United States Patent
Kulyk et al.

(10) Patent No.: US 11,730,720 B2
(45) Date of Patent: *Aug. 22, 2023

(54) ALK5 INHIBITORS

(71) Applicant: THERAVANCE BIOPHARMA R&D IP, LLC, South San Francisco, CA (US)

(72) Inventors: Svitlana Kulyk, Redwood City, CA (US); Christina Owens, Oakland, CA (US); Steven D. E. Sullivan, San Francisco, CA (US); Jennifer Kozak, Pacifica, CA (US); Adam D. Hughes, Half Moon Bay, CA (US)

(73) Assignee: Theravance Biopharma R&D IP, LLC, South San Francisco, CA (US)

( * ) Notice: Subject to any disclaimer, the term of this patent is extended or adjusted under 35 U.S.C. 154(b) by 268 days.

This patent is subject to a terminal disclaimer.

(21) Appl. No.: 17/247,225

(22) Filed: Dec. 4, 2020

(65) Prior Publication Data

US 2021/0154178 A1 May 27, 2021

Related U.S. Application Data

(63) Continuation of application No. 16/708,926, filed on Dec. 10, 2019, now Pat. No. 10,952,996.

(60) Provisional application No. 62/939,192, filed on Nov. 22, 2019, provisional application No. 62/778,142, filed on Dec. 11, 2018.

(51) Int. Cl.
| | |
|---|---|
| *A61K 31/4375* | (2006.01) |
| *A61K 9/00* | (2006.01) |
| *A61K 31/439* | (2006.01) |
| *A61K 31/4545* | (2006.01) |
| *A61K 31/4709* | (2006.01) |
| *A61K 31/496* | (2006.01) |
| *A61K 31/4985* | (2006.01) |
| *A61K 31/551* | (2006.01) |
| *A61K 45/06* | (2006.01) |
| *C07D 401/14* | (2006.01) |
| *C07D 471/04* | (2006.01) |
| *C07D 519/00* | (2006.01) |

(52) U.S. Cl.
CPC ........ *A61K 31/4375* (2013.01); *A61K 9/0073* (2013.01); *A61K 31/439* (2013.01); *A61K 31/4545* (2013.01); *A61K 31/4709* (2013.01); *A61K 31/496* (2013.01); *A61K 31/4985* (2013.01); *A61K 31/551* (2013.01); *A61K 45/06* (2013.01); *C07D 401/14* (2013.01); *C07D 471/04* (2013.01); *C07D 519/00* (2013.01)

(58) Field of Classification Search
CPC .............. A61K 31/4375; A61K 9/0073; A61K 31/439; A61K 31/4545; A61K 31/4709; A61K 31/496; A61K 31/4985; A61K 31/551; A61K 45/06; C07D 401/14; C07D 471/04; C07D 519/00
See application file for complete search history.

(56) References Cited

U.S. PATENT DOCUMENTS

| | | | |
|---|---|---|---|
| 10,952,996 B2 * | 3/2021 | Kulyk | ................ A61K 9/0073 |
| 2004/0063949 A1 | 4/2004 | Gellibert et al. | |
| 2004/0176390 A1 | 9/2004 | Blumberg et al. | |
| 2008/0319012 A1 | 12/2008 | Kim et al. | |
| 2010/0022535 A1 | 1/2010 | Lee et al. | |
| 2010/0179143 A1 | 7/2010 | Adams et al. | |
| 2020/0147234 A1 | 5/2020 | Thomas-Karyat | |
| 2020/0188370 A1 | 6/2020 | Kulyk et al. | |
| 2021/0154179 A1 * | 5/2021 | Owens | ................ C07D 487/04 |
| 2021/0387983 A1 * | 12/2021 | Brozell | ................ A61P 35/04 |

FOREIGN PATENT DOCUMENTS

| | | |
|---|---|---|
| WO | 2001062756 A1 | 8/2001 |
| WO | 2001072737 A1 | 10/2001 |
| WO | 2002040468 A1 | 5/2002 |
| WO | 2002062794 A2 | 8/2002 |
| WO | 2002088107 A1 | 11/2002 |
| WO | 2004026306 A2 | 4/2004 |
| WO | 2004026859 A1 | 4/2004 |
| WO | 2004072033 A2 | 8/2004 |
| WO | 2004111036 A1 | 12/2004 |
| WO | 2006025988 A1 | 3/2006 |
| WO | 2007059359 A2 | 5/2007 |
| WO | 2008150827 A1 | 12/2008 |
| WO | 2009150547 A2 | 12/2009 |
| WO | 2010033906 A2 | 3/2010 |
| WO | 2013009140 A2 | 1/2013 |
| WO | 2015046647 A1 | 4/2015 |
| WO | 2016081364 A1 | 5/2016 |
| WO | 2016140884 A1 | 9/2016 |
| WO | 2018017633 A1 | 1/2018 |
| WO | 2018183586 A1 | 10/2018 |

(Continued)

OTHER PUBLICATIONS

Maher; Toxicology and Applied Pharmacology 2022, 438, 115905. https://doi.org/10.1016/j.taap.2022.115905 (Year: 2022).*

(Continued)

*Primary Examiner* — Daniel R Carcanague

(74) *Attorney, Agent, or Firm* — Sheppard Mullin Richter & Hampton LLP

(57) ABSTRACT

The present disclosure provides inhibitors of activin receptor-like kinase 5 (ALK5). Also disclosed are methods to modulate the activity of ALK5 and methods of treatment of disorders mediated by ALK5.

28 Claims, No Drawings

(56) References Cited

FOREIGN PATENT DOCUMENTS

| | | | |
|---|---|---|---|
| WO | 2019005241 | A1 | 1/2019 |
| WO | 2020123453 | A2 | 6/2020 |
| WO | 2020123453 | A3 | 7/2020 |

OTHER PUBLICATIONS

Ayers et al., "Transforming growth factor-B signaling in systemic sclerosis", The Journal of Biomedical Research, 32(1): 3-12 (2018).

The Written Opinion of the International Searching Authority for PCT/US2019/065389 dated Jun. 29, 2020.

Ebrahimi et al., "Interactions between Activin-like kinase 5 (ALK5) receptor and its inhibitors and the construction of a docking descriptor-based QSAR model", Journal Braz. Chem Soc, 23(11): 2043-2053 (2012).

Gellibert et al., "Identification of 1,5-naphthyridine derivatives as a novel series of potent and selective TGF-beta type I receptor inhibitors", J.Med.Chem, 47: 4494-4506 (2004).

Jin et al., "Discovery of N-((4-([1,2,4]triazolo[1,5-a]pyridin-6-yl)-5-(6-methylpyridin-2-yl)-1H-imidazol-2-yl)methyl)-2-fluoroaniline (EW-7197): A highly potent, selective, and orally bioavailable inhibitor of TGF-beta type I receptor kinase as cancer immunotherapeutic/antifobrotic agent", J.Med.Chem., 57: 4213-1238 (2014).

Jinnin et al., "Transforming growth factor beta-inhibitor repsox downregulates collagen expression of scleroderma dermal fibroblasts and prevents bleomycin-induced mice skin fibrosis", Exp. Dermatology, 26: 1139-1143 (2017).

Kelly et al., "Nephrogenic systemic fibrosis is associated with transforming growth factor B and Smad without evidence of renin-angiotensin system involvement", Journal of the American Academy of Dermatology, 58: 1025-1030 (2008).

Li et al., "Synthesis and biological evaluation of 1-(6-methylpyridin-2-yl)-5-(quinoxalin-6-yl)-1,2,3-triazoles as transforming growth factor-beta type I receptor kinase inhibitors", Bioorganic & Med.Chem. Lett., 23: 1083-1086 (2013).

McCormick et al., "Anti-TGF-B treatment prevents skin and lung fibrosis in murine sclerodermatous graft-versus-host disease: a model for human scleroderma", The Journal of Immunology, 163: 5693-5699 (1999).

Pardali et al., "TGF-B-Induced endothelial-mesenchymal transition in fibrotic diseases", International Journal of Molecular Sciences, 18: 2157 (2017).

Ren et al., "Pharmacophore modeling and virtual screening for the discovery of new transforming growth factor-beta type I receptor (ALK5) inhibitors", Eur.J.Med.Chem., 44" 4259-4265 (2009).

Rosenbloom et al., "Human fibrotic diseases: current challenges in fibrosis research", Fibrosis: Methods and Protocols, Chapter 1, 1627: 1-23 (2017).

Song et al., "Vactosertib, a novel, orally bioavailable activin receptor-like kinase 5 inhibitor, promotes regression of fibrotic plaques in a rat model of peyronie's disease", The World of Men's Health, 12 pages (2019).

Yingling et al., "Development of TGF-B signalling inhibitors for cancer therapy", Nature Reviews: Drug Discovery, 3: 1011-1022 (2004).

Yuan et al., "Targeting the immunity protein kinases for immuno-oncology", Eur.J.Med.Chem., 163:413-427 (2019).

Zhu et al., "Design, synthesis, and antifibrosis evaluation of 4-(benzo-[c][1,2,5]thiadiazol-5-yl)-3(5)-(6-methyl-pyridin-2-yl)pyrazole and 3(5)-(6-methylpyridin-2-yl)-4-(thieno-[3,2,-c]pyridin-2-yl)pyrazole derivatives", Eur.J.Med.Chem., 180: 15-27 (2019).

\* cited by examiner

ALK5 INHIBITORS

CROSS-REFERENCE

This application is a continuation of U.S. application Ser. No. 16/708,926, filed Dec. 10, 2019; which claims the benefit of U.S. Provisional Application No. 62/778,142, filed Dec. 11, 2018, and U.S. Provisional Application No. 62/939,192, filed Nov. 22, 2019, each of which is incorporated herein by reference in its entirety.

BACKGROUND

Human fibrotic diseases such as systemic sclerosis (SSc), sclerodermatous graft vs. host disease, nephrogenic system fibrosis, and radiation-induced fibrosis, as well as cardiac, pulmonary, skin, liver, bladder and kidney fibrosis, constitute a major health problem. These diseases often progress to organ dysfunction with eventual organ failure and death due to lack of treatment available, mainly because the etiologic mechanisms of runaway fibrosis are complex, heterogeneous, and difficult to decipher. Activated myofibroblasts may be responsible for replacing normal tissues with nonfunctional fibrotic tissue. Therefore, signaling pathways responsible for stimulating profibrotic reactions in myofibroblasts have potential as targets for development of therapies to treat fibrotic diseases.

Normal tissue repair involves fibrotic reactions through homeostatic regulatory mechanisms. Uncontrolled fibrosis, however, may result in excess deposition of the extracellular matrix (ECM) macromolecules in interstitial space that stiffens over time. There are many sites along the molecular pathway leading up to myofibroblast activation, including, but not limited to, transforming growth factor-β (TGF-β) and bone morphogenic protein (BMP) signaling pathways. Of importance in this disclosure is the pathway involving transforming growth factor-β (TGF-β), TGF-β receptor I (TGF-βRI), and TGF-β receptor II (TGF-βRII).

TGF-β signaling is typically initiated by binding of a TGF-β ligand to a TGF-βRII. This in turn may recruit and phosphorylate TGF-βRI, also known as the activin receptor-like kinase 5 (ALK5). Once phosphorylated, ALK5 typically adopts an active conformation and is free to associate with and phosphorylate Smad2 or Smad3. Once phosphorylated, Smad 2 and 3 proteins then may form heterodimeric complexes with Smad4 which can translocate across the nuclear membrane and modulate Smad-mediated gene expression, including, for example, the production of collagen. Smad proteins are intracellular regulators of transcription and therefore may serve as modulators of TGF-β-regulated genes involving, inter alia, cell cycle arrest in epithelial and hematopoietic cells, control of mesenchymal cell proliferation and differentiation, wound healing, extracellular matrix production, immunosuppression and carcinogenesis.

ALK5 is believed to be the most relevant of the activin-like kinases (ALKs) in the fibrotic process (Rosenbloom, et al., *Fibrosis: Methods and Protocols, Methods in Molecular Biology*, 2017, Vol. 1627, Chapter 1, pp. 1-21). Several small molecules have been developed to inhibit the activity of ALK5 for various therapeutic indications, related mostly to oncology (see Yingling, et al., *Nature Reviews: Drug Discovery*, December 2004, Vol. 3, pp. 1011-1022).

SUMMARY OF THE INVENTION

One of the main problems with ALK5 inhibitors developed to date is that these molecules have been associated with ventricular or cardiac remodeling in preclinical safety studies resulting from significant systemic exposure from oral administration. In view of the foregoing, a need exists for small molecules that target ALK5 and for use of such compounds in the treatment of various diseases, such as cancer and fibrosis, while limiting adverse side effects. The present disclosure provides these and other related advantages. One objective of the present disclosure is to deliver a potent ALK5 inhibitor locally with minimal systemic exposure in order to address any unintended and unwanted systemic side effects of ALK5 inhibition during treatment. Therefore, in some aspects, the present disclosure provides inhaled, long-acting and lung-selective ALK5 inhibitors for the treatment of idiopathic pulmonary fibrosis. Compounds of the present disclosure may be used to treat other diseases, including, but not limited to, pulmonary fibrosis, liver fibrosis, renal glomerulosclerosis, and cancer. Compounds of the present disclosure may be used as a monotherapy or co-dosed with other therapies, whether delivered by inhalation, orally, intravenously, subcutaneously, or topically.

In certain aspects, the present disclosure provides a compound of formula I:

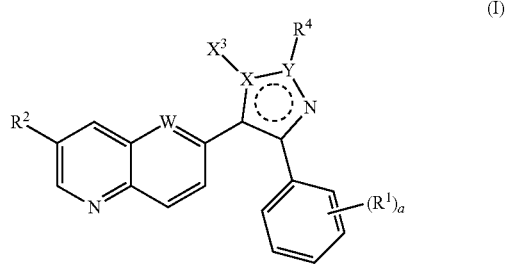

where:

W is N or C;

X and Y form a pyrrole, pyrazole, imidazole or triazole ring and X and Y is independently selected from C or N;

a is an integer from 1 to 3; each $R^1$ is independently selected from halo, —OH, —$C_{1-6}$ alkyl, and —$C_{0-2}$ alkylene-O—$C_{1-6}$ alkyl;

$R^2$ is selected from H; —NH—$(CH_2)_{0-3}R^5$; —$NHCH_2C(CH_3)_2R^5$; —$NHCH_2C(CH_3)(CH_2OCH_3)R^5$; —$NHR^5$; —$NH(CH_2)_{0-3}R^5$; —NH—$C(CH_3)_2CH_2R^5$; —$N(CH_3)R^5$; —$N(CH_3)CH_2R^5$; —$N(CH_3)CH_2CH_2R^5$; phenyl-$R^5$; pyrrolinyl; pyrrolidinyl; 3,6-diazabicyclo[3.2.0]heptanyl; 1,4-diazepanyl; piperazinyl; (2R,5R)-1,2,5-trimethylpiperazinyl; 1-methylpyridin-2(1H)-onyl; and carboxylate; or $R^2$ is selected from azetidinyl-$R^5$; piperazinyl-$R^5$; isopropylpiperazinyl-$R^5$; methylpiperazinyl-$R^5$; isopropylpiperazinyl-$R^5$; pyrrolidinyl-$R^5$; piperidinyl-$R^5$; pyrazolyl-$R^5$; triazolyl-$R^5$; 2,7-diazaspiro[4.4]nonanyl-$R^5$; 2,5-diazabicyclo[2.2.1]heptanyl-$R^5$; 5,6,7,8-tetrahydro-[1,2,4]triazolo[1,5-a]pyrazinyl; 5,6,7,8-tetrahydro-[1,2,4]triazolo[1,5-a]pyrazinyl-$R^5$; 5,6,7,8-tetrahydroimidazo[1,5-a]pyrazinyl; 3-(trifluoromethyl)-5,6,7,8-tetrahydroimidazo[1,5-a]pyrazinyl; 5,6,7,8-tetrahydroimidazo[1,2-a]pyrazinyl; 5,6,7,8-tetrahydroimidazo[1,2-a]pyrimidinyl; 5,6,7,8-tetrahydropyrido[4,3-c]pyridazine; 4,5,6,7-tetrahydro-[1,2,3]triazolo[1,5-a]pyrazinyl; 3,6-diazabicyclo[3.2.0]heptanyl-$R^5$; 2,3-dihydro-1H-imidazo[1,2-a]imidazolyl; 2,3-dihydro-1H-imidazo[1,5-a]imidazolyl; 4,5,6,7-tetrahydropyrazolo[1,5-a]pyrazinyl; 4,5,6,7-tetrahydropyrazolo[1,5-a]pyrazinyl-$R^5$; 5,6,7,8-tetrahydroimidazo[1,2-a]pyrazinyl; 5,6-dihydro-4H-imidazo[1,2-c][1,2,3]triazolyl; 2,4,5,6-tetrahydropyrrolo[2, 3-c]pyrazolyl; (R)-2-methyl-1,4-diazepanyl-R⁵; cyclohexenyl-R⁵; and cyclohexanyl-R⁵;

R³ is absent or is selected from benzyl or —C₀₋₃ alkylene-R⁷; or R³ is taken together with R⁴ to form a six-membered aromatic ring;

R⁴ is absent or taken together with R³ to form a six-membered aromatic ring;

R⁵ is selected from piperazinyl, piperidinyl, pyrrolidinyl, azetidinyl, pyridinyl, pyrrolinyl, —CH₂—R⁶, or 1,4-diazabicyclo[2.2.2]octanyl, optionally substituted with one or more methyl, ethyl, i-propyl, n-propyl, substituted or unsubstituted piperazinyl, carboxyl, carboxylate, or benzyl; methyl amine; dimethyl amine; substituted or unsubstituted cyclopentanyl; substituted or unsubstituted cyclohexanyl; —(CH₂)₀₋₃OH; —(CH₂)₀₋₃OCH₃; methyl; ethyl; i-propyl; n-propyl; halo; —CF₃; carboxamide; methyl carboxamide; dimethyl carboxamide; isopropyl carboxamide; benzyl carboxamide; N-methylacetamide; —NH₂; —NH-benzyl; —CH₂NHCH₃; —CH₂CH₂NH₂; —CH₂H₂N(CH₃)₂; —CH₂CH₂NHCH₃; —CH₂CH₂NHC(CH₃)₂; —CH₂CH₂NH-benzyl; carboxyl; carboxylate; benzyl carboxylate; methyl carboxylate; isopropyl carboxylate; substituted or unsubstituted piperazinyl; ethylazetidinyl; and 1,5-diazabicyclo[3.3.2]decanyl;

R⁶ is selected from azetidinyl, imidazolyl, and 5,6,7,8-tetrahydro-1,6-naphthyridine;

R⁷ is a heterocycle; or a pharmaceutically-acceptable salt thereof.

In some embodiments, W is N. In some embodiments, a is an integer from 1 to 3 and each R¹ is independently selected from halo, —OH, —C₁₋₆ alkyl, and —C₀₋₂ alkylene-O—C₁₋₆ alkyl. In some embodiments, a is an integer from 1 to 3 and each R¹ is independently selected from F and Cl. In some embodiments, a is 1 and R¹ is F. In some embodiments, a is 2 and R¹ is F, or R¹ is Cl and F. In some embodiments, a is 3 and R¹ is independently selected from F and Cl. In some embodiments, a is 1 or 2 and R¹ is independently selected from —CH₃, —CH₂OCH₃, and —OH. In some embodiments, W is C. In some embodiments, a is an integer from 1 to 3 and each R¹ is independently selected from F and Cl. In some embodiments, a is 1 and R¹ is Cl. In some embodiments, a is 2 and R¹ is F, or R¹ is Cl and F. In some embodiments, a is 3 and R¹ is independently selected from F and Cl.

In some embodiments, the present disclosure provides a pharmaceutical composition comprising a compound described herein and a pharmaceutically acceptable carrier. In some embodiments, the present disclosure provides a method of treating fibrosis, comprising administering to a patient a therapeutically effective amount of a compound described herein, optionally wherein the fibrosis is selected from systemic fibrosis, organ-specific fibrosis, fibrosis associated with cancer, cystic fibrosis, and fibrosis associated with autoimmune diseases. The organ-specific fibrosis may be selected from cardiac fibrosis, kidney fibrosis, pulmonary fibrosis, liver fibrosis, portal vein fibrosis, skin fibrosis, bladder fibrosis, intestinal fibrosis, peritoneal fibrosis, myelofibrosis, oral submucous fibrosis, and retinal fibrosis. In some embodiments, the pulmonary fibrosis is selected from idiopathic pulmonary fibrosis (IPF), familial pulmonary fibrosis (FPF), interstitial lung fibrosis, fibrosis associated with asthma, fibrosis associated with chronic obstructive pulmonary disease (COPD), silica-induced fibrosis, asbestos-induced fibrosis and chemotherapy-induced lung fibrosis, such as idiopathic pulmonary fibrosis (IPF). In some embodiments, the present disclosure provides a compound described herein for use in treating fibrosis. In some embodiments, the present disclosure provides the use of a compound described herein for the manufacture of a medicament for treating fibrosis.

In certain aspects, the present disclosure provides a compound of formula II:

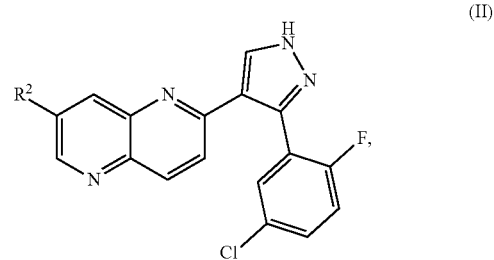

(II)

where W, X, Y, R¹, R², R³, R⁴, and a are as defined above, or a pharmaceutically acceptable salt thereof.

In certain aspects, the present disclosure provides a compound of formula III:

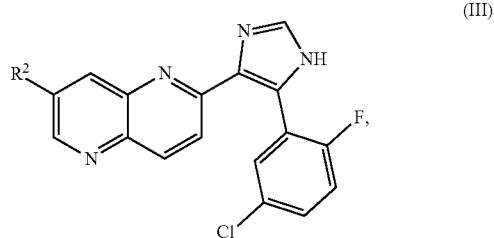

(III)

where W, X, Y, R¹, R², R³, R⁴, and a are as defined above, or a pharmaceutically acceptable salt thereof.

In certain aspects, the present disclosure provides a compound of formula IV:

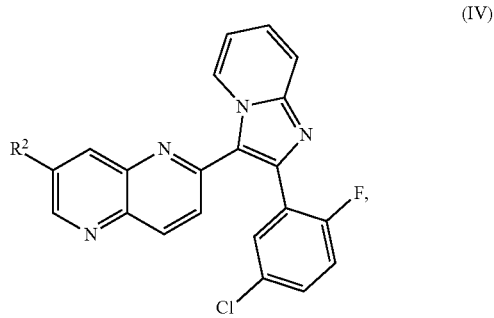

(IV)

where W, X, Y, R¹, R², R³, R⁴, and a are as defined above, or a pharmaceutically acceptable salt thereof.

In certain aspects, the present disclosure provides a compound of formula V:

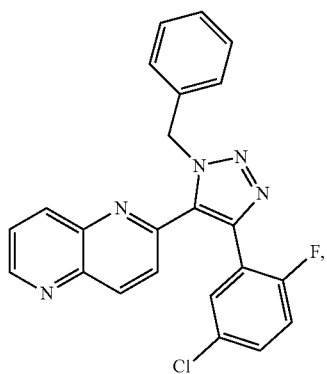

(V)

where W, X, Y, R¹, R², R³, R⁴, and a are as defined above, or a pharmaceutically acceptable salt thereof.

In certain aspects, the present disclosure provides a compound of formula VI:

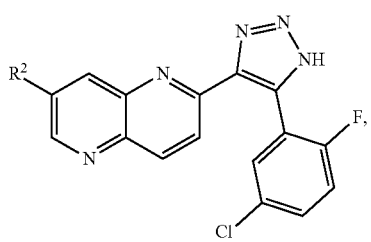

(VI)

where W, X, Y, R¹, R², R³, R⁴, and a are as defined above, or a pharmaceutically acceptable salt thereof.

In certain aspects, the present disclosure provides a compound of formula VII:

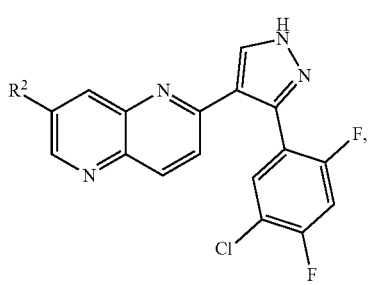

(VII)

where W, X, Y, R¹, R², R³, R⁴, and a are as defined above, or a pharmaceutically acceptable salt thereof.

In certain aspects, the present disclosure provides a compound of formula VIII:

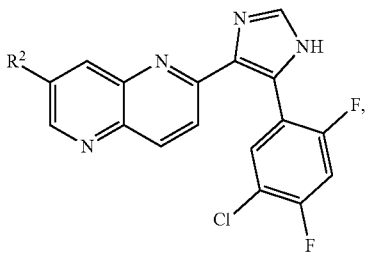

(VIII)

where W, X, Y, R¹, R², R³, R⁴, and a are as defined above, or a pharmaceutically acceptable salt thereof.

In certain aspects, the present disclosure provides a compound of formula IX:

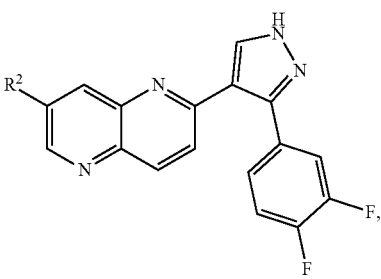

(IX)

where W, X, Y, R¹, R², R³, R⁴, and a are as defined above, or a pharmaceutically acceptable salt thereof.

In certain aspects, the present disclosure provides a compound of formula X:

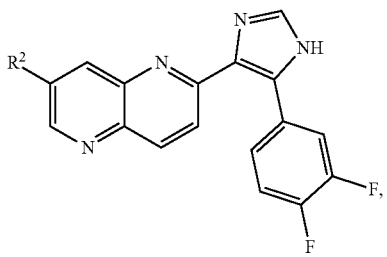

(X)

where W, X, Y, R¹, R², R³, R⁴, and a are as defined above, or a pharmaceutically acceptable salt thereof.

In certain aspects, the present disclosure provides a compound of formula XI:

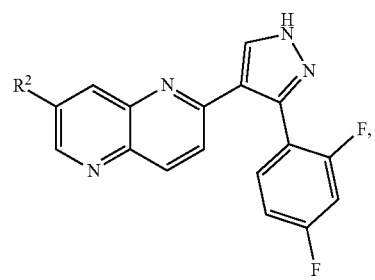

(XI)

where W, X, Y, R¹, R², R³, R⁴, and a are as defined above, or a pharmaceutically acceptable salt thereof.

In certain aspects, the present disclosure provides a compound of formula XII:

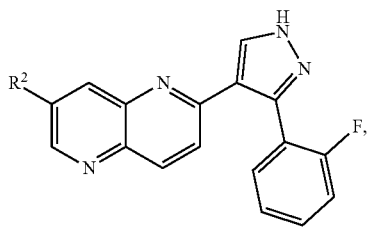

(XII)

where W, X, Y, R¹, R², R³, R⁴, and a are as defined above, or a pharmaceutically acceptable salt thereof.

In certain aspects, the present disclosure provides a compound of formula XIII:

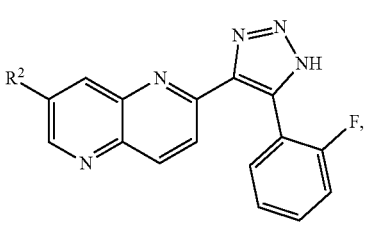

(XIII)

where W, X, Y, R¹, R², R³, R⁴, and a are as defined above, or a pharmaceutically acceptable salt thereof.

In certain aspects, the present disclosure provides a compound of formula XIV:

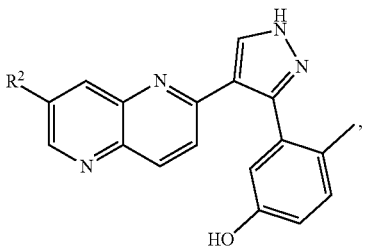

(XIV)

where W, X, Y, R¹, R², R³, R⁴, and a are as defined above, or a pharmaceutically acceptable salt thereof.

In certain aspects, the present disclosure provides a compound of formula XV:

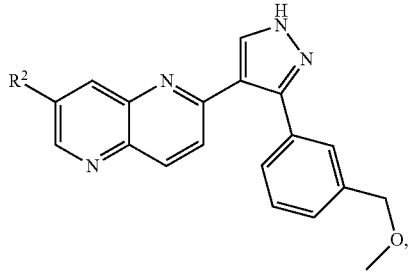

(XV)

where W, X, Y, R¹, R², R³, R⁴, and a are as defined above, or a pharmaceutically acceptable salt thereof.

In certain aspects, the present disclosure provides a compound of formula XVI:

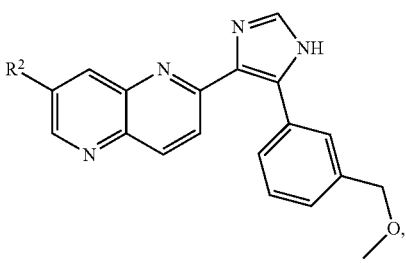

(XVI)

where W, X, Y, R¹, R², R³, R⁴, and a are as defined above, or a pharmaceutically acceptable salt thereof.

In certain aspects, the present disclosure provides a compound of formula XVII:

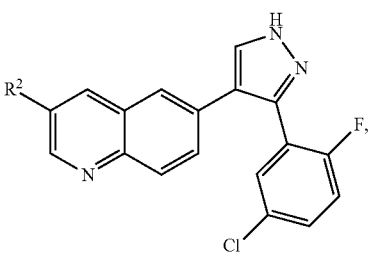

(XVII)

where W, X, Y, R¹, R², R³, R⁴, and a are as defined above, or a pharmaceutically acceptable salt thereof.

In certain aspects, the present disclosure provides a compound of formula XVIII:

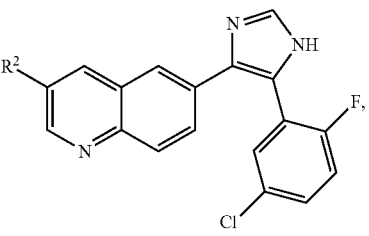

(XVIII)

where W, X, Y, R¹, R², R³, R⁴, and a are as defined above, or a pharmaceutically acceptable salt thereof.

In certain aspects, the present disclosure provides a compound of formula XIX:

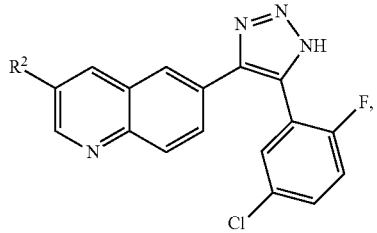
(XIX)

where W, X, Y, R¹, R², R³, R⁴, and a are as defined above, or a pharmaceutically acceptable salt thereof.

In certain aspects, the present disclosure provides a compound of formula XX:

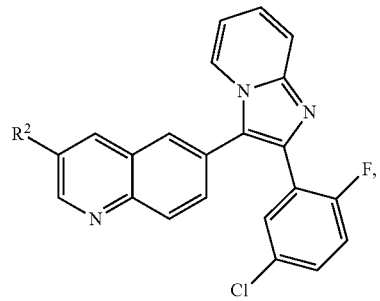
(XX)

where W, X, Y, R¹, R², R³, R⁴, and a are as defined above, or a pharmaceutically acceptable salt thereof.

In certain aspects, the present disclosure provides a compound of formula XXI:

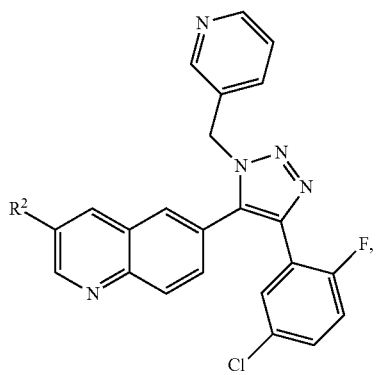
(XXI)

where W, X, Y, R¹, R², R³, R⁴, and a are as defined above, or a pharmaceutically acceptable salt thereof.

In certain aspects, the present disclosure provides a compound of formula XXII:

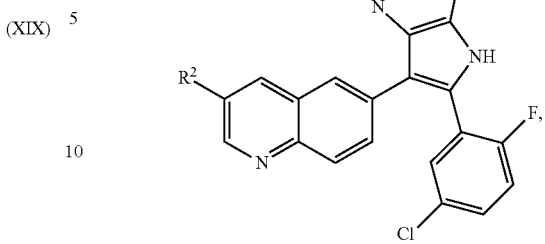
(XXII)

where W, X, Y, R¹, R², R³, R⁴, and a are as defined above, or a pharmaceutically acceptable salt thereof.

In certain aspects, the present disclosure provides a compound of formula XXIII:

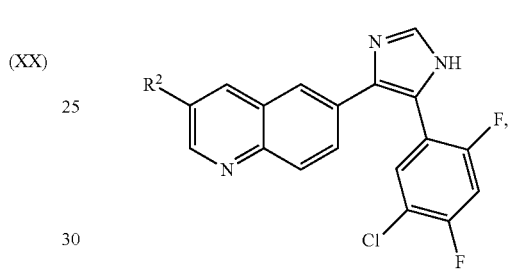
(XXIII)

where W, X, Y, R¹, R², R³, R⁴, and a are as defined above, or a pharmaceutically acceptable salt thereof.

In certain aspects, the present disclosure provides a compound of formula XXIV:

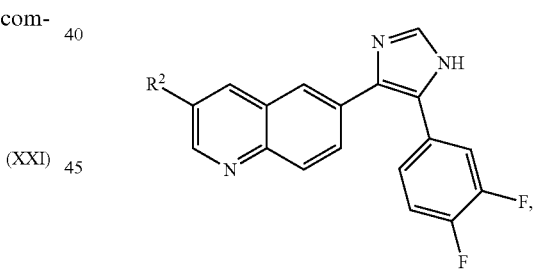
(XXIV)

where W, X, Y, R¹, R², R³, R⁴, and a are as defined above, or a pharmaceutically acceptable salt thereof.

In certain aspects, the present disclosure provides a compound of formula XXV:

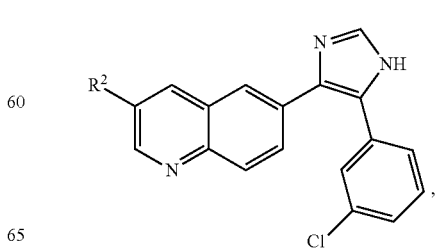
(XXV)

where W, X, Y, $R^1$, $R^2$, $R^3$, $R^4$, and a are as defined above, or a pharmaceutically acceptable salt thereof.

Another aspect of the invention relates to pharmaceutical compositions comprising a pharmaceutically acceptable carrier and a compound of the invention.

Yet another aspect of the invention relates to processes and intermediates useful for preparing compounds of the invention. Another aspect of the invention relates to a process of preparing a pharmaceutically acceptable salt of a compound of formula I, comprising contacting a compound of formula I in free acid or base form with a pharmaceutically acceptable base or acid. In other aspects, the invention relates to products prepared by any of the processes described herein, as well as novel intermediates used in such process.

The present invention provides compounds which are metabolized in vivo to compounds that have been found to possess ALK5 inhibition activity. Accordingly, compounds of the invention are expected to be useful and advantageous as therapeutic agents for treating patients suffering from a disease or disorder that is treated by inhibiting ALK5. Thus, one aspect of the invention relates to a method of treating fibrosis, comprising administering to a patient a therapeutically effective amount of a compound of the invention.

In one aspect, the invention relates to a method of treating fibrosis, comprising administering to a patient a therapeutically effective amount of the compound of formula I. Fibrosis may be systemic fibrosis, organ-specific fibrosis, fibrosis associated with cancer, cystic fibrosis, or fibrosis associated with autoimmune diseases. Organ-specific fibrosis may be cardiac fibrosis, kidney fibrosis, pulmonary fibrosis, liver fibrosis, portal vein fibrosis, skin fibrosis, bladder fibrosis, intestinal fibrosis, peritoneal fibrosis, myelofibrosis, oral submucous fibrosis, or retinal fibrosis.

In a preferred embodiment, the invention relates to the treatment of pulmonary fibrosis with the administration of a therapeutically effective amount of the compound of formula I to a patient. In particular, the pulmonary fibrosis is selected from idiopathic pulmonary fibrosis (IPF), familial pulmonary fibrosis (FPF), interstitial lung fibrosis, fibrosis associated with asthma, fibrosis associated with chronic obstructive pulmonary disease (COPD), silica-induced fibrosis, asbestos-induced fibrosis and chemotherapy-induced lung fibrosis. In a more preferred embodiment, the fibrosis is idiopathic pulmonary fibrosis (IPF).

Yet another aspect of the invention relates to the use of a compound of formula I or a pharmaceutically acceptable salt thereof, for the manufacture of a medicament, especially for the manufacture of a medicament useful for treating fibrosis. Another aspect of the invention relates to use of a compound of the invention for inhibiting ALK5 in a mammal. Other aspects and embodiments of the invention are disclosed herein.

In certain aspects, the present disclosure provides a compound of formula I:

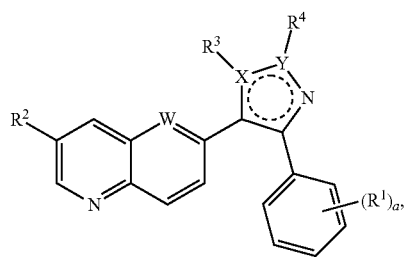

(I)

wherein:
W is N;
X and Y form a pyrrole, pyrazole, imidazole or triazole ring and X and Y are independently selected from C and N;
a is an integer from 1 to 3;
each $R^1$ is independently selected from halo, —OH, —$C_{1-6}$ alkyl, and —$C_{0-2}$ alkylene-O—$C_{1-6}$ alkyl;
$R^2$ is selected from H; —NH—$(CH_2)_{0-3}R^5$; —NHCH$_2$C(CH$_3$)$_2R^5$; —NHCH$_2$C(CH$_3$)(CH$_2$OCH$_3$)$R^5$; —NHR$^5$; —NH—C(CH$_3$)$_2$CH$_2R^5$; —N(CH$_3$)$R^5$; —N(CH$_3$)CH$_2R^5$; —N(CH$_3$)CH$_2$CH$_2R^5$; phenyl-$R^5$; pyrrolinyl; pyrrolidinyl; 3,6-diazabicyclo[3.2.0]heptanyl; 1,4-diazepanyl; piperazinyl; (2R,5R)-1,2,5-trimethylpiperazinyl; 1-methylpyridin-2(1H)-onyl; and carboxylate; or
$R^2$ is selected from azetidinyl-$R^5$; piperazinyl-$R^5$; isopropylpiperazinyl-$R^5$; methylpiperazinyl-$R^5$; isopropylpiperazinyl-$R^5$; pyrrolidinyl-$R^5$; piperidinyl-$R^5$; pyrazolyl-$R^5$; triazolyl-$R^5$; 2,7-diazaspiro[4.4]nonanyl-$R^5$; 2,5-diazabicyclo[2.2.1]heptanyl-$R^5$; 5,6,7,8-tetrahydro-[1,2,4]triazolo[1,5-a]pyrazinyl; 5,6,7,8-tetrahydro-[1,2,4]triazolo[1,5-a]pyrazinyl-$R^5$; 5,6,7,8-tetrahydroimidazo[1,5-a]pyrazinyl; 3-(trifluoromethyl)-5,6,7,8-tetrahydroimidazo[1,5-a]pyrazinyl; 5,6,7,8-tetrahydroimidazo[1,2-a]pyrazinyl; 5,6,7,8-tetrahydroimidazo[1,2-a]pyrimidinyl; 5,6,7,8-tetrahydropyrido[4,3-c]pyridazinyl; 4,5,6,7-tetrahydro-[1,2,3]triazolo[1,5-a]pyrazinyl; 3,6-diazabicyclo[3.2.0]heptanyl-$R^5$; 2,3-dihydro-1H-imidazo[1,2-a]imidazolyl; 2,3-dihydro-1H-imidazo[1,5-a]imidazolyl; 4,5,6,7-tetrahydropyrazolo[1,5-a]pyrazinyl; 4,5,6,7-tetrahydropyrazolo[1,5-a]pyrazinyl-$R^5$; 5,6,7,8-tetrahydroimidazo[1,2-a]pyrazinyl; 5,6-dihydro-4H-imidazo[1,2-c][1,2,3]triazolyl; 2,4,5,6-tetrahydropyrrolo[2,3-c]pyrazolyl; (R)-2-methyl-1,4-diazepanyl-$R^5$; cyclohexenyl-$R^5$; and cyclohexanyl-$R^5$;
$R^3$ is absent or is selected from benzyl and —$C_{0-3}$alkylene-$R^7$; or $R^3$ is taken together with $R^4$ to form a six-membered aromatic ring;
$R^4$ is absent or taken together with $R^3$ to form a six-membered aromatic ring;
$R^5$ is selected from:
piperazinyl, piperidinyl, pyrrolidinyl, azetidinyl, pyridinyl, pyrrolinyl, —CH$_2$—$R^6$, and 1,4-diazabicyclo[2.2.2]octanyl, optionally substituted with one or more methyl, ethyl, i-propyl, n-propyl, substituted or unsubstituted piperazinyl, carboxyl, carboxylate, or benzyl; and
methyl amine; dimethyl amine; substituted or unsubstituted cyclopentanyl; substituted or unsubstituted cyclohexanyl; —(CH$_2$)$_{0-3}$OH; —(CH$_2$)$_{0-3}$OCH$_3$; methyl; ethyl; i-propyl; n-propyl; halo; —CF$_3$; carboxamide; methyl carboxamide; dimethyl carboxamide; isopropyl carboxamide; benzyl carboxamide; N-methylacetamide; —NH$_2$; —NH-benzyl; —CH$_2$NHCH$_3$; —CH$_2$CH$_2$NH$_2$; —CH$_2$CH$_2$N(CH$_3$)$_2$; —CH$_2$CH$_2$NHCH$_3$; —CH$_2$CH$_2$NHC(CH$_3$)$_2$; —CH$_2$CH$_2$NH-benzyl; carboxyl; carboxylate; benzyl carboxylate; methyl carboxylate; isopropyl carboxylate; substituted or unsubstituted piperazinyl; ethylazetidinyl; and 1,5-diazabicyclo[3.3.2]decanyl;
$R^6$ is selected from azetidinyl, imidazolyl, and 5,6,7,8-tetrahydro-1,6-naphthyridine; and
$R^7$ is a heterocycle; or
a pharmaceutically acceptable salt thereof.

In some embodiments, for a compound of Formula (I), a is an integer from 1 to 3 and each $R^1$ is independently selected from F and Cl. In some embodiments, a is 1 and $R^1$ is F. In some embodiments, a is 2 and $R^1$ is F, or $R^1$ is Cl and F. In some embodiments, a is 3 and $R^1$ is independently selected from F and Cl. In some embodiments, a is 1 or 2 and $R^1$ is independently selected from —$CH_3$, —$CH_2OCH_3$, and —OH.

In certain aspects, the present disclosure provides a compound of formula I:

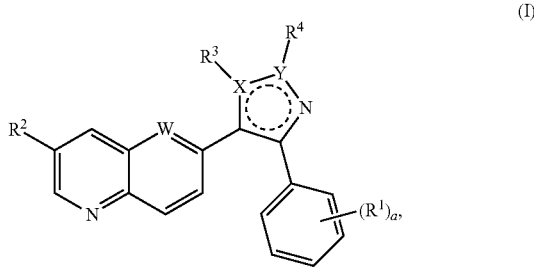

(I)

wherein:
W is CH;
X and Y form a pyrrole, pyrazole, imidazole or triazole ring and X and Y are independently selected from C and N;
a is 3;
$R^1$ is independently selected from F and Cl;
$R^2$ is selected from H; —NH—$(CH_2)_{0-3}R^5$; —$NHCH_2C(CH_3)_2R^5$; —$NHCH_2C(CH_3)(CH_2OCH_3)R^5$; —$NHR^5$; —NH—$C(CH_3)_2CH_2R^5$; —$N(CH_3)R^5$; —$N(CH_3)CH_2R^5$; —$N(CH_3)CH_2CH_2R^5$; phenyl-$R^5$; pyrrolinyl; pyrrolidinyl; 3,6-diazabicyclo[3.2.0]heptanyl; 1,4-diazepanyl; piperazinyl; (2R,5R)-1,2,5-trimethylpiperazinyl; 1-methylpyridin-2(1H)-onyl; and carboxylate; or
$R^2$ is selected from azetidinyl-$R^5$; piperazinyl-$R^5$; isopropylpiperazinyl-$R^5$; methylpiperazinyl-$R^5$; isopropylpiperazinyl-$R^5$; pyrrolidinyl-$R^5$; piperidinyl-$R^5$; pyrazolyl-$R^5$; triazolyl-$R^5$; 2,7-diazaspiro[4.4]nonanyl-$R^5$; 2,5-diazabicyclo[2.2.1]heptanyl-$R^5$; 5,6,7,8-tetrahydro-[1,2,4]triazolo[1,5-a]pyrazinyl; 5,6,7,8-tetrahydro-[1,2,4]triazolo[1,5-a]pyrazinyl-$R^5$; 5,6,7,8-tetrahydroimidazo[1,5-a]pyrazinyl; 3-(trifluoromethyl)-5,6,7,8-tetrahydroimidazo[1,5-a]pyrazinyl; 5,6,7,8-tetrahydroimidazo[1,2-a]pyrazinyl; 5,6,7,8-tetrahydroimidazo[1,2-a]pyrimidinyl; 5,6,7,8-tetrahydropyrido[4,3-c]pyridazinyl; 4,5,6,7-tetrahydro-[1,2,3]triazolo[1,5-a]pyrazinyl; 3,6-diazabicyclo[3.2.0]heptanyl-$R^5$; 2,3-dihydro-1H-imidazo[1,2-a]imidazolyl; 2,3-dihydro-1H-imidazo[1,5-a]imidazolyl; 4,5,6,7-tetrahydropyrazolo[1,5-a]pyrazinyl; 4,5,6,7-tetrahydropyrazolo[1,5-a]pyrazinyl-$R^5$; 5,6,7,8-tetrahydroimidazo[1,2-a]pyrazinyl; 5,6-dihydro-4H-imidazo[1,2-c][1,2,3]triazolyl; 2,4,5,6-tetrahydropyrrolo[2,3-c]pyrazolyl; (R)-2-methyl-1,4-diazepanyl-$R^5$; cyclohexenyl-$R^5$; and cyclohexanyl-$R^5$;
$R^3$ is absent or is selected from benzyl and —$C_{0-3}$ alkylene-$R^7$; or $R^3$ is taken together with $R^4$ to form a six-membered aromatic ring;
$R^4$ is absent or taken together with $R^3$ to form a six-membered aromatic ring;
$R^5$ is selected from:
piperazinyl, piperidinyl, pyrrolidinyl, azetidinyl, pyridinyl, pyrrolinyl, —$CH_2$—$R^6$, and 1,4-diazabicyclo[2.2.2]octanyl, optionally substituted with one or more methyl, ethyl, i-propyl, n-propyl, substituted or unsubstituted piperazinyl, carboxyl, carboxylate, or benzyl; and
methyl amine; dimethyl amine; substituted or unsubstituted cyclopentanyl; substituted or unsubstituted cyclohexanyl; —$(CH_2)_{0-3}OH$; —$(CH_2)_{0-3}OCH_3$; methyl; ethyl; i-propyl; n-propyl; halo; —$CF_3$; carboxamide;

methyl carboxamide; dimethyl carboxamide; isopropyl carboxamide; benzyl carboxamide; N-methylacetamide; —$NH_2$; —NH-benzyl; —$CH_2NHCH_3$; —$CH_2CH_2NH_2$; —$CH_2CH_2N(CH_3)_2$; —$CH_2CH_2NHCH_3$; —$CH_2CH_2NHC(CH_3)_2$; —$CH_2CH_2NH$-benzyl; carboxyl; carboxylate; benzyl carboxylate; methyl carboxylate; isopropyl carboxylate; substituted or unsubstituted piperazinyl; ethylazetidinyl; and 1,5-diazabicyclo[3.3.2]decanyl;

$R^6$ is selected from azetidinyl, imidazolyl, and 5,6,7,8-tetrahydro-1,6-naphthyridine; and $R^7$ is a heterocycle; or a pharmaceutically acceptable salt thereof.

In certain aspects, the present disclosure provides a compound of formula II, III, IV, V, VI, VII, VIII, IX, X, XI, XII, XIII, XIV, XV, XVI, XVII, XVIII, XIX, XX, XXI, XXII, or XXIII:

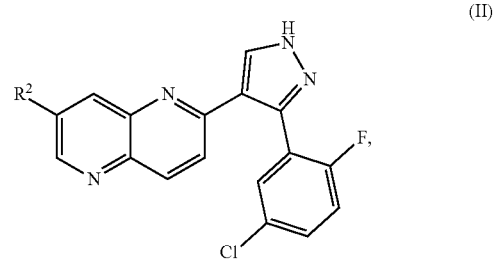

(II)

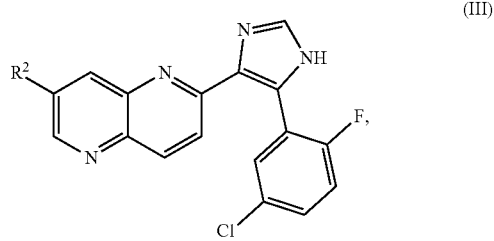

(III)

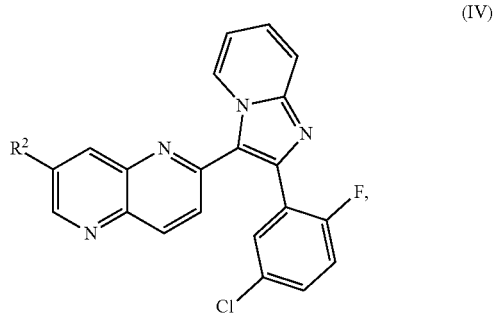

(IV)

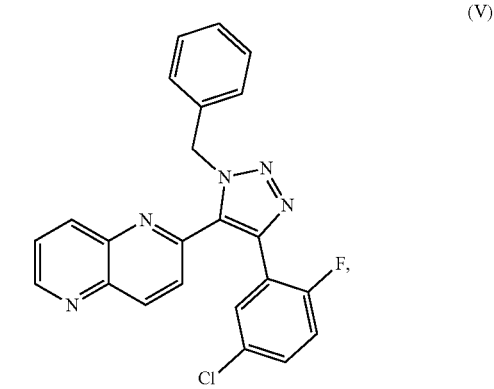 [SMILES: Fc1ccc(Cl)cc1-c1nnn(Cc2ccccc2)c1-c1ccc2ncccc2n1]

(V)

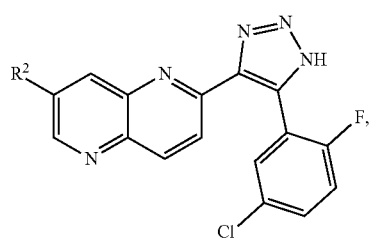
(VI)
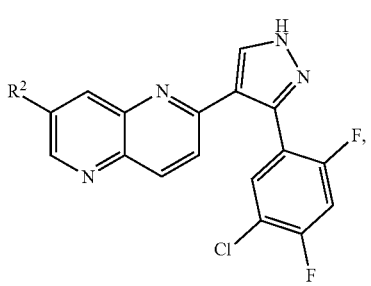
(VII)
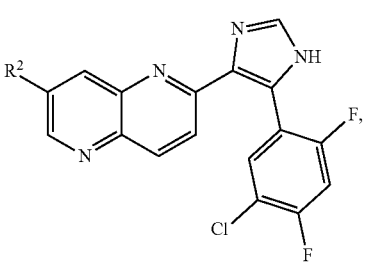
(VIII)
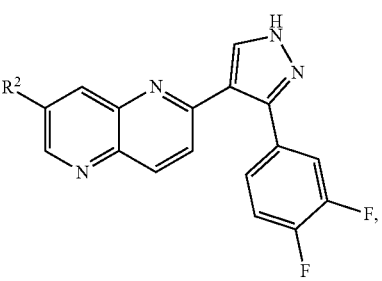
(IX)
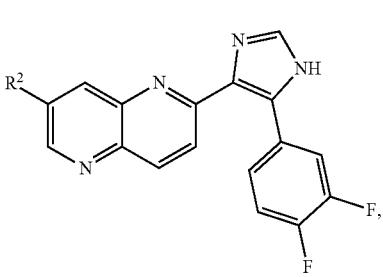
(X)
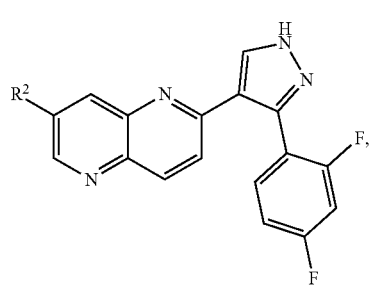
(XI)
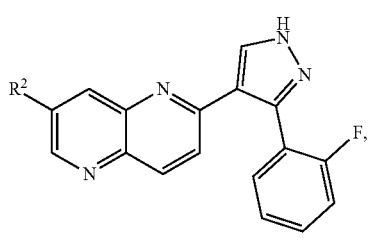
(XII)
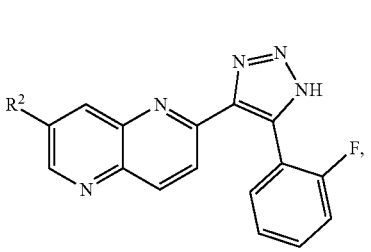
(XIII)
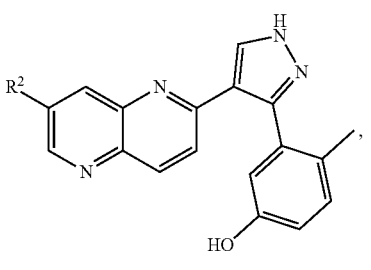
(XIV)
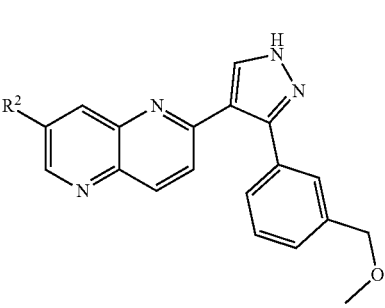
(XV)
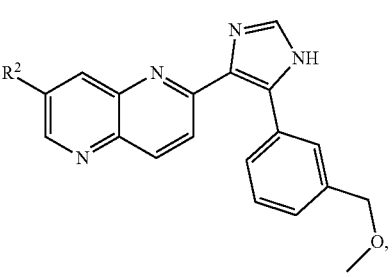
(XVI)
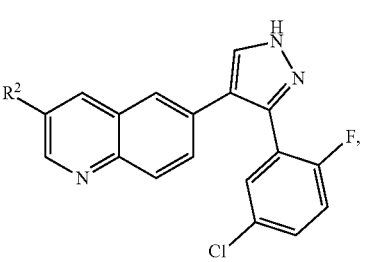
(XVII)

-continued (XVIII)
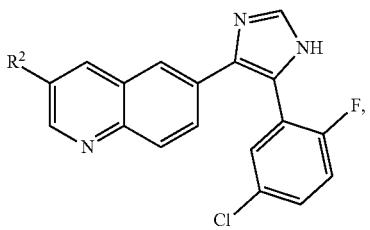

(XIX)
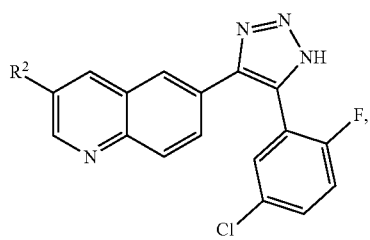

(XX)
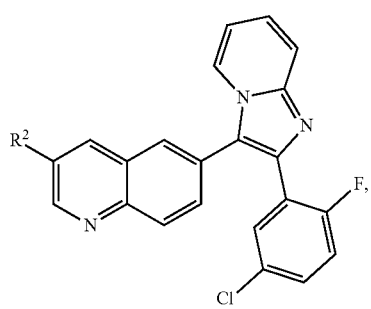

(XXI)
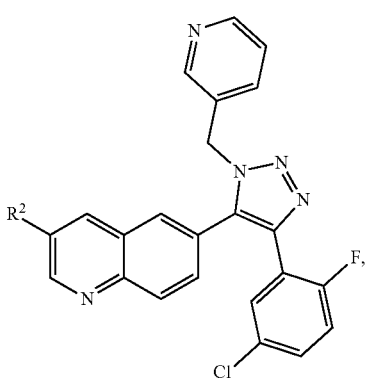

(XXII)
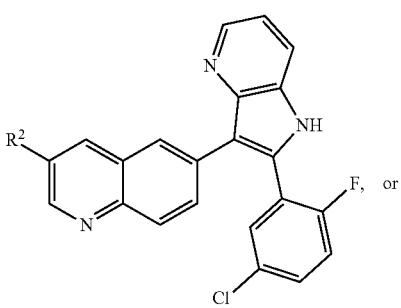

-continued (XXIII)
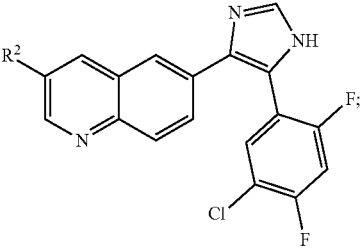

or a pharmaceutically acceptable salt thereof, wherein:

$R^2$ is selected from H; —NH—$(CH_2)_{0-3}R^5$; —NHCH$_2$C(CH$_3$)$_2$R$^5$; —NHCH$_2$C(CH$_3$)(CH$_2$OCH$_3$)R$^5$; —NHR$^5$; —NH—C(CH$_3$)$_2$CH$_2$R$^5$; —N(CH$_3$)R$^5$; —N(CH$_3$)CH$_2$R$^5$; —N(CH$_3$)CH$_2$CH$_2$R$^5$; phenyl-R$^5$; pyrrolinyl; pyrrolidinyl; 3,6-diazabicyclo[3.2.0]heptanyl; 1,4-diazepanyl; piperazinyl; (2R,5R)-1,2,5-trimethylpiperazinyl; 1-methylpyridin-2(1H)-onyl; and carboxylate; or $R^2$ is selected from azetidinyl-R$^5$; piperazinyl-R$^5$; isopropylpiperazinyl-R$^5$; methylpiperazinyl-R$^5$; isopropylpiperazinyl-R$^5$; pyrrolidinyl-R$^5$; piperidinyl-R$^5$; pyrazolyl-R$^5$; triazolyl-R$^5$; 2,7-diazaspiro[4.4]nonanyl-R$^5$; 2,5-diazabicyclo[2.2.1]heptanyl-R$^5$; 5,6,7,8-tetrahydro-[1,2,4]triazolo[1,5-a]pyrazinyl; 5,6,7,8-tetrahydro-[1,2,4]triazolo[1,5-a]pyrazinyl-R$^5$; 5,6,7,8-tetrahydroimidazo[1,5-a]pyrazinyl; 3-(trifluoromethyl)-5,6,7,8-tetrahydroimidazo[1,5-a]pyrazinyl; 5,6,7,8-tetrahydroimidazo[1,2-a]pyrazinyl; 5,6,7,8-tetrahydroimidazo[1,2-a]pyrimidinyl; 5,6,7,8-tetrahydropyrido[4,3-c]pyridazinyl; 4,5,6,7-tetrahydro-[1,2,3]triazolo[1,5-a]pyrazinyl; 3,6-diazabicyclo[3.2.0]heptanyl-R$^5$; 2,3-dihydro-1H-imidazo[1,2-a]imidazolyl; 2,3-dihydro-1H-imidazo[1,5-a]imidazolyl; 4,5,6,7-tetrahydropyrazolo[1,5-a]pyrazinyl; 4,5,6,7-tetrahydropyrazolo[1,5-a]pyrazinyl-R$^5$; 5,6,7,8-tetrahydroimidazo[1,2-a]pyrazinyl; 5,6-dihydro-4H-imidazo[1,2-c][1,2,3]triazolyl; 2,4,5,6-tetrahydropyrrolo[2,3-c]pyrazolyl; (R)-2-methyl-1,4-diazepanyl-R$^5$; cyclohexenyl-R$^5$; and cyclohexanyl-R$^5$;

$R^5$ is selected from:

piperazinyl, piperidinyl, pyrrolidinyl, azetidinyl, pyridinyl, pyrrolinyl, —CH$_2$—R$^6$, and 1,4-diazabicyclo[2.2.2]octanyl, optionally substituted with one or more methyl, ethyl, i-propyl, n-propyl, substituted or unsubstituted piperazinyl, carboxyl, carboxylate, or benzyl; and methyl amine; dimethyl amine; substituted or unsubstituted cyclopentanyl; substituted or unsubstituted cyclohexanyl; —(CH$_2$)$_{0-3}$OH; —(CH$_2$)$_{0-3}$OCH$_3$; methyl; ethyl; i-propyl; n-propyl; halo; —CF$_3$; carboxamide; methyl carboxamide; dimethyl carboxamide; isopropyl carboxamide; benzyl carboxamide; N-methylacetamide; —NH$_2$; —NH-benzyl; —CH$_2$NHCH$_3$; —CH$_2$CH$_2$NH$_2$; —CH$_2$CH$_2$N(CH$_3$)$_2$; —CH$_2$CH$_2$NHCH$_3$; —CH$_2$CH$_2$NHC(CH$_3$)$_2$; —CH$_2$CH$_2$NH-benzyl; carboxyl; carboxylate; benzyl carboxylate; methyl carboxylate; isopropyl carboxylate; substituted or unsubstituted piperazinyl; ethylazetidinyl; and 1,5-diazabicyclo[3.3.2]decanyl; and $R^6$ is selected from azetidinyl, imidazolyl, and 5,6,7,8-tetrahydro-1,6-naphthyridine.

In certain aspects, the present disclosure provides a compound of formula I:

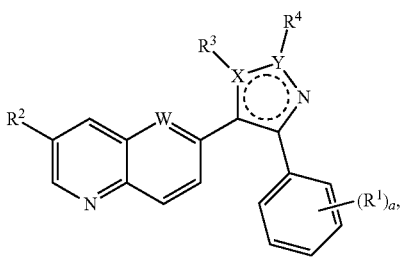

(I)

or a pharmaceutically acceptable salt thereof, wherein:

W is N or CH;

X and Y form a pyrrole, pyrazole, imidazole or triazole ring and X and Y are independently selected from C and N;

a is an integer from 0 to 3;

each $R^1$ is independently selected from halo, —OH, —$C_{1-6}$alkyl, and —$C_{0-2}$alkylene-O—$C_{1-6}$alkyl;

$R^2$ is selected from H; —NH—$(CH_2)_{0-3}R^5$; —NHCH$_2$C(CH$_3$)$_2$R$^5$; —NHCH$_2$C(CH$_3$)(CH$_2$OCH$_3$)R$^5$; —NHR$^5$; —NH—C(CH$_3$)$_2$CH$_2$R$^5$; —N(CH$_3$)R$^5$; —N(CH$_3$)CH$_2$R$^5$; —N(CH$_3$)CH$_2$CH$_2$R$^5$; phenyl-R$^5$; pyrrolinyl; pyrrolidinyl; 3,6-diazabicyclo[3.2.0]heptanyl; 1,4-diazepanyl; piperazinyl; (2R,5R)-1,2,5-trimethylpiperazinyl; 1-methylpyridin-2(1H)-onyl; and carboxylate; or $R^2$ is selected from azetidinyl-R$^5$; piperazinyl-R$^5$; isopropylpiperazinyl-R$^5$; methylpiperazinyl-R$^5$; pyrrolidinyl-R$^5$; piperidinyl-R$^5$; pyrazolyl-R$^5$; triazolyl-R$^5$; 2,7-diazaspiro[4.4]nonanyl-R$^5$; 2,5-diazabicyclo[2.2.1]heptanyl-R$^5$; 5,6,7,8-tetrahydro-[1,2,4]triazolo[1,5-a]pyrazinyl; 5,6,7,8-tetrahydro-[1,2,4]triazolo[1,5-a]pyrazinyl-R$^5$; 5,6,7,8-tetrahydroimidazo[1,5-a]pyrazinyl; 3-(trifluoromethyl)-5,6,7,8-tetrahydroimidazo[1,5-a]pyrazinyl; 5,6,7,8-tetrahydroimidazo[1,2-a]pyrazinyl; 5,6,7,8-tetrahydroimidazo[1,2-a]pyrimidinyl; 5,6,7,8-tetrahydropyrido[4,3-c]pyridazinyl; 4,5,6,7-tetrahydro-[1,2,3]triazolo[1,5-a]pyrazinyl; 3,6-diazabicyclo[3.2.0]heptanyl-R$^5$; 2,3-dihydro-1H-imidazo[1,2-a]imidazolyl; 2,3-dihydro-1H-imidazo[1,5-a]imidazolyl; 4,5,6,7-tetrahydropyrazolo[1,5-a]pyrazinyl; 4,5,6,7-tetrahydropyrazolo[1,5-a]pyrazinyl-R$^5$; 5,6,7,8-tetrahydroimidazo[1,2-a]pyrazinyl; 5,6-dihydro-4H-imidazo[1,2-c][1,2,3]triazolyl; 2,4,5,6-tetrahydropyrrolo[2,3-c]pyrazolyl; (R)-2-methyl-1,4-diazepanyl-R$^5$; cyclohexenyl-R$^5$; and cyclohexanyl-R$^5$;

$R^3$ is absent or is selected from hydrogen, benzyl, and —$C_{0-3}$alkylene-R$^7$; or R$^3$ is taken together with R$^4$ to form a six-membered aromatic ring;

$R^4$ is absent, hydrogen, or taken together with R$^3$ to form a six-membered aromatic ring;

$R^5$ is selected from:

piperazinyl, piperidinyl, pyrrolidinyl, azetidinyl, pyridinyl, pyrrolinyl, —CH$_2$—R$^6$, and 1,4-diazabicyclo[2.2.2]octanyl, each of which is optionally substituted with one or more methyl, ethyl, i-propyl, n-propyl, substituted or unsubstituted piperazinyl, carboxyl, carboxylate, or benzyl; and methyl amine; dimethyl amine; substituted or unsubstituted cyclopentanyl; substituted or unsubstituted cyclohexanyl; —(CH$_2$)$_{0-3}$OH; —(CH$_2$)$_{0-3}$OCH$_3$; methyl; ethyl; i-propyl; n-propyl; halo; —CF$_3$; carboxamide; methyl carboxamide; dimethyl carboxamide; isopropyl carboxamide; benzyl carboxamide; N-methylacetamide; —NH$_2$; —NH-benzyl; —CH$_2$NHCH$_3$; —CH$_2$CH$_2$NH$_2$; —CH$_2$CH$_2$N(CH$_3$)$_2$; —CH$_2$CH$_2$NHCH$_3$; —CH$_2$CH$_2$NHC(CH$_3$)$_2$; —CH$_2$CH$_2$NH-benzyl; carboxyl; carboxylate; benzyl carboxylate; methyl carboxylate; isopropyl carboxylate; substituted or unsubstituted piperazinyl; ethylazetidinyl; and 1,5-diazabicyclo[3.3.2]decanyl;

$R^6$ is selected from azetidinyl, imidazolyl, and 5,6,7,8-tetrahydro-1,6-naphthyridine; and $R^7$ is a heterocycle;

provided that, when $R^2$ is H:

(i) W is N; or (ii) W is CH; a is 3; and R$^1$ is independently selected from F and Cl.

In some embodiments, for a compound of Formula (I), a is an integer from 1 to 3 and each $R^1$ is independently selected from F and Cl. In some embodiments, W is N. In some embodiments, W is CH. In some embodiments, X and Y are each C. In some embodiments, X is N and Y is C. In some embodiments, X is C and Y is N. In some embodiments, X and Y are each N. In some embodiments, $R^3$ and $R^4$ are independently absent or hydrogen. In some embodiments, X is N, Y is C, and $R^3$ and $R^4$ are each hydrogen. In some embodiments, X is C, Y is N, and $R^3$ and $R^4$ are each hydrogen. In some embodiments, X and Y are each N, $R^3$ is hydrogen, and $R^4$ is absent.

In some embodiments, for a compound of Formula (I):

$R^2$ is selected from —NH—(CH$_2$)$_{0-3}$R$^5$; —NHCH$_2$C(CH$_3$)$_2$R$^5$; —NHCH$_2$C(CH$_3$)(CH$_2$OCH$_3$)R$^5$; —NHR$^5$; —NH—C(CH$_3$)$_2$CH$_2$R$^5$; —N(CH$_3$)R$^5$; —N(CH$_3$)CH$_2$R$^5$; —N(CH$_3$)CH$_2$CH$_2$R$^5$; phenyl-R$^5$; pyrrolinyl; pyrrolidinyl; 3,6-diazabicyclo[3.2.0]heptanyl; 1,4-diazepanyl; piperazinyl; (2R,5R)-1,2,5-trimethylpiperazinyl; 1-methylpyridin-2(1H)-onyl; and carboxylate; or $R^2$ is selected from azetidinyl-R$^5$; piperazinyl-R$^5$; isopropylpiperazinyl-R$^5$; methylpiperazinyl-R$^5$; pyrrolidinyl-R$^5$; piperidinyl-R$^5$; pyrazolyl-R$^5$; triazolyl-R$^5$; 2,7-diazaspiro[4.4]nonanyl-R$^5$; 2,5-diazabicyclo[2.2.1]heptanyl-R$^5$; 5,6,7,8-tetrahydro-[1,2,4]triazolo[1,5-a]pyrazinyl; 5,6,7,8-tetrahydro-[1,2,4]triazolo[1,5-a]pyrazinyl-R$^5$; 5,6,7,8-tetrahydroimidazo[1,5-a]pyrazinyl; 3-(trifluoromethyl)-5,6,7,8-tetrahydroimidazo[1,5-a]pyrazinyl; 5,6,7,8-tetrahydroimidazo[1,2-a]pyrazinyl; 5,6,7,8-tetrahydroimidazo[1,2-a]pyrimidinyl; 5,6,7,8-tetrahydropyrido[4,3-c]pyridazinyl; 4,5,6,7-tetrahydro-[1,2,3]triazolo[1,5-a]pyrazinyl; 3,6-diazabicyclo[3.2.0]heptanyl-R$^5$; 2,3-dihydro-1H-imidazo[1,2-a]imidazolyl; 2,3-dihydro-1H-imidazo[1,5-a]imidazolyl; 4,5,6,7-tetrahydropyrazolo[1,5-a]pyrazinyl; 4,5,6,7-tetrahydropyrazolo[1,5-a]pyrazinyl-R$^5$; 5,6,7,8-tetrahydroimidazo[1,2-a]pyrazinyl; 5,6-dihydro-4H-imidazo[1,2-c][1,2,3]triazolyl; 2,4,5,6-tetrahydropyrrolo[2,3-c]pyrazolyl; (R)-2-methyl-1,4-diazepanyl-R$^5$; cyclohexenyl-R$^5$; and cyclohexanyl-R$^5$.

In some embodiments, for a compound of Formula (I), $R^2$ is selected from —NH—(CH$_2$)$_{0-3}$R$^5$; —NHCH$_2$C(CH$_3$)$_2$R$^5$; —NHCH$_2$C(CH$_3$)(CH$_2$OCH$_3$)R$^5$; —NHR$^5$; —NH—C(CH$_3$)$_2$CH$_2$R$^5$; —N(CH$_3$)R$^5$; —N(CH$_3$)CH$_2$R$^5$; —N(CH$_3$)CH$_2$CH$_2$R$^5$; phenyl-R$^5$; pyrrolinyl; pyrrolidinyl; 3,6-diazabicyclo[3.2.0]heptanyl; 1,4-diazepanyl; piperazinyl; (2R,5R)-1,2,5-trimethylpiperazinyl; 1-methylpyridin-2(1H)-onyl; and carboxylate. In some embodiments, $R^2$ is selected from —NH—(CH$_2$)$_{1-3}$R$^5$; —NHCH$_2$C(CH$_3$)$_2$R$^5$; —NHCH$_2$C(CH$_3$)(CH$_2$OCH$_3$)R$^5$; —NHR$^5$; —NH—C(CH$_3$)$_2$CH$_2$R$^5$; —N(CH$_3$)R$^5$; —N(CH$_3$)CH$_2$R$^5$; and —N(CH$_3$)CH$_2$CH$_2$R$^5$. In some embodiments, $R^2$ is selected from —NH—(CH$_2$)$_{1-3}$R$^5$ and —NHR$^5$. In some embodiments, $R^2$ is selected from azetidinyl-R$^5$; piperazinyl-R$^5$; isopropylpiperazinyl-R$^5$; methylpiperazinyl-R$^5$; pyrrolidinyl-R$^5$; piperidinyl-R$^5$; pyrazolyl-R$^5$; triazolyl-R$^5$; 2,7-diazaspiro[4.4]nonanyl-R$^5$; 2,5-diazabicyclo[2.2.1]heptanyl-R$^5$;

5,6,7,8-tetrahydro-[1,2,4]triazolo[1,5-a]pyrazinyl; 5,6,7,8-tetrahydro-[1,2,4]triazolo[1,5-a]pyrazinyl-$R^5$; 5,6,7,8-tetrahydroimidazo[1,5-a]pyrazinyl; 3-(trifluoromethyl)-5,6,7,8-tetrahydroimidazo[1,5-a]pyrazinyl; 5,6,7,8-tetrahydroimidazo[1,2-a]pyrazinyl; 5,6,7,8-tetrahydroimidazo[1,2-a]pyrimidinyl; 5,6,7,8-tetrahydropyrido[4,3-c]pyridazinyl; 4,5,6,7-tetrahydro-[1,2,3]triazolo[1,5-a]pyrazinyl; 3,6-diazabicyclo[3.2.0]heptanyl-$R^5$; 2,3-dihydro-1H-imidazo[1,2-a]imidazolyl; 2,3-dihydro-1H-imidazo[1,5-a]imidazolyl; 4,5,6,7-tetrahydropyrazolo[1,5-a]pyrazinyl; 4,5,6,7-tetrahydropyrazolo[1,5-a]pyrazinyl-$R^5$; 5,6,7,8-tetrahydroimidazo[1,2-a]pyrazinyl; 5,6-dihydro-4H-imidazo[1,2-c][1,2,3]triazolyl; 2,4,5,6-tetrahydropyrrolo[2,3-c]pyrazolyl; (R)-2-methyl-1,4-diazepanyl-$R^5$; cyclohexenyl-$R^5$; and cyclohexanyl-$R^5$. In some embodiments, $R^2$ is selected from azetidinyl-$R^5$; piperazinyl-$R^5$; pyrrolidinyl-$R^5$; piperidinyl-$R^5$; pyrazolyl-$R^5$; triazolyl-$R^5$; cyclohexenyl-$R^5$; and cyclohexanyl-$R^5$. In some embodiments, $R^2$ is selected from azetidinyl-$R^5$; piperazinyl-$R^5$; and pyrrolidinyl-$R^5$.

In some embodiments, for a compound of Formula (I), $R^5$ is selected from piperazinyl, piperidinyl, pyrrolidinyl, azetidinyl, pyridinyl, and pyrrolinyl, each of which is optionally substituted with one or more methyl, ethyl, i-propyl, or n-propyl; and methyl amine; dimethyl amine; methyl; ethyl; i-propyl; n-propyl; halo; —$CF_3$; —$NH_2$; —$CH_2NHCH_3$; —$CH_2CH_2NH_2$; —$CH_2CH_2N(CH_3)_2$; —$CH_2CH_2NHCH_3$; and —$CH_2CH_2NHC(CH_3)_2$. In some embodiments, $R^5$ is selected from piperazinyl, piperidinyl, pyrrolidinyl, and azetidinyl, each of which is optionally substituted with one or more methyl, ethyl, i-propyl, or n-propyl.

In some embodiments, for a compound of Formula (I):
each $R^1$ is independently selected from F and Cl;
$R^2$ is selected from —NH—$(CH_2)_{1-3}R^5$; —NHCH$_2$C(CH$_3$)$_2$R$^5$; —NHCH$_2$C(CH$_3$)(CH$_2$OCH$_3$)R$^5$; —NHR$^5$; —NH—C(CH$_3$)$_2$CH$_2$R$^5$; —N(CH$_3$)R$^5$; —N(CH$_3$)CH$_2$R$^5$; —N(CH$_3$)CH$_2$CH$_2$R$^5$; azetidinyl-$R^5$; piperazinyl-$R^5$; pyrrolidinyl-$R^5$; piperidinyl-$R^5$; pyrazolyl-$R^5$; triazolyl-$R^5$; cyclohexenyl-$R^5$; and cyclohexanyl-$R^5$; and
$R^5$ is selected from piperazinyl, piperidinyl, pyrrolidinyl, azetidinyl, pyridinyl, and pyrrolinyl, each of which is optionally substituted with one or more methyl, ethyl, i-propyl, or n-propyl; and methyl amine; dimethyl amine; methyl; ethyl; i-propyl; n-propyl; halo; —$CF_3$; —$NH_2$; —$CH_2NHCH_3$; —$CH_2CH_2NH_2$; —$CH_2CH_2N(CH_3)_2$; —$CH_2CH_2NHCH_3$; and —$CH_2CH_2NHC(CH_3)_2$. In some embodiments, X is N, Y is C, and $R^3$ and $R^4$ are each hydrogen. In some embodiments, X is C, Y is N, and $R^3$ and $R^4$ are each hydrogen. In some embodiments, X and Y are each N, $R^3$ is hydrogen, and $R^4$ is absent.

In some embodiments, the compound of Formula (I) is a compound of Formula (II), (III) or (VII):

(II)

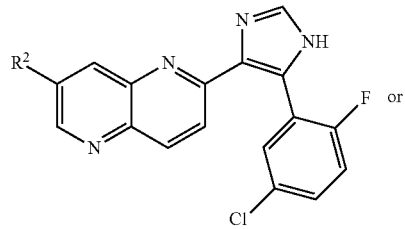

(III)

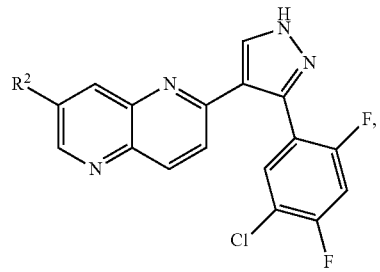

(VII)

or a pharmaceutically acceptable salt thereof, optionally wherein $R^2$ is selected from

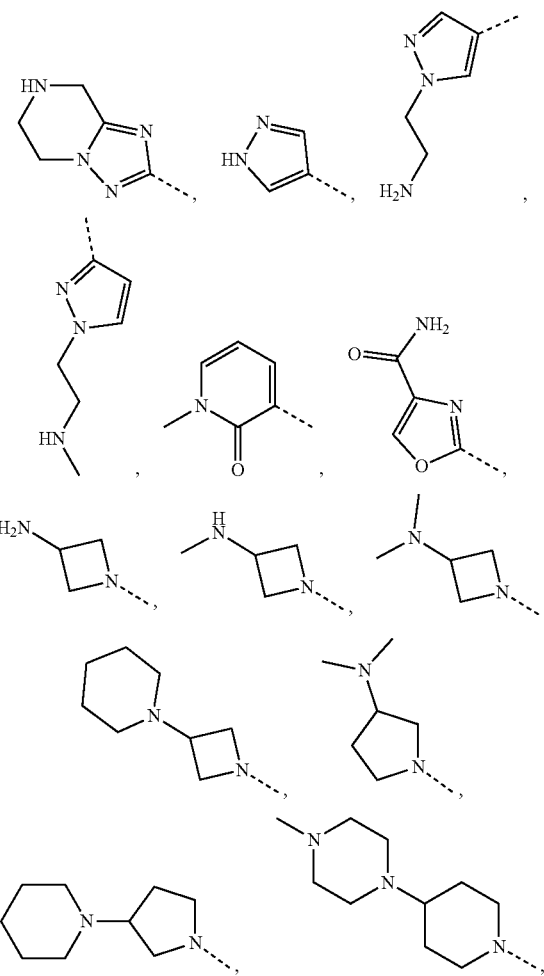

In some embodiments, the compound is a compound of Formula (II). In some embodiments, the compound is a compound of Formula (III). In some embodiments, the compound is a compound of Formula (VII).

In some embodiments, for a compound of Formula (I):
X—$R^3$ is N;
Y—$R^4$ is CH or NH;
a is an integer from 1 to 3;
each $R^1$ is independently selected from F and Cl;
$R^2$ is selected from —NH—$(CH_2)_{1-3}R^5$; —NHCH$_2$C(CH$_3$)$_2R^5$; —NH$R^5$; —NH—C(CH$_3$)$_2$CH$_2R^5$; —N(CH$_3$)$R^5$; —N(CH$_3$)CH$_2R^5$; —N(CH$_3$)CH$_2$CH$_2R^5$; and $R^5$ is selected from piperazinyl, piperidinyl, pyrrolidinyl, and pyridinyl, each of which is optionally substituted with one or more methyl, ethyl, i-propyl, or n-propyl; or
$R^2$ is selected from piperazinyl-$R^5$; pyrrolidinyl-$R^5$; piperidinyl-$R^5$; pyrazolyl-$R^5$; and triazolyl-$R^5$; and $R^5$ is selected from methyl amine; dimethyl amine; methyl; ethyl; i-propyl; n-propyl; —NH$_2$; —CH$_2$NHCH$_3$; —CH$_2$CH$_2$NH$_2$; —CH$_2$CH$_2$N(CH$_3$)$_2$; and —CH$_2$CH$_2$NHCH$_3$.

In certain aspects, the present disclosure provides a substantially pure stereoisomer of a compound described herein. In some embodiments, the stereoisomer is provided in at least 90% enantiomeric excess. In certain aspects, the present disclosure provides a compound selected from Table 1, or a pharmaceutically acceptable salt thereof. In certain aspects, the present disclosure provides a pharmaceutical composition comprising a compound or salt described herein and a pharmaceutically acceptable carrier, optionally wherein the pharmaceutical composition is formulated for inhalation.

In certain aspects, the present disclosure provides a method of inhibiting ALK5. The method may comprise contacting ALK5 with an effective amount of a compound or salt described herein. In some embodiments, the present disclosure provides a method of treating an ALK5-mediated disease or condition in a subject, comprising administering to the subject a therapeutically effective amount of a compound or salt described herein, optionally wherein the disease or condition is selected from fibrosis, alopecia and cancer. In some embodiments, the disease or condition is fibrosis. In some embodiments, the present disclosure provides a method of treating fibrosis, comprising administering to a patient a therapeutically effective amount of a compound or salt described herein. In some embodiments, the fibrosis is selected from systemic sclerosis, nephrogenic systemic fibrosis, organ-specific fibrosis, fibrosis associated with cancer, cystic fibrosis, and fibrosis associated with an autoimmune disease, optionally wherein the organ-specific fibrosis is selected from cardiac fibrosis, kidney fibrosis, pulmonary fibrosis, liver fibrosis, portal vein fibrosis, skin fibrosis, bladder fibrosis, intestinal fibrosis, peritoneal fibrosis, myelofibrosis, oral submucous fibrosis, and retinal fibrosis, and optionally wherein the pulmonary fibrosis is selected from idiopathic pulmonary fibrosis (IPF), familial pulmonary fibrosis (FPF), interstitial lung fibrosis, fibrosis associated with asthma, fibrosis associated with chronic obstructive pulmonary disease (COPD), silica-induced fibrosis, asbestos-induced fibrosis and chemotherapy-induced lung fibrosis. In some embodiments, the fibrosis is idiopathic pulmonary fibrosis (IPF). In some embodiments, the disease or condition is cancer, optionally wherein the cancer is selected from breast cancer, colon cancer, prostate cancer, lung cancer, hepatocellular carcinoma, glioblastoma, melanoma, and pancreatic cancer. In some embodiments, the lung cancer is non-small cell lung cancer. A method of the subject disclosure may comprise administering a second therapeutic agent. Optionally, the second therapeutic agent is an immunotherapeutic agent, such as a PD-1 inhibitor or a CTLA-4 inhibitor. In some embodiments, the immunotherapeutic agent is selected from pembrolizumab and durvalumab. A method of the present disclosure may further comprise administering an effective amount of radiation.

INCORPORATION BY REFERENCE

All publications and patent applications mentioned in this specification are herein incorporated by reference to the same extent as if each individual publication or patent application was specifically and individually indicated to be incorporated by reference.

DETAILED DESCRIPTION

Chemical structures are named herein according to IUPAC conventions as implemented in ChemDraw® software (Perkin Elmer, Inc., Cambridge, Mass.).

As used in the specification and claims, the singular forms "a", "an" and "the" include plural references unless the context clearly dictates otherwise.

The terms "comprising", "including," and "having" are intended to be inclusive and mean that there may be additional elements other than the listed elements. All numbers expressing quantities of ingredients, properties such as molecular weight, reaction conditions, and so forth used herein are to be understood as being modified in all instances by the term "about," unless otherwise indicated. Accordingly, the numbers set forth herein are approximations that may vary depending upon the desired properties sought to be obtained by the present invention. At least, and not as an attempt to limit the application of the doctrine of equivalents to the scope of the claims, each number should at least be construed in light of the reported significant digits and by applying ordinary rounding techniques.

The term "about," "approximately," or "approximate" is defined by a margin of error that is typically about twice the standard deviation or the half-width of a 95 percent confidence interval. The term "approximate" in other areas of the disclosure may be used to indicate standard deviation or the amount of variation or dispersion of a set of data values.

As used herein, the phrase "of the formula" or "having the formula" or "having the structure" is not intended to be limiting and is used in the same way that the term "comprising" is commonly used. For example, if one structure is depicted, it is understood that all stereoisomer and tautomer forms are encompassed, unless stated otherwise.

Lung function tests include tests to check how well the lungs work. Spirometry, for example, measures the amount of air the lungs can hold as well as how forcefully one can empty air from the lungs. The term "forced expiratory volume (FEV)" measures the amount of air a person can exhale during a forced breath. FEV1, for example, is the amount of air a person can force from their lungs in one second. The term "forced vital capacity (FVC)" is the total amount of air exhaled during an FEV test. The ratio of FEV1/FVC, also known as Index of Air Flow or Tiffeneau-Pinelli Index, is a measurement used to assess the health of a patient's lung function. A ratio of <80% indicates an obstructive defect is present in the lungs, such as chronic obstructive pulmonary disease (COPD). A ratio of >80% indicates a restrictive defect is present in the lungs, such as pulmonary fibrosis. The ratio of >80% in restrictive lung disease results from both FEV1 and FVC being reduced but that the decline in FVC is more than that of FEV1, resulting in a higher than 80% value.

The term "pharmaceutically acceptable" refers to a material that is not biologically or otherwise unacceptable when used in the invention. For example, the term "pharmaceutically acceptable carrier" refers to a material that can be incorporated into a composition and administered to a patient without causing unacceptable biological effects or interacting in an unacceptable manner with other components of the composition. Such pharmaceutically acceptable materials typically have met the required standards of toxicological and manufacturing testing, and include those materials identified as suitable inactive ingredients by the U.S. Food and Drug administration.

The term "pharmaceutically acceptable salt" means a salt prepared from a base or an acid which is acceptable for administration to a patient, such as a mammal (for example, salts having acceptable mammalian safety for a given dosage regime). However, it is understood that the salts covered by the invention are not required to be pharmaceutically acceptable salts, such as salts of intermediate compounds that are not intended for administration to a patient. Pharmaceutically acceptable salts can be derived from pharmaceutically acceptable inorganic or organic bases and from pharmaceutically acceptable inorganic or organic acids. In addition, when a compound contains both a basic moiety, such as an amine, pyridine or imidazole, and an acidic moiety such as a carboxylic acid or tetrazole, zwitterions may be formed and are included within the term "salt" as used herein. Salts derived from pharmaceutically acceptable inorganic bases include ammonium, calcium, copper, ferric, ferrous, lithium, magnesium, manganic, manganous, potassium, sodium, and zinc salts, and the like. Salts derived from pharmaceutically acceptable organic bases include salts of primary, secondary and tertiary amines, including substituted amines, cyclic amines, naturally-occurring amines and the like, such as arginine, betaine, caffeine, choline, N,N-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperadine, polyamine resins, procaine, purines, theobromine, triethylamine, trimethylamine, tripropylamine, tromethamine and the like. Salts derived from pharmaceutically acceptable inorganic acids include salts of boric, carbonic, hydrohalic (hydrobromic, hydrochloric, hydrofluoric or hydroiodic), nitric, phosphoric, sulfamic and sulfuric acids. Salts derived from pharmaceutically acceptable organic acids include salts of aliphatic hydroxyl acids (for example, citric, gluconic, glycolic, lactic, lactobionic, malic, and tartaric acids), aliphatic monocarboxylic acids (for example, acetic, butyric, formic, propionic and trifluoroacetic acids), amino acids (for example, aspartic and glutamic acids), aromatic carboxylic acids (for example, benzoic, p-chlorobenzoic, diphenylacetic, gentisic, hippuric, and triphenylacetic acids), aromatic hydroxyl acids (for example, o-hydroxybenzoic, p-hydroxybenzoic, 1-hydroxynaphthalene-2-carboxylic and 3-hydroxynaphthalene-2-carboxylic acids), ascorbic, dicarboxylic acids (for example, fumaric, maleic, oxalic and succinic acids), glucoronic, mandelic, mucic, nicotinic, orotic, pamoic, pantothenic, sulfonic acids (for example, benzenesulfonic, camphosulfonic, edisylic, ethanesulfonic, isethionic, methanesulfonic, naphthalenesulfonic, naphthalene-1,5-disulfonic, naphthalene-2,6-disulfonic and p-toluenesulfonic acids), xinafoic acid, and the like.

The term "transforming growth factor-β" can also be referred to as TGF-β, Transforming growth factor beta-1, TGF-beta-1. It is also cleaved into latency-associated peptide (LAP).

The term "TGF-β receptor II" may also be referred to as TORII, Type II TGF-β receptor, TGF-βRII, TGF-beta receptor type-2, TGFR-2, TGF-beta type II receptor, transforming growth factor-beta receptor type II, TGF-beta receptor type II or TbetaR-II.

The term "TGF-β receptor I" may also be referred to as TORT, Type I TGF-β receptor, TGF-βRI, TGF-beta receptor type-1, TGFR-1, Activin A receptor type II-like protein kinase of 53 kD, Activin receptor-like kinase 5, ALK-5, ALK5, Serine/threonine-protein kinase receptor R4, SKR4, TGF-beta type I receptor, transforming growth factor-beta receptor type I, TGF-beta receptor type I or TbetaR-I.

The term "therapeutically effective amount" means an amount sufficient to effect treatment when administered to a patient in need thereof, that is, the amount of drug needed to obtain the desired therapeutic effect. For example, a therapeutically effective amount for treating pulmonary fibrosis is an amount of compound needed to, for example, reduce, suppress, eliminate, or prevent the formation of fibrosis in a patient, or to treat the underlying cause of pulmonary fibrosis. On the other hand, the term "effective amount" means an amount sufficient to obtain a desired result, which may not necessarily be a therapeutic result. For example, an "effective amount" may be the amount needed to inhibit the enzyme.

The term "treating" or "treatment" as used herein means the treating or treatment of a disease or medical condition (such as pulmonary fibrosis) in a patient, such as a mammal (particularly a human) that includes one or more of the following: (a) preventing the disease or medical condition from occurring, i.e., preventing the reoccurrence of the disease or medical condition or prophylactic treatment of a patient that is pre-disposed to the disease or medical condition; (b) ameliorating the disease or medical condition, i.e., eliminating or causing regression of the disease or medical condition in a patient; (c) suppressing the disease or medical condition, i.e., slowing or arresting the development of the disease or medical condition in a patient; or (d) alleviating the symptoms of the disease or medical condition in a patient. For example, the term "treating pulmonary fibrosis" would include preventing fibrosis from occurring, ameliorating fibrosis, suppressing fibrosis, and alleviating the symptoms of fibrosis (for example, increasing oxygen levels in blood and improved lung function tests). The term "subject" or "patient" is intended to include those mammals, such as humans, that are in need of treatment or disease prevention or that are presently being treated for disease prevention or treatment of a specific disease or medical condition, as well as test subjects in which the compound is being evaluated or being used in an assay, for example an animal model.

All other terms used herein are intended to have their ordinary meaning as understood by those of ordinary skill in the art to which they pertain.

The compounds of the invention contain one or more chiral centers and therefore, these compounds may be prepared and used in various stereoisomeric forms. In some embodiments, in order to optimize the therapeutic activity of the compounds of the invention, e.g., to treat fibrosis, it may be desirable that the carbon atoms have a particular (R,R), (S,S), (S,R), or (R,S) configuration or are enriched in a stereoisomeric form having such configuration. In other embodiments, the compounds of the invention are present as racemic mixtures. Accordingly, the invention also relates to racemic mixtures, pure stereoisomers (e.g., enantiomers and diastereoisomers), stereoisomer-enriched mixtures, and the like unless otherwise indicated. When a chemical structure is depicted herein without any stereochemistry, it is understood that all possible stereoisomers are encompassed by such structure. Similarly, when a particular stereoisomer is shown or named herein, it will be understood by those skilled in the art that minor amounts of other stereoisomers may be present in the compositions of the invention unless otherwise indicated, provided that the utility of the composition as a whole is not eliminated by the presence of such other isomers. Individual stereoisomers may be obtained by numerous methods that are well known in the art, including chiral chromatography using a suitable chiral stationary phase or support, or by chemically converting them into diastereoisomers, separating the diastereoisomers by conventional means such as chromatography or recrystallization, then regenerating the original stereoisomer.

Additionally, where applicable, all cis-trans or E/Z isomers (geometric isomers), tautomeric forms and topoisomeric forms of the compounds of the invention are included within the scope of the invention unless otherwise specified.

The term "tautomer", as used herein, refers to each of two or more isomers of a compound that exist in equilibrium and which ready interconvert. For example, one skilled in the art would readily understand that 1,2,3-triazole exists in two tautomeric forms:

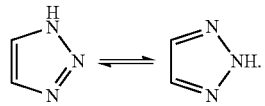 [SMILES: c1c[nH]nn1 ; c1cn[nH]n1]

Unless otherwise specified, chemical entities described herein are intended to include all possible tautomers, even when a structure depicts only one of them. For example, even though a single tautomer of a compound of Formula (I-A) may be depicted herein, the disclosure is intended to include all possible tautomers, including:

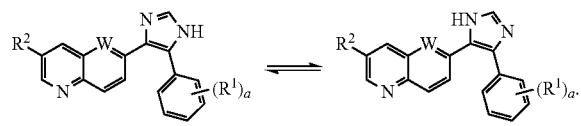

The compounds of the invention, as well as those compounds used in their synthesis, may also include isotopically-labeled compounds, that is, where one or more atoms have been enriched with atoms having an atomic mass different from the atomic mass predominately found in nature. Examples of isotopes that may be incorporated into the compounds of formula I, for example, include, but are not limited to, $^2$H, $^3$H, $^{13}$C, $^{14}$C, $^{15}$N, $^{18}$O, $^{17}$O $^{35}$S, $^{36}$Cl, and $^{18}$F. Of particular interest are compounds of formula I enriched in tritium or carbon-14 which can be used, for example, in tissue distribution studies; compounds of the invention enriched in deuterium especially at a site of metabolism resulting, for example, in compounds having greater metabolic stability; and compounds of formula I enriched in a positron emitting isotope, such as $^{11}$C, $^{18}$F, $^{15}$O and $^{13}$N, which can be used, for example, in Positron Emission Topography (PET) studies.

Unless stated otherwise, hydrogen atoms are implied in structures depicted herein as necessary to satisfy the valence requirement.

A waved line " ~ " drawn across a bond or a dashed bond " -- " are used interchangeably herein to denote where a bond disconnection or attachment occurs. For example, in the structure

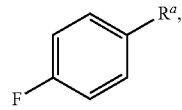

R$^a$ is attached to the para position of a fluorophenyl ring through a single bond. If R$^a$ is 2-pyridine as in

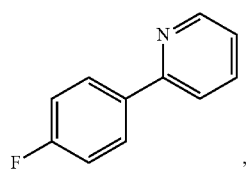 [SMILES: Fc1ccc(-c2ccccn2)cc1]

then $R^a$ may be depicted as

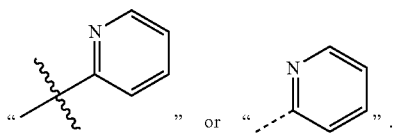

The present disclosure provides compounds that are capable of selectively binding to and/or modulating ALK5. In some embodiments, the compounds modulate ALK5 by binding to or interacting with one or more amino acids and/or one or more metal ions. The binding of these compounds may disrupt ALK5 downstream signaling.

In certain aspects, the present disclosure provides a compound of Formula (I):

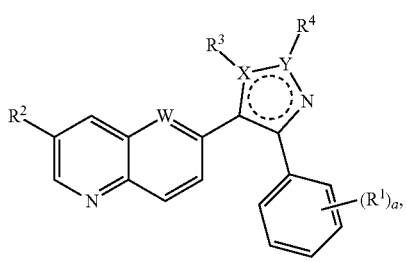

wherein:
W is N or C;
X and Y form a pyrrole, pyrazole, imidazole or triazole ring and X and Y are independently selected from C and N;
a is an integer from 1 to 3;
each $R^1$ is independently selected from halo, —OH, —$C_{1-6}$ alkyl, and —$C_{0-2}$ alkylene-O—$C_{1-6}$ alkyl;
$R^2$ is selected from H; —NH—$(CH_2)_{0-3}R^5$; —NHCH$_2$C(CH$_3$)$_2$R$^5$; —NHCH$_2$C(CH$_3$)(CH$_2$OCH$_3$)R$^5$; —NHR$^5$; —NH—C(CH$_3$)$_2$CH$_2$R$^5$; —N(CH$_3$)R$^5$; —N(CH$_3$)CH$_2$R$^5$; —N(CH$_3$)CH$_2$CH$_2$R$^5$; phenyl-R$^5$; pyrrolinyl; pyrrolidinyl; 3,6-diazabicyclo[3.2.0]heptanyl; 1,4-diazepanyl; piperazinyl; (2R,5R)-1,2,5-trimethylpiperazinyl; 1-methylpyridin-2 (1H)-onyl; and carboxylate; or
$R^2$ is selected from azetidinyl-R$^5$; piperazinyl-R$^5$; isopropylpiperazinyl-R$^5$; methylpiperazinyl-R$^5$; isopropylpiperazinyl-R$^5$; pyrrolidinyl-R$^5$; piperidinyl-R$^5$; pyrazolyl-R$^5$; triazolyl-R$^5$; 2,7-diazaspiro[4.4]nonanyl-R$^5$; 2,5-diazabicyclo[2.2.1]heptanyl-R$^5$; 5,6,7,8-tetrahydro-[1,2,4]triazolo[1,5-a]pyrazinyl; 5,6,7,8-tetrahydro-[1,2,4]triazolo[1,5-a]pyrazinyl-R$^5$; 5,6,7,8-tetrahydroimidazo[1,5-a]pyrazinyl; 3-(trifluoromethyl)-5,6,7,8-tetrahydroimidazo[1,5-a]pyrazinyl; 5,6,7,8-tetrahydroimidazo[1,2-a]pyrazinyl; 5,6,7,8-tetrahydroimidazo[1,2-a]pyrimidinyl; 5,6,7,8-tetrahydropyrido[4,3-c]pyridazinyl; 4,5,6,7-tetrahydro-[1,2,3]triazolo[1,5-a]pyrazinyl; 3,6-diazabicyclo[3.2.0]heptanyl-R$^5$; 2,3-dihydro-1H-imidazo[1,2-a]imidazolyl; 2,3-dihydro-1H-imidazo[1,5-a]imidazolyl; 4,5,6,7-tetrahydropyrazolo[1,5-a]pyrazinyl; 4,5,6,7-tetrahydropyrazolo[1,5-a]pyrazinyl-R$^5$; 5,6,7,8-tetrahydroimidazo[1,2-a]pyrazinyl; 5,6-dihydro-4H-imidazo[1,2-c][1,2,3]triazolyl; 2,4,5,6-tetrahydropyrrolo[2,3-c]pyrazolyl; (R)-2-methyl-1,4-diazepanyl-R$^5$; cyclohexenyl-R$^5$; and cyclohexanyl-R$^5$;
$R^3$ is absent or is selected from benzyl and —$C_{0-3}$ alkylene-R$^7$; or $R^3$ is taken together with $R^4$ to form a six-membered aromatic ring;

$R^4$ is absent or taken together with $R^3$ to form a six-membered aromatic ring;
$R^5$ is selected from:
piperazinyl, piperidinyl, pyrrolidinyl, azetidinyl, pyridinyl, pyrrolinyl, —CH$_2$—R$^6$, and 1,4-diazabicyclo[2.2.2]octanyl, optionally substituted with one or more methyl, ethyl, i-propyl, n-propyl, substituted or unsubstituted piperazinyl, carboxyl, carboxylate, or benzyl; and
methyl amine; dimethyl amine; substituted or unsubstituted cyclopentanyl;
substituted or unsubstituted cyclohexanyl; —(CH$_2$)$_{0-3}$OH; —(CH$_2$)$_{0-3}$OCH$_3$; methyl; ethyl; i-propyl; n-propyl; halo; —CF$_3$; carboxamide; methyl carboxamide; dimethyl carboxamide;
isopropyl carboxamide; benzyl carboxamide; N-methylacetamide; —NH$_2$; —NH-benzyl; —CH$_2$NHCH$_3$; —CH$_2$CH$_2$NH$_2$; —CH$_2$CH$_2$N(CH$_3$)$_2$; —CH$_2$CH$_2$NHCH$_3$; —CH$_2$CH$_2$NHC(CH$_3$)$_2$; —CH$_2$CH$_2$NH-benzyl; carboxyl; carboxylate; benzyl carboxylate; methyl carboxylate; isopropyl carboxylate; substituted or unsubstituted piperazinyl; ethylazetidinyl; and 1,5-diazabicyclo[3.3.2]decanyl;
$R^6$ is selected from azetidinyl, imidazolyl, and 5,6,7,8-tetrahydro-1,6-naphthyridine; and
$R^7$ is a heterocycle; or
a pharmaceutically acceptable salt thereof.

In some embodiments, for a compound of Formula (I), W is N. In some embodiments, a is an integer from 1 to 3 and each $R^1$ is independently selected from halo, —OH, —$C_{1-6}$ alkyl, and —$C_{0-2}$ alkylene-O—$C_{1-6}$ alkyl. In some embodiments, a is an integer from 1 to 3 and each $R^1$ is independently selected from F and Cl. In some embodiments, a is 1 and $R^1$ is F. In some embodiments, a is 2 and $R^1$ is F, or $R^1$ is Cl and F. In some embodiments, a is 3 and $R^1$ is independently selected from F and Cl. In some embodiments, a is 1 or 2 and $R^1$ is independently selected from —CH$_3$, —CH$_2$OCH$_3$, and —OH.

In some embodiments, for a compound of Formula (I), W is C. In some embodiments, a is an integer from 1 to 3 and each $R^1$ is independently selected from F and Cl. In some embodiments, a is 1 and $R^1$ is Cl. In some embodiments, a is 2 and $R^1$ is F, or $R^1$ is Cl and F. In some embodiments, a is 3 and $R^1$ is independently selected from F and Cl.

In certain aspects, the present disclosure provides a compound of Formula (I):

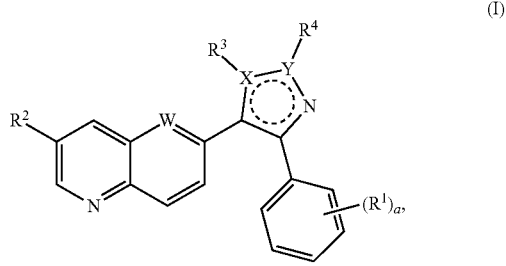

wherein:
W is N;
X and Y form a pyrrole, pyrazole, imidazole or triazole ring and X and Y are independently selected from C and N;
a is an integer from 1 to 3;
each $R^1$ is independently selected from halo, —OH, —$C_{1-6}$ alkyl, and —$C_{0-2}$ alkylene-O—$C_{1-6}$ alkyl;

R² is selected from H; —NH—(CH₂)₀₋₃R⁵; —NHCH₂C(CH₃)₂R⁵; —NHCH₂C(CH₃)(CH₂OCH₃)R⁵; —NHR⁵; —NH—C(CH₃)₂CH₂R⁵; —N(CH₃)R⁵; —N(CH₃)CH₂R⁵; —N(CH₃)CH₂CH₂R⁵; phenyl-R⁵; pyrrolinyl; pyrrolidinyl; 3,6-diazabicyclo[3.2.0]heptanyl; 1,4-diazepanyl; piperazinyl; (2R,5R)-1,2,5-trimethylpiperazinyl; 1-methylpyridin-2(1H)-onyl; and carboxylate; or R² is selected from azetidinyl-R⁵; piperazinyl-R⁵; isopropylpiperazinyl-R⁵; methylpiperazinyl-R⁵; isopropylpiperazinyl-R⁵; pyrrolidinyl-R⁵; piperidinyl-R⁵; pyrazolyl-R⁵; triazolyl-R⁵; 2,7-diazaspiro[4.4]nonanyl-R⁵; 2,5-diazabicyclo[2.2.1]heptanyl-R⁵; 5,6,7,8-tetrahydro-[1,2,4]triazolo[1,5-a]pyrazinyl; 5,6,7,8-tetrahydro-[1,2,4]triazolo[1,5-a]pyrazinyl-R⁵; 5,6,7,8-tetrahydroimidazo[1,5-a]pyrazinyl; 3-(trifluoromethyl)-5,6,7,8-tetrahydroimidazo[1,5-a]pyrazinyl; 5,6,7,8-tetrahydroimidazo[1,2-a]pyrazinyl; 5,6,7,8-tetrahydroimidazo[1,2-a]pyrimidinyl; 5,6,7,8-tetrahydropyrido[4,3-c]pyridazinyl; 4,5,6,7-tetrahydro-[1,2,3]triazolo[1,5-a]pyrazinyl; 3,6-diazabicyclo[3.2.0]heptanyl-R⁵; 2,3-dihydro-1H-imidazo[1,2-a]imidazolyl; 2,3-dihydro-1H-imidazo[1,5-a]imidazolyl; 4,5,6,7-tetrahydropyrazolo[1,5-a]pyrazinyl; 4,5,6,7-tetrahydropyrazolo[1,5-a]pyrazinyl-R⁵; 5,6,7,8-tetrahydroimidazo[1,2-a]pyrazinyl; 5,6-dihydro-4H-imidazo[1,2-c][1,2,3]triazolyl; 2,4,5,6-tetrahydropyrrolo[2,3-c]pyrazolyl; (R)-2-methyl-1,4-diazepanyl-R⁵; cyclohexenyl-R⁵; and cyclohexanyl-R⁵;

R³ is absent or is selected from benzyl and —C₀₋₃alkylene-R⁷; or R³ is taken together with R⁴ to form a six-membered aromatic ring;

R⁴ is absent or taken together with R³ to form a six-membered aromatic ring;

R⁵ is selected from:

piperazinyl, piperidinyl, pyrrolidinyl, azetidinyl, pyridinyl, pyrrolinyl, —CH₂—R⁶, and 1,4-diazabicyclo[2.2.2]octanyl, optionally substituted with one or more methyl, ethyl, i-propyl, n-propyl, substituted or unsubstituted piperazinyl, carboxyl, carboxylate, or benzyl; and methyl amine; dimethyl amine; substituted or unsubstituted cyclopentanyl; substituted or unsubstituted cyclohexanyl; —(CH₂)₀₋₃OH; —(CH₂)₀₋₃OCH₃; methyl; ethyl; i-propyl; n-propyl; halo; —CF₃; carboxamide; methyl carboxamide; dimethyl carboxamide; isopropyl carboxamide; benzyl carboxamide; N-methylacetamide; —NH₂; —NH-benzyl; —CH₂NHCH₃; —CH₂CH₂NH₂; —CH₂CH₂N(CH₃)₂; —CH₂CH₂NHCH₃; —CH₂CH₂NHC(CH₃)₂; —CH₂CH₂NH-benzyl; carboxyl; carboxylate; benzyl carboxylate; methyl carboxylate; isopropyl carboxylate; substituted or unsubstituted piperazinyl; ethylazetidinyl; and 1,5-diazabicyclo[3.3.2]decanyl;

R⁶ is selected from azetidinyl, imidazolyl, and 5,6,7,8-tetrahydro-1,6-naphthyridine; and R⁷ is a heterocycle; or a pharmaceutically acceptable salt thereof.

In certain aspects, the present disclosure provides a compound of Formula (I):

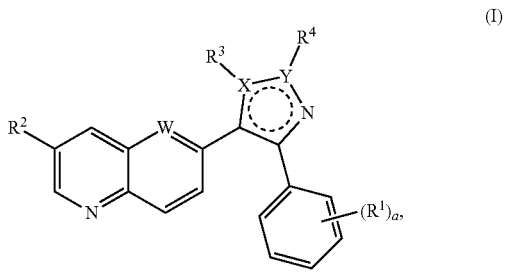

wherein:

W is CH;

X and Y form a pyrrole, pyrazole, imidazole or triazole ring and X and Y are independently selected from C and N;

a is 3;

R¹ is independently selected from F and Cl;

R² is selected from H; —NH—(CH₂)₀₋₃R⁵; —NHCH₂C(CH₃)₂R⁵; —NHCH₂C(CH₃)(CH₂OCH₃)R⁵; —NHR⁵; —NH—C(CH₃)₂CH₂R⁵; —N(CH₃)R⁵; —N(CH₃)CH₂R⁵; —N(CH₃)CH₂CH₂R⁵; phenyl-R⁵; pyrrolinyl; pyrrolidinyl; 3,6-di azabicyclo[3.2.0]heptanyl; 1,4-diazepanyl; piperazinyl; (2R,5R)-1,2,5-trimethylpiperazinyl; 1-methylpyridin-2(1H)-onyl; and carboxylate; or R² is selected from azetidinyl-R⁵; piperazinyl-R⁵; isopropylpiperazinyl-R⁵; methylpiperazinyl-R⁵; isopropylpiperazinyl-R⁵; pyrrolidinyl-R⁵; piperidinyl-R⁵; pyrazolyl-R⁵; triazolyl-R⁵; 2,7-diazaspiro[4.4]nonanyl-R⁵; 2,5-diazabicyclo[2.2.1]heptanyl-R⁵; 5,6,7,8-tetrahydro-[1,2,4]triazolo[1,5-a]pyrazinyl; 5,6,7,8-tetrahydro-[1,2,4]triazolo[1,5-a]pyrazinyl-R⁵; 5,6,7,8-tetrahydroimidazo[1,5-a]pyrazinyl; 3-(trifluoromethyl)-5,6,7,8-tetrahydroimidazo[1,5-a]pyrazinyl; 5,6,7,8-tetrahydroimidazo[1,2-a]pyrazinyl; 5,6,7,8-tetrahydroimidazo[1,2-a]pyrimidinyl; 5,6,7,8-tetrahydropyrido[4,3-c]pyridazinyl; 4,5,6,7-tetrahydro-[1,2,3]triazolo[1,5-a]pyrazinyl; 3,6-diazabicyclo[3.2.0]heptanyl-R⁵; 2,3-dihydro-1H-imidazo[1,2-a]imidazolyl; 2,3-dihydro-1H-imidazo[1,5-a]imidazolyl; 4,5,6,7-tetrahydropyrazolo[1,5-a]pyrazinyl; 4,5,6,7-tetrahydropyrazolo[1,5-a]pyrazinyl-R⁵; 5,6,7,8-tetrahydroimidazo[1,2-a]pyrazinyl; 5,6-dihydro-4H-imidazo[1,2-c][1,2,3]triazolyl; 2,4,5,6-tetrahydropyrrolo[2,3-c]pyrazolyl; (R)-2-methyl-1,4-diazepanyl-R⁵; cyclohexenyl-R⁵; and cyclohexanyl-R⁵;

R³ is absent or is selected from benzyl and —C₀₋₃alkylene-R⁷; or R³ is taken together with R⁴ to form a six-membered aromatic ring;

R⁴ is absent or taken together with R³ to form a six-membered aromatic ring;

R⁵ is selected from:

piperazinyl, piperidinyl, pyrrolidinyl, azetidinyl, pyridinyl, pyrrolinyl, —CH₂—R⁶, and 1,4-diazabicyclo[2.2.2]octanyl, optionally substituted with one or more methyl, ethyl, i-propyl, n-propyl, substituted or unsubstituted piperazinyl, carboxyl, carboxylate, or benzyl; and methyl amine; dimethyl amine; substituted or unsubstituted cyclopentanyl; substituted or unsubstituted cyclohexanyl; —(CH₂)₀₋₃OH; —(CH₂)₀₋₃OCH₃; methyl; ethyl; i-propyl; n-propyl; halo; —CF₃; carboxamide; methyl carboxamide; dimethyl carboxamide; isopropyl carboxamide; benzyl carboxamide; N-methylacetamide; —NH₂; —NH-benzyl; —CH₂NHCH₃; —CH₂CH₂NH₂; —CH₂CH₂N(CH₃)₂; —CH₂CH₂NHCH₃; —CH₂CH₂NHC(CH₃)₂; —CH₂CH₂NH-benzyl; carboxyl; carboxylate; benzyl carboxylate; methyl carboxylate; isopropyl carboxylate; substituted or unsubstituted piperazinyl; ethylazetidinyl; and 1,5-diazabicyclo[3.3.2]decanyl;

$R^6$ is selected from azetidinyl, imidazolyl, and 5,6,7,8-tetrahydro-1,6-naphthyridine; and $R^7$ is a heterocycle; or a pharmaceutically acceptable salt thereof.

In certain aspects, the compound of Formula (I) is a compound of Formula (II), (III), (IV), (V), (VI), (VII), (VIII), (IX), (X), (XI), (XII), (XIII), (XIV), (XV), (XVI), (XVII), (XVIII), (XIX), (XX), (XXI), (XXII), (XXIII), (XXIV), (XXV), (XXVI), (XXVII), (XXVIII), (XXIX), or (XXX):

(II)
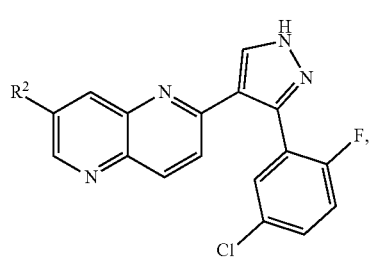

(III)
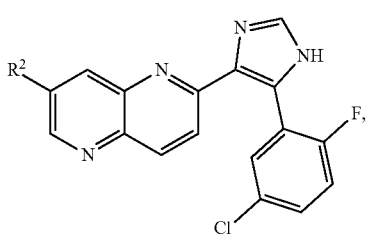

(IV)
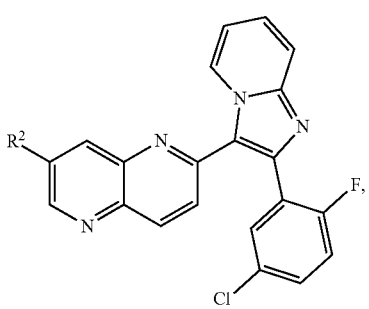

(V)
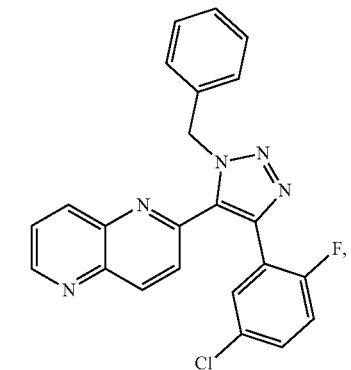

-continued (VI)
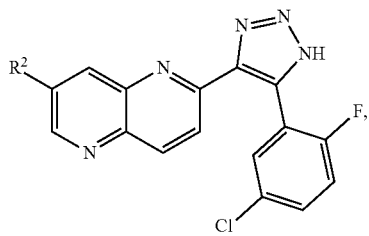

(VII)
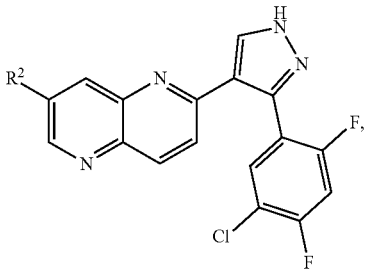

(VIII)
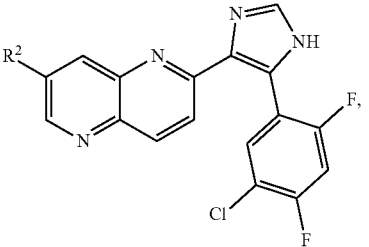

(IX)
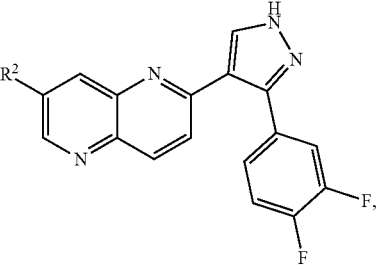

(X)
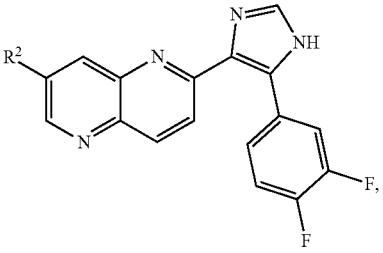

(XI)
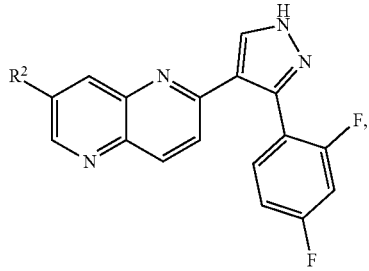

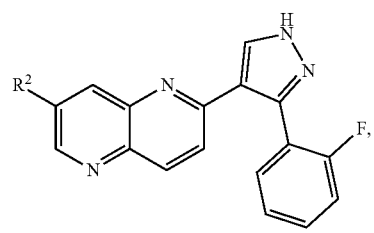 (XII)
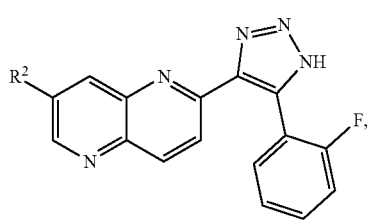 (XIII)
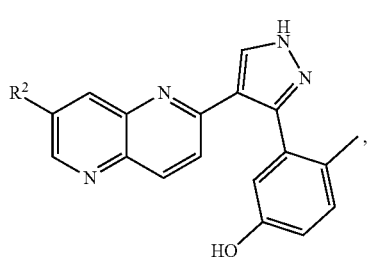 (XIV)
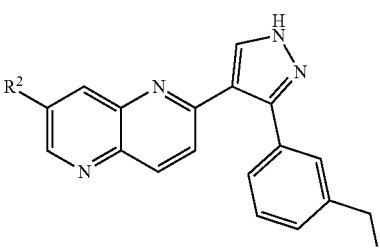 (XV)
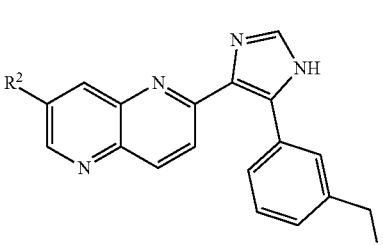 (XVI)
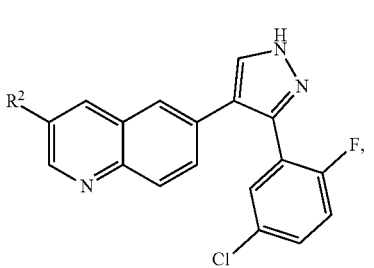 (XVII)
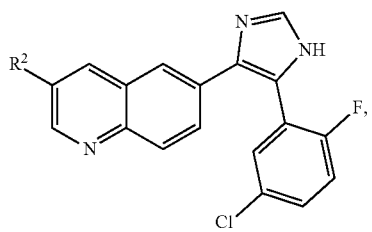 (XVIII)
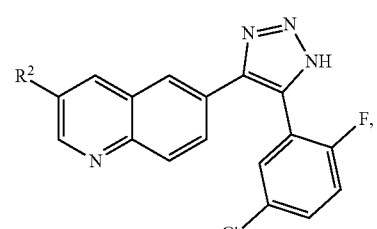 (XIX)
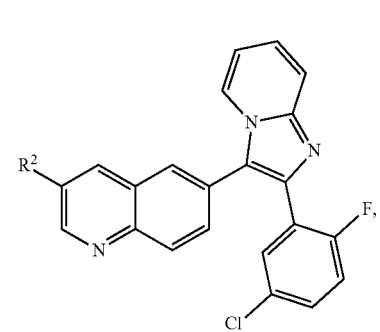 (XX)
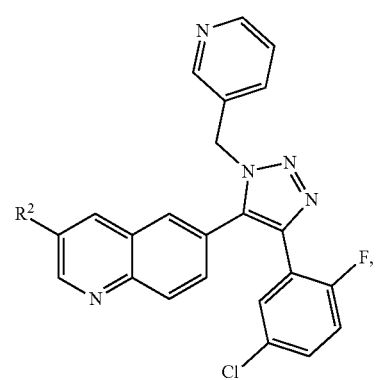 (XXI)
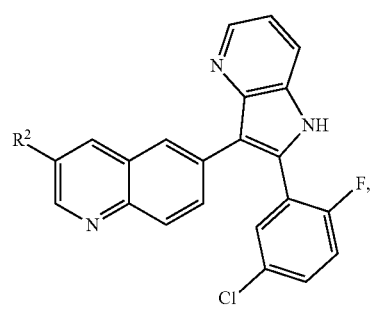 (XXII)

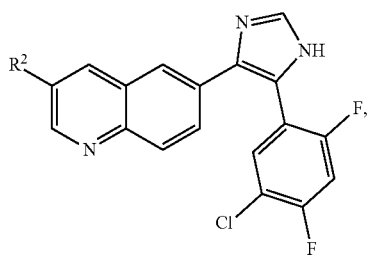
(XXIII)

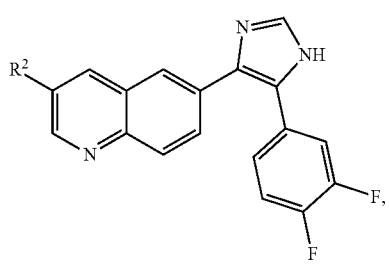
(XXIV)

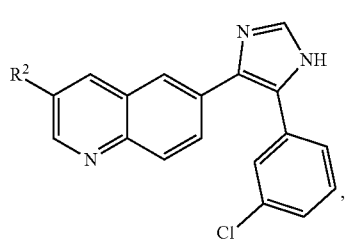
(XXV)

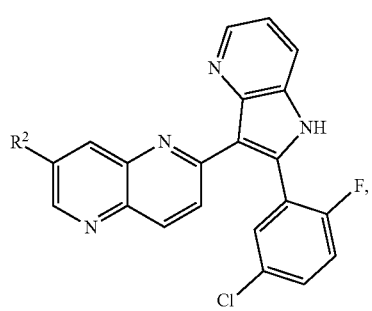
(XXVI)

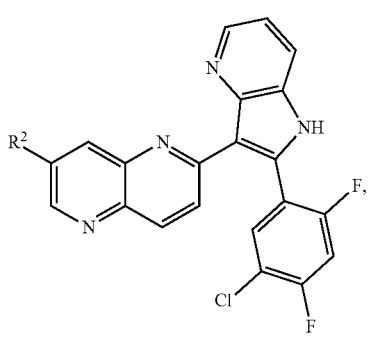
(XXVII)

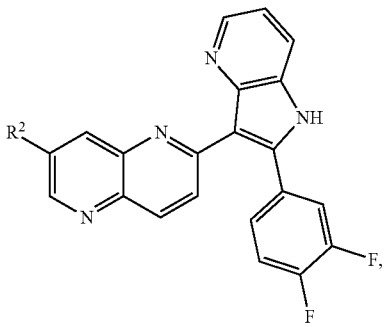
(XXVIII)

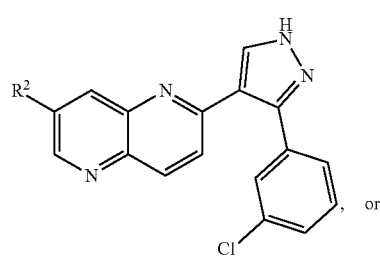
(XXIX), or

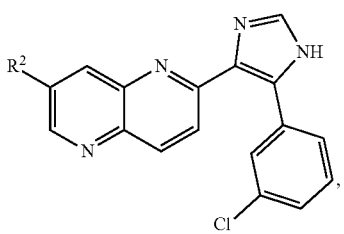
(XXX)

or a pharmaceutically acceptable salt thereof, wherein:

$R^2$ is selected from H; —NH—$(CH_2)_{0-3}R^5$; —NHCH$_2$C(CH$_3$)$_2$R$^5$; —NHCH$_2$C(CH$_3$)(CH$_2$OCH$_3$)R$^5$; —NHR$^5$; —NH—C(CH$_3$)$_2$CH$_2$R$^5$; —N(CH$_3$)R$^5$; —N(CH$_3$)CH$_2$R$^5$; —N(CH$_3$)CH$_2$CH$_2$R$^5$; phenyl-R$^5$; pyrrolinyl; pyrrolidinyl; 3,6-diazabicyclo[3.2.0]heptanyl; 1,4-diazepanyl; piperazinyl; (2R,5R)-1,2,5-trimethylpiperazinyl; 1-methylpyridin-2(1H)-onyl; and carboxylate; or $R^2$ is selected from azetidinyl-R$^5$; piperazinyl-R$^5$; isopropylpiperazinyl-R$^5$; methylpiperazinyl-R$^5$; isopropylpiperazinyl-R$^5$; pyrrolidinyl-R$^5$; piperidinyl-R$^5$; pyrazolyl-R$^5$; triazolyl-R$^5$; 2,7-diazaspiro[4.4]nonanyl-R$^5$; 2,5-diazabicyclo[2.2.1]heptanyl-R$^5$; 5,6,7,8-tetrahydro-[1,2,4]triazolo[1,5-a]pyrazinyl; 5,6,7,8-tetrahydro-[1,2,4]triazolo[1,5-a]pyrazinyl-R$^5$; 5,6,7,8-tetrahydroimidazo[1,5-a]pyrazinyl; 3-(trifluoromethyl)-5,6,7,8-tetrahydroimidazo[1,5-a]pyrazinyl; 5,6,7,8-tetrahydroimidazo[1,2-a]pyrazinyl; 5,6,7,8-tetrahydroimidazo[1,2-a]pyrimidinyl; 5,6,7,8-tetrahydropyrido[4,3-c]pyridazinyl; 4,5,6,7-tetrahydro-[1,2,3]triazolo[1,5-a]pyrazinyl; 3,6-diazabicyclo[3.2.0]heptanyl-R$^5$; 2,3-dihydro-1H-imidazo[1,2-a]imidazolyl; 2,3-dihydro-1H-imidazo[1,5-a]imidazolyl; 4,5,6,7-tetrahydropyrazolo[1,5-a]pyrazinyl; 4,5,6,7-tetrahydropyrazolo[1,5-a]pyrazinyl-R$^5$; 5,6,7,8-tetrahydroimidazo[1,2-a]pyrazinyl; 5,6-dihydro-4H-imidazo[1,2-c][1,2,3]triazolyl; 2,4,5,6-tetrahydropyrrolo[2,3-c]pyrazolyl; (R)-2-methyl-1,4-diazepanyl-R$^5$; cyclohexenyl-R$^5$; and cyclohexanyl-R$^5$;

$R^5$ is selected from:

piperazinyl, piperidinyl, pyrrolidinyl, azetidinyl, pyridinyl, pyrrolinyl, —CH$_2$—R$^6$, and 1,4-diazabicyclo[2.2.2]octanyl, optionally substituted with one or more methyl, ethyl, i-propyl, n-propyl, substituted or unsubstituted piperazinyl, carboxyl, carboxylate, or benzyl; and methyl amine; dimethyl amine; substituted or unsubstituted cyclopentanyl; substituted or unsubstituted cyclohexanyl; —$(CH_2)_{0-3}OH$; —$(CH_2)_{0-3}OCH_3$; methyl; ethyl; i-propyl; n-propyl; halo; —$CF_3$; carboxamide; methyl carboxamide; dimethyl carboxamide; isopropyl carboxamide; benzyl carboxamide; N-methylacetamide; —$NH_2$; —NH-benzyl; —$CH_2NHCH_3$; —$CH_2CH_2NH_2$; —$CH_2CH_2N(CH_3)_2$; —$CH_2CH_2NHCH_3$; —$CH_2CH_2NHC(CH_3)_2$; —$CH_2CH_2NH$-benzyl; carboxyl; carboxylate; benzyl carboxylate; methyl carboxylate; isopropyl carboxylate; substituted or unsubstituted piperazinyl; ethylazetidinyl; and 1,5-diazabicyclo[3.3.2]decanyl; and $R^6$ is selected from azetidinyl, imidazolyl, and 5,6,7,8-tetrahydro-1,6-naphthyridine.

In some embodiments, the compound of Formula (I) is a compound of Formula (II), (III), (IV), (V), (VI), (VII), (VIII), (IX), (X), (XI), (XII), (XIII), (XIV), (XV), (XVI), (XVII), (XVIII), (XIX), (XX), (XXI), (XXII), or (XXIII). In some embodiments, the compound of Formula (I) is a compound of Formula (II), (III), (IV), (VII), (VIII), (XV), (XVII), (XVIII), (XIX) or (XXIII). In some embodiments, the compound of Formula (I) is a compound of Formula (II), (III), (XVII) or (XVIII). In some embodiments, the compound of Formula (I) is a compound of Formula (II), (III) or (VII). In some embodiments, the compound of Formula (I) is a compound of Formula (II) or (III). In some embodiments, the compound of Formula (I) is a compound of Formula (II). In some embodiments, the compound of Formula (I) is a compound of Formula (III). In some embodiments, the compound of Formula (I) is a compound of Formula (VII). In some embodiments, the compound of Formula (I) is a compound of Formula (XVII) or (XVIII). In some embodiments, the compound of Formula (I) is a compound of Formula (VII), (VIII) or (XXIII).

In certain aspects, the present disclosure provides a compound of Formula (I):

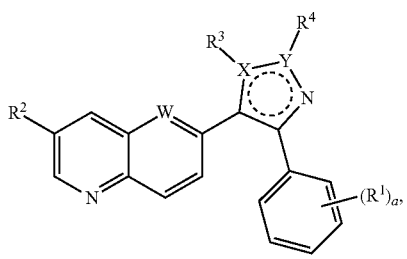

(I)

or a pharmaceutically acceptable salt thereof, wherein:
W is N or CH;
X and Y form a pyrrole, pyrazole, imidazole or triazole ring and X and Y are independently selected from C and N;
a is an integer from 0 to 3;
each $R^1$ is independently selected from halo, —OH, —$C_{1-6}$alkyl, and —$C_{0-2}$alkylene-O—$C_{1-6}$alkyl;
$R^2$ is selected from H; —NH—$(CH_2)_{0-3}R^5$; —NHCH$_2$C(CH$_3)_2R^5$; —NHCH$_2$C(CH$_3$)(CH$_2$OCH$_3$)$R^5$; —NHR$^5$; —NH—C(CH$_3$)$_2$CH$_2R^5$; —N(CH$_3$)$R^5$; —N(CH$_3$)CH$_2R^5$; —N(CH$_3$)CH$_2$CH$_2R^5$; phenyl-$R^5$; pyrrolinyl; pyrrolidinyl; 3,6-diazabicyclo[3.2.0]heptanyl; 1,4-diazepanyl; piperazinyl; (2R,5R)-1,2,5-trimethylpiperazinyl; 1-methylpyridin-2(1H)-onyl; and carboxylate; or $R^2$ is selected from azetidinyl-$R^5$; piperazinyl-$R^5$; isopropylpiperazinyl-$R^5$; methylpiperazinyl-$R^5$; isopropylpiperazinyl-$R^5$; pyrrolidinyl-$R^5$; piperidinyl-$R^5$; pyrazolyl-$R^5$; triazolyl-$R^5$; 2,7-diazaspiro[4.4]nonanyl-$R^5$; 2,5-diazabicyclo[2.2.1]heptanyl-$R^5$; 5,6,7,8-tetrahydro-[1,2,4]triazolo[1,5-a]pyrazinyl; 5,6,7,8-tetrahydro-[1,2,4]triazolo[1,5-a]pyrazinyl-$R^5$; 5,6,7,8-tetrahydroimidazo[1,5-a]pyrazinyl; 3-(trifluoromethyl)-5,6,7,8-tetrahydroimidazo[1,5-a]pyrazinyl; 5,6,7,8-tetrahydroimidazo[1,2-a]pyrazinyl; 5,6,7,8-tetrahydroimidazo[1,2-a]pyrimidinyl; 5,6,7,8-tetrahydropyrido[4,3-c]pyridazinyl; 4,5,6,7-tetrahydro-[1,2,3]triazolo[1,5-a]pyrazinyl; 3,6-diazabicyclo[3.2.0]heptanyl-$R^5$; 2,3-dihydro-1H-imidazo[1,2-a]imidazolyl; 2,3-dihydro-1H-imidazo[1,5-a]imidazolyl; 4,5,6,7-tetrahydropyrazolo[1,5-a]pyrazinyl; 4,5,6,7-tetrahydropyrazolo[1,5-a]pyrazinyl-$R^5$; 5,6,7,8-tetrahydroimidazo[1,2-a]pyrazinyl; 5,6-dihydro-4H-imidazo[1,2-c][1,2,3]triazolyl; 2,4,5,6-tetrahydropyrrolo[2,3-c]pyrazolyl; (R)-2-methyl-1,4-diazepanyl-$R^5$; cyclohexenyl-$R^5$; and cyclohexanyl-$R^5$;

$R^3$ is absent or is selected from hydrogen, benzyl, and —$C_{0-3}$ alkylene-$R^7$; or $R^3$ is taken together with $R^4$ to form a six-membered aromatic ring;

$R^4$ is absent, hydrogen, or taken together with $R^3$ to form a six-membered aromatic ring;

$R^5$ is selected from:
piperazinyl, piperidinyl, pyrrolidinyl, azetidinyl, pyridinyl, pyrrolinyl, —$CH_2$—$R^6$, and 1,4-diazabicyclo[2.2.2]octanyl, each of which is optionally substituted with one or more methyl, ethyl, i-propyl, n-propyl, substituted or unsubstituted piperazinyl, carboxyl, carboxylate, or benzyl; and methyl amine; dimethyl amine; substituted or unsubstituted cyclopentanyl; substituted or unsubstituted cyclohexanyl; —$(CH_2)_{0-3}OH$; —$(CH_2)_{0-3}OCH_3$; methyl; ethyl; i-propyl; n-propyl; halo; —$CF_3$; carboxamide; methyl carboxamide; dimethyl carboxamide; isopropyl carboxamide; benzyl carboxamide; N-methylacetamide; —$NH_2$; —NH-benzyl; —$CH_2NHCH_3$; —$CH_2CH_2NH_2$; —$CH_2CH_2N(CH_3)_2$; —$CH_2CH_2NHCH_3$; —$CH_2CH_2NHC(CH_3)_2$; —$CH_2CH_2NH$-benzyl; carboxyl; carboxylate; benzyl carboxylate; methyl carboxylate; isopropyl carboxylate; substituted or unsubstituted piperazinyl; ethylazetidinyl; and 1,5-diazabicyclo[3.3.2]decanyl;

$R^6$ is selected from azetidinyl, imidazolyl, and 5,6,7,8-tetrahydro-1,6-naphthyridine; and $R^7$ is a heterocycle;

provided that, when $R^2$ is H:
(i) W is N; or
(ii) W is CH; a is 3; and $R^1$ is independently selected from F and Cl.

In some embodiments, for a compound of Formula (I), at least one of X and Y is N. In some embodiments, X is C and Y is N, optionally wherein $R^3$ and $R^4$ are each hydrogen. In some embodiments, X is N and Y is C, optionally wherein $R^3$ and $R^4$ are each hydrogen. In some embodiments, X and Y are each N, optionally wherein $R^3$ is hydrogen and $R^4$ is absent. In some embodiments, X and Y are each C. In some embodiments, X and Y form a pyrrole ring. In some embodiments, X and Y form an imidazole ring. In some embodiments, X and Y form a triazole ring.

In some embodiments, for a compound of Formula (I), $R^3$ is absent or selected from hydrogen, benzyl and —$CH_2$-pyridyl. In some embodiments, $R^3$ is absent or hydrogen. In some embodiments, $R^4$ is absent or hydrogen. In some embodiments, $R^3$ and $R^4$ are independently absent or hydrogen.

In some embodiments, for a compound of Formula (I), $R^3$ and $R^4$ are taken together with the atoms to which they are attached to form an optionally substituted $C_{5-6}$ carbocycle or an optionally substituted 5- to 6-membered heterocycle. For example, $R^3$ and $R^4$ may be taken together with the atoms to which they are attached to form a 6-membered aromatic ring. In some embodiments, $R^3$ and $R^4$ are taken together to form

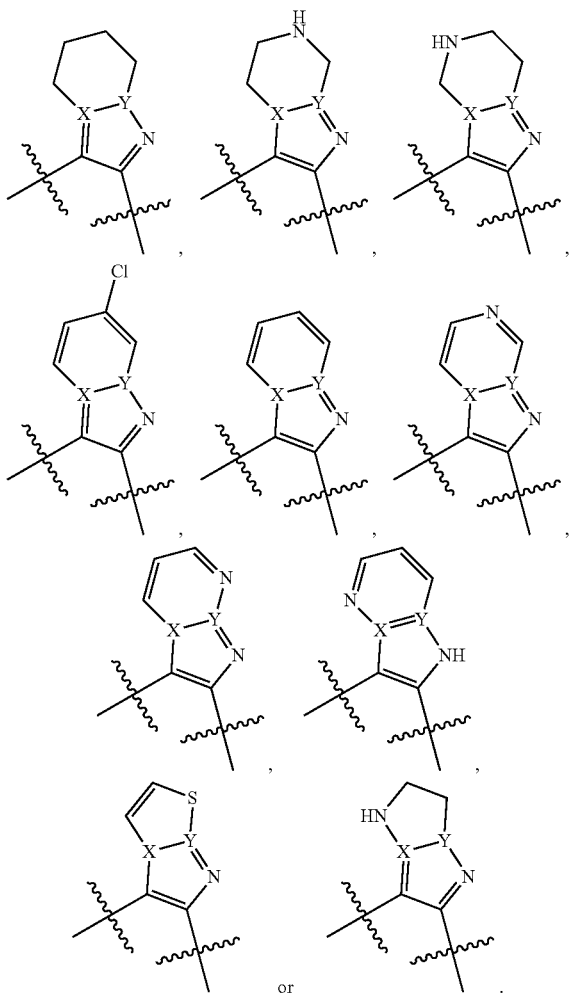

In some embodiments, $R^3$ and $R^4$ are taken together to form

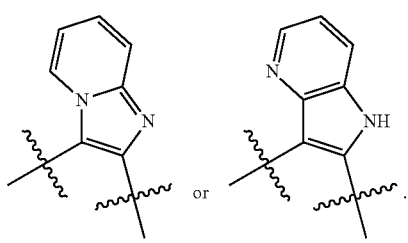 [SMILES: *c1nc2ccccn2c1* ; *c1[nH]c2cccnc2c1*]

In some embodiments, the compound of Formula (I) is a compound of Formula (I-A), (I-B) or (I-C):

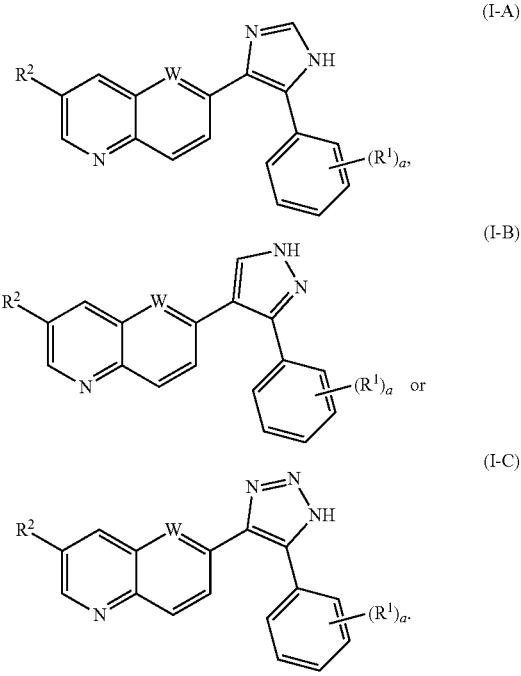

In some embodiments, for a compound of Formula (I), (I-A), (I-B) or (I-C), W is N. In some embodiments, W is CH.

In some embodiments, for a compound of Formula (I), (I-A), (I-B) or (I-C), $R^1$ is independently selected at each occurrence from halo, —OH, —CH$_3$ and —CH$_2$OCH$_3$. In some embodiments, $R^1$ is independently selected at each occurrence from Cl, F and —CH$_2$OCH$_3$. In some embodiments, $R^1$ is independently selected at each occurrence from Cl and F. In some embodiments, a is an integer from 1 to 3. In some embodiments, a is 1. In some embodiments, a is 2. In some embodiments, a is 3. In some embodiments, a is an integer from 1 to 3 and each $R^1$ is independently selected from F and Cl. In some embodiments, a is 1 or 2 and $R^1$ is independently selected from —CH$_3$, —CH$_2$OCH$_3$, and —OH. In some embodiments, a is 1 and $R^1$ is selected from Cl, F and —CH$_2$OCH$_3$. In some embodiments, a is 1 and $R^1$ is F. In some embodiments, a is 2 and each $R^1$ is independently selected from Cl, F, —OH, and —CH$_3$. In some embodiments, a is 2 and each $R^1$ is independently selected from Cl and F. In some embodiments, a is 2 and $R^1$ is F, or $R^1$ is Cl and F. In some embodiments, a is 2, the first $R^1$ is Cl and the second $R^1$ is F. In some embodiments, a is 3 and each $R^1$ is independently selected from Cl and F.

In some embodiments, for a compound of any one of Formulae (I) to (XXX):

$R^2$ is selected from —NH—(CH$_2$)$_{0-3}$R$^5$; —NHCH$_2$C(CH$_3$)$_2$R$^5$; —NHCH$_2$C(CH$_3$)(CH$_2$OCH$_3$)R$^5$; —NHR$^5$; —NH—C(CH$_3$)$_2$CH$_2$R$^5$; —N(CH$_3$)R$^5$; —N(CH$_3$)CH$_2$R$^5$; —N(CH$_3$)CH$_2$CH$_2$R$^5$; phenyl-R$^5$; pyrrolinyl; pyrrolidinyl; 3,6-diazabicyclo[3.2.0]heptanyl; 1,4-diazepanyl; piperazinyl; (2R,5R)-1,2,5-trimethylpiperazinyl; 1-methylpyridin-2(1H)-onyl; and carboxylate; or $R^2$ is selected from azetidinyl-R$^5$; piperazinyl-R$^5$; isopropylpiperazinyl-R$^5$; methylpiperazinyl-R$^5$; isopropylpiperazinyl-R$^5$; pyrrolidinyl-R$^5$; piperidinyl-R$^5$; pyrazolyl-R$^5$;

triazolyl-$R^5$; 2,7-diazaspiro[4.4]nonanyl-$R^5$; 2,5-diazabicyclo[2.2.1]heptanyl-$R^5$; 5,6,7,8-tetrahydro-[1,2,4]triazolo[1,5-a]pyrazinyl; 5,6,7,8-tetrahydro-[1,2,4]triazolo[1,5-a]pyrazinyl-$R^5$; 5,6,7,8-tetrahydroimidazo[1,5-a]pyrazinyl; 3-(trifluoromethyl)-5,6,7,8-tetrahydroimidazo[1,5-a]pyrazinyl; 5,6,7,8-tetrahydroimidazo[1,2-a]pyrazinyl; 5,6,7,8-tetrahydroimidazo[1,2-a]pyrimidinyl; 5,6,7,8-tetrahydropyrido[4,3-c]pyridazinyl; 4,5,6,7-tetrahydro-[1,2,3]triazolo[1,5-a]pyrazinyl; 3,6-diazabicyclo[3.2.0]heptanyl-$R^5$; 2,3-dihydro-1H-imidazo[1,2-a]imidazolyl; 2,3-dihydro-1H-imidazo[1,5-a]imidazolyl; 4,5,6,7-tetrahydropyrazolo[1,5-a]pyrazinyl; 4,5,6,7-tetrahydropyrazolo[1,5-a]pyrazinyl-$R^5$; 5,6,7,8-tetrahydroimidazo[1,2-a]pyrazinyl; 5,6-dihydro-4H-imidazo[1,2-c][1,2,3]triazolyl; 2,4,5,6-tetrahydropyrrolo[2,3-c]pyrazolyl; (R)-2-methyl-1,4-diazepanyl-$R^5$; cyclohexenyl-$R^5$; and cyclohexanyl-$R^5$.

In some embodiments, for a compound of any one of Formulae (I) to (XXX), $R^2$ is selected from —NH—$(CH_2)_{0-3}R^5$; —$NHCH_2C(CH_3)_2R^5$; —$NHCH_2C(CH_3)(CH_2OCH_3)R^5$; —$NHR^5$; —NH—$C(CH_3)_2CH_2R^5$; —$N(CH_3)R^5$; —$N(CH_3)CH_2R^5$; —$N(CH_3)CH_2CH_2R^5$; phenyl-$R^5$; pyrrolinyl; pyrrolidinyl; 3,6-diazabicyclo[3.2.0]heptanyl; 1,4-diazepanyl; piperazinyl; (2R,5R)-1,2,5-trimethylpiperazinyl; 1-methylpyridin-2(1H)-onyl; and carboxylate. In some embodiments, $R^2$ is selected from —NH—$(CH_2)_{1-3}R^5$; —$NHCH_2C(CH_3)_2R^5$; —$NHCH_2C(CH_3)(CH_2OCH_3)R^5$; —$NHR^5$; —NH—$C(CH_3)_2CH_2R^5$; —$N(CH_3)R^5$; —$N(CH_3)CH_2R^5$; and —$N(CH_3)CH_2CH_2R^5$. In some embodiments, $R^2$ is selected from —NH—$(CH_2)_{1-3}R^5$ and —$NHR^5$.

In some embodiments, for a compound of any one of Formulae (I) to (XXX), $R^2$ is selected from azetidinyl-$R^5$; piperazinyl-$R^5$; isopropylpiperazinyl-$R^5$; methylpiperazinyl-$R^5$; isopropylpiperazinyl-$R^5$; pyrrolidinyl-$R^5$; piperidinyl-$R^5$; pyrazolyl-$R^5$; triazolyl-$R^5$; 2,7-diazaspiro[4.4]nonanyl-$R^5$; 2,5-diazabicyclo[2.2.1]heptanyl-$R^5$; 5,6,7,8-tetrahydro-[1,2,4]triazolo[1,5-a]pyrazinyl; 5,6,7,8-tetrahydro-[1,2,4]triazolo[1,5-a]pyrazinyl-$R^5$; 5,6,7,8-tetrahydroimidazo[1,5-a]pyrazinyl; 3-(trifluoromethyl)-5,6,7,8-tetrahydroimidazo[1,5-a]pyrazinyl; 5,6,7,8-tetrahydroimidazo[1,2-a]pyrazinyl; 5,6,7,8-tetrahydroimidazo[1,2-a]pyrimidinyl; 5,6,7,8-tetrahydropyrido[4,3-c]pyridazinyl; 4,5,6,7-tetrahydro-[1,2,3]triazolo[1,5-a]pyrazinyl; 3,6-diazabicyclo[3.2.0]heptanyl-$R^5$; 2,3-dihydro-1H-imidazo[1,2-a]imidazolyl; 2,3-dihydro-1H-imidazo[1,5-a]imidazolyl; 4,5,6,7-tetrahydropyrazolo[1,5-a]pyrazinyl; 4,5,6,7-tetrahydropyrazolo[1,5-a]pyrazinyl-$R^5$; 5,6,7,8-tetrahydroimidazo[1,2-a]pyrazinyl; 5,6-dihydro-4H-imidazo[1,2-c][1,2,3]triazolyl; 2,4,5,6-tetrahydropyrrolo[2,3-c]pyrazolyl; (R)-2-methyl-1,4-diazepanyl-$R^5$; cyclohexenyl-$R^5$; and cyclohexanyl-$R^5$. In some embodiments, $R^2$ is selected from azetidinyl-$R^5$; piperazinyl-$R^5$; pyrrolidinyl-$R^5$; piperidinyl-$R^5$; pyrazolyl-$R^5$; triazolyl-$R^5$; cyclohexenyl-$R^5$; and cyclohexanyl-$R^5$. In some embodiments, $R^2$ is selected from azetidinyl-$R^5$; piperazinyl-$R^5$; and pyrrolidinyl-$R^5$.

In some embodiments, for a compound of any one of Formulae (I) to (XXX), $R^5$ is selected from
piperazinyl, piperidinyl, pyrrolidinyl, azetidinyl, pyridinyl, and pyrrolinyl, each of which is optionally substituted with one or more methyl, ethyl, i-propyl, or n-propyl; and
methyl amine; dimethyl amine; methyl; ethyl; i-propyl; n-propyl; halo; —$CF_3$; —$NH_2$; —$CH_2NHCH_3$; —$CH_2CH_2NH_2$; —$CH_2CH_2N(CH_3)_2$; —$CH_2CH_2NHCH_3$; and —$CH_2CH_2NHC(CH_3)_2$.

In some embodiments, $R^5$ is selected from piperazinyl, piperidinyl, pyrrolidinyl, and azetidinyl, each of which is optionally substituted with one or more methyl, ethyl, i-propyl, or n-propyl.

In some embodiments, for a compound of any one of Formulae (I) to (XXX), $R^2$ is selected from

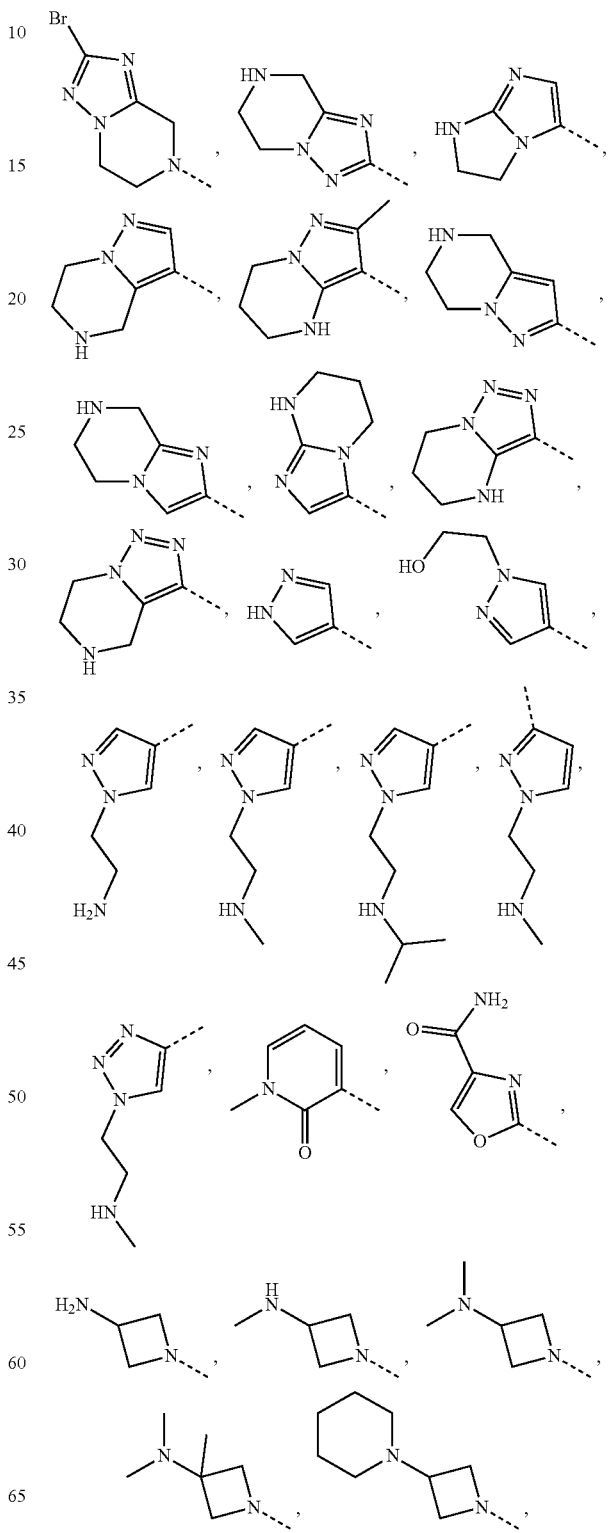

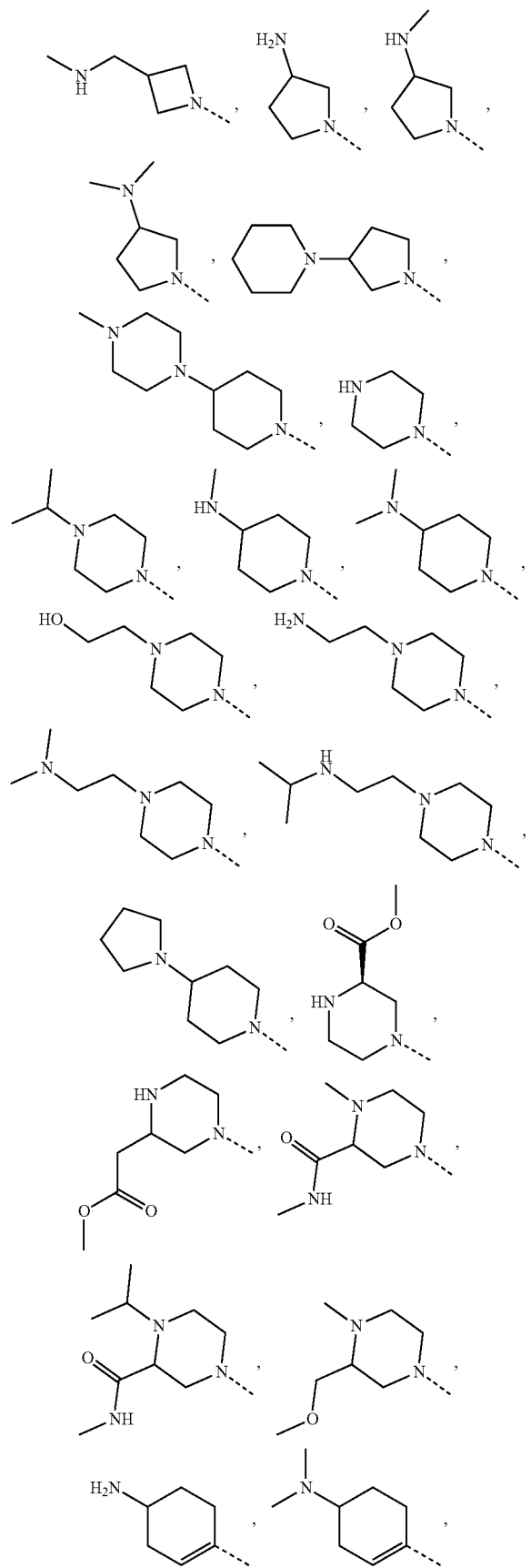
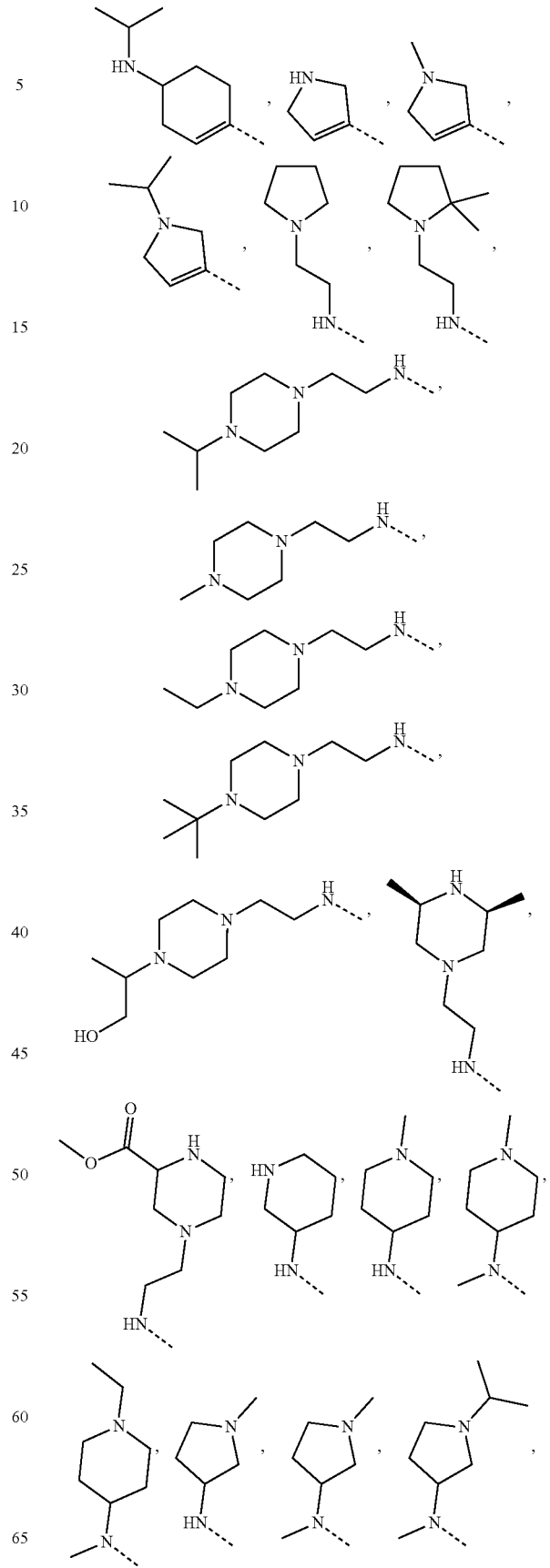

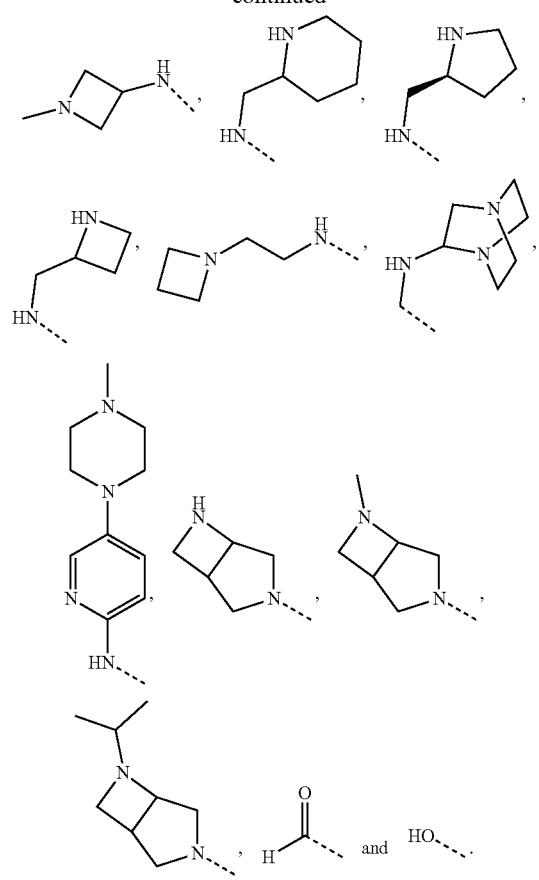
In some embodiments, R² is selected from
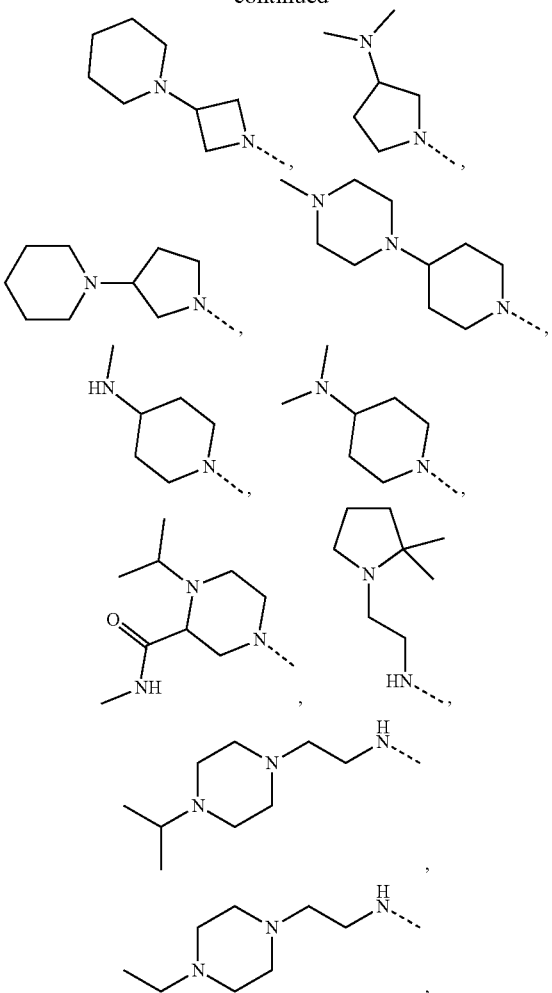
In some embodiments, R² is selected from -continued

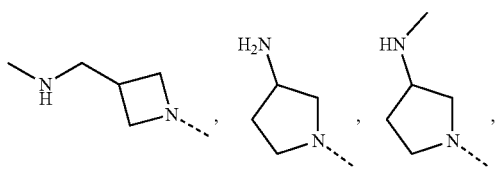

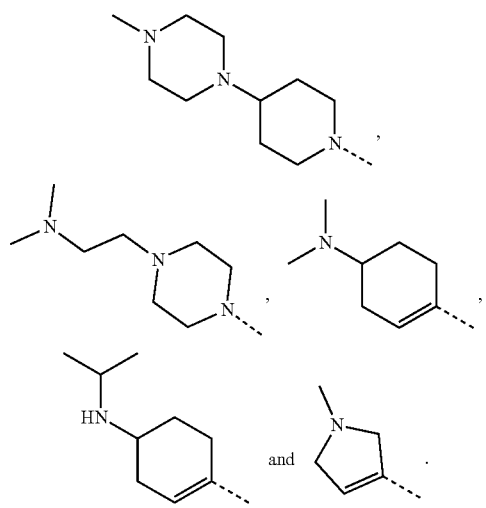

In some embodiments, R² is

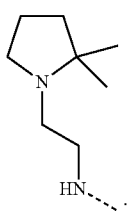

In some embodiments, R² is

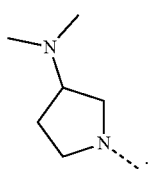

In some embodiments, R² is

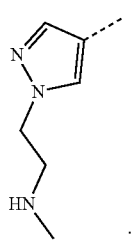

In some embodiments, R² is

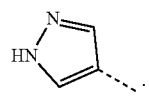

In some embodiments, R² is

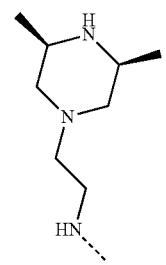

In some embodiments, R² is

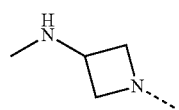

In some embodiments, R² is

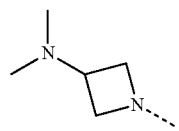

In some embodiments, for a compound of any one of Formulae (I) to (XXX), R² is -L¹L²R¹⁰, wherein:
L¹ is selected from absent; $C_{1-6}$ alkylene, $C_{3-12}$ carbocycle, and 3- to 12-membered heterocycle;
L² is selected from absent, —NH—, —C(O)O—, and —OC(O)—;
R¹⁰ is selected from:
—C(O)OR¹² and —OC(O)R¹²;
$C_{1-10}$ alkyl, optionally substituted with one or more substituents selected from —N(R¹²)₂, —C(O)OR¹², —OC(O)R¹², $C_{3-12}$ carbocycle, and 3- to 12-membered heterocycle; and
$C_{3-12}$ carbocycle and 3- to 12-membered heterocycle, wherein each $C_{3-12}$ carbocycle and 3- to 12-membered heterocycle in R¹⁰ is independently optionally substituted with one or more substituents selected from —N(R¹²)₂, —C(O)OR¹², —OC(O)R¹², and $C_{1-6}$ alkyl; and
R¹² is independently selected at each occurrence from hydrogen; and $C_{1-10}$ alkyl, $C_{3-12}$ carbocycle, and 3- to 12-membered heterocycle, each of which is optionally substituted by —NH₂, —CH₃, $C_{3-12}$ carbocycle-NH₂, or 3- to 6-membered heterocycle.

In some embodiments, for a compound of any one of Formulae (I) to (XXX), $R^2$ is -$L^1L^2R^{10}$, wherein:
  $L^1$ is absent;
  $L^2$ is selected from —C(O)O—, and —OC(O)—; and
  $R^{10}$ is selected from:
    $C_{1-10}$ alkyl, optionally substituted with one or more substituents selected from —$NH_2$, $C_{3-12}$ carbocycle, and 3- to 12-membered heterocycle; and
    $C_{3-12}$ carbocycle and 3- to 12-membered heterocycle,
    wherein each $C_{3-12}$ carbocycle and 3- to 12-membered heterocycle in $R^{10}$ is independently optionally substituted with one or more substituents selected from —$NH_2$ and $C_{1-6}$ alkyl.

In some embodiments, for a compound of any one of Formulae (I) to (XXX), $R^2$ is -$L^1L^{2-10}$, wherein:
  $L^1$ is 3- to 12-membered heterocycle;
  $L^2$ is selected from —C(O)O— and —OC(O)—; and
  $R^{10}$ is selected from:
    $C_{1-10}$ alkyl, optionally substituted with one or more substituents selected from —$NH_2$, $C_{3-12}$ carbocycle, and 3- to 12-membered heterocycle; and
    $C_{3-12}$ carbocycle and 3- to 12-membered heterocycle,
    wherein each $C_{3-12}$ carbocycle and 3- to 12-membered heterocycle in $R^{10}$ is independently optionally substituted with one or more substituents selected from —$NH_2$ and $C_{1-6}$ alkyl.

In some embodiments, for a compound of any one of Formulae (I) to (XXX), $R^2$ is -$L^1L^{2-10}$, wherein:
  $L^1$ is absent;
  $L^2$ is —NH—; and
  $R^{10}$ is selected from:
    $C_{1-10}$ alkyl, substituted with $C_{3-12}$ carbocycle or 3- to 12-membered heterocycle; and
    $C_{3-12}$ carbocycle and 3- to 12-membered heterocycle,
    wherein each $C_{3-12}$ carbocycle and 3- to 12-membered heterocycle in $R^{10}$ is substituted with —C(O)O$R^{12}$ or —OC(O)$R^{12}$;
  $R^{12}$ is independently selected at each occurrence from hydrogen; and $C_{1-10}$ alkyl, $C_{3-12}$ carbocycle, and 3- to 12-membered heterocycle, each of which is optionally substituted by —$NH_2$, —$CH_3$, $C_{3-12}$ carbocycle-$NH_2$, or 3- to 6-membered heterocycle.

In some embodiments, for a compound of Formula (I), (I-A), (I-B) or (I-C):
  X and Y are each independently selected from C and N, wherein at least one of X and Y is N;
  a is an integer from 1 to 3;
  each $R^1$ is independently selected from Cl and F;
  $R^2$ is selected from —NH—$(CH_2)_{1-3}R^5$; —NHCH$_2$C(CH$_3$)$_2R^5$; —NHCH$_2$C(CH$_3$)(CH$_2$OCH$_3$)$R^5$; —NH$R^5$; —NH—C(CH$_3$)$_2$CH$_2R^5$; —N(CH$_3$)$R^5$; —N(CH$_3$)CH$_2R^5$; —N(CH$_3$)CH$_2$CH$_2R^5$; azetidinyl-$R^5$; piperazinyl-$R^5$; pyrrolidinyl-$R^5$; piperidinyl-$R^5$; pyrazolyl-$R^5$; triazolyl-$R^5$; cyclohexenyl-$R^5$; and cyclohexanyl-$R^5$;
  $R^3$ and $R^4$ are each independently absent or hydrogen; and
  $R^5$ is selected from piperazinyl, piperidinyl, pyrrolidinyl, azetidinyl, pyridinyl, and pyrrolinyl, each of which is optionally substituted with one or more methyl, ethyl, i-propyl, or n-propyl; and methyl amine; dimethyl amine; methyl; ethyl; i-propyl; n-propyl; halo; —CF$_3$; —NH$_2$; —CH$_2$NHCH$_3$; —CH$_2$CH$_2$NH$_2$; —CH$_2$CH$_2$N(CH$_3$)$_2$; —CH$_2$CH$_2$NHCH$_3$; and —CH$_2$CH$_2$NHC(CH$_3$)$_2$.

In some embodiments, for a compound of Formula (I), (I-A), (I-B) or (I-C):
  each $R^1$ is independently selected from F and Cl;
  $R^2$ is selected from —NH—$(CH_2)_{1-3}R^5$; —NHCH$_2$C(CH$_3$)$_2R^5$; —NHCH$_2$C(CH$_3$)(CH$_2$OCH$_3$)$R^5$; —NH$R^5$; —NH—C(CH$_3$)$_2$CH$_2R^5$; —N(CH$_3$)$R^5$; —N(CH$_3$)CH$_2R^5$; —N(CH$_3$)CH$_2$CH$_2R^5$; azetidinyl-$R^5$; piperazinyl-$R^5$; pyrrolidinyl-$R^5$; piperidinyl-$R^5$; pyrazolyl-$R^5$; triazolyl-$R^5$; cyclohexenyl-$R^5$; and cyclohexanyl-$R^5$; and
  $R^5$ is selected from piperazinyl, piperidinyl, pyrrolidinyl, azetidinyl, pyridinyl, and pyrrolinyl, each of which is optionally substituted with one or more methyl, ethyl, i-propyl, or n-propyl; and methyl amine; dimethyl amine; methyl; ethyl; i-propyl; n-propyl; halo; —CF$_3$; —NH$_2$; —CH$_2$NHCH$_3$; —CH$_2$CH$_2$NH$_2$; —CH$_2$CH$_2$N(CH$_3$)$_2$; —CH$_2$CH$_2$NHCH$_3$; and —CH$_2$CH$_2$NHC(CH$_3$)$_2$.

In some embodiments, X is N, Y is C, and $R^3$ and $R^4$ are each hydrogen. In some embodiments, X is C, Y is N, and $R^3$ and $R^4$ are each hydrogen. In some embodiments, X and Y are each N, $R^3$ is hydrogen, and $R^4$ is absent.

In some embodiments, for a compound of Formula (I), (I-A), (I-B) or (I-C):
  X—$R^3$ is N;
  Y—$R^4$ is CH or NH;
  a is an integer from 1 to 3;
  each $R^1$ is independently selected from F and Cl; and
  $R^2$ is selected from —NH—$(CH_2)_{1-3}R^5$; —NHCH$_2$C(CH$_3$)$_2R^5$; —NH$R^5$; —NH—C(CH$_3$)$_2$CH$_2R^5$; —N(CH$_3$)$R^5$; —N(CH$_3$)CH$_2R^5$; and $R^5$ is selected from piperazinyl, piperidinyl, pyrrolidinyl, and pyridinyl, each of which is optionally substituted with one or more methyl, ethyl, i-propyl, or n-propyl; or
  $R^2$ is selected from piperazinyl-$R^5$; pyrrolidinyl-$R^5$; piperidinyl-$R^5$; pyrazolyl-$R^5$; and triazolyl-$R^5$; and $R^5$ is selected from methyl amine; dimethyl amine; methyl; ethyl; i-propyl; n-propyl; —NH$_2$; —CH$_2$NHCH$_3$; —CH$_2$CH$_2$NH$_2$; —CH$_2$CH$_2$N(CH$_3$)$_2$; and —CH$_2$CH$_2$NHCH$_3$.

In some embodiments, for a compound of Formula (I), (I-A), (I-B) or (I-C):
  W is N;
  X and Y are each independently selected from C and N, wherein at least one of X and Y is N;
  a is an integer from 1 to 3;
  each $R^1$ is independently selected from Cl and F;
  $R^2$ is selected from —NH—$(CH_2)_{1-3}R^5$; —NHCH$_2$C(CH$_3$)$_2R^5$; —NHCH$_2$C(CH$_3$)(CH$_2$OCH$_3$)$R^5$; —NH$R^5$; —NH—C(CH$_3$)$_2$CH$_2R^5$; —N(CH$_3$)$R^5$; —N(CH$_3$)CH$_2R^5$; —N(CH$_3$)CH$_2$CH$_2R^5$; azetidinyl-$R^5$; piperazinyl-$R^5$; pyrrolidinyl-$R^5$; piperidinyl-$R^5$; pyrazolyl-$R^5$; triazolyl-$R^5$; cyclohexenyl-$R^5$; and cyclohexanyl-$R^5$;
  $R^3$ and $R^4$ are each independently absent or hydrogen; and
  $R^5$ is selected from piperazinyl, piperidinyl, pyrrolidinyl, azetidinyl, pyridinyl, and pyrrolinyl, each of which is optionally substituted with one or more methyl, ethyl, i-propyl, or n-propyl; and methyl amine; dimethyl amine; methyl; ethyl; i-propyl; n-propyl; halo; —CF$_3$; —NH$_2$; —CH$_2$NHCH$_3$; —CH$_2$CH$_2$NH$_2$; —CH$_2$CH$_2$N(CH$_3$)$_2$; —CH$_2$CH$_2$NHCH$_3$; and —CH$_2$CH$_2$NHC(CH$_3$)$_2$.

In some embodiments, for a compound of Formula (I), (I-A), (I-B) or (I-C):
  W is N;
  a is an integer from 1 to 3;
  $R^3$ and $R^4$ are each independently absent or hydrogen; and
  $R^2$ is selected from:

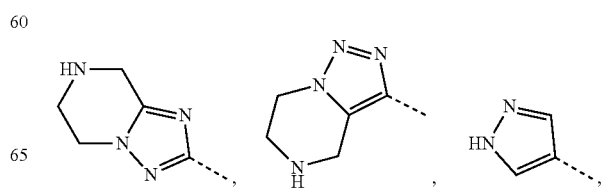

-continued
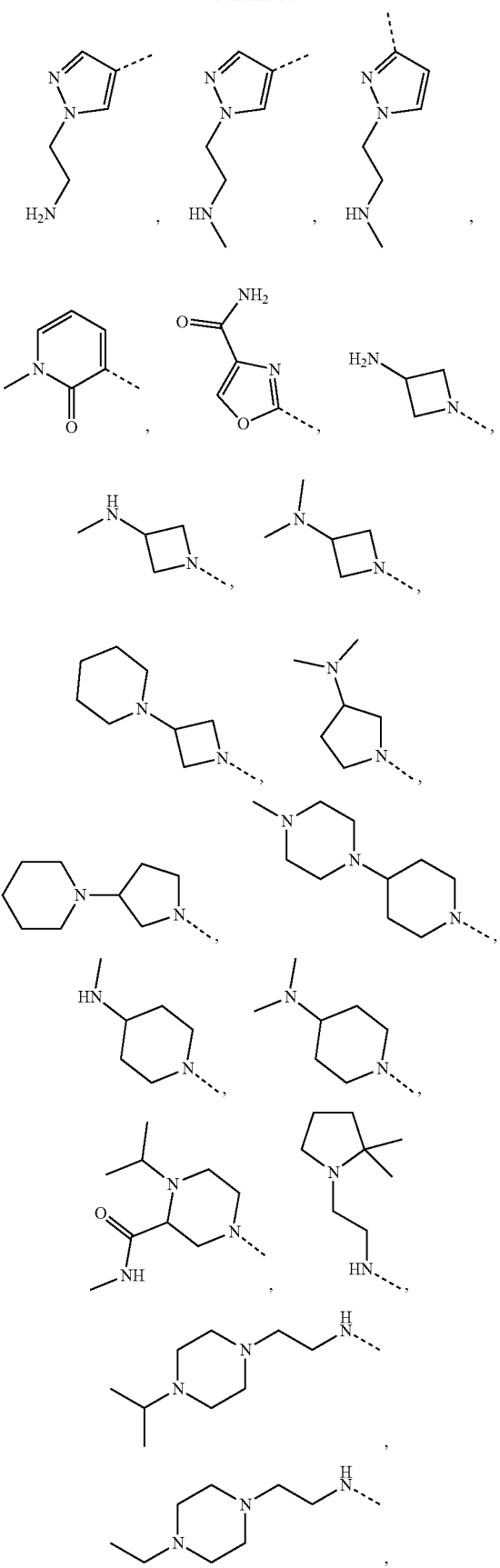
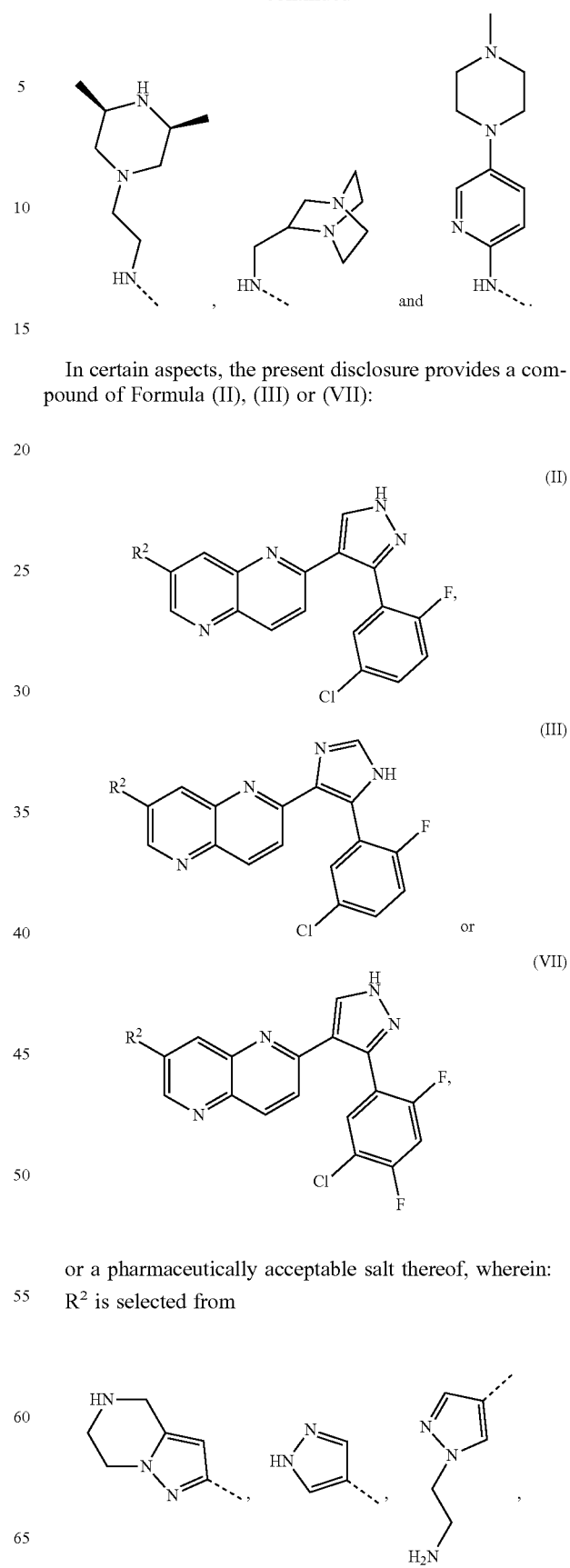
In certain aspects, the present disclosure provides a compound of Formula (II), (III) or (VII):
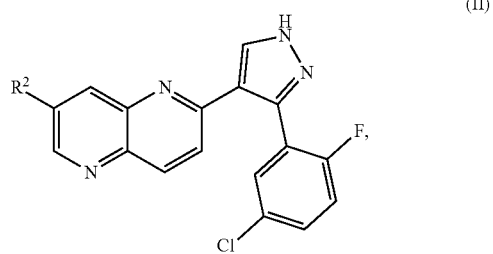
(II)
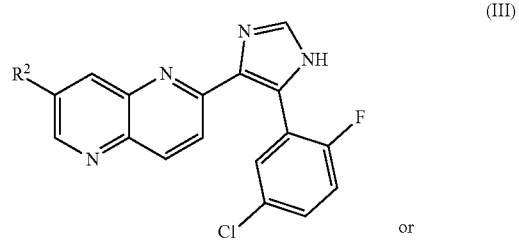
(III)
or
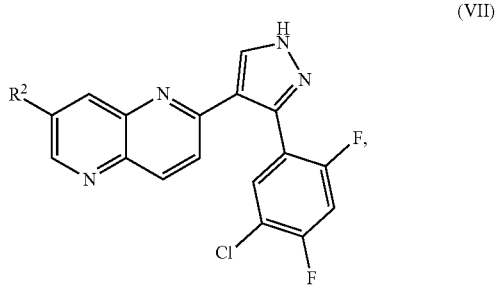
(VII)
or a pharmaceutically acceptable salt thereof, wherein:
$R^2$ is selected from

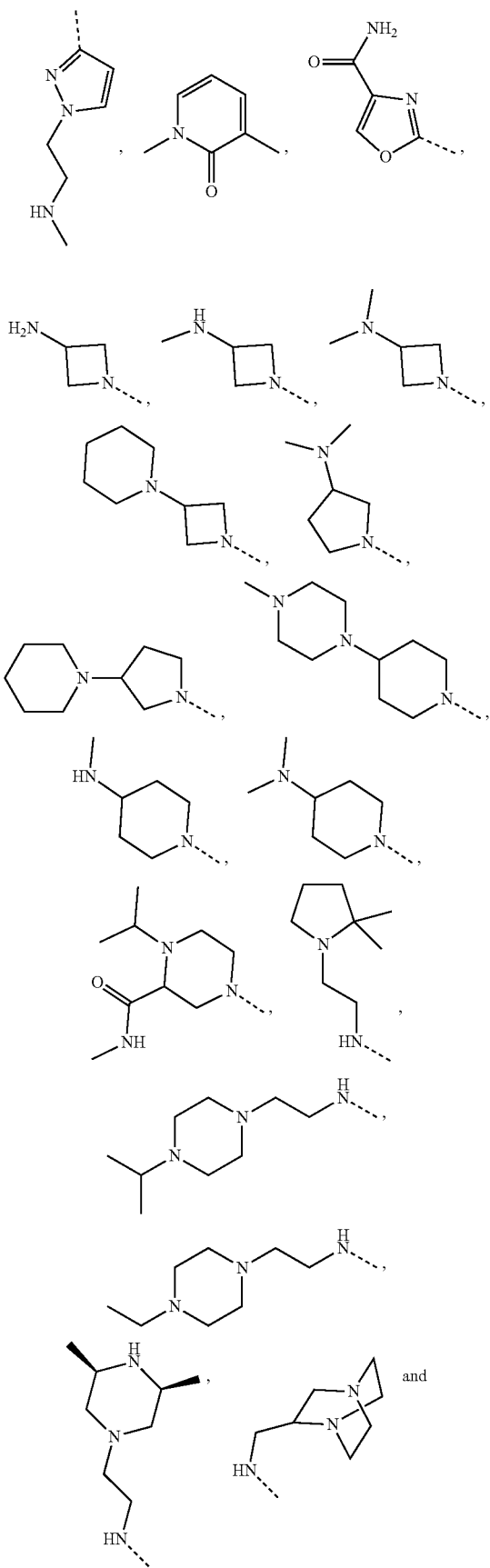

In some embodiments, the compound is a compound of Formula (II). In some embodiments, the compound is a compound of Formula (III). In some embodiments, the compound is a compound of Formula (VII).

In some embodiments, a compound of any one of Formulae (I) to (XXX) is provided as a substantially pure stereoisomer. In some embodiments, the stereoisomer is provided in at least 80% enantiomeric excess, such as at least 85%, at least 90%, at least 95%, at least 96%, at least 97%, at least 98%, at least 99% or at least 99.9% enantiomeric excess.

In some embodiments, the present disclosure provides a soft ALK5 inhibitor. As used herein, the term "soft drug" or "soft ALK5 inhibitor" refers to a biologically active compound that is converted upon entering the systemic circulation into a predictable metabolite that exhibits reduced biological activity relative to the parent compound. A soft drug preferably exerts its desired therapeutic effect locally at the target organ or tissue, then is rapidly converted to a less active metabolite upon entering the systemic circulation, thus reducing systemic exposure to the biologically active compound. Accordingly, soft drugs have a lower potential for undesired side effects relative to non-soft drug compounds having comparable biological activity. Preferably, a soft drug of the present disclosure exhibits good stability at the intended site of action (e.g., the lung), is rapidly metabolized upon entering systemic circulation, and displays more functional activity than the corresponding metabolite.

In some embodiments, a soft drug provided herein exhibits an ALK5 $pK_i$ of greater than or equal to 9, while the corresponding soft drug metabolite exhibits an ALK5 $pK_i$ of 8 or less (assessed according to the assay provided in Example 254). In some embodiments, the difference in $pK_i$ of the soft drug and the corresponding soft drug metabolite is at least 1.0, such as at least 1.1, 1.2, 1.3, 1.4, 1.5, 1.6, 1.7, 1.8, 1.9, or at least 2.0. In some embodiments, a soft drug provided herein exhibits a BEAS2B $pIC_{50}$ of greater than or equal to 7, while the corresponding soft drug metabolite exhibits a BEAS2B $pIC_{50}$ of 6 or less (assessed according to the assay provided in Example 255). In some embodiments, the difference in $pIC_{50}$ of the soft drug and the corresponding soft drug metabolite is at least 1.0, such as at least 1.1, 1.2, 1.3, 1.4, 1.5, 1.6, 1.7, 1.8, 1.9, or at least 2.0.

In some embodiments, the present disclosure provides a soft ALK5 inhibitor comprising an ester. Preferably, the ester inhibits ALK5 activity, while the corresponding carboxylic acid of the ester exhibits reduced ALK5 inhibitory activity. For example, the difference in ALK5 $pK_i$ of the ester and corresponding acid may be at least 1.0. In some embodiments, a soft drug ester of the present disclosure is administered to the lung, for example, by inhalation, and inhibits the activity of ALK5 in the lung. However, upon exiting the lung, the ester may be readily hydrolyzed to the corresponding carboxylic acid, thus reducing systemic exposure to the ester.

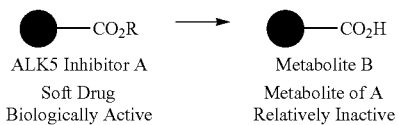

ALK5 Inhibitor A
Soft Drug
Biologically Active

Metabolite B
Metabolite of A
Relatively Inactive

The chemical entities described herein can be synthesized according to one or more illustrative schemes herein and/or techniques known in the art. Materials used herein are either commercially available or prepared by synthetic methods generally known in the art. These schemes are not limited to the compounds listed in the examples or by any particular substituents, which are employed for illustrative purposes. Although various steps are described and depicted in Schemes 1-5 and Examples 1-253, the steps in some cases may be performed in a different order than the order shown in Schemes 1-5 and Examples 1-253. Various modifications to these synthetic reaction schemes may be made and will be suggested to one skilled in the art having referred to the present disclosure. Numberings or R groups in each scheme typically have the same meanings as those defined elsewhere herein unless otherwise indicated.

Unless specified to the contrary, the reactions described herein take place at atmospheric pressure, generally within a temperature range from −10° C. to 200° C. Further, except as otherwise specified, reaction times and conditions are intended to be approximate, e.g., taking place at about atmospheric pressure within a temperature range of about −10° C. to about 110° C. over a period of about 1 to about 24 hours; reactions left to run overnight average a period of about 16 hours.

In general, compounds of the disclosure may be prepared by the following reaction schemes:

Scheme 1
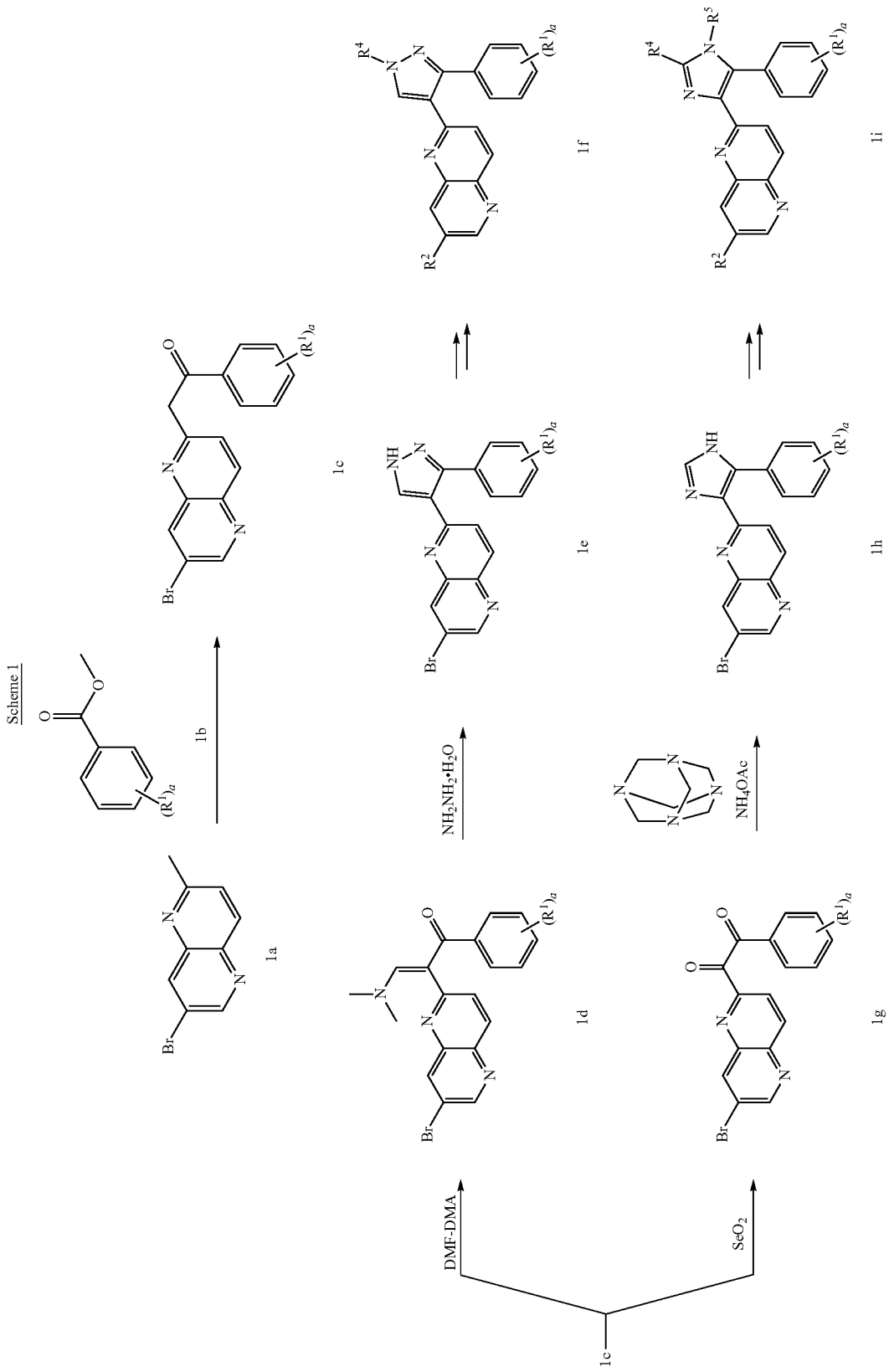

In some embodiments, a compound of Formula 1f or Formula 1i may be prepared according to Scheme 1. For example, napthyridine 1a can be reacted with unsubstituted or R¹-substituted methyl benzoate 1b to give ethanone 1c. To convert 1c to a pyrazole, 1c may first be reacted with DMF·DMA at elevated temperatures to give intermediate 1d, which can be reacted with hydrazine monohydrate to provide pyrazole 1e. Optionally, 1e may be subjected to one or more coupling reactions, and optionally one or more protecting group manipulations, to provide a pyrazole of Formula 1f. Alternatively, oxidation of 1c can provide dione 1g, which can be converted to imidazole 1h in the presence of urotropine and ammonium acetate. Optionally, 1h may be subjected to one or more coupling reactions, and optionally one or more protecting group manipulations, to provide an imidazole of Formula 1i.

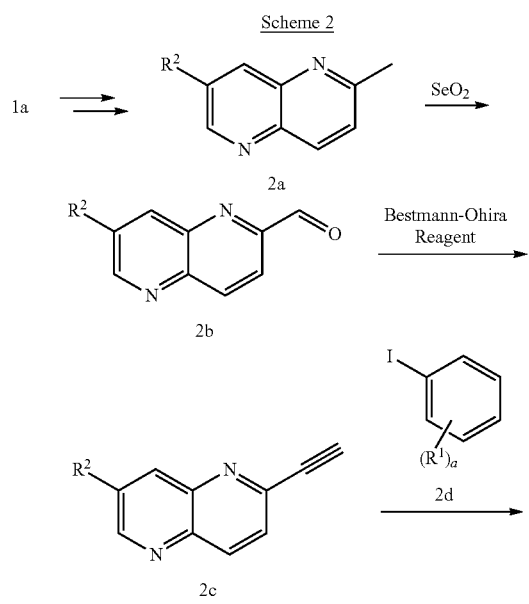

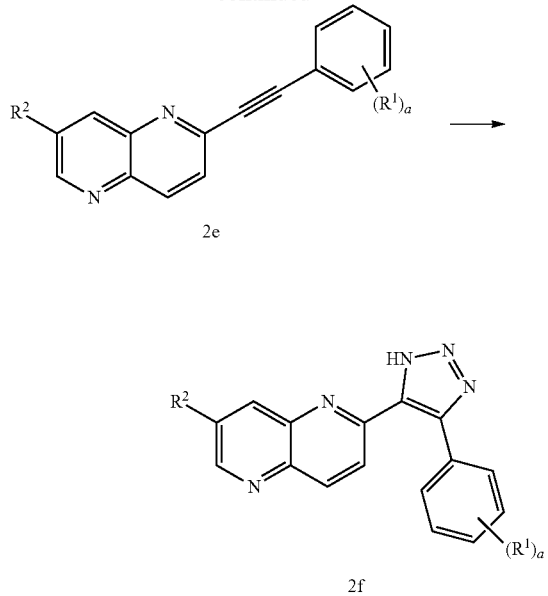

In some embodiments, a compound of Formula 2f may be prepared according to Scheme 2. For example, napthyridine 1a can be coupled to $R^2$ to afford 2a, optionally by converting 1a to (6-methyl-1,5-napthyridin-3-yl)boronic acid and then installing a desired $R^2$ group via a Suzuki reaction with I-$R^2$. Compound 2a can be oxidized to provide aldehyde 2b. The aldehyde can undergo a Seyferth-Gilbert homologation, optionally using Bestmann-Ohira reagent, to provide alkyne 2c. Cross-coupling of 2c with an unsubstituted or $R^1$-substituted iodobenzene (2d) via a Sonogashira reaction provides alkyne 2e, which can be converted to a triazole of Formula 2f in the presence of a suitable azide, such as TMS-N₃.

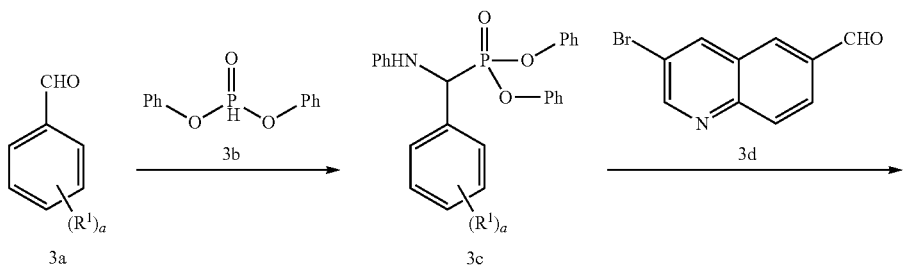

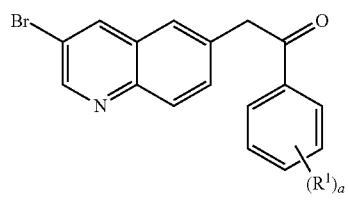

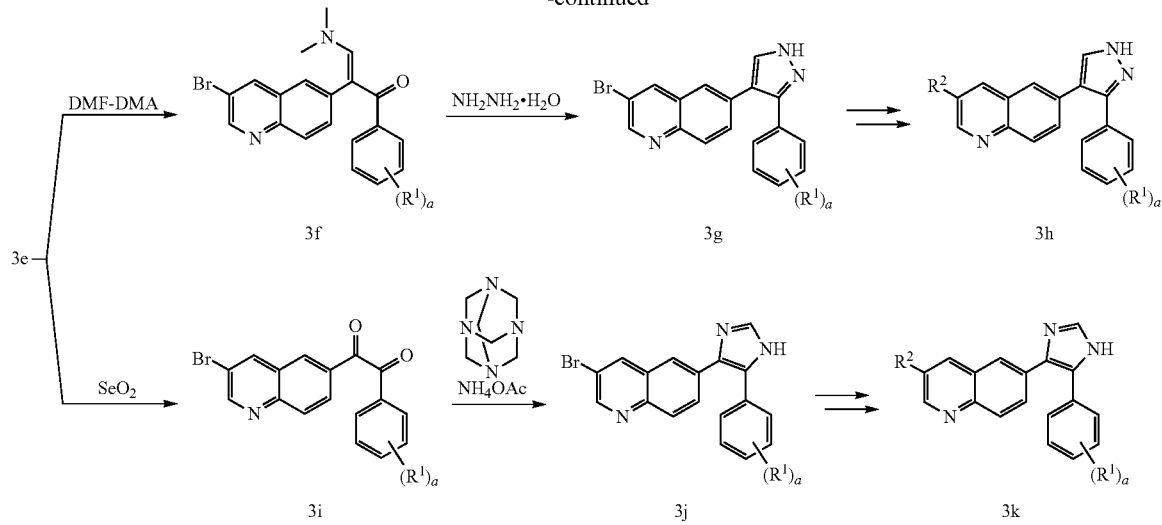

In some embodiments, a compound of Formula 3h or Formula 3k may be prepared according to Scheme 3. For example, unsubstituted or $R^1$-substituted benzaldehyde (3a) can be reacted with phosphonate 3b in the presence of $PhNH_2$ to provide 3c, which can be coupled to aldehyde 3d to give ethanone 3e. From 3e, the same general procedure outlined in Scheme 1 may be followed to provide a pyrazole of Formula 3h or an imidazole of Formula 3k.

Scheme 4

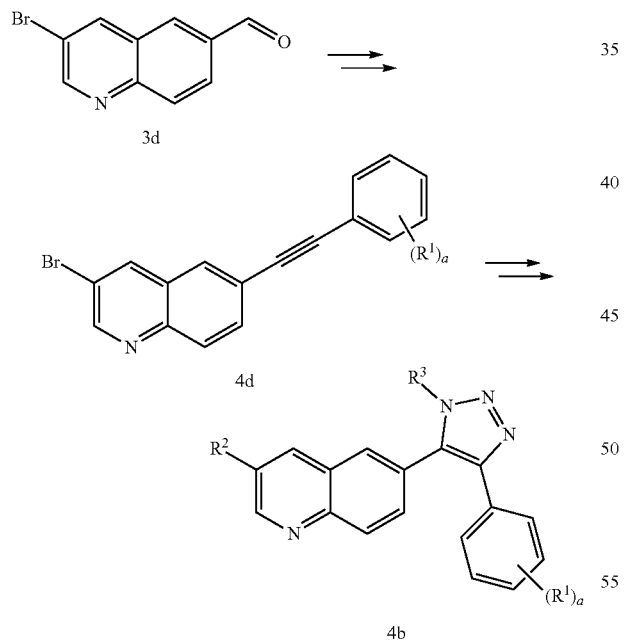

In some embodiments, a compound of Formula 4b may be prepared according to Scheme 4. For example, following the same general procedure outlined in Scheme 2, quinoline 3d can be subjected to a Seyferth-Gilbert homologation and coupled to a suitable iodobenzene via a Sonogashira reaction to provide alkyne 4a. Following cyclization to the triazole, one or more optional coupling reactions and optionally one or more protecting group manipulations may provide a triazole of Formula 4b.

Scheme 5

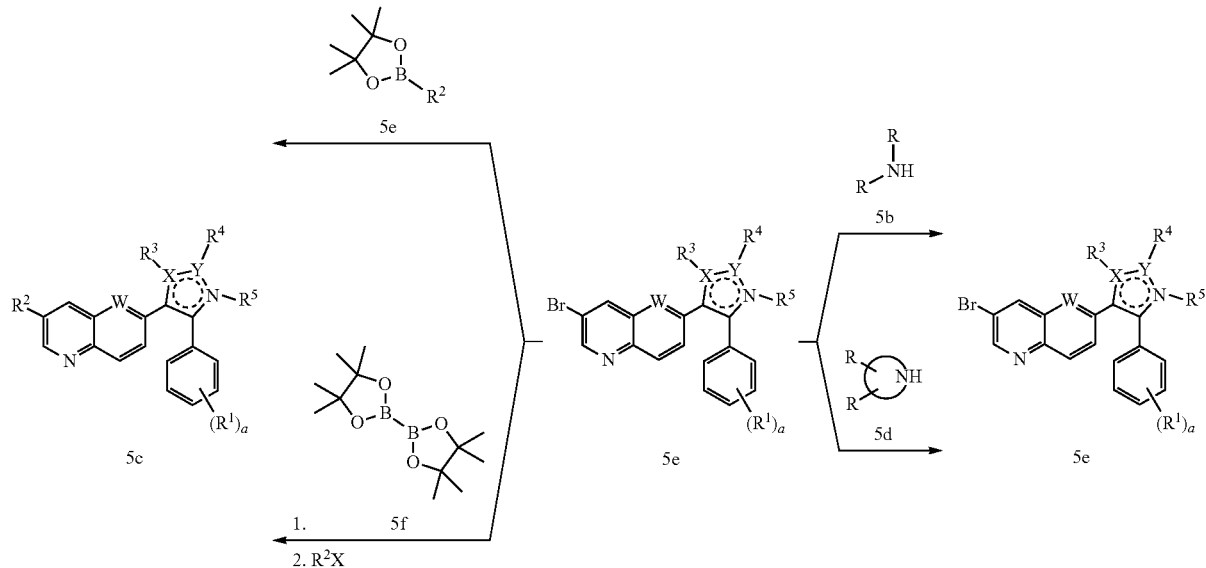

In some embodiments, a compound of Formula 5c may be prepared according to Scheme 5. For example, heteroaryl bromide 5a can be subjected to a C—N coupling reaction—optionally a Pd-catalyzed coupling reaction such as a Buchwald-Hartwig amination—with an acyclic primary or secondary amine (5b) or a cyclic secondary amine (5d) to provide a heteroaryl amine of Formula 5c. Alternatively, installation of a desired $R^2$ substituent may proceed via a Suzuki reaction, either in one step using boronic acid 5e or in two steps—wherein heteroaryl bromide 5a is first converted to the corresponding boronic acid, then coupled to a suitable halide (e.g., $R^2X$)—to give a compound of Formula 5c.

In some embodiments, a compound of the present disclosure, for example, a compound of a formula given in Table 1, is synthesized according to one of the general routes outlined in Schemes 1-5, Examples 1-253, or by methods generally known in the art. In some embodiments, exemplary compounds may include, but are not limited to, a compound or salt thereof selected from Table 1.

TABLE 1

| No. | Structure | Chemical Name | [M + H]⁺ |
|---|---|---|---|
| 1-1 | 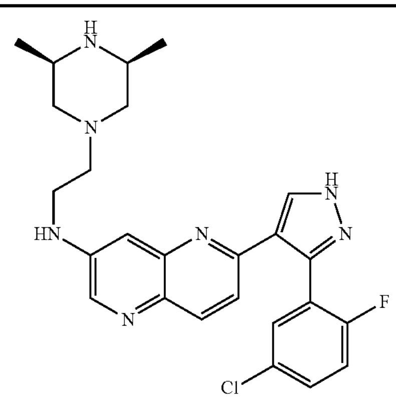 | 6-[3-(5-chloro-2-fluoro-phenyl)-1H-pyrazol-4-yl]-N-[2-[rac-(3R,5S)-3,5-dimethylpiperazin-1-yl]ethyl]-1,5-naphthyridine-3-amine | 480.1 |
| 1-2 | 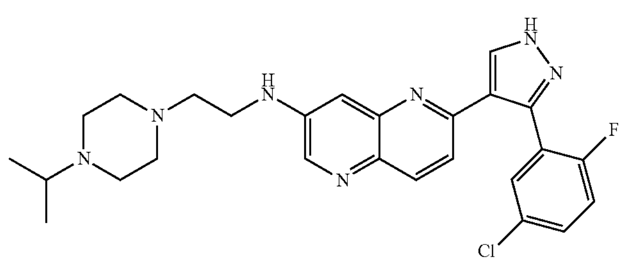 [SMILES: CC(C)N1CCN(CCNc2cnc3ccc(-c4c[nH]nc4-c4cc(Cl)ccc4F)nc3c2)CC1] | 6-[3-(5-chloro-2-fluoro-phenyl)-1H-pyrazol-4-yl]-4-yl]-N-[2-(4-isopropylpiperazin-1-yl)ethyl]-1,5-naphthyridin-3-amine | 494.2 |

TABLE 1-continued

| No. | Structure | Chemical Name | [M + H]+ |
|---|---|---|---|
| 1-3 | 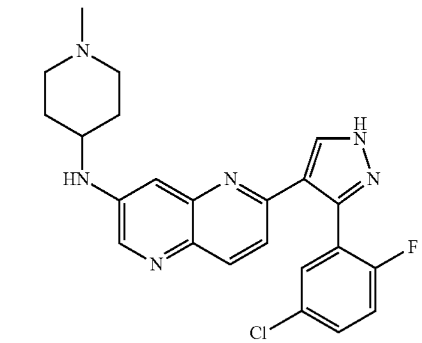 [SMILES: CN1CCC(Nc2cnc3ccc(-c4c[nH]nc4-c4cc(Cl)ccc4F)nc3c2)CC1] | 6-[3-(5-chloro-2-fluoro-phenyl)-1H-pyrazol-4-yl]-N-(1-methyl-4-piperidyl)-1,5-naphthyridine-3-amine | 437.2 |
| 1-4 | 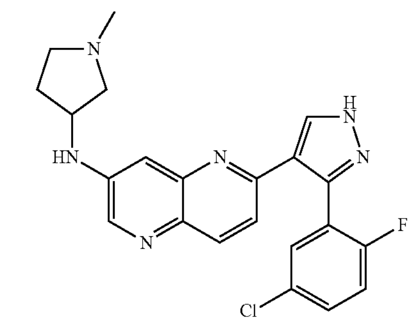 [SMILES: CN1CCC(Nc2cnc3ccc(-c4c[nH]nc4-c4cc(Cl)ccc4F)nc3c2)C1] | 6-[3-(5-chloro-2-fluoro-phenyl)-1H-pyrazol-4-yl]-N-(1-methylpyrrolidin-3-yl)-1,5-naphthyridin-3-amine | 423.1 |
| 1-5 | 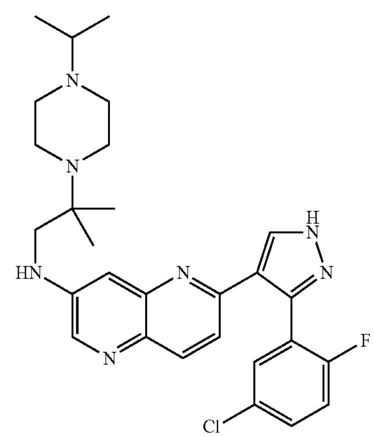 [SMILES: CC(C)N1CCN(C(C)(C)CNc2cnc3ccc(-c4c[nH]nc4-c4cc(Cl)ccc4F)nc3c2)CC1] | 6-[3-(5-chloro-2-fluoro-phenyl)-1H-pyrazol-4-yl]-N-[2-(4-isopropylpiperazin-1-yl)-2-methyl-propyl]-1,5-naphthyridin-3-amine | 522.1 |
| 1-6 | 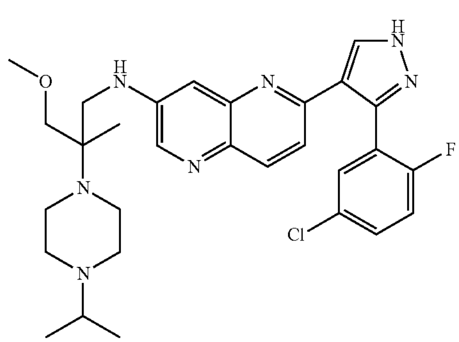 [SMILES: COCC(C)(CNc1cnc2ccc(-c3c[nH]nc3-c3cc(Cl)ccc3F)nc2c1)N1CCN(C(C)C)CC1] | 6-[3-(5-chloro-2-fluoro-phenyl)-1H-pyrazol-4-yl]-N-[2-(4-isopropylpiperazin-1-yl)-3-methoxy-2-methyl-propyl]-1,5-naphthyridin-3-amine | 552.3 |

TABLE 1-continued

| No. | Structure | Chemical Name | [M + H]+ |
|---|---|---|---|
| 1-7 | 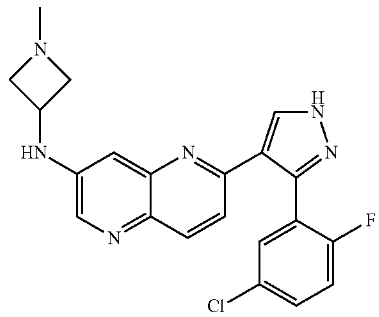 [SMILES: CN1CC(Nc2cnc3ccc(-c4c[nH]nc4-c4cc(Cl)ccc4F)nc3c2)C1] | 6-[3-(5-chloro-2-fluoro-phenyl)-1H-pyrazol-4-yl]-N-(1-methylazetidin-3-yl)-1,5-naphthyridin-3-amine | 409.1 |
| 1-8 | 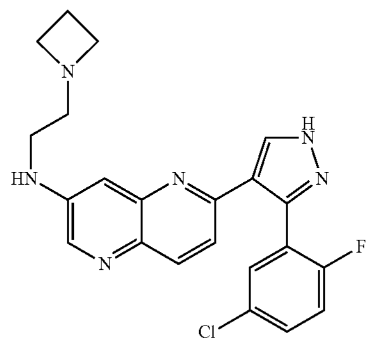 [SMILES: Fc1ccc(Cl)cc1-c1n[nH]cc1-c1ccc2ncc(NCCN3CCC3)cc2n1] | N-[2-(azetidin-1-yl)ethyl]-6-[3-(5-chloro-2-fluoro-phenyl)-1H-pyrazol-4-yl]-1,5-naphthyridin-3-amine | 423.1 |
| 1-9 | 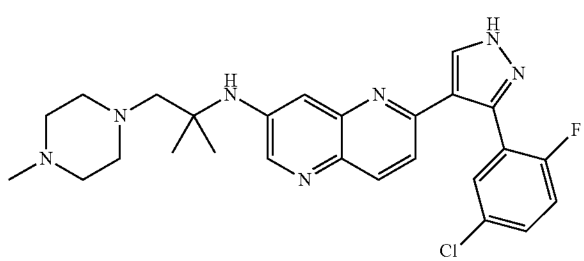 [SMILES: CN1CCN(CC(C)(C)Nc2cnc3ccc(-c4c[nH]nc4-c4cc(Cl)ccc4F)nc3c2)CC1] | 6-[3-(5-chloro-2-fluoro-phenyl)-1H-pyrazol-4-yl]-N-[1,1-dimethyl-2-(4-methylpiperazin-1-yl)ethyl]-1,5-naphthyridin-3-amine | 494.1 |
| 1-10 | 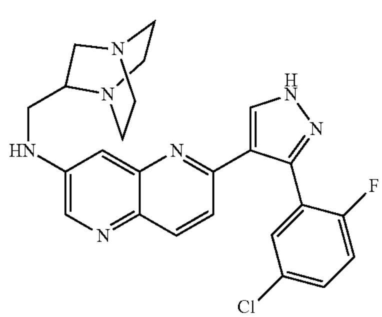 [SMILES: Fc1ccc(Cl)cc1-c1n[nH]cc1-c1ccc2ncc(NCC3CN4CCN3CC4)cc2n1] | 6-[3-(5-chloro-2-fluoro-phenyl)-1H-pyrazol-4-yl]-N-(1,4-diazabicyclo[2.2.2]octan-2-ylmethyl)-1,5-naphthyridin-3-amine | 464.1 |

TABLE 1-continued

| No. | Structure | Chemical Name | [M + H]+ |
|---|---|---|---|
| 1-11 | 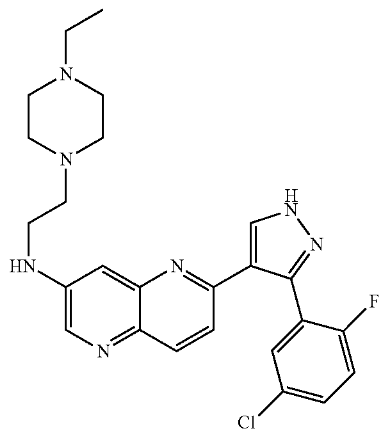 [SMILES: CCN1CCN(CCNc2cnc3ccc(-c4c[nH]nc4-c4cc(Cl)ccc4F)nc3c2)CC1] | 6-[3-(5-chloro-2-fluoro-phenyl)-1H-pyrazol-4-yl]-N-[2-(4-ethylpiperazin-1-yl)ethyl]-1,5-naphthyridin-3-amine | 480.2 |
| 1-12 | 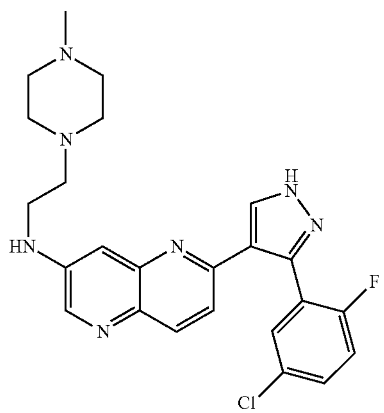 [SMILES: CN1CCN(CCNc2cnc3ccc(-c4c[nH]nc4-c4cc(Cl)ccc4F)nc3c2)CC1] | 6-[3-(5-chloro-2-fluoro-phenyl)-1H-pyrazol-4-yl]-N-[2-(4-methylpiperazin-1-yl)ethyl]-1,5-naphthyridin-3-amine | 466.2 |
| 1-13 | 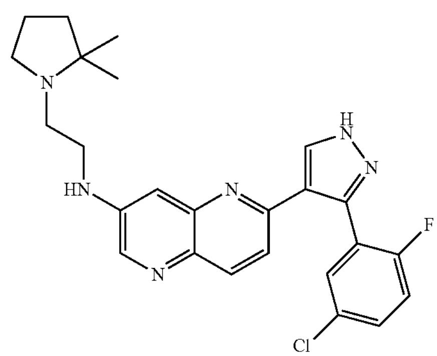 [SMILES: CC1(C)CCCN1CCNc1cnc2ccc(-c3c[nH]nc3-c3cc(Cl)ccc3F)nc2c1] | 6-[3-(5-chloro-2-fluoro-phenyl)-1H-pyrazol-4-yl]-N-[2-(2,2-dimethylpyrrolidin-1-yl)ethyl]-1,5-naphthyridin-3-amine | 465.1 |
| 1-14 | 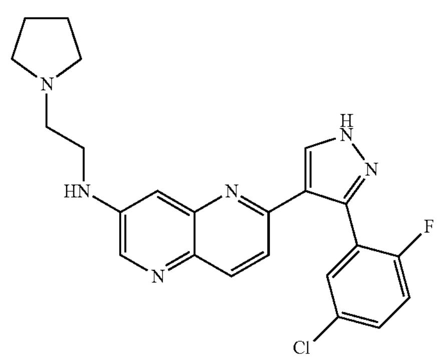 [SMILES: Fc1ccc(Cl)cc1-c1n[nH]cc1-c1ccc2ncc(NCCN3CCCC3)cc2n1] | 6-[3-(5-chloro-2-fluoro-phenyl)-1H-pyrazol-4-yl]-N-(2-pyrrolidin-1-ylethyl)-1,5-naphthyridin-3-amine | 437.1 |

TABLE 1-continued
| No. | Structure | Chemical Name | [M + H]+ |
|---|---|---|---|
| 1-15 | 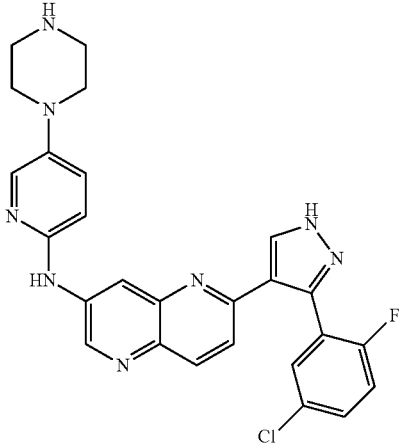 [SMILES: Fc1ccc(Cl)cc1-c1n[nH]cc1-c1ccc2ncc(Nc3ccc(N4CCNCC4)cn3)cc2n1] | 6-[3-(5-chloro-2-fluoro-phenyl)-1H-pyrazol-4-yl]-N-(5-piperazin-1-yl-2-pyridyl)-1,5-naphthyridin-3-amine | 501.1 |
| 1-16 | 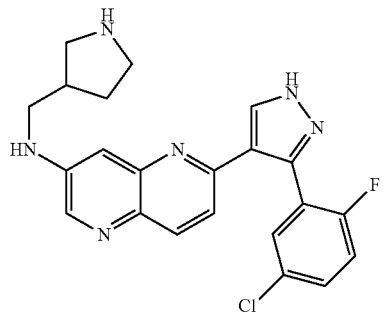 [SMILES: Fc1ccc(Cl)cc1-c1n[nH]cc1-c1ccc2ncc(NCC3CCNC3)cc2n1] | 6-[3-(5-chloro-2-fluoro-phenyl)-1H-pyrazol-4-yl]-N-(pyrrolidin-3-ylmethyl)-1,5-naphthyridin-3-amine | 423.1 |
| 1-17 | 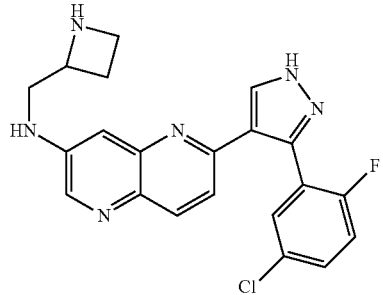 [SMILES: Fc1ccc(Cl)cc1-c1n[nH]cc1-c1ccc2ncc(NCC3CCN3)cc2n1] | N-(azetidin-2-ylmethyl)-6-[3-(5-chloro-2-fluoro-phenyl)-1H-pyrazol-4-yl]-1,5-naphthyridin-3-amine | 409.1 |
| 1-18 | 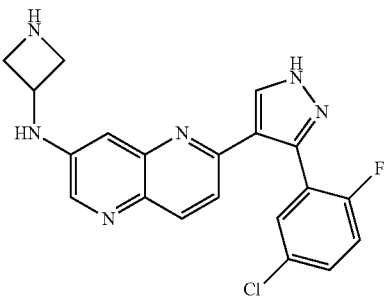 [SMILES: Fc1ccc(Cl)cc1-c1n[nH]cc1-c1ccc2ncc(NC3CNC3)cc2n1] | N-(azetidin-3-yl)-6-[3-(5-chloro-2-fluoro-phenyl)-1H-pyrazol-4-yl]-1,5-naphthyridin-3-amine | 395.1 |

TABLE 1-continued

| No. | Structure | Chemical Name | [M + H]+ |
|---|---|---|---|
| 1-19 | 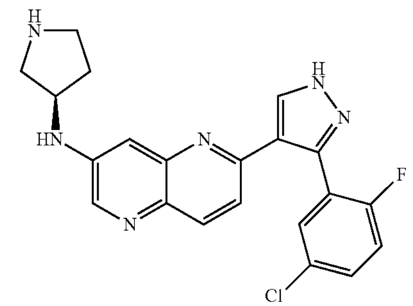 [SMILES: Fc1ccc(Cl)cc1-c1n[nH]cc1-c1ccc2ncc(N[C@@H]3CCNC3)cc2n1] | 6-[3-(5-chloro-2-fluoro-phenyl)-1H-pyrazol-4-yl]-N-[(3R)-pyrrolidin-3-yl]-1,5-naphthyridin-3-amine | 409.1 |
| 1-20 | 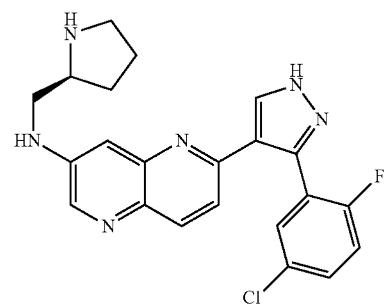 [SMILES: Fc1ccc(Cl)cc1-c1n[nH]cc1-c1ccc2ncc(NC[C@@H]3CCCN3)cc2n1] | 6-[3-(5-chloro-2-fluoro-phenyl)-1H-pyrazol-4-yl]-N-[[(2S)-pyrrolidin-2-yl]methyl]-1,5-naphthyridin-3-amine | 423.1 |
| 1-21 | 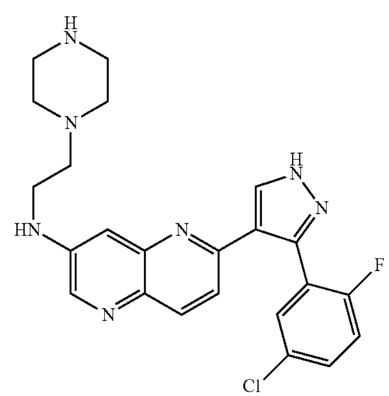 [SMILES: Fc1ccc(Cl)cc1-c1n[nH]cc1-c1ccc2ncc(NCCN3CCNCC3)cc2n1] | 6-[3-(5-chloro-2-fluoro-phenyl)-1H-pyrazol-4-yl]-N-(2-piperazin-1-ylethyl)-1,5-naphthyridin-3-amine | 452.1 |
| 1-22 | 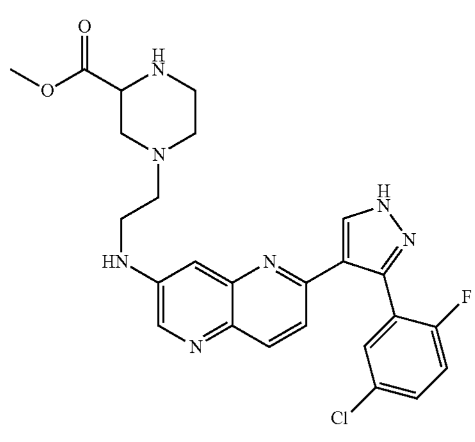 [SMILES: COC(=O)C1CN(CCNc2cnc3ccc(-c4c[nH]nc4-c4cc(Cl)ccc4F)nc3c2)CCN1] | methyl 4-[2-[[6-[3-(5-chloro-2-fluoro-phenyl)-1H-pyrazol-4-yl]-1,5-naphthyridin-3-yl]amino]ethyl]piperazine-2-carboxylate | 510.0 |

TABLE 1-continued

| No. | Structure | Chemical Name | [M + H]+ |
|---|---|---|---|
| 1-23 | 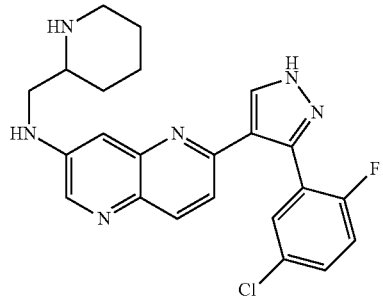 [SMILES: Fc1ccc(Cl)cc1-c1n[nH]cc1-c1ccc2ncc(NCC3CCCCN3)cc2n1] | 6-[3-(5-chloro-2-fluoro-phenyl)-1H-pyrazol-4-yl]-N-(2-piperidylmethyl)-1,5-naphthyridin-3-amine | 437.1 |
| 1-24 | 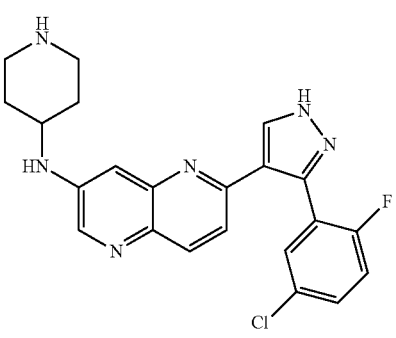 [SMILES: Fc1ccc(Cl)cc1-c1n[nH]cc1-c1ccc2ncc(NC3CCNCC3)cc2n1] | 6-[3-(5-chloro-2-fluoro-phenyl)-1H-pyrazol-4-yl]-N-(4-piperidyl)-1,5-naphthyridin-3-amine | 423.1 |
| 1-25 | 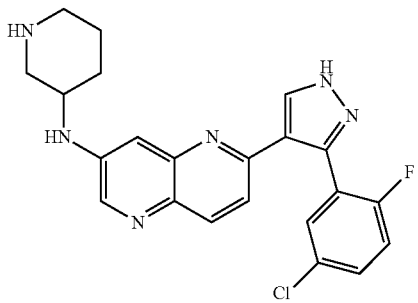 [SMILES: Fc1ccc(Cl)cc1-c1n[nH]cc1-c1ccc2ncc(NC3CCCNC3)cc2n1] | 6-[3-(5-chloro-2-fluoro-phenyl)-1H-pyrazol-4-yl]-N-(3-piperidyl)-1,5-naphthyridin-3-amine | 423.1 |
| 1-26 | 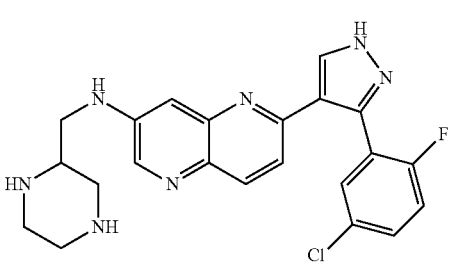 [SMILES: Fc1ccc(Cl)cc1-c1n[nH]cc1-c1ccc2ncc(NCC3CNCCN3)cc2n1] | 6-[3-(5-chloro-2-fluoro-phenyl)-1H-pyrazol-4-yl]-N-(piperazin-2-ylmethyl)-1,5-naphthyridin-3-amine | 438.1 |
| 1-27 | 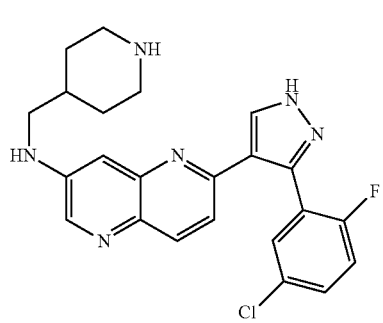 [SMILES: Fc1ccc(Cl)cc1-c1n[nH]cc1-c1ccc2ncc(NCC3CCNCC3)cc2n1] | 6-[3-(5-chloro-2-fluoro-phenyl)-1H-pyrazol-4-yl]-N-(4-piperidylmethyl)-1,5-naphthyridin-3-amine | 437.1 |

TABLE 1-continued

| No. | Structure | Chemical Name | [M + H]⁺ |
|---|---|---|---|
| 1-28 | 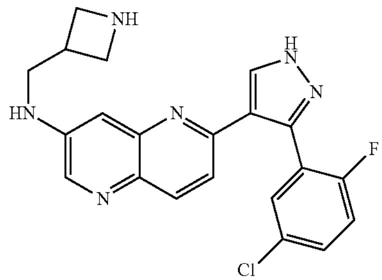 [SMILES: Fc1ccc(Cl)cc1-c1n[nH]cc1-c1ccc2ncc(NCC3CNC3)cc2n1] | N-(azetidin-3-ylmethyl)-6-[3-(5-chloro-2-fluoro-phenyl)-1H-pyrazol-4-yl]-1,5-naphthyridin-3-amine | 409.1 |
| 1-29 | 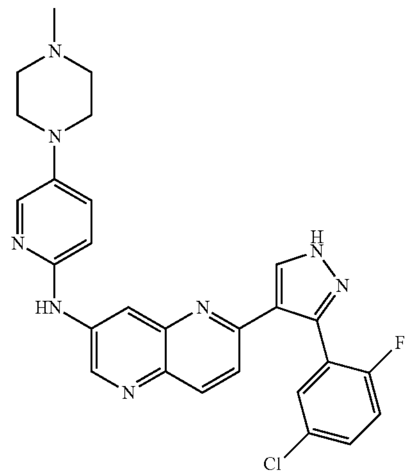 [SMILES: CN1CCN(c2ccc(Nc3cnc4ccc(-c5c[nH]nc5-c5cc(Cl)ccc5F)nc4c3)nc2)CC1] | 6-[3-(5-chloro-2-fluoro-phenyl)-1H-pyrazol-4-yl]-N-[5-(4-methylpiperazin-1-yl)-2-pyridyl]-1,5-naphthyridin-3-amine | 515.0 |
| 1-30 | 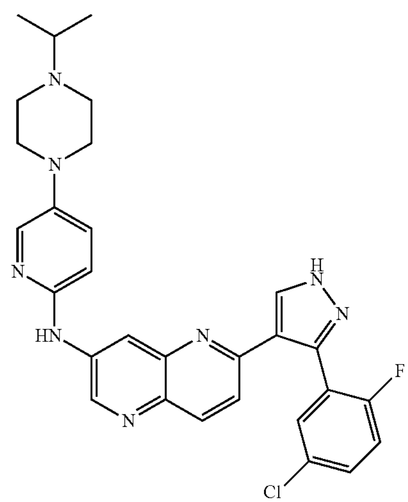 [SMILES: CC(C)N1CCN(c2ccc(Nc3cnc4ccc(-c5c[nH]nc5-c5cc(Cl)ccc5F)nc4c3)nc2)CC1] | 6-[3-(5-chloro-2-fluoro-phenyl)-1H-pyrazol-4-yl]-N-[5-(4-isopropylpiperazin-1-yl)-2-pyridyl]-1,5-naphthyridin-3-amine | 543.1 |
| 1-31 | 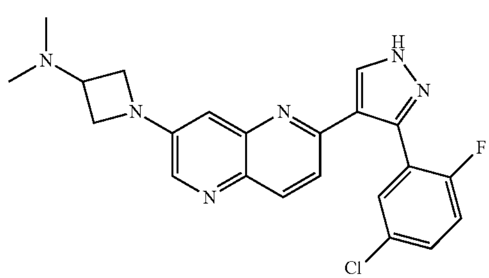 [SMILES: CN(C)C1CN(c2cnc3ccc(-c4c[nH]nc4-c4cc(Cl)ccc4F)nc3c2)C1] | 1-[6-[3-(5-chloro-2-fluoro-phenyl)-1H-pyrazol-4-yl]-1,5-naphthyridin-3-yl]-N,N-dimethyl-azetidin-3-amine | 423.1 |

TABLE 1-continued

| No. | Structure | Chemical Name | [M + H]⁺ |
|---|---|---|---|
| 1-32 | 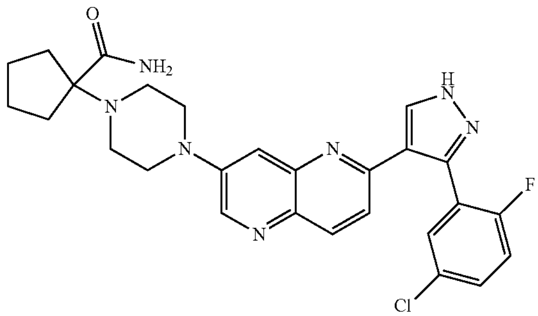 [SMILES: NC(=O)C1(N2CCN(c3cnc4ccc(-c5c[nH]nc5-c5cc(Cl)ccc5F)nc4c3)CC2)CCCC1] | 1-[4-[6-[3-(5-chloro-2-fluoro-phenyl)-1H-pyrazol-4-yl]-1,5-naphthyridin-3-yl]piperazin-1-yl]cyclopentanecarboxamide | 520.2 |
| 1-33 | 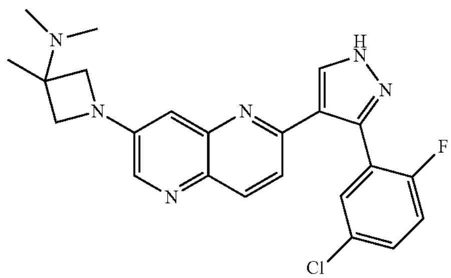 [SMILES: CN(C)C1(C)CN(c2cnc3ccc(-c4c[nH]nc4-c4cc(Cl)ccc4F)nc3c2)C1] | 1-[6-[3-(5-chloro-2-fluoro-phenyl)-1H-pyrazol-4-yl]-1,5-naphthyridin-3-yl]-N,N,3-trimethyl-azetidin-3-amine | 437.1 |
| 1-34 | AND Enantiomer | rac-(3S)-1-[6-[3-(5-chloro-2-fluoro-phenyl)-1H-pyrazol-4-yl]-1,5-naphthyridin-3-yl]-N,N-dimethyl-pyrrolidin-3-amine | 437.0 |
| 1-35 | 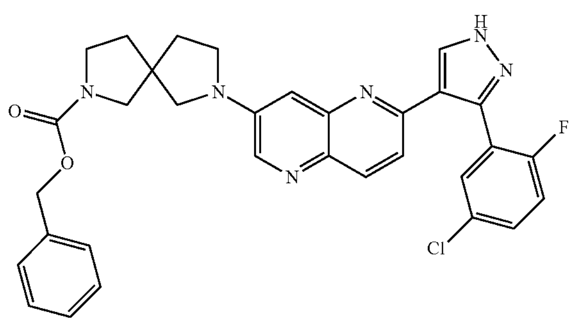 [SMILES: O=C(OCc1ccccc1)N1CCC2(CCN(c3cnc4ccc(-c5c[nH]nc5-c5cc(Cl)ccc5F)nc4c3)C2)C1] | benzyl 7-[6-[3-(5-chloro-2-fluoro-phenyl)-1H-pyrazol-4-yl]-1,5-naphthyridin-3-yl]-2,7-diazaspiro[4.4]nonane-2-carboxylate | 583.1 |
| 1-36 | 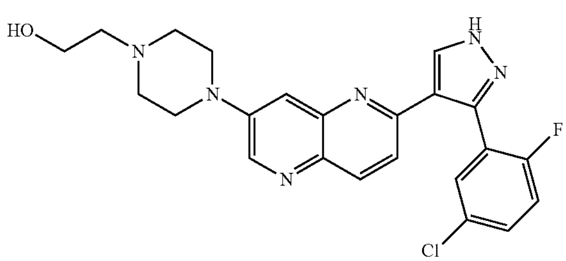 [SMILES: OCCN1CCN(c2cnc3ccc(-c4c[nH]nc4-c4cc(Cl)ccc4F)nc3c2)CC1] | 2-[4-[6-[3-(5-chloro-2-fluoro-phenyl)-1H-pyrazol-4-yl]-1,5-naphthyridin-3-yl]piperazin-1-yl]ethanol | 453.0 |

TABLE 1-continued

| No. | Structure | Chemical Name | [M + H]+ |
|---|---|---|---|
| 1-37 | 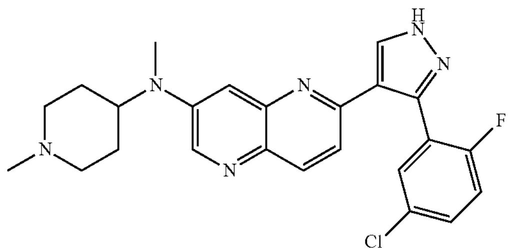 [SMILES: CN1CCC(N(C)c2cnc3ccc(-c4c[nH]nc4-c4cc(Cl)ccc4F)nc3c2)CC1] | 6-[3-(5-chloro-2-fluoro-phenyl)-1H-pyrazol-4-yl]-N-methyl-N-(1-methyl-4-piperidyl)-1,5-naphthyridin-3-amine | 451.1 |
| 1-38 | 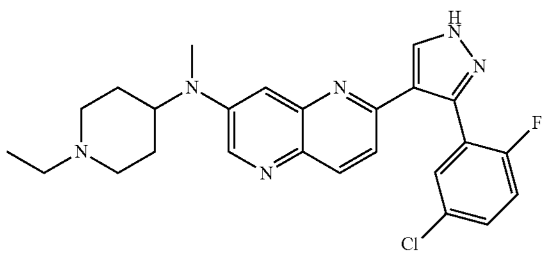 [SMILES: CCN1CCC(N(C)c2cnc3ccc(-c4c[nH]nc4-c4cc(Cl)ccc4F)nc3c2)CC1] | 6-[3-(5-chloro-2-fluoro-phenyl)-1H-pyrazol-4-yl]-N-(1-ethyl-4-piperidyl)-N-methyl-1,5-naphthyridin-3-amine | 465.1 |
| 1-39 | AND Enantiomer | 2-[3-(5-chloro-2-fluoro-phenyl)-1H-pyrazol-4-yl]-7-[rac-(3R)-3-(1-piperidyl)pyrrolidin-1-yl]-1,5-naphthyridine | 477.1 |
| 1-40 | 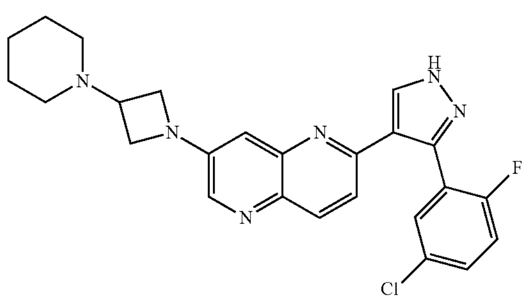 [SMILES: Fc1ccc(Cl)cc1-c1n[nH]cc1-c1ccc2ncc(N3CC(N4CCCCC4)C3)cc2n1] | 2-[3-(5-chloro-2-fluoro-phenyl)-1H-pyrazol-4-yl]-7-[3-(1-piperidyl)azetidin-1-yl]-1,5-naphthyridine | 463.2 |
| 1-41 | 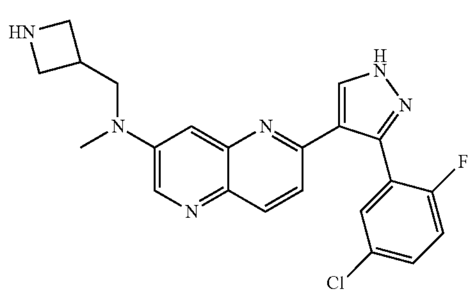 [SMILES: CN(CC1CNC1)c1cnc2ccc(-c3c[nH]nc3-c3cc(Cl)ccc3F)nc2c1] | N-(azetidin-3-ylmethyl)-6-[3-(5-chloro-2-fluoro-phenyl)-1H-pyrazol-4-yl]-N-methyl-1,5-naphthyridin-3-amine | 423.1 |

TABLE 1-continued

| No. | Structure | Chemical Name | [M + H]⁺ |
|---|---|---|---|
| 1-42 | AND Enantiomer | 2-[3-(5-chloro-2-fluoro-phenyl)-1H-pyrazol-4-yl]-7-[rac-(1R,4R)-5-methyl-2,5-diazabicyclo[2.2.1]heptan-2-yl]-1,5-naphthyridine | 435.1 |
| 1-43 | 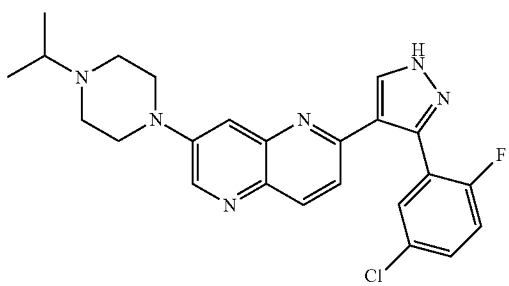 [SMILES: CC(C)N1CCN(c2cnc3ccc(-c4c[nH]nc4-c4cc(Cl)ccc4F)nc3c2)CC1] | 2-[3-(5-chloro-2-fluoro-phenyl)-1H-pyrazol-4-yl]-7-(4-isopropylpiperazin-1-yl)-1,5-naphthyridine | 451.1 |
| 1-44 | 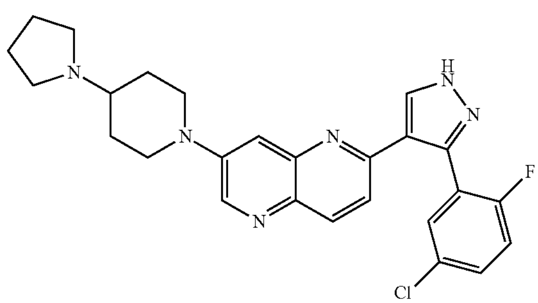 [SMILES: Fc1ccc(Cl)cc1-c1n[nH]cc1-c1ccc2ncc(N3CCC(N4CCCC4)CC3)cc2n1] | 2-[3-(5-chloro-2-fluoro-phenyl)-1H-pyrazol-4-yl]-7-(4-pyrrolidin-1-yl-1-piperidyl)-1,5-naphthyridine | 477.2 |
| 1-45 | 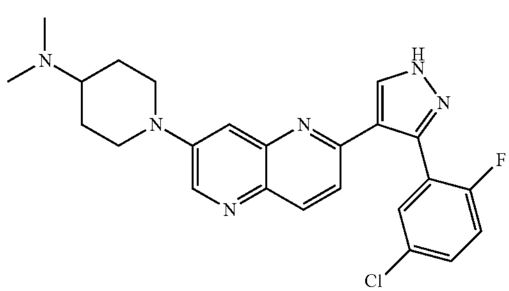 [SMILES: CN(C)C1CCN(c2cnc3ccc(-c4c[nH]nc4-c4cc(Cl)ccc4F)nc3c2)CC1] | 1-[6-[3-(5-chloro-2-fluoro-phenyl)-1H-pyrazol-4-yl]-1,5-naphthyridin-3-yl]-N,N-dimethyl-piperidin-4-amine | 451.2 |

TABLE 1-continued

| No. | Structure | Chemical Name | [M + H]+ |
|---|---|---|---|
| 1-46 | 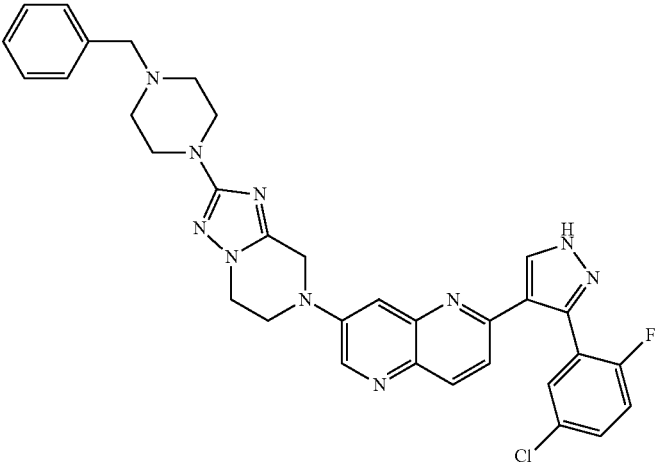 [SMILES: Fc1ccc(Cl)cc1-c1n[nH]cc1-c1ccc2ncc(N3CCn4nc(N5CCN(Cc6ccccc6)CC5)nc4C3)cc2n1] | 7-[2-(4-benzylpiperazin-1-yl)-6,8-dihydro-5H-[1,2,4]triazolo[1,5-a]pyrazin-7-yl]-2-[3-(5-chloro-2-fluoro-phenyl)-1H-pyrazol-4-yl]-1,5-naphthyridine | 621.2 |
| 1-47 | 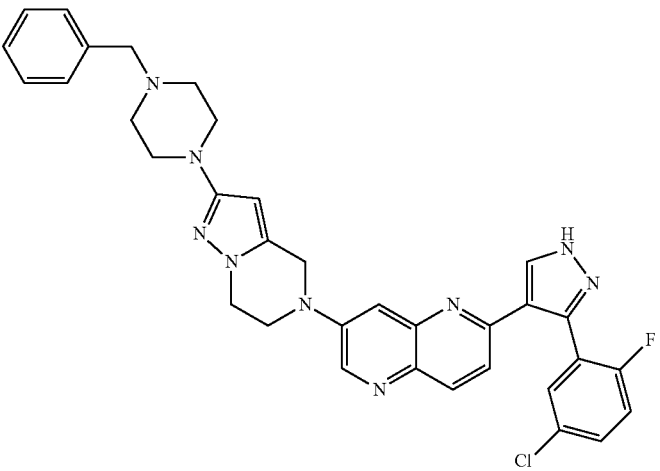 [SMILES: Fc1ccc(Cl)cc1-c1n[nH]cc1-c1ccc2ncc(N3CCn4nc(N5CCN(Cc6ccccc6)CC5)cc4C3)cc2n1] | 7-[2-(4-benzylpiperazin-1-yl)-6,7-dihydro-4H-pyrazolo[1,5-a]pyrazin-5-yl]-2-[3-(5-chloro-2-fluoro-phenyl)-1H-pyrazol-4-yl]-1,5-naphthyridine | 620.1 |
| 1-48 | 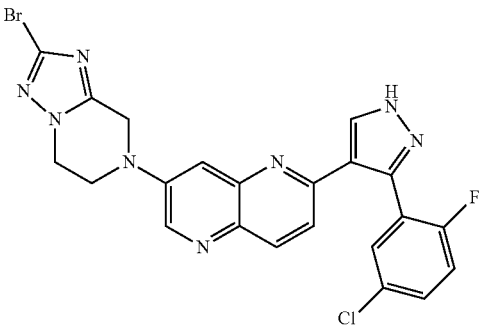 [SMILES: Fc1ccc(Cl)cc1-c1n[nH]cc1-c1ccc2ncc(N3CCn4nc(Br)nc4C3)cc2n1] | 7-(2-bromo-6,8-dihydro-5H-[1,2,4]triazolo[1,5-a]pyrazin-7-yl)-2-[3-(5-chloro-2-fluoro-phenyl)-1H-pyrazol-4-yl]-1,5-naphthyridine | 524.9 |
| 1-49 | 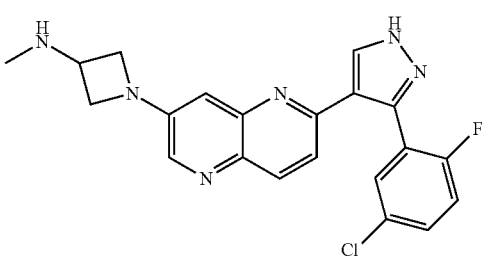 [SMILES: CNC1CN(c2cnc3ccc(-c4c[nH]nc4-c4cc(Cl)ccc4F)nc3c2)C1] | 1-[6-[3-(5-chloro-2-fluoro-phenyl)-1H-pyrazol-4-yl]-1,5-naphthyridin-3-yl]-N-methyl-azetidin-3-amine | 409.1 |

TABLE 1-continued

| No. | Structure | Chemical Name | [M + H]+ |
|---|---|---|---|
| 1-50 | AND Enantiomer | rac-(2S)-4-[6-[3-(5-chloro-2-fluoro-phenyl)-1H-pyrazol-4-yl]-1,5-naphthyridin-3-yl]piperazine-2-carboxamide | 452.1 |
| 1-51 | AND Enantiomer | rac-(2R)-4-[6-[3-(5-chloro-2-fluoro-phenyl)-1H-pyrazol-4-yl]-1,5-naphthyridin-3-yl]-N-methyl-piperazine-2-carboxamide | 466.1 |
| 1-52 | 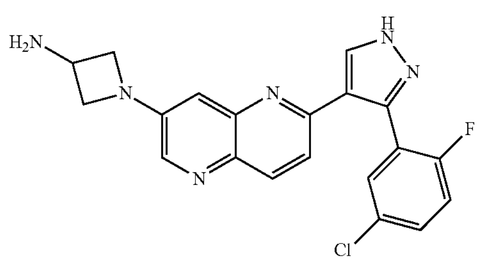 [SMILES: NC1CN(c2cnc3ccc(-c4c[nH]nc4-c4cc(Cl)ccc4F)nc3c2)C1] | 1-[6-[3-(5-chloro-2-fluoro-phenyl)-1H-pyrazol-4-yl]-1,5-naphthyridin-3-yl]azetidin-3-amine | 395.1 |
| 1-53 | 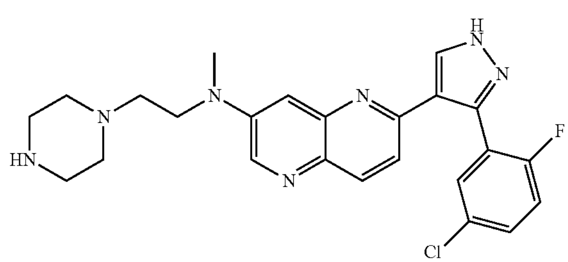 [SMILES: CN(CCN1CCNCC1)c1cnc2ccc(-c3c[nH]nc3-c3cc(Cl)ccc3F)nc2c1] | 6-[3-(5-chloro-2-fluoro-phenyl)-1H-pyrazol-4-yl]-N-methyl-N-(2-piperazin-1-ylethyl)-1,5-naphthyridin-3-amine | 466.0 |
| 1-54 | 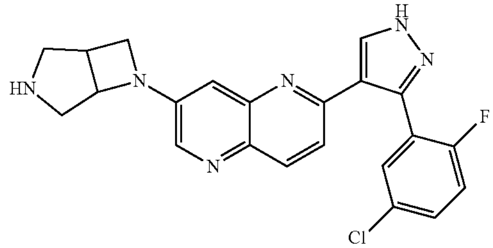 [SMILES: Fc1ccc(Cl)cc1-c1n[nH]cc1-c1ccc2ncc(N3CC4CNCC43)cc2n1] | 2-[3-(5-chloro-2-fluoro-phenyl)-1H-pyrazol-4-yl]-7-(3,6-diazabicyclo[3.2.0]heptan-6-yl)-1,5-naphthyridine | 421.1 |

TABLE 1-continued

| No. | Structure | Chemical Name | [M + H]+ |
|---|---|---|---|
| 1-55 | 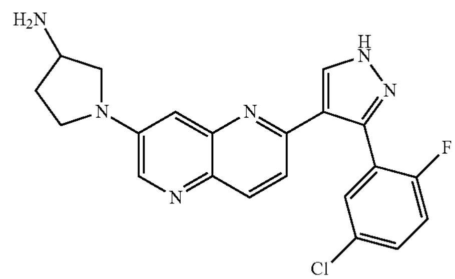 [SMILES: NC1CCN(c2cnc3ccc(-c4c[nH]nc4-c4cc(Cl)ccc4F)nc3c2)C1] | 1-[6-[3-(5-chloro-2-fluoro-phenyl)-1H-pyrazol-4-yl]-1,5-naphthyridin-3-yl]pyrrolidin-3-amine | 409.1 |
| 1-56 | 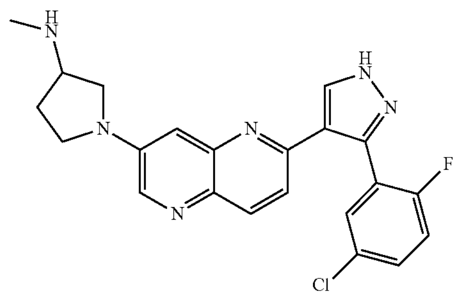 [SMILES: CNC1CCN(c2cnc3ccc(-c4c[nH]nc4-c4cc(Cl)ccc4F)nc3c2)C1] | 1-[6-[3-(5-chloro-2-fluoro-phenyl)-1H-pyrazol-4-yl]-1,5-naphthyridin-3-yl]-N-methyl-pyrrolidin-3-amine | 423.1 |
| 1-57 | 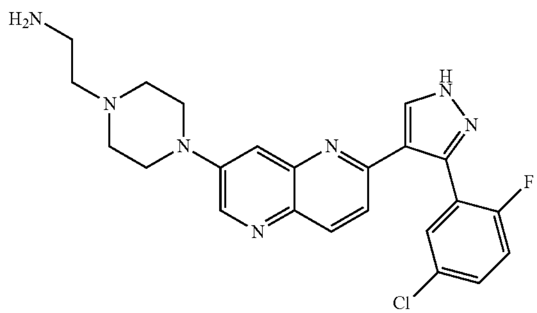 [SMILES: NCCN1CCN(c2cnc3ccc(-c4c[nH]nc4-c4cc(Cl)ccc4F)nc3c2)CC1] | 2-[4-[6-[3-(5-chloro-2-fluoro-phenyl)-1H-pyrazol-4-yl]-1,5-naphthyridin-3-yl]piperazin-1-yl]ethanamine | 452.1 |
| 1-58 | 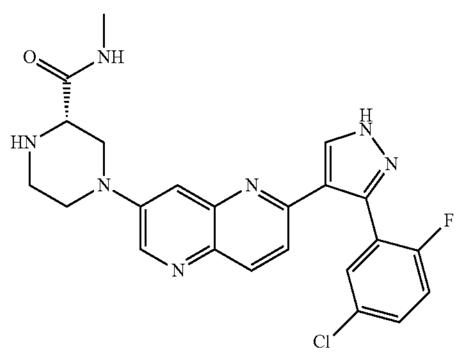 [SMILES: CNC(=O)[C@@H]1CN(c2cnc3ccc(-c4c[nH]nc4-c4cc(Cl)ccc4F)nc3c2)CCN1] | (2S)-4-[6-[3-(5-chloro-2-fluoro-phenyl)-1H-pyrazol-4-yl]-1,5-naphthyridin-3-yl]-N-methyl-piperazine-2-carboxamide | 466.1 |
| 1-59 | 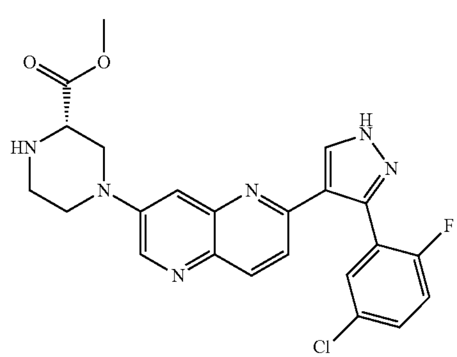 [SMILES: COC(=O)[C@@H]1CN(c2cnc3ccc(-c4c[nH]nc4-c4cc(Cl)ccc4F)nc3c2)CCN1] | methyl (2S)-4-[6-[3-(5-chloro-2-fluoro-phenyl)-1H-pyrazol-4-yl]-1,5-naphthyridin-3-yl]piperazine-2-carboxylate | 467.1 |

TABLE 1-continued

| No. | Structure | Chemical Name | [M + H]+ |
|---|---|---|---|
| 1-60 | 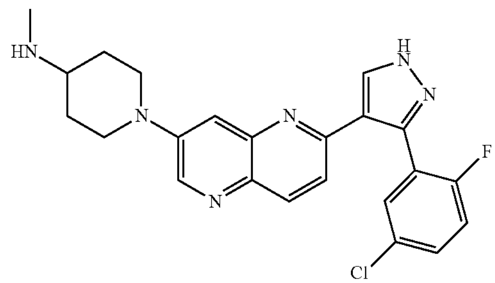 [SMILES: CNC1CCN(c2cnc3ccc(-c4c[nH]nc4-c4cc(Cl)ccc4F)nc3c2)CC1] | 1-[6-[3-(5-chloro-2-fluoro-phenyl)-1H-pyrazol-4-yl]-1,5-naphthyridin-3-yl]-N-methyl-piperidin-4-amine | 437.1 |
| 1-61 | 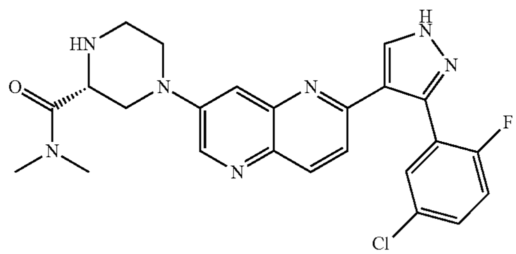 [SMILES: CN(C)C(=O)[C@H]1CN(c2cnc3ccc(-c4c[nH]nc4-c4cc(Cl)ccc4F)nc3c2)CCN1] | (2R)-4-[6-[3-(5-chloro-2-fluoro-phenyl)-1H-pyrazol-4-yl]-1,5-naphthyridin-3-yl]-N,N-dimethyl-piperazine-2-carboxamide | 480.0 |
| 1-62 | 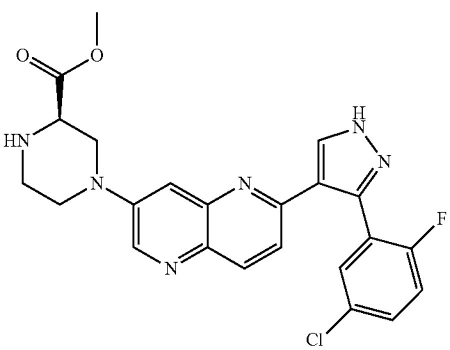 [SMILES: COC(=O)[C@H]1CN(c2cnc3ccc(-c4c[nH]nc4-c4cc(Cl)ccc4F)nc3c2)CCN1] | methyl (2R)-4-[6-[3-(5-chloro-2-fluoro-phenyl)-1H-pyrazol-4-yl]-1,5-naphthyridin-3-yl]piperazine-2-carboxylate | 467.0 |
| 1-63 | 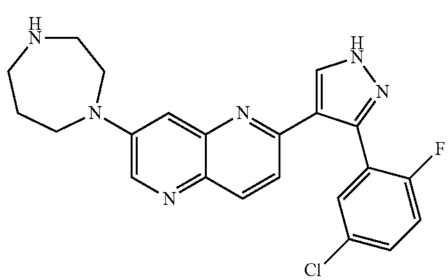 [SMILES: Fc1ccc(Cl)cc1-c1n[nH]cc1-c1ccc2ncc(N3CCCNCC3)cc2n1] | 2-[3-(5-chloro-2-fluoro-phenyl)-1H-pyrazol-4-yl]-7-(1,4-diazepan-1-yl)-1,5-naphthyridine | 423.1 |
| 1-64 | 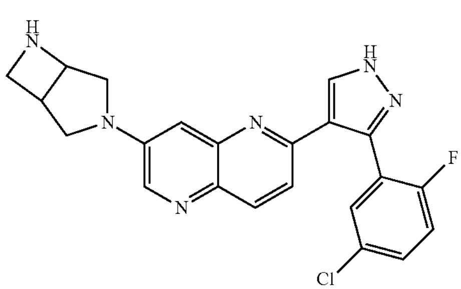 [SMILES: Fc1ccc(Cl)cc1-c1n[nH]cc1-c1ccc2ncc(N3CC4CNC4C3)cc2n1] | 2-[3-(5-chloro-2-fluoro-phenyl)-1H-pyrazol-4-yl]-7-(3,6-diazabicyclo[3.2.0]heptan-3-yl)-1,5-naphthyridine | 421.1 |

TABLE 1-continued

| No. | Structure | Chemical Name | [M + H]+ |
|---|---|---|---|
| 1-65 | 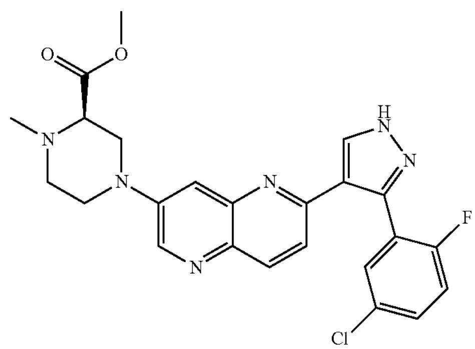 [SMILES: COC(=O)[C@H]1CN(c2cnc3ccc(-c4c[nH]nc4-c4cc(Cl)ccc4F)nc3c2)CCN1C] | methyl (2R)-4-[6-[3-(5-chloro-2-fluoro-phenyl)-1H-pyrazol-4-yl]-1,5-naphthyridin-3-yl]-1-methyl-piperazine-2-carboxylate | 481.1 |
| 1-66 | 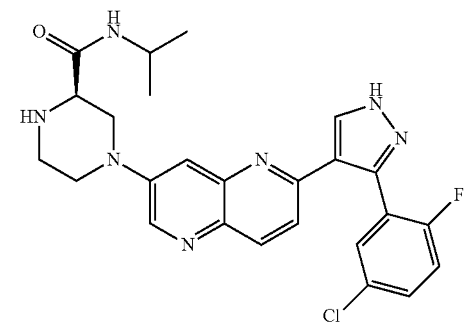 [SMILES: CC(C)NC(=O)[C@H]1CN(c2cnc3ccc(-c4c[nH]nc4-c4cc(Cl)ccc4F)nc3c2)CCN1] | (2R)-4-[6-[3-(5-chloro-2-fluoro-phenyl)-1H-pyrazol-4-yl]-1,5-naphthyridin-3-yl]-N-isopropyl-piperazine-2-carboxamide | 494.0 |
| 1-67 | 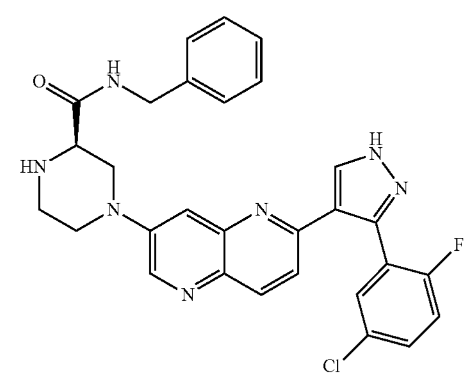 [SMILES: O=C(NCc1ccccc1)[C@H]1CN(c2cnc3ccc(-c4c[nH]nc4-c4cc(Cl)ccc4F)nc3c2)CCN1] | (2R)-N-benzyl-4-[6-[3-(5-chloro-2-fluoro-phenyl)-1H-pyrazol-4-yl]-1,5-naphthyridin-3-yl]piperazine-2-carboxamide | 542.0 |
| 1-68 | 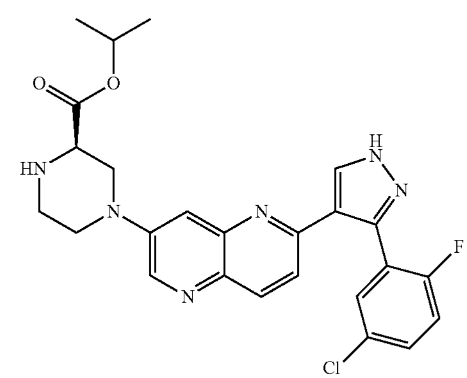 [SMILES: CC(C)OC(=O)[C@H]1CN(c2cnc3ccc(-c4c[nH]nc4-c4cc(Cl)ccc4F)nc3c2)CCN1] | isopropyl (2R)-4-[6-[3-(5-chloro-2-fluoro-phenyl)-1H-pyrazol-4-yl]-1,5-naphthyridin-3-yl]piperazine-2-carboxylate | 495.0 |

TABLE 1-continued

| No. | Structure | Chemical Name | [M + H]+ |
|---|---|---|---|
| 1-69 | 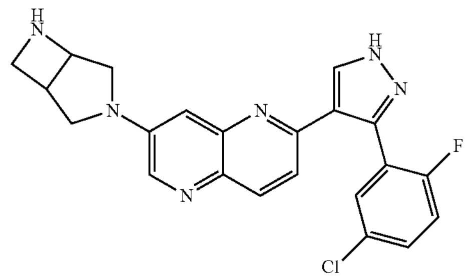 [SMILES: Fc1ccc(Cl)cc1-c1n[nH]cc1-c1ccc2ncc(N3CC4CNC4C3)cc2n1] | 2-[3-(5-chloro-2-fluoro-phenyl)-1H-pyrazol-4-yl]-7-(3,6-diazabicyclo[3.2.0]heptan-3-yl)-1,5-naphthyridine | 421.1 |
| 1-70 | 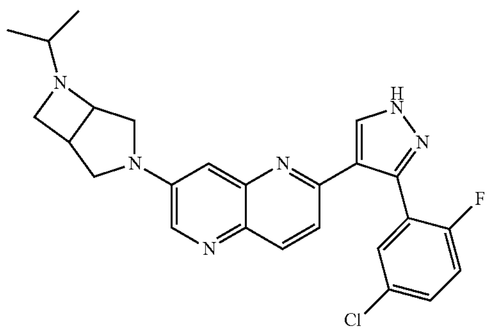 [SMILES: CC(C)N1CC2CN(c3cnc4ccc(-c5c[nH]nc5-c5cc(Cl)ccc5F)nc4c3)CC21] | 2-[3-(5-chloro-2-fluoro-phenyl)-1H-pyrazol-4-yl]-7-(6-isopropyl-3,6-diazabicyclo[3.2.0]heptan-3-yl)-1,5-naphthyridine | 463.1 |
| 1-71 | 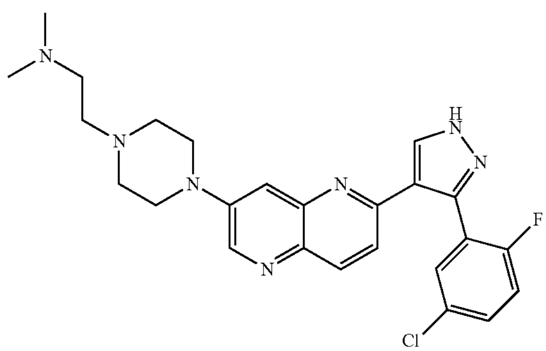 [SMILES: CN(C)CCN1CCN(c2cnc3ccc(-c4c[nH]nc4-c4cc(Cl)ccc4F)nc3c2)CC1] | 2-[4-[6-[3-(5-chloro-2-fluoro-phenyl)-1H-pyrazol-4-yl]-1,5-naphthyridin-3-yl]piperazin-1-yl]-N,N-dimethyl-ethanamine | 480.2 |
| 1-72 | 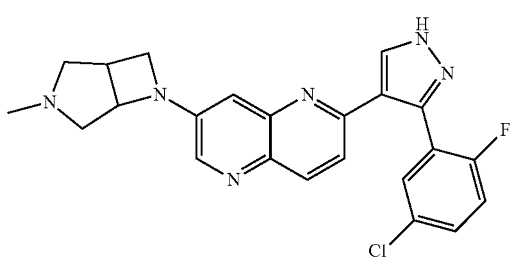 [SMILES: CN1CC2CN(c3cnc4ccc(-c5c[nH]nc5-c5cc(Cl)ccc5F)nc4c3)C2C1] | 2-[3-(5-chloro-2-fluoro-phenyl)-1H-pyrazol-4-yl]-7-(3-methyl-3,6-diazabicyclo[3.2.0]heptan-6-yl)-1,5-naphthyridine | 435.1 |
| 1-73 | 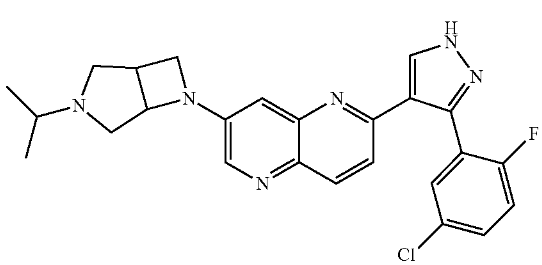 [SMILES: CC(C)N1CC2CN(c3cnc4ccc(-c5c[nH]nc5-c5cc(Cl)ccc5F)nc4c3)C2C1] | 2-[3-(5-chloro-2-fluoro-phenyl)-1H-pyrazol-4-yl]-7-(3-isopropyl-3,6-diazabicyclo[3.2.0]heptan-6-yl)-1,5-naphthyridine | 463.1 |

TABLE 1-continued

| No. | Structure | Chemical Name | [M + H]⁺ |
|---|---|---|---|
| 1-74 | 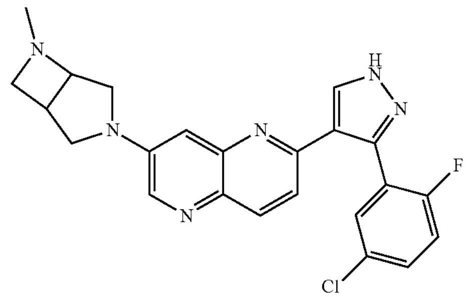 [SMILES: CN1CC2CN(c3cnc4ccc(-c5c[nH]nc5-c5cc(Cl)ccc5F)nc4c3)CC21] | 2-[3-(5-chloro-2-fluoro-phenyl)-1H-pyrazol-4-yl]-7-(6-methyl-3,6-diazabicyclo[3.2.0]heptan-3-yl)-1,5-naphthyridine | 435.1 |
| 1-75 | AND Enantiomer | 2-[3-(5-chloro-2-fluoro-phenyl)-1H-pyrazol-4-yl]-7-[rac-(2R,5R)-2,4,5-trimethylpiperazin-1-yl]-1,5-naphthyridine | 451.2 |
| 1-76 | 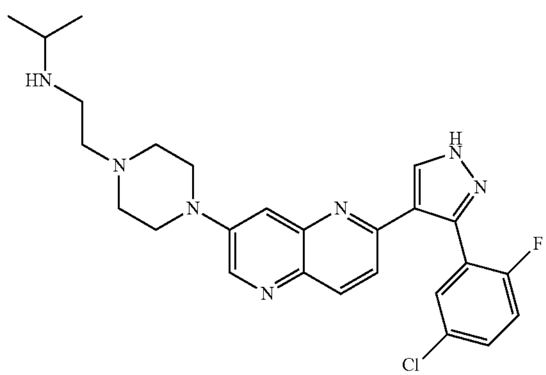 [SMILES: CC(C)NCCN1CCN(c2cnc3ccc(-c4c[nH]nc4-c4cc(Cl)ccc4F)nc3c2)CC1] | N-[2-[4-[6-[3-(5-chloro-2-fluoro-phenyl)-1H-pyrazol-4-yl]-1,5-naphthyridin-3-yl]piperazin-1-yl]ethyl]propan-2-amine | 494.2 |
| 1-77 | AND Enantiomer | rac-(2R)-4-[6-[3-(5-chloro-2-fluoro-phenyl)-1H-pyrazol-4-yl]-1,5-naphthyridin-3-yl]-N,1-dimethyl-piperazine-2-carboxamide | 480.1 |

TABLE 1-continued

| No. | Structure | Chemical Name | [M + H]⁺ |
|---|---|---|---|
| 1-78 | AND Enantiomer | rac-(2R)-4-[6-[3-(5-chloro-2-fluoro-phenyl)-1H-pyrazol-4-yl]-1,5-naphthyridin-3-yl]-1-isopropyl-N-methyl-piperazine-2-carboxamide | 508.2 |
| 1-79 | AND Enantiomer | 6-[3-(5-chloro-2-fluoro-phenyl)-1H-pyrazol-4-yl]-N-methyl-N-[rac-(3R)-1-methylpyrrolidin-3-yl]-1,5-naphthyridin-3-amine | 437.1 |
| 1-80 | AND Enantiomer | 2-[3-(5-chloro-2-fluoro-phenyl)-1H-pyrazol-4-yl]-7-[rac-(3R)-3-(methoxymethyl)-4-methyl-piperazin-1-yl]-1,5-naphthyridine | 467.1 |
| 1-81 | AND Enantiomer | rac-(2S)-4-[6-[3-(5-chloro-2-fluoro-phenyl)-1H-pyrazol-4-yl]-1,5-naphthyridin-3-yl]-N,1-dimethyl-piperazine-2-carboxamide | 480.1 |
| 1-82 | AND Enantiomer | 2-[3-(5-chloro-2-fluoro-phenyl)-1H-pyrazol-4-yl]-7-[rac-(3S)-4-isopropyl-3-methyl-1,4-diazepan-1-yl]-1,5-naphthyridine | 479.1 |

TABLE 1-continued

| No. | Structure | Chemical Name | [M + H]+ |
|---|---|---|---|
| 1-83 | 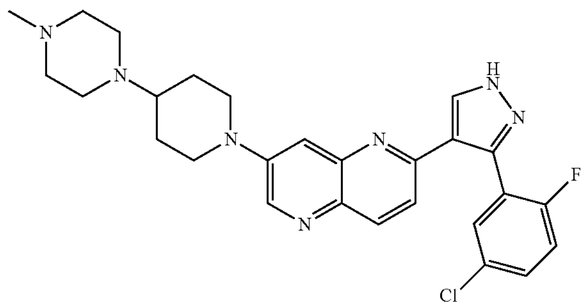 [SMILES: CN1CCN(C2CCN(c3cnc4ccc(-c5c[nH]nc5-c5cc(Cl)ccc5F)nc4c3)CC2)CC1] | 2-[3-(5-chloro-2-fluoro-phenyl)-1H-pyrazol-4-yl]-7-[4-(4-methylpiperazin-1-yl)-1-piperidyl]-1,5-naphthyridine | 507.0 |
| 1-84 | 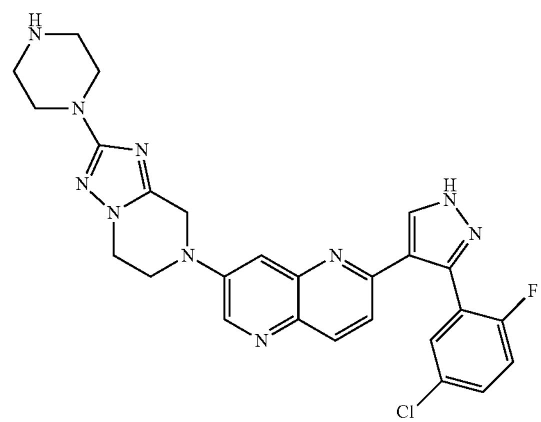 [SMILES: Fc1ccc(Cl)cc1-c1n[nH]cc1-c1ccc2ncc(N3CCn4nc(N5CCNCC5)nc4C3)cc2n1] | 2-[3-(5-chloro-2-fluoro-phenyl)-1H-pyrazol-4-yl]-7-(2-piperazin-1-yl-6,8-dihydro-5H-[1,2,4]triazolo[1,5-a]pyrazin-7-yl)-1,5-naphthyridine | 530.1 |
| 1-85 | 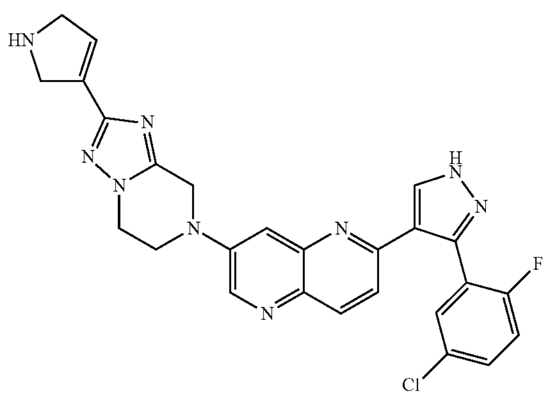 [SMILES: Fc1ccc(Cl)cc1-c1n[nH]cc1-c1ccc2ncc(N3CCn4nc(C5=CCNC5)nc4C3)cc2n1] | 2-[3-(5-chloro-2-fluoro-phenyl)-1H-pyrazol-4-yl]-7-[2-(2,5-dihydro-1H-pyrrol-3-yl)-6,8-dihydro-5H-[1,2,4]triazolo[1,5-a]pyrazin-7-yl]-1,5-naphthyridine | 514.0 |
| 1-86 | 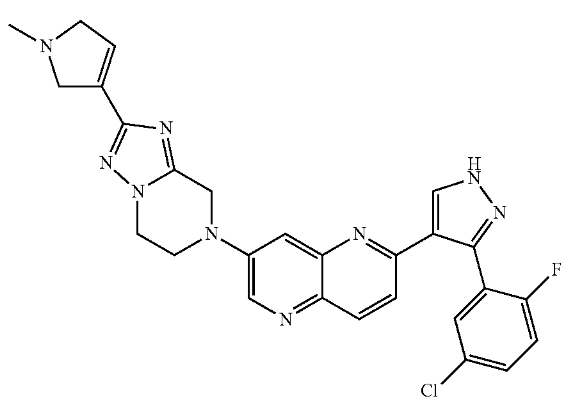 [SMILES: CN1CC=C(c2nc3n(n2)CCN(c2cnc4ccc(-c5c[nH]nc5-c5cc(Cl)ccc5F)nc4c2)C3)C1] | 2-[3-(5-chloro-2-fluoro-phenyl)-1H-pyrazol-4-yl]-7-[2-(1-methyl-2,5-dihydropyrrol-3-yl)-6,8-dihydro-5H-[1,2,4]triazolo[1,5-a]pyrazin-7-yl]-1,5-naphthyridine | 528.0 |

TABLE 1-continued

| No. | Structure | Chemical Name | [M + H]⁺ |
|---|---|---|---|
| 1-87 | 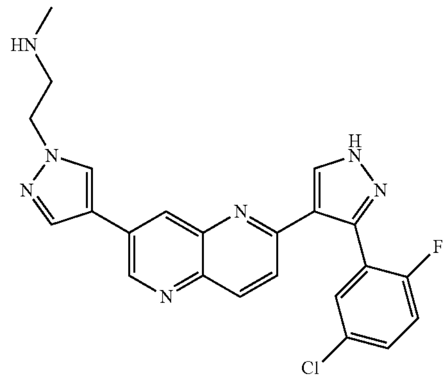 [SMILES: CNCCn1cc(-c2cnc3ccc(-c4c[nH]nc4-c4cc(Cl)ccc4F)nc3c2)cn1] | 2-[4-[6-[3-(5-chloro-2-fluoro-phenyl)-1H-pyrazol-4-yl]-1,5-naphthyridin-3-yl]pyrazol-1-yl]-N-methyl-ethanamine | 448.2 |
| 1-88 | 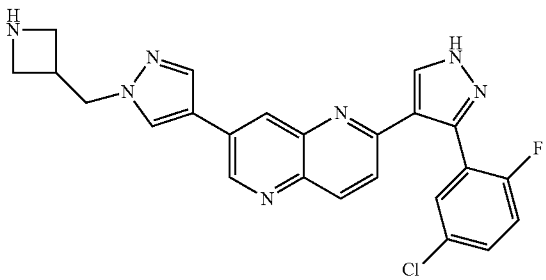 [SMILES: Fc1ccc(Cl)cc1-c1n[nH]cc1-c1ccc2ncc(-c3cnn(CC4CNC4)c3)cc2n1] | 7-[1-(azetidin-3-ylmethyl)pyrazol-4-yl]-2-[3-(5-chloro-2-fluoro-phenyl)-1H-pyrazol-4-yl]-1,5-naphthyridine | 460.0 |
| 1-89 | 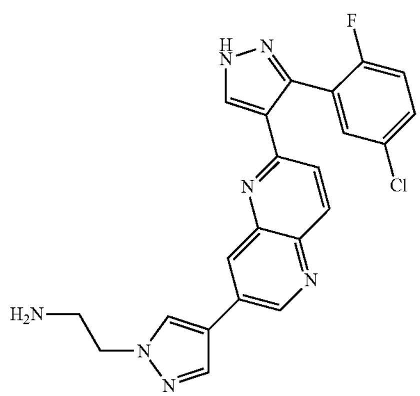 [SMILES: NCCn1cc(-c2cnc3ccc(-c4c[nH]nc4-c4cc(Cl)ccc4F)nc3c2)cn1] | 2-[4-[6-[3-(5-chloro-2-fluoro-phenyl)-1H-pyrazol-4-yl]-1,5-naphthyridin-3-yl]pyrazol-1-yl]ethanamine | 434.1 |
| 1-90 | 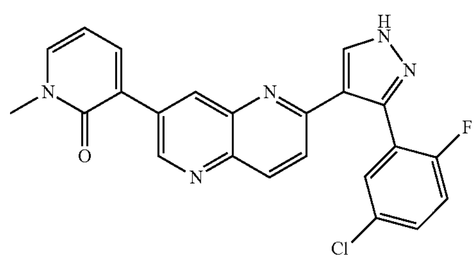 [SMILES: Cn1cccc(-c2cnc3ccc(-c4c[nH]nc4-c4cc(Cl)ccc4F)nc3c2)c1=O] | 3-[6-[3-(5-chloro-2-fluoro-phenyl)-1H-pyrazol-4-yl]-1,5-naphthyridin-3-yl]-1-methyl-pyridin-2-one | 432.1 |
| 1-91 | 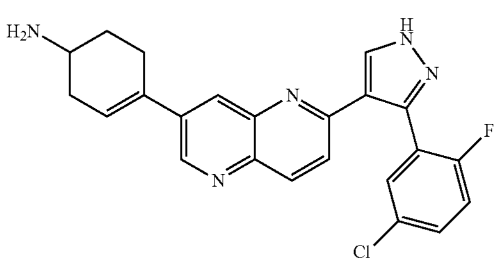 [SMILES: NC1CC=C(c2cnc3ccc(-c4c[nH]nc4-c4cc(Cl)ccc4F)nc3c2)CC1] | 4-[6-[3-(5-chloro-2-fluoro-phenyl)-1H-pyrazol-4-yl]-1,5-naphthyridin-3-yl]cyclohex-3-en-1-amine | 420.1 |

TABLE 1-continued

| No. | Structure | Chemical Name | [M + H]+ |
|---|---|---|---|
| 1-92 | 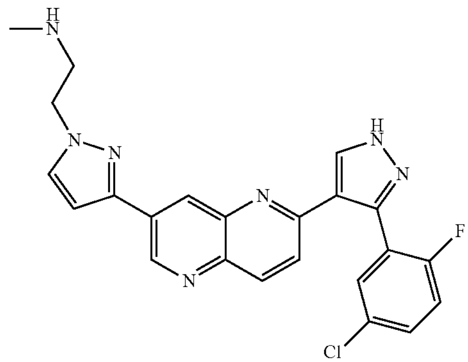 [SMILES: CNCCn1ccc(-c2cnc3ccc(-c4c[nH]nc4-c4cc(Cl)ccc4F)nc3c2)n1] | 2-[3-[6-[3-(5-chloro-2-fluoro-phenyl)-1H-pyrazol-4-yl]-1,5-naphthyridin-3-yl]pyrazol-1-yl]-N-methyl-ethanamine | 448.1 |
| 1-93 | 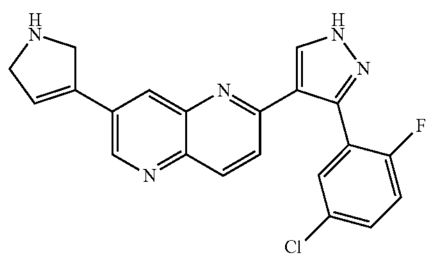 [SMILES: Fc1ccc(Cl)cc1-c1n[nH]cc1-c1ccc2ncc(C3=CCNC3)cc2n1] | 2-[3-(5-chloro-2-fluoro-phenyl)-1H-pyrazol-4-yl]-7-(2,5-dihydro-1H-pyrrol-3-yl)-1,5-naphthyridine | 392.0 |
| 1-94 | 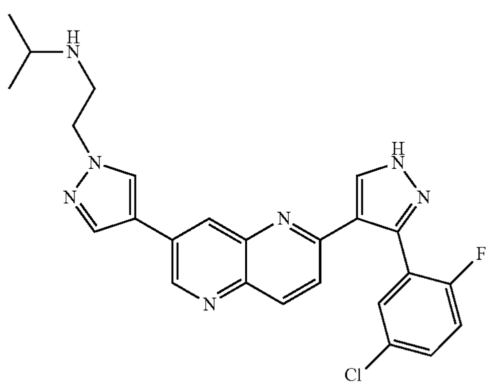 [SMILES: CC(C)NCCn1cc(-c2cnc3ccc(-c4c[nH]nc4-c4cc(Cl)ccc4F)nc3c2)cn1] | N-[2-[4-[6-[3-(5-chloro-2-fluoro-phenyl)-1H-pyrazol-4-yl]-1,5-naphthyridin-3-yl]pyrazol-1-yl]ethyl]propan-2-amine | 476.1 |
| 1-95 | 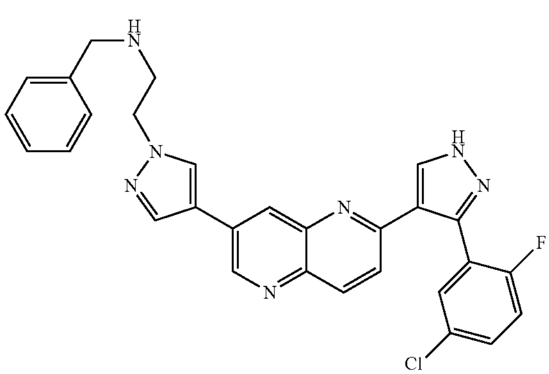 [SMILES: Fc1ccc(Cl)cc1-c1n[nH]cc1-c1ccc2ncc(-c3cnn(CCNCc4ccccc4)c3)cc2n1] | N-benzyl-2-[4-[6-[3-(5-chloro-2-fluoro-phenyl)-1H-pyrazol-4-yl]-1,5-naphthyridin-3-yl]pyrazol-1-yl]ethanamine | 524.2 |

TABLE 1-continued

| No. | Structure | Chemical Name | [M + H]+ |
|---|---|---|---|
| 1-96 | 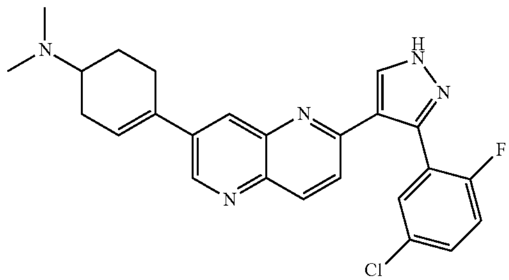 [SMILES: CN(C)C1CC=C(c2cnc3ccc(-c4c[nH]nc4-c4cc(Cl)ccc4F)nc3c2)CC1] | 4-[6-[3-(5-chloro-2-fluoro-phenyl)-1H-pyrazol-4-yl]-1,5-naphthyridin-3-yl]-N,N-dimethyl-cyclohex-3-en-1-amine | 448.2 |
| 1-97 | 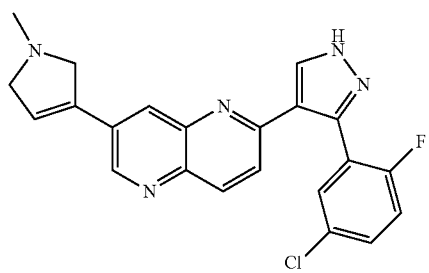 [SMILES: CN1CC=C(c2cnc3ccc(-c4c[nH]nc4-c4cc(Cl)ccc4F)nc3c2)C1] | 2-[3-(5-chloro-2-fluoro-phenyl)-1H-pyrazol-4-yl]-7-(1-methyl-2,5-dihydropyrrol-3-yl)-1,5-naphthyridine | 406.1 |
| 1-98 | 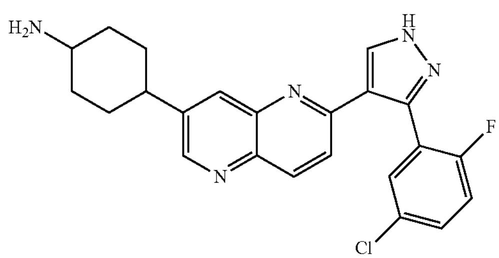 [SMILES: NC1CCC(c2cnc3ccc(-c4c[nH]nc4-c4cc(Cl)ccc4F)nc3c2)CC1] | 4-[6-[3-(5-chloro-2-fluoro-phenyl)-1H-pyrazol-4-yl]-1,5-naphthyridin-3-yl]cyclohexanamine | 422.1 |
| 1-99 | 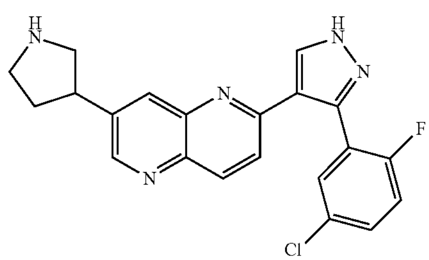 [SMILES: Fc1ccc(Cl)cc1-c1n[nH]cc1-c1ccc2ncc(C3CCNC3)cc2n1] | 2-[3-(5-chloro-2-fluoro-phenyl)-1H-pyrazol-4-yl]-7-pyrrolidin-3-yl-1,5-naphthyridine | 394.0 |
| 1-100 | 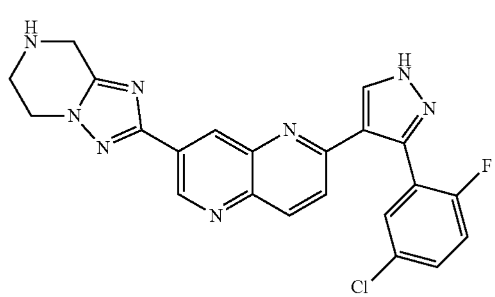 [SMILES: Fc1ccc(Cl)cc1-c1n[nH]cc1-c1ccc2ncc(-c3nc4n(n3)CCNC4)cc2n1] | 2-[3-(5-chloro-2-fluoro-phenyl)-1H-pyrazol-4-yl]-7-(5,6,7,8-tetrahydro-[1,2,4]triazolo[1,5-a]pyrazin-2-yl)-1,5-naphthyridine | 447.0 |

TABLE 1-continued

| No. | Structure | Chemical Name | [M + H]+ |
|---|---|---|---|
| 1-101 | 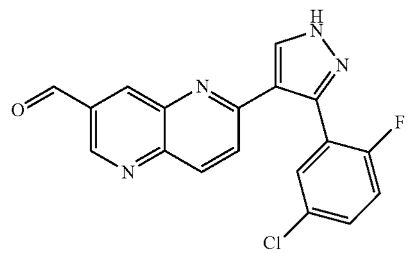 [SMILES: O=Cc1cnc2ccc(-c3c[nH]nc3-c3cc(Cl)ccc3F)nc2c1] | 6-[3-(5-chloro-2-fluoro-phenyl)-1H-pyrazol-4-yl]-1,5-naphthyridine-3-carbaldehyde | 353.2 |
| 1-102 | 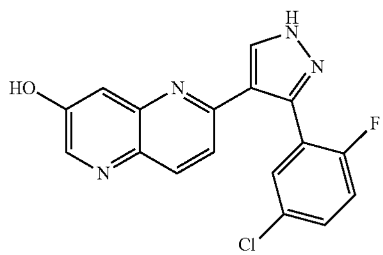 [SMILES: Oc1cnc2ccc(-c3c[nH]nc3-c3cc(Cl)ccc3F)nc2c1] | 6-[3-(5-chloro-2-fluoro-phenyl)-1H-pyrazol-4-yl]-1,5-naphthyridin-3-ol | 341.1 |
| 1-103 | 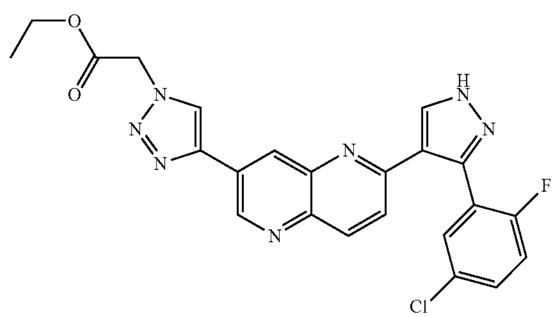 [SMILES: CCOC(=O)Cn1cc(-c2cnc3ccc(-c4c[nH]nc4-c4cc(Cl)ccc4F)nc3c2)nn1] | ethyl 2-[4-[6-[3-(5-chloro-2-fluoro-phenyl)-1H-pyrazol-4-yl]-1,5-naphthyridin-3-yl]triazol-1-yl]acetate | 478.1 |
| 1-104 | 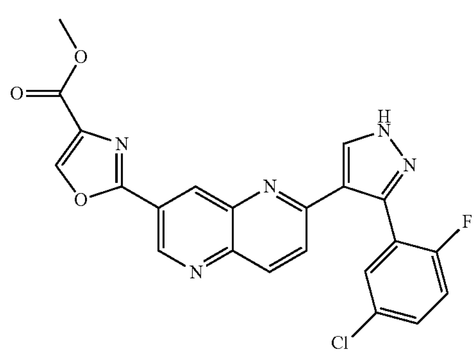 [SMILES: COC(=O)c1coc(-c2cnc3ccc(-c4c[nH]nc4-c4cc(Cl)ccc4F)nc3c2)n1] | methyl 2-[6-[3-(5-chloro-2-fluoro-phenyl)-1H-pyrazol-4-yl]-1,5-naphthyridin-3-yl]oxazole-4-carboxylate | 450.1 |
| 1-105 | 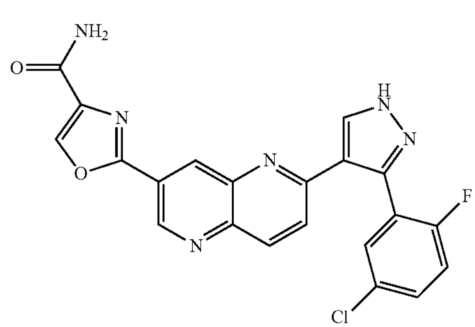 [SMILES: NC(=O)c1coc(-c2cnc3ccc(-c4c[nH]nc4-c4cc(Cl)ccc4F)nc3c2)n1] | 2-[6-[3-(5-chloro-2-fluoro-phenyl)-1H-pyrazol-4-yl]-1,5-naphthyridin-3-yl]oxazole-4-carboxamide | 435.0 |

TABLE 1-continued

| No. | Structure | Chemical Name | [M + H]⁺ |
|---|---|---|---|
| 1-106 | 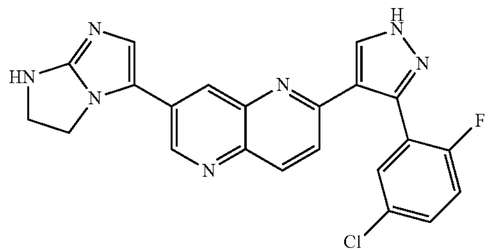 [SMILES: Fc1ccc(Cl)cc1-c1n[nH]cc1-c1ccc2ncc(-c3cnc4n3CCN4)cc2n1] | 2-[3-(5-chloro-2-fluoro-phenyl)-1H-pyrazol-4-yl]-7-(6,7-dihydro-5H-imidazo[1,2-a]imidazol-3-yl)-1,5-naphthyridine | 432.1 |
| 1-107 | 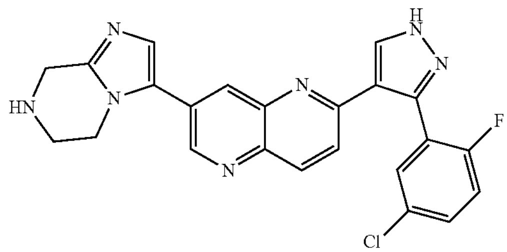 [SMILES: Fc1ccc(Cl)cc1-c1n[nH]cc1-c1ccc2ncc(-c3cnc4n3CCNC4)cc2n1] | 2-[3-(5-chloro-2-fluoro-phenyl)-1H-pyrazol-4-yl]-7-(5,6,7,8-tetrahydroimidazo[1,2-a]pyrazin-3-yl)-1,5-naphthyridine | 446.1 |
| 1-108 | 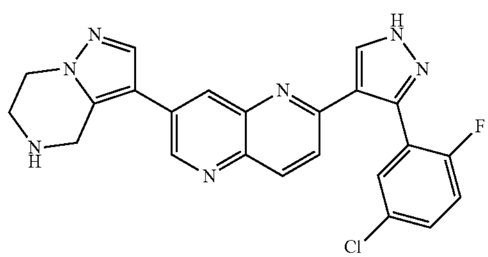 [SMILES: Fc1ccc(Cl)cc1-c1n[nH]cc1-c1ccc2ncc(-c3cnn4c3CNCC4)cc2n1] | 2-[3-(5-chloro-2-fluoro-phenyl)-1H-pyrazol-4-yl]-7-(4,5,6,7-tetrahydropyrazolo[1,5-a]pyrazin-3-yl)-1,5-naphthyridine | 446.1 |
| 1-109 | 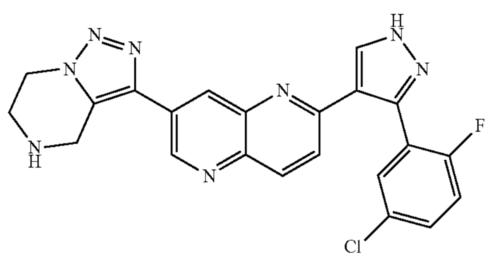 [SMILES: Fc1ccc(Cl)cc1-c1n[nH]cc1-c1ccc2ncc(-c3nnn4c3CNCC4)cc2n1] | 2-[3-(5-chloro-2-fluoro-phenyl)-1H-pyrazol-4-yl]-7-(4,5,6,7-tetrahydrotriazolo[1,5-a]pyrazin-3-yl)-1,5-naphthyridine | 447.0 |
| 1-110 | 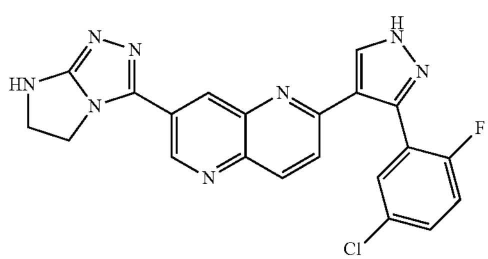 [SMILES: Fc1ccc(Cl)cc1-c1n[nH]cc1-c1ccc2ncc(-c3nnc4n3CCN4)cc2n1] | 2-[3-(5-chloro-2-fluoro-phenyl)-1H-pyrazol-4-yl]-7-(6,7-dihydro-5H-imidazo[2,1-c][1,2,4]triazol-3-yl)-1,5-naphthyridine | 433.0 |
| 1-111 | 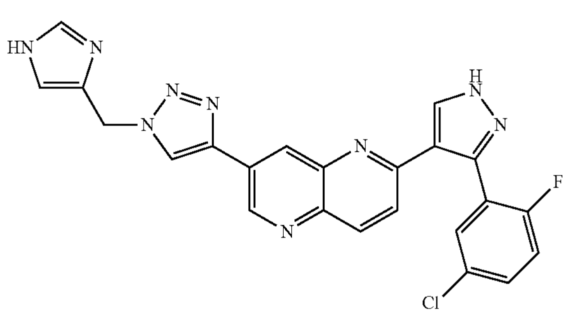 [SMILES: Fc1ccc(Cl)cc1-c1n[nH]cc1-c1ccc2ncc(-c3cn(Cc4c[nH]cn4)nn3)cc2n1] | 2-[3-(5-chloro-2-fluoro-phenyl)-1H-pyrazol-4-yl]-7-[1-(1H-imidazol-4-ylmethyl)triazol-4-yl]-1,5-naphthyridine | 427.1 |

TABLE 1-continued

| No. | Structure | Chemical Name | [M + H]+ |
|---|---|---|---|
| 1-112 | 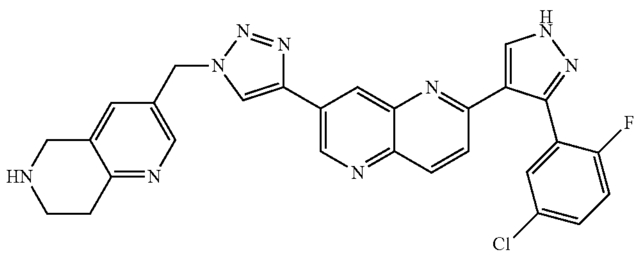 [SMILES: Fc1ccc(Cl)cc1-c1n[nH]cc1-c1ccc2ncc(-c3cn(Cc4cnc5c(c4)CNCC5)nn3)cc2n1] | 2-[3-(5-chloro-2-fluoro-phenyl)-1H-pyrazol-4-yl]-7-[1-(5,6,7,8-tetrahydro-1,6-naphthyridin-3-ylmethyl)triazol-4-yl]-1,5-naphthyridine | 538.2 |
| 1-113 | 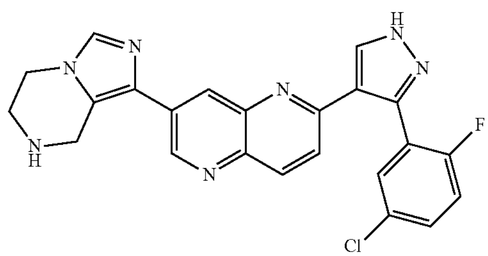 [SMILES: Fc1ccc(Cl)cc1-c1n[nH]cc1-c1ccc2ncc(-c3ncn4c3CNCC4)cc2n1] | 2-[3-(5-chloro-2-fluoro-phenyl)-1H-pyrazol-4-yl]-7-(5,6,7,8-tetrahydroimidazo[1,5-a]pyrazin-1-yl)-1,5-naphthyridine | 446.1 |
| 1-114 | 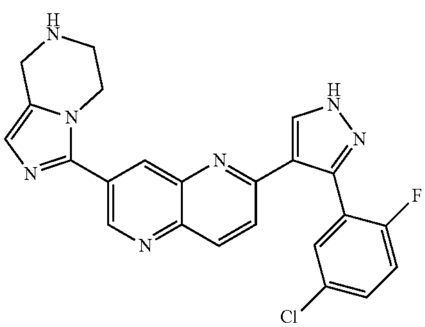 [SMILES: Fc1ccc(Cl)cc1-c1n[nH]cc1-c1ccc2ncc(-c3ncc4n3CCNC4)cc2n1] | 2-[3-(5-chloro-2-fluoro-phenyl)-1H-pyrazol-4-yl]-7-(5,6,7,8-tetrahydroimidazo[1,5-a]pyrazin-3-yl)-1,5-naphthyridine | 446.1 |
| 1-115 | 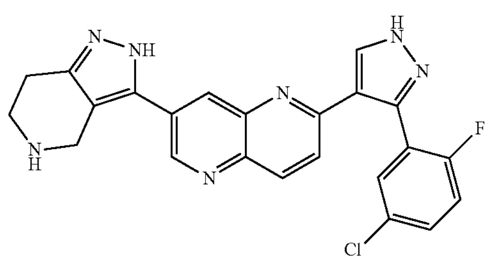 [SMILES: Fc1ccc(Cl)cc1-c1n[nH]cc1-c1ccc2ncc(-c3[nH]nc4c3CNCC4)cc2n1] | 2-[3-(5-chloro-2-fluoro-phenyl)-1H-pyrazol-4-yl]-7-(4,5,6,7-tetrahydro-2H-pyrazolo[4,3-c]pyridin-3-yl)-1,5-naphthyridine | 446.1 |
| 1-116 | 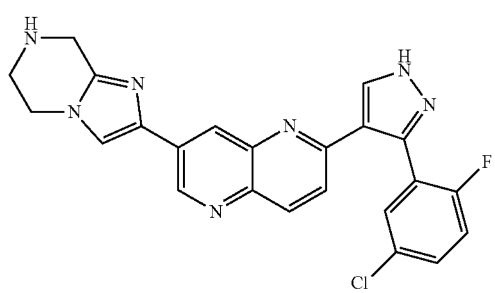 [SMILES: Fc1ccc(Cl)cc1-c1n[nH]cc1-c1ccc2ncc(-c3cn4c(n3)CNCC4)cc2n1] | 2-[3-(5-chloro-2-fluoro-phenyl)-1H-pyrazol-4-yl]-7-(5,6,7,8-tetrahydroimidazo[1,2-a]pyrazin-2-yl)-1,5-naphthyridine | 446.1 |

TABLE 1-continued

| No. | Structure | Chemical Name | [M + H]⁺ |
|---|---|---|---|
| 1-117 | 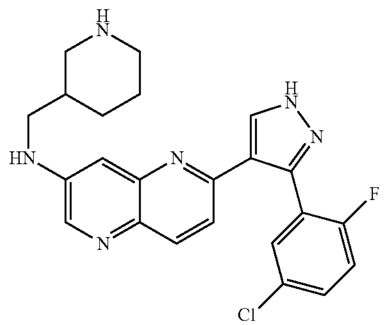 [SMILES: Fc1ccc(Cl)cc1-c1n[nH]cc1-c1ccc2ncc(NCC3CCCNC3)cc2n1] | 6-[3-(5-chloro-2-fluoro-phenyl)-1H-pyrazol-4-yl]-N-(3-piperidylmethyl)-1,5-naphthyridin-3-amine | 437.1 |
| 1-118 | 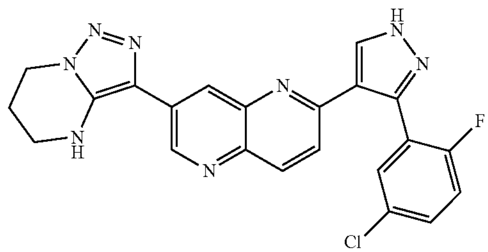 [SMILES: Fc1ccc(Cl)cc1-c1n[nH]cc1-c1ccc2ncc(-c3nnn4c3NCCC4)cc2n1] | 2-[3-(5-chloro-2-fluoro-phenyl)-1H-pyrazol-4-yl]-7-(4,5,6,7-tetrahydrotriazolo[1,5-a]pyrimidin-3-yl)-1,5-naphthyridine | 447.0 |
| 1-119 | 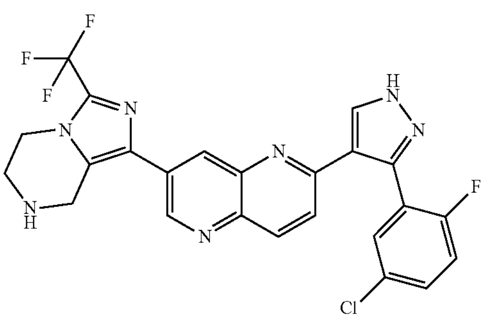 [SMILES: Fc1ccc(Cl)cc1-c1n[nH]cc1-c1ccc2ncc(-c3nc(C(F)(F)F)n4c3CNCC4)cc2n1] | 2-[3-(5-chloro-2-fluoro-phenyl)-1H-pyrazol-4-yl]-7-[3-(trifluoromethyl)-5,6,7,8-tetrahydroimidazo[1,5-a]pyrazin-1-yl]-1,5-naphthyridine | 514.0 |
| 1-120 | 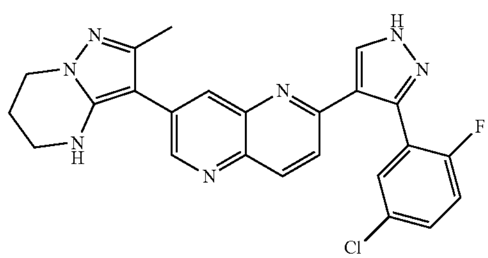 [SMILES: Cc1nn2c(c1-c1cnc3ccc(-c4c[nH]nc4-c4cc(Cl)ccc4F)nc3c1)NCCC2] | 2-[3-(5-chloro-2-fluoro-phenyl)-1H-pyrazol-4-yl]-7-(2-methyl-4,5,6,7-tetrahydropyrazolo[1,5-a]pyrimidin-3-yl)-1,5-naphthyridine | 460.1 |
| 1-121 | 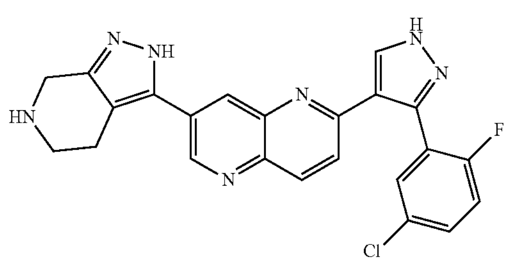 [SMILES: Fc1ccc(Cl)cc1-c1n[nH]cc1-c1ccc2ncc(-c3[nH]nc4c3CCNC4)cc2n1] | 2-[3-(5-chloro-2-fluoro-phenyl)-1H-pyrazol-4-yl]-7-(4,5,6,7-tetrahydro-2H-pyrazolo[3,4-c]pyridin-3-yl)-1,5-naphthyridine | 446.1 |

TABLE 1-continued

| No. | Structure | Chemical Name | [M + H]+ |
|---|---|---|---|
| 1-122 | 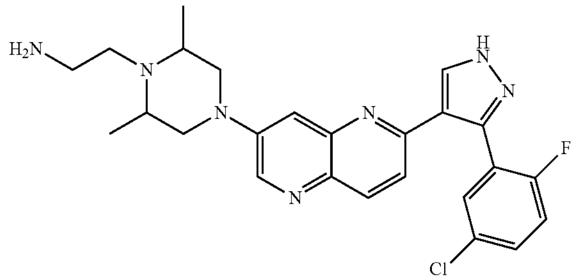 [SMILES: CC1CN(c2cnc3ccc(-c4c[nH]nc4-c4cc(Cl)ccc4F)nc3c2)CC(C)N1CCN] | 2-[4-[6-[3-(5-chloro-2-fluoro-phenyl)-1H-pyrazol-4-yl]-1,5-naphthyridin-3-yl]-2,6-dimethyl-piperazin-1-yl]ethanamine | 480.2 |
| 1-123 | 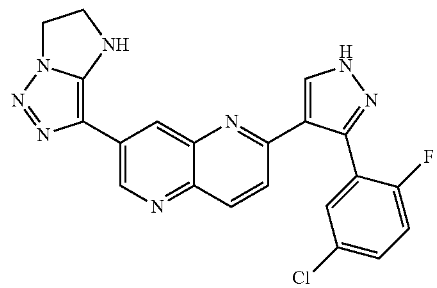 [SMILES: Fc1ccc(Cl)cc1-c1n[nH]cc1-c1ccc2ncc(-c3nnn4c3NCC4)cc2n1] | 2-[3-(5-chloro-2-fluoro-phenyl)-1H-pyrazol-4-yl]-7-(5,6-dihydro-4H-imidazo[1,2-c]triazol-3-yl)-1,5-naphthyridine | 433.1 |
| 1-124 | 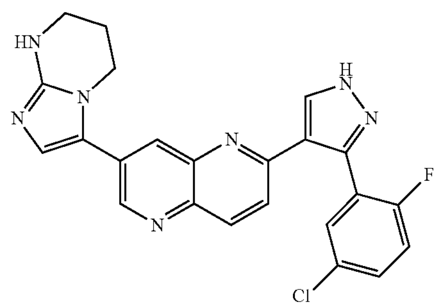 [SMILES: Fc1ccc(Cl)cc1-c1n[nH]cc1-c1ccc2ncc(-c3cnc4n3CCCN4)cc2n1] | 2-[3-(5-chloro-2-fluoro-phenyl)-1H-pyrazol-4-yl]-7-(5,6,7,8-tetrahydroimidazo[1,2-a]pyrimidin-3-yl)-1,5-naphthyridine | 446.0 |
| 1-125 | 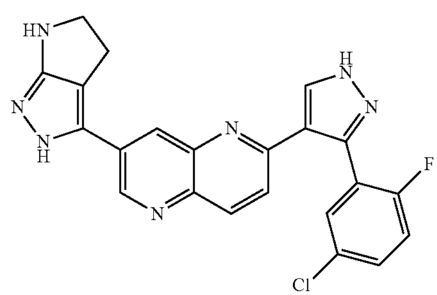 [SMILES: Fc1ccc(Cl)cc1-c1n[nH]cc1-c1ccc2ncc(-c3[nH]nc4c3CCN4)cc2n1] | 2-[3-(5-chloro-2-fluoro-phenyl)-1H-pyrazol-4-yl]-7-(2,4,5,6-tetrahydropyrrolo[2,3-c]pyrazol-3-yl)-1,5-naphthyridine | 432.0 |
| 1-126 | 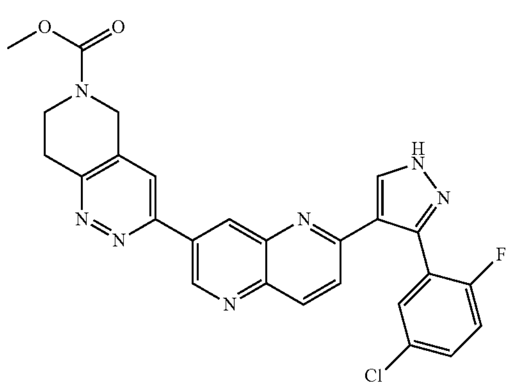 [SMILES: COC(=O)N1CCc2nnc(-c3cnc4ccc(-c5c[nH]nc5-c5cc(Cl)ccc5F)nc4c3)cc2C1] | methyl 3-[6-[3-(5-chloro-2-fluoro-phenyl)-1H-pyrazol-4-yl]-1,5-naphthyridin-3-yl]-7,8-dihydro-5H-pyrido[4,3-c]pyridazine-6-carboxylate | 516.0 |

TABLE 1-continued

| No. | Structure | Chemical Name | [M + H]+ |
|---|---|---|---|
| 1-127 | 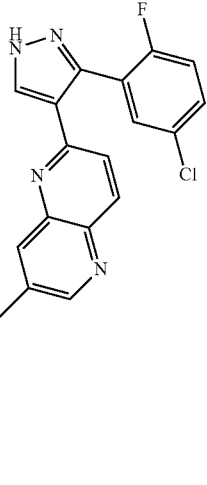 | ethyl 2-[2-[4-[6-[3-(5-chloro-2-fluoro-phenyl)-1H-pyrazol-4-yl]-1,5-naphthyridin-3-yl]pyrazol-1-yl]ethylamino]acetate | 520.1 |
| 1-128 | 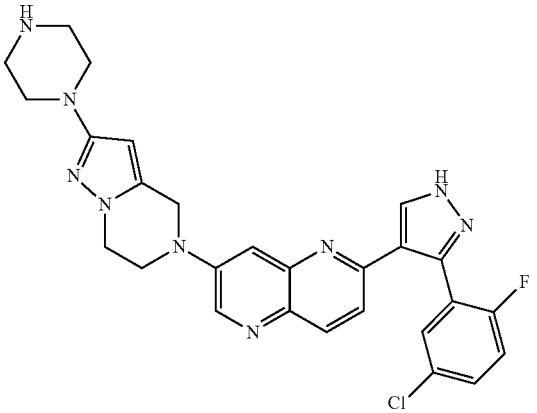 [SMILES: Fc1ccc(Cl)cc1-c1n[nH]cc1-c1ccc2ncc(N3CCn4nc(N5CCNCC5)cc4C3)cc2n1] | 2-[3-(5-chloro-2-fluoro-phenyl)-1H-pyrazol-4-yl]-7-(2-piperazin-1-yl-6,7-dihydro-4H-pyrazolo[1,5-a]pyrazin-5-yl)-1,5-naphthyridine | 531.1 |
| 1-129 | 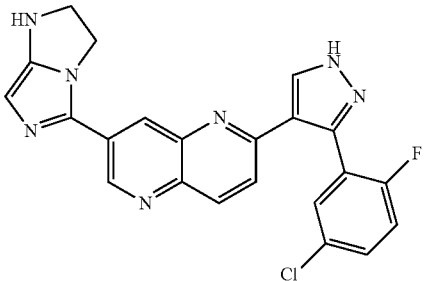 [SMILES: Fc1ccc(Cl)cc1-c1n[nH]cc1-c1ccc2ncc(-c3ncc4n3CCN4)cc2n1] | 2-[3-(5-chloro-2-fluoro-phenyl)-1H-pyrazol-4-yl]-7-(2,3-dihydro-1H-imidazo[1,2-c]imidazol-5-yl)-1,5-naphthyridine | 432.0 |
| 1-130 | 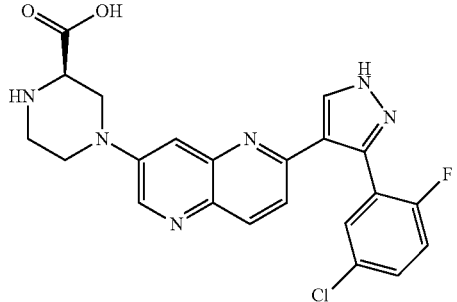 [SMILES: O=C(O)[C@H]1CN(c2cnc3ccc(-c4c[nH]nc4-c4cc(Cl)ccc4F)nc3c2)CCN1] | (2R)-4-[6-[3-(5-chloro-2-fluoro-phenyl)-1H-pyrazol-4-yl]-1,5-naphthyridin-3-yl]piperazine-2-carboxylic acid | 453.1 |

TABLE 1-continued

| No. | Structure | Chemical Name | [M + H]+ |
|---|---|---|---|
| 1-131 | 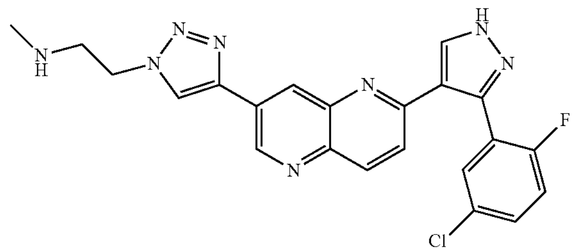 [SMILES: CNCCn1cc(-c2cnc3ccc(-c4c[nH]nc4-c4cc(Cl)ccc4F)nc3c2)nn1] | 2-[4-[6-[3-(5-chloro-2-fluoro-phenyl)-1H-pyrazol-4-yl]-1,5-naphthyridin-3-yl]triazol-1-yl]-N-methyl-ethanamine | 449.0 |
| 1-132 | 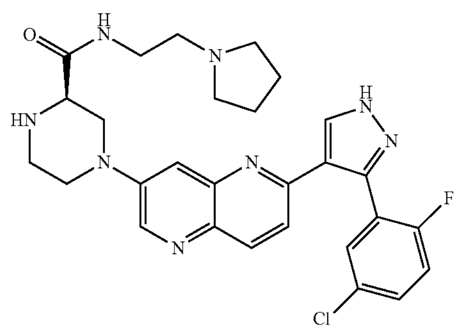 [SMILES: O=C(NCCN1CCCC1)[C@H]1CN(c2cnc3ccc(-c4c[nH]nc4-c4cc(Cl)ccc4F)nc3c2)CCN1] | (2R)-4-[6-[3-(5-chloro-2-fluoro-phenyl)-1H-pyrazol-4-yl]-1,5-naphthyridin-3-yl]-N-(2-pyrrolidin-1-ylethyl)piperazine-2-carboxamide | 549.1 |
| 1-133 | 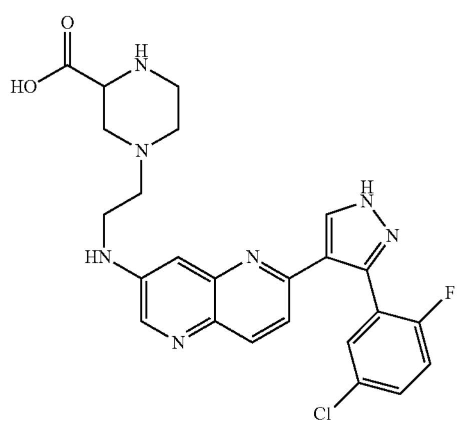 [SMILES: O=C(O)C1CN(CCNc2cnc3ccc(-c4c[nH]nc4-c4cc(Cl)ccc4F)nc3c2)CCN1] | 4-[2-[[6-[3-(5-chloro-2-fluoro-phenyl)-1H-pyrazol-4-yl]-1,5-naphthyridin-3-yl]amino]ethyl]piperazine-2-carboxylic acid | 496.1 |
| 1-134 | 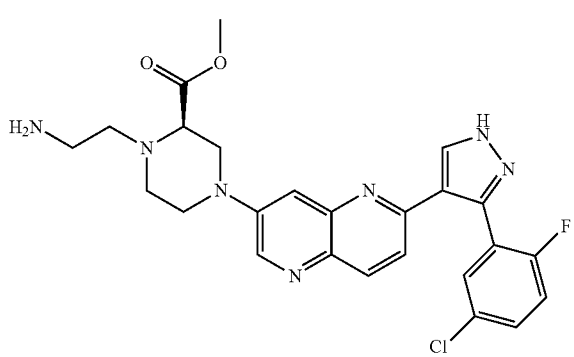 [SMILES: COC(=O)[C@H]1CN(c2cnc3ccc(-c4c[nH]nc4-c4cc(Cl)ccc4F)nc3c2)CCN1CCN] | methyl (2R)-1-(2-aminoethyl)-4-[6-[3-(5-chloro-2-fluoro-phenyl)-1H-pyrazol-4-yl]-1,5-naphthyridin-3-yl]piperazine-2-carboxylate | 510.2 |

TABLE 1-continued

| No. | Structure | Chemical Name | [M + H]+ |
|---|---|---|---|
| 1-135 | 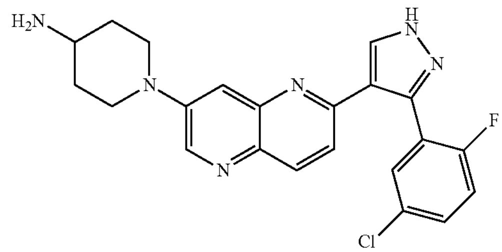 [SMILES: NC1CCN(c2cnc3ccc(-c4c[nH]nc4-c4cc(Cl)ccc4F)nc3c2)CC1] | 1-[6-[3-(5-chloro-2-fluoro-phenyl)-1H-pyrazol-4-yl]-1,5-naphthyridin-3-yl]piperidin-4-amine | 423.1 |
| 1-136 | 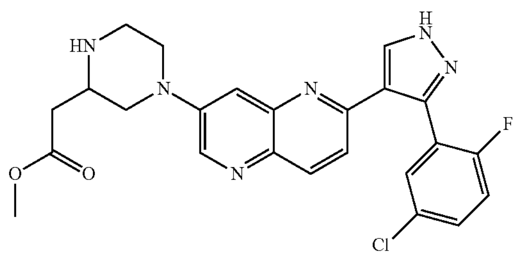 [SMILES: COC(=O)CC1CN(c2cnc3ccc(-c4c[nH]nc4-c4cc(Cl)ccc4F)nc3c2)CCN1] | methyl 2-[4-[6-[3-(5-chloro-2-fluoro-phenyl)-1H-pyrazol-4-yl]-1,5-naphthyridin-3-yl]piperazin-2-yl]acetate | 481.0 |
| 2-1 | 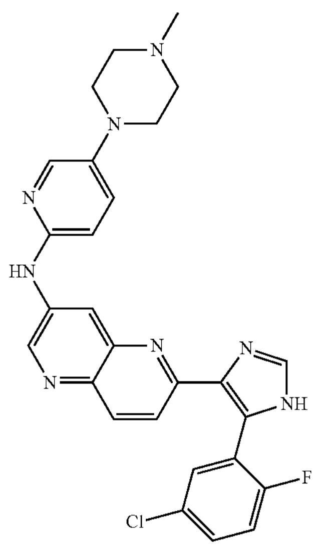 [SMILES: CN1CCN(c2ccc(Nc3cnc4ccc(-c5nc[nH]c5-c5cc(Cl)ccc5F)nc4c3)nc2)CC1] | 6-[5-(5-chloro-2-fluoro-phenyl)-1H-imidazol-4-yl]-N-[5-(4-methylpiperazin-1-yl)-2-pyridyl]-1,5-naphthyridin-3-amine | 545.1 |
| 2-2 | 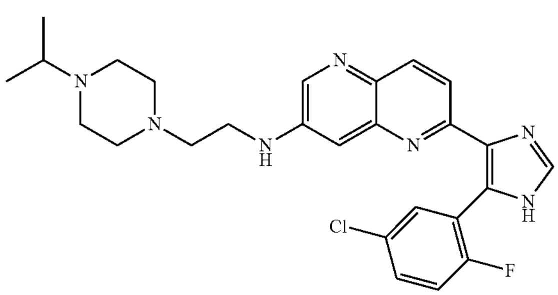 [SMILES: CC(C)N1CCN(CCNc2cnc3ccc(-c4nc[nH]c4-c4cc(Cl)ccc4F)nc3c2)CC1] | 6-[5-(5-chloro-2-fluoro-phenyl)-1H-imidazol-4-yl]-N-[2-(4-isopropylpiperazin-1-yl)ethyl]-1,5-naphthyridin-3-amine | 494.2 |

TABLE 1-continued

| No. | Structure | Chemical Name | [M + H]+ |
|---|---|---|---|
| 2-3 | 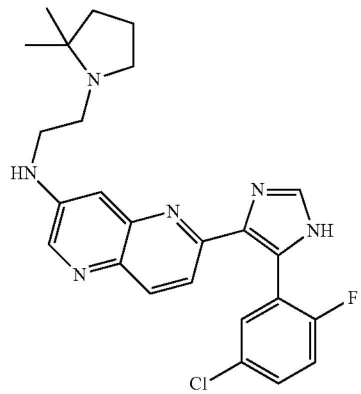 [SMILES: CC1(C)CCCN1CCNc1cnc2ccc(-c3nc[nH]c3-c3cc(Cl)ccc3F)nc2c1] | 6-[5-(5-chloro-2-fluoro-phenyl)-1H-imidazol-4-yl]-N-[2-(2,2-dimethylpyrrolidin-1-yl)ethyl]-1,5-naphthyridin-3-amine | 465.0 |
| 2-4 | 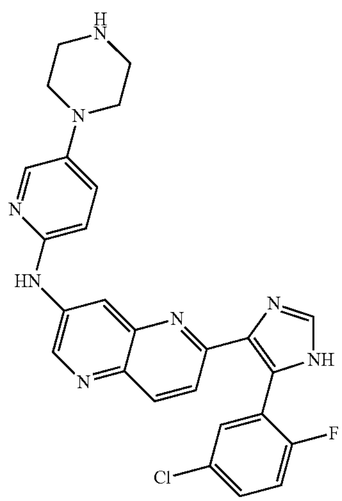 [SMILES: Fc1ccc(Cl)cc1-c1[nH]cnc1-c1ccc2ncc(Nc3ccc(N4CCNCC4)cn3)cc2n1] | 6-[5-(5-chloro-2-fluoro-phenyl)-1H-imidazol-4-yl]-N-(5-piperazin-1-yl-2-pyridyl)-1,5-naphthyridin-3-amine | 501.1 |
| 2-5 | 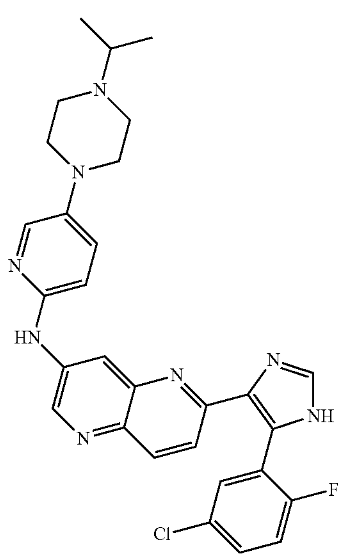 [SMILES: CC(C)N1CCN(c2ccc(Nc3cnc4ccc(-c5nc[nH]c5-c5cc(Cl)ccc5F)nc4c3)nc2)CC1] | 6-[5-(5-chloro-2-fluoro-phenyl)-1H-imidazol-4-yl]-N-[5-(4-isopropylpiperazin-1-yl)-2-pyridyl]-1,5-naphthyridin-3-amine | 543.1 |

TABLE 1-continued

| No. | Structure | Chemical Name | [M + H]+ |
|---|---|---|---|
| 2-6 | 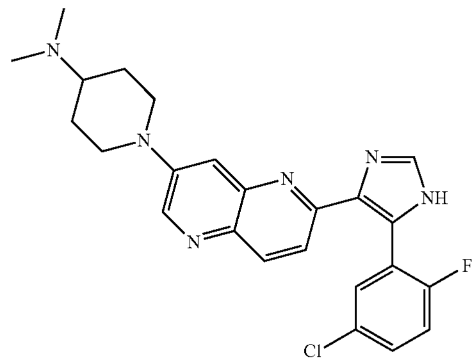 [SMILES: CN(C)C1CCN(c2cnc3ccc(-c4nc[nH]c4-c4cc(Cl)ccc4F)nc3c2)CC1] | 1-[6-[5-(5-chloro-2-fluoro-phenyl)-1H-imidazol-4-yl]-1,5-naphthyridin-3-yl]-N,N-dimethyl-piperidin-4-amine | 451.1 |
| 2-7 | 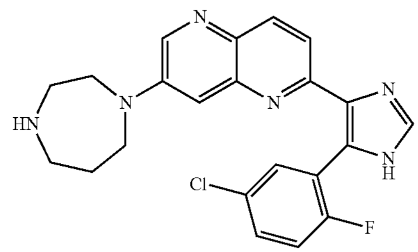 [SMILES: Fc1ccc(Cl)cc1-c1[nH]cnc1-c1ccc2ncc(N3CCCNCC3)cc2n1] | 2-[5-(5-chloro-2-fluoro-phenyl)-1H-imidazol-4-yl]-7-(1,4-diazepan-1-yl)-1,5-naphthyridine | 423.1 |
| 2-8 | 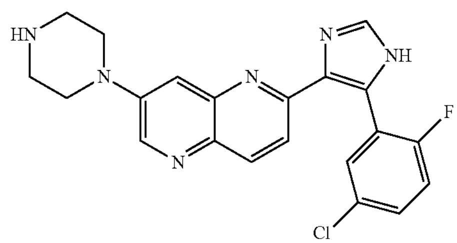 [SMILES: Fc1ccc(Cl)cc1-c1[nH]cnc1-c1ccc2ncc(N3CCNCC3)cc2n1] | 2-[5-(5-chloro-2-fluoro-phenyl)-1H-imidazol-4-yl]-7-piperazin-1-yl-1,5-naphthyridine | 409.2 |
| 2-9 | 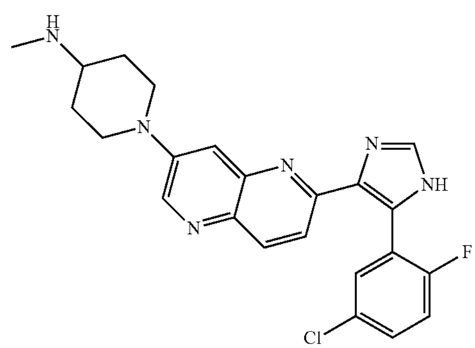 [SMILES: CNC1CCN(c2cnc3ccc(-c4nc[nH]c4-c4cc(Cl)ccc4F)nc3c2)CC1] | 1-[6-[5-(5-chloro-2-fluoro-phenyl)-1H-imidazol-4-yl]-1,5-naphthyridin-3-yl]-N-methyl-piperidin-4-amine | 437.1 |
| 2-10 | 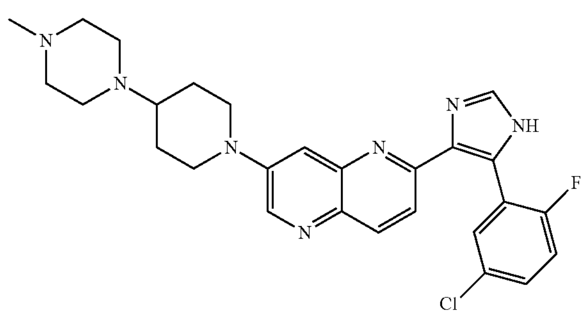 [SMILES: CN1CCN(C2CCN(c3cnc4ccc(-c5nc[nH]c5-c5cc(Cl)ccc5F)nc4c3)CC2)CC1] | 2-[5-(5-chloro-2-fluoro-phenyl)-1H-imidazol-4-yl]-7-[4-(4-methylpiperazin-1-yl)-1-piperidyl]-1,5-naphthyridine | 506.2 |

TABLE 1-continued

| No. | Structure | Chemical Name | [M + H]+ |
|---|---|---|---|
| 2-11 | AND Enantiomer | rac-(3S)-1-(6-[5-(5-chloro-2-fluoro-phenyl)-1H-imidazol-4-yl]-1,5-naphthyridin-3-yl]-N,N-dimethyl-pyrrolidin-3-amine | 437.1 |
| 2-13 | 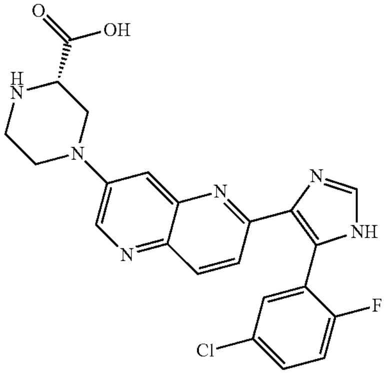 [SMILES: O=C(O)[C@@H]1CN(c2cnc3ccc(-c4nc[nH]c4-c4cc(Cl)ccc4F)nc3c2)CCN1] | (2S)-4-[6-[5-(5-chloro-2-fluoro-phenyl)-1H-imidazol-4-yl]-1,5-naphthyridin-3-yl]piperazine-2-carboxylic acid | 453.1 |
| 2-14 | 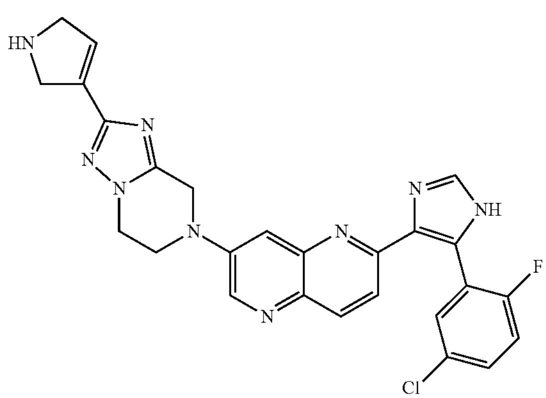 [SMILES: Fc1ccc(Cl)cc1-c1[nH]cnc1-c1ccc2ncc(N3CCn4nc(C5=CCNC5)nc4C3)cc2n1] | 2-[5-(5-chloro-2-fluoro-phenyl)-1H-imidazol-4-yl]-7-[2-(2,5-dihydro-1H-pyrrol-3-yl)-6,8-dihydro-5H-[1,2,4]triazolo[1,5-a]pyrazin-7-yl]-1,5-naphthyridine | 514.0 |
| 2-15 | 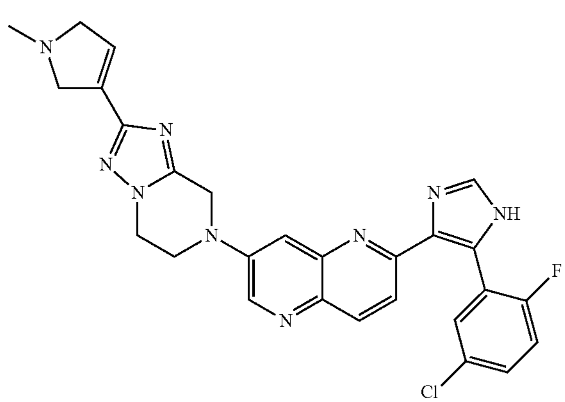 [SMILES: CN1CC=C(c2nc3n(n2)CCN(c2cnc4ccc(-c5nc[nH]c5-c5cc(Cl)ccc5F)nc4c2)C3)C1] | 2-[5-(5-chloro-2-fluoro-phenyl)-1H-imidazol-4-yl]-7-[2-(1-methyl-2,5-dihydropyrrol-3-yl)-6,8-dihydro-5H-[1,2,4]triazolo[1,5-a]pyrazin-7-yl]-1,5-naphthyridine | 528.0 |

TABLE 1-continued

| No. | Structure | Chemical Name | [M + H]+ |
|---|---|---|---|
| 2-16 | 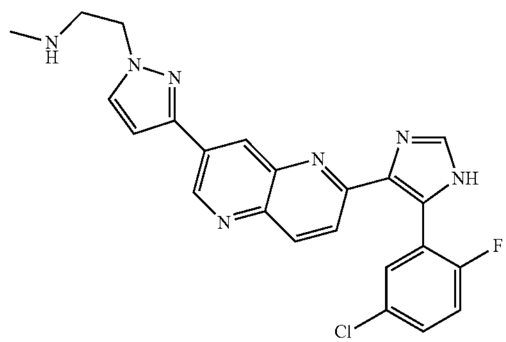 [SMILES: CNCCn1ccc(-c2cnc3ccc(-c4nc[nH]c4-c4cc(Cl)ccc4F)nc3c2)n1] | 2-[3-[6-[5-(5-chloro-2-fluoro-phenyl)-1H-imidazol-4-yl]-1,5-naphthyridin-3-yl]pyrazol-1-yl]-N-methyl-ethanamine | 448.1 |
| 2-17 | 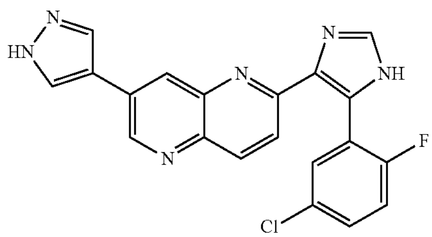 [SMILES: Fc1ccc(Cl)cc1-c1[nH]cnc1-c1ccc2ncc(-c3cn[nH]c3)cc2n1] | 2-[5-(5-chloro-2-fluoro-phenyl)-1H-imidazol-4-yl]-7-(1H-pyrazol-4-yl)-1,5-naphthyridine | 390.9 |
| 2-18 | 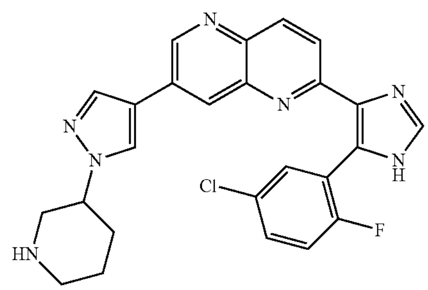 [SMILES: Fc1ccc(Cl)cc1-c1[nH]cnc1-c1ccc2ncc(-c3cnn(C4CCCNC4)c3)cc2n1] | 2-[5-(5-chloro-2-fluoro-phenyl)-1H-imidazol-4-yl]-7-[1-(3-piperidyl)pyrazol-4-yl]-1,5-naphthyridine | 474.1 |
| 2-19 | 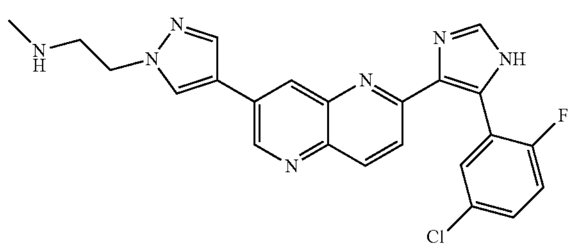 [SMILES: CNCCn1cc(-c2cnc3ccc(-c4nc[nH]c4-c4cc(Cl)ccc4F)nc3c2)cn1] | 2-[4-[6-[5-(5-chloro-2-fluoro-phenyl)-1H-imidazol-4-yl]-1,5-naphthyridin-3-yl]pyrazol-1-yl]-N-methyl-ethanamine | 448.1 |
| 2-20 | 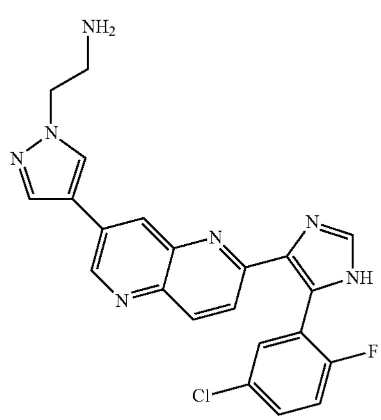 [SMILES: NCCn1cc(-c2cnc3ccc(-c4nc[nH]c4-c4cc(Cl)ccc4F)nc3c2)cn1] | 2-[4-[6-[5-(5-chloro-2-fluoro-phenyl)-1H-imidazol-4-yl]-1,5-naphthyridin-3-yl]pyrazol-1-yl]ethanamine | 434.0 |

TABLE 1-continued

| No. | Structure | Chemical Name | [M + H]+ |
|---|---|---|---|
| 2-21 | 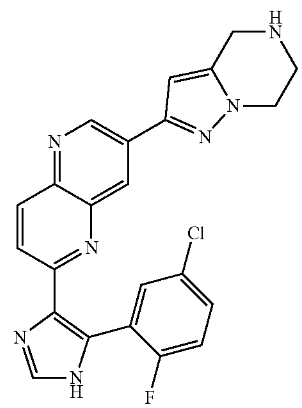 [SMILES: Fc1ccc(Cl)cc1-c1[nH]cnc1-c1ccc2ncc(-c3cc4n(n3)CCNC4)cc2n1] | 2-[5-(5-chloro-2-fluoro-pheyl)-1H-imidazol-4-yl]-7-(4,5,6,7-tetrahydropyrazolo[1,5-a]pyrazin-2-yl)-1,5-naphthyridine | 446.0 |
| 2-22 | 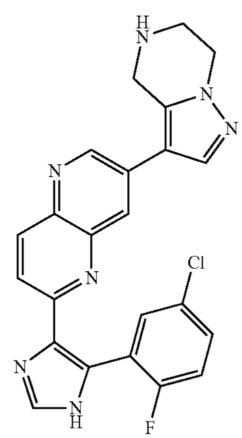 [SMILES: Fc1ccc(Cl)cc1-c1[nH]cnc1-c1ccc2ncc(-c3cnn4c3CNCC4)cc2n1] | 2-[5-(5-chloro-2-fluoro-phenyl)-1H-imidazol-4-yl]-7-(4,5,6,7-tetrahydropyrazolo[1,5-a]pyrazin-3-yl)-1,5-naphthyridine | 446.1 |
| 2-23 | 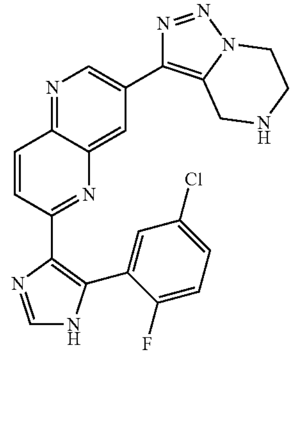 [SMILES: Fc1ccc(Cl)cc1-c1[nH]cnc1-c1ccc2ncc(-c3nnn4c3CNCC4)cc2n1] | 2-[5-(5-chloro-2-fluoro-phenyl)-1H-imidazol-4-yl]-7-(4,5,6,7-tetrahydrotriazolo[1,5-a]pyrazin-3-yl)-1,5-naphthyridine | 447.2 |

TABLE 1-continued

| No. | Structure | Chemical Name | [M + H]+ |
|---|---|---|---|
| 2-24 | 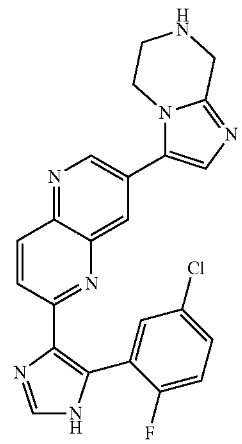 [SMILES: Fc1ccc(Cl)cc1-c1[nH]cnc1-c1ccc2ncc(-c3cnc4n3CCNC4)cc2n1] | 2-[5-(5-chloro-2-fluoro-phenyl)-1H-imidazol-4-yl]-7-(5,6,7,8-tetrahydroimidazo[1,2-a]pyrazin-3-yl)-1,5-naphthyridine | 446.0 |
| 2-25 | 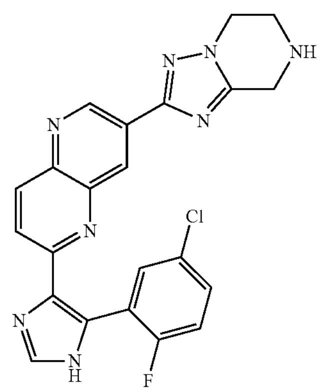 [SMILES: Fc1ccc(Cl)cc1-c1[nH]cnc1-c1ccc2ncc(-c3nc4n(n3)CCNC4)cc2n1] | 2-[5-(5-chloro-2-fluoro-phenyl)-1H-imidazol-4-yl]-7-(5,6,7,8-tetrahydro-[1,2,4]triazolo[1,5-a]pyrazin-2-yl)-1,5-naphthyridine | 447.0 |
| 2-26 | 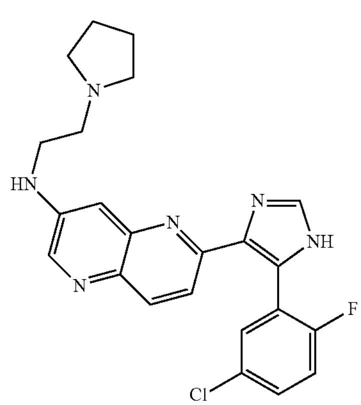 [SMILES: Fc1ccc(Cl)cc1-c1[nH]cnc1-c1ccc2ncc(NCCN3CCCC3)cc2n1] | 6-[5-(5-chloro-2-fluoro-phenyl)-1H-imidazol-4-yl]-N-(2-pyrrolidin-1-ylethyl)-1,5-naphthyridin-3-amine | 437.2 |

TABLE 1-continued

| No. | Structure | Chemical Name | [M + H]+ |
|---|---|---|---|
| 2-27 | 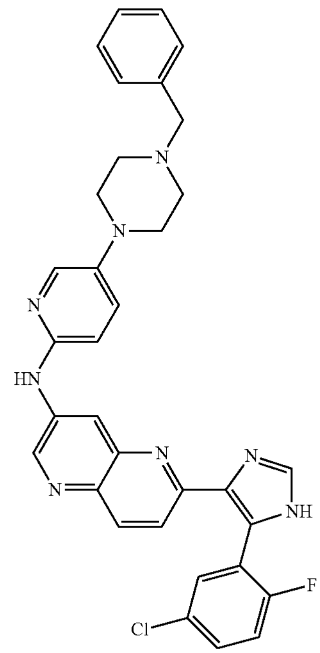 [SMILES: Fc1ccc(Cl)cc1-c1[nH]cnc1-c1ccc2ncc(Nc3ccc(N4CCN(Cc5ccccc5)CC4)cn3)cc2n1] | N-[5-(4-benzylpiperazin-1-yl)-2-pyridyl]-6-[5-(5-chloro-2-fluoro-phenyl)-1H-imidazol-4-yl]-1,5-naphthyridin-3-amine | 591.0 |
| 2-28 | 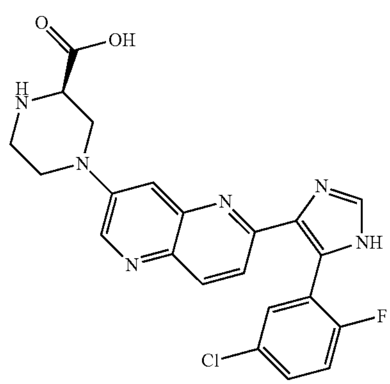 [SMILES: O=C(O)[C@H]1CN(c2cnc3ccc(-c4nc[nH]c4-c4cc(Cl)ccc4F)nc3c2)CCN1] | (2R)-4-[6-[5-(5-chloro-2-fluoro-phenyl)-1H-imidazol-4-yl]-1,5-naphthyridin-3-yl]piperazine-2-carboxylic acid | 453.1 |
| 2-29 | 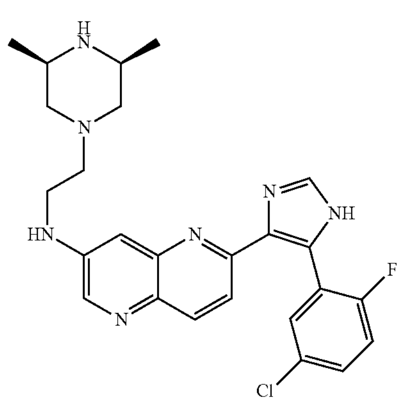 [SMILES: C[C@@H]1CN(CCNc2cnc3ccc(-c4nc[nH]c4-c4cc(Cl)ccc4F)nc3c2)C[C@H](C)N1] | 6-[5-(5-chloro-2-fluoro-phenyl)-1H-imidazol-4-yl]-N-[2-[rac-(3R,5S)-3,5-dimethylpiperazin-1-yl]ethyl]-1,5-naphthyridin-3-amine | 480.2 |

TABLE 1-continued

| No. | Structure | Chemical Name | [M + H]+ |
|---|---|---|---|
| 2-30 | 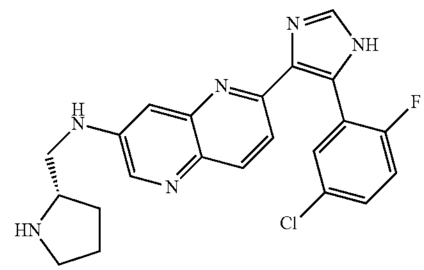 [SMILES: Fc1ccc(Cl)cc1-c1[nH]cnc1-c1ccc2ncc(NC[C@@H]3CCCN3)cc2n1] | 6-[5-(5-chloro-2-fluoro-phenyl)-1H-imidazol-4-yl]-N-[[(2S)-pyrrolidin-2-yl]methyl]-1,5-naphthyridin-3-amine | 423.0 |
| 2-31 | 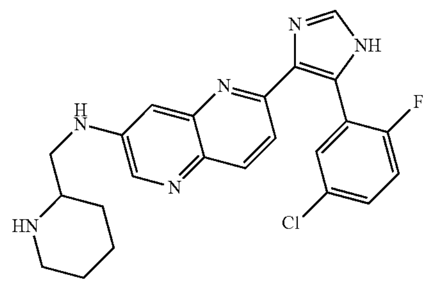 [SMILES: Fc1ccc(Cl)cc1-c1[nH]cnc1-c1ccc2ncc(NCC3CCCCN3)cc2n1] | 6-[5-(5-chloro-2-fluoro-phenyl)-1H-imidazol-4-yl]-N-(2-piperidylmethyl)-1,5-naphthyridin-3-amine | 437.1 |
| 2-32 | 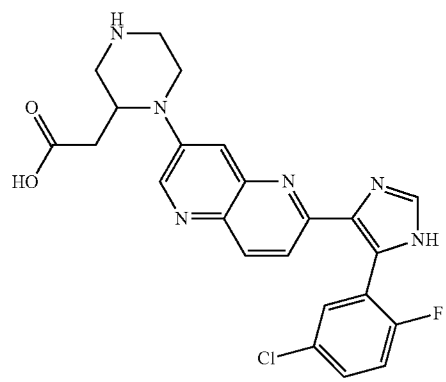 [SMILES: O=C(O)CC1CNCCN1c1cnc2ccc(-c3nc[nH]c3-c3cc(Cl)ccc3F)nc2c1] | 2-[1-[6-[5-(5-chloro-2-fluoro-phenyl)-1H-imidazol-4-yl]-1,5-naphthyridin-3-yl]piperazin-2-yl]acetic acid | 467.1 |
| 2-33 | 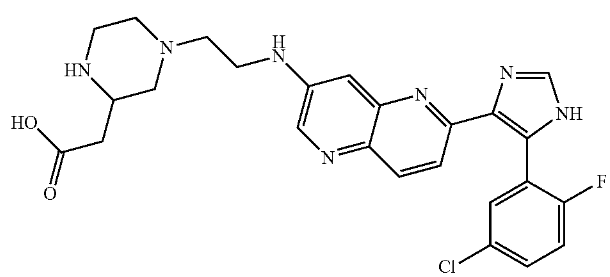 [SMILES: O=C(O)CC1CN(CCNc2cnc3ccc(-c4nc[nH]c4-c4cc(Cl)ccc4F)nc3c2)CCN1] | 2-[5-[2-[[6-[5-(5-chloro-2-fluoro-phenyl)-1H-imidazol-4-yl]-1,5-naphthyridin-3-yl]amino]ethyl]piperazin-2-yl]acetic acid | 510.1 |
| 2-34 | 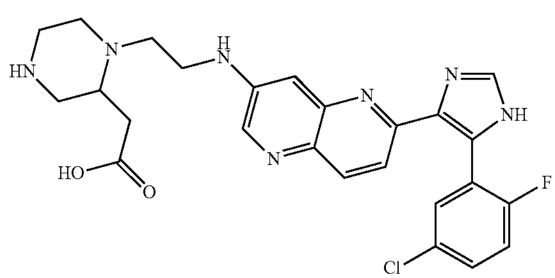 [SMILES: O=C(O)CC1CNCCN1CCNc1cnc2ccc(-c3nc[nH]c3-c3cc(Cl)ccc3F)nc2c1] | 2-[1-[2-[[6-[5-(5-chloro-2-fluoro-phenyl)-1H-imidazol-4-yl]-1,5-naphthyridin-3-yl]amino]ethyl]piperazin-2-yl]acetic acid | 510.1 |

TABLE 1-continued

| No. | Structure | Chemical Name | [M + H]+ |
|---|---|---|---|
| 2-35 | 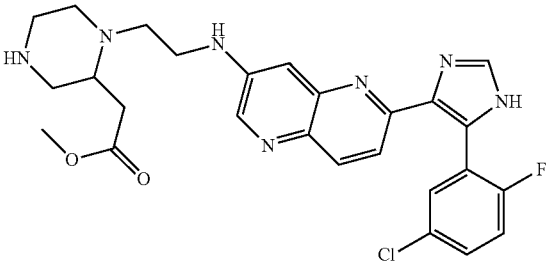 [SMILES: COC(=O)CC1CNCCN1CCNc1cnc2ccc(-c3nc[nH]c3-c3cc(Cl)ccc3F)nc2c1] | methyl 2-[1-[2-[[6-[5-(5-chloro-2-fluoro-phenyl)-1H-imidazol-4-yl]-1,5-naphthyridin-3-yl]amino]ethyl]piperazin-2-yl]acetate | 524.1 |
| 2-36 | 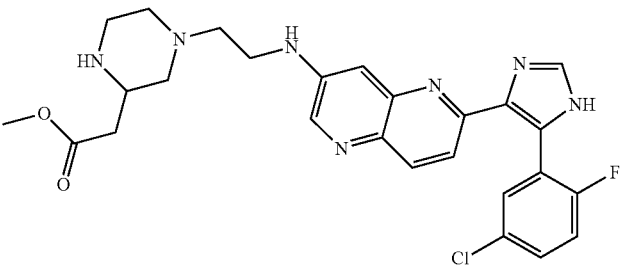 [SMILES: COC(=O)CC1CN(CCNc2cnc3ccc(-c4nc[nH]c4-c4cc(Cl)ccc4F)nc3c2)CCN1] | methyl 2-[4-[2-[[6-[5-(5-chloro-2-fluoro-phenyl)-1H-imidazol-4-yl]-1,5-naphthyridin-3-yl]amino]ethyl]piperazin-2-yl]acetate | 524.0 |
| 2-37 | 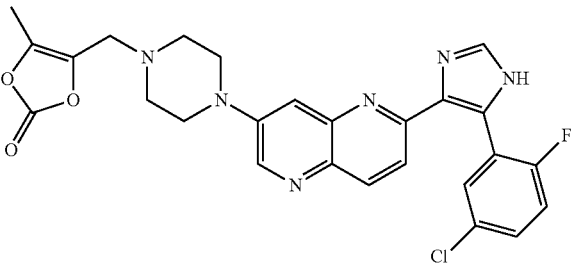 [SMILES: Cc1oc(=O)oc1CN1CCN(c2cnc3ccc(-c4nc[nH]c4-c4cc(Cl)ccc4F)nc3c2)CC1] | 4-[[4-[6-[5-(5-chloro-2-fluoro-phenyl)-1H-imidazol-4-yl]-1,5-naphthyridin-3-yl]piperazin-1-yl]methyl]-5-methyl-1,3-dioxol-2-one | 521.1 |
| 2-38 | 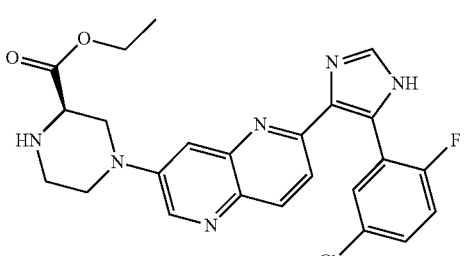 | ethyl (2R)-4-[6-[5-(5-chloro-2-fluoro-phenyl)-1H-imidazol-4-yl]-1,5-naphthyridin-3-yl]piperazine-2-carboxylate | 481.0 |
| 3-1 | 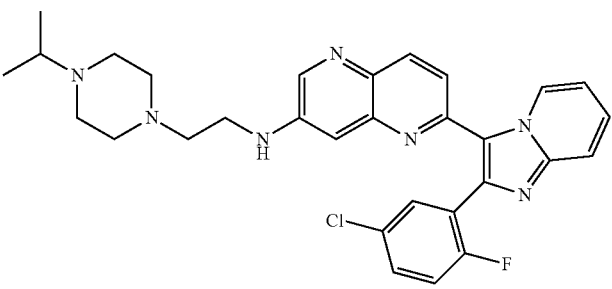 [SMILES: CC(C)N1CCN(CCNc2cnc3ccc(-c4c(-c5cc(Cl)ccc5F)nc5ccccn45)nc3c2)CC1] | 6-[2-(5-chloro-2-fluoro-phenyl)imidazo[1,2-a]pyridin-3-yl]-N-[2-(4-isopropylpiperazin-1-yl)ethyl]-1,5-naphthyridin-3-amine | 544.2 |

TABLE 1-continued

| No. | Structure | Chemical Name | [M + H]+ |
|---|---|---|---|
| 3-2 | 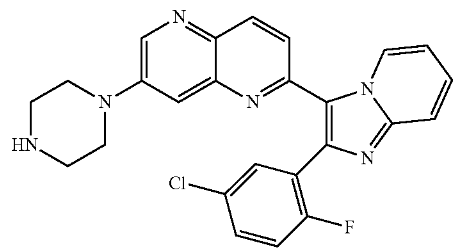 [SMILES: Fc1ccc(Cl)cc1-c1nc2ccccn2c1-c1ccc2ncc(N3CCNCC3)cc2n1] | 2-[2-(5-chloro-2-fluoro-phenyl)imidazo[1,2-a]pyridin-3-yl]-7-piperazin-1-yl-1,5-naphthyridine | 459.1 |
| 3-3 | 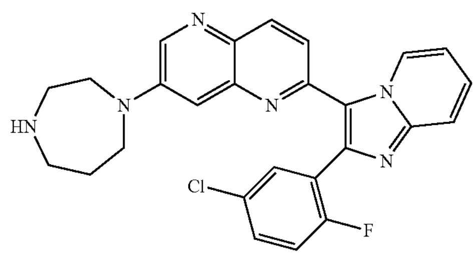 | 2-[2-(5-chloro-2-fluoro-phenyl)imidazo[1,2-a]pyridin-3-yl]-7-(1,4-diazepan-1-yl)-1,5-naphthyridine | 473.1 |
| 3-4 | AND Enantiomer | rac-(3S)-1-[6-[2-(5-chloro-2-fluoro-phenyl)imidazo[1,2-a]pyridin-3-yl]-1,5-naphthyridin-3-yl]-N,N-dimethyl-pyrrolidin-3-amine | 487.1 |
| 3-5 | 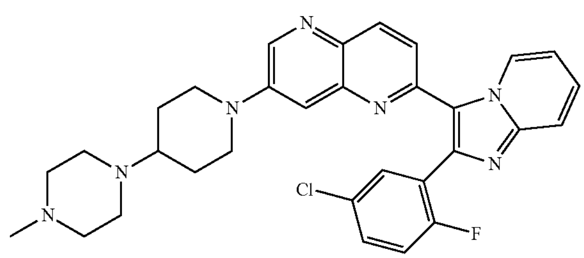 [SMILES: CN1CCN(C2CCN(c3cnc4ccc(-c5c(-c6cc(Cl)ccc6F)nc6ccccn56)nc4c3)CC2)CC1] | 2-[2-(5-chloro-2-fluoro-phenyl)imidazo[1,2-a]pyridin-3-yl]-7-[4-(4-methylpiperazin-1-yl)-1-piperidyl]-1,5-naphthyridine | 556.2 |
| 3-6 | 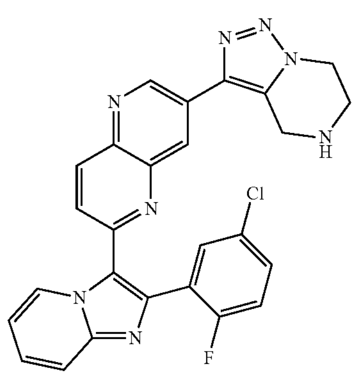 [SMILES: Fc1ccc(Cl)cc1-c1nc2ccccn2c1-c1ccc2ncc(-c3nnn4c3CNCC4)cc2n1] | 2-[2-(5-chloro-2-fluoro-phenyl)imidazo[1,2-a]pyridin-3-yl]-7-(4,5,6,7-tetrahydrotriazolo[1,5-a]pyrazin-3-yl)-1,5-naphthyridine | 497.1 |

TABLE 1-continued

| No. | Structure | Chemical Name | [M + H]+ |
|---|---|---|---|
| 3-7 | 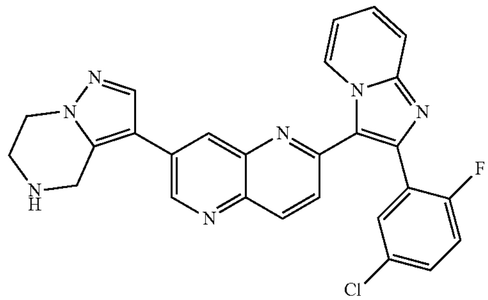 [SMILES: Fc1ccc(Cl)cc1-c1nc2ccccn2c1-c1ccc2ncc(-c3cnn4c3CNCC4)cc2n1] | 2-[2-(5-chloro-2-fluoro-phenyl)imidazo[1,2-a]pyridin-3-yl]-7-(4,5,6,7-tetrahydropyrazolo[1,5-a]pyrazin-3-yl)-1,5-naphthyridine | 496.1 |
| 3-8 | 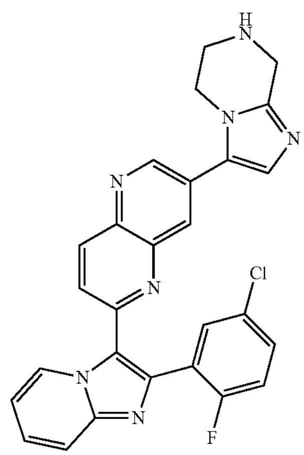 [SMILES: Fc1ccc(Cl)cc1-c1nc2ccccn2c1-c1ccc2ncc(-c3cnc4n3CCNC4)cc2n1] | 2-[2-(5-chloro-2-fluoro-phenyl)imidazo[1,2-a]pyridin-3-yl]-7-(5,6,7,8-tetrahydroimidazo[1,2-a]pyrazin-3-yl)-1,5-naphthyridine | 496.1 |
| 3-9 | 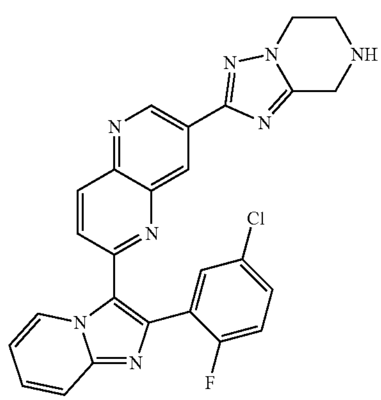 [SMILES: Fc1ccc(Cl)cc1-c1nc2ccccn2c1-c1ccc2ncc(-c3nc4n(n3)CCNC4)cc2n1] | 2-[2-(5-chloro-2-fluoro-phenyl)imidazo[1,2-a]pyridin-3-yl]-7-(5,6,7,8-tetrahydro-[1,2,4]triazolo[1,5-a]pyrazin-2-yl)-1,5-naphthyridine | 497.1 |
| 3-10 | 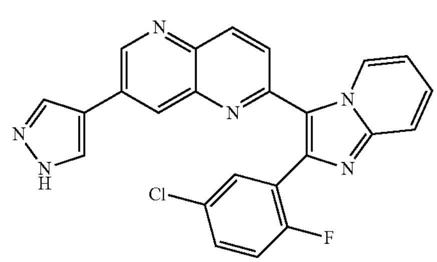 [SMILES: Fc1ccc(Cl)cc1-c1nc2ccccn2c1-c1ccc2ncc(-c3cn[nH]c3)cc2n1] | 2-[2-(5-chloro-2-fluoro-phenyl)imidazo[1,2-a]pyridin-3-yl]-7-(1H-pyrazol-4-yl)-1,5-naphthyridine | 441.1 |

TABLE 1-continued

| No. | Structure | Chemical Name | [M + H]⁺ |
|---|---|---|---|
| 4-1 | 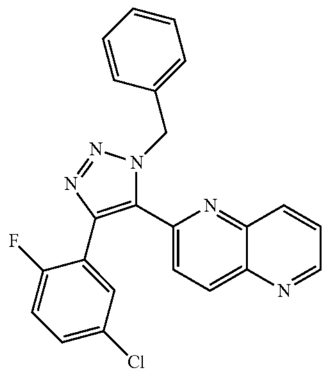 [SMILES: Fc1ccc(Cl)cc1-c1nnn(Cc2ccccc2)c1-c1ccc2ncccc2n1] | 2-[3-benzyl-5-(5-chloro-2-fluoro-phenyl)triazol-4-yl]-1,5-naphthyridine | 416.2 |
| 4-2 | 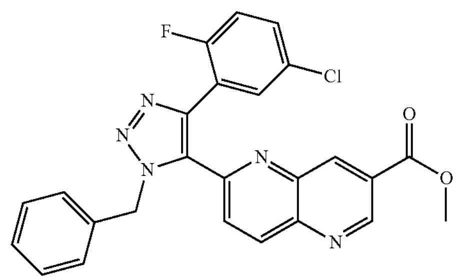 [SMILES: COC(=O)c1cnc2ccc(-c3c(-c4cc(Cl)ccc4F)nnn3Cc3ccccc3)nc2c1] | methyl 6-[3-benzyl-5-(5-chloro-2-fluoro-phenyl)triazol-4-yl]-1,5-naphthyridine-3-carboxylate | 474.0 |
| 5-1 | 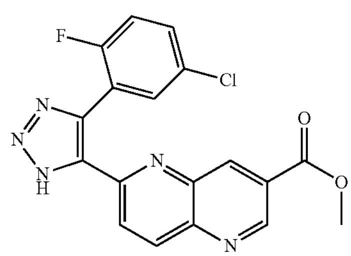 [SMILES: COC(=O)c1cnc2ccc(-c3[nH]nnc3-c3cc(Cl)ccc3F)nc2c1] | methyl 6-[4-(5-chloro-2-fluoro-phenyl)-1H-triazol-5-yl]-1,5-naphthyridine-3-carboxylate | 384.0 |
| 5-2 | 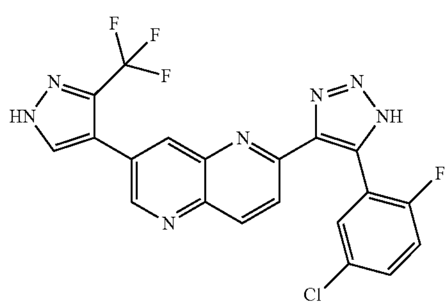 [SMILES: Fc1ccc(Cl)cc1-c1[nH]nnc1-c1ccc2ncc(-c3c[nH]nc3C(F)(F)F)cc2n1] | 2-[5-(5-chloro-2-fluoro-phenyl)-1H-triazol-4-yl]-7-[3-(trifluoromethyl)-1H-pyrazol-4-yl]-1,5-naphthyridine | 460.9 |
| 6-1 | 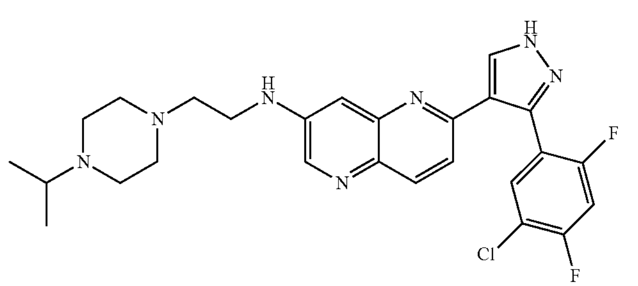 [SMILES: CC(C)N1CCN(CCNc2cnc3ccc(-c4c[nH]nc4-c4cc(Cl)c(F)cc4F)nc3c2)CC1] | 6-[3-(5-chloro-2,4-difluoro-phenyl)-1H-pyrazol-4-yl]-N-[2-(4-isopropylpiperazin-1-yl)ethyl]-1,5-naphthyridin-3-amine | 512.2 |

TABLE 1-continued

| No. | Structure | Chemical Name | [M + H]⁺ |
|---|---|---|---|
| 6-2 | 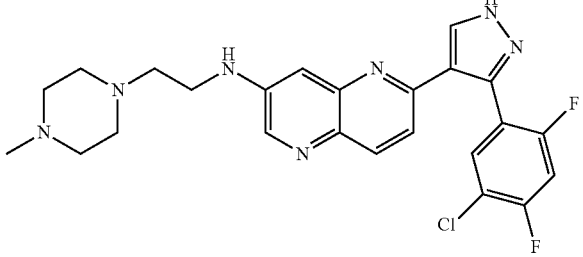 | 6-[3-(5-chloro-2,4-difluoro-phenyl)-1H-pyrazol-4-yl]-N-[2-(4-methylpiperazin-1-yl)ethyl]-1,5-naphthyridin-3-amine | 484.1 |
| 6-3 | 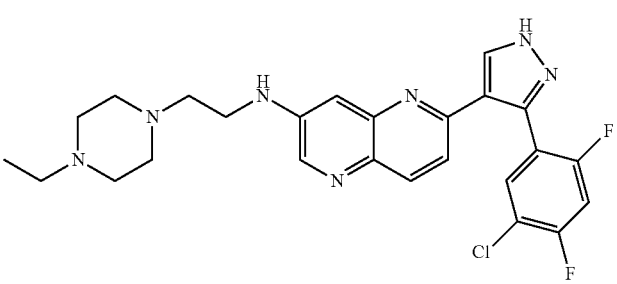 [SMILES: CCN1CCN(CCNc2cnc3ccc(-c4c[nH]nc4-c4cc(Cl)c(F)cc4F)nc3c2)CC1] | 6-[3-(5-chloro-2,4-difluoro-phenyl)-1H-pyrazol-4-yl]-N-[2-(4-ethylpiperazin-1-yl)ethyl]-1,5-naphthyridin-3-amine | 498.1 |
| 6-4 | 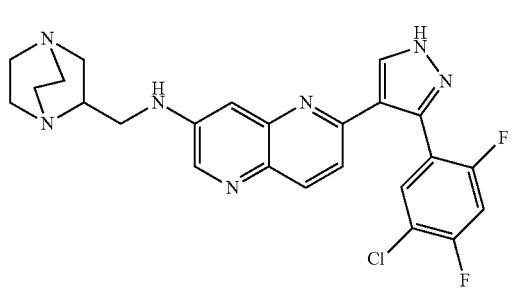 [SMILES: Fc1cc(F)c(-c2n[nH]cc2-c2ccc3ncc(NCC4CN5CCN4CC5)cc3n2)cc1Cl] | 6-[3-(5-chloro-2,4-difluoro-phenyl)-1H-pyrazol-4-yl]-N-(1,4-diazabicyclo[2.2.2]octan-2-ylmethyl)-1,5-naphthyridin-3-amine | 482.1 |
| 6-5 | 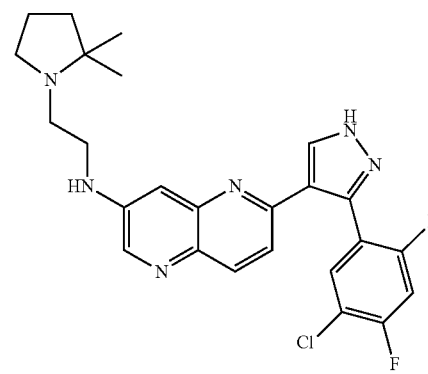 | 6-[3-(5-chloro-2,4-difluoro-phenyl)-1H-pyrazol-4-yl]-N-[2-(2,2-dimethylpyrrolidin-1-yl)ethyl]-1,5-naphthyridin-3-amine | 483.0 |
| 6-6 | 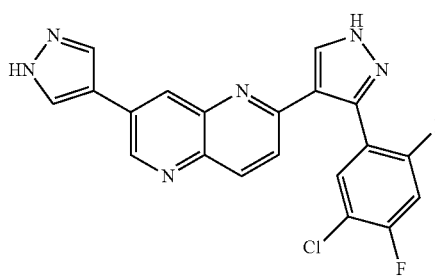 | 2-[3-(5-chloro-2,4-difluoro-phenyl)-1H-pyrazol-4-yl]-7-(1H-pyrazol-4-yl)-1,5-naphthyridine | 409.0 |

TABLE 1-continued

| No. | Structure | Chemical Name | [M + H]+ |
|---|---|---|---|
| 6-7 | 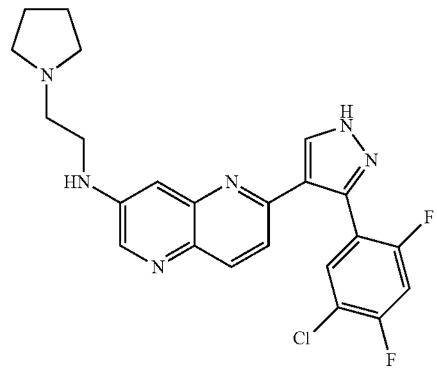 [SMILES: Fc1cc(F)c(-c2n[nH]cc2-c2ccc3ncc(NCCN4CCCC4)cc3n2)cc1Cl] | 6-[3-(5-chloro-2,4-difluoro-phenyl)-1H-pyrazol-4-yl]-N-(2-pyrrolidin-1-ylethyl)-1,5-naphthyridin-3-amine | 455.2 |
| 6-8 | 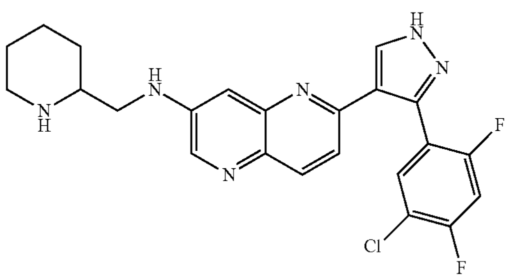 [SMILES: Fc1cc(F)c(-c2n[nH]cc2-c2ccc3ncc(NCC4CCCCN4)cc3n2)cc1Cl] | 6-[3-(5-chloro-2,4-difluoro-phenyl)-1H-pyrazol-4-yl]-N-(2-piperidylmethyl)-1,5-naphthyridin-3-amine | 455.1 |
| 6-9 | 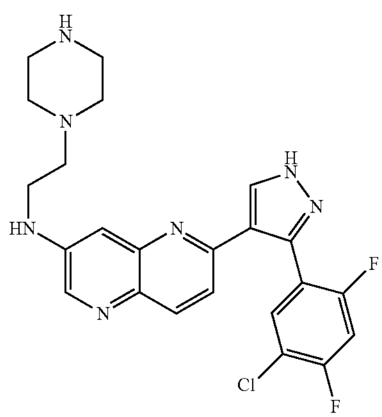 [SMILES: Fc1cc(F)c(-c2n[nH]cc2-c2ccc3ncc(NCCN4CCNCC4)cc3n2)cc1Cl] | 6-[3-(5-chloro-2,4-difluoro-phenyl)-1H-pyrazol-4-yl]-N-(2-piperazin-1-ylethyl)-1,5-naphthyridin-3-amine | 470.1 |
| 6-10 | 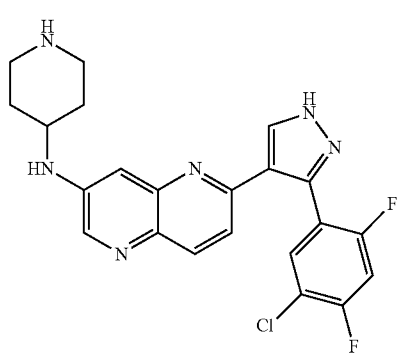 [SMILES: Fc1cc(F)c(-c2n[nH]cc2-c2ccc3ncc(NC4CCNCC4)cc3n2)cc1Cl] | 6-[3-(5-chloro-2,4-difluoro-phenyl)-1H-pyrazol-4-yl]-N-(4-piperidyl)-1,5-naphthyridin-3-amine | 441.1 |

TABLE 1-continued

| No. | Structure | Chemical Name | [M + H]⁺ |
|---|---|---|---|
| 6-11 | 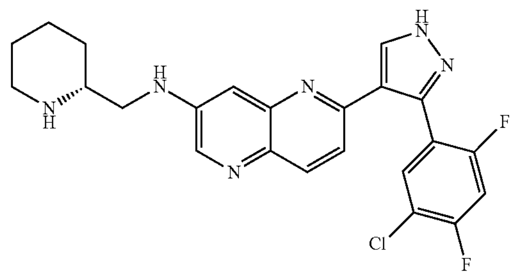 [SMILES: Fc1cc(F)c(-c2n[nH]cc2-c2ccc3ncc(NC[C@H]4CCCCN4)cc3n2)cc1Cl] | 6-[3-(5-chloro-2,4-difluoro-phenyl)-1H-pyrazol-4-yl]-N-[[(2R)-2-piperidyl]methyl]-1,5-naphthyridin-3-amine | 455.1 |
| 6-12 | 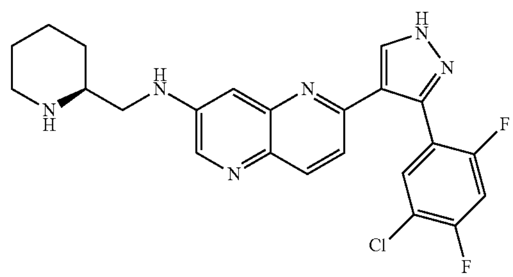 [SMILES: Fc1cc(F)c(-c2n[nH]cc2-c2ccc3ncc(NC[C@@H]4CCCCN4)cc3n2)cc1Cl] | 6-[3-(5-chloro-2,4-difluoro-phenyl)-1H-pyrazol-4-yl]-N-[[(2S)-2-piperidyl]methyl]-1,5-naphthyridin-3-amine | 455.1 |
| 6-13 | 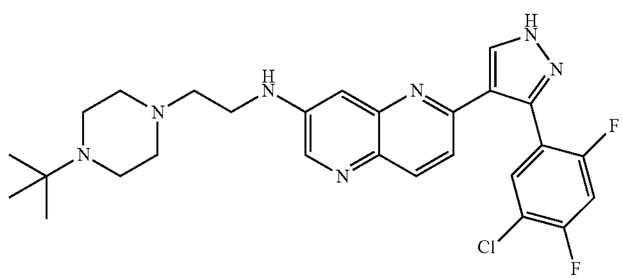 [SMILES: CC(C)(C)N1CCN(CCNc2cnc3ccc(-c4c[nH]nc4-c4cc(Cl)c(F)cc4F)nc3c2)CC1] | N-[2-(4-tert-butylpiperazin-1-yl)ethyl]-6-[3-(5-chloro-2,4-difluoro-phenyl)-1H-pyrazol-4-yl]-1,5-naphthyridin-3-amine | 526.2 |
| 6-14 | 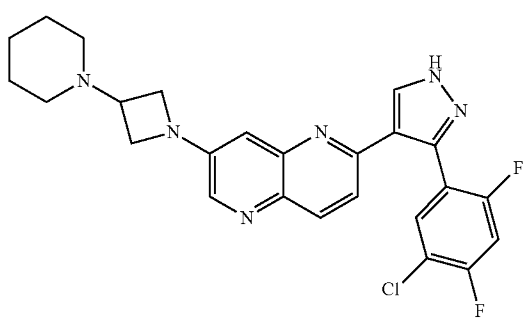 [SMILES: Fc1cc(F)c(-c2n[nH]cc2-c2ccc3ncc(N4CC(N5CCCCC5)C4)cc3n2)cc1Cl] | 2-[3-(5-chloro-2,4-difluoro-phenyl)-1H-pyrazol-4-yl]-7-[3-(1-piperidyl)azetidin-1-yl]-1,5-naphthyridine | 481.1 |
| 6-15 | 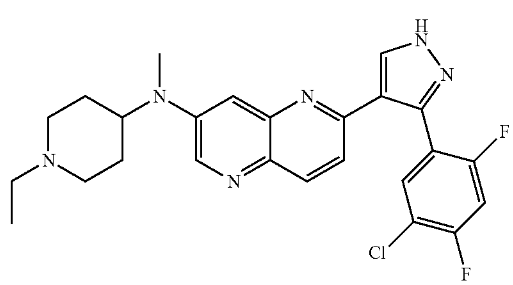 [SMILES: CCN1CCC(N(C)c2cnc3ccc(-c4c[nH]nc4-c4cc(Cl)c(F)cc4F)nc3c2)CC1] | 6-[3-(5-chloro-2,4-difluoro-phenyl)-1H-pyrazol-4-yl]-N-(1-ethyl-4-piperidyl)-N-methyl-1,5-naphthyridin-3-amine | 483.1 |

TABLE 1-continued

| No. | Structure | Chemical Name | [M + H]+ |
|---|---|---|---|
| 6-16 | 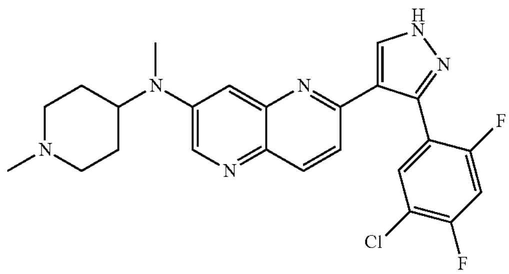 [SMILES: CN1CCC(N(C)c2cnc3ccc(-c4c[nH]nc4-c4cc(Cl)c(F)cc4F)nc3c2)CC1] | 6-[3-(5-chloro-2,4-difluoro-phenyl)-1H-pyrazol-4-yl]-N-methyl-N-(1-methyl-4-piperidyl)-1,5-naphthyridin-3-amine | 469.2 |
| 6-17 | 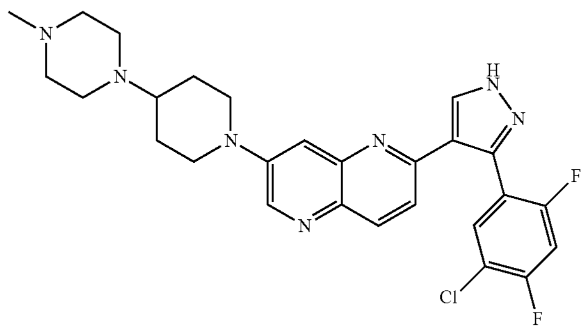 [SMILES: CN1CCN(C2CCN(c3cnc4ccc(-c5c[nH]nc5-c5cc(Cl)c(F)cc5F)nc4c3)CC2)CC1] | 2-[3-(5-chloro-2,4-difluoro-phenyl)-1H-pyrazol-4-yl]-7-[4-(4-methylpiperazin-1-yl)-1-piperidyl]-1,5-naphthyridine | 524.2 |
| 6-18 | 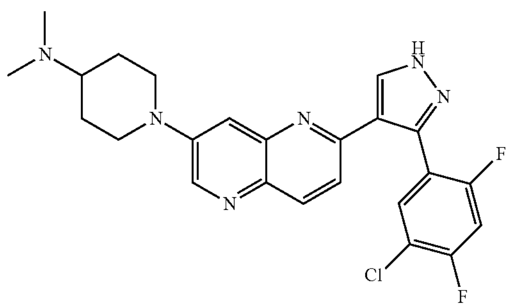 [SMILES: CN(C)C1CCN(c2cnc3ccc(-c4c[nH]nc4-c4cc(Cl)c(F)cc4F)nc3c2)CC1] | 1-[6-[3-(5-chloro-2,4-difluoro-phenyl)-1H-pyrazol-4-yl]-1,5-naphthyridin-3-yl]-N,N-dimethyl-piperidin-4-amine | 469.1 |
| 6-19 | 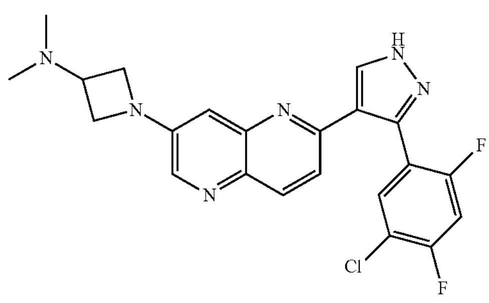 [SMILES: CN(C)C1CN(c2cnc3ccc(-c4c[nH]nc4-c4cc(Cl)c(F)cc4F)nc3c2)C1] | 1-[6-[3-(5-chloro-2,4-difluoro-phenyl)-1H-pyrazol-4-yl]-1,5-naphthyridin-3-yl]-N,N-dimethyl-azetidin-3-amine | 441.1 |
| 6-20 | 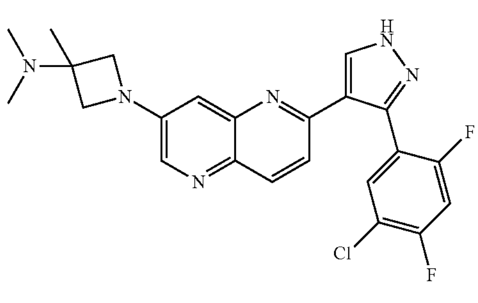 [SMILES: CN(C)C1(C)CN(c2cnc3ccc(-c4c[nH]nc4-c4cc(Cl)c(F)cc4F)nc3c2)C1] | 1-[6-[3-(5-chloro-2,4-difluoro-phenyl)-1H-pyrazol-4-yl]-1,5-naphthyridin-3-yl]-N,N,3-trimethyl-azetidin-3-amine | 455.0 |

TABLE 1-continued

| No. | Structure | Chemical Name | [M + H]⁺ |
|---|---|---|---|
| 6-21 | AND Enantiomer | 2-[3-(5-chloro-2,4-difluoro-phenyl)-1H-pyrazol-4-yl]-7-[rac-(3R)-3-(1-piperidyl)pyrrolidin-1-yl]-1,5-naphthyridine | 495.1 |
| 6-22 | AND Enantiomer | rac-(3S)-1-[6-[3-(5-chloro-2,4-difluoro-phenyl)-1H-pyrazol-4-yl]-1,5-naphthyridin-3-yl]-N,N-dimethyl-pyrrolidin-3-amine | 455.0 |
| 6-23 | 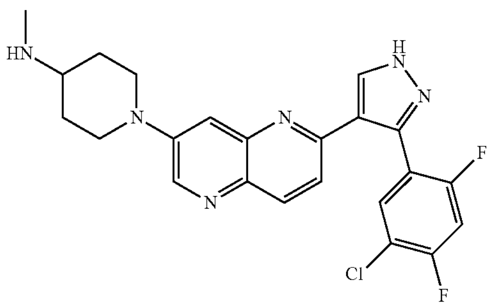 [SMILES: CNC1CCN(c2cnc3ccc(-c4c[nH]nc4-c4cc(Cl)c(F)cc4F)nc3c2)CC1] | 1-[6-[3-(5-chloro-2,4-difluoro-phenyl)-1H-pyrazol-4-yl]-1,5-naphthyridin-3-yl]-N-methyl-piperidin-4-amine | 455.1 |
| 6-24 | 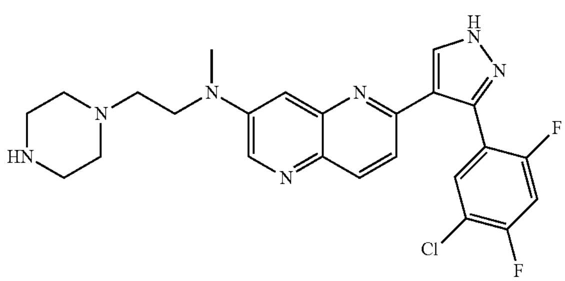 [SMILES: CN(CCN1CCNCC1)c1cnc2ccc(-c3c[nH]nc3-c3cc(Cl)c(F)cc3F)nc2c1] | 6-[3-(5-chloro-2,4-difluoro-phenyl)-1H-pyrazol-4-yl]-N-methyl-N-(2-piperazin-1-ylethyl)-1,5-naphthyridin-3-amine | 484.0 |
| 6-25 | AND Enantiomer | rac-(2R)-4-[6-[3-(5-chloro-2,4-difluoro-phenyl)-1H-pyrazol-4-yl]-1,5-naphthyridin-3-yl]-N-methyl-piperazine-2-carboxamide | 484.0 |

TABLE 1-continued

| No. | Structure | Chemical Name | [M + H]+ |
|---|---|---|---|
| 6-26 | 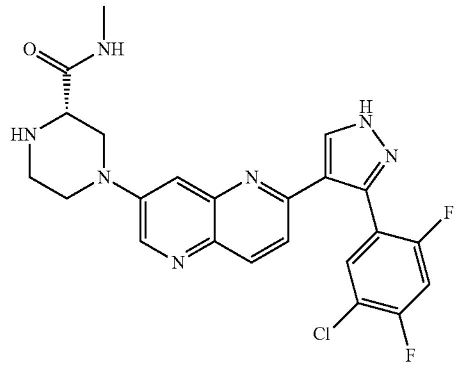 [SMILES: CNC(=O)[C@@H]1CN(c2cnc3ccc(-c4c[nH]nc4-c4cc(Cl)c(F)cc4F)nc3c2)CCN1] | (2S)-4-[6-[3-(5-chloro-2,4-difluoro-phenyl)-1H-pyrazol-4-yl]-1,5-naphthyridin-3-yl]-N-methyl-piperazine-2-carboxamide | 484.0 |
| 6-27 | 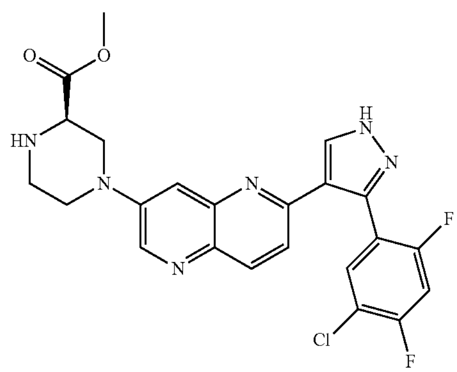 [SMILES: COC(=O)[C@H]1CN(c2cnc3ccc(-c4c[nH]nc4-c4cc(Cl)c(F)cc4F)nc3c2)CCN1] | methyl (2R)-4-[6-[3-(5-chloro-2,4-difluoro-phenyl)-1H-pyrazol-4-yl]-1,5-naphthyridin-3-yl]piperazine-2-carboxylate | 485.0 |
| 6-28 | 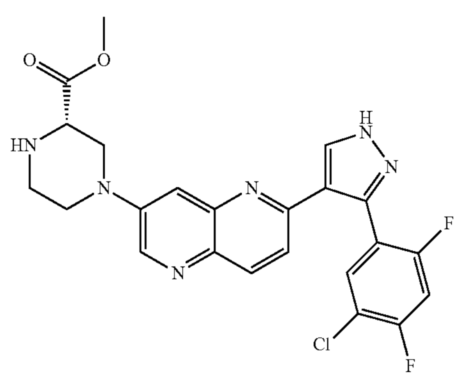 [SMILES: COC(=O)[C@@H]1CN(c2cnc3ccc(-c4c[nH]nc4-c4cc(Cl)c(F)cc4F)nc3c2)CCN1] | methyl (2S)-4-[6-[3-(5-chloro-2,4-difluoro-phenyl)-1H-pyrazol-4-yl]-1,5-naphthyridin-3-yl]piperazine-2-carboxylate | 485.1 |
| 6-29 | 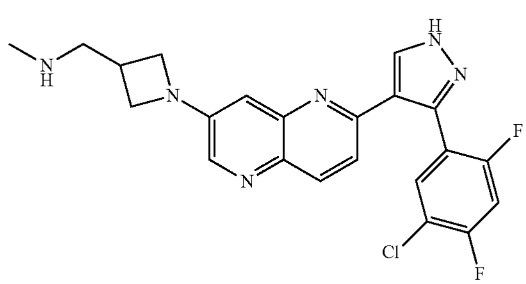 [SMILES: CNCC1CN(c2cnc3ccc(-c4c[nH]nc4-c4cc(Cl)c(F)cc4F)nc3c2)C1] | 1-[1-[6-[3-(5-chloro-2,4-difluoro-phenyl)-1H-pyrazol-4-yl]-1,5-naphthyridin-3-yl]azetidin-3-yl]-N-methyl-methanamine | 441.1 |

TABLE 1-continued

| No. | Structure | Chemical Name | [M + H]+ |
|---|---|---|---|
| 6-30 | 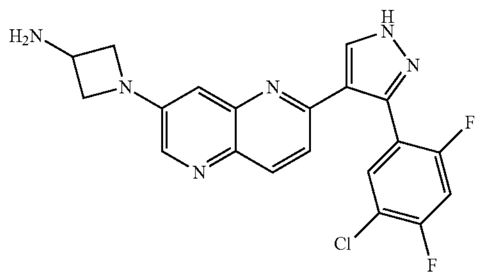 [SMILES: NC1CN(c2cnc3ccc(-c4c[nH]nc4-c4cc(Cl)c(F)cc4F)nc3c2)C1] | 1-[6-[3-(5-chloro-2,4-difluoro-phenyl)-1H-pyrazol-4-yl]-1,5-naphthyridin-3-yl]azetidin-3-amine | 413.1 |
| 6-31 | 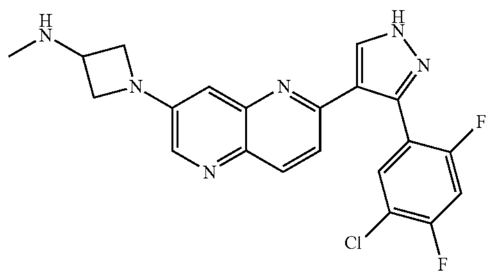 [SMILES: CNC1CN(c2cnc3ccc(-c4c[nH]nc4-c4cc(Cl)c(F)cc4F)nc3c2)C1] | 1-[6-[3-(5-chloro-2,4-difluoro-phenyl)-1H-pyrazol-4-yl]-1,5-naphthyridin-3-yl]-N-methyl-azetidin-3-amine | 427.1 |
| 6-32 | 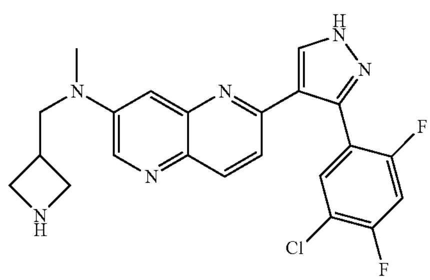 [SMILES: CN(CC1CNC1)c1cnc2ccc(-c3c[nH]nc3-c3cc(Cl)c(F)cc3F)nc2c1] | N-(azetidin-3-ylmethyl)-6-[3-(5-chloro-2,4-difluoro-phenyl)-1H-pyrazol-4-yl]-N-methyl-1,5-naphthyridin-3-amine | 441.0 |
| 6-33 | 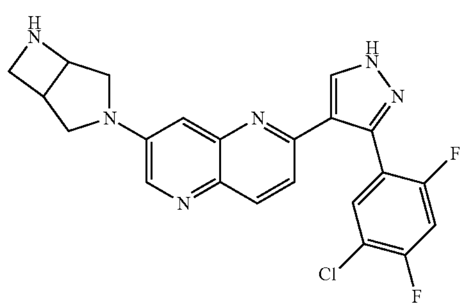 [SMILES: Fc1cc(F)c(-c2n[nH]cc2-c2ccc3ncc(N4CC5CNC5C4)cc3n2)cc1Cl] | 2-[3-(5-chloro-2,4-difluoro-phenyl)-1H-pyrazol-4-yl]-7-(3,6-diazabicyclo[3.2.0]heptan-3-yl)-1,5-naphthyridine | 439.1 |
| 6-34 | 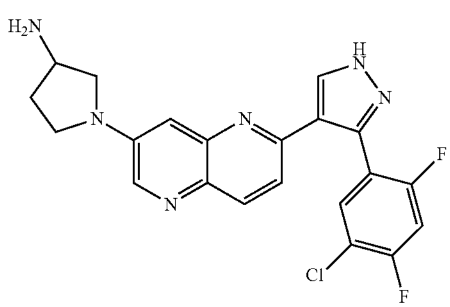 [SMILES: NC1CCN(c2cnc3ccc(-c4c[nH]nc4-c4cc(Cl)c(F)cc4F)nc3c2)C1] | 1-[6-[3-(5-chloro-2,4-difluoro-phenyl)-1H-pyrazol-4-yl]-1,5-naphthyridin-3-yl]pyrrolidin-3-amine | 427.1 |

TABLE 1-continued

| No. | Structure | Chemical Name | [M + H]+ |
|---|---|---|---|
| 6-35 | 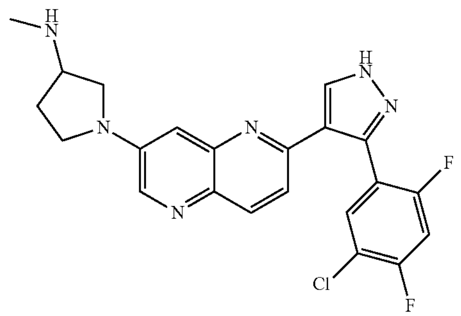 [SMILES: CNC1CCN(c2cnc3ccc(-c4c[nH]nc4-c4cc(Cl)c(F)cc4F)nc3c2)C1] | 1-[6-[3-(5-chloro-2,4-difluoro-phenyl)-1H-pyrazol-4-yl]-1,5-naphthyridin-3-yl]-N-methyl-pyrrolidin-3-amine | 441.0 |
| 6-36 | 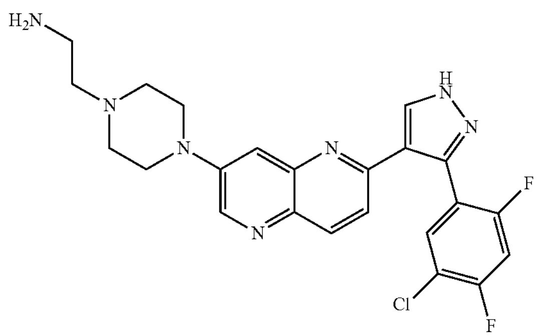 [SMILES: NCCN1CCN(c2cnc3ccc(-c4c[nH]nc4-c4cc(Cl)c(F)cc4F)nc3c2)CC1] | 2-[4-[6-[3-(5-chloro-2,4-difluoro-phenyl)-1H-pyrazol-4-yl]-1,5-naphthyridin-3-yl]piperazin-1-yl]ethanamine | 470.1 |
| 6-37 | 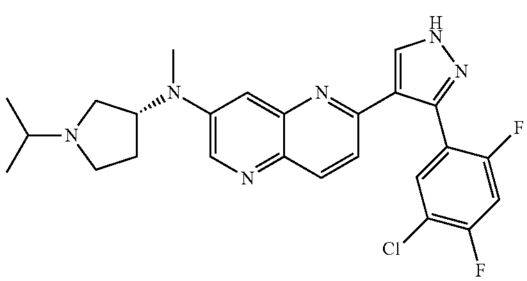 [SMILES: CC(C)N1CC[C@@H](N(C)c2cnc3ccc(-c4c[nH]nc4-c4cc(Cl)c(F)cc4F)nc3c2)C1] | 6-[3-(5-chloro-2,4-difluoro-phenyl)-1H-pyrazol-4-yl]-N-[(3R)-1-isopropylpyrrolidin-3-yl]-N-methyl-1,5-naphthyridin-3-amine | 483.0 |
| 6-38 | 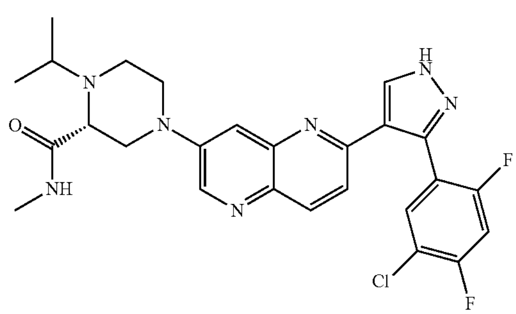 [SMILES: CNC(=O)[C@H]1CN(c2cnc3ccc(-c4c[nH]nc4-c4cc(Cl)c(F)cc4F)nc3c2)CCN1C(C)C] | (2R)-4-[6-[3-(5-chloro-2,4-difluoro-phenyl)-1H-pyrazol-4-yl]-1,5-naphthyridin-3-yl]-1-isopropyl-N-methyl-piperazine-2-carboxamide | 526.1 |

TABLE 1-continued

| No. | Structure | Chemical Name | [M + H]⁺ |
|---|---|---|---|
| 6-39 | 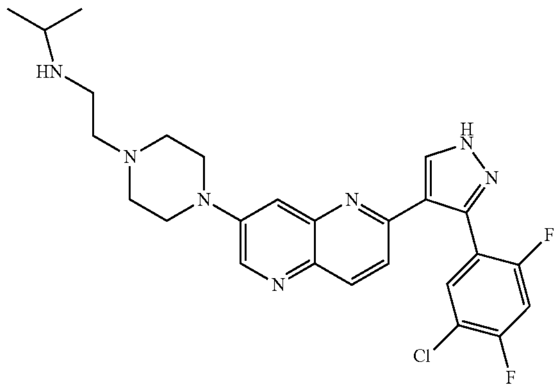 [SMILES: CC(C)NCCN1CCN(c2cnc3ccc(-c4c[nH]nc4-c4cc(Cl)c(F)cc4F)nc3c2)CC1] | N-[2-[4-[6-[3-(5-chloro-2,4-difluoro-phenyl)-1H-pyrazol-4-yl]-1,5-naphthyridin-3-yl]piperazin-1-yl]ethyl]propan-2-amine | 512.2 |
| 6-40 | 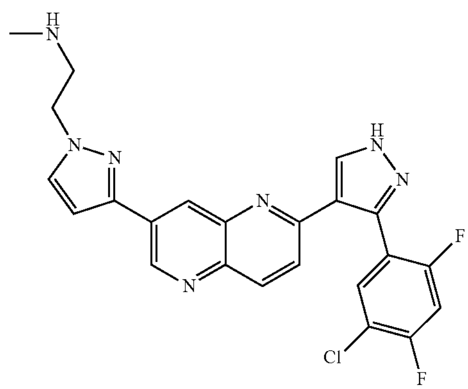 [SMILES: CNCCn1ccc(-c2cnc3ccc(-c4c[nH]nc4-c4cc(Cl)c(F)cc4F)nc3c2)n1] | 2-[3-[6-[3-(5-chloro-2,4-difluoro-phenyl)-1H-pyrazol-4-yl]-1,5-naphthyridin-3-yl]pyrazol-1-yl]-N-methyl-ethanamine | 466.1 |
| 6-41 | 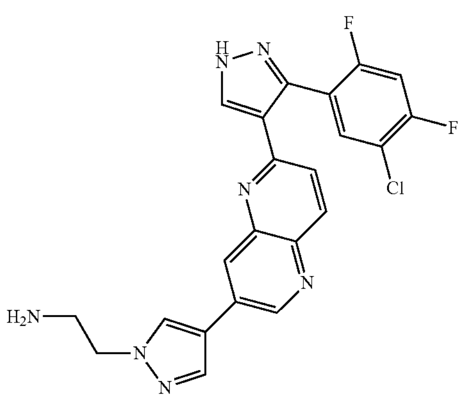 [SMILES: NCCn1cc(-c2cnc3ccc(-c4c[nH]nc4-c4cc(Cl)c(F)cc4F)nc3c2)cn1] | 2-[4-[6-[3-(5-chloro-2,4-difluoro-phenyl)-1H-pyrazol-4-yl]-1,5-naphthyridin-3-yl]pyrazol-1-yl]ethanamine | 452.1 |
| 6-42 | 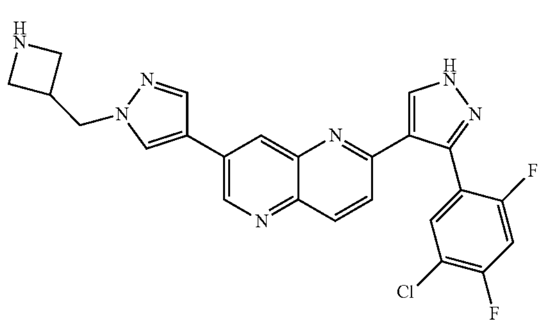 [SMILES: Fc1cc(F)c(-c2n[nH]cc2-c2ccc3ncc(-c4cnn(CC5CNC5)c4)cc3n2)cc1Cl] | 7-[1-(azetidin-3-ylmethyl)pyrazol-4-yl]-2-[3-(5-chloro-2,4-difluoro-phenyl)-1H-pyrazol-4-yl]-1,5-naphthyridine | 478.0 |

TABLE 1-continued

| No. | Structure | Chemical Name | [M + H]+ |
|---|---|---|---|
| 6-43 | 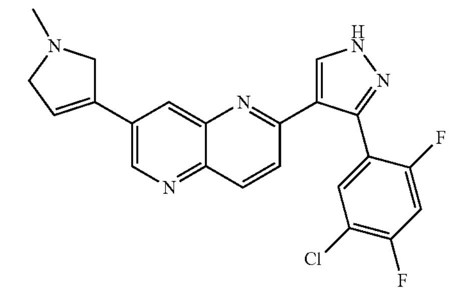 [SMILES: CN1CC=C(c2cnc3ccc(-c4c[nH]nc4-c4cc(Cl)c(F)cc4F)nc3c2)C1] | 2-[3-(5-chloro-2,4-difluoro-phenyl)-1H-pyrazol-4-yl]-7-(1-methyl-2,5-dihydropyrrol-3-yl)-1,5-naphthyridine | 424.1 |
| 6-44 | 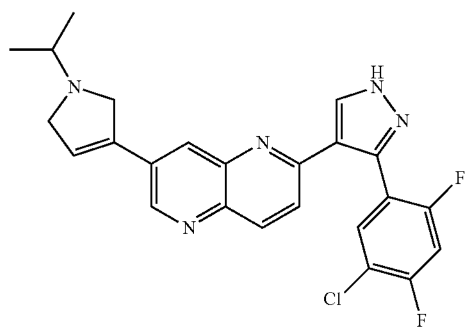 [SMILES: CC(C)N1CC=C(c2cnc3ccc(-c4c[nH]nc4-c4cc(Cl)c(F)cc4F)nc3c2)C1] | 2-[3-(5-chloro-2,4-difluoro-phenyl)-1H-pyrazol-4-yl]-7-(1-isopropyl-2,5-dihydropyrrol-3-yl)-1,5-naphthyridine | 452.0 |
| 6-45 | 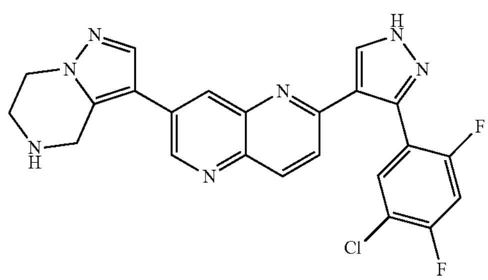 [SMILES: Fc1cc(F)c(-c2n[nH]cc2-c2ccc3ncc(-c4cnn5c4CNCC5)cc3n2)cc1Cl] | 2-[3-(5-chloro-2,4-difluoro-phenyl)-1H-pyrazol-4-yl]-7-(4,5,6,7-tetrahydropyrazolo[1,5-a]pyrazin-3-yl)-1,5-naphthyridine | 464.0 |
| 6-46 | 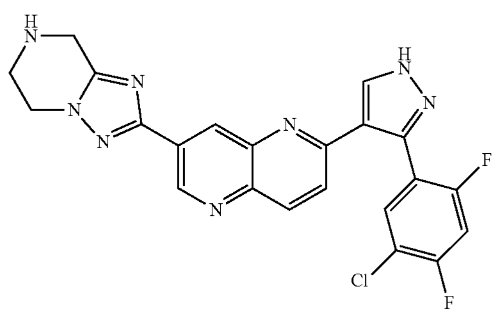 [SMILES: Fc1cc(F)c(-c2n[nH]cc2-c2ccc3ncc(-c4nc5n(n4)CCNC5)cc3n2)cc1Cl] | 2-[3-(5-chloro-2,4-difluoro-phenyl)-1H-pyrazol-4-yl]-7-(5,6,7,8-tetrahydro-[1,2,4]triazolo[1,5-a]pyrazin-2-yl)-1,5-naphthyridine | 465.0 |
| 6-47 | 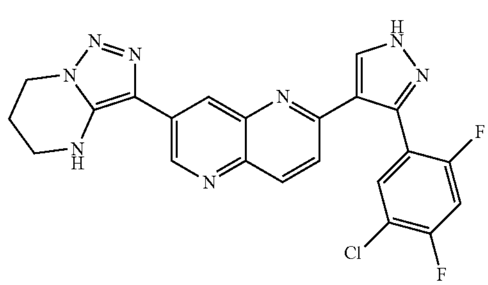 [SMILES: Fc1cc(F)c(-c2n[nH]cc2-c2ccc3ncc(-c4nnn5c4NCCC5)cc3n2)cc1Cl] | 2-[3-(5-chloro-2,4-difluoro-phenyl)-1H-pyrazol-4-yl]-7-(4,5,6,7-tetrahydrotriazolo[1,5-a]pyrimidin-3-yl)-1,5-naphthyridine | 465.0 |

TABLE 1-continued

| No. | Structure | Chemical Name | [M + H]+ |
|---|---|---|---|
| 6-48 | 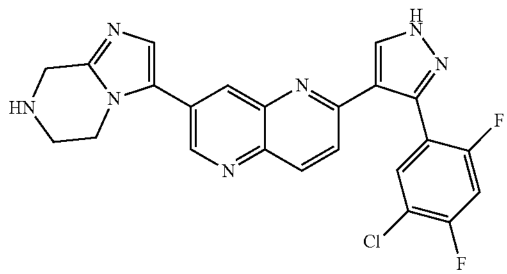 [SMILES: Fc1cc(F)c(-c2n[nH]cc2-c2ccc3ncc(-c4cnc5n4CCNC5)cc3n2)cc1Cl] | 2-[3-(5-chloro-2,4-difluoro-phenyl)-1H-pyrazol-4-yl]-7-(5,6,7,8-tetrahydroimidazo[1,2-a]pyrazin-3-yl)-1,5-naphthyridine | 464.0 |
| 6-49 | 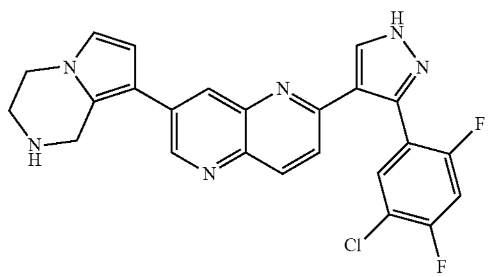 [SMILES: Fc1cc(F)c(-c2n[nH]cc2-c2ccc3ncc(-c4ccn5c4CNCC5)cc3n2)cc1Cl] | 2-[3-(5-chloro-2,4-difluoro-phenyl)-1H-pyrazol-4-yl]-7-(5,6,7,8-tetrahydroimidazo[1,5-a]pyrazin-1-yl)-1,5-naphthyridine | 464.1 |
| 6-50 | 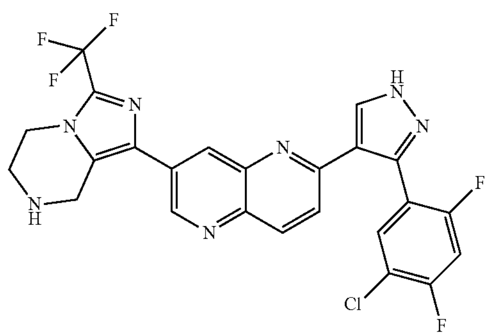 [SMILES: Fc1cc(F)c(-c2n[nH]cc2-c2ccc3ncc(-c4nc(C(F)(F)F)n5c4CNCC5)cc3n2)cc1Cl] | 2-[3-(5-chloro-2,4-difluoro-phenyl)-1H-pyrazol-4-yl]-7-[3-(trifluoromethyl)-5,6,7,8-tetrahydroimidazo[1,5-a]pyrazin-1-yl]-1,5-naphthyridine | 532.0 |
| 6-51 | 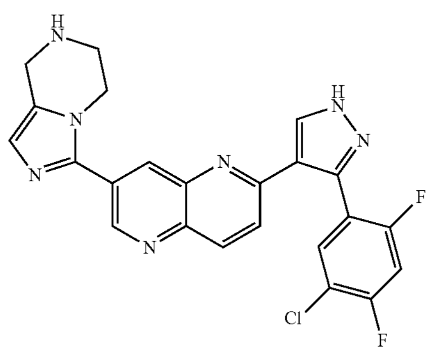 [SMILES: Fc1cc(F)c(-c2n[nH]cc2-c2ccc3ncc(-c4ncc5n4CCNC5)cc3n2)cc1Cl] | 2-[3-(5-chloro-2,4-difluoro-phenyl)-1H-pyrazol-4-yl]-7-(5,6,7,8-tetrahydroimidazo[1,5-a]pyrazin-3-yl)-1,5-naphthyridine | 464.0 |
| 6-52 | 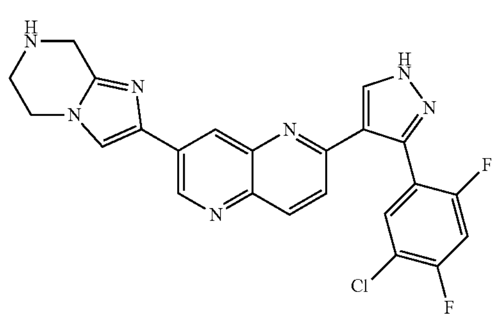 [SMILES: Fc1cc(F)c(-c2n[nH]cc2-c2ccc3ncc(-c4cn5c(n4)CNCC5)cc3n2)cc1Cl] | 2-[3-(5-chloro-2,4-difluoro-phenyl)-1H-pyrazol-4-yl]-7-(5,6,7,8-tetrahydroimidazo[1,2-a]pyrazin-2-yl)-1,5-naphthyridine | 464.1 |

TABLE 1-continued

| No. | Structure | Chemical Name | [M + H]+ |
|---|---|---|---|
| 6-53 | 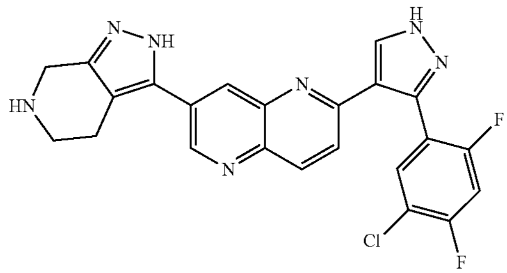 [SMILES: Fc1cc(F)c(-c2n[nH]cc2-c2ccc3ncc(-c4[nH]nc5c4CCNC5)cc3n2)cc1Cl] | 2-[3-(5-chloro-2,4-difluoro-phenyl)-1H-pyrazol-4-yl]-7-(4,5,6,7-tetrahydro-2H-pyrazolo[3,4-c]pyridin-3-yl)-1,5-naphthyridine | 464.1 |
| 6-54 | 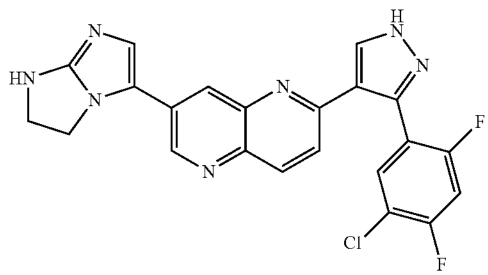 [SMILES: Fc1cc(F)c(-c2n[nH]cc2-c2ccc3ncc(-c4cnc5n4CCN5)cc3n2)cc1Cl] | 2-[3-(5-chloro-2,4-difluoro-phenyl)-1H-pyrazol-4-yl]-7-(6,7-dihydro-5H-imidazo[1,2-a]imidazol-3-yl)-1,5-naphthyridine | 450.0 |
| 6-55 | 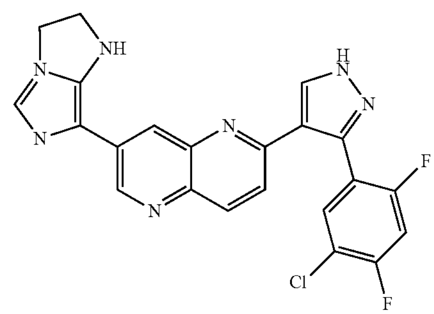 | 2-[3-(5-chloro-2,4-difluoro-phenyl)-1H-pyrazol-4-yl]-7-(2,3-dihydro-1H-imidazo[1,5-a]imidazol-7-yl)-1,5-naphthyridine | 450.1 |
| 6-56 | 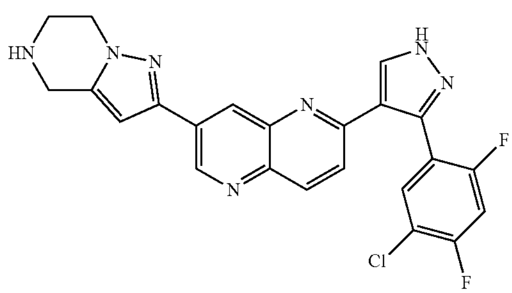 [SMILES: Fc1cc(F)c(-c2n[nH]cc2-c2ccc3ncc(-c4cc5n(n4)CCNC5)cc3n2)cc1Cl] | 2-[3-(5-chloro-2,4-difluoro-phenyl)-1H-pyrazol-4-yl]-7-(4,5,6,7-tetrahydropyrazolo[1,5-a]pyrazin-2-yl)-1,5-naphthyridine | 464.0 |
| 6-57 | 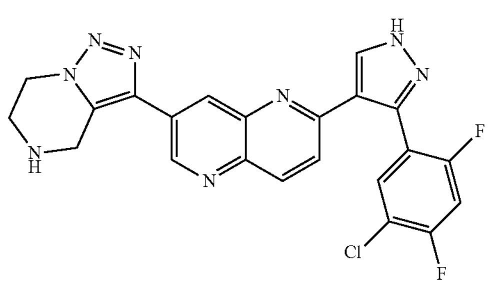 [SMILES: Fc1cc(F)c(-c2n[nH]cc2-c2ccc3ncc(-c4nnn5c4CNCC5)cc3n2)cc1Cl] | 2-[3-(5-chloro-2,4-difluoro-phenyl)-1H-pyrazol-4-yl]-7-(4,5,6,7-tetrahydrotriazolo[1,5-a]pyrazin-3-yl)-1,5-naphthyridine | 465.0 |

TABLE 1-continued

| No. | Structure | Chemical Name | [M + H]+ |
|---|---|---|---|
| 6-58 | 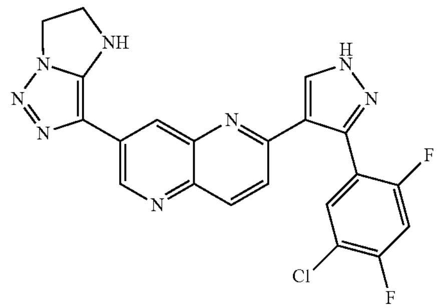 [SMILES: Fc1cc(F)c(-c2n[nH]cc2-c2ccc3ncc(-c4nnn5c4NCC5)cc3n2)cc1Cl] | 2-[3-(5-chloro-2,4-difluoro-phenyl)-1H-pyrazol-4-yl]-7-(5,6-dihydro-4H-imidazo[1,2-c]triazol-3-yl)-1,5-naphthyridine | 451.1 |
| 6-59 | 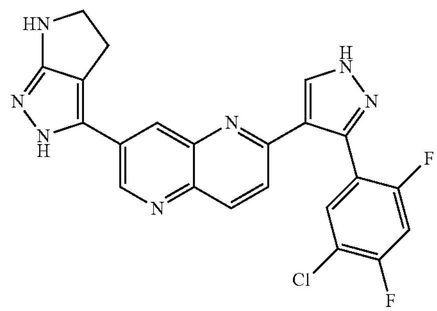 [SMILES: Fc1cc(F)c(-c2n[nH]cc2-c2ccc3ncc(-c4[nH]nc5c4CCN5)cc3n2)cc1Cl] | 2-[3-(5-chloro-2,4-difluoro-phenyl)-1H-pyrazol-4-yl]-7-(2,4,5,6-tetrahydropyrrolo[2,3-c]pyrazol-3-yl)-1,5-naphthyridine | 450.0 |
| 6-60 | 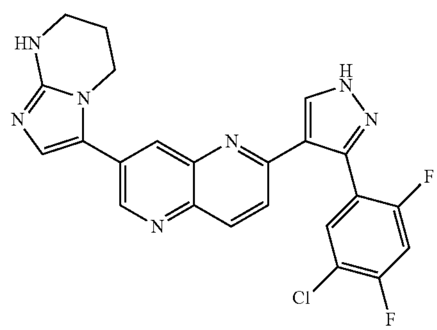 [SMILES: Fc1cc(F)c(-c2n[nH]cc2-c2ccc3ncc(-c4cnc5n4CCCN5)cc3n2)cc1Cl] | 2-[3-(5-chloro-2,4-difluoro-phenyl)-1H-pyrazol-4-yl]-7-(5,6,7,8-tetrahydroimidazo[1,2-a]pyrimidin-3-yl)-1,5-naphthyridine | 464.0 |
| 6-61 | 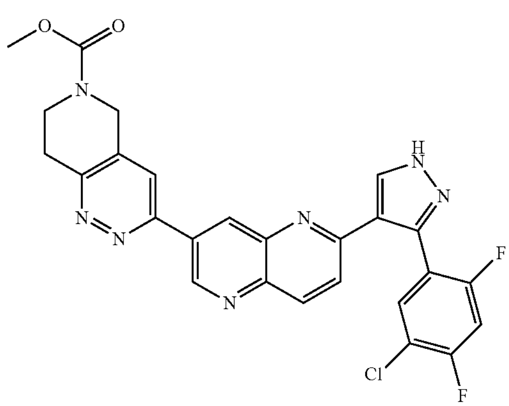 [SMILES: COC(=O)N1CCc2nnc(-c3cnc4ccc(-c5c[nH]nc5-c5cc(Cl)c(F)cc5F)nc4c3)cc2C1] | methyl 3-[6-[3-(5-chloro-2,4-difluoro-phenyl)-1H-pyrazol-4-yl]-1,5-naphthyridin-3-yl]-7,8-dihydro-5H-pyrido[4,3-c]pyridazine-6-carboxylate | 534.0 |

TABLE 1-continued

| No. | Structure | Chemical Name | [M + H]+ |
|---|---|---|---|
| 6-62 | 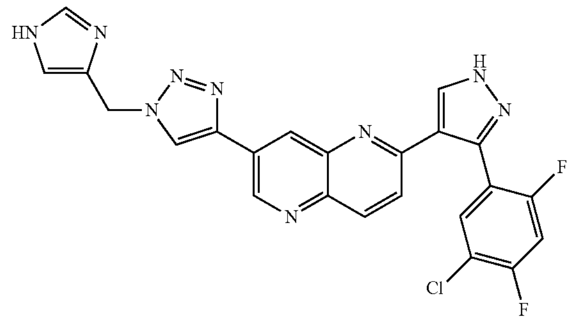 [SMILES: Fc1cc(F)c(-c2n[nH]cc2-c2ccc3ncc(-c4cn(Cc5c[nH]cn5)nn4)cc3n2)cc1Cl] | 2-[3-(5-chloro-2,4-difluoro-phenyl)-1H-pyrazol-4-yl]-7-[1-(1H-imidazol-4-ylmethyl)triazol-4-yl]-1,5-naphthyridine | 489.9 |
| 6-63 | 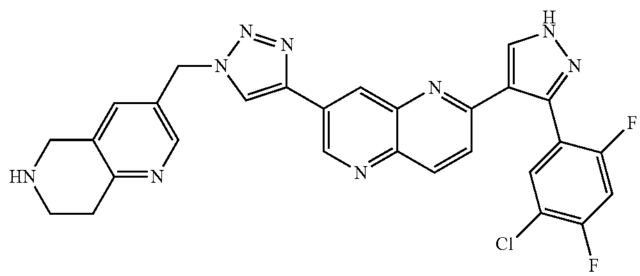 [SMILES: Fc1cc(F)c(-c2n[nH]cc2-c2ccc3ncc(-c4cn(Cc5cnc6c(c5)CNCC6)nn4)cc3n2)cc1Cl] | 2-[3-(5-chloro-2,4-difluoro-phenyl)-1H-pyrazol-4-yl]-7-[1-(5,6,7,8-tetrahydro-1,6-naphthyridin-3-ylmethyl)triazol-4-yl]-1,5-naphthyridine | 556.1 |
| 6-64 | 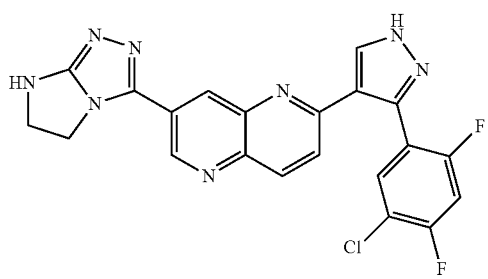 [SMILES: Fc1cc(F)c(-c2n[nH]cc2-c2ccc3ncc(-c4nnc5n4CCN5)cc3n2)cc1Cl] | 2-[3-(5-chloro-2,4-difluoro-phenyl)-1H-pyrazol-4-yl]-7-(6,7-dihydro-5H-imidazo[2,1-c][1,2,4]triazol-3-yl)-1,5-naphthyridine | 451.1 |
| 6-65 | 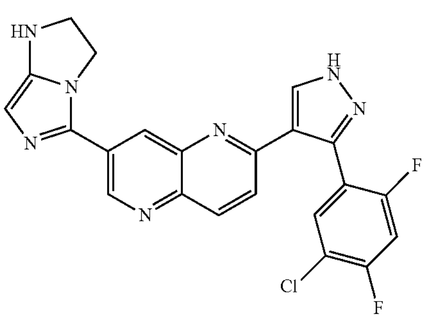 [SMILES: Fc1cc(F)c(-c2n[nH]cc2-c2ccc3ncc(-c4ncc5n4CCN5)cc3n2)cc1Cl] | 2-[3-(5-chloro-2,4-difluoro-phenyl)-1H-pyrazol-4-yl]-7-(2,3-dihydro-1H-imidazo[1,2-c]imidazol-5-yl)-1,5-naphthyridine | 450.0 |
| 6-66 | 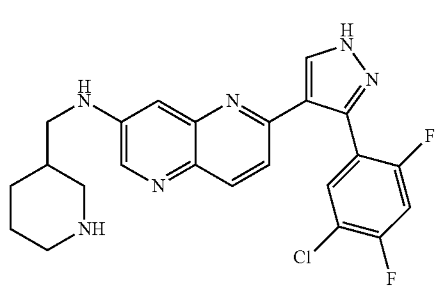 [SMILES: Fc1cc(F)c(-c2n[nH]cc2-c2ccc3ncc(NCC4CCCNC4)cc3n2)cc1Cl] | 6-[3-(5-chloro-2,4-difluoro-phenyl)-1H-pyrazol-4-yl]-N-(3-piperidylmethyl)-1,5-naphthyridin-3-amine | 455.0 |

TABLE 1-continued

| No. | Structure | Chemical Name | [M + H]+ |
|---|---|---|---|
| 6-67 | 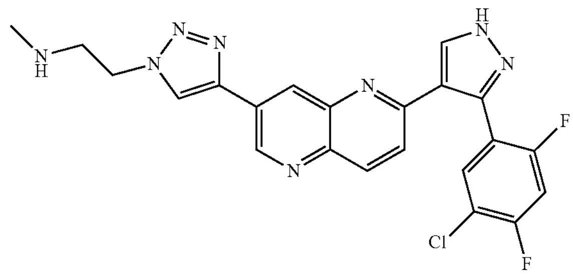 [SMILES: CNCCn1cc(-c2cnc3ccc(-c4c[nH]nc4-c4cc(Cl)c(F)cc4F)nc3c2)nn1] | 2-[4-[6-[3-(5-chloro-2,4-difluoro-phenyl)-1H-pyrazol-4-yl]-1,5-naphthyridin-3-yl]triazol-1-yl]-N-methyl-ethanamine | 467.0 |
| 6-68 | 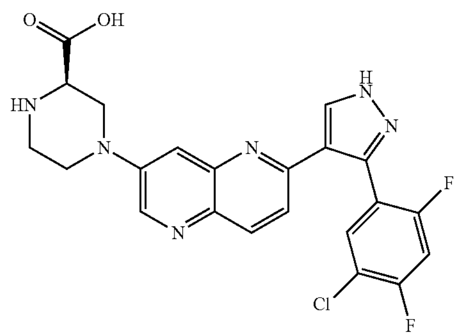 [SMILES: O=C(O)[C@H]1CN(c2cnc3ccc(-c4c[nH]nc4-c4cc(Cl)c(F)cc4F)nc3c2)CCN1] | (2R)-4-[6-[3-(5-chloro-2,4-difluoro-phenyl)-1H-pyrazol-4-yl]-1,5-naphthyridin-3-yl]piperazine-2-carboxylic acid | 471.1 |
| 6-71 | 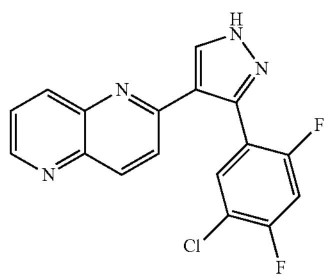 [SMILES: Fc1cc(F)c(-c2n[nH]cc2-c2ccc3ncccc3n2)cc1Cl] | 2-[3-(5-chloro-2,4-difluoro-phenyl)-1H-pyrazol-4-yl]-1,5-naphthyridine | 342.9 |
| 6-72 | 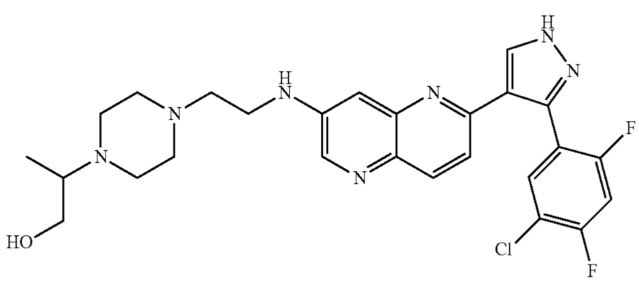 [SMILES: CC(CO)N1CCN(CCNc2cnc3ccc(-c4c[nH]nc4-c4cc(Cl)c(F)cc4F)nc3c2)CC1] | 2-[4-[2-[[6-[3-(5-chloro-2,4-difluoro-phenyl)-1H-pyrazol-4-yl]-1,5-naphthyridin-3-yl]amino]ethyl]piperazin-1-yl]propan-1-ol | 528.1 |
| 6-73 | AND Enantiomer | 6-[3-(5-chloro-2,4-difluoro-phenyl)-1H-pyrazol-4-yl]-N-[[rac-(2S)-pyrrolidin-2-yl]methyl]-1,5-naphthyridin-3-amine | 441.1 |

TABLE 1-continued

| No. | Structure | Chemical Name | [M + H]+ |
|---|---|---|---|
| 6-74 | 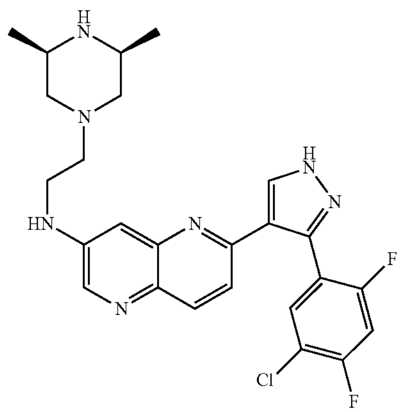 [SMILES: C[C@@H]1CN(CCNc2cnc3ccc(-c4c[nH]nc4-c4cc(Cl)c(F)cc4F)nc3c2)C[C@H](C)N1] | 6-[3-(5-chloro-2,4-difluoro-phenyl)-1H-pyrazol-4-yl]-N-[2-[rac-(3R,5S)-3,5-dimethylpiperazin-1-yl]ethyl]-1,5-naphthyridin-3-amine | 498.1 |
| 6-75 | 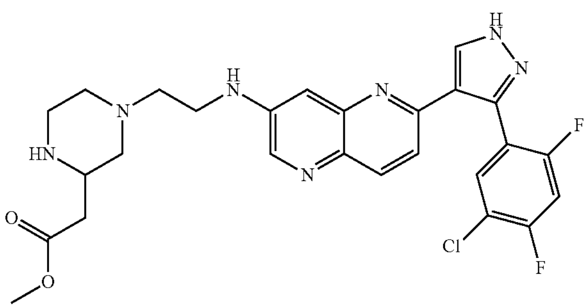 [SMILES: COC(=O)CC1CN(CCNc2cnc3ccc(-c4c[nH]nc4-c4cc(Cl)c(F)cc4F)nc3c2)CCN1] | methyl 2-[4-[2-[[6-[3-(5-chloro-2,4-difluoro-phenyl)-1H-pyrazol-4-yl]-1,5-naphthyridin-3-yl]amino]ethyl]piperazin-2-yl]acetate | 542.0 |
| 7-1 | 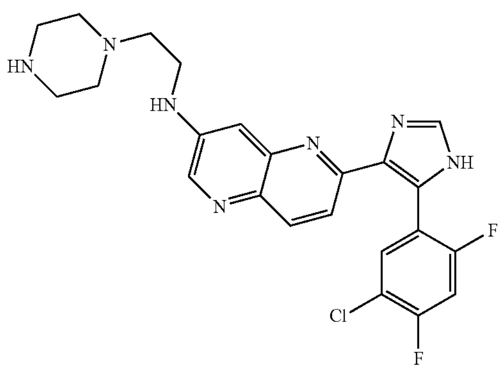 [SMILES: Fc1cc(F)c(-c2[nH]cnc2-c2ccc3ncc(NCCN4CCNCC4)cc3n2)cc1Cl] | 6-[5-(5-chloro-2,4-difluoro-phenyl)-1H-imidazol-4-yl]-N-(2-piperazin-1-ylethyl)-1,5-naphthyridin-3-amine | 470.1 |
| 7-2 | 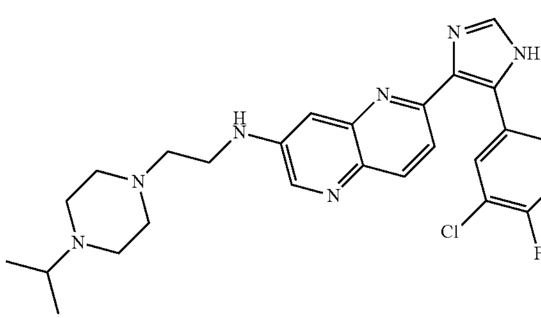 | 6-[5-(5-chloro-2,4-difluoro-phenyl)-1H-imidazol-4-yl]-N-[2-(4-isopropylpiperazin-1-yl)ethyl]-1,5-naphthyridin-3-amine | 512.2 |

TABLE 1-continued

| No. | Structure | Chemical Name | [M + H]+ |
|---|---|---|---|
| 7-3 | 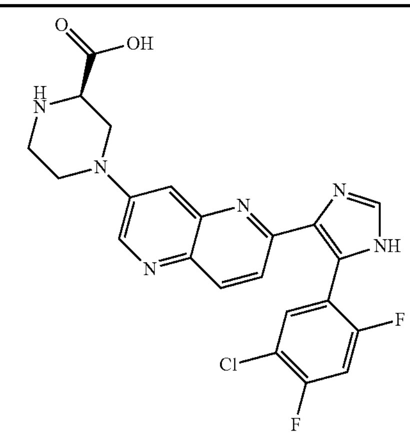 | (2R)-4-[6-[5-(5-chloro-2,4-difluoro-phenyl)-1H-imidazol-4-yl]-1,5-naphthyridin-3-yl]piperazine-2-carboxylic acid | 471.1 |
| 7-4 | 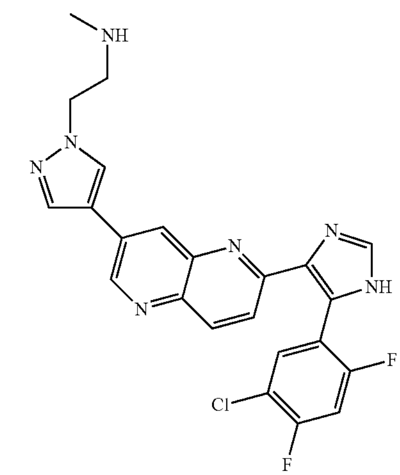 [SMILES: CNCCn1cc(-c2cnc3ccc(-c4nc[nH]c4-c4cc(Cl)c(F)cc4F)nc3c2)cn1] | 2-[4-[6-[5-(5-chloro-2,4-difluoro-phenyl)-1H-imidazol-4-yl]-1,5-naphthyridin-3-yl]pyrazol-1-yl]-N-methyl-ethanamine | 466.1 |
| 7-5 | 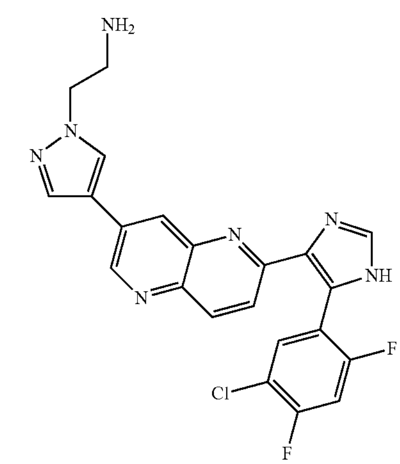 [SMILES: NCCn1cc(-c2cnc3ccc(-c4nc[nH]c4-c4cc(Cl)c(F)cc4F)nc3c2)cn1] | 2-[4-[6-[5-(5-chloro-2,4-difluoro-phenyl)-1H-imidazol-4-yl]-1,5-naphthyridin-3-yl]pyrazol-1-yl]ethanamine | 452.0 |

TABLE 1-continued

| No. | Structure | Chemical Name | [M + H]+ |
|---|---|---|---|
| 7-6 | 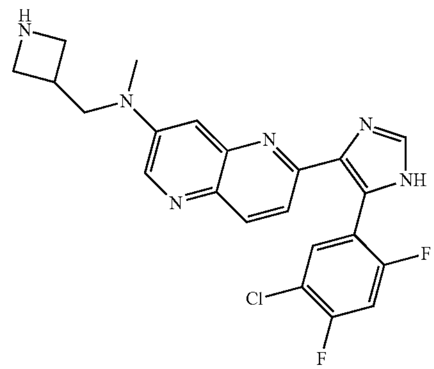 [SMILES: CN(CC1CNC1)c1cnc2ccc(-c3nc[nH]c3-c3cc(Cl)c(F)cc3F)nc2c1] | N-(azetidin-3-ylmethyl)-6-[5-(5-chloro-2,4-difluoro-phenyl)-1H-imidazol-4-yl]-N-methyl-1,5-naphthyridin-3-amine | 441.0 |
| 7-7 | 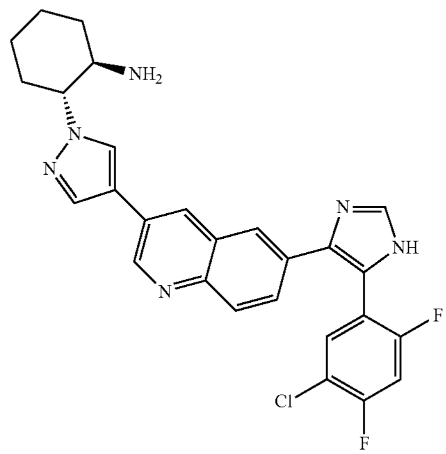 [SMILES: N[C@@H]1CCCC[C@H]1n1cc(-c2cnc3ccc(-c4nc[nH]c4-c4cc(Cl)c(F)cc4F)cc3c2)cn1] | (1R,2R)-2-[4-[6-[5-(5-chloro-2,4-difluoro-phenyl)-1H-imidazol-4-yl]-3-quinolyl]pyrazol-1-yl]cyclohexanamine | 505.1 |
| 8-1 | 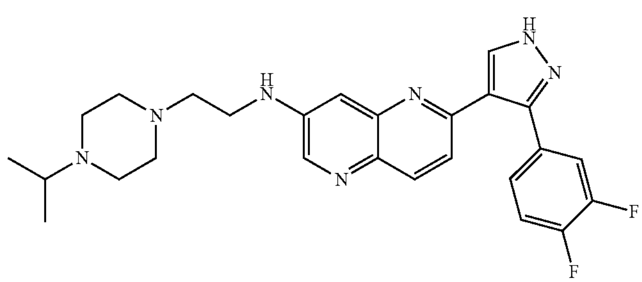 [SMILES: CC(C)N1CCN(CCNc2cnc3ccc(-c4c[nH]nc4-c4ccc(F)c(F)c4)nc3c2)CC1] | 6-[3-(3,4-difluorophenyl)-1H-pyrazol-4-yl]-N-[2-(4-isopropylpiperazin-1-yl)ethyl]-1,5-naphthyridin-3-amine | 478.6 |
| 8-2 | 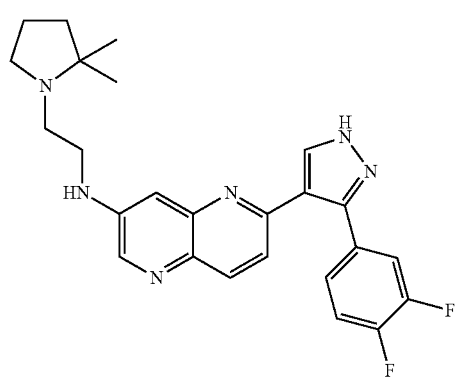 [SMILES: CC1(C)CCCN1CCNc1cnc2ccc(-c3c[nH]nc3-c3ccc(F)c(F)c3)nc2c1] | 6-[3-(3,4-difluorophenyl)-1H-pyrazol-4-yl]-N-[2-(2,2-dimethylpyrrolidin-1-yl)ethyl]-1,5-naphthyridin-3-amine | 449.2 |

TABLE 1-continued

| No. | Structure | Chemical Name | [M + H]+ |
|---|---|---|---|
| 8-3 | 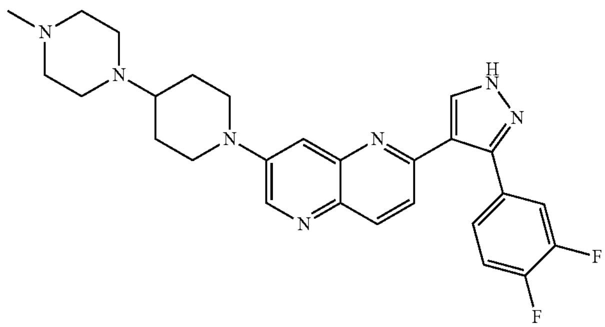 [SMILES: CN1CCN(C2CCN(c3cnc4ccc(-c5c[nH]nc5-c5ccc(F)c(F)c5)nc4c3)CC2)CC1] | 2-[3-(3,4-difluorophenyl)-1H-pyrazol-4-yl]-7-[4-(4-methylpiperazin-1-yl)-1-piperidyl]-1,5-naphthyridine | 490.3 |
| 8-4 | 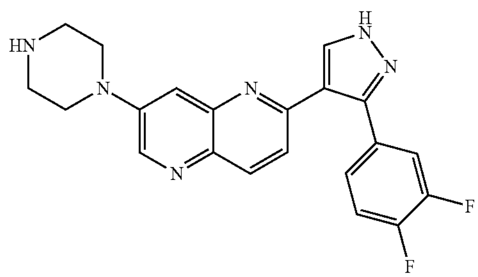 [SMILES: Fc1ccc(-c2n[nH]cc2-c2ccc3ncc(N4CCNCC4)cc3n2)cc1F] | 2-[3-(3,4-difluorophenyl)-1H-pyrazol-4-yl]-7-piperazin-1-yl-1,5-naphthyridine | 393.2 |
| 8-5 | AND Enantiomer | rac-(3S)-1-[6-[3-(3,4-difluorophenyl)-1H-pyrazol-4-yl]-1,5-naphthyridin-3-yl]-N,N-dimethyl-pyrrolidin-3-amine | 421.1 |
| 8-6 | 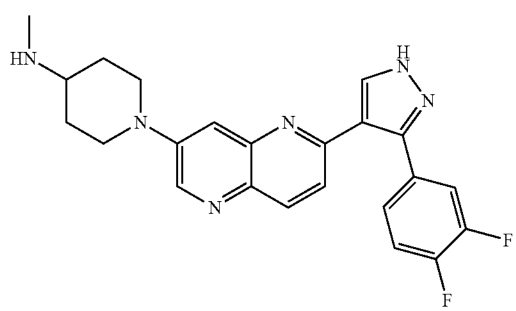 [SMILES: CNC1CCN(c2cnc3ccc(-c4c[nH]nc4-c4ccc(F)c(F)c4)nc3c2)CC1] | 1-[6-[3-(3,4-difluorophenyl)-1H-pyrazol-4-yl]-1,5-naphthyridin-3-yl]-N-methyl-piperidin-4-amine | 421.1 |
| 8-7 | 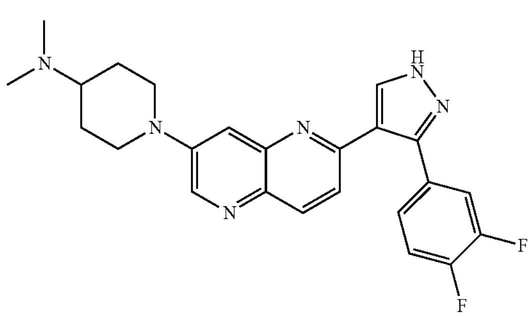 [SMILES: CN(C)C1CCN(c2cnc3ccc(-c4c[nH]nc4-c4ccc(F)c(F)c4)nc3c2)CC1] | 1-[6-[3-(3,4-difluorophenyl)-1H-pyrazol-4-yl]-1,5-naphthyridin-3-yl]-N,N-dimethyl-piperidin-4-amine | 435.1 |

TABLE 1-continued

| No. | Structure | Chemical Name | [M + H]+ |
|---|---|---|---|
| 8-8 | 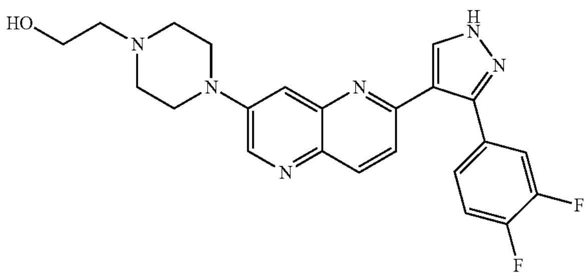 [SMILES: OCCN1CCN(c2cnc3ccc(-c4c[nH]nc4-c4ccc(F)c(F)c4)nc3c2)CC1] | 2-[4-[6-[3-(3,4-difluorophenyl)-1H-pyrazol-4-yl]-1,5-naphthyridin-3-yl]piperazin-1-yl]ethanol | 437.0 |
| 8-9 | 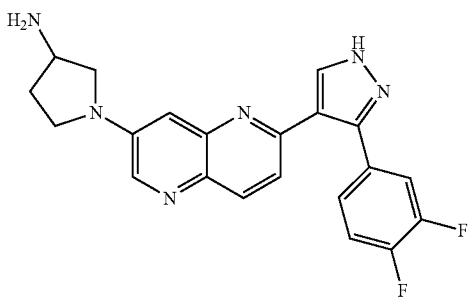 [SMILES: NC1CCN(c2cnc3ccc(-c4c[nH]nc4-c4ccc(F)c(F)c4)nc3c2)C1] | 1-[6-[3-(3,4-difluorophenyl)-1H-pyrazol-4-yl]-1,5-naphthyridin-3-yl]pyrrolidin-3-amine | 393.1 |
| 8-10 | 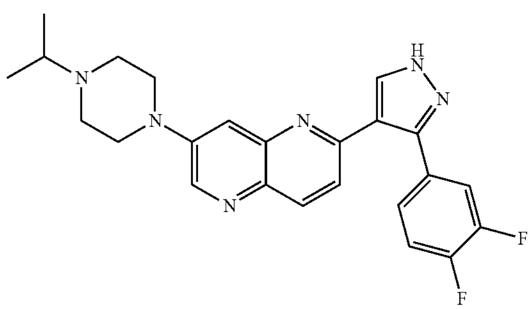 [SMILES: CC(C)N1CCN(c2cnc3ccc(-c4c[nH]nc4-c4ccc(F)c(F)c4)nc3c2)CC1] | 2-[3-(3,4-difluorophenyl)-1H-pyrazol-4-yl]-7-(4-isopropylpiperazin-1-yl)-1,5-naphthyridine | 435.1 |
| 8-11 | 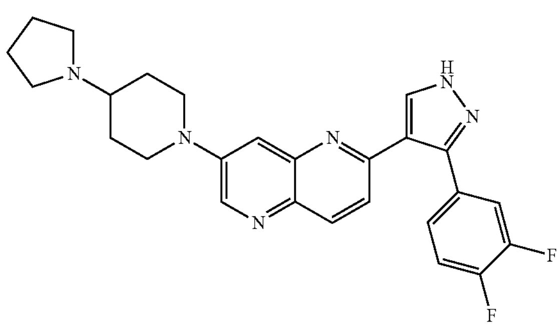 [SMILES: Fc1ccc(-c2n[nH]cc2-c2ccc3ncc(N4CCC(N5CCCC5)CC4)cc3n2)cc1F] | 2-[3-(3,4-difluorophenyl)-1H-pyrazol-4-yl]-7-(4-pyrrolidin-1-yl-1-piperidyl)-1,5-naphthyridine | 461.1 |

TABLE 1-continued

| No. | Structure | Chemical Name | [M + H]+ |
|---|---|---|---|
| 8-12 | 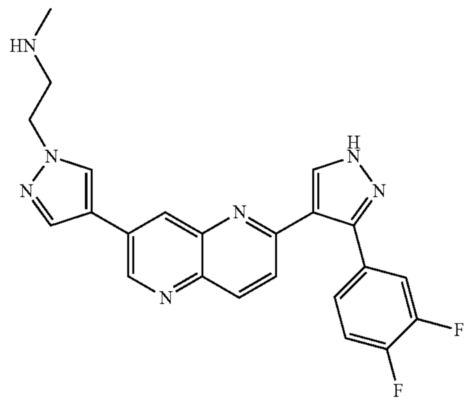 [SMILES: CNCCn1cc(-c2cnc3ccc(-c4c[nH]nc4-c4ccc(F)c(F)c4)nc3c2)cn1] | 2-[4-[6-[3-(3,4-difluorophenyl)-1H-pyrazol-4-yl]-1,5-naphthyridin-3-yl]pyrazol-1-yl]-N-methyl-ethanamine | 432.2 |
| 8-13 | 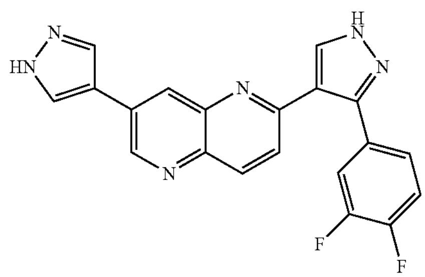 [SMILES: Fc1ccc(-c2n[nH]cc2-c2ccc3ncc(-c4cn[nH]c4)cc3n2)cc1F] | 2-[3-(3,4-difluorophenyl)-1H-pyrazol-4-yl]-7-(1H-pyrazol-4-yl)-1,5-naphthyridine | 375.1 |
| 8-14 | 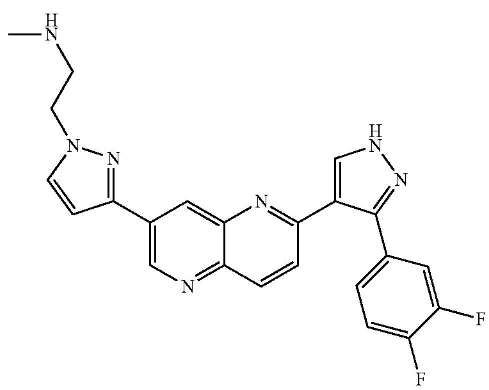 [SMILES: CNCCn1ccc(-c2cnc3ccc(-c4c[nH]nc4-c4ccc(F)c(F)c4)nc3c2)n1] | 2-[3-[6-[3-(3,4-difluorophenyl)-1H-pyrazol-4-yl]-1,5-naphthyridin-3-yl]pyrazol-1-yl]-N-methyl-ethanamine | 432.1 |
| 8-15 | 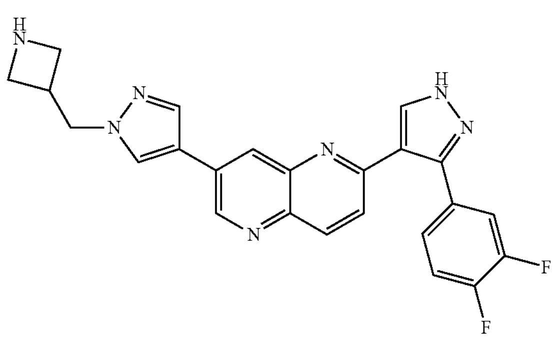 [SMILES: Fc1ccc(-c2n[nH]cc2-c2ccc3ncc(-c4cnn(CC5CNC5)c4)cc3n2)cc1F] | 7-[1-(azetidin-3-ylmethyl)pyrazol-4-yl]-2-[3-(3,4-difluorophenyl)-1H-pyrazol-4-yl]-1,5-naphthyridine | 444.1 |

TABLE 1-continued

| No. | Structure | Chemical Name | [M + H]+ |
|---|---|---|---|
| 8-16 | 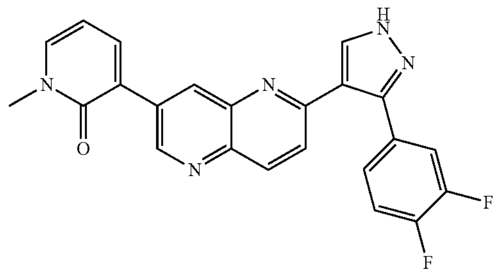 [SMILES: Cn1cccc(-c2cnc3ccc(-c4c[nH]nc4-c4ccc(F)c(F)c4)nc3c2)c1=O] | 3-[6-[3-(3,4-difluorophenyl)-1H-pyrazol-4-yl]-1,5-naphthyridin-3-yl]-1-methyl-pyridin-2-one | 416.2 |
| 8-17 | 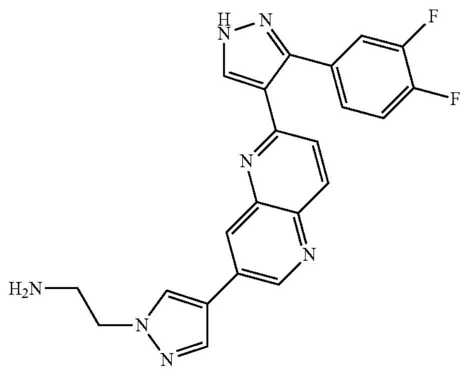 [SMILES: NCCn1cc(-c2cnc3ccc(-c4c[nH]nc4-c4ccc(F)c(F)c4)nc3c2)cn1] | 2-[4-[6-[3-(3,4-difluorophenyl)-1H-pyrazol-4-yl]-1,5-naphthyridin-3-yl]pyrazol-1-yl]ethanamine | 418.1 |
| 8-18 | 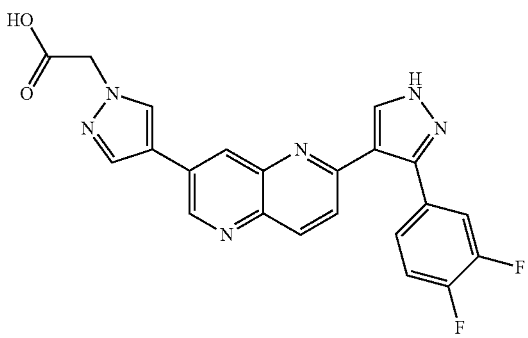 [SMILES: O=C(O)Cn1cc(-c2cnc3ccc(-c4c[nH]nc4-c4ccc(F)c(F)c4)nc3c2)cn1] | 2-[4-[6-[3-(3,4-difluorophenyl)-1H-pyrazol-4-yl]-1,5-naphthyridin-3-yl]pyrazol-1-yl]acetic acid | 433.1 |
| 8-19 | 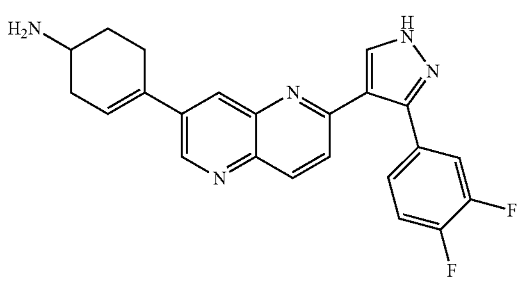 [SMILES: NC1CC=C(c2cnc3ccc(-c4c[nH]nc4-c4ccc(F)c(F)c4)nc3c2)CC1] | 4-[6-[3-(3,4-difluorophenyl)-1H-pyrazol-4-yl]-1,5-naphthyridin-3-yl]cyclohex-3-en-1-amine | 404.1 |
| 8-20 | 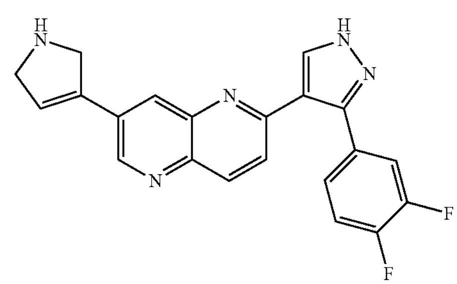 [SMILES: Fc1ccc(-c2n[nH]cc2-c2ccc3ncc(C4=CCNC4)cc3n2)cc1F] | 2-[3-(3,4-difluorophenyl)-1H-pyrazol-4-yl]-7-(2,5-dihydro-1H-pyrrol-3-yl)-1,5-naphthyridine | 376.2 |

TABLE 1-continued

| No. | Structure | Chemical Name | [M + H]+ |
|---|---|---|---|
| 8-21 | 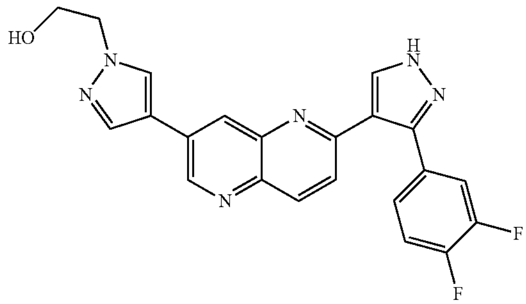 [SMILES: OCCn1cc(-c2cnc3ccc(-c4c[nH]nc4-c4ccc(F)c(F)c4)nc3c2)cn1] | 2-[4-[6-[3-(3,4-difluorophenyl)-1H-pyrazol-4-yl]-1,5-naphthyridin-3-yl]pyrazol-1-yl]ethanol | 419.1 |
| 8-22 | 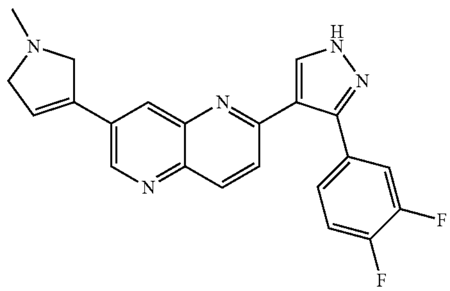 [SMILES: CN1CC=C(c2cnc3ccc(-c4c[nH]nc4-c4ccc(F)c(F)c4)nc3c2)C1] | 2-[3-(3,4-difluorophenyl)-1H-pyrazol-4-yl]-7-(1-methyl-2,5-dihydropyrrol-3-yl)-1,5-naphthyridine | 390.1 |
| 8-23 | 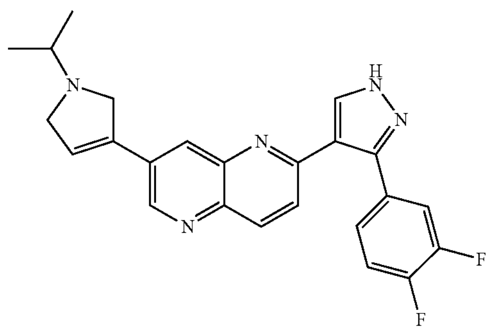 [SMILES: CC(C)N1CC=C(c2cnc3ccc(-c4c[nH]nc4-c4ccc(F)c(F)c4)nc3c2)C1] | 2-[3-(3,4-difluorophenyl)-1H-pyrazol-4-yl]-7-(1-isopropyl-2,5-dihydropyrrol-3-yl)-1,5-naphthyridine | 418.2 |
| 8-24 | 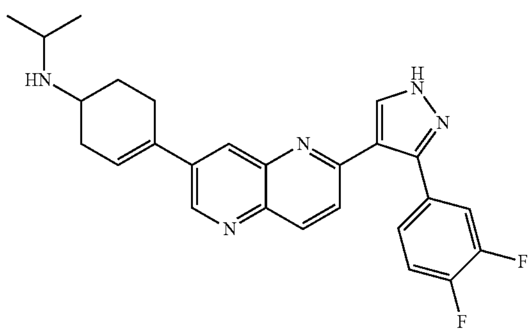 [SMILES: CC(C)NC1CC=C(c2cnc3ccc(-c4c[nH]nc4-c4ccc(F)c(F)c4)nc3c2)CC1] | 4-[6-[3-(3,4-difluorophenyl)-1H-pyrazol-4-yl]-1,5-naphthyridin-3-yl]-N-isopropyl-cyclohex-3-en-1-amine | 446.0 |
| 8-25 | 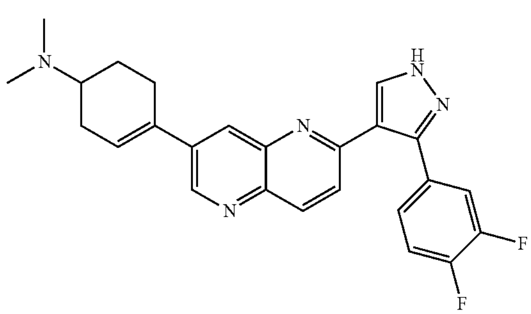 [SMILES: CN(C)C1CC=C(c2cnc3ccc(-c4c[nH]nc4-c4ccc(F)c(F)c4)nc3c2)CC1] | 4-[6-[3-(3,4-difluorophenyl)-1H-pyrazol-4-yl]-1,5-naphthyridin-3-yl]-N,N-dimethyl-cyclohex-3-en-1-amine | 432.0 |

TABLE 1-continued

| No. | Structure | Chemical Name | [M + H]+ |
|---|---|---|---|
| 8-26 | 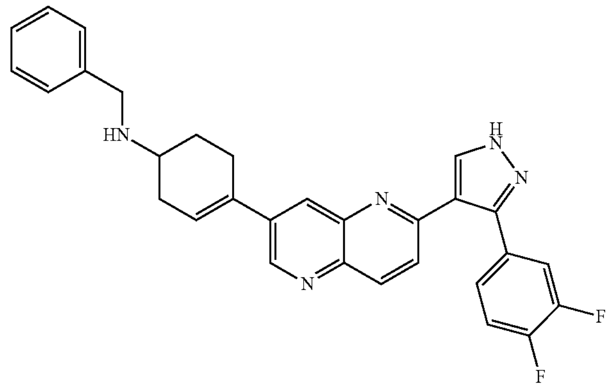 [SMILES: Fc1ccc(-c2n[nH]cc2-c2ccc3ncc(C4=CCC(NCc5ccccc5)CC4)cc3n2)cc1F] | N-benzyl-4-[6-[3-(3,4-difluorophenyl)-1H-pyrazol-4-yl]-1,5-naphthyridin-3-yl]cyclohex-3-en-1-amine | 494.1 |
| 8-27 | 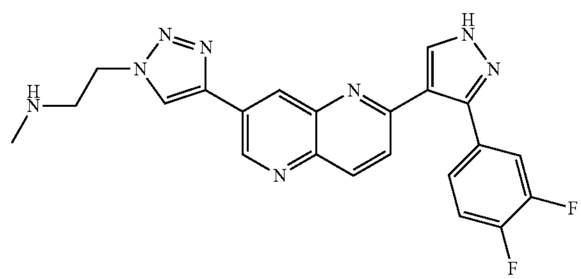 [SMILES: CNCCn1cc(-c2cnc3ccc(-c4c[nH]nc4-c4ccc(F)c(F)c4)nc3c2)nn1] | 2-[4-[6-[3-(3,4-difluorophenyl)-1H-pyrazol-4-yl]-1,5-naphthyridin-3-yl]triazol-1-yl]-N-methyl-ethanamine | 433.0 |
| 9-1 | 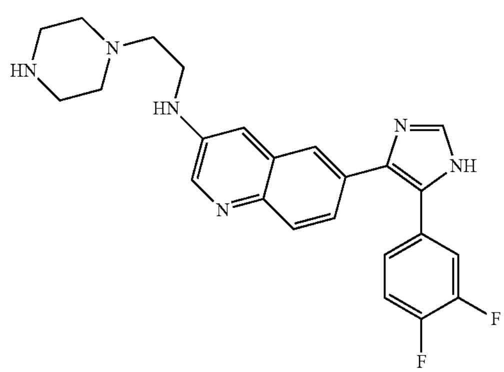 [SMILES: Fc1ccc(-c2[nH]cnc2-c2ccc3ncc(NCCN4CCNCC4)cc3c2)cc1F] | 6-[5-(3,4-difluorophenyl)-1H-imidazol-4-yl]-N-(2-piperazin-1-ylethyl)-1,5-naphthyridin-3-amine | 436.1 |
| 9-2 | 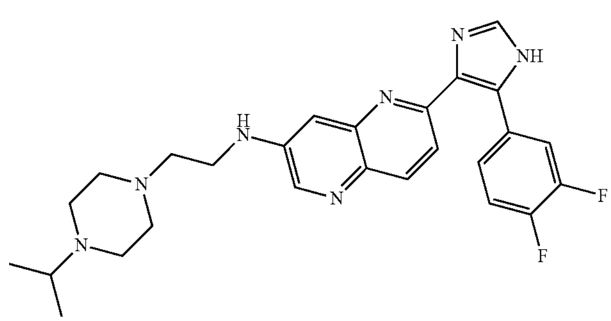 [SMILES: CC(C)N1CCN(CCNc2cnc3ccc(-c4nc[nH]c4-c4ccc(F)c(F)c4)nc3c2)CC1] | 6-[5-(3,4-difluorophenyl)-1H-imidazol-4-yl]-N-[2-(4-isopropylpiperazin-1-yl)ethyl]-1,5-naphthyridin-3-amine | 478.2 |

TABLE 1-continued

| No. | Structure | Chemical Name | [M + H]⁺ |
|---|---|---|---|
| 9-3 | 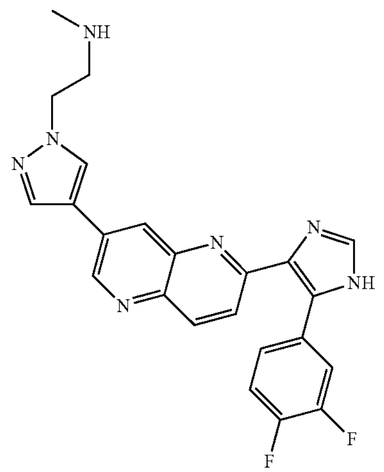 [SMILES: CNCCn1cc(-c2cnc3ccc(-c4nc[nH]c4-c4ccc(F)c(F)c4)nc3c2)cn1] | 2-[4-[6-[5-(3,4-difluorophenyl)-1H-imidazol-4-yl]-1,5-naphthyridin-3-yl]pyrazol-1-yl]-N-methyl-ethanamine | 432.2 |
| 10-1 | 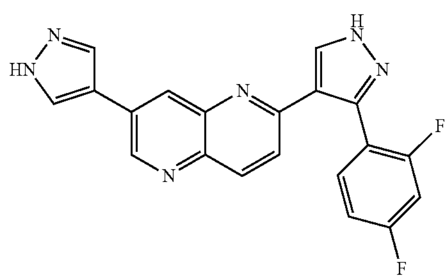 [SMILES: Fc1ccc(-c2n[nH]cc2-c2ccc3ncc(-c4cn[nH]c4)cc3n2)c(F)c1] | 2-[3-(2,4-difluorophenyl)-1H-pyrazol-4-yl]-7-(1H-pyrazol-4-yl)-2,5-naphthyridine | 357.1 |
| 10-2 | 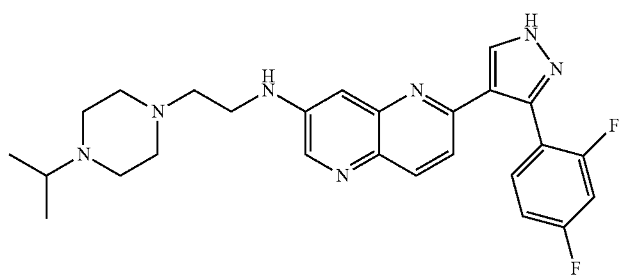 [SMILES: CC(C)N1CCN(CCNc2cnc3ccc(-c4c[nH]nc4-c4ccc(F)cc4F)nc3c2)CC1] | 6-[3-(2,4-difluorophenyl)-1H-pyrazol-4-yl]-N-[2-(4-isopropylpiperazin-1-yl)ethyl]-1,5-naphthyridin-3-amine | 478.0 |
| 11-1 | 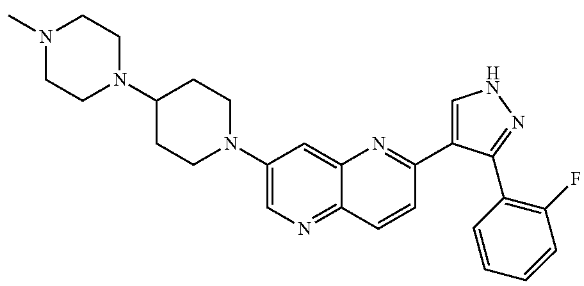 [SMILES: CN1CCN(C2CCN(c3cnc4ccc(-c5c[nH]nc5-c5ccccc5F)nc4c3)CC2)CC1] | 2-[3-(2-fluorophenyl)-1H-pyrazol-4-yl]-7-[4-(4-methylpiperazin-1-yl)-1-piperidyl]-1,5-naphthyridine | 472.3 |
| 11-2 | 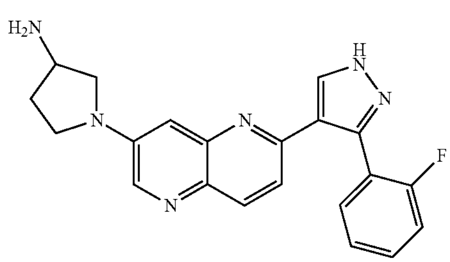 [SMILES: NC1CCN(c2cnc3ccc(-c4c[nH]nc4-c4ccccc4F)nc3c2)C1] | 1-[6-[3-(2-fluorophenyl)-1H-pyrazol-4-yl]-1,5-naphthyridin-3-yl]pyrrolidin-3-amine | 375.2 |

TABLE 1-continued

| No. | Structure | Chemical Name | [M + H]+ |
|---|---|---|---|
| 11-3 | 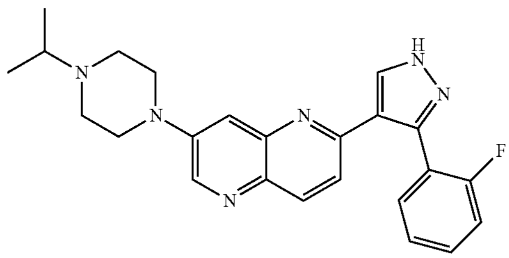 [SMILES: CC(C)N1CCN(c2cnc3ccc(-c4c[nH]nc4-c4ccccc4F)nc3c2)CC1] | 2-[3-(2-fluorophenyl)-1H-pyrazol-4-yl]-7-(4-isopropylpiperazin-1-yl)-1,5-naphthyridine | 417.2 |
| 11-4 | 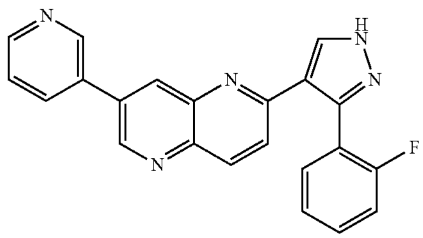 [SMILES: Fc1ccccc1-c1n[nH]cc1-c1ccc2ncc(-c3cccnc3)cc2n1] | 2-[3-(2-fluorophenyl)-1H-pyrazol-4-yl]-7-(3-pyridyl)-1,5-naphthyridine | 368.2 |
| 12-1 | 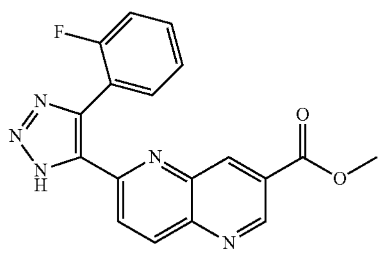 [SMILES: COC(=O)c1cnc2ccc(-c3[nH]nnc3-c3ccccc3F)nc2c1] | methyl 6-[4-(2-fluorophenyl)-1H-triazol-5-yl]-1,5-naphthyridine-3-carboxylate | 350.0 |
| 12-2 | 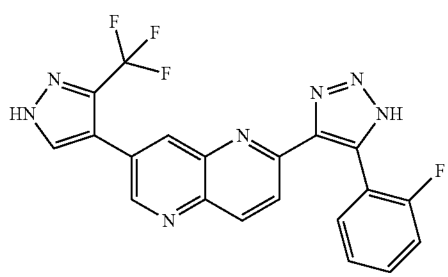 [SMILES: Fc1ccccc1-c1[nH]nnc1-c1ccc2ncc(-c3c[nH]nc3C(F)(F)F)cc2n1] | 2-[5-(2-fluorophenyl)-1H-triazol-4-yl]-7-[3-(trifluoromethyl)-1H-pyrazol-4-yl]-1,5-naphthyridine | 426.0 |
| 13-1 | 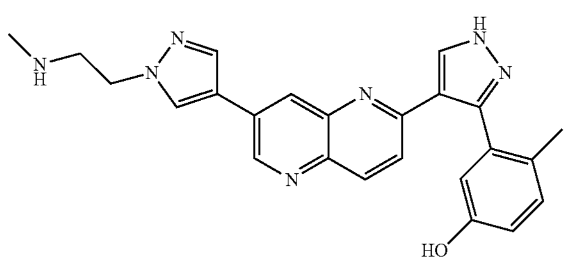 | 4-methyl-3-[4-[7-[1-[2-(methylamino)ethyl]pyrazol-4-yl]-1,5-naphthyridin-2-yl]-1H-pyrazol-3-yl]phenol | 426.1 |
| 14-1 | 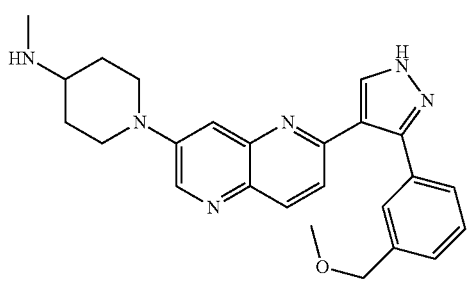 [SMILES: CNC1CCN(c2cnc3ccc(-c4c[nH]nc4-c4cccc(COC)c4)nc3c2)CC1] | 1-[6-[3-[3-(methoxymethyl)phenyl]-1H-pyrazol-4-yl]-1,5-naphthyridin-3-yl]-N-methyl-piperidin-4-amine | 429.2 |

TABLE 1-continued

| No. | Structure | Chemical Name | [M + H]+ |
|---|---|---|---|
| 14-2 | 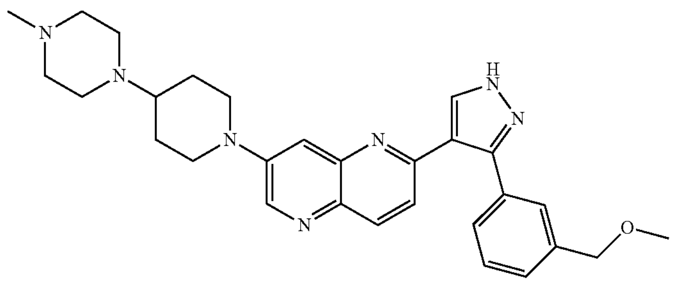 | 2-[3-(3-(methoxymethyl)phenyl]-1H-pyrazol-4-yl]-7-[4-(4-methylpiperazin-1-yl)-1-piperidyl]-1,5-naphthyridine | 498.3 |
| 14-3 | 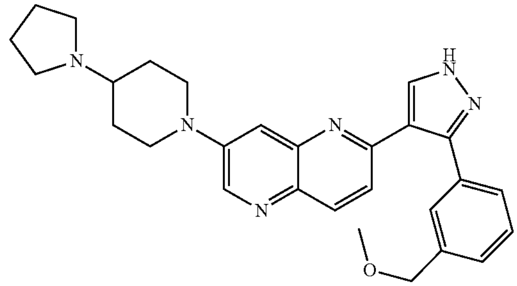 [SMILES: COCc1cccc(-c2n[nH]cc2-c2ccc3ncc(N4CCC(N5CCCC5)CC4)cc3n2)c1] | 2-[3-[3-(methoxymethyl)phenyl]-1H-pyrazol-4-yl]-7-(4-pyrrolidin-1-yl-1-piperidyl)-1,5-naphthyridine | 469.1 |
| 14-4 | AND Enantiomer | rac-(3S)-1-[6-[3-[3-(methoxymethyl)phenyl]-1H-pyrazol-4-yl]-1,5-naphthyridin-3-yl]-N,N-dimethyl-pyrrolidin-3-amine | 429.1 |
| 14-5 | 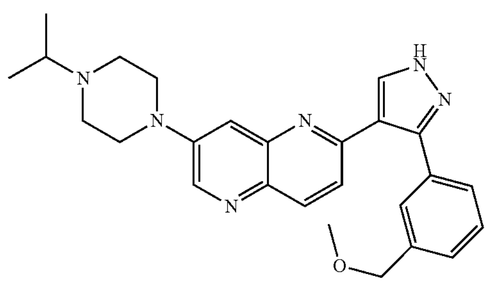 [SMILES: COCc1cccc(-c2n[nH]cc2-c2ccc3ncc(N4CCN(C(C)C)CC4)cc3n2)c1] | 7-(4-isopropylpiperazin-1-yl)-2-[3-[3-(methoxymethyl)phenyl]-1H-pyrazol-4-yl]-1,5-naphthyridine | 443.2 |
| 14-6 | 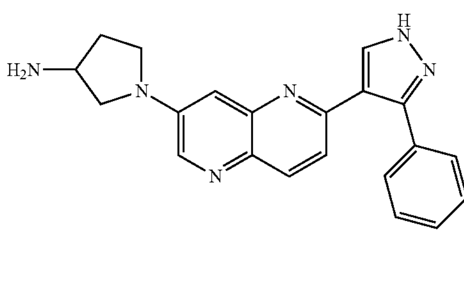 | 1-[6-[3-[3-(methoxymethyl)phenyl]-1H-pyrazol-4-yl]-1,5-naphthyridin-3-yl]pyrrolidin-3-amine | 401.2 |

TABLE 1-continued

| No. | Structure | Chemical Name | [M + H]+ |
|---|---|---|---|
| 14-7 | 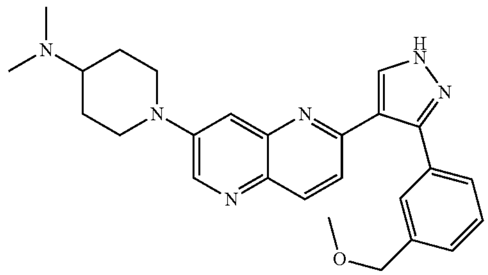 [SMILES: COCc1cccc(-c2n[nH]cc2-c2ccc3ncc(N4CCC(N(C)C)CC4)cc3n2)c1] | 1-[6-[3-[3-(methoxymethyl)phenyl]-1H-pyrazol-4-yl]-1,5-naphthyridin-3-yl]-N,N-dimethyl-piperidin-4-amine | 443.2 |
| 14-8 | 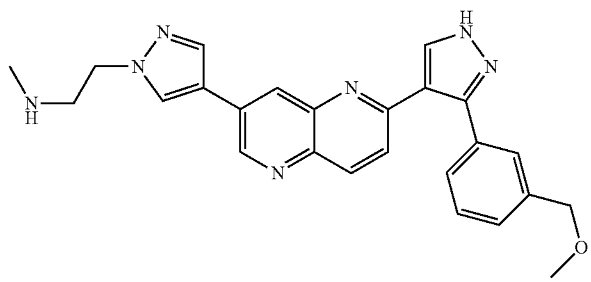 [SMILES: CNCCn1cc(-c2cnc3ccc(-c4c[nH]nc4-c4cccc(COC)c4)nc3c2)cn1] | 2-[4-[6-[3-[3-(methoxymethyl)phenyl]-1H-pyrazol-4-yl]-1,5-naphthyridin-3-yl]pyrazol-1-yl]-N-methylethanamine | 440.2 |
| 14-9 | 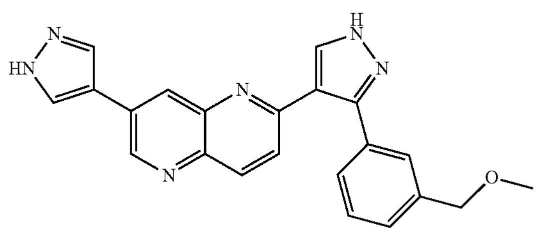 [SMILES: COCc1cccc(-c2n[nH]cc2-c2ccc3ncc(-c4cn[nH]c4)cc3n2)c1] | 2-[3-[3-(methoxymethyl)phenyl]-1H-pyrazol-4-yl]-7-(1H-pyrazol-4-yl)-1,5-naphthyridine | 383.2 |
| 14-10 | 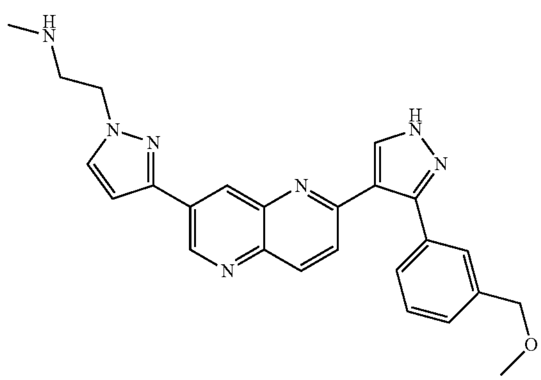 [SMILES: CNCCn1ccc(-c2cnc3ccc(-c4c[nH]nc4-c4cccc(COC)c4)nc3c2)n1] | 2-[3-[6-[3-[3-(methoxymethyl)phenyl]-1H-pyrazol-4-yl]-1,5-naphthyridin-3-yl]pyrazol-1-yl]-N-methyl-ethanamine | 440.2 |
| 14-11 | 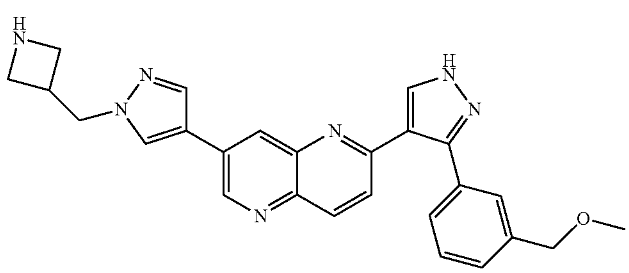 [SMILES: COCc1cccc(-c2n[nH]cc2-c2ccc3ncc(-c4cnn(CC5CNC5)c4)cc3n2)c1] | 7-[1-(azetidin-3-ylmethyl)pyrazol-4-yl]-2-[3-[3-(methoxymethyl)phenyl]-1H-pyrazol-4-yl]-1,5-naphthyridine | 452.1 |

TABLE 1-continued

| No. | Structure | Chemical Name | [M + H]⁺ |
|---|---|---|---|
| 14-12 | 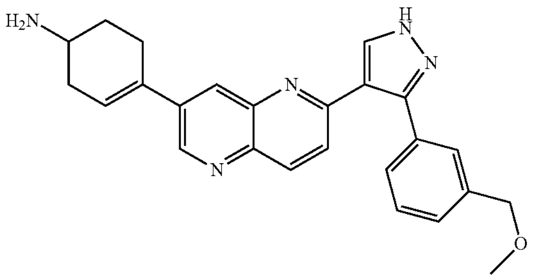 [SMILES: COCc1cccc(-c2n[nH]cc2-c2ccc3ncc(C4=CCC(N)CC4)cc3n2)c1] | 4-[6-[3-[3-(methoxymethyl)phenyl]-1H-pyrazol-4-yl]-1,5-naphthyridin-3-yl]cyclohex-3-en-1-amine | 412.2 |
| 14-13 | 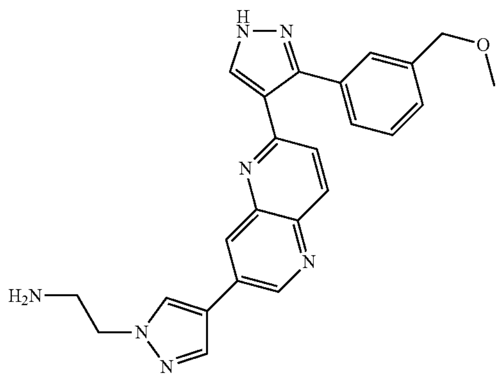 [SMILES: COCc1cccc(-c2n[nH]cc2-c2ccc3ncc(-c4cnn(CCN)c4)cc3n2)c1] | 2-[4-[6-[3-[3-(methoxymethyl)phenyl]-1H-pyrazol-4-yl]-1,5-naphthyridin-3-yl]pyrazol-1-yl]ethanamine | 426.1 |
| 14-14 | 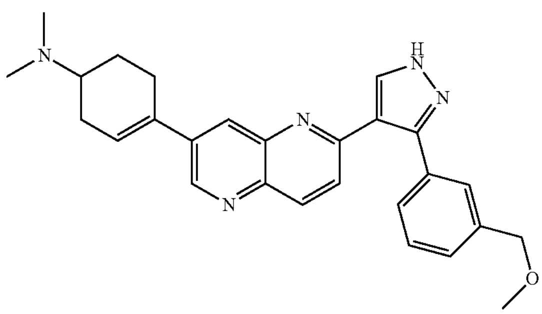 [SMILES: COCc1cccc(-c2n[nH]cc2-c2ccc3ncc(C4=CCC(N(C)C)CC4)cc3n2)c1] | 4-[6-[3-[3-(methoxymethyl)phenyl]-1H-pyrazol-4-yl]-1,5-naphthyridin-3-yl]-N,N-dimethyl-cyclohex-3-en-1-amine | 440.1 |
| 14-15 | 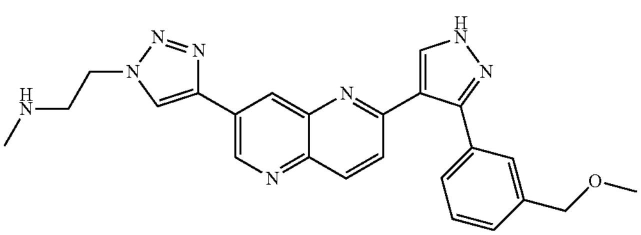 | 2-[4-[6-[3-[3-(methoxymethyl)phenyl]-1H-pyrazol-4-yl]-1,5-naphthyridin-3-yl]triazol-1-yl]-N-methyl-ethanamine | 441.1 |
| 14-16 | 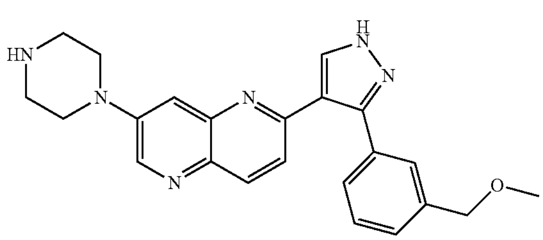 [SMILES: COCc1cccc(-c2n[nH]cc2-c2ccc3ncc(N4CCNCC4)cc3n2)c1] | 2-[3-[3-(methoxymethyl)phenyl]-1H-pyrazol-4-yl]-7-piperazin-1-yl-1,5-naphthyridine | 401.3 |

TABLE 1-continued

| No. | Structure | Chemical Name | [M + H]+ |
|---|---|---|---|
| 14-17 | 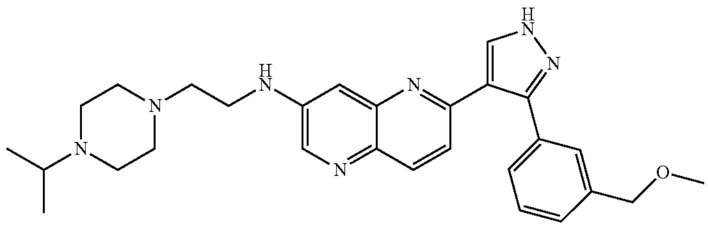 [SMILES: COCc1cccc(-c2n[nH]cc2-c2ccc3ncc(NCCN4CCN(C(C)C)CC4)cc3n2)c1] | N-[2-(4-isopropylpiperazin-1-yl)ethyl]-6-[3-[3-(methoxymethyl)phenyl]-1H-pyrazol-4-yl]-1,5-naphthyridin-3-amine | 486.2 |
| 14-18 | 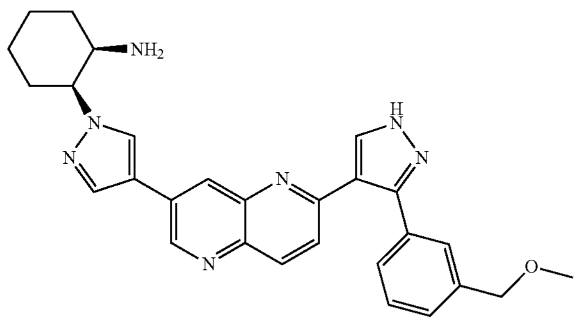 [SMILES: COCc1cccc(-c2n[nH]cc2-c2ccc3ncc(-c4cnn([C@H]5CCCC[C@H]5N)c4)cc3n2)c1] | (1R,2S)-2-[4-[6-[3-[3-(methoxymethyl)phenyl]-1H-pyrazol-4-yl]-1,5-naphthyridin-3-yl]pyrazol-1-yl]cyclohexanamine | 480.1 |
| 15-1 | 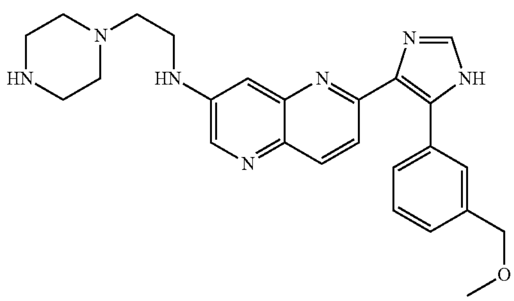 [SMILES: COCc1cccc(-c2[nH]cnc2-c2ccc3ncc(NCCN4CCNCC4)cc3n2)c1] | 6-[5-[3-(methoxymethyl)phenyl]-1H-imidazol-4-yl]-N-(2-piperazin-1-ylethyl)-1,5-naphthyridin-3-amine | 444.1 |
| 15-2 | 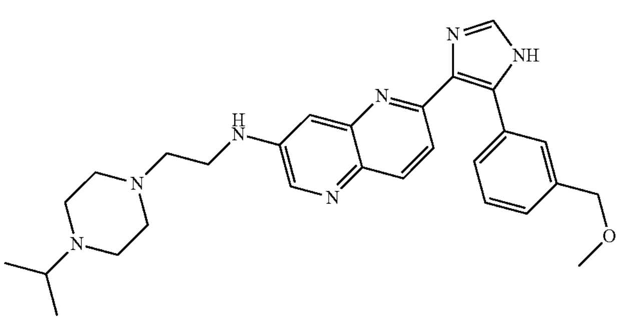 [SMILES: COCc1cccc(-c2[nH]cnc2-c2ccc3ncc(NCCN4CCN(C(C)C)CC4)cc3n2)c1] | N-[2-(4-isopropoylpiperazin-1-yl)ethyl]-6-[5-[3-(methoxymethyl)phenyl]-1H-imidazol-4-yl]-1,5-naphthyridin-3-amine | 486.2 |

TABLE 1-continued

| No. | Structure | Chemical Name | [M + H]+ |
|---|---|---|---|
| 15-3 | 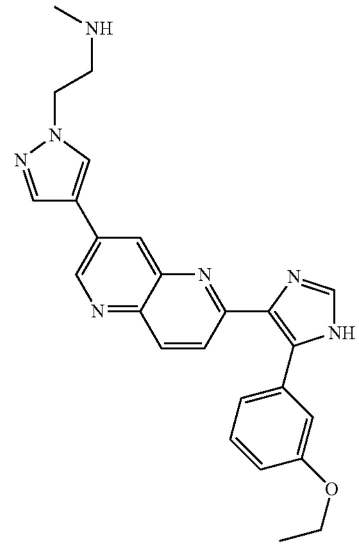 [SMILES: CCOc1cccc(-c2[nH]cnc2-c2ccc3ncc(-c4cnn(CCNC)c4)cc3n2)c1] | 2-[4-[6-[5-[3-(methoxymethyl)phenyl]-1H-imidazol-4-yl]-1,5-naphthyridin-3-yl]pyrazol-1-yl]-N-methyl-ethanamine | 440.1 |
| 15-4 | 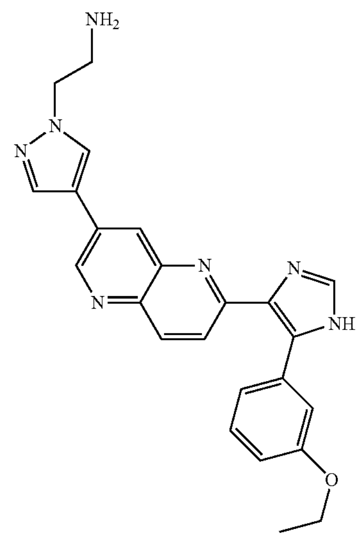 [SMILES: CCOc1cccc(-c2[nH]cnc2-c2ccc3ncc(-c4cnn(CCN)c4)cc3n2)c1] | 2-[4-[6-[5-[3-(methoxymethyl)phenyl]-1H-imidazol-4-yl]-1,5-naphthyridin-3-yl]pyrazol-1-yl]ethanamine | 426.0 |
| 16-1 | 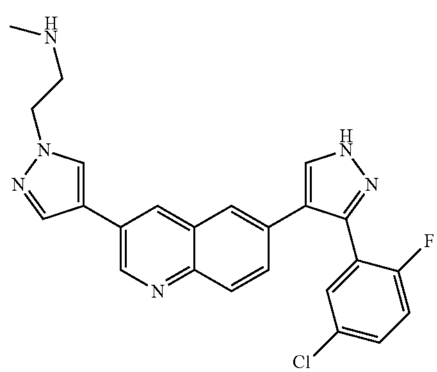 [SMILES: CNCCn1cc(-c2cnc3ccc(-c4c[nH]nc4-c4cc(Cl)ccc4F)cc3c2)cn1] | 2-[4-[6-[3-(5-chloro-2-fluoro-phenyl)-1H-pyrazol-4-yl]-3-quinolyl]pyrazol-1-yl]-N-methyl-ethanamine | 447.1 |

TABLE 1-continued

| No. | Structure | Chemical Name | [M + H]+ |
|-----|-----------|---------------|----------|
| 16-2 | 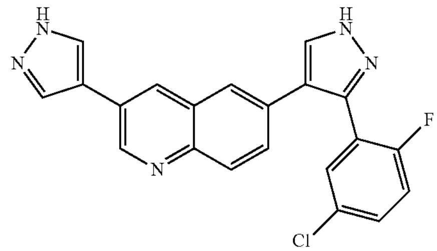 [SMILES: Fc1ccc(Cl)cc1-c1n[nH]cc1-c1ccc2ncc(-c3cn[nH]c3)cc2c1] | 6-[3-(5-chloro-2-fluoro-phenyl)-1H-pyrazol-4-yl]-3-(1H-pyrazol-4-yl)quinoline | 390.1 |
| 16-3 | AND Enantiomer | rac-(3S)-1-[6-[3-(5-chloro-2-fluoro-phenyl)-1H-pyrazol-4-yl]-3-quinolyl]-N,N-dimethyl-pyrrolidin-3-amine | 436.1 |
| 16-4 | 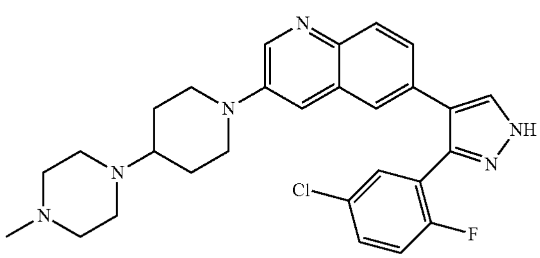 [SMILES: CN1CCN(C2CCN(c3cnc4ccc(-c5c[nH]nc5-c5cc(Cl)ccc5F)cc4c3)CC2)CC1] | 6-[3-(5-chloro-2-fluoro-phenyl)-1H-pyrazol-4-yl]-3-[4-(4-methylpiperazin-1-yl)-1-piperidyl]quinoline | 505.1 |
| 16-5 | 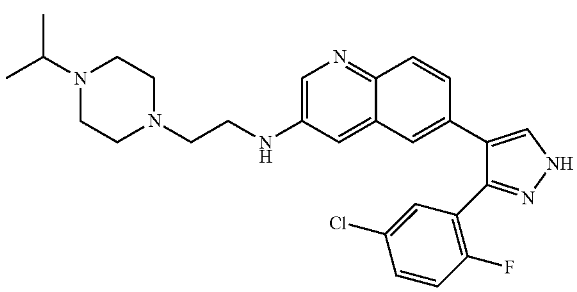 [SMILES: CC(C)N1CCN(CCNc2cnc3ccc(-c4c[nH]nc4-c4cc(Cl)ccc4F)cc3c2)CC1] | 6-[3-(5-chloro-2-fluoro-phenyl)-1H-pyrazol-4-yl]-N-[2-(4-isopropylpiperazin-1-yl)ethyl]quinolin-3-amine | 493.1 |
| 17-1 | 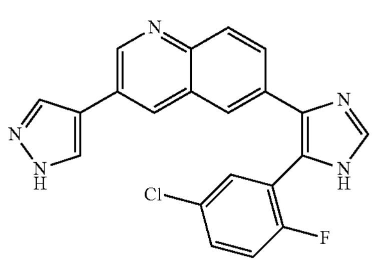 [SMILES: Fc1ccc(Cl)cc1-c1[nH]cnc1-c1ccc2ncc(-c3cn[nH]c3)cc2c1] | 6-[5-(5-chloro-2-fluoro-phenyl)-1H-imidazol-4-yl]-3-(1H-pyrazol-4-yl)quinoline | 390.1 |

TABLE 1-continued

| No. | Structure | Chemical Name | [M + H]⁺ |
|---|---|---|---|
| 17-2 | 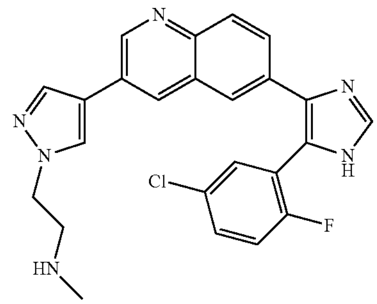 [SMILES: CNCCn1cc(-c2cnc3ccc(-c4nc[nH]c4-c4cc(Cl)ccc4F)cc3c2)cn1] | 2-[4-[6-[5-(5-chloro-2-fluoro-phenyl)-1H-imidazol-4-yl]-3-quinolyl]pyrazol-1-yl]-N-methyl-ethanamine | 447.2 |
| 17-3 | 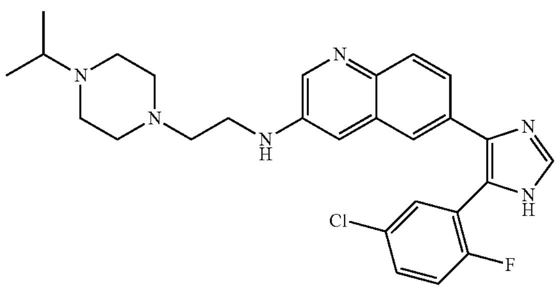 [SMILES: CC(C)N1CCN(CCNc2cnc3ccc(-c4nc[nH]c4-c4cc(Cl)ccc4F)cc3c2)CC1] | 6-[5-(5-chloro-2-fluoro-phenyl)-1H-imidazol-4-yl]-N-[2-(4-isopropylpiperazin-1-yl)ethyl]quinolin-3-amine | 493.2 |
| 17-4 | 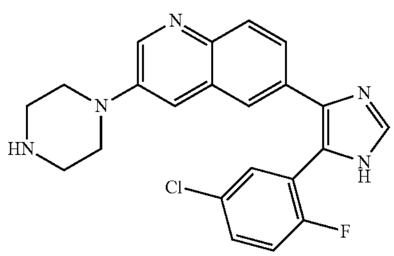 [SMILES: Fc1ccc(Cl)cc1-c1[nH]cnc1-c1ccc2ncc(N3CCNCC3)cc2c1] | 6-[5-(5-chloro-2-fluoro-phenyl)-1H-imidazol-4-yl]-3-piperazin-1-yl-quinoline | 408.2 |
| 17-5 | AND Enantiomer | rac-(3S)-1-[6-[5-(5-chloro-2-fluoro-phenyl)-1H-imidazol-4-yl]-3-quinolyl]-N,N-dimethyl-pyrrolidin-3-amine | 436.2 |
| 17-6 | 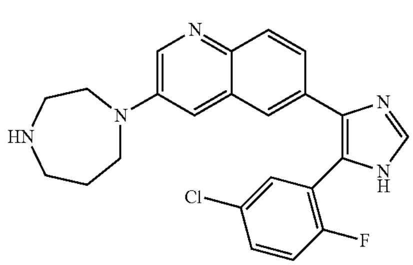 | 6-[5-(5-chloro-2-fluoro-phenyl)-1H-imidazol-4-yl]-3-(1,4-diazepan-1-yl)quinoline | 422.2 |

TABLE 1-continued

| No. | Structure | Chemical Name | [M + H]+ |
|---|---|---|---|
| 17-7 | 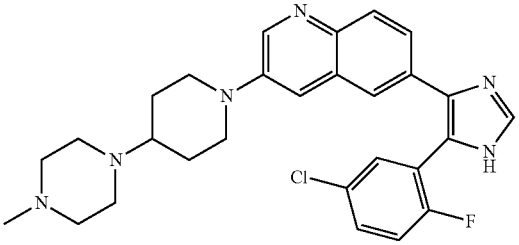 [SMILES: CN1CCN(C2CCN(c3cnc4ccc(-c5nc[nH]c5-c5cc(Cl)ccc5F)cc4c3)CC2)CC1] | 6-[5-(5-chloro-2-fluoro-phenyl)-1H-imidazol-4-yl]-3-[4-(4-methylpiperazin-1-yl)-1-piperidyl]quinoline | 505.2 |
| 17-8 | 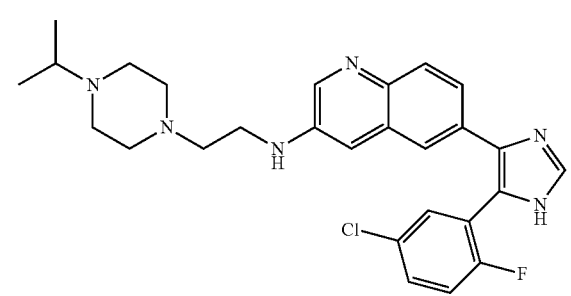 | 6-[5-(5-chloro-2-fluoro-phenyl)-1H-imidazol-4-yl]-N-[2-(4-isopropylpiperazin-1-yl)ethyl]quinolin-3-amine | 493.2 |
| 17-9 | 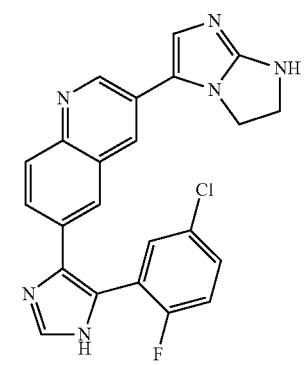 [SMILES: Fc1ccc(Cl)cc1-c1[nH]cnc1-c1ccc2ncc(-c3cnc4n3CCN4)cc2c1] | 6-[5-(5-chloro-2-fluoro-phenyl)-1H-imidazol-4-yl]-3-(6,7-dihydro-5H-imidazo[1,2-a]imidazol-3-yl)quinoline | 431.1 |
| 17-10 | 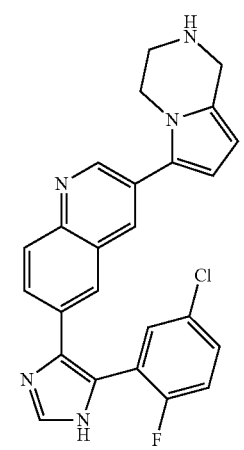 [SMILES: Fc1ccc(Cl)cc1-c1[nH]cnc1-c1ccc2ncc(-c3ccc4n3CCNC4)cc2c1] | 6-[5-(5-chloro-2-fluoro-phenyl)-1H-imidazol-4-yl]-3-(5,6,7,8-tetrahydroimidazo[1,2-a]pyrazin-3-yl)quinoline | 445.1 |

TABLE 1-continued

| No. | Structure | Chemical Name | [M + H]+ |
|---|---|---|---|
| 17-11 | 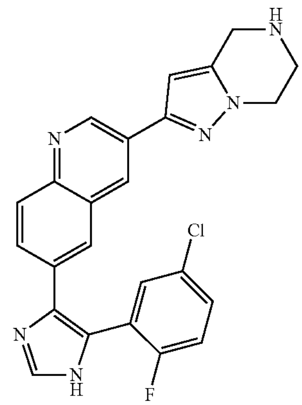 [SMILES: Fc1ccc(Cl)cc1-c1[nH]cnc1-c1ccc2ncc(-c3cc4n(n3)CCNC4)cc2c1] | 6-[5-(5-chloro-2-fluoro-phenyl)-1H-imidazol-4-yl]-3-(4,5,6,7-tetrahydropyrazolo[1,5-a]pyrazin-2-yl)quinoline | 445.1 |
| 17-12 | 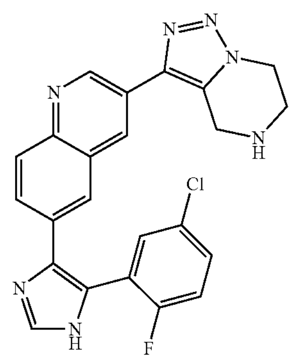 [SMILES: Fc1ccc(Cl)cc1-c1[nH]cnc1-c1ccc2ncc(-c3nnn4c3CNCC4)cc2c1] | 6-[5-(5-chloro-2-fluoro-phenyl)-1H-imidazol-4-yl]-3-(4,5,6,7-tetrahydrotriazolo[1,5-a]pyrazin-3-yl)quinoline | 446.1 |
| 17-13 | 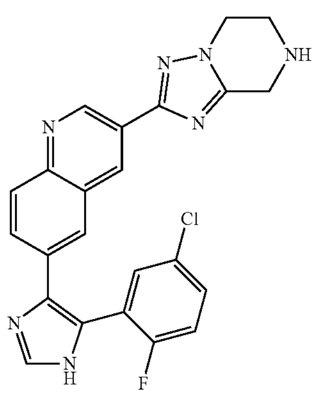 [SMILES: Fc1ccc(Cl)cc1-c1[nH]cnc1-c1ccc2ncc(-c3nc4n(n3)CCNC4)cc2c1] | 6-[5-(5-chloro-2-fluoro-phenyl)-1H-imidazol-4-yl]-3-(5,6,7,8-tetrahydro-[1,2,4]triazolo[1,5-a]pyrazin-2-yl)quinoline | 446.1 |
| 17-14 | 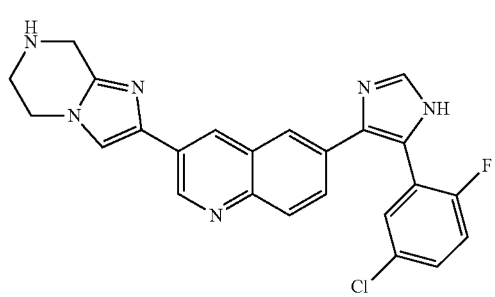 [SMILES: Fc1ccc(Cl)cc1-c1[nH]cnc1-c1ccc2ncc(-c3cn4c(n3)CNCC4)cc2c1] | 6-[5-(5-chloro-2-fluoro-phenyl)-1H-imidazol-4-yl]-3-(5,6,7,8-tetrahydroimidazo[1,2-a]pyrazin-2-yl)quinoline | 445.1 |

TABLE 1-continued

| No. | Structure | Chemical Name | [M + H]+ |
|---|---|---|---|
| 17-15 | 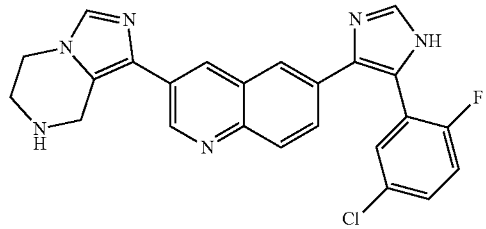 [SMILES: Fc1ccc(Cl)cc1-c1[nH]cnc1-c1ccc2ncc(-c3ncn4c3CNCC4)cc2c1] | 6-[5-(5-chloro-2-fluoro-phenyl)-1H-imidazol-4-yl]-3-(4,5,6,7-tetrahydropyrazolo[1,5-a]pyrazin-3-yl)quinoline | 445.1 |
| 18-1 | 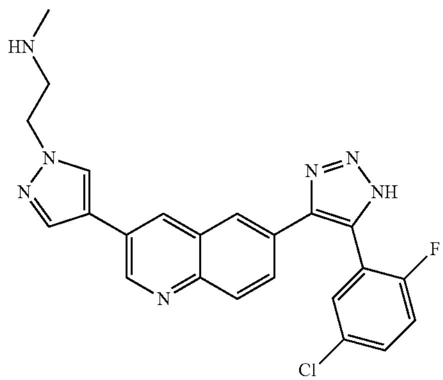 [SMILES: CNCCn1cc(-c2cnc3ccc(-c4nn[nH]c4-c4cc(Cl)ccc4F)cc3c2)cn1] | 2-[4-[6-[5-(5-chloro-2-fluoro-phenyl)-1H-triazol-4-yl]-3-quinolyl]pyrazol-1-yl]-N-methyl-ethanamine | 448.1 |
| 18-2 | 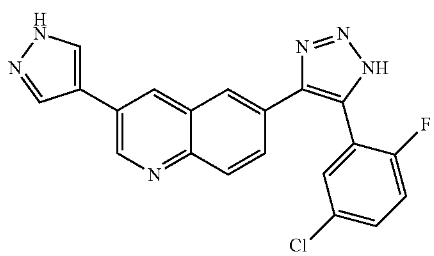 [SMILES: Fc1ccc(Cl)cc1-c1[nH]nnc1-c1ccc2ncc(-c3cn[nH]c3)cc2c1] | 6-[5-(5-chloro-2-fluoro-phenyl)-1H-triazol-4-yl]-3-(1H-pyrazol-4-yl)quinoline | 391.0 |
| 18-3 | 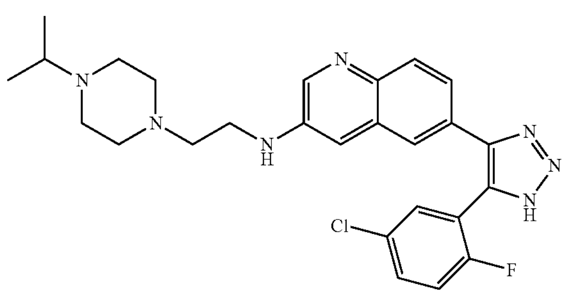 [SMILES: CC(C)N1CCN(CCNc2cnc3ccc(-c4nn[nH]c4-c4cc(Cl)ccc4F)cc3c2)CC1] | 6-[5-(5-chloro-2-fluoro-phenyl)-1H-triazol-4-yl]-N-[2-(4-isopropylpiperazin-1-yl)ethyl]quinolin-3-amine | 495.2 |
| 18-4 | AND Enantiomer | rac-(3S)-1-[6-[5-(5-chloro-2-fluoro-phenyl)-1H-triazol-4-yl]-3-quinolyl]-N,N-dimethyl-pyrrolidin-3-amine | 437.1 |

TABLE 1-continued

| No. | Structure | Chemical Name | [M + H]+ |
|---|---|---|---|
| 18-5 | 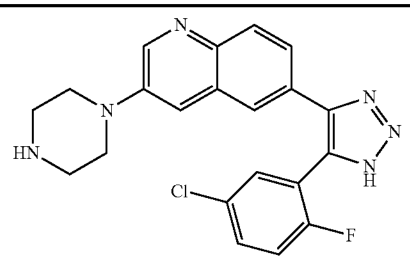 | 6-[5-(5-chloro-2-fluoro-phenyl)-1H-triazol-4-yl]-3-piperazin-1-yl-quinoline | 409.1 |
| 18-6 | 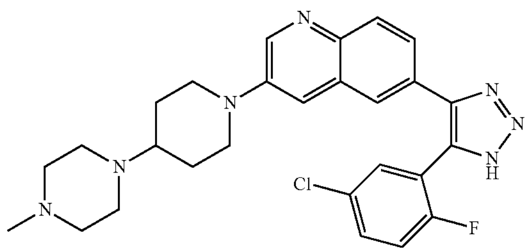 [SMILES: CN1CCN(C2CCN(c3cnc4ccc(-c5nn[nH]c5-c5cc(Cl)ccc5F)cc4c3)CC2)CC1] | 6-[5-(5-chloro-2-fluoro-phenyl)-1H-triazol-4-yl]-3-[4-(4-methylpiperazin-1-yl)-1-piperidyl]quinoline | 507.2 |
| 18-7 | 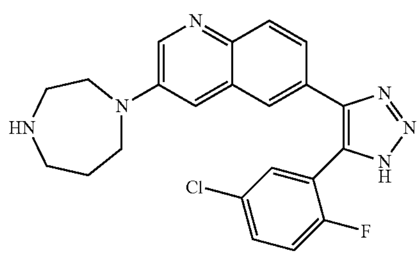 [SMILES: Fc1ccc(Cl)cc1-c1[nH]nnc1-c1ccc2ncc(N3CCCNCC3)cc2c1] | 6-[5-(5-chloro-2-fluoro-phenyl)-1H-triazol-4-yl]-3-(1,4-diazepan-1-yl)quinoline | 423.1 |
| 19-1 | 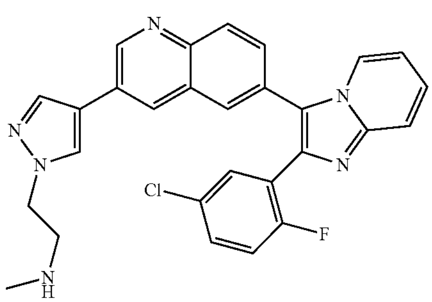 [SMILES: CNCCn1cc(-c2cnc3ccc(-c4c(-c5cc(Cl)ccc5F)nc5ccccn45)cc3c2)cn1] | 2-[4-[6-[2-(5-chloro-2-fluoro-phenyl)imidazo[1,4-a]pyridin-3-yl]-3-quinolyl]pyrazol-1-yl]-N-methyl-ethanamine | 497.1 |
| 19-2 | 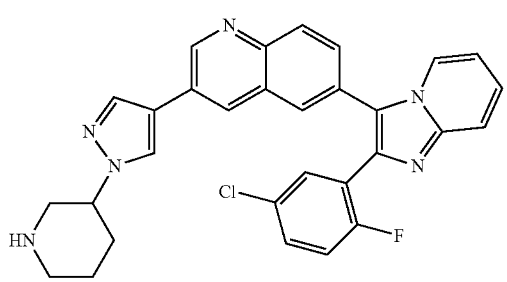 [SMILES: Fc1ccc(Cl)cc1-c1nc2ccccn2c1-c1ccc2ncc(-c3cnn(C4CCCNC4)c3)cc2c1] | 6-[2-(5-chloro-2-fluoro-phenyl)imidazo[1,2-a]pyridin-3-yl]-3-[1-(3-piperidyl)pyrazol-4-yl]quinoline | 523.1 |
| 19-3 | 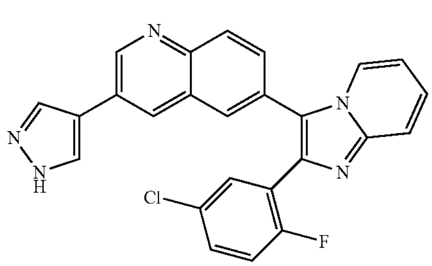 [SMILES: Fc1ccc(Cl)cc1-c1nc2ccccn2c1-c1ccc2ncc(-c3cn[nH]c3)cc2c1] | 6-[2-(5-chloro-2-fluoro-phenyl)imidazo[1,2-a]pyridin-3-yl]-3-(1H-pyrazol-4-yl)quinoline | 439.9 |

TABLE 1-continued

| No. | Structure | Chemical Name | [M + H]⁺ |
|---|---|---|---|
| 19-4 | 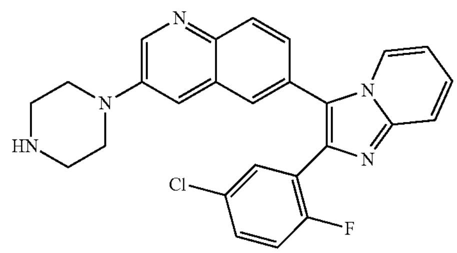 | 6-[2-(5-chloro-2-fluoro-phenyl)imidazo[1,2-a]pyridin-3-yl]-3-piperazin-1-yl-quinoline | 458.0 |
| 19-5 | 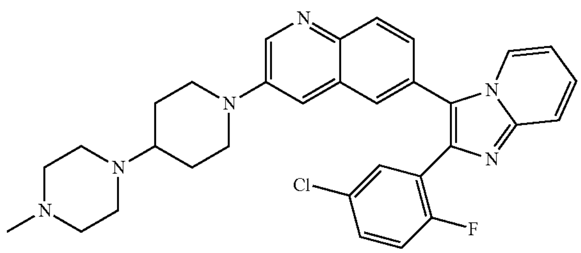 [SMILES: CN1CCN(C2CCN(c3cnc4ccc(-c5c(-c6cc(Cl)ccc6F)nc6ccccn56)cc4c3)CC2)CC1] | 6-[2-(5-chloro-2-fluoro-phenyl)imidazo[1,2-a]pyridin-3-yl]-3-[4-(4-methylpiperazin-1-yl)-1-piperidyl]quinoline | 555.2 |
| 19-6 | 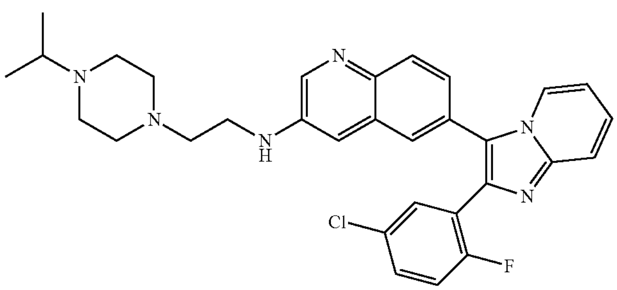 [SMILES: CC(C)N1CCN(CCNc2cnc3ccc(-c4c(-c5cc(Cl)ccc5F)nc5ccccn45)cc3c2)CC1] | 6-[2-(5-chloro-2-fluoro-phenyl)imidazo[1,2-a]pyridin-3-yl]-N-[2-(4-isopropylpiperazin-1-yl)ethyl]quinolin-3-amine | 543.1 |
| 19-7 | AND Enantiomer | rac-(3S)-1-[6-[2-(5-chloro-2-fluoro-phenyl)imidazo[1,2-a]pyridin-3-yl]-3-quinolyl]-N,N-dimethyl-pyrrolidin-3-amine | 486.0 |
| 19-8 | 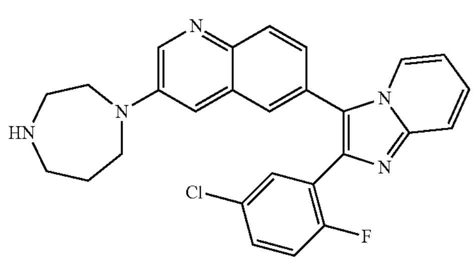 [SMILES: Fc1ccc(Cl)cc1-c1nc2ccccn2c1-c1ccc2ncc(N3CCCNCC3)cc2c1] | 6-[2-(5-chloro-2-fluoro-phenyl)imidazo[1,2-a]pyridin-3-yl]-3-(1,4-diazepan-1-yl)quinoline | 472.0 |

TABLE 1-continued

| No. | Structure | Chemical Name | [M + H]+ |
|---|---|---|---|
| 20-1 | 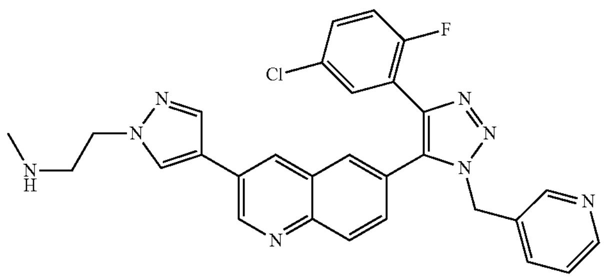 [SMILES: CNCCn1cc(-c2cnc3ccc(-c4c(-c5cc(Cl)ccc5F)nnn4Cc4cccnc4)cc3c2)cn1] | 2-[4-[6-[5-(5-chloro-2-fluoro-phenyl)-3-(3-pyridylmethyl)triazol-4-yl]-3-quinolyl]pyrazol-1-yl]-N-methyl-ethanamine | 539.1 |
| 21-1 | 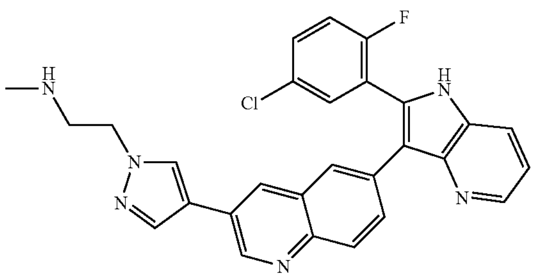 [SMILES: CNCCn1cc(-c2cnc3ccc(-c4c(-c5cc(Cl)ccc5F)[nH]c5cccnc45)cc3c2)cn1] | 2-[4-[6-[2-(5-chloro-2-fluoro-phenyl)-1H-pyrrolo[3,2-b]pyridin-3-yl]-3-quinolyl]pyrazol-1-yl]-N-methyl-ethanamine | 497.0 |
| 22-1 | 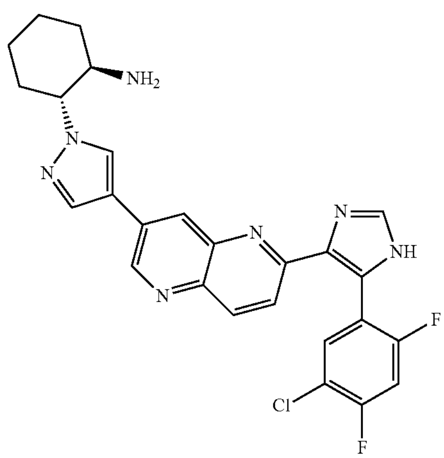 [SMILES: N[C@@H]1CCCC[C@H]1n1cc(-c2cnc3ccc(-c4nc[nH]c4-c4cc(Cl)c(F)cc4F)nc3c2)cn1] | (1R,2R)-2-[4-[6-[5-(5-chloro-2,4-difluoro-phenyl)-1H-imidazol-4-yl]-1,5-naphthyridin-3-yl]pyrazol-1-yl]cyclohexanamine | 506.1 |
| 22-2 | 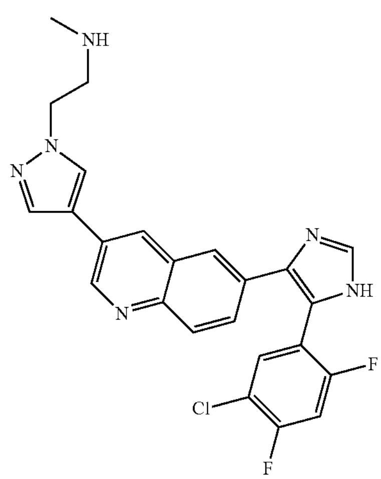 [SMILES: CNCCn1cc(-c2cnc3ccc(-c4nc[nH]c4-c4cc(Cl)c(F)cc4F)cc3c2)cn1] | 2-[4-[6-[5-(5-chloro-2,4-difluoro-phenyl)-1H-imidazol-4-yl]-3-quinolyl]pyrazol-1-yl]-N-methyl-ethanamine | 465.0 |

TABLE 1-continued

| No. | Structure | Chemical Name | [M + H]+ |
|---|---|---|---|
| 22-3 | 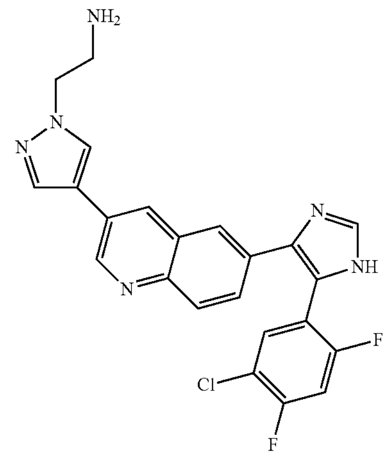 [SMILES: NCCn1cc(-c2cnc3ccc(-c4nc[nH]c4-c4cc(Cl)c(F)cc4F)cc3c2)cn1] | 2-[4-[6-[5-(5-chloro-2,4-difluoro-phenyl)-1H-imidazol-4-yl]-3-quinolyl]pyrazol-1-yl]ethanamine | 450.9 |
| 22-4 | 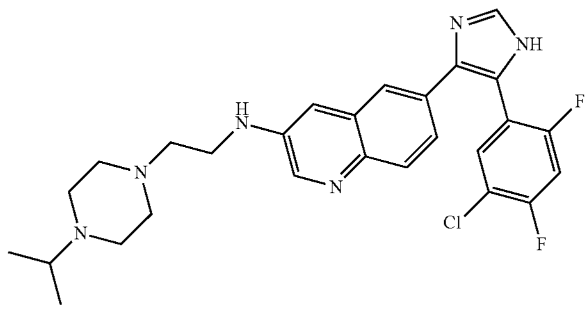 [SMILES: CC(C)N1CCN(CCNc2cnc3ccc(-c4nc[nH]c4-c4cc(Cl)c(F)cc4F)cc3c2)CC1] | 6-[5-(5-chloro-2,4-difluoro-phenyl)-1H-imidazol-4-yl]-N-[2-(4-isopropylpiperazin-1-yl)ethyl]quinolin-3-amine | 511.1 |
| 22-5 | 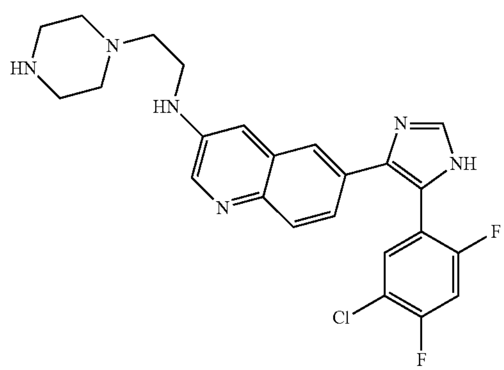 [SMILES: Fc1cc(F)c(-c2[nH]cnc2-c2ccc3ncc(NCCN4CCNCC4)cc3c2)cc1Cl] | 6-[5-(5-chloro-2,4-difluoro-phenyl)-1H-imidazol-4-yl]-N-(2-piperazin-1-ylethyl)quinolin-3-amine | 469.0 |
| 22-6 | 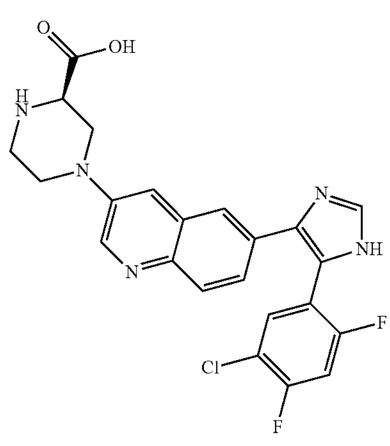 [SMILES: O=C(O)[C@H]1CN(c2cnc3ccc(-c4nc[nH]c4-c4cc(Cl)c(F)cc4F)cc3c2)CCN1] | (2R)-4-[6-[5-(5-chloro-2,4-difluoro-phenyl)-1H-imidazol-4-yl]-3-quinolyl]piperazine-2-carboxylic acid | 470.0 |

TABLE 1-continued
| No. | Structure | Chemical Name | [M + H]+ |
|---|---|---|---|
| 23-1 | 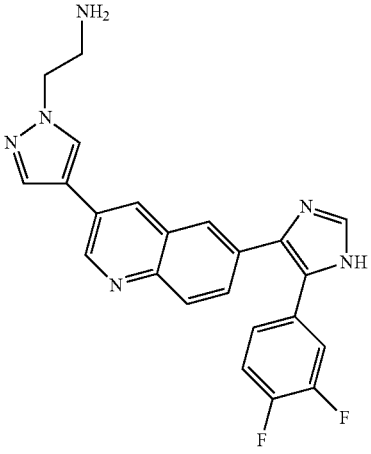 [SMILES: NCCn1cc(-c2cnc3ccc(-c4nc[nH]c4-c4ccc(F)c(F)c4)cc3c2)cn1] | 2-[4-[6-[5-(3,4-difluorophenyl)-1H-imidazol-4-yl]-3-quinolyl]pyrazol-1-yl]ethanamine | 417.1 |
| 23-2 | 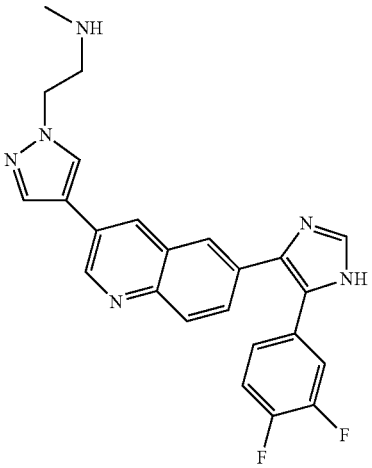 [SMILES: CNCCn1cc(-c2cnc3ccc(-c4nc[nH]c4-c4ccc(F)c(F)c4)cc3c2)cn1] | 2-[4-[6-[5-(3,4-difluorophenyl)-1H-imidazol-4-yl]-3-quinolyl]pyrazol-1-yl]-N-methyl-ethanamine | 431.2 |
| 23-3 | 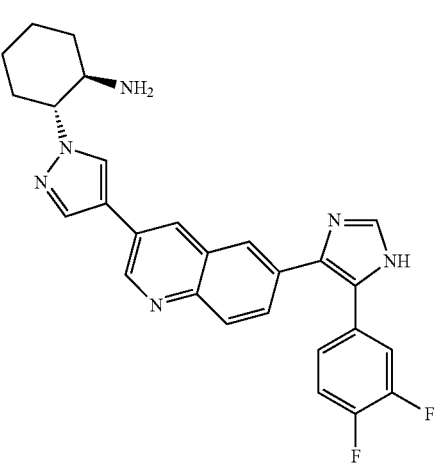 [SMILES: N[C@@H]1CCCC[C@H]1n1cc(-c2cnc3ccc(-c4nc[nH]c4-c4ccc(F)c(F)c4)cc3c2)cn1] | (1R,2R)-2-[4-[6-[5-(3,4-difluorophenyl)-1H-imidazol-4-yl]-3-quinolyl]pyrazol-1-yl]cyclohexanamine | 471.0 |

TABLE 1-continued
| No. | Structure | Chemical Name | [M + H]+ |
|---|---|---|---|
| 23-4 | 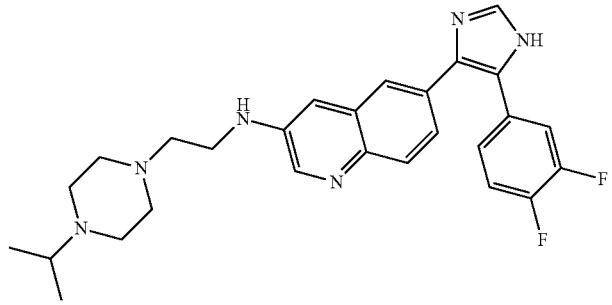 [SMILES: CC(C)N1CCN(CCNc2cnc3ccc(-c4nc[nH]c4-c4ccc(F)c(F)c4)cc3c2)CC1] | 6-[5-(3,4-difluorophenyl)-1H-imidazol-4-yl]-N-[2-(4-isopropylpiperazin-1-yl)ethyl]quinolin-3-amine | 477.2 |
| 23-5 | 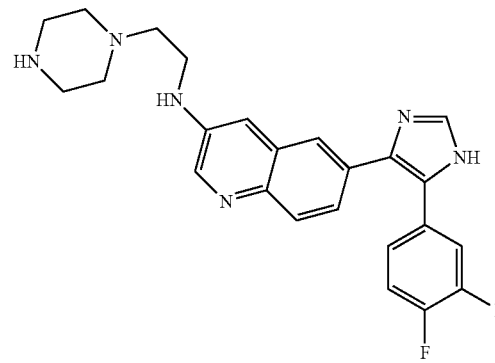 | 6-[5-(3,4-difluorophenyl)-1H-imidazol-4-yl]-N-(2-piperazin-1-ylethyl)quinolin-3-amine | 435.1 |
| 24-1 | 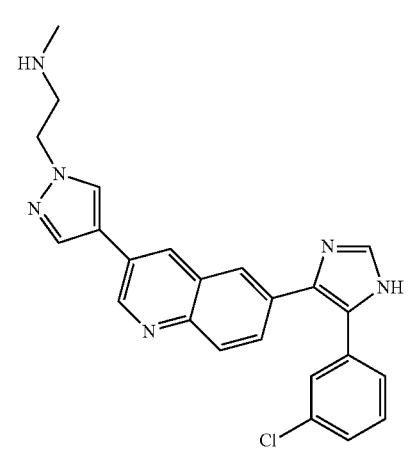 [SMILES: CNCCn1cc(-c2cnc3ccc(-c4nc[nH]c4-c4cccc(Cl)c4)cc3c2)cn1] | 2-[4-[6-[5-(3-chlorophenyl)-1H-imidazol-4-yl]-3-quinolyl]pyrazol-1-yl]-N-methyl-ethanamine | 429.0 |
| 24-2 | 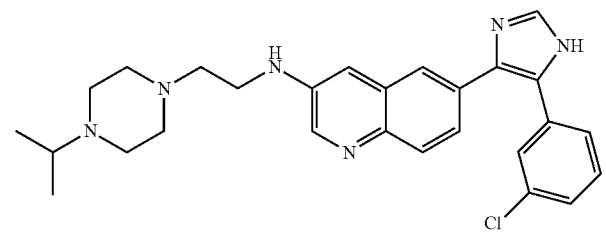 [SMILES: CC(C)N1CCN(CCNc2cnc3ccc(-c4nc[nH]c4-c4cccc(Cl)c4)cc3c2)CC1] | 6-[5-(3-chlorophenyl)-1H-imidazol-4-yl]-N-[2-(4-isopropylpiperazin-1-yl)ethyl]quinolin-3-amine | 475.1 |

TABLE 1-continued

| No. | Structure | Chemical Name | [M + H]+ |
|---|---|---|---|
| 24-3 | 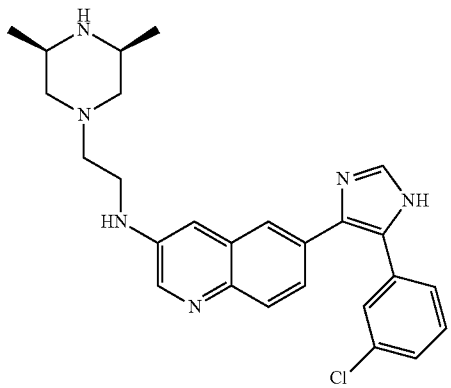 [SMILES: C[C@@H]1CN(CCNc2cnc3ccc(-c4nc[nH]c4-c4cccc(Cl)c4)cc3c2)C[C@H](C)N1] | 6-[5-(3-chlorophenyl)-1H-imidazol-4-yl]-N-[2-[(3R,5S)-3,5-dimethylpiperazin-1-yl]ethyl]quinolin-3-amine | 461.1 |
| 24-4 | 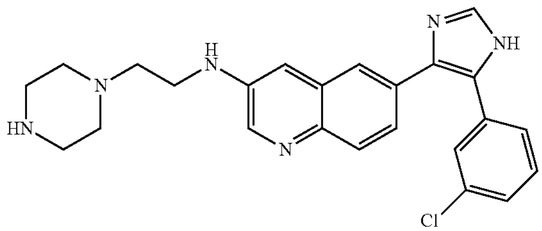 [SMILES: Clc1cccc(-c2[nH]cnc2-c2ccc3ncc(NCCN4CCNCC4)cc3c2)c1] | 6-[5-(3-chlorophenyl)-1H-imidazol-4-yl]-N-(2-piperazin-1-ylethyl)quinolin-3-amine | 433.0 |
| 25-1 | 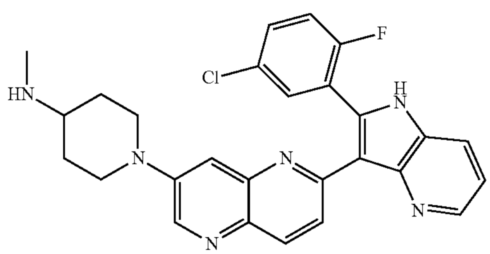 [SMILES: CNC1CCN(c2cnc3ccc(-c4c(-c5cc(Cl)ccc5F)[nH]c5cccnc45)nc3c2)CC1] | 1-[6-[2-(5-chloro-2-fluoro-phenyl)-1H-pyrrolo[3,2-b]pyridin-3-yl]-1,5-naphthyridin-3-yl]-N-methyl-piperazin-4-amine | 487.0 |
| 25-2 | 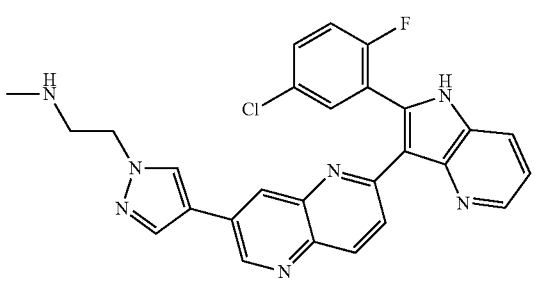 [SMILES: CNCCn1cc(-c2cnc3ccc(-c4c(-c5cc(Cl)ccc5F)[nH]c5cccnc45)nc3c2)cn1] | 2-[4-[6-[2-(5-chloro-2-fluoro-phenyl)-1H-pyrrolo[3,2-b]pyridin-3-yl]-1,5-naphthyridin-3-yl]pyrazol-1-yl]-N-methyl-ethanamine | 498.0 |
| 26-1 | 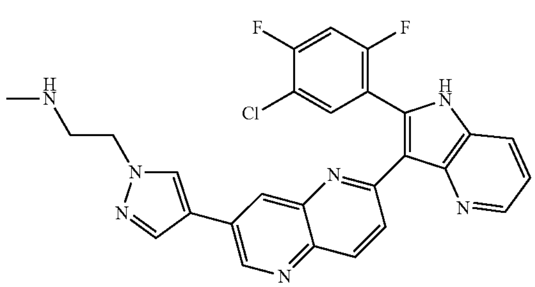 [SMILES: CNCCn1cc(-c2cnc3ccc(-c4c(-c5cc(Cl)c(F)cc5F)[nH]c5cccnc45)nc3c2)cn1] | 2-[4-[6-[2-(5-chloro-2,4-difluoro-phenyl)-1H-pyrrolo[3,2-b]pyridin-3-yl]-1,5-naphthyridin-3-yl]pyrazol-1-yl]-N-methyl-ethanamine | 516.0 |

TABLE 1-continued

| No. | Structure | Chemical Name | [M + H]+ |
|---|---|---|---|
| 27-1 | 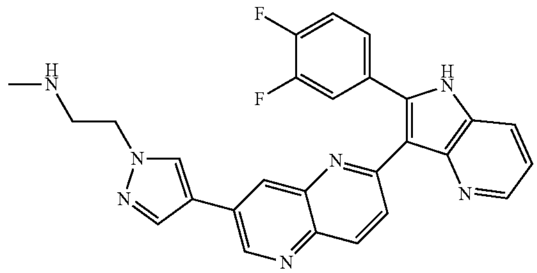 [SMILES: CNCCn1cc(-c2cnc3ccc(-c4c(-c5ccc(F)c(F)c5)[nH]c5cccnc45)nc3c2)cn1] | 2-[4-[6-[2-(3,4-difluorophenyl)-1H-pyrrolo[3,2-b]pyridin-3-yl]-1,5-naphthyridin-3-yl]pyrazol-1-yl]-N-methyl-ethanamine | 482.0 |
| 28-1 | 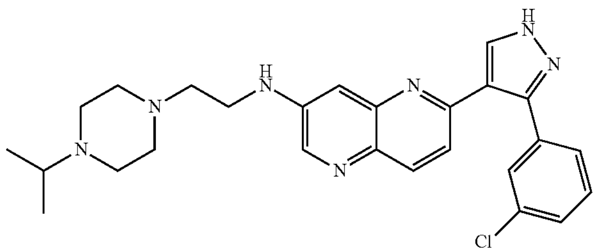 [SMILES: CC(C)N1CCN(CCNc2cnc3ccc(-c4c[nH]nc4-c4cccc(Cl)c4)nc3c2)CC1] | 6-[3-(3-chlorophenyl)-1H-pyrazol-4-yl]-N-[2-(4-isopropylpiperazin-1-yl)ethyl]-1,5-naphthyridin-3-amine | 476.2 |
| 29-1 | 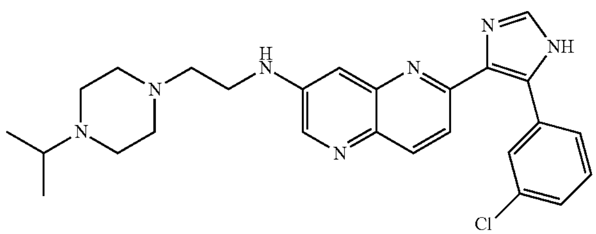 [SMILES: CC(C)N1CCN(CCNc2cnc3ccc(-c4nc[nH]c4-c4cccc(Cl)c4)nc3c2)CC1] | 6-[5-(3-chlorophenyl)-1H-imidazol-4-yl]-N-[2-(4-isopropylpiperazin-1-yl)ethyl]-1,5-naphthyridin-3-amine | 476.1 |
| 29-2 | 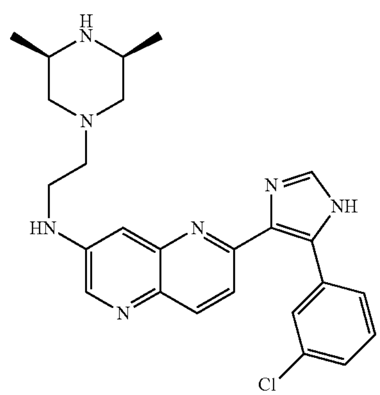 [SMILES: C[C@@H]1CN(CCNc2cnc3ccc(-c4nc[nH]c4-c4cccc(Cl)c4)nc3c2)C[C@H](C)N1] | 6-[5-(3-chlorophenyl)-1H-imidazol-4-yl]-N-[2-[rac-(3R,5S)-3,5-dimethylpiperazin-1-yl]ethyl]-1,5-naphthyridin-3-amine | 462.1 |
| 29-3 | 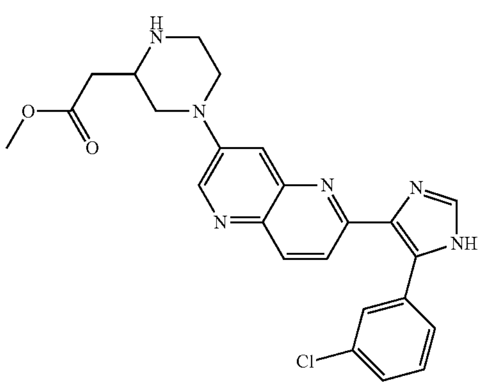 [SMILES: COC(=O)CC1CN(c2cnc3ccc(-c4nc[nH]c4-c4cccc(Cl)c4)nc3c2)CCN1] | methyl 2-[4-[6-[5-(3-chlorophenyl)-1H-imidazol-4-yl]-1,5-naphthyridin-3-yl]piperazin-2-yl]acetate | 463.0 |

| No. | Structure | Chemical Name | [M + H]⁺ |
|---|---|---|---|
| 29-4 | 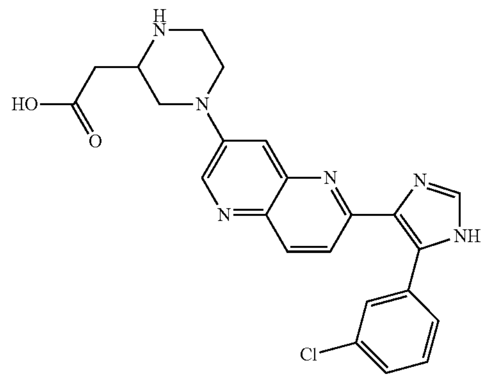 [SMILES: O=C(O)CC1CN(c2cnc3ccc(-c4nc[nH]c4-c4cccc(Cl)c4)nc3c2)CCN1] | 2-[4-[6-[5-(3-chlorophenyl)-1H-imidazol-4-yl]-1,5-naphthyridin-3-yl]piperazin-2-yl]acetic acid | 449.1 |

Methods

In some aspects, the present disclosure provides a method of inhibiting TGFβ signaling, comprising contacting a cell with an effective amount of a compound disclosed herein, such as a compound of any one of Formulae (I) to (XXX). In some embodiments, the present disclosure provides a method of inhibiting ALK5, comprising contacting ALK5 with an effective amount of a compound disclosed herein. Inhibition of ALK5 or TGFβ signaling can be assessed by a variety of methods known in the art. Non-limiting examples include a showing of (a) a decrease in kinase activity of ALK5; (b) a decrease in binding affinity between the TGFβ/TGFβ-RII complex and ALK5; (c) a decrease in the levels of phosphorylated intracellular signaling molecules downstream in the TGFβ signaling pathway, such as a decrease in pSMAD2 or pSMAD3 levels; (d) a decrease in binding of ALK5 to downstream signaling molecules, such as SMAD2 and SMAD3; and/or (e) an increase in ATP levels or a decrease in ADP levels. Kits and commercially available assays can be utilized for determining one or more of the above.

In some aspects, the present disclosure provides a method of treating an ALK5-mediated disease or condition in a subject, comprising administering to the subject a therapeutically effective amount of a compound disclosed herein. In some embodiments, the disease or condition is selected from fibrosis and cancer. In some embodiments, the disease or condition is alopecia. In some embodiments, the disease is a neurodegenerative disease, such as Alzheimer's disease. In some embodiments, the present disclosure provides a method of reversing symptoms of aging. For example, the method may enhance neurogenesis, reduce neuroinflammation, improve cognitive performance, regenerate liver tissue, and reduce p16 levels.

In some aspects, the present disclosure provides a method of treating fibrosis, comprising administering to a patient an effective amount of a compound disclosed herein. In some embodiments, the fibrosis is mediated by ALK5. In some embodiments, the fibrosis is selected from systemic sclerosis, systemic fibrosis, organ-specific fibrosis, kidney fibrosis, pulmonary fibrosis, liver fibrosis, portal vein fibrosis, skin fibrosis, bladder fibrosis, intestinal fibrosis, peritoneal fibrosis, myelofibrosis, oral submucous fibrosis, and retinal fibrosis. In some embodiments, the fibrosis is pulmonary fibrosis, such as idiopathic pulmonary fibrosis (IPF), familial pulmonary fibrosis (FPF), interstitial lung fibrosis, fibrosis associated with asthma, fibrosis associated with chronic obstructive pulmonary disease (COPD), silica-induced fibrosis, asbestos-induced fibrosis or chemotherapy-induced lung fibrosis. In some embodiments, the fibrosis is idiopathic pulmonary fibrosis (IPF).

In some aspects, the present disclosure provides a method of treating cancer, comprising administering to a patient an effective amount of a compound disclosed herein. In some embodiments, the cancer is mediated by ALK5. In some embodiments, the cancer is selected from breast cancer, colon cancer, prostate cancer, lung cancer, hepatocellular carcinoma, glioblastoma, melanoma and pancreatic cancer. In some embodiments, the cancer is lung cancer, such as non-small cell lung cancer. In some aspects, the present disclosure provides a method of treating cancer, such as non-small cell lung cancer, comprising administering to a patient an effective amount of a compound disclosed herein and an immunotherapeutic agent. In some embodiments, the cancer is stage III non-small cell lung cancer. In some embodiments, the method further comprises administering radiation to the patient. In some embodiments, the immunotherapeutic agent is a PD-1 inhibitor or a CTLA-4 inhibitor. In some embodiments, the immunotherapeutic agent is selected from atezolizumab, avelumab, nivolumab, pembrolizumab, durvalumab, BGB-A317, tremelimumab and ipilimumab. In some embodiments, the immunotherapeutic agent is selected from pembrolizumab and durvalumab.

The compounds described herein, including compounds of any one of Formulae (I) to (XXX), are ALK5 inhibitors that limit the activity of TGFβ. TGFβ is one of several factors involved in the initiation and development of fibrotic diseases throughout the body. As such, the compounds of the disclosure are expected to be useful for the treatment, prevention and/or reduction of fibrosis in a patient by administering a therapeutically effective amount of a compound disclosed herein. By inhibiting ALK5, the compound is expected to potentiate the formation of fibrosis in areas of the body that suffer from excessive deposition of the extracellular matrix. Those areas are described below.

Systemic Fibrotic Diseases

Systemic sclerosis (SSc) is an autoimmune disorder that affects the skin and internal organs and results in autoantibody production, vascular endothelial activation of small blood vessels, and tissue fibrosis as a result of fibroblast dysfunction. Transforming growth factor β (TGF-β) has been identified as a regulator of pathological fibrogenesis in SSc (Ayers, N. B., et al., *Journal of Biomedical Research*, 2018, 32(1), pp. 3-12). According to the authors, "understanding the essential role TGF-β pathways play in the pathology of systemic sclerosis could provide a potential outlet for treatment and a better understanding of this severe disease." In some embodiments, the present disclosure provides a method of treating SSc, comprising administering to a subject an effective amount of a compound disclosed herein.

Multifocal fibrosclerosis (MF) and idiopathic multifocal fibrosclerosis (IMF) are disorders characterized by fibrous lesions at varying sites and include retroperitoneal fibrosis, mediastinal fibrosis and Riedel's thyroiditis. Both multifocal fibrosclerosis and idiopathic multifocal fibrosclerosis are considered to be an outcome of $IgG_4$-associated fibrosis/disease and TGF-β is believed to be one factor involved in the initiation and development of fibrosis (Pardali, E., et. al., *Int. J. Mol. Sci.*, 18, 2157, pp. 1-22). In some embodiments, the present disclosure provides a method of treating multifocal fibrosclerosis or idiopathic multifocal fibrosclerosis, comprising administering to a subject an effective amount of a compound disclosed herein.

In some embodiments, the present disclosure provides a method of treating nephrogenic systemic fibrosis, comprising administering to a subject an effective amount of a compound disclosed herein. Nephrogenic systemic fibrosis is a rare disease occurring mainly in people with advanced kidney failure with or without dialysis. In a study performed by Kelly et al. (*J. Am. Acad. Dermatol.*, 2008, 58, 6, pp. 1025-1030), it was shown that TGF-β, as well as Smad 2/3, appear to be associated with fibrosis seen in nephrogenic systemic fibrosis.

Sclerodermatous graft-versus-host disease (GVHD) is a prevalent complication of allogeneic hematopoietic stem cell graft appearing two to three months after allogeneic bone marrow transplantation. The disease results in production of autoantibodies and fibrosis of skin and inner organs. Using a murine cutaneous GVHD model, it has been shown that progression of early skin and lung disease can be inhibited with TGF-β neutralizing antibodies (McCormick, L. L., et al., *J. Immunol.*, 1999, 163, pp. 5693-5699). In some embodiments, the present disclosure provides a method of treating sclerodermatous GVHD, comprising administering to a subject an effective amount of a compound disclosed herein.

Organ-Specific Fibrotic Diseases

Cardiac fibrosis refers to the abnormal thickening of heart valves due to the abnormal proliferation of cardiac fibroblasts resulting in excess deposition of ECM in heart muscle. Fibroblasts secrete collagen, which serves as structural support for the heart. However, when collagen is excessively secreted in the heart, wall and valve thickening can result in tissue build-up on the tricuspid and pulmonary valves. This in turn causes loss of flexibility and ultimately valvular dysfunction leading to heart failure. A specific type of cardiac fibrosis is hypertension-associated cardiac fibrosis as described by J. Diez (*J. Clin. Hypertens.*, 2007, July 9(7), pp. 546-550). According to Diez, changes in the composition of cardiac tissue develop in hypertensive patients with left ventricular hypertrophy and lead to structural remodeling of the heart tissue. One change relates to the disruption of the equilibrium between the synthesis and degradation of collagen types I and III molecules, resulting in excessive accumulation of collagen fibers in the heart tissue. Other types of cardiac fibrosis include post-myocardial infarction and Chagas disease-induced myocardial fibrosis. In Chagas disease, transforming growth factor β (TGF-β1) has been implicated in Chagas disease physiopathology, where animal models suggest that the TGF-β1-pathway is up-regulated during infection (Araujo-Jorge, T. C., et al., *Clin. Pharmacol. Ther.*, 2012, 92(5), pp. 613-621; Curvo, E., *Mem Inst Oswaldo Cruz*, 2018, Vol. 113(4), e170440, pp. 1-8). In some embodiments, the present disclosure provides a method of treating various forms of cardiac fibrosis, such as hypertension-associated cardiac fibrosis, post-myocardial infarction or Chagas disease-induced myocardial fibrosis, comprising administering to a subject an effective amount of a compound disclosed herein.

Renal fibrosis encompasses a variety of disorders associated with the aberrant expression and activity of TGF-β, including, but not limited to, diabetic and hypertensive nephropathy, urinary tract obstruction-induced kidney fibrosis, inflammatory/autoimmune-induced kidney fibrosis, aristolochic acid nephropathy, progressive kidney fibrosis, and polysystic kidney disease. As discussed above, fibrosis involves an excess accumulation of the ECM, which in turn causes loss of function when normal tissue is replaced with scar tissue (Wynn, T. A., J Clin Invest., 2007, 117, pp. 524-529). As early as 2005, ALK5 inhibitors were being studied in models for renal disease (Laping, N. J., *Current Opinion in Pharmacology*, 2003, 3, pp. 204-208). In some embodiments, the present disclosure provides a method of treating renal fibrosis, comprising administering to a subject an effective amount of a compound disclosed herein.

One fibrotic disease that has been particularly difficult to treat is idiopathic pulmonary fibrosis (IPF). IPF is a chronic, progressive and fatal fibrotic lung disease with survival only improved by lung transplantation. Current oral therapies such as nintedanib and pirfenidone have been shown to slow the progression of the disease, but have adverse effects that lead to discontinuation and lack of compliance by the patient. Although there are other therapies in development targeting various pathways, an unmet need remains for patients with IPF.

Although ALK5 is an important and known component in the fibrotic disease pathway, the efficacy of ALK5 inhibitors in IPF have not been realized due to systemic adverse effects, especially in the heart. Thus, one of the goals of this disclosure is to develop ALK5 inhibitors with high lung selectivity and rapid clearance. One preferred embodiment of this disclosure is to treat patients with idiopathic pulmonary fibrosis with a compound described herein, for example, by once or twice daily administration of inhalable ALK5 inhibitor having minimal systemic exposure. The inhaled ALK5 inhibitor may be administered as a monotherapy or co-dosed with other orally available IPF therapies. In some embodiments, the present disclosure provides a method of treating idiopathic pulmonary fibrosis, comprising administering to a subject an effective amount of a compound disclosed herein. In some embodiments, the compound is administered by inhalation.

Familial pulmonary fibrosis is a hereditary disease where two or more family members have confirmed IPF. In some embodiments, the present disclosure provides a method of treating familial pulmonary fibrosis, comprising administering to a subject an effective amount of a compound disclosed herein.

Other types of interstitial lung diseases include, but are not limited to, (1) interstitial pneumonia caused by bacteria, viruses, or fungi; (2) nonspecific interstitial pneumonitis usually associated with autoimmune conditions such as rheumatoid arthritis or scleroderma; (3) hypersensitivity pneumonitis caused by inhalation of dust, mold, or other irritants; (4) cryptogenic organizing pneumonia; (5) acute interstitial pneumonitis; (6) desquamative interstitial pneumonitis; (7) sarcoidosis; and (8) drug-induced interstitial lung disease. In some embodiments, the present disclosure provides a method of treating an interstitial lung disease, comprising administering to a subject an effective amount of a compound disclosed herein.

Both transforming growth factor (TGF)-beta(1) and activin-A have been implicated in airway remodeling in asthma (Kariyawasam, H. H., *J Allergy Clin Immunol.*, 2009, September, 124(3), pp. 454-462). In some embodiments, the present disclosure provides a method of treating asthma, comprising administering to a subject an effective amount of a compound disclosed herein.

Chronic obstructive pulmonary disease (COPD) is a pulmonary disorder characterized by a poorly reversible and progressive airflow limitation caused by airway inflammation and emphysema, whereas IPF is associated with impaired diffusion capacity (Chilosi, M., et al., *Respir. Res.*, 2012, 13(1), 3, pp. 1-9). Both diseases, however, demonstrate a progressive loss of alveolar parenchyma leading to severe impairment of respiratory function. Fibrosis associated with emphysema is known and research has demonstrated TGF-β1 involvement in chronic sinus disease, pulmonary fibrosis, asthma, and COPD (Yang, Y. C., et al., *Allergy*, 2012, 67, pp. 1193-1202). In some embodiments, the present disclosure provides a method of treating COPD, comprising administering to a subject an effective amount of a compound disclosed herein.

Other types of lung injury that result in fibrosis include silica-induced pneumoconiosis (silicosis), asbestos-induced pulmonary fibrosis (asbestosis), and chemotherapeutic agent-induced pulmonary fibrosis. In some embodiments, the present disclosure provides a method of treating injury-induced fibrosis, comprising administering to a subject an effective amount of a compound disclosed herein.

In some embodiments, the present disclosure provides a method of treating liver fibrosis, comprising administering to a subject an effective amount of a compound disclosed herein. Fibrosis develops in the liver when it is repeatedly or continuously damaged, for example, in patients with chronic hepatitis. TGF-β signaling participates in all stages of disease progression, from initial liver injury through inflammation and fibrosis, to cirrhosis and cancer (Fabregat, I., et al., *The FEBS* 1, 2016, 283(12), pp. 2219-2232).

A related condition involves fibrosis resulting from idiopathic non-cirrhotic portal hypertension (INCPH). This disease is of uncertain etiology characterized by periportal fibrosis and involvement of small and medium branches of the portal vein. According to Nakanuma et al., small portal veins and skin findings are similar between patients with scleroderma and INCPH (Nakanuma, Y., *Hepatol. Res.*, 2009, 39, pp. 1023-1031). Transforming growth factor-β (TGF-β) and connective tissue growth factor, which are fibrosis-related and vascular endothelial growth factors, respectively, increase in serum, skin, and the portal vein, suggesting that these could be mechanisms of the portal vein occlusion in INCPH. Moreover, endothelial mesenchymal transition (EndMT) theory was proposed by Kitao et al. based on these findings (Kitao, A., et al., *Am. J. Pathol.*, 2009, 175, pp. 616-626). The increase of TGF-β in sera may act as a potent inducer of EndMT. In some embodiments, the present disclosure provides a method of treating INCPH, comprising administering to a subject an effective amount of a compound disclosed herein.

Other types of liver fibrosis include alcoholic and non-alcoholic liver fibrosis, hepatitis C-induced liver fibrosis, primary biliary cirrhosis or cholangitis, and parasite-induced liver fibrosis (schistosomiasis). In some embodiments, the present disclosure provides a method of treating alcoholic liver fibrosis, non-alcoholic liver fibrosis, hepatitis C-induced liver fibrosis, primary biliary cirrhosis, primary biliary cholangitis, or parasite-induced liver fibrosis (schistosomiasis), comprising administering to a subject an effective amount of a compound disclosed herein.

Fibrotic skin conditions include, but are not limited to, hypertrophic scarring, keloids, and localized or systemic sclerosis (scleroderma). As discussed previously, TGF-β is a potent stimulus of connective tissue accumulation, and has been implicated in the pathogenesis of scleroderma and other fibrotic disorders (Lakos, G., et al., *Am. J. Pathol.*, 2004, 165(1), pp. 203-217). Lakos et. al. demonstrated that Smad3 functions as a key intracellular signal transducer for profibrotic TGF-β responses in normal skin fibroblasts and found that the targeted disruption of TGF-β/Smad3 signaling modulated skin fibrosis in the mouse model of scleroderma. In some embodiments, the present disclosure provides a method of treating skin fibrosis, comprising administering to a subject an effective amount of a compound disclosed herein.

Other types of organ-specific fibrosis or fibrotic diseases involving the TGF-β pathway, include but are not limited to, radiation-induced fibrosis (various organs), bladder fibrosis, intestinal fibrosis, peritoneal sclerosis, diffuse fasciitis, Dupuytren's disease, myelofibrosis, oral submucous fibrosis, and retinal fibrosis. In some embodiments, the present disclosure provides a method of treating radiation-induced fibrosis, bladder fibrosis, intestinal fibrosis, peritoneal sclerosis, diffuse fasciitis, Dupuytren's disease, myelofibrosis, oral submucous fibrosis, or retinal fibrosis, comprising administering to a subject an effective amount of a compound disclosed herein.

Although one of the goals of this disclosure is to treat fibrotic diseases locally or in a targeted way, the compounds described herein may also be used to treat patients systemically. Diseases that may be treated systemically, include, for example, oncologic diseases such as glioblastoma, pancreatic cancer and heptocellular carcinoma, breast cancer metastasized to lungs, non-small cell lung cancer, small cell lung cancer, cystic fibrosis, and metastasis of other forms of primary cancer subtypes. Some of the forgoing diseases may also be treated locally as well.

Other fibrotic diseases that compounds disclosed herein may treat include angioedema, anti-aging, and alopecia. Alopecia includes alopecia totalis, alopecia universalis, androgenetic alopecia, alopecia areata, diffuse alopecia, postpartum alopecia, and traction alopecia.

Other Indications

In certain aspects, the present disclosure provides a method of reversing one or more symptoms of aging, comprising administering to a subject an ALK5 inhibitor. The method may further comprise administering an activator of the MAPK pathway, such as oxytocin. The method may be effective in one or more of enhancing neurogenesis in the hippocampus, reducing neuroinflammation, improving cognitive ability, reducing liver adiposity, reducing liver fibrosis, and decreasing the number of $p16^+$ cells. In some embodiments, a method described herein increases stem cell activity. The increase in stem cell activity may allow the subject to generate new muscle fibers and/or to form new neurons in the hippocampus. Treatment with an ALK5 inhibitor, such as a compound described herein, may prevent or slow the onset of age-related diseases, such as Alzheimer's disease. (see Mehdipour, M. et al. *Aging* 2018, 10, 5628-5645).

Pharmaceutical Compositions

In some aspects, the present disclosure provides a pharmaceutical composition. The pharmaceutical composition may comprise a compound disclosed herein, such as a compound of any one of Formulae (I) to (XXX), and a pharmaceutically acceptable carrier. In some embodiments, the pharmaceutical composition is formulated for oral administration. In some embodiments, the pharmaceutical composition is formulated for inhalation. In some embodiments, the pharmaceutical composition comprises a compound disclosed herein and an additional therapeutic agent. Non-limiting examples of such therapeutic agents are described herein below.

Pharmaceutical compositions typically include at least one pharmaceutically acceptable carrier, diluent or excipient and at least one compound of any one of Formulae (I) to (XXX), or a compound provided in Table 1—described herein as the active agent. The active agent may be provided in any form suitable for the particular mode of administration, such as a free base, a free acid, or a pharmaceutically acceptable salt. Additionally, the methods and pharmaceutical compositions of the present disclosure include the use of N-oxides, crystalline forms (e.g., polymorphs), as well as metabolites of these compounds having similar activity. All tautomers of the compounds described herein are included within the scope of the present disclosure. Additionally, the compounds described herein encompass unsolvated as well as solvated forms with pharmaceutically acceptable solvents such as water, ethanol and the like.

Suitable routes of administration include, but are not limited to, oral, intravenous, rectal, vaginal, aerosol, pulmonary, nasal, transmucosal, topical, transdermal, otic, ocular, and parenteral modes of administration. In addition, by way of example only, parenteral delivery includes intramuscular, subcutaneous, intravenous, intramedullary injections, as well as intrathecal, direct intraventricular, intraperitoneal, intralymphatic, and intranasal injections.

In certain embodiments, a compound described herein is administered in a local rather than systemic manner, for example, via injection of the compound directly into an organ, often in a depot preparation or sustained release formulation. In some embodiments, a long acting formulation is administered by implantation (e.g., subcutaneously or intramuscularly) or by intramuscular injection. In some embodiments, a compound described herein is provided in the form of a rapid release formulation, an extended release formulation, or an intermediate release formulation. In some embodiments, a compound described herein is provided in the form of a nebulized formulation. In some embodiments, a compound described herein is administered locally to the lungs by inhalation.

Compounds of the present disclosure are effective over a wide dosage range. For example, in the treatment of adult humans, dosages from 0.01 to 1000 mg, 0.5 to 100 mg, 1 to 50 mg, or from 5 to 40 mg per day may be administered to a subject in need thereof. The exact dosage will depend upon the route of administration, the form in which the compound is administered, the subject to be treated, the body weight of the subject to be treated, and the preference and experience of the attending physician.

A compound of the present disclosure may be administered in a single dose. In some embodiments, a compound of the disclosure is administered in multiple doses, such as about once, twice, three times, four times, five times, six times, or more than six times per day. In some embodiments, dosing is about once a month, one every two weeks, once a week, or once every other day. In some embodiments, a compound of the disclosure and an additional therapeutic agent are administered together about once per day to about 6 times per day. In some embodiments, the administration continues for more than about 6, 10, 14, 28 days, two months, six months, or more than about one year. In some embodiments, a dosing schedule is maintained as long as necessary. A compound of the present disclosure may be administered chronically on an ongoing basis, e.g., for the treatment of chronic effects.

Pharmaceutical compositions of the present disclosure typically contain a therapeutically effective amount of a compound of the present disclosure. Those skilled in the art will recognize, however, that a pharmaceutical composition may contain more than a therapeutically effective amount, e.g., bulk compositions, or less than a therapeutically effective amount, e.g., individual unit doses designed for co-administration to achieve a therapeutically effective amount.

Typically, pharmaceutical compositions of the present disclosure contain from about 0.01 to about 95% by weight of the active agent; including, for example, from about 0.05 to about 30% by weight; and from about 0.1% to about 10% by weight of the active agent.

Any conventional carrier or excipient may be used in the pharmaceutical compositions of the present disclosure. The choice of a particular carrier or excipient, or combinations of carriers or excipients, will depend on the mode of administration being used to treat a particular patient or type of medical condition or disease state. Additionally, the carriers or excipients used in the pharmaceutical compositions of this disclosure may be commercially-available. Conventional formulation techniques are described in Remington: The Science and Practice of Pharmacy, 20th Edition, Lippincott Williams & White, Baltimore, Md. (2000); and H. C. Ansel et al., Pharmaceutical Dosage Forms and Drug Delivery Systems, 7th Edition, Lippincott Williams & White, Baltimore, Md. (1999).

Representative examples of materials which can serve as pharmaceutically acceptable carriers include, but are not limited to, the following: sugars, such as lactose, glucose and sucrose; starches, such as corn starch and potato starch; cellulose, such as microcrystalline cellulose and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical compositions.

Pharmaceutical compositions are typically prepared by thoroughly and intimately mixing or blending the active agent with a pharmaceutically-acceptable carrier and one or more optional ingredients. The resulting uniformly blended mixture can then be shaped or loaded into tablets, capsules, pills and the like using conventional procedures and equipment.

In one aspect, the pharmaceutical composition is suitable for inhaled administration. Pharmaceutical compositions for inhaled administration are typically in the form of an aerosol or a powder. Such compositions are generally administered using inhaler delivery devices, such as a dry powder inhaler (DPI), a metered-dose inhaler (MDI), a nebulizer inhaler, or a similar delivery device.

In a particular embodiment, the pharmaceutical composition is administered by inhalation using a dry powder inhaler. Such dry powder inhalers typically administer the pharmaceutical composition as a free-flowing powder that is dispersed in a patient's air-stream during inspiration. In order to achieve a free-flowing powder composition, the therapeutic agent is typically formulated with a suitable excipient such as lactose, starch, mannitol, dextrose, polylactic acid (PLA), polylactide-co-glycolide (PLGA) or combinations thereof. Typically, the therapeutic agent is micronized and combined with a suitable carrier to form a composition suitable for inhalation.

A representative pharmaceutical composition for use in a dry powder inhaler comprises lactose and a micronized form of a compound disclosed herein. Such a dry powder composition can be made, for example, by combining dry milled lactose with the therapeutic agent and then dry blending the components. The composition is then typically loaded into a dry powder dispenser, or into inhalation cartridges or capsules for use with a dry powder delivery device.

Dry powder inhaler delivery devices suitable for administering therapeutic agents by inhalation are described in the art and examples of such devices are commercially available. For example, representative dry powder inhaler delivery devices or products include Aeolizer (Novartis); Airmax (IVAX); ClickHaler (Innovata Biomed); Diskhaler (GlaxoSmithKline); Diskus/Accuhaler (GlaxoSmithKline); Ellipta (GlaxoSmithKline); Easyhaler (Orion Pharma); Eclipse (Aventis); FlowCaps (Hovione); Handihaler (Boehringer Ingelheim); Pulvinal (Chiesi); Rotahaler (GlaxoSmithKline); SkyeHaler/Certihaler (SkyePharma); Twisthaler (Schering-Plough); Turbuhaler (AstraZeneca); Ultrahaler (Aventis); and the like.

A pharmaceutical composition of the present disclosure may be administered by inhalation using a metered-dose inhaler. Such metered-dose inhalers typically discharge a measured amount of a therapeutic agent using a compressed propellant gas. Accordingly, pharmaceutical compositions administered using a metered-dose inhaler typically comprise a solution or suspension of the therapeutic agent in a liquefied propellant. Any suitable liquefied propellant may be employed, including hydrofluoroalkanes (HFAs), such as 1,1,1,2-tetrafluoroethane (HFA 134a) and 1,1,1,2,3,3,3-heptafluoro-n-propane, (HFA 227); and chlorofluorocarbons, such as $CCl_3F$. In a particular embodiment, the propellant is a hydrofluoroalkane. In some embodiments, the hydrofluoroalkane formulation contains a co-solvent, such as ethanol or pentane, and/or a surfactant, such as sorbitan trioleate, oleic acid, lecithin, and glycerin.

A representative pharmaceutical composition for use in a metered-dose inhaler comprises from about 0.01% to about 5% by weight of a compound of the present disclosure; from about 0% to about 20% by weight ethanol; and from about 0% to about 5% by weight surfactant; with the remainder being an HFA propellant. Such compositions are typically prepared by adding chilled or pressurized hydrofluoroalkane to a suitable container containing the therapeutic agent, ethanol (if present) and the surfactant (if present). To prepare a suspension, the therapeutic agent is micronized and then combined with the propellant. The composition is then loaded into an aerosol canister, which typically forms a portion of a metered-dose inhaler device.

Metered-dose inhaler devices suitable for administering therapeutic agents by inhalation are described in the art and examples of such devices are commercially available. For example, representative metered-dose inhaler devices or products include AeroBid Inhaler System (Forest Pharmaceuticals); Atrovent Inhalation Aerosol (Boehringer Ingelheim); Flovent (GlaxoSmithKline); Maxair Inhaler (3M); Proventil Inhaler (Schering); Serevent Inhalation Aerosol (GlaxoSmithKline); and the like.

A pharmaceutical composition of the present disclosure may be administered by inhalation using a nebulizer inhaler. Such nebulizer devices typically produce a stream of high velocity air that causes the pharmaceutical composition to spray as a mist that is carried into the patient's respiratory tract. Accordingly, when formulated for use in a nebulizer inhaler, the therapeutic agent can be dissolved in a suitable carrier to form a solution. Alternatively, the therapeutic agent can be micronized or nanomilled and combined with a suitable carrier to form a suspension.

A representative pharmaceutical composition for use in a nebulizer inhaler comprises a solution or suspension comprising from about 0.05 μg/mL to about 20 mg/mL of a compound of the present disclosure and excipients compatible with nebulized formulations. In one embodiment, the solution has a pH of about 3 to about 8.

Nebulizer devices suitable for administering therapeutic agents by inhalation are described in the art and examples of such devices are commercially available. For example, representative nebulizer devices or products include the Respimat® Softmist™ Inhalaler (Boehringer Ingelheim); the AERx® Pulmonary Delivery System (Aradigm Corp.); the PARI LC Plus® Reusable Nebulizer or PARI eFlow® rapid Nebulizer System (Pari GmbH); and the like.

A pharmaceutical composition of the present disclosure may be prepared in a dosage form intended for oral administration. Suitable pharmaceutical compositions for oral administration may be in the form of capsules, tablets, pills, lozenges, cachets, dragees, powders, granules; or as a solution or a suspension in an aqueous or non-aqueous liquid; or as an oil-in-water or water-in-oil liquid emulsion; or as an elixir or syrup; and the like; each containing a predetermined amount of a compound of the present invention as an active ingredient.

When intended for oral administration in a solid dosage form, the pharmaceutical compositions of the invention will typically comprise the active agent and one or more pharmaceutically-acceptable carriers, such as sodium citrate or dicalcium phosphate. Optionally or alternatively, such solid dosage forms may also comprise: fillers or extenders, binders, humectants, solution retarding agents, absorption accelerators, wetting agents, absorbents, lubricants, coloring agents, and buffering agents. Release agents, wetting agents, coating agents, sweetening, flavoring and perfuming agents, preservatives and antioxidants can also be present in the present pharmaceutical compositions.

Alternative formulations may include controlled release formulations, liquid dosage forms for oral administration, transdermal patches, and parenteral formulations. Conventional excipients and methods of preparation of such alternative formulations are described, for example, in the reference by Remington, supra.

The following non-limiting examples illustrate representative pharmaceutical compositions of the present disclosure.

Dry Powder Composition

A micronized compound of the present disclosure (1 g) is blended with milled lactose (25 g). This blended mixture is then loaded into individual blisters of a peelable blister pack in an amount sufficient to provide between about 0.1 mg to about 4 mg of the compound per dose. The contents of the blisters are administered using a dry powder inhaler.

Dry Powder Composition

A micronized compound of the present disclosure (1 g) is blended with milled lactose (20 g) to form a bulk composition having a weight ratio of compound to milled lactose of 1:20. The blended composition is packed into a dry powder inhalation device capable of delivering between about 0.1 mg to about 4 mg of the compound per dose.

Metered-Dose Inhaler Composition

A micronized compound of the present disclosure (10 g) is dispersed in a solution prepared by dissolving lecithin (0.2 g) in demineralized water (200 mL). The resulting suspension is spray dried and then micronized to form a micronized composition comprising particles having a mean diameter less than about 1.5 µm. The micronized composition is then loaded into metered-dose inhaler cartridges containing pressurized 1,1,1,2-tetrafluoroethane in an amount sufficient to provide about 0.1 mg to about 4 mg of the compound per dose when administered by the metered dose inhaler.

Nebulizer Composition

A representative nebulizer composition is as follows. A compound of the present disclosure (2 g of free-base equivalents) is dissolved in a solution containing 80 mL reverse-osmosis water, 0.1-1% by weight of anhydrous citric acid, and 0.5-1.5 equivalents of hydrochloric acid, followed by addition of sodium hydroxide to adjust the pH to 3.5 to 5.5. Thereafter, between 4-6% by weight of D-mannitol is added and solution q.s. to 100 mL. The solution is then filtered through a 0.2 µm filter and stored at room temperature prior to use. The solution is administered using a nebulizer device that provides about 0.1 mg to about 4 mg of the compound per dose.

Kits

In certain aspects, the present disclosure provides a kit comprising one or more unit doses of a compound or pharmaceutical composition described herein, optionally wherein the kit further comprises instructions for using the compound or pharmaceutical composition. In some embodiments, the kit comprises a carrier, package, or container that is compartmentalized to receive one or more containers, such as vials, tubes, and the like, each of the container(s) comprising one of the separate elements to be used in a method described herein. Suitable containers include, for example, bottles, vials, syringes, and test tubes. The containers may be formed from a variety of materials, such as glass or plastic.

The articles of manufacture provided herein may contain packaging materials. Packaging materials for use in packaging pharmaceutical products include those found in, e.g., U.S. Pat. Nos. 5,323,907, 5,052,558 and 5,033,252. Examples of pharmaceutical packaging materials include, but are not limited to, blister packs, bottles, tubes, inhalers, pumps, bags, vials, containers, syringes, bottles, and any packaging material suitable for a selected formulation and intended mode of administration and treatment. For example, the container(s) may include one or more compounds described herein, optionally in a composition or in combination with another agent as disclosed herein. The container(s) may optionally have a sterile access port (for example, the container is an intravenous solution bag or a vial having a stopper pierceable by a hypodermic injection needle). Such kits may optionally comprise a compound with an identifying description or label or instructions relating to its use in the methods described herein.

In some embodiments, a kit includes one or more containers, each with one or more of various materials (such as reagents, optionally in concentrated form, and/or devices) desirable from a commercial and user standpoint for use of a compound described herein. Nonlimiting examples of such materials include, but are not limited to, buffers, diluents, filters, needles, syringes, carrier, package, container, vial and/or tube labels listing contents and/or instructions for use, and package inserts with instructions for use. A set of instructions will also typically be included. A label is optionally on or associated with the container. For example, a label is on a container when letters, numbers or other characters forming the label are attached, molded, or etched onto the container itself, a label is associated with a container when it is present within a receptacle or carrier that also holds the container, e.g., as a package insert. In addition, a label is used to indicate that the contents are to be used for a specific therapeutic application. In addition, the label indicates directions for use of the contents, such as in the methods described herein. In certain embodiments, the pharmaceutical composition is presented in a pack or dispenser device which contains one or more unit dosage forms containing a compound provided herein. The pack may contain metal or plastic foil, such as a blister pack. In some embodiments, the pack or dispenser device is accompanied by instructions for administration. Optionally, the pack or dispenser is accompanied with a notice associated with the container in a form prescribed by a governmental agency regulating the manufacture, use, or sale of pharmaceuticals, which notice is reflective of approval by the agency of the form of the drug for human or veterinary administration. Such notice, for example, is the labeling approved by the U.S. Food and Drug Administration for prescription drugs, or the approved product insert. In some embodiments, compositions containing a compound provided herein formulated in a compatible pharmaceutical carrier are prepared, placed in an appropriate container, and labeled for treatment of an indicated condition.

Combination Therapy

The compounds and pharmaceutical compositions of the disclosure may be used in combination with one or more therapeutic agents which act by the same mechanism or by a different mechanism to treat a disease. The one or more agents may be administered sequentially or simultaneously, in separate compositions or in the same composition. Useful classes of agents for combination therapy include, but are not limited to, compounds used to treat cardiac, kidney, pulmonary, liver, skin, immunological and oncological conditions.

In practicing any of the subject methods, an ALK5 inhibitor and a second therapeutic agent can be administered sequentially, wherein the two agents are introduced into a subject at two different time points. The two time points can be separated by more than 2 hours, 1 or more days, 1 or more weeks, 1 or more months, or according to any intermittent regimen schedule disclosed herein.

In some embodiments, the ALK5 inhibitor and the second therapeutic agent are administered simultaneously. The two agents may form part of the same composition, or the two agents may be provided in one or more unit doses.

In some embodiments, the ALK5 inhibitor or the second therapeutic agent are administered parenterally, orally, inhalatively, intraperitoneally, intravenously, intraarterially, transdermally, intramuscularly, liposomally, via local delivery by catheter or stent, subcutaneously, intraadiposally, or intrathecally. As used herein, a therapeutically effective amount of a combination of an ALK5 inhibitor and a second therapeutic agent refers to a combination of an ALK5 inhibitor and a second therapeutic agent, wherein the combination is sufficient to affect the intended application, including but not limited to, disease treatment, as defined herein. Also contemplated in the subject methods is the use of a sub-therapeutic amount of an ALK5 inhibitor and a second therapeutic agent in combination for treating an intended disease condition. The individual components of the combination, though present in sub-therapeutic amounts, synergistically yield an efficacious effect and/or reduced a side effect in an intended application.

The amount of the ALK5 inhibitor and the second therapeutic agent administered may vary depending upon the intended application (in vitro or in vivo), or the subject and disease condition being treated, e.g., the weight and age of the subject, the severity of the disease condition, the manner of administration and the like, which can readily be determined by one of ordinary skill in the art.

Measuring an immune response and/or the inhibition of biological effects of ALK5 can comprise performing an assay on a biological sample, such as a sample from a subject. Any of a variety of samples may be selected, depending on the assay. Examples of samples include, but are not limited to blood samples (e.g. blood plasma or serum), exhaled breath condensate samples, bronchoalveolar lavage fluid, sputum samples, urine samples, and tissue samples.

A subject being treated with an ALK5 inhibitor and a second therapeutic agent may be monitored to determine the effectiveness of treatment, and the treatment regimen may be adjusted based on the subject's physiological response to treatment. For example, if inhibition of a biological effect of ALK5 inhibition is above or below a threshold, the dosing amount or frequency may be decreased or increased, respectively. Alternatively, the treatment regimen may be adjusted with respect to an immune response. The methods can further comprise continuing the therapy if the therapy is determined to be efficacious. The methods can comprise maintaining, tapering, reducing, or stopping the administered amount of a compound or compounds in the therapy if the therapy is determined to be efficacious. The methods can comprise increasing the administered amount of a compound or compounds in the therapy if it is determined not to be efficacious. Alternatively, the methods can comprise stopping therapy if it is determined not to be efficacious. In some embodiments, treatment with an ALK5 inhibitor and a second therapeutic agent is discontinued if inhibition of the biological effect is above or below a threshold, such as in a lack of response or an adverse reaction. The biological effect may be a change in any of a variety of physiological indicators.

Specific agents that may be used in combination with the compounds disclosed herein include, but are not limited to, OFEV® (nintedanib) and Esbriet® (pirfenidone). In some embodiments, a compound disclosed herein is administered in combination with pirfenidone, optionally wherein the pirfenidone is administered by inhalation. In some embodiments, the present disclosure provides a method of treating fibrosis, such as idiopathic pulmonary fibrosis, in a subject, comprising administering to the subject an ALK5 inhibitor, such as a compound disclosed in Table 1, and nintedanib or pirfenidone. In some embodiments, the present disclosure provides a method of treating cancer, such as lung cancer, in a subject, comprising administering to the subject an ALK5 inhibitor, such as a compound disclosed in Table 1, and nintedanib or pirfenidone.

In some embodiments, the present disclosure provides a method for treating a proliferative disorder (e.g., lung cancer) in a subject in need thereof, comprising administering to said subject an ALK5 inhibitor and an immunotherapeutic agent. TGF-β has been shown to regulate lymphocyte differentiation, suppress T cell proliferation and to enhance tumor growth. Moreover, TGF-β has been shown to prevent optimal activation of the immune system in immunotherapy-resistant patients (see Löffek, S. *J. Oncolo.* 2018, 1-9; incorporated herein by reference in its entirety). Not wishing to be bound by any particular theory, the present inventors expect that inhibition of ALK5 may enhance the efficacy of a particular immunotherapy. As such, treatment with an immunotherapeutic agent, such as durvalumab or pembrolizumab, and an ALK5 inhibitor, such as a compound of the present disclosure, is expected to improve the clinical outcome of a subject with cancer, such as a subject with non-small cell lung cancer. The combination is expected to produce a synergistic effect. A synergistic combination is also expected for a triple combination of radiation therapy, immunotherapy, and ALK5 inhibition. In addition, the ALK5 inhibitor, even when administered locally (e.g., to the lung by inhalation), may stimulate both local and systemic immune responses, allowing for the treatment of primary or metastatic tumors in tissues beyond the site of the local delivery. For example, an inhaled ALK5 inhibitor may be administered in combination with an immunotherapeutic agent to treat melanoma, renal cell carcinoma, colon cancer, or breast cancer.

In some embodiments, the ALK5 inhibitor and the immunotherapeutic agent are administered sequentially or simultaneously. In some embodiments, the ALK5 inhibitor and the immunotherapeutic agent are more effective in treating the proliferative disorder than either agent alone. In some embodiments, the ALK5 inhibitor and the immunotherapeutic agent yield a synergistic effect in treating the proliferative disorder. The synergistic effect may be a therapeutic effect that is greater than either agent used alone in comparable amounts under comparable conditions. The synergistic effect may be a therapeutic effect that is greater than results expected by adding the effects of each agent alone. In some embodiments, the proliferative disorder is a cancer condition. In some embodiments, the cancer condition is lung cancer, such as non-small cell lung cancer.

The term "immunotherapeutic agent" refers to any agent that induces, enhances, suppresses or otherwise modifies an immune response. This includes the administration of an active agent to, or any type of intervention or process performed on, the subject, with the objective of modifying an immune response. An immunotherapeutic agent may, for example, increase or enhance the effectiveness or potency of an existing immune response in a subject, for example, by stimulating mechanisms that enhance the endogenous host immune response or overcoming mechanisms that suppress the endogenous host immune response.

"Immune response" refers to the action of a cell of the immune system including, for example, B lymphocytes, T lymphocytes, natural killer (NK) cells, macrophages, eosinophils, mast cells, myeloid-derived suppressor cells, dendritic cells and neutrophils and soluble macromolecules produced by any of these cells or the liver (including antibodies, cytokines and complement), that results in selective targeting, binding to, damage to, destruction of, and/or elimination of invading pathogens, cells or tissues infected with pathogens, cancerous or other abnormal cells, or, in cases of autoimmunity or pathological inflammation, normal human cells or tissues, from the body of a subject.

In one embodiment, an immunotherapeutic agent may comprise a PD-1 inhibitor. In another embodiment, an immunotherapeutic agent may comprise a CTLA-4 inhibitor. In still another embodiment, an immunotherapeutic agent may comprise a B7 inhibitor.

Exemplary PD-1 inhibitors: A PD-1 inhibitor suitable for use in the subject methods can be selected from a variety of types of molecules. For example, the PD-1 inhibitor can be a biological or chemical compound, such as an organic or inorganic molecule, peptide, peptide mimetic, antibody or an antigen-binding fragment of an antibody. Some exemplary classes of agents suitable for use in the subject methods are detailed in the sections below. A PD-1 inhibitor for use in the present disclosure can be any PD-1 inhibitor that is known in the art, and can include any entity that, upon administration to a patient, results in inhibition of the PD-1 pathway in the patient. A PD-1 inhibitor can inhibit PD-1 by any biochemical mechanism, including disruption of any one or more of PD-1/PD-L1, PD1/PD-L2 and PD-L1/CD80 interactions.

In some embodiments, the PD-1 inhibitor is a molecule that inhibits the binding of PD-1 to its ligand binding partners. In a specific aspect, the PD-1 ligand binding partners are PD-L1 and/or PD-L2. In another embodiment, a PD-1 inhibitor is a molecule that inhibits the binding of PD-L1 to its binding partners. In a specific aspect, PD-L1 binding partners are PD1 and/or CD80. In another embodiment, the PD-1 inhibitor is a molecule that inhibits the binding of PD-L2 to its binding partners. In a specific aspect, a PD-L2 binding partner is PD1. The inhibitor may be an antibody, an antigen binding fragment thereof, an immunoadhesin, a fusion protein or oligopeptide.

In some embodiments, the PD-1 inhibitor is an anti-PD-1 antibody. In some further embodiments, the anti-PD-1 antibody is capable of inhibiting binding between PD-1 and PD-L1. In another embodiment, the anti-PD-1 antibody is capable of inhibiting binding between PD-1 and PD-L2. In some embodiments, the PD-1 inhibitor is an anti-PD-L1 antibody. In some embodiments, the anti-PD-L1 antibody is capable of inhibiting binding between PD-L1 and PD-1 and/or between PD-L1 and CD80. In some embodiments, the PD-1 inhibitor is an anti-PD-L2 antibody. In some further embodiments, the anti-PD-L2 antibody is capable of inhibiting binding between PD-1 and PD-L2. In yet another embodiment, the PD-1 inhibitor is nivolumab or pembrolizumab. In some embodiments, the PD-1 inhibitor is selected from atezolizumab, avelumab, nivolumab, pembrolizumab, durvalumab and BGB-A317.

Inhibition of the PD-1 pathway can enhance the immune response to cancerous cells in a patient. The interaction between PD-1 and PD-L1 impairs T cell response as manifested by a decrease in tumor-infiltrating lymphocytes (TILs) and a decrease in T-cell receptor mediated proliferation, resulting in T cell anergy, exhaustion or apoptosis, and immune evasion by the cancerous cells. This immune suppression can be reversed by inhibiting the local interaction between PD-L1 and PD-1 using a PD-1 inhibitor, including, for example, an anti-PD-1 and/or an anti-PD-L1 Ab. A PD-1 inhibitor may improve or restore antitumor T-cell functions.

Anti-PD-1 antibodies suitable for use in the disclosure can be generated using methods well known in the art. Exemplary PD-1 inhibitors include, but are not limited to: nivolumab (BMS936558), pembrolizumab (MK-3475), pidilizumab (CT-011), AMP-224, AMP-514, BMS-936559, RG7446 (MPDL3280A), MDX-1106 (Medarex Inc.), MSB0010718C, MEDI4736, and HenGrui mAB005 (WO 15/085847). Further PD-1 antibodies and other PD-1 inhibitors include those described in WO 04/056875, WO 06/121168, WO 07/005874, WO 08/156712, WO 09/014708, WO 09/114335, WO 09/101611, WO 10/036959, WO 10/089411, WO 10/027827, WO 10/077634, WO 11/066342, WO 12/145493, WO 13/019906, WO 13/181452, WO 14/022758, WO 14/100079, WO 14/206107, WO 15/036394, WO 15/085847, WO 15/112900, WO 15/112805, WO 15/112800, WO 15/109124, WO 15/061668, WO 15/048520, WO 15/044900, WO 15/036927, WO 15/035606; U. S. Pub. No. 2015/0071910; and U.S. Pat. Nos. 7,488,802; 7,521,051; 7,595,048; 7,722, 868; 7,794, 710; 8,008,449; 8,354,509; 8,383,796; 8,652,465; and 8,735,553; all of which are incorporated herein by reference. Some anti-PD-1 antibodies are commercially available, for example from ABCAM (AB137132), BIOLEGEND (EH12.2H7, RMP 1-14) and AFFYMETRIX EBIOSCIENCE (J105, J116, M1H4).

Exemplary CTLA-4 inhibitors: A CTLA-4 inhibitor suitable for use in the subject methods can be selected from a variety of types of molecules. For example, the CTLA-4 inhibitor can be a biological or chemical compound, such as an organic or inorganic molecule, peptide, peptide mimetic, antibody or an antigen-binding fragment of an antibody. Some exemplary classes of agents suitable for use in the subject methods are detailed in the sections below. A CTLA-4 inhibitor for use in the present disclosure can be any CTLA-4 inhibitor that is known in the art, and can include any entity that, upon administration to a patient, results in inhibition of the CTLA-4 pathway in the patient. A CTLA-4 inhibitor can inhibit CTLA-4 by any biochemical mechanism, including disruption of either one or both of CTLA-4/CD80 and CTLA-4/CD86 interactions.

In some embodiments, the CTLA-4 inhibitor is a molecule that inhibits the binding of CTLA-4 to its ligand binding partners. In a specific aspect, the CTLA-4 ligand binding partners are CD80 and/or CD86. In another embodiment, a CTLA-4 inhibitor is a molecule that inhibits the binding of CD80 to its binding partners. In a specific aspect, a CD80 binding partner is CTLA-4. In another embodiment, the CTLA-4 inhibitor is a molecule that inhibits the binding of CD86 to its binding partners. In a specific aspect, a CD86 binding partner is CTLA-4. The inhibitor may be an antibody, an antigen binding fragment thereof, an immunoadhesin, a fusion protein or oligopeptide.

In some embodiments, the CTLA-4 inhibitor is an anti-CTLA-4 antibody. In some further embodiments, the anti-CTLA-4 antibody is capable of inhibiting binding between CTLA-4 and CD80. In another embodiment, the anti-CTLA-4 antibody is capable of inhibiting binding between CTLA-4 and CD86. In some embodiments, the CTLA-4 inhibitor is an anti-CD80 antibody. In some embodiments, the anti-CD80 antibody is capable of inhibiting binding between CTLA-4 and CD80. In some embodiments, the CTLA-4 inhibitor is an anti-CD86 antibody. In some further embodiments, the anti-CD86 antibody is capable of inhibiting binding between CTLA-4 and CD86. In yet another embodiment, the CTLA-4 inhibitor is tremelimumab or ipilimumab.

Inhibition of the CTLA-4 pathway can enhance the immune response to cancerous cells in a patient. The interaction between CTLA-4 and one of its natural ligands, CD80 and CD86, delivers a negative regulatory signal to T cells. This immune suppression can be reversed by inhibiting the local interaction between CD80 or CD86 and CTLA-4 using a CTLA-4 inhibitor, including, for example, an anti-CTLA-4 Ab, anti-CD80 Ab or an antiCD86 Ab. A CTLA-4 inhibitor may improve or restore antitumor T-cell functions.

Anti-CTLA-4 antibodies suitable for use in the disclosure can be generated using methods well known in the art.

Exemplary CTLA-4 inhibitors include but are not limited to tremelimumab and ipilimumab (also known as 10D1 or MDX-010). Further CTLA-4 antibodies and other CTLA-4 inhibitors include those described in WO 98/042752, WO 00/037504, WO 01/014424 and WO 04/035607; U. S. Pub. Nos. 2002/0039581, 2002/086014 and 2005/0201994; U.S. Pat. Nos. 5,811,097; 5,855,887; 5,977,318; 6,051,227; 6,207, 156; 6,682,736; 6,984,720; 7, 109,003; 7, 132,281; 7,605,238; 8, 143,379; 8,318,916; 8,435,516; 8,784,815; and 8,883,984; EP Pat. No. 1212422; Hurwitz et al., PNAS 1998, 95(17): 10067-10071; Camacho et al., J Clin Oncology 2004, 22(145): abstract no. 2505 (antibody CP675206); and Mokyr, et al., Cancer Research 1998, 58:5301-5304; each of which is incorporated herein by reference.

Also provided herein is a pharmaceutical composition comprising a compound of the disclosure or a pharmaceutically acceptable salt thereof and one or more other therapeutic agents. The therapeutic agent may be selected from the classes of agents specified above and from the lists of specific agents described above. In some embodiments, the pharmaceutical composition is suitable for delivery to the lungs. In some embodiments, the pharmaceutical composition is suitable for inhaled or nebulized administration. In some embodiments, the pharmaceutical composition is a dry powder or a liquid composition.

Further, in a method aspect, the disclosure provides a method of treating a disease or disorder in a mammal comprising administering to the mammal a compound of the disclosure or a pharmaceutically acceptable salt thereof and one or more other therapeutic agents.

When used in combination therapy, the agents may be formulated in a single pharmaceutical composition, or the agents may be provided in separate compositions that are administered simultaneously or at separate times, by the same or by different routes of administration. Such compositions can be packaged separately or may be packaged together as a kit. The two or more therapeutic agents in the kit may be administered by the same route of administration or by different routes of administration.

EXAMPLES

The following Reaction Schemes/Preparations and Examples are provided to illustrate specific embodiments of the invention. These specific embodiments, however, are not intended to limit the scope of the invention in any way unless specifically indicated.

The following abbreviations have the following meanings unless otherwise indicated and any other abbreviations used herein and not defined have their standard, generally accepted meaning:

AcOH=acetic acid
AcONa=sodium acetate
ACN=acetonitrile
Atm=atmosphere
Boc$_2$O=di-tert-butyl dicarbonate
(Bpin)$_2$=bis(pinacolato)diboron
BrettPhos=2-(dicyclohexylphosphino)3,6-dimethoxy-2',4',6'-triisopropyl-1,1'-biphenyl
BrettPhos Pd G4=N-substituted 2-aminobiphenylpalladium methanesulfonate precatalyst
BSA=bovine serum albumin, Fraction V
Cp*RuCl(PPh$_3$)$_2$=pentamethylcyclopentadienylbis (triphenylphosphine)ruthenium(II) chloride
d=day(s)
DCE=1,2-dichloroethane
DCM=dichloromethane or methylene chloride
DHP=dihydropyran
DIAD=diisopropylazodicarboxylate
DIBAH=diisobutylaluminium hydride
DIPEA=N,N-diisopropylethylamine
DMA or DMAc=dimethylacetamide
DMAP=4-dimethylaminopyridine
DMEDA=1,2-bis(methylamino)ethane
DMF=N,N-dimethylformamide
DMSO=dimethyl sulfoxide
DPPA=diphenylphosphoryl azide
DTT=dithiothreitol
EDCI=N-ethyl-N'-(3-dimethylaminopropyl) carbodiimide hydrochloride
EDTA=ethylenediaminetetraacetic acid
EGTA=ethylene glycol-bis(β-aminoethyl ether)-N,N,N',N'-tetraacetic acid
EtOH=ethanol
EtOAc or EA=ethyl acetate
g=gram(s)
h=hour(s)
HATU=N,N,N',N'-tetramethyl-O-(7-azabenzotriazol-1-yOuronium hexafluorophosphate
HEPES=4-(2-hydroxyethyl)-1-piperazine ethane sulfonic acid
HOBT=hydroxybenzotriazole
i-PrOBPin=2-isopropyl-4,4,5,5-tetramethyl-1,3,2-dioxaborolane
KHMDS=potassium bis(trimethylsilyl)amide
LDA=lithium diisopropylamide
LiHDMS=hexamethyldisilazane lithium salt
MeCN=acetonitrile
MeOH=methanol
min=minute(s)
MTBE=methyl tert-butyl ether
NBS=N-bromosuccinimide
Pd(dppf)Cl$_2$=[1,1'-bis(diphenylphosphino)ferrocene]-dichloropalladium(II)
Pd/C=palladium on activated carbon, 10% loading
Pd$_2$(dba)$_3$=tris(dibenzylideneacetone)dipalladium(O)
PE=petroleum ether
RT, rt, or r.t.=room temperature
RuPhos=2-dicyclohexylphosphino-2',6'-diisopropoxybiphenyl
RuPhos Pd G2=chloro(2-dicyclohexylphosphino-2',6'-diisopropoxy-1,1'-biphenyl)[2-(2'-amino-1,1'-biphenyl)]palladium(II)
RuPhos Pd G4=ligand for Buchwald 4$^{th}$ generation Palladacycle
SEMCl=2-(trimethylsilyl)ethoxymethyl chloride
SPhos Pd G3=(2-dicyclohexylphosphino-2',6'-dimethoxybiphenyl) [2-(2'-amino-1,1'-biphenyl)]palladium (II) methanesulfonate
TBAB=tetrabutylammonium bromide
TBSCl=tert-butyldimethylchlorosilane
t-BuOK=potassium tert-butoxide
TEA, Et$_3$N=triethylamine
TFA=trifluoroacetic acid
THF=tetrahydrofuran
TMS=tetramethylsilane
TosCl=p-toluenesulfonyl chloride
Tris-HCl=tris(hydroxymethyl)aminomethane hydrochloride
Tween-20=polyoxyethylene sorbitan monolaurate
Xantphos=4,5-bis(diphenylphosphino)-9,9-dimethylxanthene
XPhos Pd G4=Buchwald 4$^{th}$ generation palladacycle Unless noted otherwise, all materials, such as reagents, starting materials and solvents, were purchased from commercial suppliers (such as Sigma-Aldrich, Fluka Riedel-de Haen, and the like) and were used without further purification.

Reactions were run under nitrogen atmosphere, unless noted otherwise. The progress of reactions was monitored by thin layer chromatography (TLC), analytical high performance liquid chromatography (anal. HPLC), and mass spectrometry, the details of which are given in specific examples.

Reactions were worked up as described specifically in each preparation for example; commonly reaction mixtures were purified by extraction and other purification methods such as temperature-, and solvent-dependent crystallization, and precipitation. In addition, reaction mixtures were routinely purified by preparative HPLC, typically using Microsorb C18 and Microsorb BDS column packings and conventional eluents. Progress of reactions was typically measured by liquid chromatography mass spectrometry (LCMS). Characterization of isomers was done by Nuclear Overhauser effect spectroscopy (NOE). Characterization of reaction products was routinely carried out by mass and $^1$H-NMR spectrometry. For NMR measurement, samples were dissolved in deuterated solvent (CD$_3$OD, CDCl$_3$, or DMSO-d$_6$), and $^1$H-NMR spectra were acquired with a Varian Gemini 2000 instrument (400 MHz) under standard observation conditions. Mass spectrometric identification of compounds was typically conducted using an electrospray ionization method (ESMS) with an Applied Biosystems (Foster City, Calif.) model API 150 EX instrument or an Agilent (Palo Alto, Calif.) model 1200 LC/MSD instrument.

Example 1: Synthesis of
7-bromo-2-methyl-1,5-napthyridine (1)

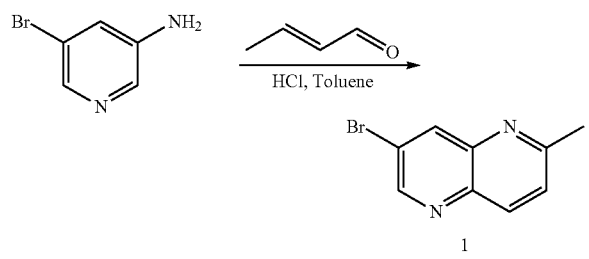

(E)-but-2-enal (30.66 g, 437 mmol) in toluene (90 mL) was added dropwise to 5-bromopyridin-3-amine (18.0 g, 104.0 mmol) in HCl (1.8 L, 6 M) at 100° C. and the mixture was stirred for 1 h at 100° C. A further amount of (E)-but-2-enal (30.66 g, 437 mmol) in toluene (90 mL) was added in one portion and the mixture was stirred at 100° C. for another 4 h. The solvent was removed in vacuum to dryness and the pH of the residue was adjusted to pH 8.0 with NaHCO$_3$ solid. This procedure was repeated four times and the crude products were combined and purified by column chromatography (PE:EA=100:1 to 5:1) to yield title compound 1 as a yellow solid (71 g, 95% purity, 15.3% yield). [M+H]$^+$ calcd for C$_9$H$_8$BrN$_2$ 222.99, found 222.9. $^1$H NMR (400 MHz, CDCl$_3$) δ 8.89 (d, J=1.6 Hz, 1H), 8.46 (d, J=1.6 Hz, 1H), 8.23 (d, J=8.8 Hz, 1H), 7.50 (d, J=8.4 Hz, 1H), 2.76 (s, 3H).

Example 2: Synthesis of tert-butyl 5-bromo-2,3-dihydro-1H-imidazo[1,2-a]imidazole-1-carboxylate (4)

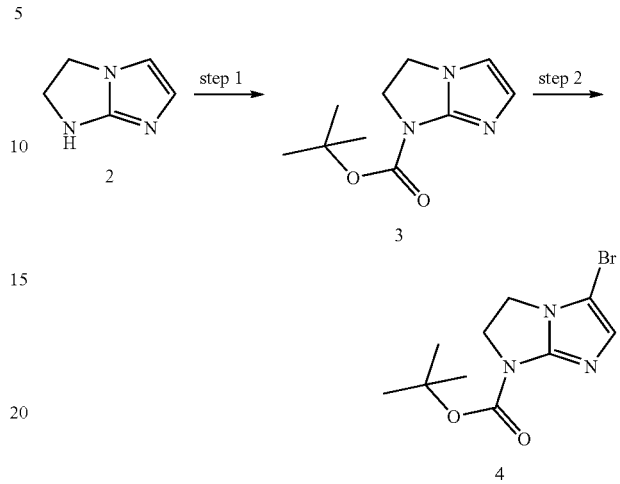

Step 1: To a cooled to 0° C. stirring solution of compound 2 (10.0 g, 91.6 mmol), triethylamine (9.00 g, 88.9 mmol), and DMAP (0.500 g, 4.09 mmol) in chloroform (200 mL), Boc$_2$O (20.0 g, 91.6 mmol) was added dropwise over 30 min and the reaction mass was stirred for 16 h at rt. Then, the volatiles were evaporated and the crude product was subjected to silica gel column chromatography (hexane/MTBE) to give 19.2 g (91.8 mmol, 90%) of compound 3.

Step 2: To a solution of compound 3 (10.0 g, 47.8 mmol) in THF (200 mL) 2M solution of LDA in THF (48 mL) was added at −80° C. In 1 h dibromotetrafluoroethane (24.5 g, 94.3 mmol) was added dropwise at the same temperature. In 15 min the reaction mixture was poured into brine (300 mL) and immediately extracted with MTBE (300 mL). The solvent was evaporated and the residue was purified by the column chromatography (chloroform/hexane) to give 4.00 g (13.9 mmol, 28%) of title compound 4 as a white solid. [M+H]$^+$ calcd for C$_{10}$H$_{14}$BrN$_3$O$_2$ 288.04, found 288.2. $^1$H NMR (400 MHz, CDCl$_3$) δ 6.72 (s, 1H), 4.34 (t, J=7.6 Hz, 2H), 3.98 (t, J=7.6 Hz, 2H) 1.53 (s, 9H).

Example 3: Synthesis of tert-butyl 7-iodo-2,3-dihydro-1H-imidazo[1,5-a]imidazole-1-carboxylate (7)

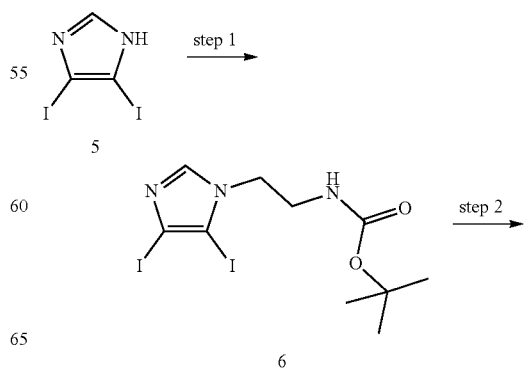

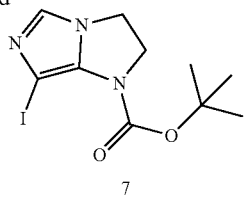

Step 1: To a suspension of NaH (2.75 g, 68.8 mmol) in DMF (50 mL) a solution of 4,5-diiodo-1H-imidazole 5 (20.0 g, 62.5 mmol) in DMF (400 mL) was added dropwise and the resulting mixture was stirred until the gas evolution ceased. Then, a solution of 1-[(tert-butoxycarbonyl)amino]-2-chloroethane (11.2 g, 62.5 mmol) in DMF (100 mL) was added and the reaction mass was left to stir overnight at rt. The resulting mixture was concentrated to ½ of the initial volume and poured onto crushed ice. The precipitated solid was collected by filtration and dried to obtain 24.6 g (53.1 mmol, 85%) of compound 6.

Step 2: A solution of compound 6 (11.6 g, 25.0 mmol) in acetonitrile (100 mL) was stirred for 15 min at 40° C. under flow of argon. Then, $K_2CO_3$ (6.91 g, 50.0 mmol), CuI (0.714 g, 3.75 mmol), and DMEDA (0.556 g, 6.31 mmol) were added and the reaction mass was maintained at 80° C. for 21 h. The insoluble solid was filtered off and the filtrate was concentrated under reduced pressure. The crude product was purified by silica gel column chromatography to give 1.26 g (3.76 mmol, 15%) of title compound 7 as a light-yellow solid. [M+H]+ calcd for $C_{10}H_{14}IN_3O_2$ 336.02, found 336.0. ¹H NMR (400 MHz, DMSO-d₆) δ 8.21 (s, 1H), 4.48 (m, 2H), 4.06 (m, 2H), 1.55 (s, 9H).

Example 4: Synthesis of tert-butyl 5-bromo-2,3-dihydro-1H-imidazo[1,5-a]imidazole-1-carboxylate (9)

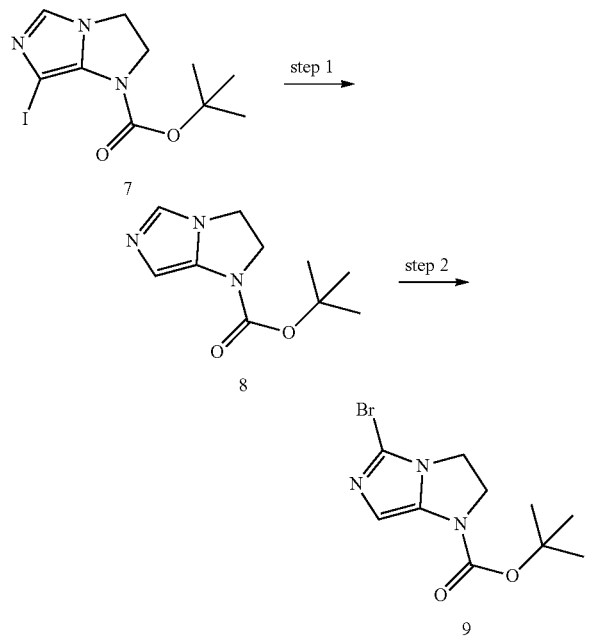

Step 1: A mixture of compound 7 (1.00 g, 2.98 mmol) and Pd/C (0.150 g, 10% wt.) in methanol was stirred overnight under an atmosphere of hydrogen, and then filtered. The filtrate was evaporated under reduced pressure to obtain 0.498 g (2.38 mmol, 80%) of compound 8.

Step 2: To a cooled to −78° C. stirring solution of compound 8 (0.498 g, 2.38 mmol) in anhydrous THF (20 mL) 2.5M solution of n-BuLi in hexanes (1.05 mL, 2.62 mmol of n-BuLi) was added dropwise over 15 min and the resulting mixture was stirred for 15 min at the same temperature. Then, a solution of dibromotetrafluoroethane (0.681 g, 2.62 mmol) in THF (10 mL) was added and the reaction mass was stirred for further 1 h at −78° C. The reaction was quenched with aqueous $NH_4Cl$, warmed up to r.t., diluted with brine, and extracted with dichloromethane. The organic extract was dried over $Na_2SO_4$, and evaporated under reduced pressure. The residue was purified by silica gel column chromatography to give 0.104 g (0.360 mmol, 15%) of title compound 9 as a white solid. [M+H]+ calcd for $C_{10}H_4BrN_3O_2$ 288.04, found 288.0. ¹H NMR (400 MHz, CDCl₃) δ 5.55 (s, 1H), 4.40 (t, J=8.7 Hz, 2H), 4.09 (t, J=8.7 Hz, 2H), 1.53 (s, 9H).

Example 5: Synthesis of tert-butyl 2-bromo-6,7-dihydropyrazolo[1,5-a]pyrimidine-4 (5H)-carboxylate (17)

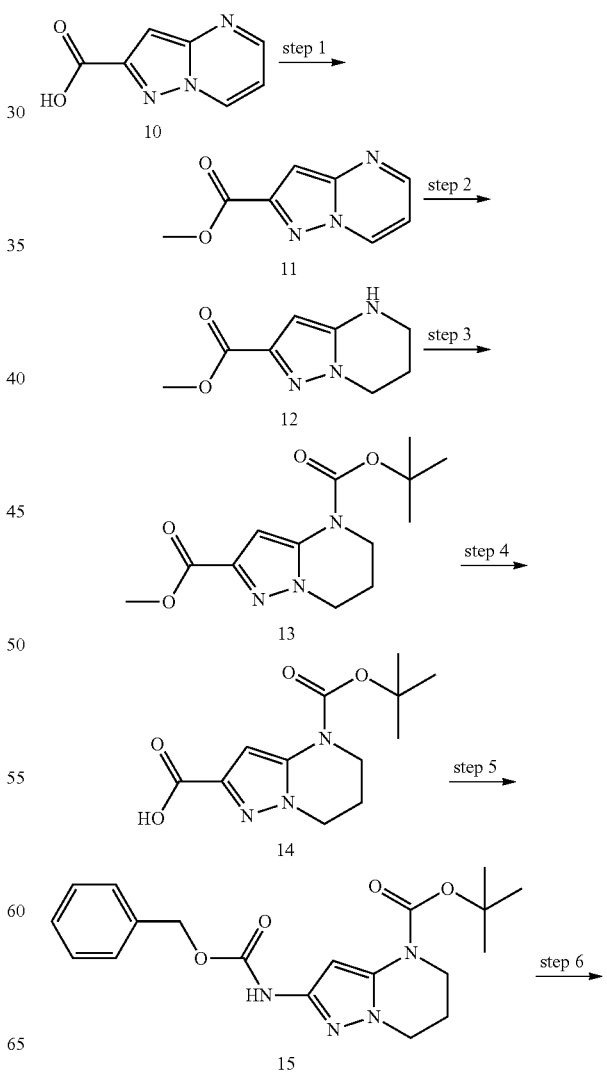

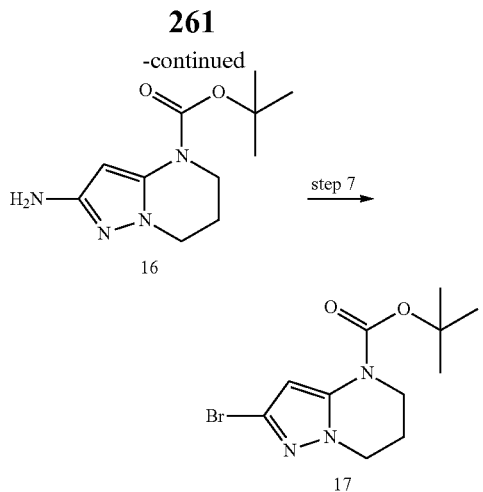

Step 1: A solution of compound 10 (80.0 g, 490 mmol) and H₂SO₄ (2.40 g, 24.5 mmol) in methanol (500 mL) was refluxed for 12 h and then evaporated under reduced pressure. The residue was mixed with aqueous NaHCO₃. The insoluble solid was collected by filtration, washed with water, and dried to obtain 78.1 g (441 mmol, 90%) of compound 11.

Step 2: A mixture of compound 11 (75.0 g, 423 mmol), Pd/C (4.00 g, 10% wt.), and methanol (600 mL) was stirred for 16 h at r.t. under pressure of hydrogen (3 atm.). Then, the catalyst was filtered off and the filtrate was evaporated under reduced pressure. The resulting solid was dried to obtain 57.4 g (317 mmol, 75%) of compound 12.

Step 3: To a solution of compound 12 (50.0 g, 276 mmol) and Boc₂O (72.2 g, 331 mmol) in THF (400 mL) 1M LiHMDS in THF (304 mL, 304 mmol of LiHMDS) was added dropwise at r.t. and the reaction mass was stirred for 12 h at r.t. The mixture was diluted with NaHCO₃ solution and extracted with ethyl acetate. The organic extract was dried over Na₂SO₄ and evaporated under reduced pressure. The residue was triturated with hexane and dried to obtain 46.7 g (166 mmol, 60%) of compound 13, pure enough for the next step.

Step 4: A mixture of compound 13 (45.0 g, 160 mmol), water (20 mL), methanol (200 mL), and NaOH (9.60 g, 240 mmol) was stirred for 8 h at r.t. Then, MeOH was distilled off and the residue was mixed with crushed ice. 10% hydrochloric acid was added until pH 6 and the product was extracted with dichloromethane. The organic extract was washed with NaHCO₃, dried over Na₂SO₄, and evaporated under reduced pressure. The residue was triturated with hexane and dried to obtain 29.9 g (112 mmol, 70%) of compound 14.

Step 5: A mixture of compound 14 (25.0 g, 93.5 mmol), triethylamine (10.4 g, 103 mmol), DPPA (28.3 g, 103 mmol), and toluene (300 mL) was stirred at 80° C. for 4 h, cooled to 40° C., and treated with benzyl alcohol (25.3 g, 234 mmol). The reaction mass was refluxed for 8 h and then evaporated under reduced pressure. The residue was dissolved in ethyl acetate. The solution was extracted with aqueous NaHSO₄, water, and aqueous NaHCO₃, dried over Na₂SO₄, and evaporated under reduced pressure. The residue was purified by silica gel column chromatography to give 7.09 g (28.1 mmol, 30%) of compound 15.

Step 6: A mixture of compound 15 (7.00 g, 27.7 mmol), Pd/C (1.00 g, 10% wt.), and methanol (60 mL) was stirred for 12 h at r.t. under atmosphere of hydrogen (balloon pressure, 1 atm) and then filtered through a pad of celite. The filtrate was evaporated under reduced pressure and the residue was triturated with MTBE and filtered to obtain 4.62 g (19.4 mmol, 70%) of compound 16.

Step 7: To a cooled to 0° C. stirring solution of compound 16 (4.50 g, 18.9 mmol) and p-toluenesulfonic acid (3.91 g, 22.7 mmol) in acetonitrile (50 mL) TBAB (7.32 g, 22.7 mmol), CuBr₂ (0.211 g, 0.945 mmol), tert-butyl nitrite (2.34 g, 22.7 mmol) were added and the reaction mass was stirred for 2 h at 0° C. and then for 6 h at r.t. The obtained mixture was diluted with an aqueous NaHCO₃ solution and extracted with ethyl acetate. The organic extract was washed with an aqueous citric acid solution and brine, dried over Na₂SO₄, and evaporated under reduced pressure. The residue was purified by silica gel column chromatography to give 0.228 g (756 mmol, 4%) of target compound 17 as a white solid. [M+H]⁺ calcd for $C_{11}H_{16}BrN_3O_2$ 302.06, found 302.2. ¹H NMR (400 MHz, CDCl₃) δ 6.5 (s br, 1H), 4.12 (t, J=5.5 Hz, 2H), 3.78 (t, J=4.3 Hz, 2H), 2.14 (m, 2H), 1.55 (s, 9H).

Example 6: Synthesis of tert-butyl 3-bromo-6,7-dihydroimidazo[1,2-a]pyrimidine-8(5H)-carboxylate (20)

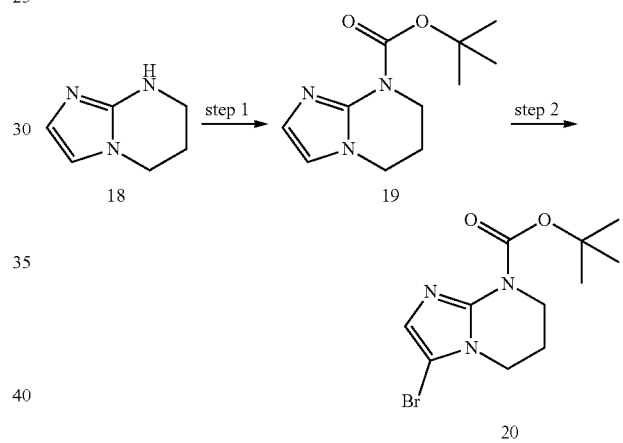

Step 1: To a cooled to −10° C. solution of compound 18 (24.8 g, 201 mmol), triethylamine (24.5 g, 242 mmol), and DMAP (2.46 g, 20.1 mmol) in dichloromethane (450 mL), Boc₂O (52.8 g, 242 mmol) was added dropwise. The mixture was stirred for 30 min at −10° C., then warmed to r.t. and left to stir overnight. The next day the reaction mixture was evaporated under vacuum. The residue was subjected to silica gel column chromatography to give 30.0 g (134 mmol, 67%) of compound 19.

Step 2: To a cooled to −78° C. solution of compound 19 (7.39 g, 33.1 mmol) in THF (100 mL) a solution of LDA (18.5 mL, 23% in hexane, 40.0 mmol) was added dropwise and the mixture was left to stir for 1.5 h at −78° C. Then, dibromotetrafluoroethane (12.9 g, 49.6 mmol) was added dropwise at −78° C. The mixture was stirred 30 min at the same temperature, then warmed to room temperature and diluted with water (200 mL). The obtained solution was extracted with ethyl acetate (3×200 mL). The combined organic layers were dried with disodium sulfate and evaporated under vacuum. After flash chromatography 4.00 g (13.2 mmol, 40%) of pure title compound 20 as a white solid. [M+H]⁺ calcd for $C_{11}H_{16}BrN_3O_2$ 302.06, found 302.2. ¹H NMR (500 MHz, CDCl₃) δ 6.88 (s, 1H), 3.86 (m, 4H), 2.15 (pent, J=7.0 Hz, 2H), 1.56 (s, 9H).

Example 7: Synthesis of tert-butyl 7-bromo-2,3-dihydro-1H-imidazo[1,2-b]pyrazole-1-carboxylate (22)

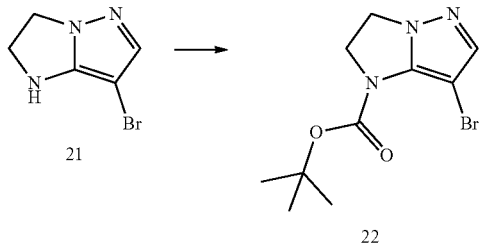 [SMILES: Brc1cnn2c1NCC2 ; CC(C)(C)OC(=O)N1CCn2ncc(Br)c21]

To a stirring solution of compound 21 hydrobromide (1.21 g, 4.50 mmol), in anhydrous DMF (10 mL) NaH (60% dispersion in mineral oil, 0.420 g, 10.5 mmol) and DMAP (0.055 g, 0.450 mmol) were added followed by Boc$_2$O (2.00 g, 9.16 mmol). The reaction mass was left to stir overnight at room temperature and then diluted with water (50 mL). The product was extracted with dichloromethane (3×50 mL). The organic extract was washed with water, dried over Na$_2$SO$_4$, and evaporated under reduced pressure. The residue was purified by silica gel column chromatography to give 1.09 g (3.78 mmol, 84%) of title compound 22 as a white solid. C$_{10}$H$_{14}$BrN$_3$O$_2$ 288.04, found 288.2. $^1$H NMR (500 MHz, CDCl$_3$) δ 7.65 (s, 1H), 4.42 (t, J=7.8 Hz, 2H), 4.25 (t, J=7.8 Hz, 2H), 1.58 (s, 9H).

Example 8: Synthesis of tert-butyl 3-bromo-6,7-dihydropyrazolo[1,5-a]pyrimidine-4 (5H)-carboxylate (24)

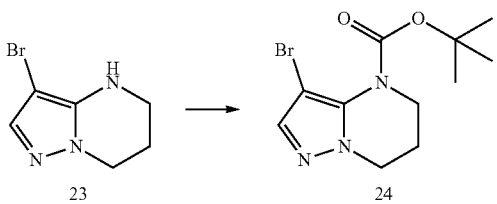 [SMILES: Brc1cnn2c1NCCC2 ; CC(C)(C)OC(=O)N1CCCn2ncc(Br)c21]

To a stirring solution of compound 23 (3.00 g, 14.8 mmol), in anhydrous THF (60 mL) NaH (60% dispersion in mineral oil, 0.750 g, 17.9 mmol) and DMAP (0.182 g, 1.50 mmol) were added followed by Boc$_2$O (6.50 g, 29.8 mmol). The reaction mass was left to stir overnight at room temperature and then diluted with water (100 mL). The product was extracted with ethyl acetate (3×10 mL). The organic extract was washed with water, dried over Na$_2$SO$_4$, and evaporated under reduced pressure. The residue was purified by silica gel column chromatography to give 2.70 g (8.94 mmol, 60%) of target compound 24 as a white solid. [M+H]$^+$ calcd for C$_{11}$H$_{16}$BrN$_3$O$_2$ 302.06, found 302.2. $^1$H NMR (400 MHz, CDCl$_3$) δ 7.39 (s, 1H), 4.18 (t, J=5.8 Hz, 2H), 3.78 (t, J=5.8 Hz, 2H), 2.15 (pent, J=5.8 Hz, 2H), 1.52 (s, 9H).

Example 9: Synthesis of tert-butyl 3-bromo-4,5-dihydropyrrolo[2,3-c]pyrazole-6(1H)-carboxylate (30)

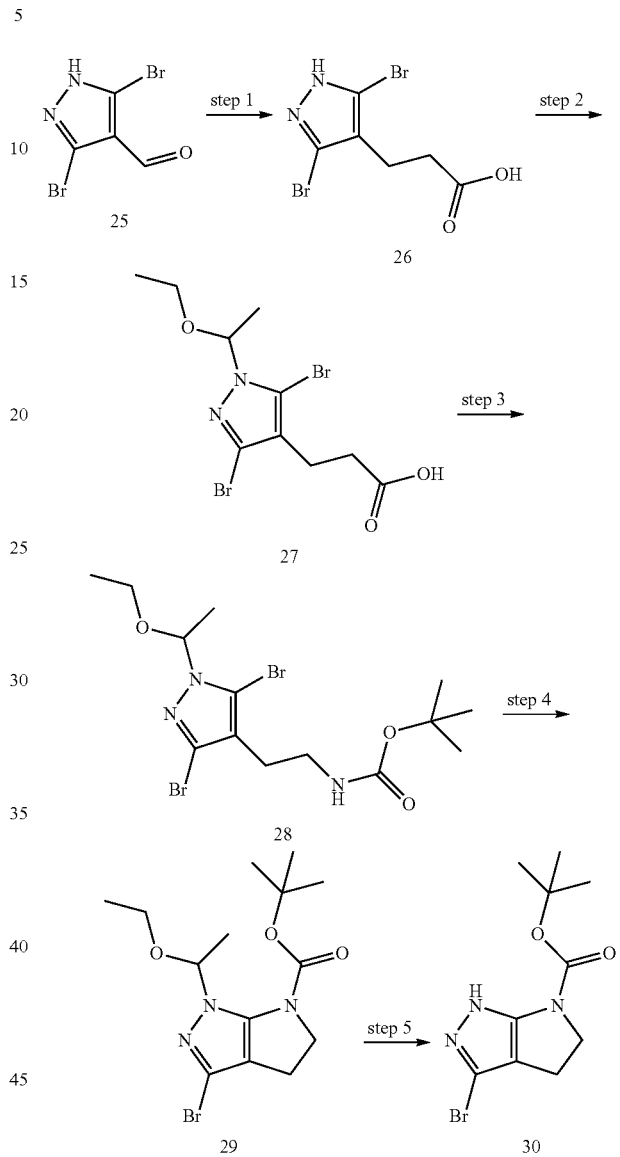

Step 1: Triethylamine (19.0 mL, 136 mmol) was added dropwise to stirred formic acid (12.5 mL, 321 mmol) at 5° C. To the resulting reagent were added DMF (150 mL), Meldrum's acid (13.2 g, 91.7 mmol), and aldehyde 25 (23.3 g, 91.7 mmol). The reaction mixture was stirred at 80° C. for 10 h and then evaporated under reduced pressure. The residue was triturated with water (300 ml) and acidified with conc. aq. hydrochloric acid until pH 2. The formed product was filtered, dried on air, and recrystallized to obtain 13.5 g (45.3 mmol, 50%) of compound 26.

Step 2: To a solution of compound 26 (13.5 g, 45.3 mmol) in dichloromethane (100 mL) TFA (0.350 mL, 4.57 mmol) and ethyl vinyl ether (6.50 mL, 68.0 mmol) were added and the reaction mass was stirred overnight at r.t. The obtained mixture was washed with water (3×50 mL), dried over Na$_2$SO$_4$, and evaporated under reduced pressure to give 15.0 g (40.5 mmol, 89%) of compound 27.

Step 3: A mixture of compound 27 (15.0 g, 40.5 mmol), triethylamine (9.00 mL, 64.6 mmol), and DPPA (13.4 g, 48.7 mmol) in t-BuOH (200 mL) was refluxed for 24 h, cooled to r.t., diluted with ethyl acetate (200 mL), washed with brine (2×200 mL), dried over Na$_2$SO$_4$, and evaporated under reduced pressure. The residue was subjected to silica gel column chromatography to give 5.00 g (11.3 mmol, 28%) of compound 28.

Step 4: To a cooled to 0° C. stirring solution of compound 28 (5.00 g, 11.3 mmol) in acetonitrile (100 mL) CuI (0.290 g, 1.52 mmol), DMEDA (0.44 mL, 4.09 mmol), and K$_2$CO$_3$ (2.64 g, 19.1 mmol) were added under argon and the reaction mass was refluxed overnight. The insoluble solid was filtered off and the filtrate was evaporated under reduced pressure. The residue was purified by silica gel column chromatography to give 1.50 g (4.16 mmol, 37%) of compound 29.

Step 5: To a solution of compound 29 (1.50 g, 4.16 mmol) in methanol (50 mL) p-toluenesulfonic acid (0.072 g, 0.420 mmol) was added and the reaction mass was stirred overnight at r.t. Then, the mixture was diluted with ethyl acetate (100 mL), washed with water (2×100 mL) and brine (2×50 mL), dried over Na$_2$SO$_4$, and evaporated under reduced pressure to obtain 0.490 g (1.70 mmol, 41%) of title compound 30 as a white solid. [M+H]$^+$ calcd for C$_{10}$H$_{14}$BrN$_3$O$_2$ 288.04, found 288.0. $^1$H NMR (400 MHz, CDCl$_3$) δ 9.6 (s br, 1H), 4.32 (m, 2H), 2.89 (t, J=8.6 Hz, 2H), 1.54 (s, 9H).

Example 10: Synthesis of tert-butyl 3-bromo-6,7-dihydro[1,2,3]triazolo[1,5-a]pyrimidine-4(5H)-carboxylate (36)

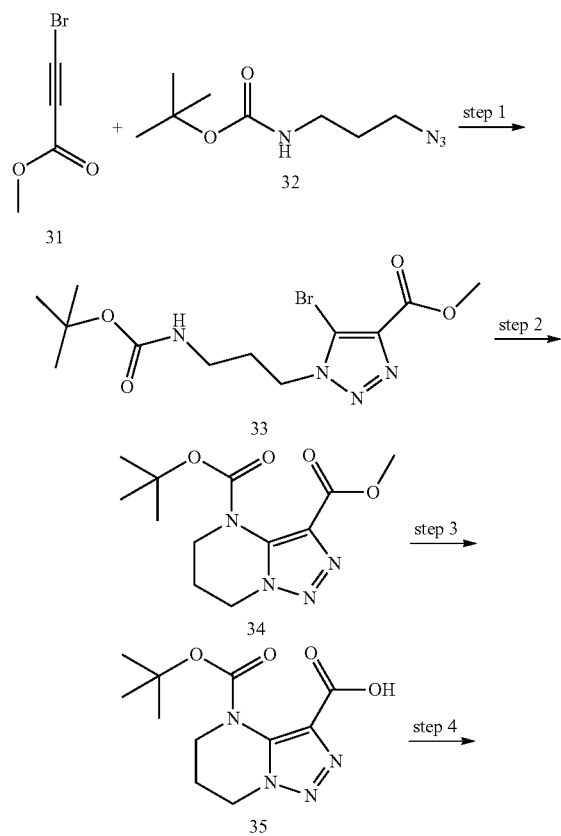

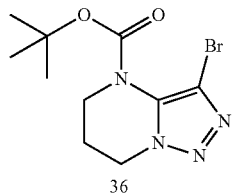

Step 1: To a stirring solution of compound 31 (15.0 g, 92.0 mmol) in THF (300 mL) compound 32 (18.4 g, 91.9 mmol) and Cu(OAc)$_2$ (3.00 g, 16.5 mmol) were added and the reaction mass was stirred for 48 h at r.t. Then the solvent was distilled off and the residue was dissolved in ethyl acetate. The solution was washed with 1N aqueous NH$_4$Cl, dried over Na$_2$SO$_4$, and evaporated under reduced pressure. The residue was recrystallized from hexane/2-propanol 9:1 mixture and dried to obtain 12.7 g (35.0 mmol, 38%) of compound 33.

Step 2: To a solution of compound 33 (12.7 g, 35.0 mmol) in toluene (200 mL) t-BuOK (4.30 g, 38.3 mmol) and Pd(OAc)$_2$ were added under argon and the reaction mass was stirred for 12 h at 110° C. under an inert atmosphere. The obtained mixture was filtered and the filtrate was washed with water, dried over Na$_2$SO$_4$, and evaporated under reduced pressure. The obtained solid was purified by silica gel column chromatography eluting with MTBE to give 4.20 g (14.9 mmol, 43%) of compound 34.

Step 3: To a stirring solution of NaOH (0.900 g, 22.5 mmol) in water (30 mL) compound 34 (4.20 g, 14.9 mmol) was added and the reaction mass was stirred for 12 h. Then, ice (40 g) was added thereto and the obtained mixture was acidified until pH 2 with HCl. The product was extracted with ethyl acetate (4×60 mL). The organic extract was dried over Na$_2$SO$_4$ and evaporated under reduced pressure to obtain 2.90 g (10.8 mmol, 76%) of compound 35.

Step 4: To a cooled to 0° C. stirring solution of compound 35 (1.80 g, 6.71 mmol) and NaHCO$_3$ (0.600 g, 7.14 mmol) in methanol (30 mL) Br$_2$ (0.350 mL, 6.83 mmol) was added and the reaction mass was stirred overnight at r.t. Then the volatiles were evaporated and water (100 mL) was added to the residue. The insoluble solid was collected by filtration and purified by silica gel column chromatography to give 0.600 g (1.98 mmol, 30%) of title compound 36 as a white solid. [M+H]$^+$ calcd for C$_{10}$H$_{15}$BrN$_4$O$_2$ 303.05, found 303.2. $^1$H NMR (500 MHz, CDCl$_3$) δ 4.46 (t, J=7.7 Hz, 2H), 3.83 (t, J=6.4 Hz, 2H), 2.20 (m, 2H), 1.54 (s, 9H).

Example 11: Synthesis of tert-butyl 3-bromo-5,6-dihydro-4H-imidazo[1,2-c][1,2,3]triazole-4-carboxylate (41)

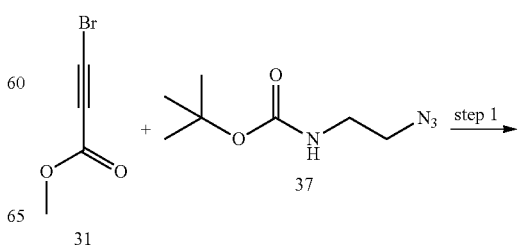

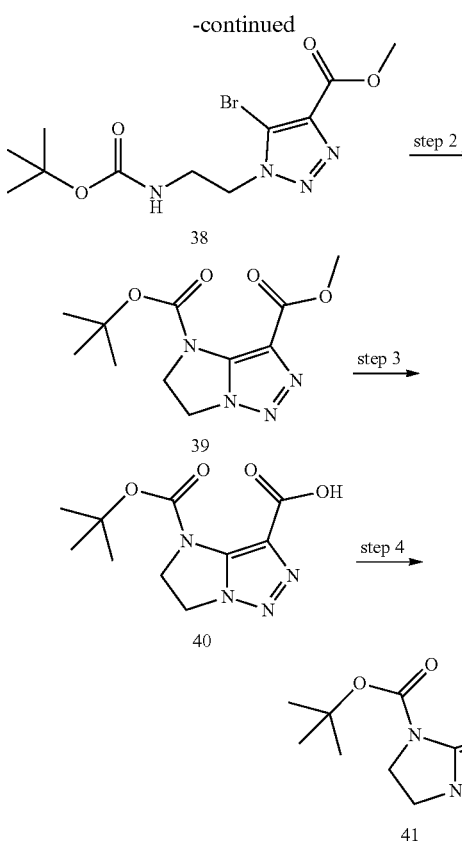

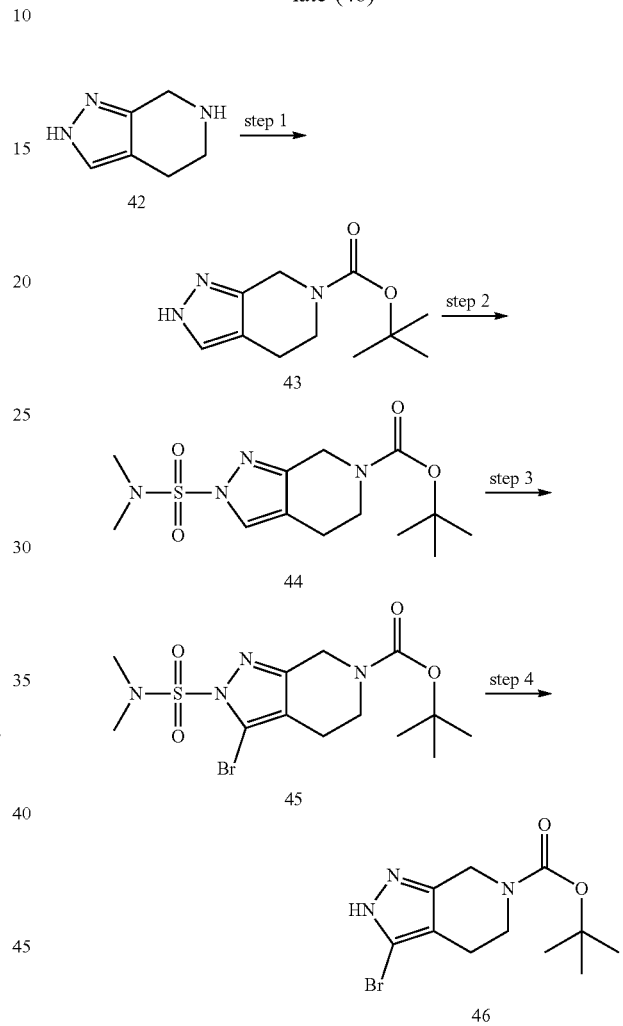

Step 1: To a solution of compound 31 (15.0 g, 92.0 mmol) in THF (300 mL) compound 37 (17.0 g, 91.3 mmol) and Cu(OAc)$_2$ (3.00 g, 16.5 mmol) were added and the reaction mass was stirred for 48 h at r.t. Then THF was distilled off and the residue was dissolved in ethyl acetate. The solution was washed with 1N aqueous NH$_4$Cl, dried over Na$_2$SO$_4$, and evaporated under reduced pressure. The residue was recrystallized from hexane/2-propanol 9:1 mixture to obtain 8.40 g (24.1 mmol, 26%) of compound 38.

Step 2: To a stirring solution of compound 38 (8.40 g, 24.1 mmol) in anhydrous dioxane (200 mL) Cs$_2$CO$_3$ (17.0 g, 52.2 mmol), Xantphos (0.700 g, 1.21 mmol), and Pd$_2$(dba)$_3$ (0.600 g, 0.655 mmol) were added under argon and the reaction mass was stirred for 12 h at 100° C. Then the reaction mass was filtered and the filter cake was rinsed with dioxane. The filtrate and rinses were evaporated under reduced pressure and the residue was purified by silica gel column chromatography to give 3.10 g (11.6 mmol, 49%) of compound 39.

Step 3: To a stirring solution of NaOH (0.700 g, 17.5 mmol) in water (20 mL) compound 39 (3.10 g, 11.6 mmol) was added and the reaction mass was stirred for 12 h. Then, ice (30 g) was added thereto and the obtained mixture was acidified until pH 2 with hydrochloric acid. The product was extracted with ethyl acetate (4×50 mL). The organic extract was dried over Na$_2$SO$_4$ and evaporated under reduced pressure to obtain 2.20 g (8.65 mmol, 76%) of compound 40.

Step 4: To a cooled to 0° C. stirring solution of compound 40 (2.20 g, 8.65 mmol) and NaHCO$_3$ (0.800 g, 9.52 mmol) in methanol (30 mL) Br$_2$ (0.450 mL, 8.79 mmol) was added and the reaction mass was stirred overnight at r.t. Then the volatiles were evaporated and water (100 mL) was added to the residue. The insoluble solid was collected by filtration and purified by silica gel column chromatography to give 0.560 g (1.94 mmol, 23%) of target compound 41 as a white solid. [M+H]$^+$ calcd for C$_9$H$_{13}$BrN$_4$O$_2$ 289.02, found 289.0. $^1$H NMR (400 MHz, CDCl$_3$) δ 4.61 (t, J=8.9 Hz, 2H), 4.50 (t, J=8.9 Hz, 2H), 1.59 (s, 9H).

Example 12: Synthesis of tert-butyl 3-bromo-2,4,5,7-tetrahydro-6H-pyrazolo[3,4-c]pyridine-6-carboxylate (46)

Step 1: To a solution of compound 42 (10.0 g, 81.2 mmol) and triethylamine (8.63 g, 85.3 mmol) in dichloromethane (200 mL) Boc$_2$O (18.6 g, 85.3 mmol) was added and the reaction mass was stirred overnight at r.t. The resulting mixture was washed with water, dried over Na$_2$SO$_4$, and evaporated under reduced pressure to obtain 16.7 g (74.7 mmol, 92%) of compound 43.

Step 2: To a cooled to 0° C. stirring solution of compound 43 (15.0 g, 67.2 mmol) in THF (200 mL) NaH (60% dispersion in mineral oil, 2.82 g, 70.6 mmol) was added and the reaction mass was warmed up to r.t. and stirred for 20 min. Then, a solution of N,N-dimethylsulfamoyl chloride (10.1 g, 70.6 mmol) in THF (100 mL) was added and the reaction mass was stirred overnight at 50° C. The volatiles were evaporated and the residue was dissolved in dichloromethane (200 mL). The solution was washed with water (3×100 mL), dried over Na$_2$SO$_4$, and evaporated under reduced pressure. The crude product was subjected to silica gel column chromatography to give 15.5 g (47.0 mmol, 70%) of compound 44.

Step 3: To a cooled to −78° C. stirring solution of compound 44 (15.0 g, 45.4 mmol) in THF (300 mL) 1M solution of LDA in hexanes (48 mL, 48.0 mmol) was added and the mixture was stirred for 30 min at −78° C. Then, 1,2-dibromo-1,1,2,2-tetrafluoroethane (12.5 g, 48.0 mmol) was added, the obtained mixture was stirred for 30 min at −78° C. and then overnight at r.t. The volatiles were evaporated and the residue was dissolved in dichloromethane. The solution was washed with water, dried over $Na_2SO_4$, and evaporated under reduced pressure to obtain 16.4 g (40.0 mmol, 88%) of compound 45.

Step 4: A mixture of compound 45 (0.819 g, 2.00 mmol), NaOH (0.240 g, 6.00 mmol), and methanol (10 mL) was refluxed for 8 h and then evaporated under reduced pressure. The residue was partitioned between water and dichloromethane and acidified with $H_3PO_4$. The product was extracted with dichloromethane (3×20 mL). The organic extract was dried over $Na_2SO_4$, and evaporated under reduced pressure. The residue was purified by silica gel column chromatography to give 0.393 g (1.30 mmol, 65%) of title compound 46 as a white solid. [M+H]$^+$ calcd for $C_{11}H_{16}BrN_3O_2$ 302.06, found 302.0. $^1$H NMR (400 MHz, $CDCl_3$) δ 4.58 (s, 2H), 3.65 (m, 2H), 2.50 (m, 2H), 1.47 (s, 9H).

Example 13: Synthesis of tert-butyl 6-bromo-2,3-dihydro-1H-imidazo[1,2-a]imidazole-1-carboxylate (48)

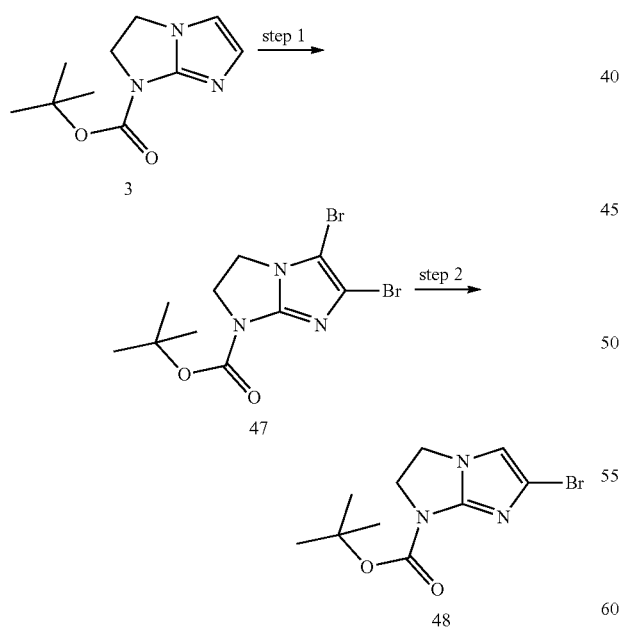

Step 1: To a solution of compound 3 (10.5 g, 50.0 mmol) in chloroform (500 mL) a solution of NBS (26.7 g, 150 mmol) in chloroform (100 mL) was added dropwise over 2 h. After that, the reaction mixture was treated with 2M solution of $Na_2SO_3$ (200 mL) and evaporated to dryness. The residue was purified using the column chromatography (hexane/$CHCl_3$) to yield 1.80 g (4.90 mmol, 10%) of compound 47.

Step 2: To a solution of compound 47 (1.84 g, 5.00 mmol) in anhydrous THF (100 mL), 0.8M i-PrMgCl in THF (6.25 mL) was added at −40° C. In 2 h the reaction mixture was treated with brine and the crude product was extracted with chloroform. The solvent was removed under reduce pressure and the residue was purified by column chromatography (hexane/MTBE) to yield 0.600 g (2.08 mmol, 60%) of title compound 48 as a white solid. [M+H]$^+$ calcd for $C_{10}H_{14}BrN_3O_2$ 288.04, found 288.0. $^1$H NMR (400 MHz, $CDCl_3$) δ 6.67 (s, 1H), 4.31 (t, J=7.7 Hz, 2H), 4.07 (t, J=7.7 Hz, 2H), 1.56 (s, 9H).

Example 14: Synthesis of tert-butyl 6-bromo-2,3-dihydro-1H-imidazo[1,2-b]pyrazole-1-carboxylate (54)

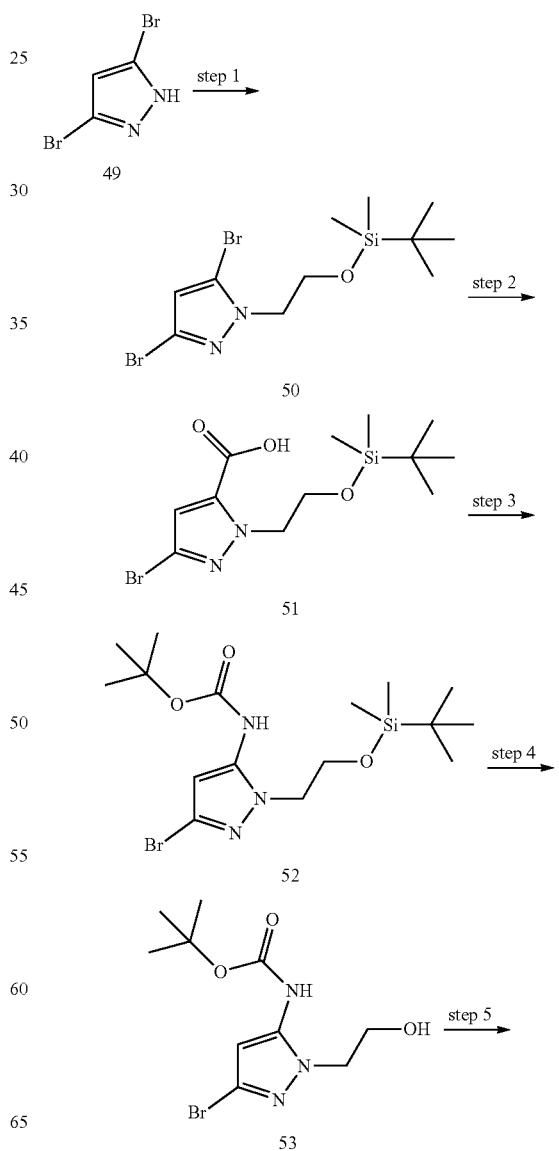

-continued

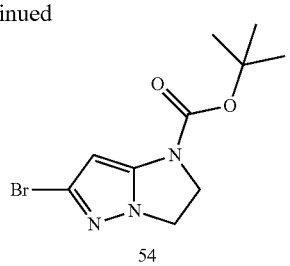

Step 1: To a solution of compound 49 (10.0 g, 44.2 mmol) in DMF (50 mL) Cs$_2$CO$_3$ (28.9 g, 88.7 mmol)' was added followed by (2-bromoethoxy)-tert-butyldimethylsilane (11.1 g, 46.5 mmol) at 20° C. The mixture was then heated to 75° C. and stirred for 16 h. The reaction was quenched with cold water (500 mL) and extracted with ethyl acetate (3×200 mL). The organics were washed with brine (5×150 mL), dried over Na$_2$SO$_4$, filtered, and concentrated under reduced pressure. The residue was purified by chromatography (silica gel, hexane to 80:20 hexane/ethyl acetate) to afford 14.7 g (38.3 mmol, 86%) of compound 50 as a light yellow oil.

Step 2: To a cooled to -90° C. solution of compound 50 (10.0 g, 26.0 mmol) in anhydrous THF (300 mL) 2.5M solution of n-BuLi in hexanes (11 mL, 27.3 mmol of n-BuLi) was added maintaining the inner temperature below -80° C. Upon completion of the addition the reaction mixture was maintained for additional 45 minutes, after which time freshly crushed dry ice was added in one portion. The cooling bath was removed and the reaction was stirred at room temperature overnight. The volatiles were evaporated. The lithium salt of the desired acid was recrystallized from petroleum ether (CAUTION: this salt is better soluble in organic solvents rather than in water), dissolved in water (200 mL), and acidified with H$_3$PO$_4$. The product was extracted with MTBE (3×100 mL). The organic extract was dried over Na$_2$SO$_4$, filtered, and concentrated under reduced pressure to afford 7.50 g (21.5 mmol, 82%) of compound 51 as a beige powder.

Step 3: To a suspension of compound 51 (5.00 g, 14.3 mmol) in anhydrous t-BuOH (100 mL), triethylamine (6.10 mL, 43.8 mmol) was added. After the clear solution was formed, DPPA (3.70 mL, 17.2 mmol) was added at 20° C. The mixture was then gradually warmed to 90° C. and stirred for 1 h resulting in gas evolution occurred upon heating. The reaction mixture was cooled down to 75° C., left overnight, and evaporated. The residue was quenched with saturated K$_2$CO$_3$ and extracted with MTBE (3×150 mL). The insoluble materials were filtered off. The organics were dried over Na$_2$SO$_4$, filtered, and concentrated under reduced pressure. The residue was purified by chromatography (silica gel, MTBE) to afford 4.70 g (11.2 mmol, 78%) of compound 52 as a light yellow solid.

Step 4: To a solution of compound 52 (4.00 g, 9.51 mmol) in anhydrous acetonitrile (75 mL) potassium fluoride (1.65 g, 28.5 mmol) was added and the reaction was stirred at 60° C. overnight. The reaction mixture was then evaporated under reduced pressure. The crude material was purified by chromatography (silica gel, MTBE) to afford 2.20 g (7.19 mmol, 75%) of compound 53 as beige crystals.

Step 5: To a solution of compound 53 (1.25 g, 4.08 mmol) in anhydrous THF (75 mL) tri-nbutylphosphine (1.12 mL, 4.50 mmol) and DIAD (0.910 g, 4.50 mmol) were added at 0° C. under nitrogen. The solution was then stirred at room temperature for 2.5 h. The insoluble solid was filtered off, and the filtrate was concentrated under residue pressure. Water was added to the residue, and the obtained suspension was extracted with ethyl acetate. The extract was washed sequentially with water and brine, and then dried over anhydrous Na$_2$SO$_4$. The crude material was purified by chromatography (silica gel, MTBE) to afford 0.70 g (2.43 mmol, 60%) of title compound 54 as a white powder. C$_{10}$H$_{14}$BrN$_3$O$_2$ 288.04, found 288.2. $^1$H NMR (400 MHz, CDCl$_3$) δ 5.70 (s, 1H), 4.31 (m, 4H), 1.55 (s, 9H).

Example 15: Synthesis of methyl 5-chloro-2-fluorobenzoatone (56)

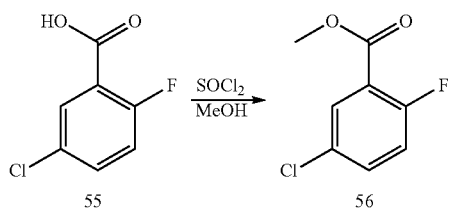

To a mixture of 5-chloro-2-fluorobenzoic acid 55 (80 g, 458.3 mmol) in MeOH (800 mL), SOCl$_2$ (162 g, 1374.9 mmol) was added dropwise. The reaction was stirred at 15° C. for 16 h before being concentrated in vacuo. The concentrate was then diluted with H$_2$O (500 mL) and adjusted to pH 8 by adding saturated aqueous NaHCO$_3$. The mixture was extracted with EtOAc (3×300 mL). The combined organic layers were washed with brine (2×300 mL), dried with Na$_2$SO$_4$, concentrated in vacuum and purified by column chromatography (PE:EA=100:1 to 20:1) to yield compound 56 as colourless oil (80 g, 95% purity, 93% yield). [M+H]$^+$ calcd for C$_8$H$_7$ClFO$_2$ 189.01, found 189.0. $^1$H NMR (400 MHz, Chlorophorm-d) δ 7.95 (dd, J=6.0, 2.8 Hz, 1H), 7.52-7.46 (m, 1H), 7.14 (t, J=5.6 Hz, 1H), 3.96 (s, 3H).

Example 16: Synthesis of 2-(7-bromo-1,5-naphthyridin-2-yl)-1-(5-chloro-2-fluorophenyl)ethan-1-one (57)

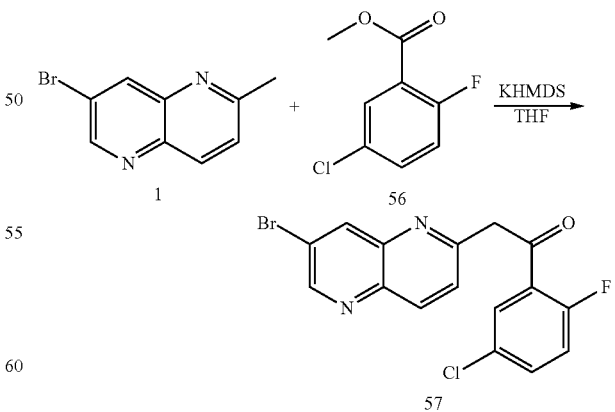

KHMDS (81 mL, 81.08 mmol, 1M) was added dropwise to a mixture of compound 1 (9 g, 40.54 mmol) and compound 56 (23 g, 121.62 mmol) in THF (250 mL) at -78° C. The mixture was then stirred at -78° C. for 1 h before being warmed to 15° C. and stirred for another 30 min. The mixture was quenched with H₂O (400 mL) to form a yellow solid precipitate. This procedure was repeated once and the combined precipitate was filtered. The resultant filter cake was washed with H₂O (50 mL) and further titrated with PE/EA=5:1 (180 mL) to yield intermediate 57 as a yellow solid (27 g, 95% purity, 88% yield). [M+H]⁺ calcd for C₁₆H₉BrClFN₂O, 378.96, found 378.9.

Example 17: Synthesis of 7-bromo-2-(3-(5-chloro-2-fluorophenyl)-1-(tetrahydro-2H-pyran-2-yl)-1H-pyrazol-4-yl)-1,5-naphthyridine (60)

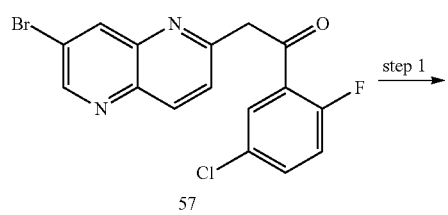

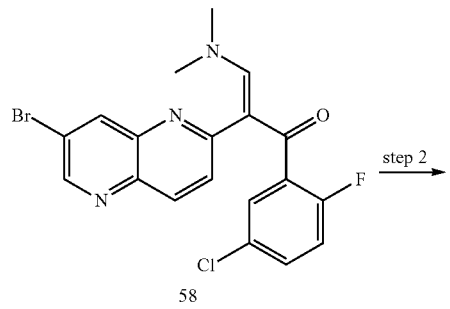

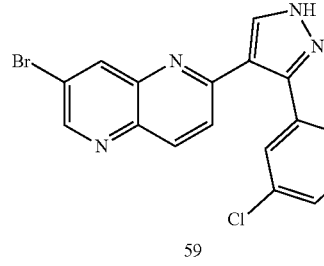

Step 1: (E)-2-(7-Bromo-1,5-naphthyridin-2-yl)-1-(5-chloro-2-fluorophenyl)-3-(dimethylamino)prop-2-en-1-one (58). A solution of compound 57 (20 g, 52.68 mmol) in DMF-DMA (500 mL) was stirred for 6.5 h at 80° C. under N₂. The mixture was concentrated in vacuum to obtain crude compound 58 (23 g) as black oil which was used in directly in Step 2. [M+H]⁺ calcd for C₁₉H₁₄BrClFN₃O, 434.01, found 433.9.

Step 2: 7-Bromo-2-(3-(5-chloro-2-fluorophenyl)-1H-pyrazol-4-yl)-1,5-naphthyridine (59). To a solution of compound 58 (23 g, 52.68 mmol, crude) in MeCN (360 mL) was added AcOH (23 g, 383.01 mmol) and hydrazine hydrate (15 g, 299.70 mmol). The mixture was stirred at 15° C. for 16 h. The reaction was filtered and the filter cake was washed with H₂O (50 mL, 3×), then washed with MeCN (3×50 mL). The filter cake was concentrated in vacuum to obtain title compound 59 (16.5 g) as yellow solid. [M+H]⁺ calcd for C₁₇H₉BrClFN₄ 402.98, found 403.0.

Step 3: 7-Bromo-2-(3-(5-chloro-2-fluorophenyl)-1-(tetrahydro-2H-pyran-2-yl)-1H-pyrazol-4-yl)-1,5-naphthyridine (60). To a solution of compound 59 (16.5 g, 40.88 mmol) in THF (200 mL) was added MsOH (50 drops, catalytic amount) and DHP (18.0 g, 213.98 mmol). The mixture was stirred at 80° C. for 2 h under N₂. The reaction was concentrated in vacuum to give a residue, which was diluted with sat. NaHCO₃ aq (150 mL) and then extracted with EA (3×200 mL). The combined organic layers were concentrated in vacuum and purified by trituration (PE/EA=1/1, 80 mL) to afford compound 60 (14.0 g) as gray solid (14 g, 99% purity, 70% yield). [M+H]⁺ calcd for C₂₂H₁₇BrClFN₄O 487.03, found 487.2. ¹H NMR (400 MHz, DMSO-d₆) δ 8.97 (d, J=2.2 Hz, 1H), 8.84 (s, 1H), 8.39 (d, J=8.9 Hz, 1H), 8.15 (d, J=2.2 Hz, 1H), 7.97 (d, J=8.9 Hz, 1H), 7.65-7.54 (m, 2H), 7.32 (t, J=9.1 Hz, 1H), 5.58 (dd, J=9.9, 2.6 Hz, 1H), 4.06-3.97 (m, 1H), 3.72 (ddd, J=11.5, 8.0, 5.7 Hz, 1H), 2.27-2.11 (m, 1H), 2.10-1.90 (m, 2H), 1.81-1.65 (m, 1H), 1.60 (p, J=4.7 Hz, 2H).

Example 18: Synthesis of (6-(3-(5-chloro-2-fluorophenyl)-1-(tetrahydro-2H-pyran-2-yl)-1H-pyrazol-4-yl)-1,5-naphthyridin-3-yl)boronic acid (61)

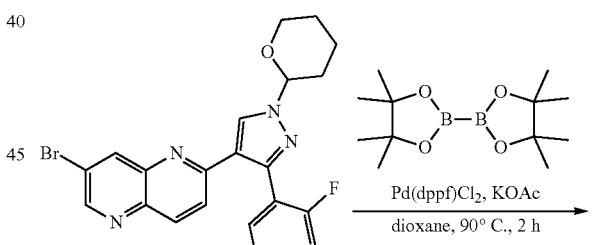

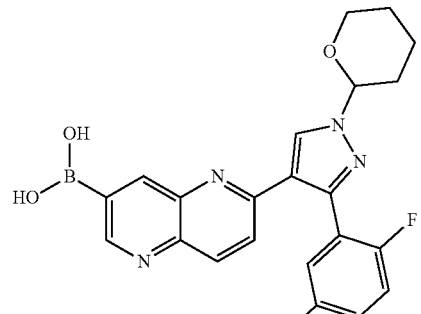

To a solution of compound 60 (7.5 g, 15.4 mmol), 4,4,4',4',5,5,5',5'-octamethyl-2,2'-bi(1,3,2-dioxaborolane) (5.9 g, 23.1 mmol) and KOAc (4.5 g, 46.2 mmol) in dioxane (230 mL) was added Pd(dppf)Cl$_2$ (563 mg, 0.7 mmol). The mixture was stirred at 90° C. for 2 h under N$_2$. The mixture was diluted with H$_2$O (250 mL), the aqueous phase was extracted with EA (200 mL×3). The organic phase was washed with brine, dried over anhydrous Na$_2$SO$_4$, filtered and concentrated under vacuum. The residue was combined was purified by prep-HPLC (Phenomenex Gemini C18 250×50 mm×10 μm, water (0.05% ammonia hydroxide v/v) to afford title compound 61 as a white solid (3.4 g, 99% purity, 45% yield). [M+H]$^+$ calcd for C$_{22}$H$_{19}$BClFN$_4$O$_3$ 453.13, found 453.0. $^1$H NMR (400 MHz, Methanol-d$_4$) δ 9.06 (s, 1H), 8.59 (s, 1H), 8.48 (s, 1H), 8.29 (d, J=8.9 Hz, 1H), 7.79 (d, J=8.9 Hz, 1H), 7.67 (dd, J=6.1, 2.8 Hz, 1H), 7.49 (dt, J=8.8, 4.3, 2.8 Hz, 1H), 7.13 (t, J=9.1 Hz, 1H), 5.59 (dd, J=9.8, 2.8 Hz, 1H), 4.14 (d, J=11.3 Hz, 1H), 3.83 (td, J=11.3, 2.8 Hz, 1H), 2.39-1.98 (m, 3H), 1.94-1.59 (m, 2H), 1.35-1.10 (m, 1H).

Example 19: Synthesis of 6-(3-(5-chloro-2-fluoro-phenyl)-1-(tetrahydro-2H-pyran-2-yl)-1H-pyrazol-4-yl)-1,5-naphthyridine-3-carbaldehyde (64)

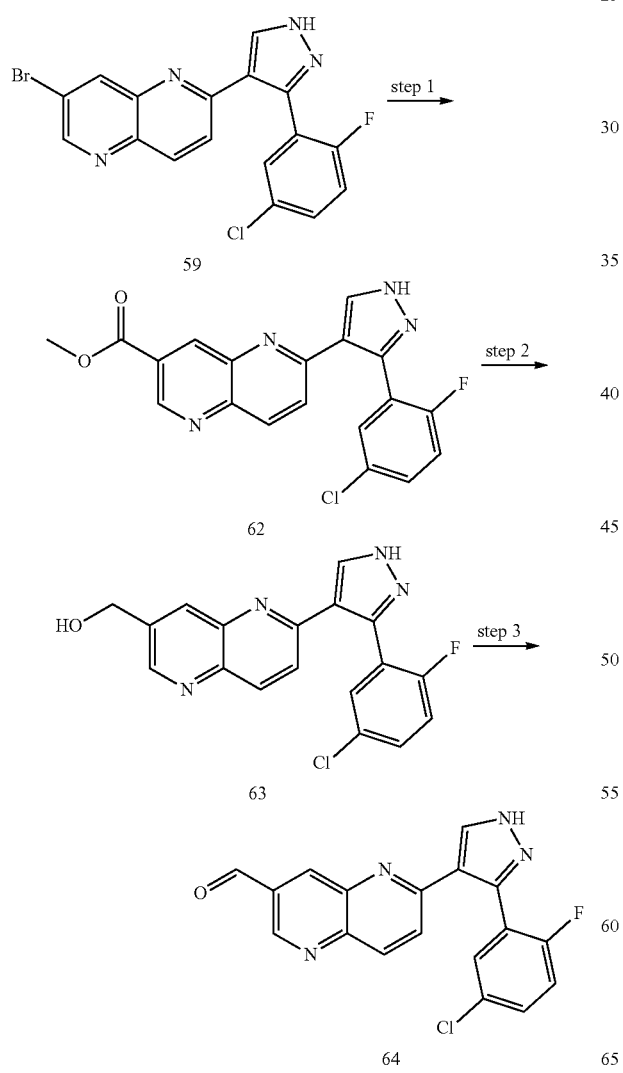

Step 1: Methyl 6-(3-(5-chloro-2-fluorophenyl)-1H-pyrazol-4-yl)-1,5-naphthyridine-3-carboxylate (62). A solution of compound 59 (5.7 g, 14.1 mmol), Xantphos (1.6 g, 2.8 mmol) and NaOAc (1.7 g, 21.2 mmol) in MeOH (50 mL) and DMF (50 mL) was added Pd(OAc)$_2$ (943 mg, 4.2 mmol) under N$_2$ atmosphere. The reaction was stirred at 80° C. for 48 h under CO (50 psi). The reaction was concentrated in vacuum. The residue was purified by column chromatography (20-100% EA in PE) to afford compound 62 as yellow solid (3.5 g, 80% purity, 64% yield). [M+H]$^+$ calcd for C$_{19}$H$_{12}$ClFN$_4$O$_2$ 382.06, found 382.9.

Step 2: (6-(3-(5-Chloro-2-fluorophenyl)-1H-pyrazol-4-yl)-1,5-naphthyridin-3-yl)methanol (63). To a mixture of compound 62 (3×1.17 g, 3×3.06 mmol) in THF (3×100 mL) at −10° C. was added LiAlH$_4$ (3×232 mg, 3×6.12 mmol) in portions. The mixture was stirred at −10° C. for 10 min. The resulting mixture was diluted with sat. sodium potassium tartrate aq. (300 mL) and extracted with EtOAc (3×300 mL). The combined organic portions were dried (Na$_2$SO$_4$), concentrated in vacuum and purified by column chromatography (50%-100% EA in PE; 0-10% MeOH in EA) to afford compound 63 as yellow solid (2.3 g, 96% purity, 70% yield). [M+H]$^+$ calcd for C$_{18}$H$_{12}$ClFN$_4$O, 354.07, found 355.0.

Step 3: 6-(3-(5-Chloro-2-fluorophenyl)-1H-pyrazol-4-yl)-1,5-naphthyridine-3-carbaldehyde (64). To a solution of compound 63 (2×0.9 g, 2×2.5 mmol) in THF (2×12 mL) was added MnO$_2$ (2×1.1 g, 2×12.5 mmol). The mixture was stirred at 70° C. for 16 h. The mixture was filtered and concentrated in vacuum, then purified by prep-HPLC to obtain compound 64 as white solid (760 mg, 96% purity, 33% yield). [M+H]$^+$ calcd for C$_{18}$H$_{10}$ClFN$_4$O 353.05, found 352.9. $^1$H NMR (400 MHz, DMSO-d$_6$) δ 13.66 (s, 1H), 10.27 (s, 1H), 9.26 (d, J=2.0 Hz, 1H), 8.72 (s, 1H), 8.48-8.40 (m, 2H), 8.09 (d, J=8.9 Hz, 1H), 7.78-7.49 (m, 2H), 7.34-7.29 (m, 1H).

Example 20: Synthesis of 2-(3-(5-chloro-2-fluoro-phenyl)-1-(tetrahydro-2H-pyran-2-yl)-1H-pyrazol-4-yl)-7-ethynyl-1,5-naphthyridine (65)

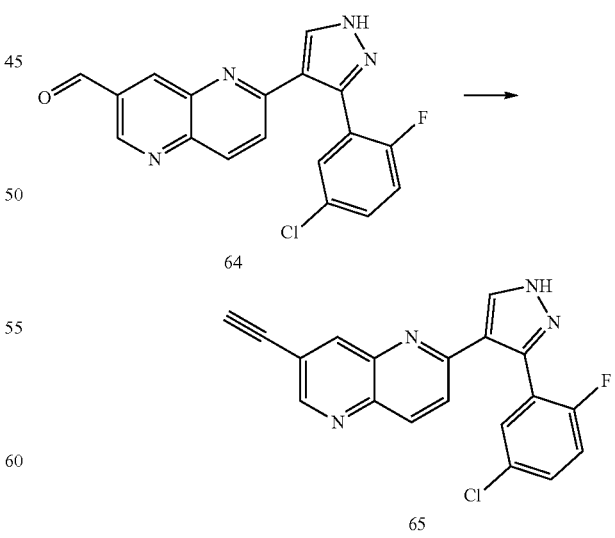

To a slurry of compound 64 (200 mg, 0.567 mmol) in MeOH (5.6 mL) cooled to 0° C. was added dimethyl (1-diazo-2-oxopropyl)phosphonate (0.119 mL, 0.794 mmol)

followed by K₂CO₃ (157 mg, 1.134 mmol). The resultant mixture (thick slurry) was stirred in a cooling ice bath allowed to reach room temperature overnight. The mixture was then concentrated in vacuo, dry-loaded onto silica gel and purified using RediSep Silica 12 g Gold CombiFlash® column with 0 to 15% MeOH-DCM as eluent. The title compound 65 was concentrated in vacuo to yield 138 mg (66.3% yield, 95% purity). [M+H]⁺ calcd for $C_{19}H_{10}ClFN_4$ 349.07, found 349.0.

Example 21: Synthesis of 6-(3-(5-chloro-2-fluorophenyl)-1H-pyrazol-4-yl)-N-(2-((3S,5R)-3,5-dimethylpiperazin-1-yl)ethyl)-1,5-naphthyridin-3-amine (1-1

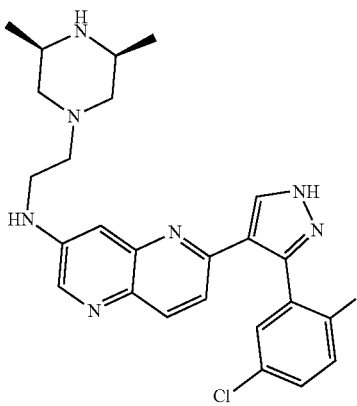

2-((3S,5R)-3,5-dimethylpiperazin-1-yl)ethan-1-amine (26.6 mg, 0.169 mmol) was added of compound 60 (75 mg, 0.154 mmol), BrettPhos (8.25 mg, 0.015 mmol) and BrettPhos Pd G4 (14.15 mg, 0.015 mmol) followed by cesium carbonate (150 mg, 0.461 mmol) and dioxane (1538 μl). The resulting mixture was stirred at 95° C. for 16 h. The residue was then treated with 1 mL of TFA and stirred at 50° C. for 1 h until THP protecting group was fully removed. The resulting mixture was concentrated and purified by preparative HPLC chromatography using a gradient (10 to 50%) of acetonitrile in water with 0.05% trifluoroacetic acid to yield a TFA salt of the title compound (15 mg). [M+H]⁺ calcd for $C_{25}H_{27}ClFN_7$ 480.21, found 480.1.

Example 22: Synthesis of 6-(3-(5-chloro-2-fluorophenyl)-1H-pyrazol-4-yl)-N-(5-(piperazin-1-yl)pyridin-2-yl)-1,5-naphthyridin-3-amine (1-15)

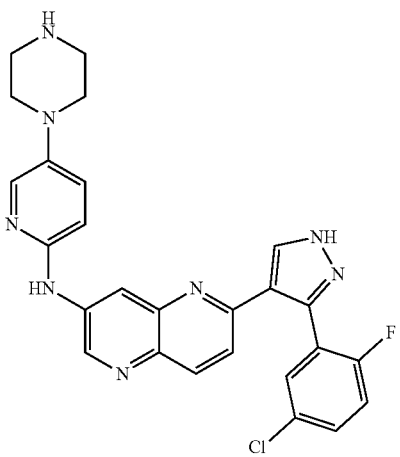 [SMILES: Fc1ccc(Cl)cc1-c1n[nH]cc1-c1ccc2ncc(Nc3ccc(N4CCNCC4)cn3)cc2n1]

A vial of 7-bromo-2-(3-(5-chloro-2-fluorophenyl)-1-(tetrahydro-2H-pyran-2-yl)-1H-pyrazol-4-yl)-1,5-naphthyridine, tert-Butyl 4-(6-aminopyridin-3-yl)piperazine-1-carboxylate (33.7 mg, 0.121 mmol), BrettPhos Pd G4 (18.58 mg, 0.020 mmol), BrettPhos (10.83 mg, 0.020 mmol), and cesium carbonate (99 mg, 0.303 mmol) in 1,4-Dioxane (673 μl) was heated to 85° C. for 16 h. The residue was then treated with 1 mL of TFA and stirred at 50° C. for 1 h until THP and Boc protecting groups were fully removed. The resulting mixture was concentrated and purified by preparative HPLC chromatography using a gradient (2 to 40%) of acetonitrile in water with 0.05% trifluoroacetic acid to yield a TFA salt of the title compound (21.1 mg). [M+H]⁺ calcd for $C_{26}H_{22}ClFN_8$ 501.16, found 501.1.

Example 23: Synthesis of 6-(3-(5-chloro-2-fluorophenyl)-1H-pyrazol-4-yl)-N-(5-(4-methylpiperazin-1-yl)pyridin-2-yl)-1,5-naphthyridin-3-amine (1-29)

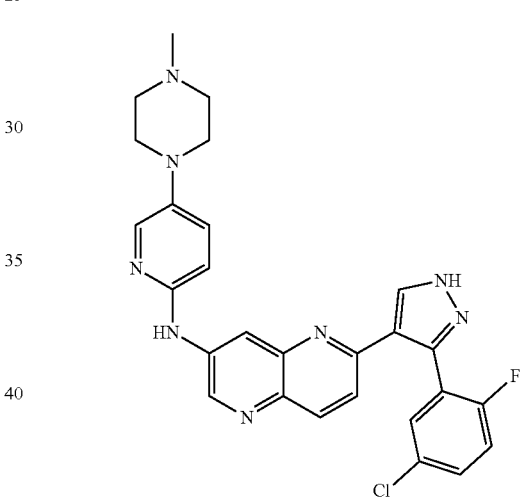

A mixture of 6-(3-(5-chloro-2-fluorophenyl)-1H-pyrazol-4-yl)-N-(5-(piperazin-1-yl)pyridin-2-yl)-1,5-naphthyridin-3-amine (11.2 mg, 0.022 mmol), AcOH (1.282 μl, 0.022 mmol), and formaldehyde (3.33 μL, 0.045 mmol) was stirred for 1 h in methanol (250 μL) before adding sodium triacetoxyborohydride (14.24 mg, 0.067 mmol). The resulting mixture was allowed to stir 16 h at room temperature. The resulting mixture was concentrated and purified by preparative HPLC chromatography using a gradient (15 to 32%) of acetonitrile in water with 0.05% trifluoroacetic acid to yield a TFA salt of the title compound (4.5 mg). [M+H]⁺ calcd for $C_{27}H_{24}ClFN_8$ 515.18, found 515.0. ¹H NMR (400 MHz, Methanol-d₄) δ 9.04-8.98 (m, 1H), 8.91 (d, J=2.5 Hz, 1H), 8.39 (s, 1H), 8.33 (d, J=8.7 Hz, 1H), 8.07 (dd, J=3.0, 0.7 Hz, 1H), 7.69 (dd, J=6.1, 2.7 Hz, 1H), 7.57-7.45 (m, 3H), 7.21-7.12 (m, 1H), 7.00 (dd, J=9.0, 0.7 Hz, 1H), 4.92-4.81 (m, 2H), 3.77 (s, 2H), 3.63 (s, 2H), 3.08 (s, 2H), 2.99 (s, 3H).

Example 24: Synthesis of 6-(3-(5-chloro-2-fluorophenyl)-1H-pyrazol-4-yl)-N-(5-(4-isopropylpiperazin-1-yl)pyridin-2-yl)-1,5-naphthyridin-3-amine (1-30)

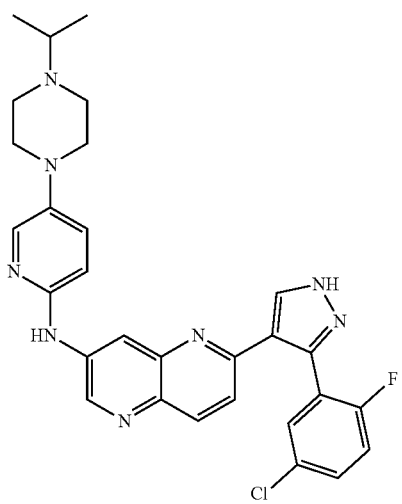 [SMILES: CC(C)N1CCN(c2ccc(Nc3cnc4ccc(-c5c[nH]nc5-c5cc(Cl)ccc5F)nc4c3)nc2)CC1]

A mixture of 6-(3-(5-chloro-2-fluorophenyl)-1H-pyrazol-4-yl)-N-(5-(piperazin-1-yl)pyridin-2-yl)-1,5-naphthyridin-3-amine (11.2 mg, 0.022 mmol), AcOH (1.282 µL, 0.022 mmol), and acetone (3.33 µL, 0.045 mmol) was stirred for 1 h in methanol (250 µL) before adding sodium triacetoxyborohydride (14.24 mg, 0.067 mmol). The resulting mixture was allowed to stir 16 h at room temperature. The resulting mixture was concentrated and purified by preparative HPLC chromatography using a gradient (15 to 32%) of acetonitrile in water with 0.05% trifluoroacetic acid to yield a TFA salt of the title compound (4.5 mg). [M+H]$^+$ calcd for $C_{29}H_{28}ClFN_8$ 543.27, found 543.1.

Example 25: Synthesis of 2-(4-benzylpiperazin-1-yl)-5,6,7,8-tetrahydro-[1,2,4]triazolo[1,5-a]pyrazine

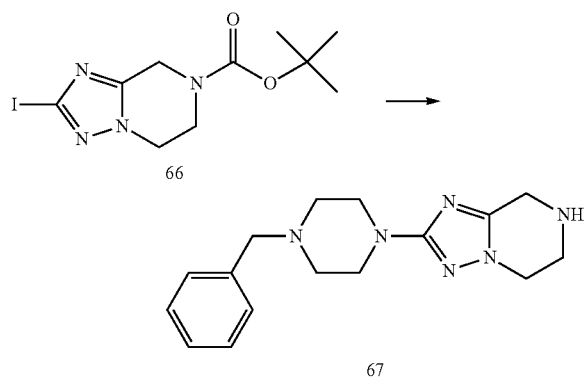

To a vial containing compound 66 (46.4 mg, 0.132 mmol), n-benzylpiperazine (46.7 mg, 0.265 mmol), RuPhos (12.35 mg, 0.026 mmol), RuPhos PD G4 (22.51 mg, 0.026 mmol), and sodium tert-butoxide (38.2 mg, 0.397 mmol) was added 1,4-dioxane (0.8 mL) and subsequently sparged with nitrogen for 5 min. The resulting yellow reaction mixture was capped stirred at 100° C. for 16 h. The reaction was filtered through a plug of celite, washed with THF (5 mL) and concentrated in vacuo. The resulting residue was treated with TFA (0.5 mL) and stirred at 50° C. for 1 h. The crude product was concentrated in vacuo, and purified by reverse phase chromatography using a gradient (0 to 50%) of acetonitrile in water with 0.05% trifluoroacetic acid to yield a TFA salt of the title intermediate 67 (29 mg). [M+H]$^+$ calcd for $C_{16}H_{22}N_6$ 299.19, found 299.0.

Example 26: Synthesis of 2-(4-benzylpiperazin-1-yl)-4,5,6,7-tetrahydropyrazolo[1,5-a]pyrazine

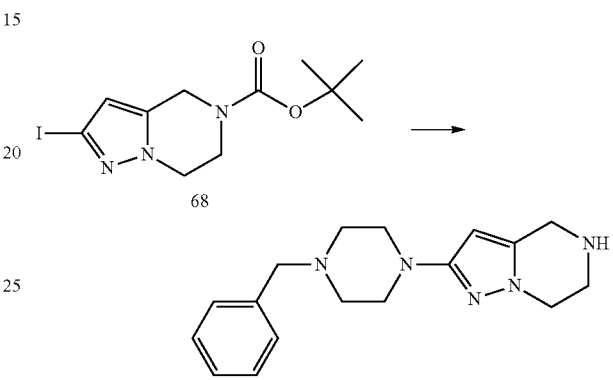

To a vial containing compound 68 (40.0 mg, 0.132 mmol), n-benzylpiperazine (46.7 mg, 0.265 mmol), RuPhos (12.35 mg, 0.026 mmol), RuPhos PD G4 (22.51 mg, 0.026 mmol), and sodium tert-butoxide (38.2 mg, 0.397 mmol) was added 1,4-dioxane (0.8 ml) and subsequently sparged with nitrogen for 5 min. The resulting yellow reaction mixture was capped stirred at 100° C. for 16 h. The reaction was filtered through a plug of celite, washed with THF (5 mL) and concentrated in vacuo. The resulting residue was treated with TFA (0.5 mL) and stirred at 50° C. for 1 h. The crude product was concentrated in vacuo, and purified by reverse phase chromatography using a gradient (0 to 50%) of acetonitrile in water with 0.05% trifluoroacetic acid to yield a TFA salt of the title intermediate 69 (49 mg). [M+H]$^+$ calcd for $C_{17}H_{23}N_5$ 298.20, found 298.0.

Example 27: Synthesis of 1-(6-(3-(5-chloro-2-fluorophenyl)-1H-pyrazol-4-yl)-1,5-naphthyridin-3-yl)-N,N-dimethylazetidin-3-amine (1-31)

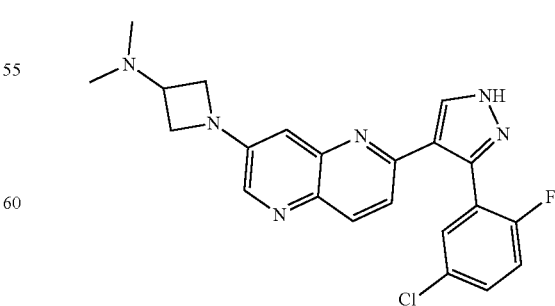

To a vial charged with compound 60 (32 mg, 0.066 mmol) and 3-(dimethylamino)azetidine dihydrochloride (23 mg, 0.066 mmol) was added RuPhos, (3.08 mg, 6.60 μmol), RuPhos Pd G2 (5.13 mg, 6.60 μmol) and cesium carbonate, (65 mg, 0.198 mmol). To the resulting mixture was added dioxane (600 μL) and subsequently sparged with nitrogen for 5 min. The resulting yellow reaction mixture was capped stirred at 85° C. for 16 h. The reaction was filtered through a plug of celite, washed with THF (5 mL) and concentrated in vacuo. The resulting residue was treated with 1 mL of TFA and stirred at 45° C. for 1 h. The crude product was concentrated in vacuo, and purified by preparative HPLC chromatography using a gradient (17 to 31%) of acetonitrile in water with 0.05% trifluoroacetic acid to yield a TFA salt of the title compound (23.1 mg). [M+H]$^+$ calcd for $C_{22}H_{20}ClFN_6$ 423.14, found 423.1. $^1$H NMR (400 MHz, Methanol-d$_4$) δ 8.56 (d, J=2.6 Hz, 1H), 8.50 (d, J=8.7 Hz, 1H), 8.47 (s, 1H), 7.70 (dd, J=6.1, 2.7 Hz, 1H), 7.52 (ddd, J=8.9, 4.4, 2.7 Hz, 1H), 7.47 (d, J=8.7 Hz, 1H), 7.20-7.13 (m, 1H), 7.11 (d, J=2.5 Hz, 1H), 4.57 (dd, J=9.9, 7.7 Hz, 2H), 4.48-4.36 (m, 3H), 2.99 (s, 6H).

Example 28: Synthesis of 1-(6-(3-(5-chloro-2-fluorophenyl)-1H-pyrazol-4-yl)-1,5-naphthyridin-3-yl)-N-methylazetidin-3-amine (1-49)

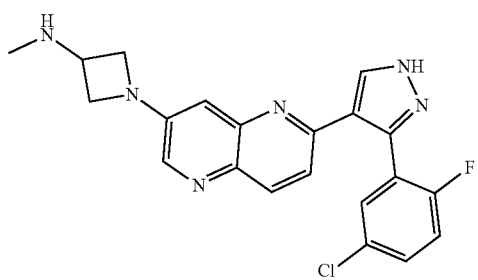 [SMILES: CNC1CN(c2cnc3ccc(-c4c[nH]nc4-c4cc(Cl)ccc4F)nc3c2)C1]

To a vial charged with compound 60 (32 mg, 0.066 mmol) and tert-butyl azetidin-3-yl(methyl)carbamate hydrochloride (13 mg, 0.072 mmol) was added RuPhos, (3.08 mg, 6.60 μmol), RuPhos Pd G2 (5.13 mg, 6.60 μmol) and cesium carbonate, (65 mg, 0.198 mmol). To the resulting mixture was added dioxane (600 μL) and subsequently sparged with nitrogen for 5 min. The resulting yellow reaction mixture was capped stirred at 85° C. for 16 h. The reaction was filtered through a plug of celite, washed with THF (5 mL) and concentrated in vacuo. The resulting residue was treated with 1 mL of TFA and stirred at 45° C. for 1 h. The crude product was concentrated in vacuo, and purified by preparative HPLC chromatography using a gradient (12 to 38%) of acetonitrile in water with 0.05% trifluoroacetic acid to yield a TFA salt of the title compound (10.4 mg). [M+H]$^+$ calcd for $C_{21}H_{18}ClFN_6$ 409.13, found 409.1. $^1$H NMR (400 MHz, Methanol-d$_4$) δ 8.47 (d, J=2.7 Hz, 1H), 8.38 (s, 1H), 8.33 (dd, J=8.7, 0.6 Hz, 1H), 7.68 (dd, J=6.2, 2.7 Hz, 1H), 7.55-7.47 (m, 1H), 7.47 (d, J=8.7 Hz, 1H), 7.21-7.11 (m, 1H), 7.06 (d, J=2.0 Hz, 1H), 4.55-4.46 (m, 2H), 4.33-4.21 (m, 3H), 2.81 (s, 3H).

Example 29: Synthesis of (2R)-1-(tert-butoxycarbonyl)-4-(6-(3-(5-chloro-2-fluorophenyl)-1-(tetrahydro-2H-pyran-2-yl)-1H-pyrazol-4-yl)-1,5-naphthyridin-3-yl)piperazine-2-carboxylic acid (71)

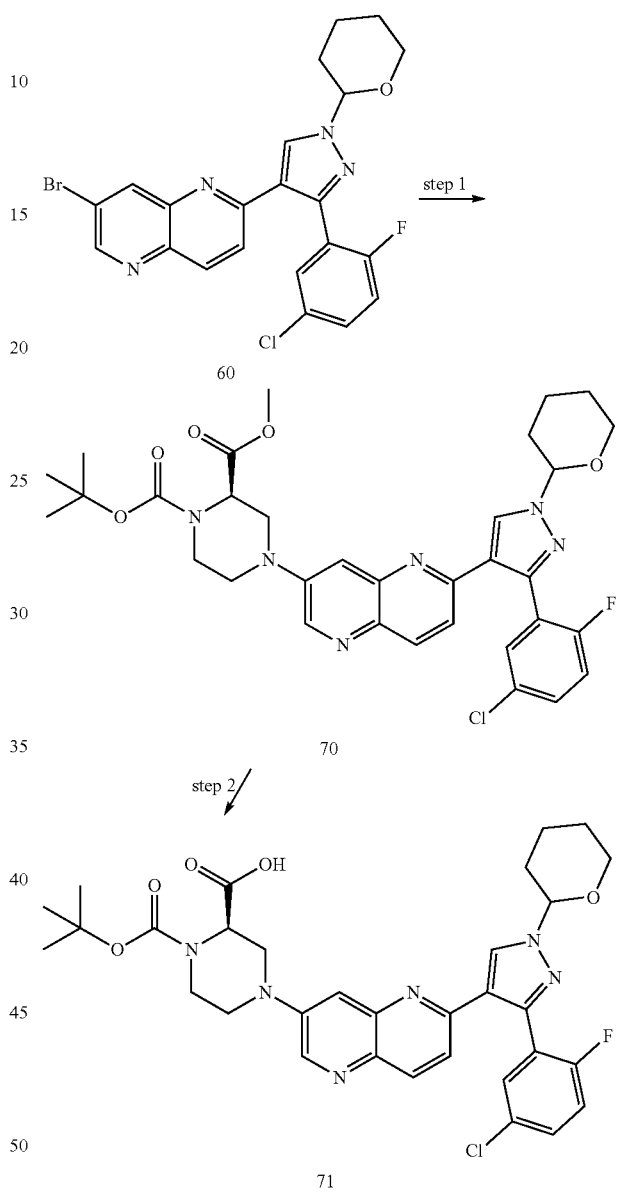

Step 1: 1-(tert-butyl) 2-methyl (2R)-4-(6-(3-(5-chloro-2-fluorophenyl)-1-(tetrahydro-2H-pyran-2-yl)-1H-pyrazol-4-yl)-1,5-naphthyridin-3-yl)piperazine-1,2-dicarboxylate (70). To a vial charged with compound 60 (70 mg, 0.144 mmol) and 1-(tert-butyl) 2-methyl (R)-piperazine-1,2-dicarboxylate (45.6 mg, 0.187 mmol) was added RuPhos, (13.39 mg, 0.029 mmol), RuPhos Pd G4 (24.41 mg, 0.028 mmol) and cesium carbonate, (140 mg, 0.431 mmol). To the resulting mixture was added dioxane (718 μL) and subsequently sparged with nitrogen for 5 min. The resulting yellow reaction mixture was capped stirred at 85° C. for 2.5 h. The reaction was cooled and concentrated in vacuo. The resulting residue was purified by normal phase column chromatography using a gradient (5 to 90%) of ethyl acetate in hexanes to yield title intermediate 70 as a light brown oil (81.2 mg, 87% yield). [M+H]+ calcd for $C_{33}H_{36}ClFN_6O_5$ 651.24, found 651.0.

Step 2: (2R)-1-(tert-butoxycarbonyl)-4-(6-(3-(5-chloro-2-fluorophenyl)-1-(tetrahydro-2H-pyran-2-yl)-1H-pyrazol-4-yl)-1,5-naphthyridin-3-yl)piperazine-2-carboxylic acid (71). To a vial of compound 70 (81.2 mg, 0.125 mmol) in 1:1 MeOH:THF (1248 μL) was added LiOH as a 1M solution in H2O (624 μL, 0.624 mmol). The resulting mixture was stirred for 16 h at room temperature. The reaction was concentrated in vacuo, yielding the title intermediate 71 as a crude product. The resulting solid was used as is in the following reactions as a fraction of the resulting total mass and the assumption of 100% theoretical yield. [M+H]+ calcd for $C_{32}H_{34}ClFN_6O_5$ 637.23, found 637.0.

Example 30: Synthesis of (R)-4-(6-(3-(5-Chloro-2-fluorophenyl)-1H-pyrazol-4-yl)-1,5-naphthyridin-3-yl)-N-isopropylpiperazine-2-carboxamide (1-66)

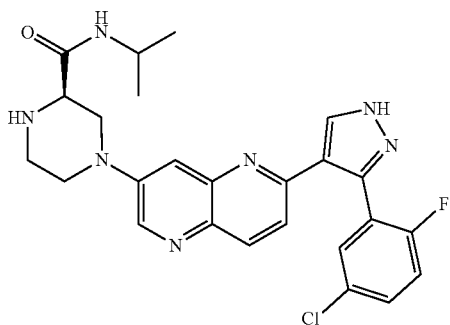 [SMILES: CC(C)NC(=O)[C@H]1CN(c2cnc3ccc(-c4c[nH]nc4-c4cc(Cl)ccc4F)nc3c2)CCN1]

A vial of compound 71 (12 mg, 0.019 mmol), DIPEA (9.87 μL, 0.057 mmol), and HATU (9.31 mg, 0.024 mmol) in DMF (0.306 ml) was stirred for 30 min before adding isopropylamine (3.34 mg, 0.057 mmol). The resulting mixture was stirred for 16 h at room temperature. Afterwards, the reaction was concentrated in vacuo. The resulting residue was treated with 0.5 mL of TFA and stirred at 50° C. for 1 h. The crude product was concentrated in vacuo, and purified by preparative HPLC chromatography using a gradient (15 to 55%) of acetonitrile in water with 0.05% trifluoroacetic acid to yield a TFA salt of the title compound (3.4 mg). [M+H]+ calcd for $C_{25}H_{25}ClFN_7O$, 494.18, found 494.0.

Example 31: Synthesis of 7-(3,6-diazabicyclo[30.2.0]heptan-3-yl)-2-(3-(5-chloro-2-fluorophenyl)-1H-pyrazol-4-yl)-1,5-naphthyridine (1-69)

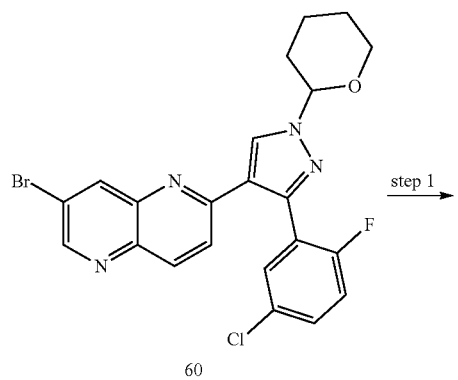

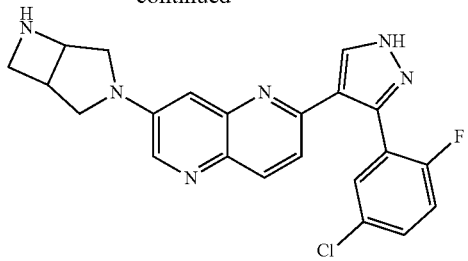

To a vial charged with 60 (50 mg, 0.103 mmol) and tert-butyl 3,6-diazabicyclo[3.2.0]heptane-6-carboxylate (22 mg, 0.113 mmol) was added RuPhos, (9.57 mg, 0.021 mmol), RuPhos Pd G4 (17.43 mg, 0.021 mmol) and cesium carbonate, (100 mg, 0.308 mmol). To the resulting mixture was added dioxane (500 μL) and subsequently sparged with nitrogen for 5 min. The resulting yellow reaction mixture was capped stirred at 85° C. for 16 h. The reaction was cooled and then concentrated in vacuo. The resulting residue was treated with 1 mL of TFA and stirred at 50° C. for 1 h. The crude product was concentrated in vacuo, and purified by preparative HPLC chromatography using a gradient (5 to 45%) of acetonitrile in water with 0.05% trifluoroacetic acid to yield a TFA salt of the title compound (29 mg). [M+H]+ calcd for $C_{22}H_{18}ClFN_6$ 421.13, found 421.1.

Example 32: Synthesis of 2-(3-(5-chloro-2-fluorophenyl)-112-pyrazol-4-yl)-7-(6-isopropyl-3,6-diazabicyclo[3.2.0]heptan-3-yl)-1,5-naphthyridine (1-70)

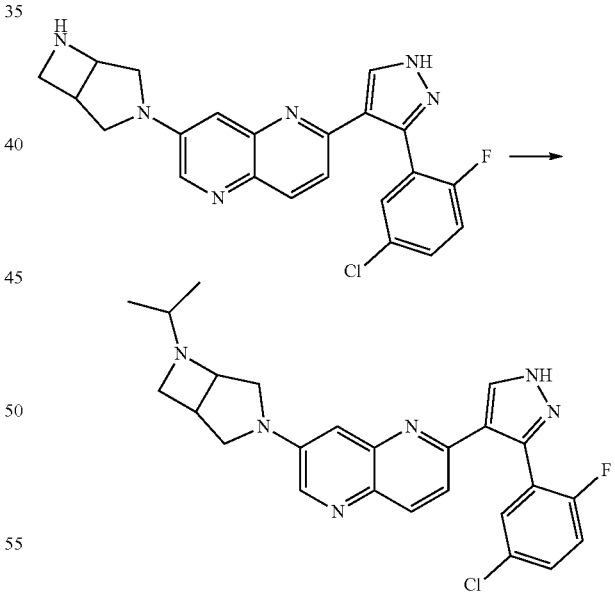

To a vial charged with 7-(3,6-diazabicyclo[3.2.0]heptan-3-yl)-2-(3-(5-chloro-2-fluorophenyl)-1H-pyrazol-4-yl)-1,5-naphthyridine (9.01 mg, 0.021 mmol) and MeOH (253 μL) was added acetic acid (1.289 mg, 0.021 mmol) and acetone (7.88 μL, 0.107 mmol). The resulting reaction was stirred for 30 min at rt before adding sodium triacetoxyborohydride (11.26 mg, 0.053 mmol), and then continued to stir at rt for 21 h. The reaction was quenched by the addition of H2O and then concentrated in vacuo. The resulting residue was puri-

285 fied by preparative HPLC chromatography using a gradient (5 to 45%) of acetonitrile in water with 0.05% trifluoroacetic acid to yield a TFA salt of the title compound (8.0 mg). [M+H]+ calcd for $C_{25}H_{24}ClFN_6$ 463.17, found 463.1.

Example 33: Synthesis of 2-(3-(5-chloro-2-fluorophenyl)-1H-pyrazol-4-yl)-7-(2-(piperazin-1-yl)-6,7-dihydropyrazolo[1,5-a]pyrazin-5 (4H)-yl)-1,5-naphthyridine (1-84)

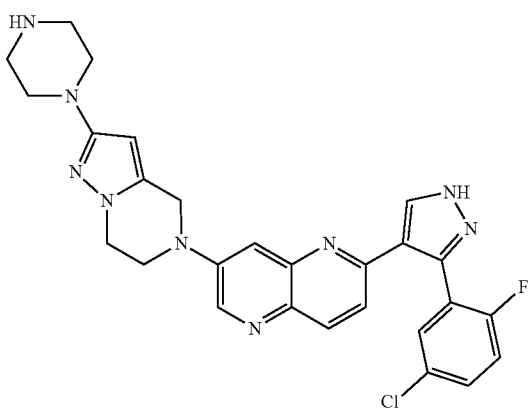 [SMILES: Fc1ccc(Cl)cc1-c1n[nH]cc1-c1ccc2ncc(N3CCn4nc(N5CCNCC5)cc4C3)cc2n1]

To a vial charged with compound 60 (20 mg, 0.041 mmol) and 2-(4-benzylpiperazin-1-yl)-4,5,6,7-tetrahydropyrazolo[1,5-a]pyrazine (22 mg, 0.054 mmol) was added RuPhos, (3.83 mg, 0.008 mmol), RuPhos Pd G4 (6.98 mg, 0.008 mmol) and cesium carbonate, (40 mg, 0.123 mmol). To the resulting mixture was added dioxane (410 µL) and subsequently sparged with nitrogen for 5 min. The resulting yellow reaction mixture was capped stirred at 85° C. for 16 h. The reaction was filtered through a plug of celite, washed with THF (5 mL) and concentrated in vacuo. The resulting residue was dissolved in ethanol (354 µL), followed by the addition of palladium, 10% wt. on carbon, wet (2.263 mg, 2.127 µmol). The reaction was placed under hydrogen atmosphere and heated to 40° C. for 16 h. The reaction was filtered through a plug of celite, washed with THF (5 mL) and concentrated in vacuo. The resulting residue was treated with TFA (0.5 mL) and stirred at 50° C. for 1 h. The crude product was concentrated in vacuo, and purified by preparative HPLC chromatography using a gradient (19 to 33%) of acetonitrile in water with 0.05% trifluoroacetic acid to yield a TFA salt of the title compound (2.4 mg). [M+H]+ calcd for $C_{27}H_{25}ClFN_9$ 530.20 found 530.1.

286

Example 34: Synthesis of 7-(2-bromo-5,6-dihydro-[1,2,4]triazolo[1,5-a]pyrazin-7(8H)-yl)-2-(3-(5-chloro-2-fluorophenyl)-1-(tetrahydro-2H-pyran-2-yl)-1H-pyrazol-4-yl)-1,5-naphthyridine (72)

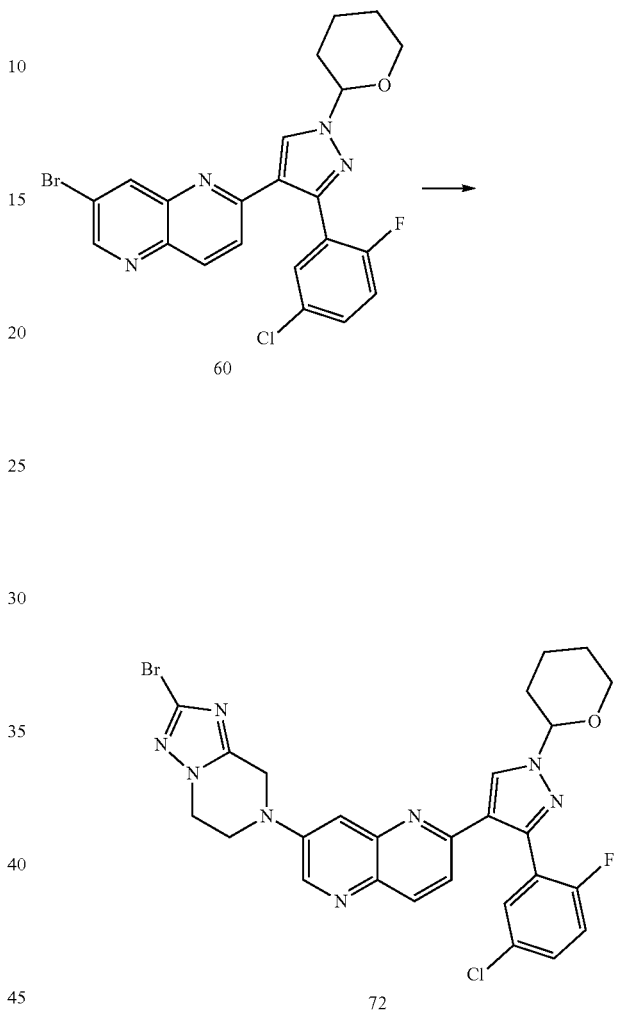

To a vial charged with compound 60 (60 mg, 0.112 mmol) and 2-bromo-5,6,7,8-tetrahydro-[1,2,4]triazolo[1,5-a]pyrazine (29.7 mg, 0.146 mmol) was added RuPhos, (10.49 mg, 0.022 mmol), RuPhos Pd G4 (19.11 mg, 0.022 mmol) and cesium carbonate, (110 mg, 0.337 mmol). To the resulting mixture was added dioxane (562 µL) and subsequently sparged with nitrogen for 5 min. The resulting yellow reaction mixture was capped stirred at 95° C. for 16 h. The reaction was filtered through a plug of celite, washed with THF (5 mL) and concentrated in vacuo. The resulting residue was purified by normal phase column chromatography using a gradient (0 to 100%) of ethyl acetate in hexanes to yield the title intermediate 72 (38 mg). [M+H]+ calcd for $C_{27}H_{23}BrClFN_8O$, 609.09, found 609.0.

Example 35: Synthesis of 2-(3-(5-chloro-2-fluoro-phenyl)-1H-pyrazol-4-yl)-7-(2-(2,5-dihydro-1H-pyrrol-3-yl)-5,6-dihydro-[1,2,4]triazolo[1,5-a]pyrazin-7(8H)-yl)-1,5-naphthyridine (1-85)

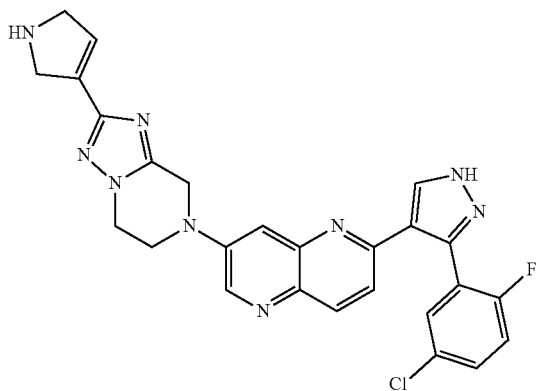 [SMILES: Fc1ccc(Cl)cc1-c1n[nH]cc1-c1ccc2ncc(N3CCn4nc(C5=CCNC5)nc4C3)cc2n1]

A vial containing 72 (38 mg, 0.062 mmol), sodium carbonate (19.81 mg, 0.187 mmol), [1,1'-bis(diphenylphosphino)ferrocene]dichloropalladium(ii) (9.12 mg, 0.012 mmol), and 1-boc-2,5-dihydro-1H-pyrrole-3-boronic acid, pinacol ester 2 (22.07 mg, 0.075 mmol) in 2:1 1,4-dioxane (415 µL):water (208 µL) was sparged with nitrogen for 5 min before heating to 85° C. for 16 h. The reaction cooled and then concentrated in vacuo. The resulting residue was treated with TFA (0.5 mL) and stirred at 50° C. for 1 h. The crude product was concentrated in vacuo, and purified by preparative HPLC chromatography using a gradient (10 to 45%) of acetonitrile in water with 0.05% trifluoroacetic acid to yield a TFA salt of the title compound (20.4 mg). [M+H]$^+$ calcd for $C_{21}H_{18}ClFN_6$ 514.16, found 514.0.

Example 36: Synthesis of 2-(3-(5-chloro-2-fluoro-phenyl)-1H-pyrazol-4-yl)-7-(2-(1-methyl-2,5-dihydro-1H-pyrrol-3-yl)-5,6-dihydro-[1,2,4]triazolo[1,5-a]pyrazin-7(8H)-yl)-1,5-naphthyridine (1-86)

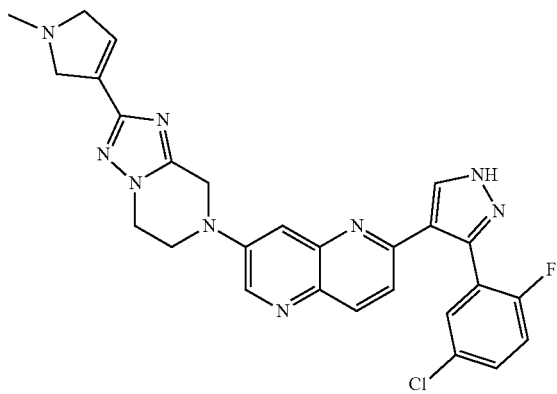 [SMILES: CN1CC=C(c2nc3n(n2)CCN(c2cnc4ccc(-c5c[nH]nc5-c5cc(Cl)ccc5F)nc4c2)C3)C1]

To a vial containing 2-(3-(5-chloro-2-fluorophenyl)-1H-pyrazol-4-yl)-7-(2-(2,5-dihydro-1H-pyrrol-3-yl)-5,6-dihydro-[1,2,4]triazolo[1,5-a]pyrazin-7(8H)-yl)-1,5-naphthyridine (10 mg, 0.019 mmol) in methanol (250 µL) was added AcOH (1.114 µL, 0.019 mmol) and stirred at rt for 1 h. Afterwards, sodium triacetoxyborohydride (12.37 mg, 0.058 mmol) was added and stirred at rt for 16 h. The crude product was concentrated in vacuo, and purified by preparative HPLC chromatography using a gradient (10 to 50%) of acetonitrile in water with 0.05% trifluoroacetic acid to yield a TFA salt of the title compound (3.6 mg). [M+H]$^+$ calcd for $C_{21}H_{18}ClFN_6$ 528.17, found 528.0.

Example 37: Synthesis of 2-(4-(6-(3-(5-chloro-2-fluorophenyl)-1H-pyrazol-4-yl)-1,5-naphthyridin-3-yl)-1H-pyrazol-1-yl)-N-methylethan-1-amine (1-87)

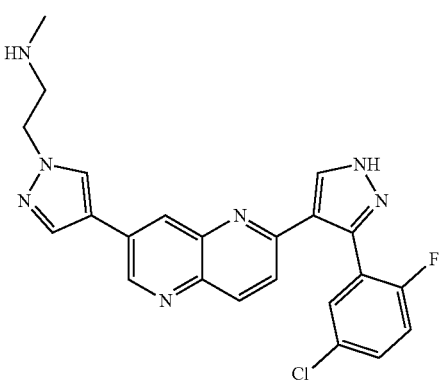 [SMILES: CNCCn1cc(-c2cnc3ccc(-c4c[nH]nc4-c4cc(Cl)ccc4F)nc3c2)cn1]

To a vial charged with 7-bromo-2-(3-(5-chloro-2-fluorophenyl)-1-(tetrahydro-2H-pyran-2-yl)-1H-pyrazol-4-yl)-1,5-naphthyridine (35 mg, 0.072 mmol) and carbamic acid, N-methyl-N-[2-[4-(4,4,5,5-tetramethyl-1,3,2-dioxaborolan-2-yl)-1H-pyrazol-1-yl]ethyl]-, 1,1-dimethylethyl ester (30.2 mg, 0.086 mmol) was added potassium phosphate, tribasic, anhydrous, (45.7 mg, 0.215 mmol), XPhos Pd G4 (6.17 mg, 7.18 µmop and 2-dicyclohexylphosphino-2',4',6'-triisopropylbiphenyl 1 g (3.42 mg, 7.18 µmop. The mixture was purged with nitrogen before water (144 µL) and dioxane (144 µL) was added and the resulting slurry was stirred at 85° C. for 1.5 h, then cooled to room temperature and filtered through a plug of celite, washed with THF (5 mL) and concentrated in GeneVac®. The dark residue was treated with 1.2 mL of TFA and stirred at 55° C. and for 1 h before being concentrated, filtered and purified by preparative HPLC chromatography a gradient (20 to 55%) of acetonitrile in water with 0.05% trifluoroacetic acid to yield TFA salt of the title compound (29.5 mg, 100% purity, 60.8%). [M+H]$^+$ calcd for $C_{23}H_{19}ClFN_7$ 448.14, found 448.2. $^1$H NMR (400 MHz, DMSO-d$_6$) δ 9.19 (d, J=2.2 Hz, 1H), 8.55 (s, br, 1H), 8.48 (s, br, 1H), 8.53 (d, J=0.8 Hz, 1H) 8.29 (d, J=0.8 Hz, 1H), 8.27 (dd, J=8.8, 0.9 Hz, 1H) 8.12 (d, J=2.2 Hz, 0.9 Hz 1H), 7.72 (d, J=8.8 Hz, 1H) 7.69-7.65 (m, 1H), 7.60-7.51 (m, 1H), 7.29 (t, J=9.1 Hz, 1H), 4.47 (t, J=6.0 Hz, 2H), 3.42 (qnt, J=6.0 Hz, 2H), 2.59 (t, J=5.3 Hz, 3H).

Example 38: Synthesis of 3-(6-(3-(5-chloro-2-fluorophenyl)-1H-pyrazol-4-yl)-1,5-naphthyridin-3-yl)-1-methylpyridin-2(1H)-one (1-90)

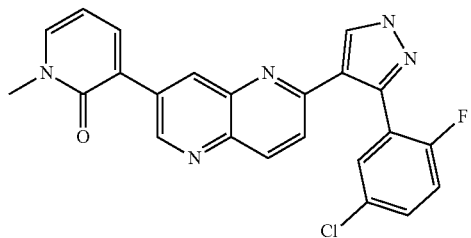 [SMILES: Cn1cccc(-c2cnc3ccc(-c4c[nH]nc4-c4cc(Cl)ccc4F)nc3c2)c1=O]

The procedure provided in Example 37 was also used to make the title compound except that cesium carbonate-25 g (58.4 mg, 0.179 mmol) was substituted for anhydrous $K_3PO_4$. Additionally, after degassing nitrogen, dioxane (287 μL) was added and the yellow reaction mixture was capped prior to stirring at 100° C. overnight. Similar to above, the reaction product was then filtered through celite, washed with THF (5 mL) and concentrated in GeneVac®. The residue was then treated with 1.2 mL of TFA and stirred at 55° C. for 1 h. The resulting product was concentrated and purified by preparative HPLC chromatography a gradient (10 to 50%) of acetonitrile in water with 0.05% trifluoroacetic acid to yield TFA salt of the title compound (5.6 mg). $[M+H]^+$ calcd for $C_{23}H_{15}ClFN_5O$ 432.09, found 432.1. $^1H$ NMR (400 MHz, Methanol-$d_4$) δ 9.20 (s, br, 1H), 8.45 (dd, J=2.1, 0.8 Hz, 1H), 8.40 (s, 1H), 8.30 (dd, J=8.8, 0.8 Hz, 1H), 7.90 (dd, J=7.1, 2.0 Hz, 1H), 7.84-7.73 (m, 2H), 7.64 (dd, J=6.1, 2.7 Hz, 1H), 7.48 (ddd, J=8.8, 4.3, 2.7 Hz, 1H), 7.15 (dd, J=9.5, 8.8 Hz, 1H), 6.54 (t, J=7.1 Hz, 1H), 3.67 (s, 3H).

Example 39: Synthesis of 4-(6-(3-(5-chloro-2-fluorophenyl)-1H-pyrazol-4-yl)-1,5-naphthyridin-3-yl)cyclohex-3-en-1-amine (1-91)

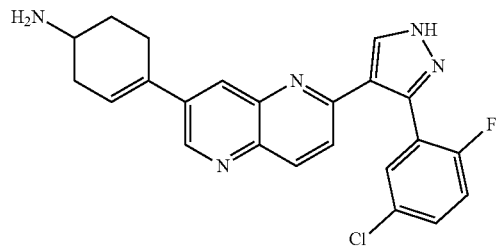 [SMILES: NC1CC=C(c2cnc3ccc(-c4c[nH]nc4-c4cc(Cl)ccc4F)nc3c2)CC1]

A vial of 7-bromo-2-(3-(5-chloro-2-fluorophenyl)-1-(tetrahydro-2H-pyran-2-yl)-1H-pyrazol-4-yl)-1,5-naphthyridine (39.4 mg. 0.081 mmol), sodium carbonate (25.7 mg, 0.242 mmol), [1,1'-bis(diphenylphosphino)ferrocene]dichloropalladium(II) (11.81 mg, 0.016 mmol), and 4-(N-boc-amino)cyclohex-1-enyl-1-boronic acid pinacol ester (33.9 mg, 0.105 mmol) in 1,4-dioxane (269 μL)/water (135 μL) was sparged with a steam of nitrogen for 5 min before heating to 95° C. overnight. The reaction mixture was cooled to room temperature and concentrated in GeneVac®. TFA (500 μL) was added and the resulting mixture was heated to 50° C. for 1 hour before being concentrated and purified by preparative HPLC chromatography a gradient (10 to 50%) of acetonitrile in water with 0.05% trifluoroacetic acid to yield TFA salt of the title compound (28.5 mg) $[M+H]^+$ calcd for $C_{23}K_{19}ClFN_5$ 420.13, found 420.1. $^1H$ NMR (400 MHz, Methanol-$d_4$) δ 9.03 (d, J=2.2 Hz, 1H), 8.38 (s, 1H), 8.28 (dd, J=8.9, 0.8 Hz, 1H), 8.09 (dd, J=2.2, 0.8 Hz, 1H), 7.73 (d, J=8.8 Hz, 1H), 7.66 (dd, J=6.1, 2.7 Hz, 1H), 7.49 (ddd, J=8.8, 4.3, 2.7 Hz, 1H), 7.20-7.09 (m, 1H), 6.43 (td, J=3.3, 1.7 Hz, 1H), 3.52 (s, 1H), 2.75 (s, 3H), 2.45-2.21 (m, 1H), 2.02-1.86 (m, 2H).

Example 40: Synthesis of N-(2-(4-(6-(3-(5-chloro-2-fluorophenyl)-1H-pyrazol-4-yl)-1,5-naphthyridin-3-yl)-1H-pyrazol-1-yl)ethyl)propan-2-amine (1-94)

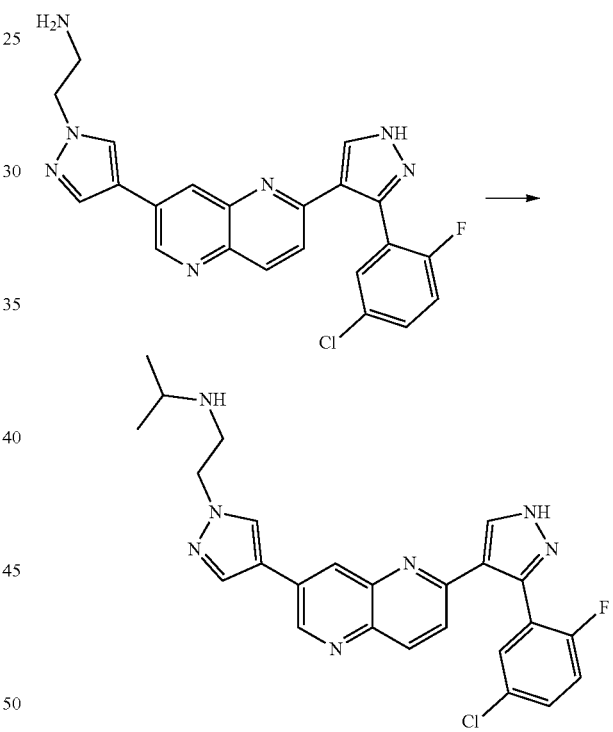

A vial of 2-(4-(6-(3-(5-chloro-2-fluorophenyl)-1H-pyrazol-4-yl)-1,5-naphthyridin-3-yl)-1H-pyrazol-1-yl)ethan-1-amine, 2TFA (15 mg, 0.023 mmol), acetone (2.5 μL, 0.034 mmol) and AcOH (1.297 μL, 0.023 mmol) in MeOH (0.25 mL) was allowed to stir for 1 hour at RT before adding sodium triacetoxyborohydride (9.61 mg, 0.045 mmol). The resulting mixture was allowed to stir for 16 hrs at RT before being quenched with $H_2O$ (0.5 mL) and concentrated in GeneVac®. The dark residue was purified by preparative HPLC chromatography a gradient (15 to 55%) of acetonitrile in water with 0.05% trifluoroacetic acid to yield TFA salt of the title compound (4.6 mg). $[M+H]^+$ calcd for $C_{25}H_{23}ClFN_7$ 476.17, found 476.1.

Example 41: Synthesis of 4-(6-(3-(5-chloro-2-fluorophenyl)-1H-pyrazol-4-yl)-1,5-naphthyridin-3-yl)-N,N-dimethylcyclohex-3-en-1-amine (1-96)

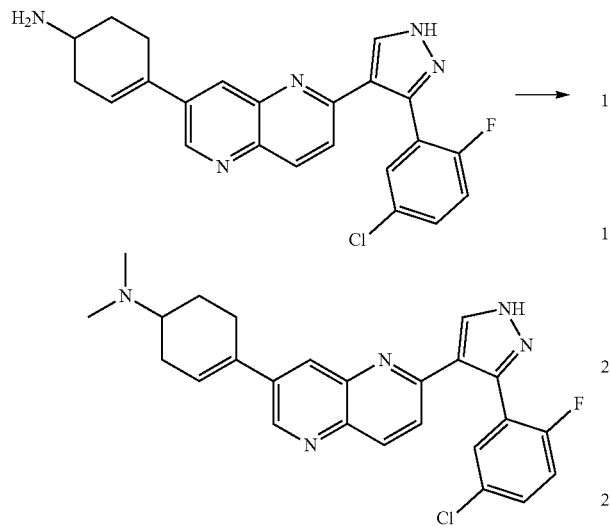

A vial of 2-(3-(5-chloro-2-fluorophenyl)-1H-pyrazol-4-yl)-7-(2,5-dihydro-1H-pyrrol-3-yl)-1,5-naphthyridine (11 mg, 0.026 mmol), AcOH (1.5 µL, 0.026 mmol) and formaldehyde solution 37 wt. % in water (3.90 µL, 0.052 mmol) was stirred for 60 min in Methanol (250 µL) before sodium triacetoxyborohydride (16.66 mg, 0.079 mmol) was added. The resulting mixture was allowed to stir overnight at RT before being quenched with H$_2$O (0.5 mL) and concentrated in GeneVac®. The dark residue was purified by preparative HPLC chromatography a gradient (22 to 40%) of acetonitrile in water with 0.05% trifluoroacetic acid to yield TFA salt of the title compound (5.7 mg). [M+H]$^+$ calcd for C$_{25}$H$_{23}$ClFN$_5$ 448.16, found 448.2. $^1$H NMR (400 MHz, Methanol-d$_4$) δ 9.04 (d, J=2.2 Hz, 1H), 8.39 (s, 1H), 8.29 (dd, J=8.9, 0.8 Hz, 1H), 8.10 (dd, J=2.3, 0.8 Hz, 1H), 7.75 (d, J=8.9 Hz, 1H), 7.66 (dd, J=6.1, 2.7 Hz, 1H), 7.49 (ddd, J=8.8, 4.3, 2.7 Hz, 1H), 7.15 (dd, J=9.5, 8.8 Hz, 1H), 6.49-6.41 (m, 1H), 3.60 (s, 1H), 2.96 (s, 7H), 3.03-2.72 (m, 2H), 2.72-2.52 (m, 1H), 2.38 (s, 1H), 2.05-1.84 (m, 1H).

Example 42: Synthesis of 4-(6-(3-(5-chloro-2-fluorophenyl)-1H-pyrazol-4-yl)-1,5-naphthyridin-3-yl)cyclohexan-1-amine (1-98)

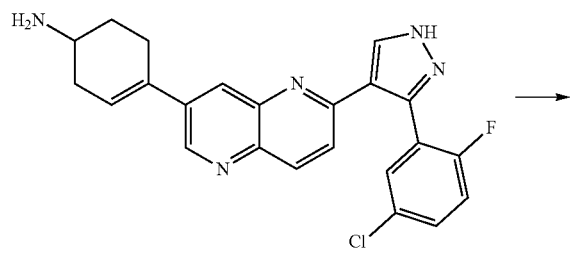

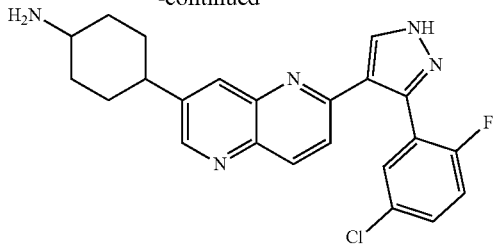

To a vial containing 4-(6-(3-(5-chloro-2-fluorophenyl)-1H-pyrazol-4-yl)-1,5-naphthyridin-3-yl)cyclohex-3-en-1-amine (11 mg, 0.026 mmol) in MeOH (262 µl) was added ammonium formate (10.57 mg, 0.168 mmol) and palladium on carbon (1.729 mg, 1.624 µmol) and the resulting mixture was stirred at 70° C. for 1 h. The mixture was filtered through a pad of celite, washed with MeOH (1 mL), concentrated in GeneVac®. The residue was purified by preparative HPLC chromatography a gradient (22 to 40%) of acetonitrile in water with 0.05% trifluoroacetic acid to yield TFA salt of the title compound (4.9 mg). [M+H]$^+$ calcd for C$_{23}$H$_{21}$ClFN$_5$ 422.15, found 422.1.

Example 43: Synthesis of 2-(3-(5-chloro-2-fluorophenyl)-1H-pyrazol-4-yl)-7-(5,6,7,8-tetrahydro-[1,2,4]triazolo[1,5-a]pyrazin-2-yl)-1,5-naphthyridine (1-100)

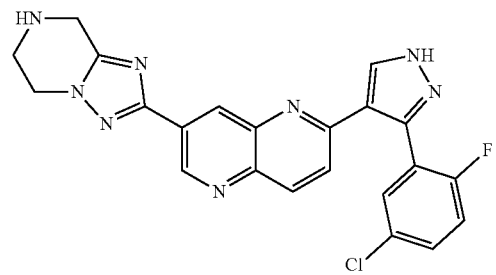 [SMILES: Fc1ccc(Cl)cc1-c1n[nH]cc1-c1ccc2ncc(-c3nc4n(n3)CCNC4)cc2n1]

A vial was charged with 61 (20 mg, 0.044 mmol), tert-butyl 2-iodo-5,6-dihydro[1,2,4]triazolo[1,5-a]pyrazine-7(8h)-carboxylate (19 mg, 0.053 mmol), dicyclohexyl(2',4',6'-triisopropyl-[1,1'-biphenyl]-2-yl)phosphine (2.106 mg, 4.42 µmol) and Xphos Pd G4 (3.80 mg, 4.42 µmol) and the content of the vial was purged with nitrogen before dioxane (100 µL) and stock solution of potassium phosphate, tribasic, anhydrous (28.1 mg, 0.133 mmol) in water (100 µL) was added. The reaction vial was stirred at 85° C. overnight before being filtered through a pad of celite and washed on a filter with 3 mL of THF. The filtrates were concentrated and treated with 0.8 mL of TFA at 50° C. The resulting mixture was concentrated and purified by preparative HPLC chromatography a gradient (20 to 40%) of acetonitrile in water with 0.05% trifluoroacetic acid to yield a TFA salt of the title compound (9.9 mg). [M+H]$^+$ calcd for C$_{22}$H$_{16}$ClFN$_8$ 447.12, found 447.0. $^1$H NMR (400 MHz, DMSO-d$_6$) δ 9.73 (s br, 1H), 9.42 (d, J=2.1 Hz, 1H), 8.61 (s, 1H), 8.36 (dd, J=8.9, 0.9 Hz, 1H), 8.31 (dd, J=2.1, 0.9 Hz, 1H), 7.98 (d, J=8.9 Hz, 1H), 7.66 (dd, J=6.2, 2.7 Hz, 1H), 7.58 (ddd, J=9.1, 4.2, 2.7 Hz, 1H), 7.30 (t, J=9.1 Hz, 1H), 6.47 (s, 1H), 4.64 (s, 2H), 4.48 (t, J=5.8 Hz, 2H), 3.76 (t, J=5.8 Hz, 2H).

Example 44: Synthesis of 1-(7-bromo-1,5-naphthyridin-2-yl)-2-(5-chloro-2-fluorophenyl)ethane-1,2-dione (73)

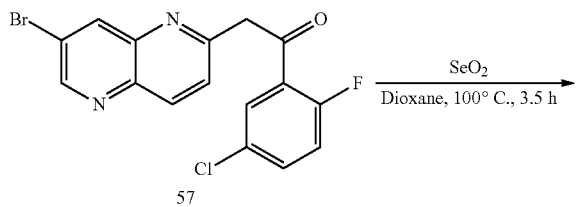

A solution of 57 (10.9 g, 28.7 mmol), SeO$_2$ (15.9 g, 144 mmol) in dioxane (200 mL) was stirred at 100° C. for 3.5 h. The reaction mixture was filtered through a pad of celite. The filtrate was concentrated in vacuum to give 73 as a yellow solid (11 g, 97% yield, 82% purity). [M+H]$^+$ calcd for C$_{16}$H$_7$BrClFN$_2$O$_2$ 392.95, found 393.0.

Example 45: Synthesis of 7-bromo-2-(5-(5-chloro-2-fluorophenyl)-1H-imidazol-4-yl)-1,5-naphthyridine (75)

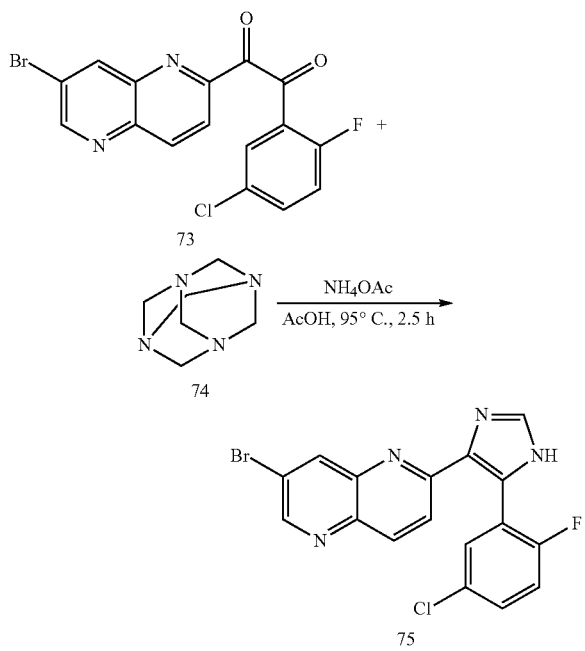

A solution of 73 (11.0 g, 22.92 mmol), 1,3,5,7-tetraazaadamantane 74 (9.6 g, 68.76 mmol) and NH$_4$OAc (10.6 g, 137.5 mmol) in AcOH (100 mL) was heated to 95° C. After 30 min., additional AcOH (100 mL) was added, and the reaction mixture was stirred for 2 h. The reaction mixture was concentrated in vacuo and basified with sat. aq. NaHCO$_3$ (300 mL) to pH 9. The mixture was extracted with EA (3×400 mL). Combined organic phase was washed with brine (2×400 mL), dried over Na$_2$SO$_4$, filtered, and concentrated under vacuum to give a residue. The residue was purified by column (EA:MeOH=1:0 to 10:1) to yield 75 as yellow solid (6.0 g, 55% yield, 95% purity). [M+H]$^+$ calcd for C$_{17}$H$_9$BrClFN$_4$ 402.98, found 403.1.

Example 46: Synthesis of 7-bromo-2-(5-(5-chloro-2-fluorophenyl)-1-((2-(trimethylsilyl)ethoxy)methyl)-1H-imidazol-4-yl)-1,5-naphthyridine (76)

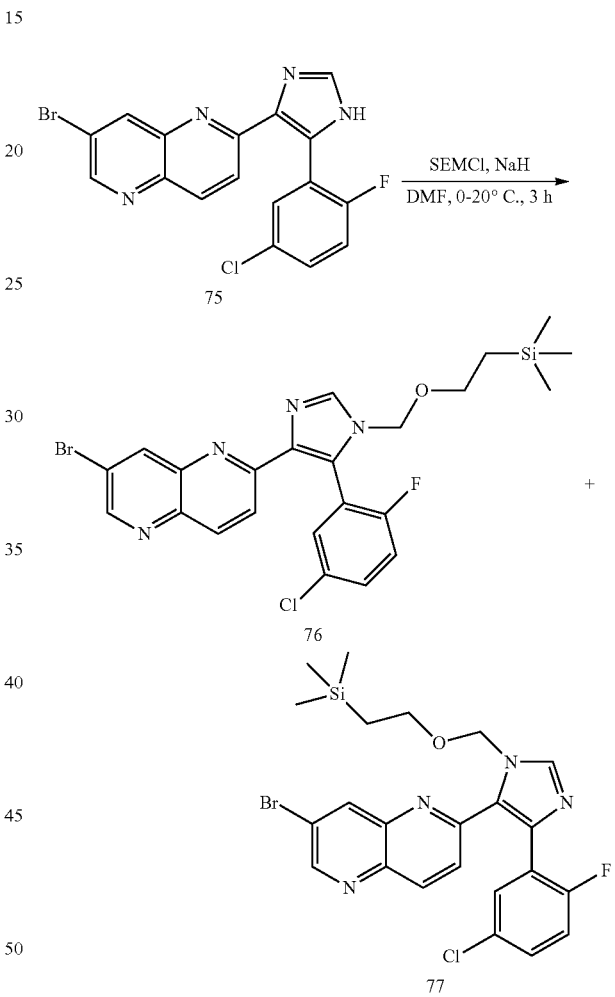

To a solution of 75 (6.0 g, 14.86 mmol) in DMF (120 mL) was added NaH (773 mg, 19.32 mmol) at 0° C. The reaction mixture was stirred at 0° C. for 1 h. SEMCl (3.0 g, 17.83 mmol) was then added to the mixture. The reaction mixture was stirred at 20° C. for 2 h. The reaction mixture was diluted with H$_2$O (200 mL), extracted with EA (3×300 mL). The organic layer was washed with brine (2×300 mL), dried over Na$_2$SO$_4$, filtered, and concentrated in vacuo. The residue was purified by column (PE:EA=10:0 to 3:1) to afford 76 and 77 as yellow solids (76, 3.3 g, 42% yield, 98% purity; 77, 3.5 g, 44% yield, 97% purity). [M+H]$^+$ calcd for (76 and 77) C$_{23}$H$_{23}$BrClFN$_4$OSi 533.06, found 533.2. $^1$H NMR (400 MHz, DMSO-d$_6$) δ 8.93 (d, J=2.0 Hz, 1H), 8.49-8.38 (m, 2H), 8.25 (s, 1H), 7.87-7.81 (m, 1H), 7.72-

7.62 (m, 2H), 7.42 (t, J=8.9 Hz, 1H), 5.32 (s, 2H), 3.42 (t, J=8.2 Hz, 2H), 0.78 (t, J=8.2 Hz, 2H), −0.08 (s, 9H) and $^1$H NMR (400 MHz, DMSO-$d_6$) δ 9.08 (d, J=2.2 Hz, 1H), 8.77 (dd, J=2.2, 0.9 Hz, 1H), 8.39 (dd, J=8.8, 1.0 Hz, 1H), 8.26 (s, 1H), 7.71 (dd, J=6.3, 2.8 Hz, 1H), 7.59 (d, J=8.8 Hz, 1H), 7.48 (ddd, J=8.8, 4.2, 2.8 Hz, 1H), 7.20 (dd, J=9.9, 8.8 Hz, 1H), 5.87 (s, 2H), 3.36-3.29 (m, 2H), 0.60 (dd, J=8.6, 7.4 Hz, 2H), −0.29 (s, 9H).

Example 47: Synthesis of (1-(2-((tert-butoxycarbonyl)(methyl)amino)ethyl)-1H-pyrazol-3-yl)boronic acid (80)

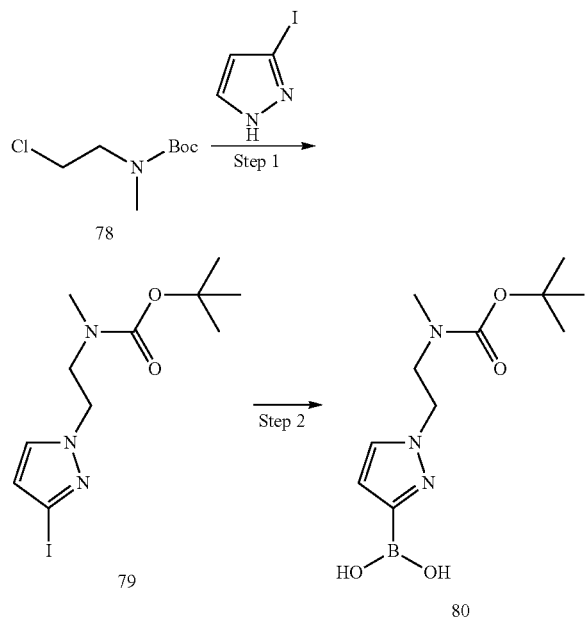

Step 1: A mixture of 3-iodo-1H-pyrazole (5.0 g, 25.9 mmol), 78 (9.8 g, 51.2 mmol), cesium carbonate (16.7 g, 51.2 mmol) in DMF (100 mL) was stirred at 20° C. for 12 h. The reaction mixture was diluted with water (50 mL), extracted with EA (200 mL×3). The organic layer was washed with brine (100 mL×3), dried over sodium sulfate, filtered, and concentrated in vacuum. The residue was purified by silica gel column chromatography (EA/PE=1/50 to 1/10) to afford product 79 (4.0 g, 45%) as colorless oil.

Step 2: To a mixture of 79 (6.0 g, 17.1 mmol), i-PrOBPin (4.8 g, 25.7 mmol) in THF (100 mL) was added i-PrMgCl (17.1 mL, 34.2 mmol) at 0° C. The reaction mixture was stirred at RT for 12 h. The mixture was concentrated in vacuum to afford crude 80 (10 g, 33% purity) as a brown solid. The material was either used directly in subsequent reactions or purified by prep-HPLC: Phenomenex Synergi C18 550×50×10 um, contains 0.05% HCl in $H_2O$, 35%~50% MeCN in $H_2O$. 4.5 g of crude material resulted only in 450 mg of pure 80 (24% yield, 95% purity) as a yellow solid.). [M+H]$^+$ calcd $C_{11}H_{20}BN_3O_3$ 270.15, found 270.3.

Example 48: Synthesis of 6-(5-(5-chloro-2-fluorophenyl)-1H-imidazol-4-yl)-N-(5-(4-methylpiperazin-1-yl)pyridin-2-yl)-1,5-naphthyridin-3-amine (2-1)

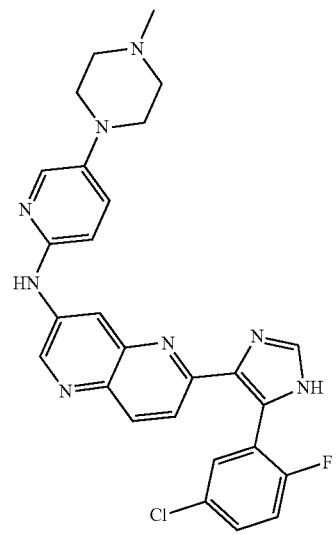 [SMILES: CN1CCN(c2ccc(Nc3cnc4ccc(-c5nc[nH]c5-c5cc(Cl)ccc5F)nc4c3)nc2)CC1]

Compound 76 (80 mg, 0.150 mmol) and 5-(4-methylpiperazin-1-yl)pyridin-2-amine (34.6 mg, 0.180 mmol) was added BrettPhos, (8.04 mg, 0.015 mmol), BrettPhos Pd G4 (13.79 mg, 0.015 mmol) and cesium carbonate, (146 mg, 0.450 mmol). To the resulting mixture was added dioxane (749 µL) and subsequently sparged with nitrogen for 5 min. The resulting yellow reaction mixture was capped stirred at 95° C. for 16 h. The reaction was filtered through a plug of celite, washed with THF (10 mL) and concentrated in vacuo. The resulting residue was dissolved in 1,2-dichloroethane (0.2 mL) and then treated with 6N aq. HCl (0.1 mL) and stirred at 80° C. for 3 h. The crude product was concentrated in vacuo, and purified by preparative HPLC chromatography using a gradient (5 to 40%) of acetonitrile in water with 0.05% trifluoroacetic acid to yield a TFA salt of the title compound (40 mg). [M+H]$^+$ calcd for $C_{27}H_{24}ClFN_8$ 515.18 found 515.1.

Example 49: Synthesis of 6-(5-(5-chloro-2-fluorophenyl)-1H-imidazol-4-yl)-N-(5-(4-isopropylpiperazin-1-yl)pyridin-2-yl)-1,5-naphthyridin-3-amine (2-5)

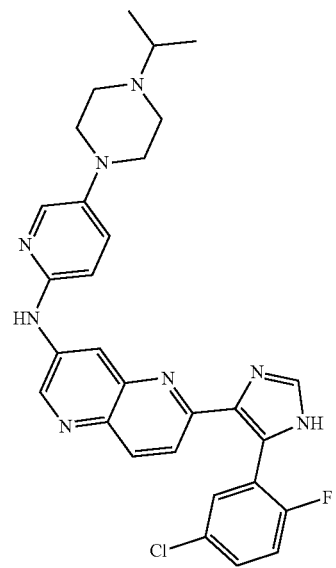 [SMILES: CC(C)N1CCN(c2ccc(Nc3cnc4ccc(-c5nc[nH]c5-c5cc(Cl)ccc5F)nc4c3)nc2)CC1]

To a vial charged with 6-(5-(5-Chloro-2-fluorophenyl)-1H-imidazol-4-yl)-N-(5-(piperazin-1-yl)pyridin-2-yl)-1,5-naphthyridin-3-amine (25 mg, 0.050 mmol) dissolved in DCE (0.33 mL) and methanol (0.16 mL) was added acetic acid (10 μL, 0.175 mmol) and acetone (50 μL, 0.681 mmol) and was stirred at 55° C. for 2 h. Afterwards, the reaction was treated with sodium triacetoxyborohydride (31.7 mg, 0.150 mmol). The resulting mixture was capped and let stir at RT for 16 h. Afterwards, the reaction was quenched by the addition of H$_2$O, and concentrated in vacuo. The resulting material was purified by preparative HPLC chromatography using a gradient (5 to 45%) of acetonitrile in water with 0.05% trifluoroacetic acid to yield a TFA salt of the title compound (6.4 mg). [M+H]+ calcd for $C_{29}H_{28}ClFN_8$ 543.21 found 543.1.

Example 50: Synthesis of 1-(6-(5-(5-chloro-2-fluorophenyl)-1H-imidazol-4-yl)-1,5-naphthyridin-3-yl)-N,N-dimethylpiperidin-4-amine (2-6)

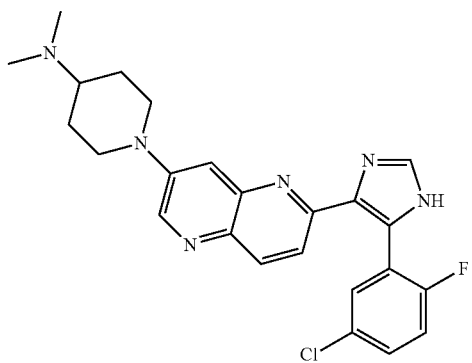 [SMILES: CN(C)C1CCN(c2cnc3ccc(-c4nc[nH]c4-c4cc(Cl)ccc4F)nc3c2)CC1]

To a vial charged with compound 76 (30 mg, 0.056 mmol) and 4-(dimethylamino)piperidine (9.37 mg, 0.073 mmol) was added RuPhos, (5.24 mg, 0.011 mmol), RuPhos Pd G2 (9.56 mg, 0.011 mmol) and sodium tert-butoxide, (16.2 mg, 0.169 mmol). To the resulting mixture was added 1,4-dioxane (375 μL) and subsequently sparged with nitrogen for 5 min. The resulting yellow reaction mixture was capped stirred at 85° C. for 16 h. The reaction was filtered through a plug of celite, washed with THF (5 mL) and concentrated in vacuo. The resulting residue was dissolved in 1,2-dichloroethane (0.2 mL) and then treated with 6N aq. HCl (0.2 mL) and stirred at 80° C. for 3 h. The crude product was concentrated in vacuo, and purified by preparative HPLC chromatography using a gradient (5 to 45%) of acetonitrile in water with 0.05% trifluoroacetic acid to yield a TFA salt of the title compound (18.6 mg). [M+H]+ calcd for $C_{24}H_{24}ClFN_6$ 451.17 found 451.1. $^1$H NMR (400 MHz, Methanol-d$_4$) δ 8.99-8.90 (m, 2H), 8.28 (dd, J=8.7, 0.7 Hz, 1H), 7.78 (dd, J=6.1, 2.7 Hz, 1H), 7.73-7.60 (m, 2H), 7.48 (dd, J=8.7, 1.0 Hz, 1H), 7.37 (t, J=9.2 Hz, 1H), 4.23 (d, J=13.2 Hz, 1H), 3.58-3.43 (m, 1H), 3.13-2.88 (m, 3H), 2.92 (s, 6H), 2.31-2.22 (m, 2H), 1.91 (qd, J=12.2, 4.1 Hz, 2H).

Example 51: Synthesis of (S)-4-(6-(5-(5-chloro-2-fluorophenyl)-1H-imidazol-4-yl)-1,5-naphthyridin-3-yl)piperazine-2-carboxylic acid (2-13)

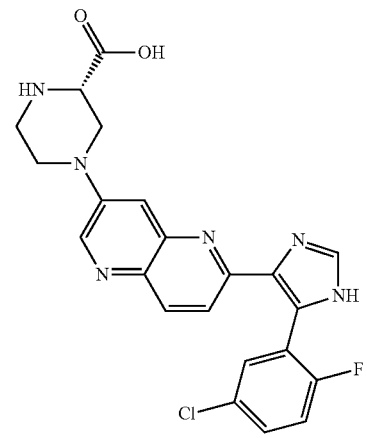 [SMILES: O=C(O)[C@@H]1CN(c2cnc3ccc(-c4nc[nH]c4-c4cc(Cl)ccc4F)nc3c2)CCN1]

A vial of 76, (S)-1-N-boc-piperazine-2-carboxylic acid methyl ester (26.0 mg, 0.107 mmol), cesium carbonate (80 mg, 0.246 mmol), RuPhos Pd G4 (13.95 mg, 0.016 mmol), 2-dicyclohexylphosphino-2',6'-diisopropoxybiphenyl (7.65 mg, 0.016 mmol) in 1,4-dioxane (410 μL) was heated to 85° C. for 16 h. Following that the mixture was concentrated in vacuum and treated with 200 μL of 6 N aq HCl and 200 μL of dichloroethane. The reaction mixture was heated to 80° C. for 3 h until fully deprotected and ester hydrolyzed to carboxylic acid. The resulting dark mixture was concentrated and purified by preparative HPLC chromatography using a gradient (12 to 40%) of acetonitrile in water with 0.05% trifluoroacetic acid to yield a TFA salt of the title compound (13.3 mg) as a yellow solid. [M+H]+ calcd for $C_{22}H_{18}ClFN_6O_2$ 453.12, found 453.1. $^1$H NMR (400 MHz, Methanol-d$_4$) δ 8.94 (d, J=2.8 Hz, 1H), 8.68 (s, 1H), 8.26 (d, J=8.7 Hz, 1H), 7.77 (dd, J=6.1, 2.7 Hz, 1H), 7.70 (d, J=2.8 Hz, 1H), 7.60 (ddd, J=8.9, 4.4, 2.7 Hz, 1H), 7.56 (dd, J=8.7, 1.0 Hz, 1H), 7.31 (t, J=9.1 Hz, 1H), 4.33 (dd, J=9.1, 3.6 Hz, 1H), 4.18 (dd, J=13.6, 3.3 Hz, 1H), 3.92 (m, 1H), 3.70-3.51 (m, 3H), 3.51-3.31 (m, 1H).

Example 52: Synthesis of 2-(5-(5-chloro-2-fluorophenyl)-1H-imidazol-4-yl)-7-(2-(2,5-dihydro-1H-pyrrol-3-yl)-5,6-dihydro-[1,2,4]triazolo[1,5-a]pyrazin-7(8H)-yl)-1,5-naphthyridine (2-14)

76 →<sup>Step 1</sup>

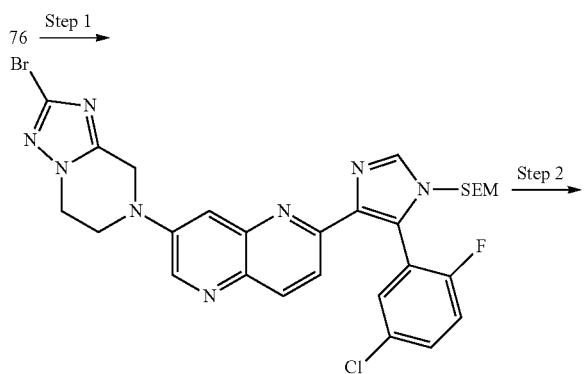

→ Step 2

-continued

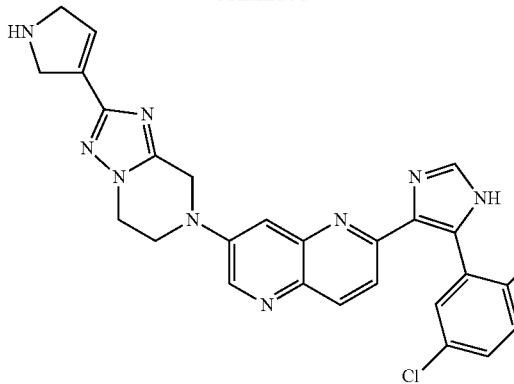

Step 1: A vial of 2-bromo-5H,6H,7H,8H-[1,2,4]triazolo[1,5-a]pyrazine (29.7 mg, 0.146 mmol), 76 (60 mg, 0.112 mmol), cesium carbonate (110 mg, 0.337 mmol), RuPhos PD G4 (19.11 mg, 0.022 mmol), and 2-dicyclohexylphosphino-2',6'-diisopropoxybiphenyl (10.49 mg, 0.022 mmol) in 1,4-dioxane (562 µL) was heated at 96° C. for 16 h. The reaction was cooled and filtered through a pad of celite and concentrated in vacuum. The crude material was purified vial normal phase chromatography (0-100% EA:Hexanes) yielding the heteroaryl bromide intermediate (43 mg, 58%) a beige powder. [M+H]+ calcd for $C_{28}H_{29}BrClFN_8OSi$ 655.11, found 655.0.

Step 2: A vial of heteroaryl bromide from step 1 (40.9 mg, 0.62 mmol), sodium carbonate (19.81 mg, 0.187 mmol), [1,1-bis(diphenylphosphino)ferrocene]di-chloropalladium(11) (9.12 mg, 0.012 mmol), and 1-boc-2,5-dihydro-1H-pyrrole-3-boronic acid, pinacol ester 2 (22.07 mg, 0.075 mmol) in 1,4-dioxane (415 µL) and water (208 µL) was sparged for 5 min before heating to 85° C. for 16 h. Following that the reaction was cooled and concentrated in the vacuum. Then 200 µL of 6N aq HCl and 200 µL of dichloroethane were added the reactions. The reaction mixture was heated to 80° C. for 3 hours until fully deprotected. The crude mixtures were dissolved in 15% ACN in $H_2O$, filtered, and purified by preparative HPLC chromatography using a gradient (5 to 45%) of acetonitrile in water with 0.05% trifluoroacetic acid to yield a TFA salt of the title compound (16.8 mg) as a yellow solid. [M+H]+ calcd for $C_{26}H_{21}ClFN_9$ 514.16, found 514.0.

Example 53: Synthesis of 2-(5-(5-chloro-2-fluorophenyl)-1H-imidazol-4-yl)-7-(2-(1-methyl-2,5-dihydro-1H-pyrrol-3-yl)-5,6-dihydro-[1,2,4]triazolo[1,5-a]pyrazin-7(8H)-yl)-1,5-naphthyridine (2-15)

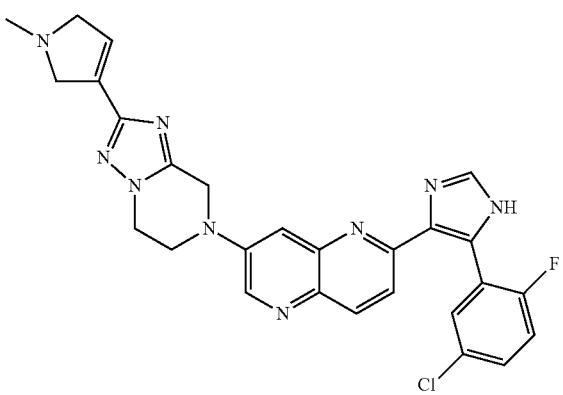 [SMILES: CN1CC=C(c2nc3n(n2)CCN(c2cnc4ccc(-c5nc[nH]c5-c5cc(Cl)ccc5F)nc4c2)C3)C1]

A vial of formaldehyde solution, 37 wt. % in water (2.90 µl, 0.039 mmol), acetic acid (1.114 µL, 0.019 mmol), and Compound 2-13 (10 mg, 0.019 mmol) in MeOH (0.250 mL) was stirred at RT for 1 h before adding sodium triacetoxyborohydride (12.37 mg, 0.058 mmol). The resulting mixture was allowed to stir at RT for 16 h. The reaction was quenched with $H_2O$ (0.5 mL) and concentrated in vacuum. The residue was purified by preparative HPLC chromatography using a gradient (5 to 45%) of acetonitrile in water with 0.05% trifluoroacetic acid to yield a TFA salt of the title compound (5 mg) as a yellow solid. [M+H]+ calcd for $C_{27}H_{23}ClFN_9$ 528.18, found 528.0.

Example 54: Synthesis of 2-(3-(6-(5-(5-chloro-2-fluorophenyl)-1H-imidazol-4-yl)-1,5-naphthyridin-3-yl)-1H-pyrazol-1-yl)-N-methylethan-1-amine (2-16)

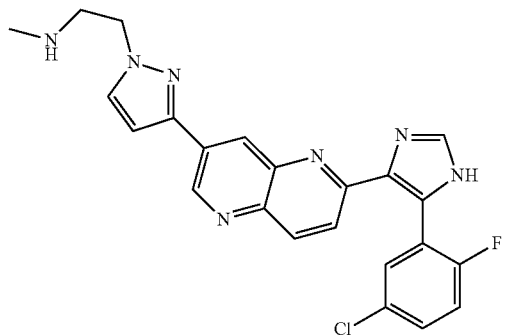 [SMILES: CNCCn1ccc(-c2cnc3ccc(-c4nc[nH]c4-c4cc(Cl)ccc4F)nc3c2)n1]

A content of the vial of 76 (32.3 mg, 0.060 mmol), 80 (27.2 mg, 0.091 mmol), sodium carbonate (19.2 mg, 0.181 mmol), and [1,1-bis(diphenylphosphino)ferrocene]di-chloropalladium(11) (8.84 mg, 0.012 mmol) in 1,4-dioxane (269 µL) and water (134 µL) was sparged with $N_2$ for 5 min before heating to 96° C. for 16 h. The mixture was concentrated in vacuum and treated with 100 µL, of 6N aq HCl and 300 µL of dichloroethane. The reaction mixture was heated to 80° C. for 16 h. The resulting dark mixture was concentrated and purified by preparative HPLC chromatography using a gradient (10 to 32%) of acetonitrile in water with 0.05% trifluoroacetic acid to yield a TFA salt of the title compound (14.4 mg) as a yellow solid. [M+H]+ calcd for $C_{23}H_{19}ClFN_7$ 448.14, found 448.1.

Example 55: Synthesis of 2-(5-(5-chloro-2-fluorophenyl)-1H-imidazol-4-yl)-7-(4,5,6,7-tetrahydropyrazolo[1,5-a]pyrazin-2-yl)-1,5-naphthyridine (2-21)

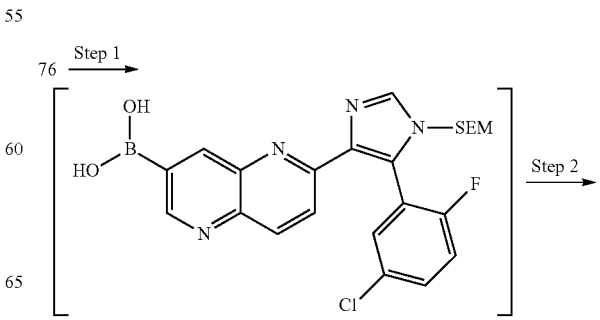

301
-continued

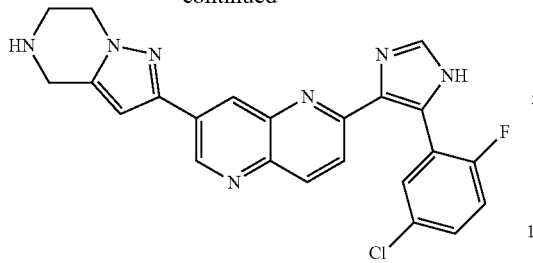

302
-continued

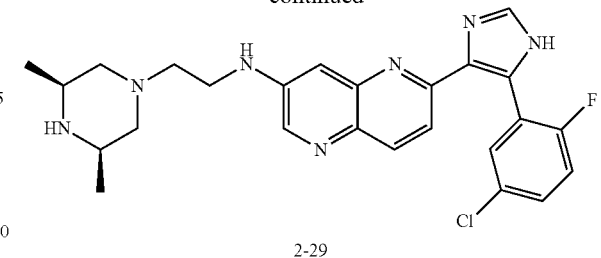

2-29

Step 1: A vial of 76 (500 mg, 0.937 mmol), potassium acetate (276 mg, 2.81 mmol), bis(pinacolato)diboron (309 mg, 1.217 mmol), and [1,1-bis(diphenylphosphino)-ferrocene]dichloropalladium(II) (137 mg, 0.187 mmol) in 1,4-dioxane (4.4 mL) was sparged for 10 min with $N_2$ before being heated at 85° C. for 16 h. This mixture was cooled and used in step 2 as a 0.2M stock solution.

Step 2: To a vial of (6-(5-(5-chloro-2-fluorophenyl)-1-((2-(trimethylsilyl)ethoxy)methyl)-1H-imidazol-4-yl)-1,5-naphthyridin-3-yl)boronic acid (286 µL, 0.060 mmol) (0.2 M in dioxane) was added tert-butyl 2-bromo-6,7-dihydropyrazolo[1,5-a]pyrazine-5(4H)-carboxylate (21.8 mg, 0.072 mmol), [1,1-bis(diphenylphosphino)ferrocene]di-chloropalladium(II) (8.80 mg, 0.012 mmol), and sodium carbonate (19.12 mg, 0.180 mmol). water (143 µL) was added to each reaction and the reactions were sparged with $N_2$ for 5 min before heating to 94° C. The reaction mixture was cooled and concentrated in the vacuum. Then 200 µL of 6N aq HCl and 200 µL of dichloroethane were added the reaction and the resulting was heated at 80° C. for 3 h. The resulting mixture was concentrated and purified by preparative HPLC chromatography using a gradient (15 to 29%) of acetonitrile in water with 0.05% trifluoroacetic acid to yield a TFA salt of the title compound (20.5 mg) as a yellow solid. $[M+H]^+$ calcd for $C_{23}H_{17}ClFN_7$ 446.12, found 446.0. $^1H$ NMR (400 MHz, Methanol-$d_4$) δ 9.46 (d, J=2.1 Hz, 1H), 9.12 (s, 1H), 8.74 (dd, J=2.1, 0.9 Hz, 1H), 8.41 (dd, J=8.8, 0.9 Hz, 1H), 7.81 (dd, J=6.1, 2.7 Hz, 1H), 7.72 (dd, J=8.8, 1.0 Hz, 1H), 7.69 (ddd, J=9.1, 4.4, 2.7 Hz, 1H), 7.39 (t, J=9.1 Hz, 1H), 6.98 (t, J=1.0 Hz, 1H), 4.64 (s, 2H), 4.57 (t, J=5.9 Hz, 2H), 3.88 (d, J=5.9 Hz, 2H).

Example 56: Synthesis 6-(5-(5-chloro-2-fluorophenyl)-1H-imidazol-4-yl)-N-(2-((3S,5R)-3,5-dimethylpiperazin-1-yl)ethyl)-1,5-naphthyridin-3-amine (2-29)

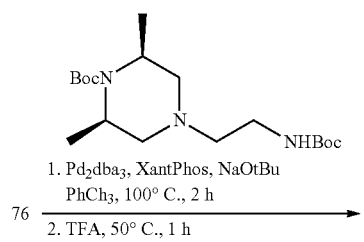

76
1. $Pd_2dba_3$, XantPhos, NaOtBu
   $PhCH_3$, 100° C., 2 h
2. TFA, 50° C., 1 h To a solution of 76 (33.30 mg, 0.062 mmol) and tert-butyl (2S,6R)-4-(2-((tert-butoxycarbonyl)amino)ethyl)-2,6-dimethylpiperazine-1-carboxylate (27.0 mg, 0.075 mmol) in $PhCH_3$ (0.249 ml) was added $Pd_2dba_3$ (1.43 mg, 1.56 µmop, XantPhos (0.90 mg, 1.56 µmop and sodium tert-butoxide (18.0 mg, 0.187 mmol). The resulting mixture was degassed with $N_2$ and heated to 100° C. for 2 h. The reaction was filtered through a plug of celite and concentrated in vacuo. The resulting residue was dissolved in TFA (0.50 mL) and heated to 50° C. for 1 h. The crude product was concentrated in vacuo and purified by preparative HPLC chromatography using a gradient (2 to 60%) of acetonitrile in water with 0.05% trifluoroacetic acid to yield a TFA salt of the title compound (33.4 mg). $[M+H]^+$ calcd for $C_{25}H_{27}ClFN_7$ 480.20 found 480.2. $^1H$ NMR (601 MHz, Methanol-$d_4$) δ 9.29 (s, 1H), 8.88 (d, J=2.7 Hz, 1H), 8.39 (d, J=8.8 Hz, 1H), 8.02 (d, J=2.7 Hz, 1H), 7.80 (dd, J=6.0, 2.7 Hz, 1H), 7.72 (ddd, J=9.0, 4.4, 2.7 Hz, 1H), 7.55 (dd, J=8.9, 0.9 Hz, 1H), 7.42 (t, J=9.1 Hz, 1H), 4.02-3.93 (comp m, 6H), 3.67 (t, J=6.1 Hz, 2H), 3.39 (t, J=13.3 Hz, 2H), 1.46 (d, J=6.5 Hz, 6H).

Example 57: Synthesis of 2-bromo-2-(7-bromo-1,5-naphthyridin-2-yl)-1-(5-chloro-2-fluorophenyl)ethan-1-one (81)

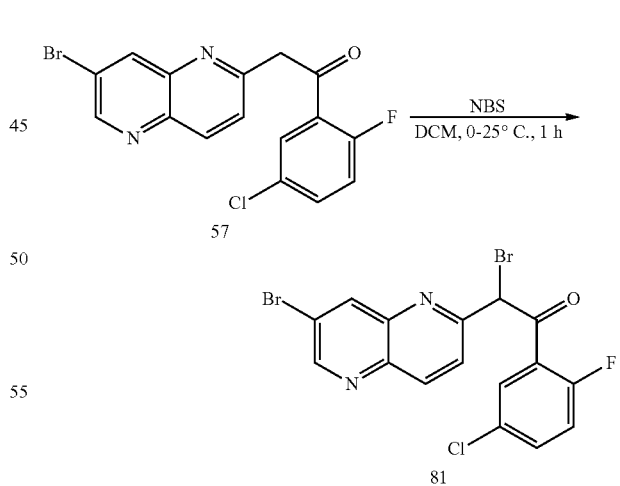

To a mixture of 57 (3.3 g, 8.7 mmol) in DCM (85 mL) cooled to 0° C., NBS (1.6 g, 8.7 mmol) was added and the mixture was stirred at 25° C. for 1 h. The mixture was concentrated and purified by column chromatography (PE: EA=50:1 to 30:1) to afford 81 (4.1 g) as yellow solid (4.1 g, 75% yield, 73% purity). $[M+H]^+$ calcd for $C_{16}H_8Br_2ClFN_2O$, 456.88, found 456.8.

Example 58: Synthesis of 7-bromo-2-(2-(5-chloro-2-fluorophenyl)imidazo[1,2-a]pyridin-3-yl)-1,5-naphthyridine (83)

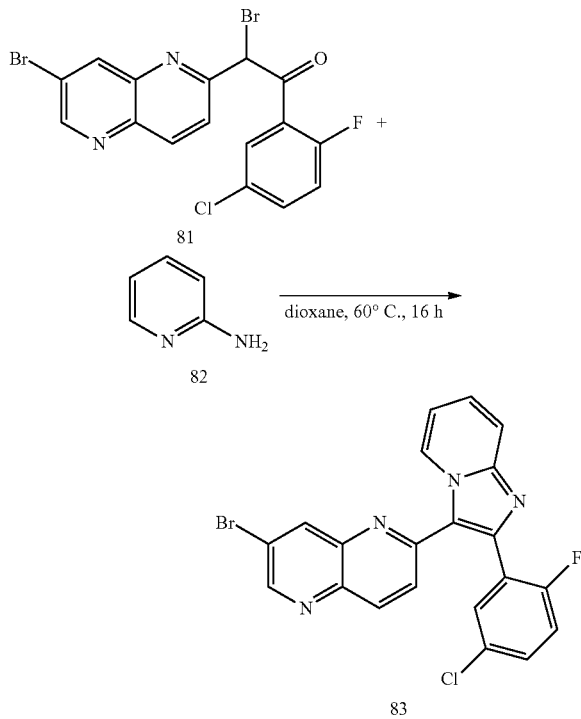

To a mixture of 81 (4.1 g, 8.94 mmol) in dioxane (65 mL) was added pyridin-2-amine 82 (2.5 g, 26.83 mmol), the mixture was stirred at 60° C. for 16 h. The reaction was combined with two additional lots, concentrated in vacuo to obtain a yellow solid. The yellow solid was purified by column chromatography (PE:EA=30:1 to 10:1) and triturated with PE:EA=1:1 (40 mL), the filter cake was collected and dried in vacuo to afford 83 as a white solid (2.0 g, 40% yield, 97% purity).). [M+H]+ calcd for 452.99, found 452.9. $^1$H NMR (400 MHz, Chloroform-d) δ 9.85 (dd, J=7.1, 1.2 Hz, 1H), 8.97 (d, J=2.2 Hz, 1H), 8.67 (d, J=2.2 Hz, 1H), 8.23 (d, J=8.9 Hz, 1H), 7.88-7.77 (m, 2H), 7.58 (dd, J=8.9, 1.1 Hz, 1H), 7.51-7.40 (m, 2H), 7.14-7.02 (m, 2H).

Example 59: Synthesis of 6-(2-(5-chloro-2-fluorophenyl)imidazo[1,2-a]pyridin-3-yl)-N-(2-(4-isopropylpiperazin-1-yl)ethyl)-1,5-naphthyridin-3-amine (3-1)

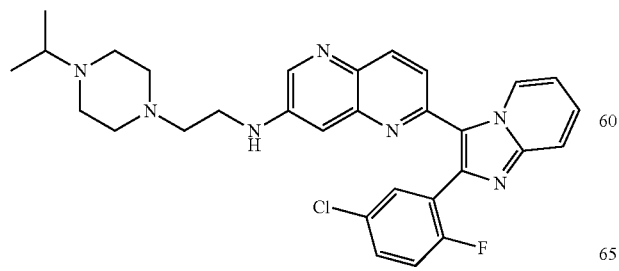

A vial of 83 (30 mg, 0.066 mmol), 2-(4-isopropyl-piperazin-1-yl)-ethylamine (13.62 mg, 0.080 mmol), sodium tert-butoxide (19.11 mg, 0.199 mmol), BrettPhos, 1 g bottle (3.56 mg, 6.63 μmol), and BrettPhos Pd G4 (6.10 mg, 6.63 μmop in 1,4-dioxane (331 μL) (degassed with $N_2$) was heated to 90° C. overnight. Following that the the reaction mixture was filtered through a pad of celite, washed on a filter with THF (4 mL). The combined filtrates were concentrated and purified by preparative HPLC chromatography using a gradient (18 to 32%) of acetonitrile in water with 0.05% trifluoroacetic acid to yield a TFA salt of the title compound (mg). [M+H]+ calcd for $C_{30}H_{31}ClFN_7$ 544.23, found 544.2.

Example 60: Synthesis of 2-(2-(5-chloro-2-fluorophenyl)imidazo[1,2-a]pyridin-3-yl)-7-(piperazin-1-yl)-1,5-naphthyridine (3-2)

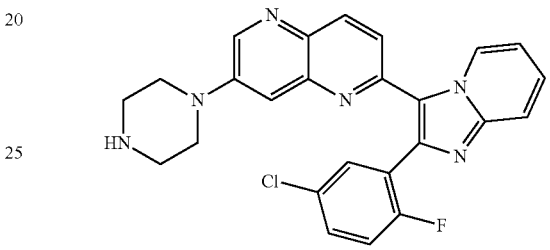

Step 1: A content of the vial of 83 (30 mg, 0.066 mmol), 2-dicyclohexylphosphino-2',6'-diisopropoxybiphenyl(6.17 mg, 0.013 mmol), 1-boc-piperazine (14.78 mg, 0.079 mmol), sodium tert-butoxide (19.06 mg, 0.198 mmol) and RuPhos Pd G2 (10.27 mg, 0.013 mmol) in 1,4-dioxane (220 μL) was sparged with nitrogen heated to 90° C. for 16 h.

Step 2: 4M hydrogen chloride in dioxane (300 μl, 0.066 mmol) was added to reaction mixture and the solution was allowed to stir for 2 hours at RT. The resulting mixture was concentrated and purified by preparative HPLC chromatography using a gradient (19 to 33%) of acetonitrile in water with 0.05% trifluoroacetic acid to yield a TFA salt of the title compound (45 mg). [M+H]+ calcd for $C_{25}H_{20}ClFN_6$ 459.14, found 459.1.

Example 61: Synthesis of 2-(2-(5-chloro-2-fluorophenyl)imidazo[1,2-a]pyridin-3-yl)-7-(4,5,6,7-tetrahydro-[1,2,3]triazolo[1,5-a]pyrazin-3-yl)-1,5-naphthyridine (3-6)

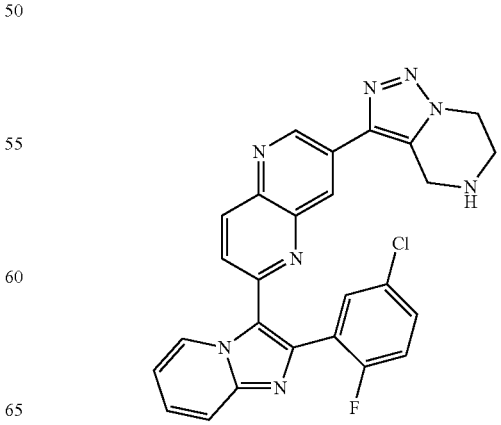

Step 1: A vial of 83 (338 mg, 0.745 mmol), bis(pinacolato)diboron (265 mg, 1.044 mmol), [1,1-bis(diphenylphosphino)ferrocene]dichloropalladium(II) (109 mg, 0.149 mmol), and potassium acetate (220 mg, 2.237 mmol) in 1,4-dioxane (3.5 mL) was sparged with $N_2$ for 5 min before being heated at 85° C. overnight. The reaction mixture was concentrated and the crude material was used in step 2 without further purification.

Step 2: A vial of crude (6-(2-(5-chloro-2-fluorophenyl)imidazo[1,2-a]pyridin-3-yl)-1,5-naphthyridin-3-yl)boronic acid obtained in step 1 (33.5 mg, 0.080 mmol), tert-butyl 3-bromo-6,7-dihydro-[1,2,3]triazolo[1,5-a]pyrazine-5(4H)-carboxylate (36.3 mg, 0.120 mmol), sodium carbonate (0.025 g, 0.240 mmol) and [1,1'-bis(diphenylphosphino)ferrocene]palladium(II) dichloride (9.21 mg, 0.016 mmol) in water (0.150 mL) and 1,4-dioxane (0.300 mL) was sparged for 10 min with $N_2$ before being heated to 94° C. for 18 h. The reaction mixture was cooled, concentrated in vacuum and used in step 3.

Step 3: TFA (300 μL) was added to residue and the resulting dark solution was heated to 60° C. for 1 h. The resulting mixture was concentrated and purified by preparative HPLC chromatography using a gradient (5 to 45%) of acetonitrile in water with 0.05% trifluoroacetic acid to yield a TFA salt of the title compound (32.7 mg). $[M+H]^+$ calcd for $C_{26}H_{18}ClFN_8$ 497.13, found 497.1. $^1H$ NMR (400 MHz, Methanol-$d_4$) δ 9.83 (dt, J=7.0, 1.1 Hz, 1H), 9.41 (d, J=2.2 Hz, 1H), 8.75 (dd, J=2.2, 0.9 Hz, 1H), 8.35 (dd, J=8.9, 0.9 Hz, 1H), 7.87-7.77 (m, 2H), 7.70 (ddd, J=9.0, 6.8, 1.3 Hz, 1H), 7.63 (dd, J=8.9, 0.7 Hz, 1H), 7.59 (ddd, J=8.9, 4.3, 2.7 Hz, 1H), 7.31-7.19 (m, 2H), 5.06 (s, 2H), 4.91-4.81 (m, 2H), 3.91 (dd, J=6.3, 5.4 Hz, 2H).

Example 62: Synthesis of 1,5-naphthyridine 1-oxide (85)

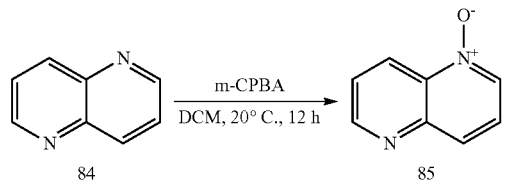 [SMILES: c1cnc2cccnc2c1 ; [O-][n+]1cccc2ncccc21]

To a solution of 1,5-naphthyridine 84 (24.0 g, 184 mmol) in DCM (500 mL) was added m-CPBA (47.7 g, 277 mmol) in several portions. The mixture was stirred for 12 h at 20° C. It was quenched with sat. aq. sodium sulfite (200 mL) and sat. aq. sodium bicarbonate (100 mL). It was extracted with DCM (3×300 mL). The combined organic layers were concentrated in vacuum. The residue was purified by column chromatography (DCM:MeOH 30:1 to 20:1) to afford 85 as yellow solid (13.0 g, 46% yield, 95% purity). $[M+H]^+$ calcd for $C_8H_6N_2O$, 147.06, found 147.1.

Example 63: Synthesis of 2-bromo-1,5-naphthyridine (86)

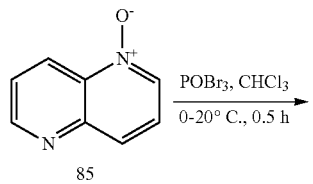

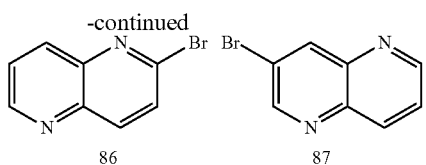

To a solution of 85 (2.0 g, 13.68 mmol) in $CHCl_3$ (60 mL) was added phosphorus oxybromide (5.9 g, 20.52 mmol) in several portions at 0° C. The mixture was stirred for 15 min at 0° C. Then it was stirred for 15 min at 20° C. It was quenched with sat. aq. sodium bicarbonate (100 mL). It was extracted with DCM (3×200 mL). The combined organic layers were concentrated in vacuum. The residue was purified with column chromatography (PE:EA=7:1 to 5:1) to provide 86 as a yellow solid (4.8 g, 21% yield, 89% purity) and 87 as a yellow solid (3.9 g, 17% yield, 97% purity). $[M+H]^+$ calcd for $C_8H_5BrN_2$ 208.97, found 209.0.

Example 64: Synthesis of 2-((trimethylsilyl)ethynyl)-1,5-naphthyridine (89)

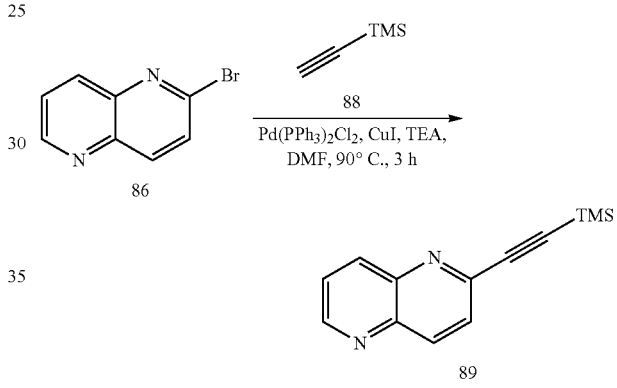

To a solution of 86 (4.8 g, 22.96 mmol), ethynyltrimethylsilane 88 (3.4 g, 34.44 mmol), copper (I) iodide (438 mg, 2.30 mmol) and triethylamine (4.6 g, 45.92 mmol) in DMF (40 mL) was added $Pd(PPh_3)_2Cl_2$ (806 mg, 1.15 mmol) under $N_2$. It was stirred at 90° C. for 3 h. The mixture was poured into water (40 mL), and the suspension was filtrated out. The aqueous phase was extracted with EA (3×100 mL). The combined organic layers were washed with brine (3×100 mL), and dried over sodium sulfate. After concentration, the crude product was purified by column chromatography (PE:EA=7:1 to 5:1) to yield 89 as a yellow solid (4.0 g, 77% yield, 82% purity). $[M+H]^+$ calcd for $C_{13}H_{14}N_2Si$, 227.10, found 227.0.

Example 65: Synthesis of 2-ethynyl-1,5-naphthyridine (90)

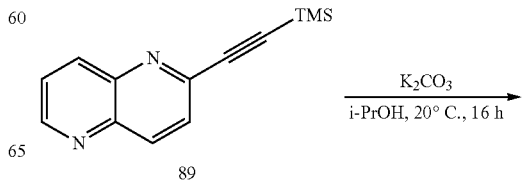

-continued

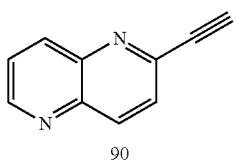

90

To a solution of 89 (1.9 g, 8.39 mmol) in isopropanol (40 mL) was added potassium carbonate (3.5 g, 25.17 mmol). It was stirred at 20° C. for 16 h. The reaction mixture was washed with water (50 mL), extracted with DCM (3×80 mL). The organic layer was washed with brine (3×80 mL), dried over sodium sulfate, filtered, and concentrated in vacuum to give a residue. The residue was purified by column chromatography (PE:EA=5:1 to 3:1) to afford 90 as yellow solid (1.7 g, 68% yield, 99% purity). [M+H]$^+$ calcd for $C_{10}H_6N_2$ 155.06, found 155.0. $^1$H NMR (400 MHz, CDCl$_3$) δ 8.99 (dd, J=4.0, 1.6 Hz, 1H), 8-41-8.38 (m, 2H), 7.79 (d, J=8.8 Hz, 1H), 7.68 (dd, J=8.4, 4.0 Hz, 1H). 3.32 (s, 1H).

Example 66: Synthesis of 2-((5-chloro-2-fluorophenyl)ethynyl)-1,5-naphthyridine (92)

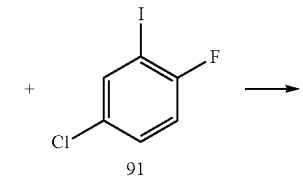

90     91

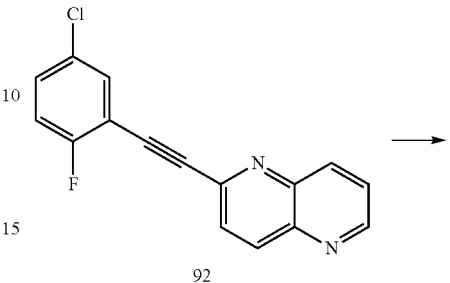

92

To a vial of 90 (30 mg, 0.195 mmol) in THF (256 µL) was added 4-chloro-1-fluoro-2-iodobenzene 91 and triethylamine (256 µL). The reaction mixture was sparged for 5 min with N$_2$. Copper (I) iodide (7.41 mg, 0.039 mmol) and Pd(PPh$_3$)$_4$ (22.49 mg, 0.019 mmol) were then added to the mixture. The reaction was allowed to stir at 80° C. overnight filtered through a pad of celite and the crude product was used in the following reaction after solvent removal in vacuum. [M+H]$^+$ calcd for $C_{10}H_6N_2$ 283.04, found 283.0.

Example 67: Synthesis of 2-(1-benzyl-4-(5-chloro-2-fluorophenyl)-1H-1,2,3-triazol-5-yl)-1,5-naphthyridine (4-1)

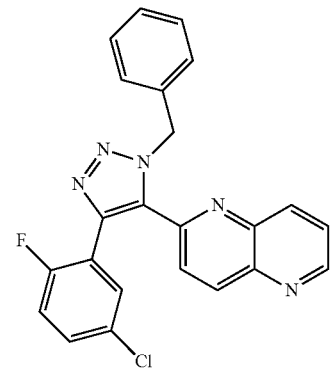

92

A vial of crude 92 (0.055 g, 0.195 mmol), benzyl azide (0.029 g, 0.215 mmol), and Cp*RuCl(PPh$_3$)$_2$ (7.76 mg, 9.75 µmop in 1,4-dioxane (1.300 mL) was sparged for 5 min. The reaction mixture was heated at 80° C. overnight. The resulting mixture was concentrated and purified by preparative HPLC chromatography using a gradient (56 to 71%) of acetonitrile in water with 0.05% trifluoroacetic acid to yield a TFA salt of the title compound as less polar isomer (4.7 mg). [M+H]$^+$ calcd for $C_{23}H_{15}ClFN_5$ 416.11, found 416.2. $^1$H NMR (400 MHz, Methanol-d$_4$) δ 9.02 (dd, J=4.3, 1.6 Hz, 1H), 8.55 (ddd, J=8.6, 1.6, 0.9 Hz, 1H), 8.30 (dd, J=8.8, 0.9 Hz, 1H), 7.87 (dd, J=8.6, 4.3 Hz, 1H), 7.78 (dd, J=6.2, 2.7 Hz, 1H), 7.51-7.42 (m, 2H), 7.18-7.02 (m, 6H), 6.09 (d, J=0.6 Hz, 2H).

Example 68: Synthesis of 3-bromo-1,5-naphthyridine (87)

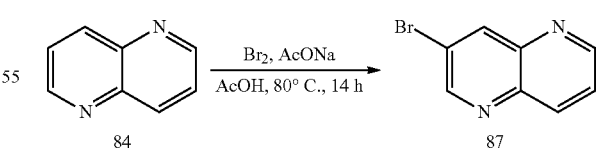

84     87

To a mixture of 84 (30 g, 230.5 mmol) and AcONa (37.8 g, 461.0 mmol) in AcOH (350 mL) was added dropwise a solution of Br$_2$ (12.9 mL, 253.5 mmol) in AcOH (50 mL) at 80° C. The mixture was stirred for 14 h at 80° C. The reaction was combined with two additional reactions. The total mixture was concentrated to remove AcOH, then diluted with water (200 mL) slowly, neutralized to pH=7, extracted with EA (3×500 mL). The combined organic phase was washed with brine (150 mL), dried with anhydrous Na₂SO₄ and concentrated under vacuum, and purified by silica column (PE:EA=100:1 to 10:1) to afford 87 as a white solid (57 g, 39% yield).

Example 69: Synthesis of 7-bromo-1,5-naphthyridine 1-oxide (93)

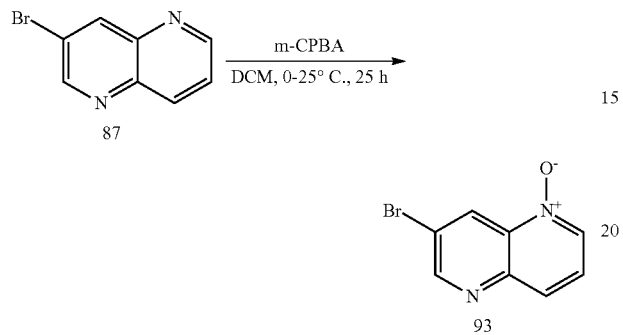

A solution of 87 (13 g, 62.2 mmol) in DCM (250 mL) was added m-CPBA (12.9 g, 74.6 mmol) in portions at 0° C. The mixture was stirred for 25 h at 25° C. The reaction mixture was washed with saturated Na₂SO₃ (200 mL) and saturated NaHCO₃ (300 mL) sequentially, and then washed with brine (300 mL), dried over Na₂SO₄ and filtered. The filtrate was concentrated to afford the crude product which was purified by column chromatography (DCM:MeOH=100:1 to 50:1) to afford 93 as a yellow solid (10 g, 71% yield).

Example 70: Synthesis of 7-bromo-1,5-naphthyridin-2(1H)-one (94)

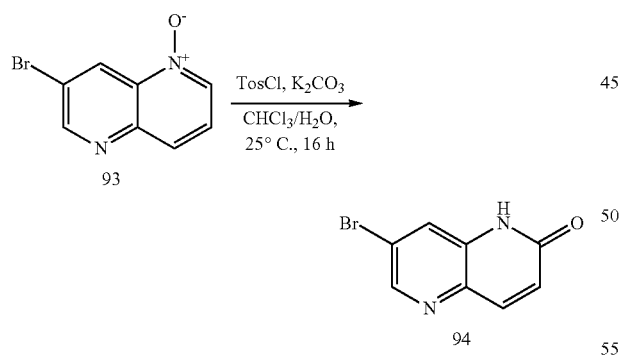

To a mixture of 93 (10.0 g, 44.4 mmol) and K₂CO₃ (20.9 g, 151.0 mmol) in H₂O (33 mL) and CHCl₃ (100 mL) was added TosCl (10.2 g, 53.3 mmol). The mixture was stirred for 25 h at 16° C. and combined with a second reaction. The reaction mixture was diluted with water (200 mL) and filtered. The filter cake was washed with water (100 mL) and concentrated to afford 94 as a white solid (24 g, 83% yield). ¹H NMR (400 MHz, DMSO-d₆) δ 12.0 (s, br, 1H), 8.53 (d, J=2.0 Hz, 1H), 7.92 (d, J=9.6 Hz, 1H), 7.84 (d, J=2.0 Hz, 1H), 6.77 (d, J=2.0 Hz, 1H).

Example 71: Synthesis of methyl 6-oxo-5,6-dihydro-1,5-naphthyridine-3-carboxylate (95)

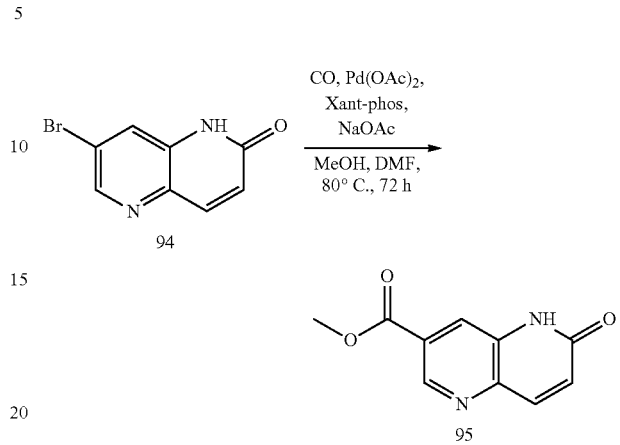

A solution of 94 (7.5 g, 33.3 mmol), Xant-phos (3.9 g, 6.66 mmol) and NaOAc (4.1 g, 50.0 mmol) in MeOH (150 mL) and DMF (30 mL) was added Pd(OAc)₂ (2.2 g, 9.99 mmol) under N₂ atmosphere. The reaction was stirred at 80° C. for 72 h under CO (50 psi). The mixture was concentrated to afford crude 95 as a grey solid (12 g, 53% purity). Due to the poor solubility, the crude product was used directly for the next step. [M+H]⁺ calcd for C₁₀H₈N₂O₃ 205.06, found 205.1.

Example 72: Synthesis of methyl 6-bromo-1,5-naphthyridine-3-carboxylate (96)

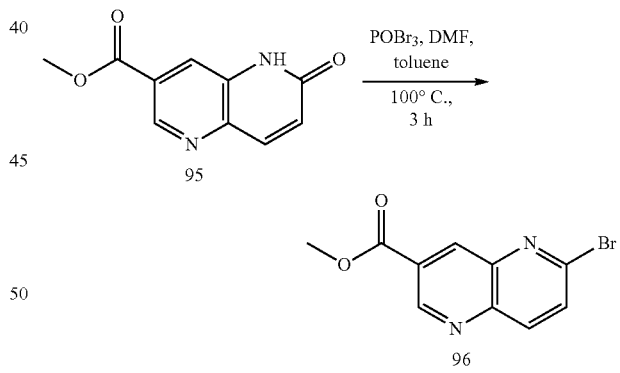

A solution of 95 (11.0 g, 53.9 mmol), POBr₃ (30.9 g, 107.7 mmol) and DMF (0.2 mL) in toluene (120 mL) was stirred at 100° C. for 3 h. The solution was concentrated in vacuo. The residue was basified to pH 8 with aq. NaHCO₃, extracted with DCM (3×300 mL), dried over Na₂SO₄, filtered and concentrated in vacuo. The solid was washed with a solution of DCM and EA (50 mL, DCM:EA=1:2) to obtain pure 96 as grey solid (5 g, 90% purity). The filtrate was concentrated in vacuo and purified by silica column using gradient of 0 to 100% of DCM in PE to obtain crude 96 as yellow solid (2 g, 50% yield). [M+H]⁺ calcd for C₁₀H₇BrN₂O₂ 266.98, found 266.9.

Example 73: Synthesis of methyl 6-((trimethylsilyl)ethynyl)-1,5-naphthyridine-3-carboxylate (97)

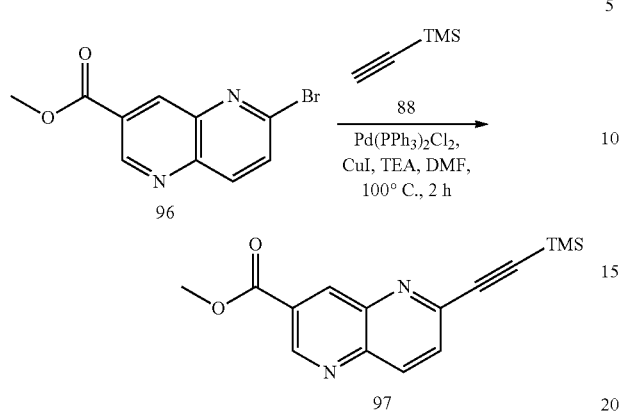

To a solution of 96 (5.0 g, 18.7 mmol), 88 (2.8 g, 28.1 mmol), copper (I) iodide (356 mg, 1.87 mmol) and TEA (3.8 g, 37.4 mmol) in DMF (80 mL) was added $Pd(PPh_3)_2Cl_2$ (1.3 g, 1.87 mmol) under $N_2$. It was stirred at 100° C. for 2 h. $H_2O$ (150 mL) was added, extracted with EA (400 mL), washed with brine (3×100 mL), dried over $Na_2SO_4$, filtered and concentrated in vacuo. The residue was purified by column to obtain 97 as yellow solid (3.5 g, 66% yield, 87% purity). $[M+H]^+$ calcd for $C_{15}H_{16}N_2O_2Si$, 285.11, found 285.1.

Example 74: Synthesis of methyl 6-ethynyl-1,5-naphthyridine-3-carboxylate (98)

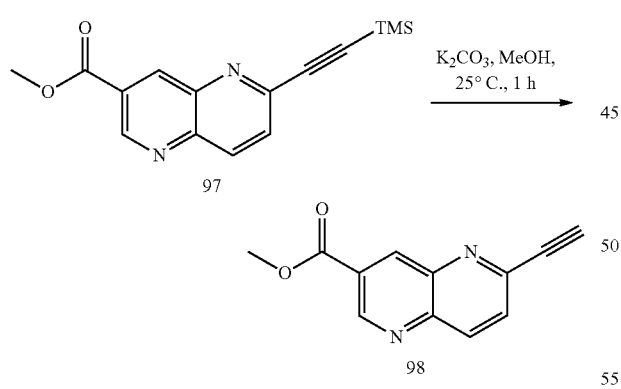

A solution of 97 (3.5 g, 12.3 mmol) and $K_2CO_3$ (3.4 g, 24.6 mmol) in MeOH (100 mL) was stirred at 25° C. for 1 h. The solution was concentrated in vacuo. $H_2O$ (200 mL) was added and extracted with EA (3×300 mL), dried over $Na_2SO_4$, filtered and concentrated in vacuo to obtain 98 as grey solid (2.6 g, 99% yield, 98% purity). $[M+H]^+$ calcd for $C_{12}H_8N_2O_2$ 213.07, found 213.0. $^1H$ NMR (400 MHz, Chloroform-d) δ 9.53 (d, J=2.0 Hz, 1H), 9.02 (t, J=2.0, 0.9 Hz, 1H), 8.44 (dd, J=8.7, 0.9 Hz, 1H), 7.87 (d, J=8.7 Hz, 1H), 4.06 (s, 3H), 3.38 (s, 1H).

Example 75: Synthesis of methyl 6-((5-chloro-2-fluorophenyl)ethynyl)-1,5-naphthyridine-3-carboxylate (99)

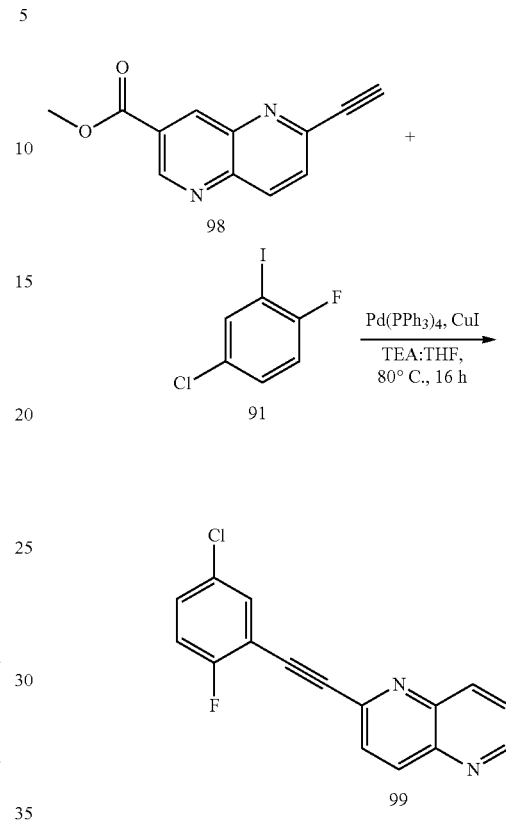

To a vial of 98 (50 mg, 0.236 mmol) in THF (310 μL) was added 91 and TEA (310 μL). The reaction mixture was sparged for 5 min with $N_2$. Copper (I) iodide (8.97 mg, 0.047 mmol) and $Pd(PPh_3)_4$ (27.2 mg, 0.024 mmol) were then added. The reaction was allowed to stir at 80° C. for 16 h. The reaction was filtered through a pad of celite, concentrated, and the crude product 99 was used directly in the following reaction. $[M+H]^+$ calcd for $C_{18}H_{10}ClFN_2O_2$ 341.04 found 341.0.

Example 76: Synthesis of methyl 6-(4-(5-chloro-2-fluorophenyl)-1H-1,2,3-triazol-5-yl)-1,5-naphthyridine-3-carboxylate (5-1)

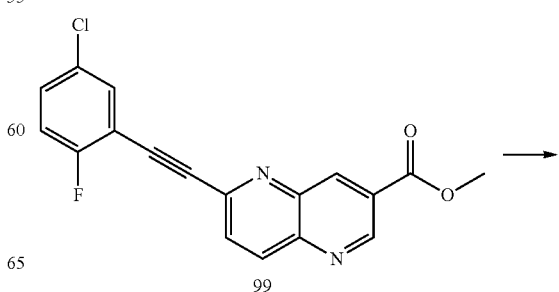

-continued

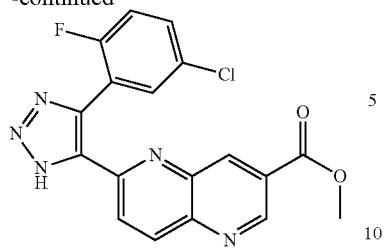

To a solution of 99 (33 mg, 0.098 mmol) in dry DMF (653 µL) was added trimethylsilyl azide (51.8 µL, 0.392 mmol). The reaction mixture was allowed to stir at 100° C. for 16 h. The reaction mixture was concentrated and purified by preparative HPLC chromatography using a gradient (40 to 90%) of acetonitrile in water with 0.05% trifluoroacetic acid to yield a TFA salt of the title compound (2.2 mg). $[M+H]^+$ calcd for $C_{18}H_{11}ClFN_5O2$ 384.07, found 384.0.

Example 77: Synthesis of 4-iodo-3-(trifluoromethyl)-1H-pyrazole (101)

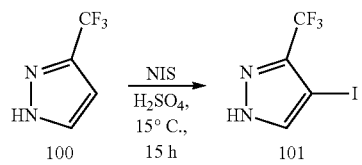

To a solution of 100 (30.0 g, 147.0 mmol) in $H_2SO_4$ (600 mL, 50%) was added N-iodosuccinimide (39.7 g, 176.4 mmol). The mixture was stirred at 15° C. for 3 h. The reaction was diluted with $H_2O$ (800 mL) and stirred at 15° C. for another 12 h. The mixture was filtered and the filter cake was washed with $H_2O$ (3×300 mL), then concentrated in vacuum to obtain 101 (40.0 g, 69% yield, 99% purity) as white solid. $[M+H]^+$ calcd for $C_4H_2F_3IN_2$ 262.92, found 262.8.

Example 78: Synthesis of 4-iodo-1-(tetrahydro-2H-pyran-2-yl)-3-(trifluoromethyl)-1H-pyrazole

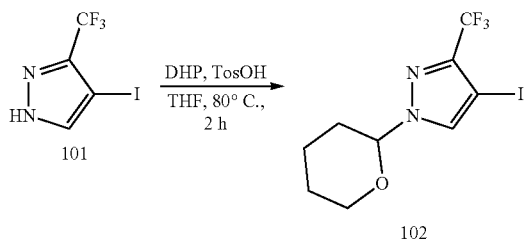

To a solution of 101 (25.0 g, 95.4 mmol) in THF (300 mL) was added TosOH (1.6 g, 9.5 mmol) and dihydropyran (40.1 g, 477.0 mmol). The mixture was stirred for 2 h at 80° C. The reaction was diluted with sat. sodium bicarbonate aq. (300 mL) and extracted with EA (300 mL*3). The combined organic layers were dried ($Na_2SO_4$) and concentrated in vacuum. The residue was purified by column (0-5% of EA in PE) to afford crude 102 (33.0 g) as light yellow oil.

Example 79: Synthesis of 2-methyl-7-(1-(tetrahydro-2H-pyran-2-yl)-3-(trifluoromethyl)-1H-pyrazol-4-yl)-1,5-naphthyridine (104)

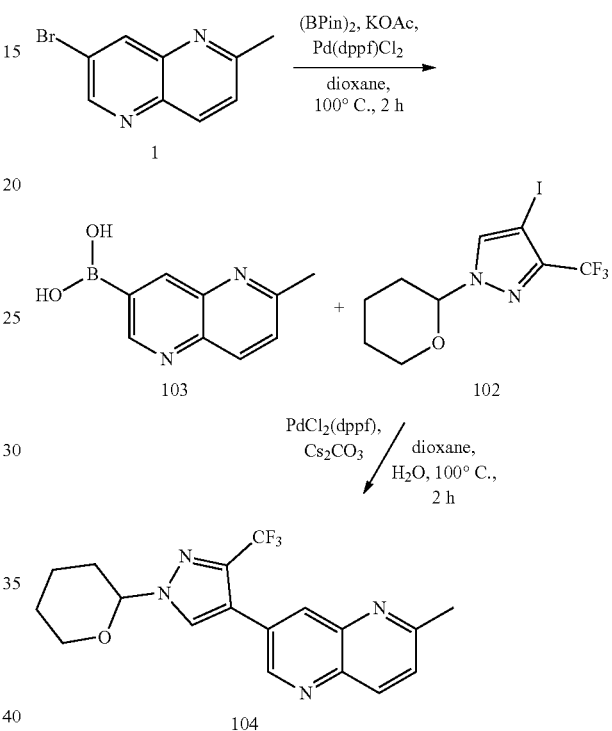

To a mixture of 1 (5.0 g, 22.4 mmol) and bis(pinacolato) diboron (6.8 g, 26.8 mmol) in dioxane (80 mL) was added Pd(dppf)Cl$_2$ (1.6 g, 2.2 mmol) and potassium acetate (6.6 g, 67.2 mmol). The mixture was heated at 100° C. for 2 h under $N_2$. The mixture was diluted with $H_2O$ (200 mL) and extracted with EA (3×200 mL). The combined organic layers were dried ($Na_2SO_4$) and concentrated in vacuum to obtained crude 103 (6.0 g) as black oil which was used directly in the following reaction. $[M+H]^+$ calcd for $C_9H_9BN_2O_2$ 189.09, found 189.1. A mixture of 103 (6.0 g, 22.4 mmol, crude) in dioxane (100 mL) and $H_2O$ (10 mL) was added 102 (15.5 g, 44.8 mmol), PdCl$_2$(dppf) (1.6 g, 2.2 mmol), Cs$_2$CO$_3$ (14.6 g, 44.8 mmol). The mixture was stirred at 100° C. for 2 h under $N_2$ atmosphere. The reaction was diluted with $H_2O$ (100 mL) and extracted with EA (3×120 mL). The combined organic layers were dried ($Na_2SO_4$) and concentrated in vacuum. The residue was purified by column (10-50% of EA in PE) to afford 104 (8.0 g, 87% yield, 88% purity) as brown oil. $[M+H]^+$ calcd for $C_{18}H_{17}F_3N_4O$, 363.14, found 363.0.

Example 80: Synthesis of 7-(1-(tetrahydro-2H-pyran-2-yl)-3-(trifluoromethyl)-1H-pyrazol-4-yl)-1,5-naphthyridine-2-carbaldehyde (105)

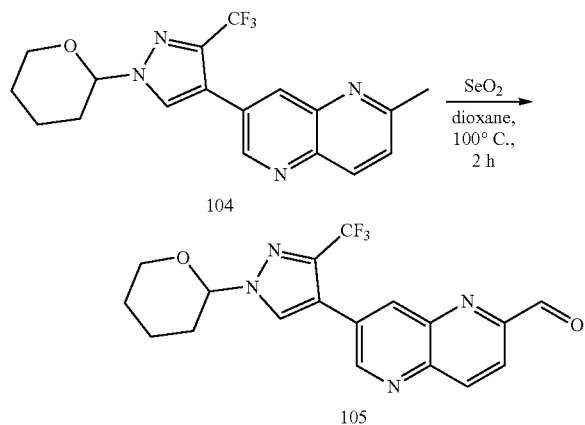

To a solution of 104 (9.4 g, 25.9 mmol) in dioxane (100 mL) was added SeO₂ (3.5 g, 31.1 mmol). The mixture was stirred at 100° C. for 2 h under N₂ atmosphere. The reaction was filtered and concentrated in vacuum, then purified by column (10-50% of EA in PE) to obtain 105 (4.8 g, 49% yield) as red solid. $^1$H NMR (400 MHz, DMSO-d₆) δ 10.7 (d, J=0.8 Hz, 1H), 9.26 (d, J=2.0 Hz, 1H), 8.83 (s, 1H), 8.67 (d, J=8.4 Hz, 1H), 8.60 (d, J=2.0 Hz, 1H), 8.23 (d, J=8.4 Hz, 1H) 5.63 (dd, J=9.6, 2.4 1H), 4.03-3.99 (m, 1H), 3.76-3.71 (m, 1H), 2.18-1.96 (m, 3H), 2.82-2.65 (m, 1H), 1.62-1.57 (m, 2H).

Example 81: Synthesis of 2-ethynyl-7-(1-(tetrahydro-2H-pyran-2-yl)-3-(trifluoromethyl)-1H-pyrazol-4-yl)-1,5-naphthyridine (106)

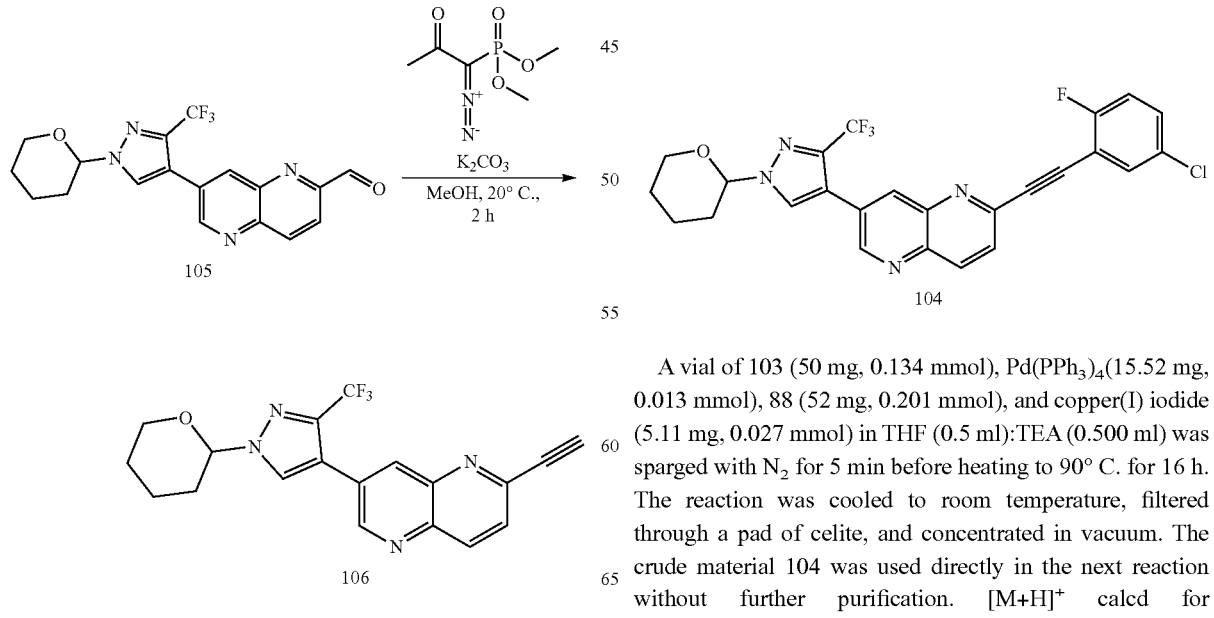

To a solution of 105 (3.8 g, 10.1 mmol) in MeOH (76 mL) was added potassium carbonate (2.8 g, 20.2 mmol) and dimethyl (1-diazo-2-oxopropyl)phosphonate (3.9 g, 20.2 mmol). The mixture was stirred at 20° C. for 2 h. The mixture was diluted with H₂O (300 mL) and extracted with EA (200 mL*3). The combined organic phase was dried over Na₂SO₄, concentrated in vacuum and purified by preparative HPLC using a gradient (5 to 30%) of acetonitrile in water with 0.05% ammonia hydroxide obtain 106 (2.4 g, 50% yield, 96% purity) as white solid. [M+H]⁺ calcd for $C_{19}H_{15}F_3N_4O$ 373.12, found 373.0. $^1$H NMR (400 MHz, DMSO-d₆) δ 9.13 (d, J=2.2 Hz, 1H), 8.77 (s, 1H), 8.48 (t, J=8.7, 0.9 Hz, 1H), 8.39 (d, J=2.2 Hz, 1H), 7.92 (d, J=8.7 Hz, 1H), 5.62 (dd, J=9.7, 2.7 Hz, 1H), 4.65 (s, 1H), 4.00 (dt, J=12.2, 3.6 Hz, 1H), 3.78-3.66 (m, 1H), 2.27-1.88 (m, 3H), 1.79-1.68 (m, 1H), 1.60 (q, J=4.9, 4.4 Hz, 2H).

Example 82: Synthesis of 2-((5-chloro-2-fluorophenyl)ethynyl)-7-(1-(tetrahydro-2H-pyran-2-yl)-3-(trifluoromethyl)-1H-pyrazol-4-yl)-1,5-naphthyridine

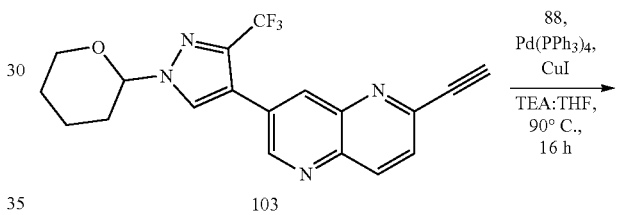

A vial of 103 (50 mg, 0.134 mmol), Pd(PPh₃)₄ (15.52 mg, 0.013 mmol), 88 (52 mg, 0.201 mmol), and copper(I) iodide (5.11 mg, 0.027 mmol) in THF (0.5 ml):TEA (0.500 ml) was sparged with N₂ for 5 min before heating to 90° C. for 16 h. The reaction was cooled to room temperature, filtered through a pad of celite, and concentrated in vacuum. The crude material 104 was used directly in the next reaction without further purification. [M+H]⁺ calcd for $C_{25}H_{17}ClF_4N_4O$, 501.10, found 501.0.

Example 83: Synthesis of 2-(5-(5-chloro-2-fluorophenyl)-1H-1,2,3-triazol-4-yl)-7-(3-(trifluoromethyl)-1H-pyrazol-4-yl)-1,5-naphthyridine (5-2)

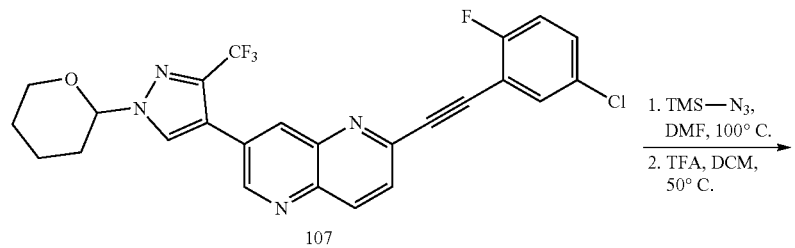

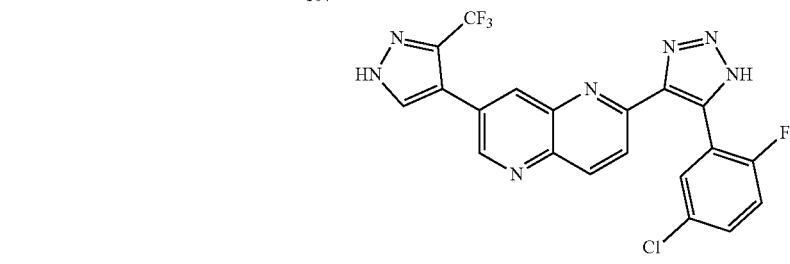

To a vial of 107 (0.067 g, 0.134 mmol, crude) in DMF (1 ml) was added TMS-N$_3$ (0.071 ml, 0.536 mmol). The reaction was heated to 100° C. for 16 h. The reaction was cooled to room temperature and concentrated in vacuum. The crude material was redissolved in DCM (0.300 ml) and TFA (0.300 ml, 3.89 mmol) was added. The mixture was allowed to stir for 1 hour at 50° C. The reaction was concentrated in vacuum and purified by preparative HPLC chromatography using a gradient (30 to 90%) of acetonitrile in water with 0.05% trifluoroacetic acid to yield a TFA salt of the title compound (10.3 mg). [M+H]$^+$ calcd for C$_{20}$H$_{10}$ClF$_4$N$_7$ 460.06, found 460.9.

Example 84: Synthesis of methyl 5-chloro-2,4-difluorobenzoate (109)

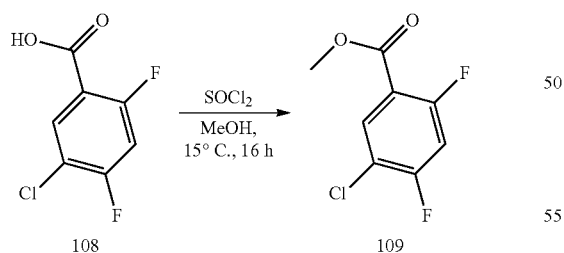

To a solution of 5-chloro-2,4-difluorobenzoic acid (108) (35.0 g, 181.77 mmol) in MeOH (300 mL), SOCl$_2$ (64.9 g, 545.31 mmol) was added dropwise. The reaction was stirred at 15° C. for 16 h. The reaction was concentrated in vacuum, then diluted with H$_2$O (500 mL) and adjusted to pH 8 by adding sat. NaHCO$_3$ aq, extracted with EtOAc (3×300 mL). The combined organic layers were washed with brine (2×300 mL), dried with (Na$_2$SO$_4$), concentrated in vacuo and purified by column chromatography (PE:EA=100:1 to 20:1) to yield title compound 109 as white solid (30.0 g, 95% purity, 80% yield). $^1$H NMR (400 MHz, CDCl$_3$) δ 8.03 (t, J=8.0 Hz, 1H), 6.98 (t, J=9.6 Hz, 1H), 3.92 (s, 3H).

Example 85: Synthesis of 2-(7-bromo-1,5-naphthyridin-2-yl)-1-(5-chloro-2,4-difluorophenyl)ethan-1-one (110)

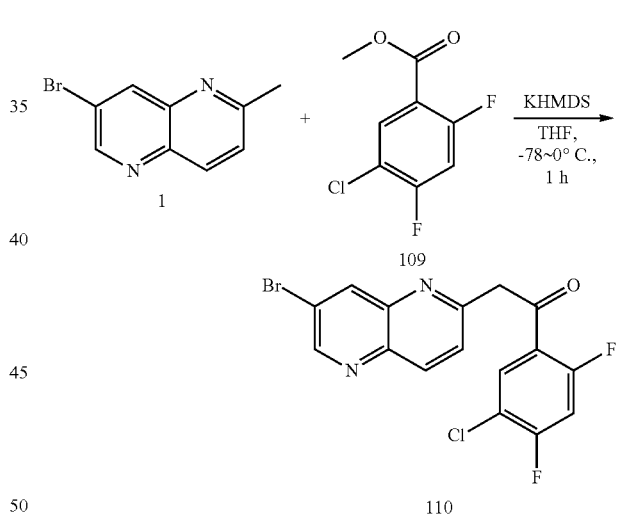

To a solution of 1 (10.0 g, 45.0 mmol) and 109 (23.3 g, 112.6 mmol) in THF (200 mL), KHMDS (90.0 mL, 90.0 mmol, 1.0 M/L) was added dropwise at −78° C. The mixture was stirred at −78° C. for 30 min. Then the mixture was stirred at 0° C. for 30 min. The mixture was quenched with H$_2$O (200 mL) and filtered. The resultant filter cake was washed with PE:EA (1:1, 50 mL, 2×) and H$_2$O (20 mL, 3×) prior to being was concentrated in vacuo to afford title compound 110 as yellow solid (14.0 g, 70% purity, 78% yield). [M+H]$^+$ calcd for C$_{16}$H$_8$BrClF$_2$N$_2$O, 396.95, found 397.0.

Example 86: Synthesis of (Z)-2-(7-bromo-1,5-naphthyridin-2-yl)-1-(5-chloro-2,4-difluorophenyl)-3-(dimethylamino)prop-2-en-1-one (111)

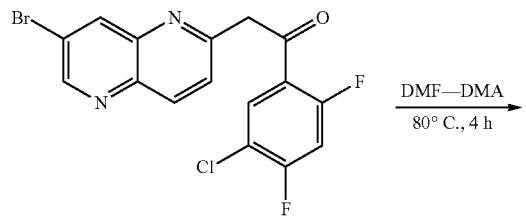

110

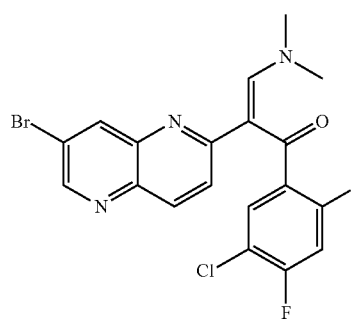

111

A solution of 110 (14.0 g, 35.2 mmol) in DMF-DMA (300 mL) was stirred at 80° C. for 4 h under a N₂ atmosphere. The mixture was concentrated in vacuo to obtain crude 111 as black oil (14.9 g, crude), which was used directly in Example 87 below. [M+H]⁺ calcd for $C_{19}H_{13}BrClF_2N_3O$, 451.99, found 451.9.

Example 87: Synthesis of 7-bromo-2-(3-(5-chloro-2,4-difluorophenyl)-1H-pyrazol-4-yl)-1,5-naphthyridine (112)

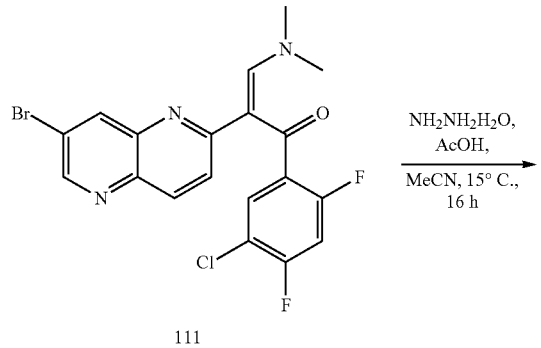

111

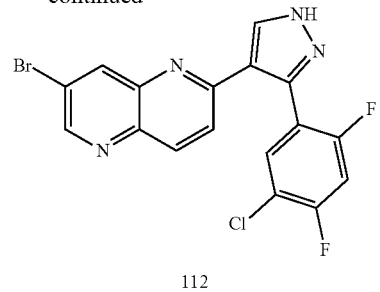

112

To a solution of 111 (14.9 g, 32.91 mmol, crude) in MeCN (200 mL), AcOH (14.0 g, 233.66 mmol) and NH₂NH₂H₂O (9.0 g, 181.00 mmol) was added. The mixture was stirred at 15° C. for 16 h. The reaction was filtered and the filter cake was washed with MeCN (30 mL, 3×), then washed with H₂O (30 mL, 3×). The filter cake was dried to obtain title compound 112 as red solid (5.5 g, 37% yield, 87% purity). [M+H]⁺ calcd for $C_{17}H_8BrClF_2N_4$ 420.96, found 421.1. ¹H NMR (400 MHz, DMSO-d₆) δ 8.93 (s, J=8.0 Hz, 1H), 8.34 (d, J=9.2 Hz, 1H), 8.17 (d, J=1.6 Hz, 1H), 7.98 (d, J=8.8 Hz, 1H), 7.81 (t, J=8.0 Hz, 1H), 7.59 (t, J=9.6 Hz, 1H).

Example 88: Synthesis of 7-bromo-2-(3-(5-chloro-2,4-difluorophenyl)-1-(tetrahydro-2H-pyran-2-yl)-1H-pyrazol-4-yl)-1,5-naphthyridine (113)

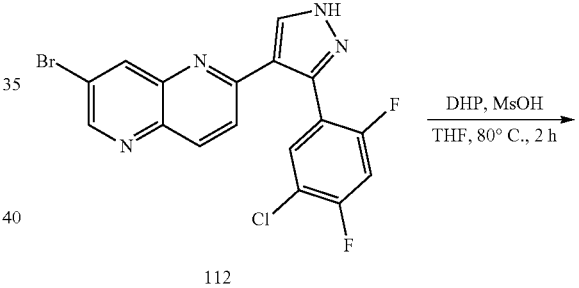

112

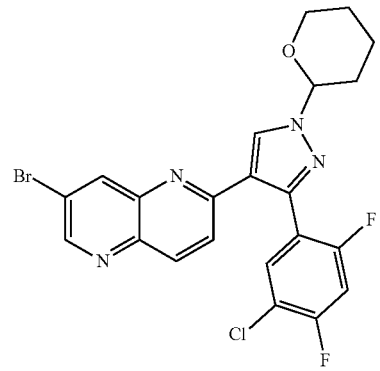

113

To a solution of 112 (5.5 g, 13.05 mmol) in THF (60 mL), MsOH (15 drops, catalytic amount) and DHP (5.5 g, 65.22 mmol) was added. The mixture was stirred at 80° C. for 2 h under N₂. The reaction was diluted with sat. NaHCO₃aq (150 mL) and extracted with EA (3×200 mL). The combined organic layers were washed with brine (3×200 mL), dried (Na₂SO₄) and concentrated in vacuo. The residue was purified by column chromatography (PE:EA=100:1 to 5:1)

and further purified by prep-HPLC (Phenomenex Gemini C18, 250×50 mm×10 μm, water (0.05% ammonia hydroxide)—ACN, 5-30%, 100 mL/min) to afford 113 as yellow solid (5.1 g, 77% yield, 95% purity). [M+H]⁺ calcd for $C_{22}H_{16}BrClF_2N_4O$ 505.02, found 505.0. ¹H NMR (400 MHz, CDCl₃) δ 8.88 (d, J=2.0 Hz, 1H), 8.30-8.32 (m, 2H), 8.23 (d, J=8.8 Hz, 1H), 7.77 (t, J=8.0 Hz, 1H), 7.55 (d, J=8.8 Hz, 1H, 6.93 (t, J=8.8 Hz, 1H). 5.50 (t, J=8.0 Hz, 1H), 4.13-4.16 (m, 1H), 3.74-3.80 (m, 1H), 2.20-2.21 (m, 2H), 2.08-2.20 (m, 1H), 1.64-1.76 (m, 3H).

Example 89: Synthesis of 2-(3-(5-chloro-2,4-difluorophenyl)-1-(tetrahydro-2H-pyran-2-yl)-1H-pyrazol-4-yl)-7-(4,4,5,5-tetramethyl-1,3,2-dioxaborolan-2-yl)-1,5-naphthyridine (114)

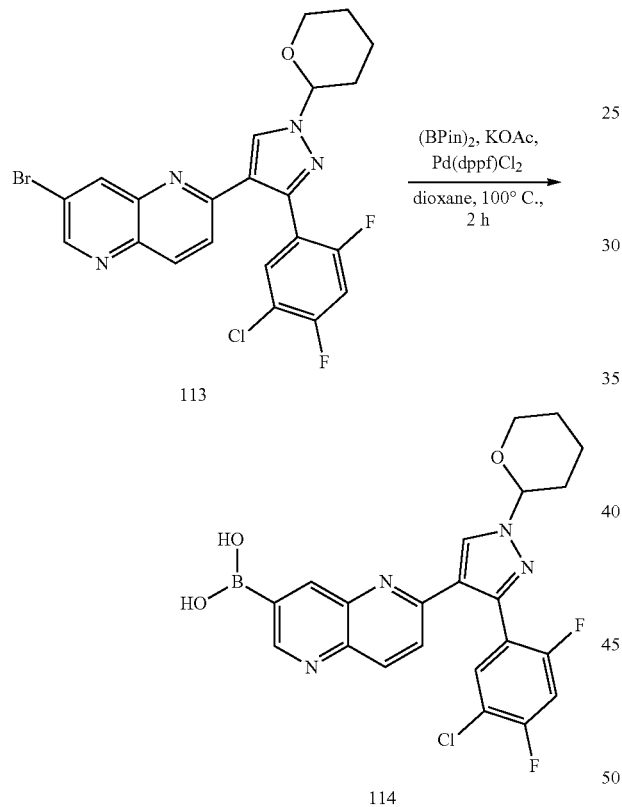

To a mixture of compound 113 (2.8 g, 5.53 mmol) and (BPin)₂ (2.1 g, 8.30 mmol) in dioxane (60 mL) was added Pd(dppf)Cl₂ (405 mg, 0.553 mmol) and KOAc (1.6 g, 16.6 mmol). The mixture was stirred at 100° C. for 2 h under N₂ atmosphere. The reaction was filtered, concentrated in vacuum. The residue was purified by normal phase column chromatography (50% of EA in PE) to obtain compound 114 as a yellow oil (2.78 g, 91% yield, 92% purity). $C_{22}H_{18}BClF_2N_4O_3$ 471.11, found 471.2 ¹H NMR (400 MHz, DMSO-d₆) δ 9.00 (d, J=1.6 Hz, 1H), 8.84 (s, 1H), 8.38 (d, J=8.9 Hz, 1H), 8.15 (d, J=1.6 Hz, 1H), 8.03 (d, J=8.9 Hz, 1H), 7.94 (s, 2H), 7.83 (t, J=7.8 Hz, 1H), 7.61 (t, J=9.6 Hz, 1H), 5.57 (dd, J=9.7, 2.5 Hz, 1H), 4.07-3.97 (m, 1H), 3.72 (dt, J=11.8, 6.7 Hz, 1H), 2.10-2.02 (m, 2H), 1.77-1.72 (m, 1H), 1.62-1.57 (m, 3H).

Example 90: Synthesis of 2-(3-(5-chloro-2,4-difluorophenyl)-1-(tetrahydro-2H-pyran-2-yl)-1H-pyrazol-4-yl)-7-ethynyl-1,5-naphthyridine (118)

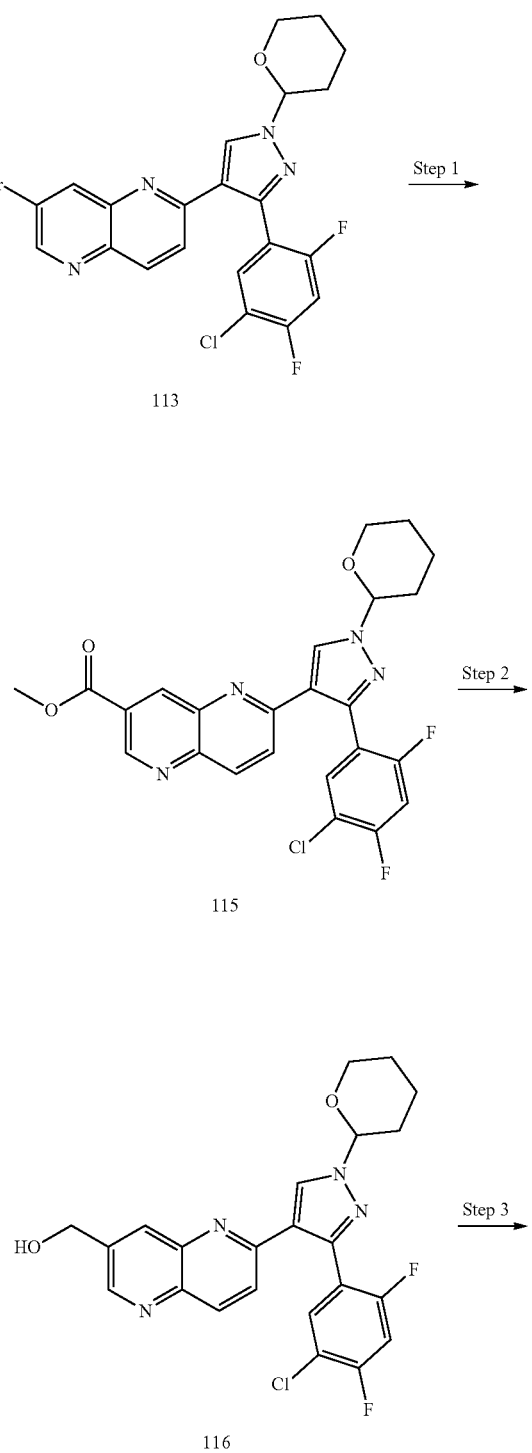

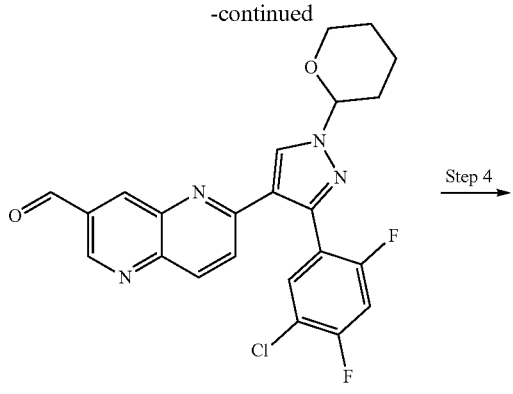

117

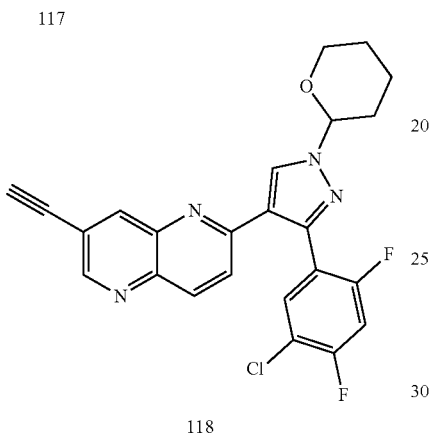

118

Step 1: A solution of 113 (5.0 g, 9.9 mmol), Xantphos (1.2 g, 2.0 mmol) and sodium acetate (1.2 g, 14.9 mmol) in methanol (50 mL) and THF (50 mL) was added palladium (II) acetate (673 mg, 3.0 mmol) under $N_2$ atmosphere. The reaction was stirred at 80° C. for 48 h under CO (50 psi). The reaction was concentrated in vacuum and purified by silica gel column chromatography (10%-50% of EA in PE) to obtain 115 (4.6 g, 95% yield, 98% purity) as yellow solid. $[M+H]^+$ calcd for $C_{24}H_{19}ClF_2N_4O_3$ 485.11, found 485.0.

Step 2: To a solution of ester 115 (1.2 g×3, 2.47 mmol×3) in THF (100 mL×3) at −30° C. was added LiAlH$_4$ (187 mg×3, 4.94 mmol×3) in portions. The mixture was stirred at −30° C. for 15 min. The resulting mixture was diluted with sat. aq. sodium potassium tartrate (200 mL) and extracted with EtOAc (3×200 mL). The combined organics were dried over sodium sulfate, concentrated in vacuum and purified by silica gel column chromatography to afford alcohol 116 (2.6 g, 60% yield, 96% purity) as yellow solid. $[M+H]^+$ calcd for $C_{23}H_{19}ClF_2N_4O_2$ 457.11, found 457.0.

Step 3: To a solution of 116 (2.6 g, 5.7 mmol) in THF (50 mL) was added MnO$_2$ (5.0 g, 57.0 mmol). The mixture was stirred at 70° C. for 16 h and monitored by TLC. Upon complete conversion the reaction was filtered, concentrated in vacuum and purified by column to obtain aldehyde 117 (920 mg, 35% yield, 100% purity) as light yellow solid. $[M+H]^+$ calcd for $C_{23}H_{17}ClF_2N_4O_3$ 455.10, found 455.0. $^1$H NMR (400 MHz, DMSO-d$_6$) δ 10.28 (s, 1H), 9.26 (d, J=1.9 Hz, 1H), 8.92 (s, 1H), 8.50-8.41 (m, 2H), 8.15 (d, J=8.8 Hz, 1H), 7.81 (dd, J=8.4, 7.2 Hz, 1H), 7.59 (t, J=9.6 Hz, 1H), 5.58 (dd, J=9.8, 2.6 Hz, 1H), 4.07-3.92 (m, 1H), 3.72 (ddd, J=11.5, 8.0, 5.8 Hz, 1H), 2.28-2.14 (m, 1H), 2.12-1.95 (m, 2H), 1.84-1.66 (m, 1H), 1.61 (dq, J=9.3, 5.3, 4.6 Hz, 2H).

Step 4: To a slurry of aldehyde 117 (210 mg, 0.462 mmol) in methanol (5.7 mL) cooled to 0° C. was added dimethyl (1-diazo-2-oxopropyl)phosphonate (0.097 mL, 0.646 mmol) followed potassium carbonate (128 mg, 0.923 mmol). The yellow slurry was stirred while the cooling ice bath was allowed to slowly expire overnight. After 18 h the mixture was concentrated and the residue was purified using silica gel column chromatography (0 to 15% methanol in DCM gradient) to give 118 (140 mg, 61% yield, 90% purity) as a white solid. $[M+H]^+$ calcd for $C_{24}H_{17}ClF_2N_4O$, 451.11, found 451.0.

Example 91: Synthesis of 6-(3-(5-chloro-2,4-difluorophenyl)-1H-pyrazol-4-yl)-N-(2-(4-isopropylpiperazin-1-yl)ethyl)-1,5-naphthyridin-3-amine (6-1)

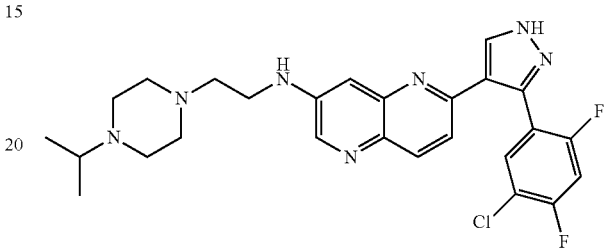

To compound 113 (65 mg, 0.129 mmol) and 2-(4-isopropyl-piperazin-1-yl)-ethylamine (25.3 mg, 0.148 mmol) was added BrettPhos, (6.90 mg, 0.013 mmol), BrettPhos Pd G4 (11.83 mg, 0.013 mmol) and cesium carbonate, (123 mg, 0.386 mmol). To the resulting mixture was added dioxane (500 µL) and subsequently sparged with nitrogen for 5 min. The resulting yellow reaction mixture was capped stirred at 105° C. for 16 h. The reaction was filtered through a plug of celite, washed with THF (10 mL) and concentrated in vacuo. The resulting residue was treated with 2 mL of TFA and stirred at 55° C. for 1 h. The crude product was concentrated in vacuo and purified by preparative HPLC chromatography using a gradient (20 to 35%) of acetonitrile in water with 0.05% trifluoroacetic acid to yield a TFA salt of the title compound (27.3 mg). $[M+H]^+$ calcd for $C_{26}H_{28}ClF_2N_7$ 512.21, found 512.2. $^1$H NMR (601 MHz, Acetonitrile-d$_3$) δ 8.60 (s, 1H), 8.57 (s, 1H), 8.36 (d, J=8.6 Hz, 1H), 7.66 (t, J=7.6 Hz, 1H), 7.62 (s, 1H), 7.24 (d, J=8.6 Hz, 1H), 7.13 (t, J=9.4 Hz, 1H), 3.75-3.61 (m, 6H), 3.61-3.47 (m, 5H), 3.41-3.36 (m, 2H), 1.34 (d, J=6.6 Hz, 6H).

Example 92: Synthesis of N-(2-(4-(tert-butyl)piperazin-1-yl)ethyl)-6-(3-(5-chloro-2,4-difluorophenyl)-1H-pyrazol-4-yl)-1,5-naphthyridin-3-amine (6-13)

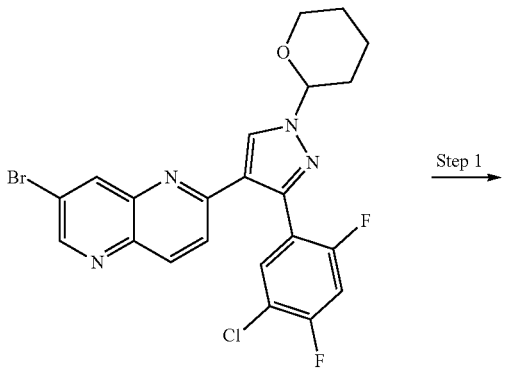

113

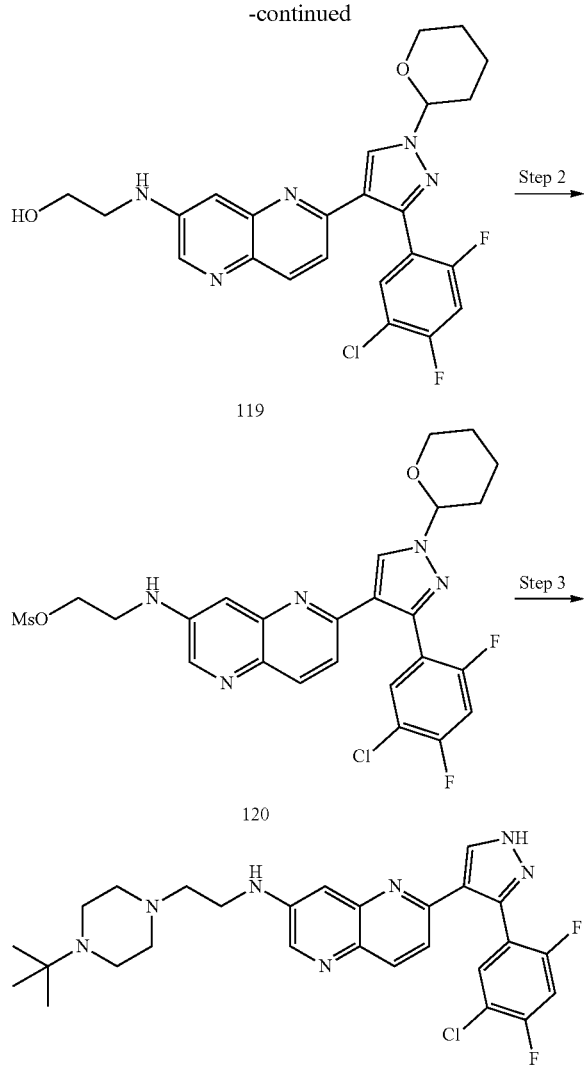

119

120

Step 1: Preparation of 2-((6-(3-(5-chloro-2,4-difluorophenyl)-1-(tetrahydro-2H-pyran-2-yl)-1H-pyrazol-4-yl)-1,5-naphthyridin-3-yl)amino)ethan-1-ol. To a vial charged with compound 113 (200 mg, 0.395 mmol) and ethanolamine (0.028 mL, 0.455 mmol) was added BrettPhos (21.23 mg, 0.040 mmol), BrettPhos Pd G4 (36.4 mg, 0.040 mmol), and cesium carbonate (387 mg, 1.186 mmol). The resulting mixture was purged with nitrogen for 5 min and dioxane (2.3 mL) was added. The resulting yellow mixture was capped and stirred at 90° C. for 16 h. The resulting mixture was cooled and filtered through a plug of celite, washed with THF (20 mL) and then concentrated in vacuo. The resulting residue was purified by silica column chromatography using a gradient (0 to 15%) of methanol in DCM to yield the title intermediate 119 (88.9 mg). [M+H]$^+$ calcd for $C_{24}H_{22}ClF_2N_5O_2$ 486.14 found 486.

Step 2: Preparation of 2-((6-(3-(5-chloro-2,4-difluorophenyl)-1-(tetrahydro-2H-pyran-2-yl)-1H-pyrazol-4-yl)-1,5-naphthyridin-3-yl)amino)ethyl methanesulfonate (120). To a vial charged with compound 119 (31.5 mg, 0.065 mmol) dissolved in DCM (648 µL) was added triethylamine (18.07 µL, 0.130 mmol) and the resulting mixture was cooled to 0° C. before being treated with methanesulfonyl chloride (10.03 µL, 0.130 mmol). The resulting mixture was let stir and warm to RT over 2 h. Afterwards, the reaction was quenched with saturated sodium bicarbonate solution, extracted with DCM. The combined organics dried over sodium sulfate, filtered, and then concentrated in vacuo. This yielded a dried crude mixture containing the title intermediate 120, which was used without further purification. [M+H]$^+$ calcd for $C_{25}H_{24}ClF_2N_5O_4S$, 564.12 found 564.

Step 3: Preparation of N-(2-(4-(tert-Butyl)piperazin-1-yl)ethyl)-6-(3-(5-chloro-2,4-difluorophenyl)-1H-pyrazol-4-yl)-1,5-naphthyridin-3-amine. To a vial charged with compound 120 from the previous step dissolved in dry acetonitrile (650 µL) was added 1-tert-butylpiperazine (18.44 mg, 0.130 mmol) and DIPEA (28.3 µL, 0.162 mmol). The resulting mixture was capped and stirred at 80° C. for 16 h. Afterwards, the reaction was concentrated in vacuo. The resulting residue was treated with 1.0 mL of TFA and stirred at 55° C. for 1 h. The crude product was concentrated in vacuo, and purified by preparative HPLC chromatography using a gradient (10 to 40%) of acetonitrile in water with 0.05% trifluoroacetic acid to yield a TFA salt of the title compound (27.3 mg). [M+H]$^+$ calcd for $C_{27}H_{30}ClF_2N_7$ 526.22 found 526.2. $^1$H NMR (400 MHz, Methanol-d$_4$) δ 8.64 (d, J=2.6 Hz, 1H), 8.45 (s, 1H), 8.42 (d, J=8.5 Hz, 1H), 7.84 (dd, J=8.1, 7.3 Hz, 1H), 7.38 (d, J=8.6 Hz, 1H), 7.25 (t, J=9.5 Hz, 1H), 7.08 (d, J=2.3 Hz, 1H), 3.66-3.51 (m, 2H), 3.43 (t, J=6.1 Hz, 2H), 3.28-3.21 (m, 2H), 3.21-3.13 (m, 2H), 2.84 (t, J=6.1 Hz, 2H), 2.64-2.49 (m, 2H), 1.43 (s, 9H).

Example 93: Synthesis of 2-(3-(5-chloro-2,4-difluorophenyl)-1H-pyrazol-4-yl)-7-(3-(piperidin-1-yl)azetidin-1-yl)-1,5-naphthyridine (6-14)

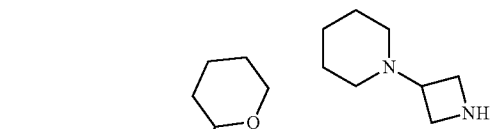

1. RuPhos Pd G4, RuPhos, Cs$_2$CO$_3$
   1,4-Dioxane, 85° C., 16 h
2. TFA, 50° C., 1 h

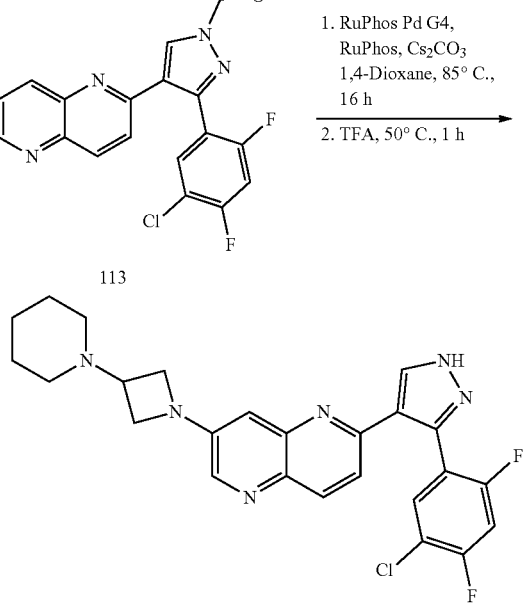

113

A vial of 113 (30 mg, 0.059 mmol), RuPhos Pd G4 (10.09 mg, 0.012 mmol), RuPhos (5.54 mg, 0.012 mmol), cesium carbonate (58.0 mg, 0.178 mmol), and 1-(3-azetidinyl)piperidine (10.0 mg, 0.071 mmol) in 1,4-dioxane (0.5 mL) was heated to 85° C. for 16 h. The reaction mixture was filtered through a pad of celite and concentrated in vacuum. TFA (300 µL) was added to the residue and heated to 50° C. for 1 h. TFA was removed in vacuum and the residue was purified by preparative HPLC chromatography using a gradient (10 to 80%) of acetonitrile in water with 0.05% trifluoroacetic acid to yield a TFA salt of the title compound (10.0 mg). [M+H]$^+$ calcd for $C_{25}H_{23}ClF_2N_6$ 481.16, found 481.1.

Example 94: Synthesis of 1-(6-(3-(5-chloro-2,4-difluorophenyl)-1H-pyrazol-4-yl)-1,5-naphthyridin-3-yl)-N-methylpiperidin-4-amine (6-23)

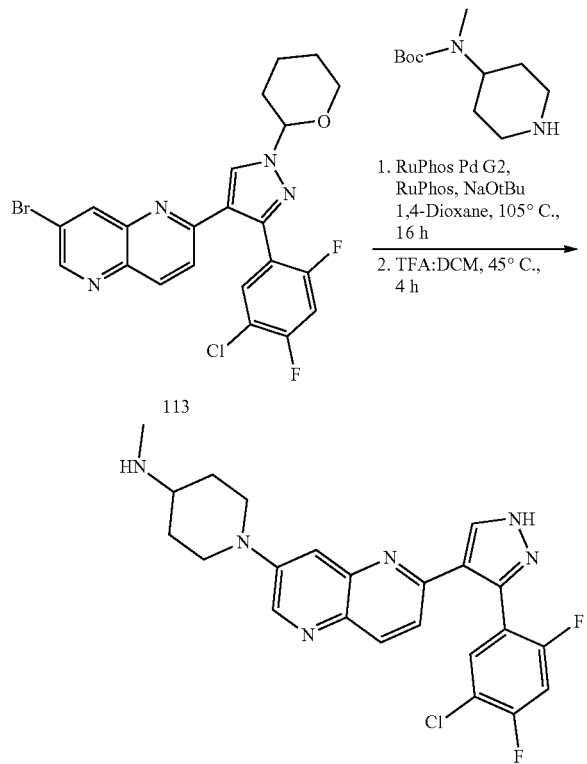

A vial of 113 (45 mg, 0.044 mmol), RuPhos Pd G2 (3.42 mg, 0.004 mmol), RuPhos (2.05 mg, 0.004 mmol), sodium tert-butoxide (13.0 mg, 0.132 mmol), and 4-n-boc-4-n-methylaminopiperidine (71.0 mg, 0.066 mmol) in 1,4-Dioxane (0.4 mL) was heated to 105° C. for 16 h. The reaction mixture was filtered through a pad of celite and concentrated in vacuum. A mixture of 1:1 TFA:DCM (1 mL) was added to the residue and heated to 45° C. for 4 h until THP and Boc protecting groups were fully removed. TFA was removed in vacuum and the residue was purified by preparative HPLC chromatography using a gradient (10 to 80%) of acetonitrile in water with 0.05% trifluoroacetic acid to yield a TFA salt of the title compound (6.6 mg). [M+H]$^+$ calcd for $C_{23}H_{21}ClF_2N_6$ 455.15, found 455.1. $^1$H NMR (400 MHz, Methanol-d4) δ 9.03 (d, J=2.8 Hz, 1H), 8.51 (s, 1H), 8.46 (dd, J=8.7, 0.7 Hz, 1H), 7.84 (dd, J=8.2, 7.2 Hz, 1H), 7.56-7.48 (m, 2H), 7.28-7.17 (m, 1H), 4.26 (d, J=13.3 Hz, 2H), 3.39 (tt, J=11.6, 4.1 Hz, 1H), 3.17 (ddd, J=13.7, 12.3, 2.5 Hz, 2H), 2.76 (s, 3H), 2.32-2.26 (m, 2H), 1.77 (qd, J=12.3, 4.1 Hz, 2H).

Example 95: Synthesis of (R)-6-(3-(5-chloro-2,4-difluorophenyl)-1H-pyrazol-4-yl)-N-(1-isopropylpyrrolidin-3-yl)-N-methyl-1,5-naphthyridin-3-amine (6-37)

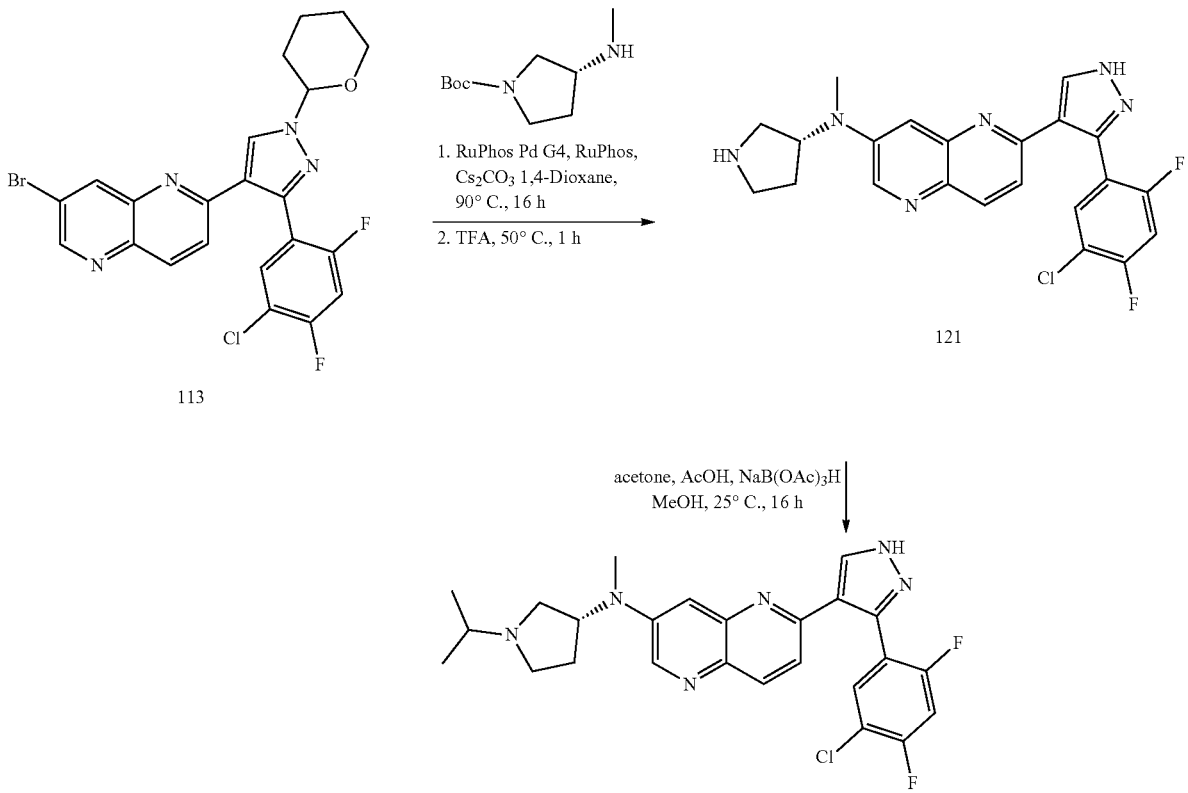

A vial of 113 (30 mg, 0.059 mmol), RuPhos Pd G4 (10.09 mg, 0.012 mmol), RuPhos (5.54 mg, 0.012 mmol), cesium carbonate (58.0 mg, 0.178 mmol), and (r)-tert-butyl 3-(methylamino)pyrrolidine-1-carboxylate (14.0 mg, 0.071 mmol) in 1,4-dioxane (0.5 mL) was heated to 85° C. for 16 h. The reaction mixture was filtered through a pad of celite and concentrated in vacuum. TFA (300 µL) was added to the residue and heated to 50° C. for 1 h until THP and Boc protecting groups were fully removed. TFA was removed in vacuum and the residue was purified by preparative HPLC chromatography using a gradient (10 to 80%) of acetonitrile in water with 0.05% trifluoroacetic acid to yield a TFA salt of (R)-6-(3-(5-chloro-2,4-difluorophenyl)-1H-pyrazol-4-yl)-N-methyl-N-(pyrrolidin-3-yl)-1,5-naphthyridin-3-amine (121) (16.8 mg). [M+H]$^+$ calcd for $C_{22}H_{19}ClF_2N_6$ 441.13, found 441.1. A vial of compound 121 (9.38 mg, 0.021 mmol), acetone (3.13 µL, 0.043 mmol), and AcOH (1.218 µL, 0.021 mmol) in methanol (0.2 mL) was stirred at 25° C. for 1 h before adding sodium triacetoxyborohydride (13.53 mg, 0.064 mmol). The resulting mixture was allowed to stir at 25° C. for 16 h. The reaction was quenched with $H_2O$ (0.2 mL) and concentrated in vacuum. The residue was purified by preparative HPLC chromatography using a gradient (5 to 65%) of acetonitrile in water with 0.05% trifluoroacetic acid to yield a TFA salt of the title compound (6.6 mg). [M+H]$^+$ calcd for $C_{25}H_{25}ClF_2N_6$ 483.18, found 483.0.

Example 96: Synthesis of 2-(3-(6-(3-(5-chloro-2,4-difluorophenyl)-1H-pyrazol-4-yl)-1,5-naphthyridin-3-yl)-1H-pyrazol-1-yl)-N-methylethan-1-amine (6-40)

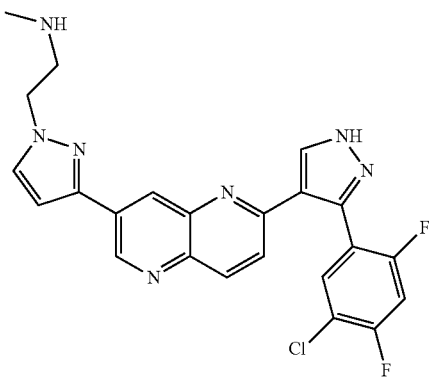 [SMILES: CNCCn1ccc(-c2cnc3ccc(-c4c[nH]nc4-c4cc(Cl)c(F)cc4F)nc3c2)n1]

A vial of 113 (33.7 mg, 0.067 mmol), 80 (26.9 mg, 0.100 mmol) sodium carbonate (21.18, 0.200 mmol), and [1,1-bis(diphenylphosphino)ferrocene]dichloropalladium(II) (8.84 mg, 0.012 mmol) in 1,4-dioxane (269 µL) and water (134 µL) was sparged with $N_2$ for 5 min before being heated to 96° C. for 18 h. Following that the mixture was concentrated in the vacuum and treated with 300 µL of TFA at to 50° C. for 1 h. The resulting mixture was concentrated and purified by preparative HPLC chromatography using a gradient (18 to 42%) of acetonitrile in water with 0.05% trifluoroacetic acid to yield a TFA salt of the title compound (24.1 mg) as a light yellow solid. [M+H]$^+$ calcd for $C_{23}H_{18}ClF_2N_7$ 466.13, found 466.1. $^1$H NMR (400 MHz, Methanol-$d_4$) δ 9.40 (d, J=2.0 Hz, 1H), 8.47 (dd, J=2.0, 0.9 Hz, 1H), 8.41 (s, 1H), 8.31 (dd, J=8.9, 0.8 Hz, 1H), 7.87-7.75 (m, 3H), 7.22 (t, J=9.4 Hz, 1H), 6.97 (d, J=2.4 Hz, 1H), 4.64-4.57 (m, 2H), 3.63-3.57 (m, 2H), 2.80 (s, 3H).

Example 97: Synthesis of 2-(3-(5-chloro-2,4-difluorophenyl)-1H-pyrazol-4-yl)-7-(1-methyl-2,5-dihydro-1H-pyrrol-3-yl)-1,5-naphthyridine (6-43)

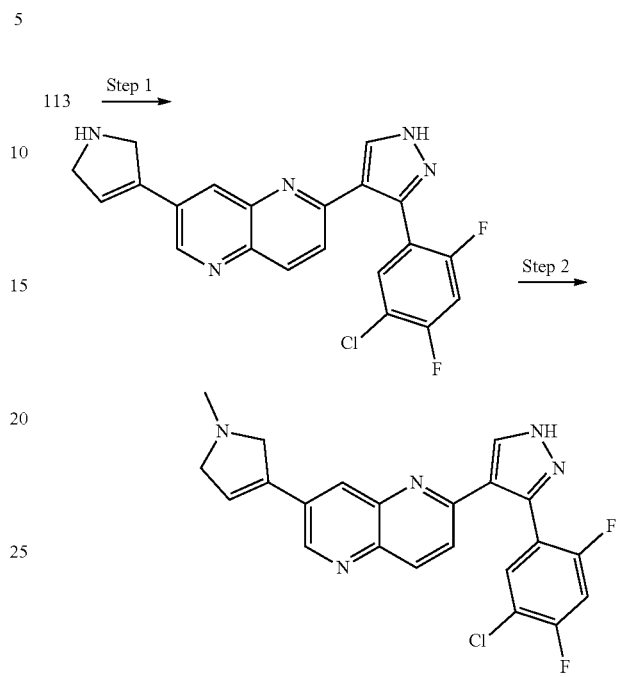

Step 1: A vial of 113 (30.6 mg, 0.61 mmol), sodium carbonate (19.25 mg, 0.182 mmol), [1,1-bis(diphenylphosphino)ferrocene]dichloropalladium(II) (8.86 mg, 0.012 mmol), and 1-boc-2,5-dihydro-1H-pyrrole-3-boronic acid, pinacol ester (23.23 mg, 0.079 mmol) in 1,4-dioxane (202 µL) and water (101 µL) was sparged with $N_2$ for 5 minutes before heating to 95° C. for 18 h. The reaction mixture was cooled and concentrated in vacuum. TFA (500 µL) was added and the dark solution was heated to 50° C. for 1 h. The resulting mixture was concentrated and purified by preparative HPLC chromatography using a gradient (8 to 20%) of acetonitrile in water with 0.05% trifluoroacetic acid to yield a TFA salt of the intermediate 2-(3-(5-chloro-2,4-difluorophenyl)-1H-pyrazol-4-yl)-7-(2,5-dihydro-1-pyrrol-3-yl)-1,5-naphthyridine (19.8 mg) as a white solid. [M+H]$^+$ calcd for $C_{21}H_{14}ClF_2N_5$ 410.09, found 410.0.

Step 2: A vial of 2-(3-(5-chloro-2,4-difluorophenyl)-1H-pyrazol-4-yl)-7-(2,5-dihydro-1-pyrrol-3-yl)-1,5-naphthyridine (11.6 mg, 0.028 nnol), acetic acid (1.620 µL, 0.028 mmol), and formaldehyde solution, 37 wt. % in water (4.21 µL, 0.057 mmol) was stirred for 60 min in methanol (250 µL) before adding sodium triacetoxyborohydride (17.99 mg, 0.085 mmol). The resulting mixture was allowed to stir for 18 h at RT. The reaction mixtures were quenched with water (0.5 mL), concentrated and purified by preparative HPLC chromatography using a gradient (25 to 40%) of acetonitrile in water with 0.05% trifluoroacetic acid to yield a TFA salt of the title compound (7 mg) as a light yellow solid. [M+H]$^+$ calcd for $C_{22}H_{16}ClF_2N_5$ 424.11, found 424.1. $^1$H NMR (400 MHz, Methanol-$d_4$) δ 9.13 (d, J=2.2 Hz, 1H), 8.40 (s, 1H), 8.32 (dd, J=8.8, 0.9 Hz, 1H), 8.01 (d, J=2.2 Hz, 1H), 7.85 (d, J=8.8 Hz, 1H), 7.83-7.74 (m, 1H), 7.20 (t, J=9.4 Hz, 1H), 6.73 (t, J=2.2 Hz, 1H), 4.73-4.38 (m, 3H), 4.30-4.17 (m, 1H), 3.15 (s, 3H).

Example 98: Synthesis of 2-(3-(5-chloro-2,4-difluorophenyl)-1H-pyrazol-4-yl)-7-(4,5,6,7-tetrahydropyrazolo[1,5-a]pyrazin-3-yl)-1,5-naphthyridine (6-45)

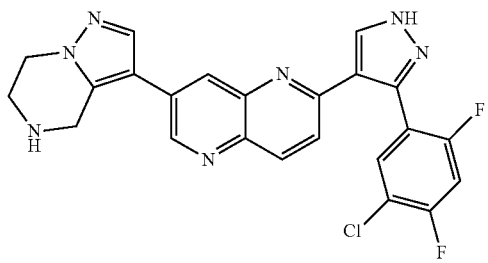 [SMILES: Fc1cc(F)c(-c2n[nH]cc2-c2ccc3ncc(-c4cnn5c4CNCC5)cc3n2)cc1Cl]

To a vial containing tert-butyl 3-bromo-6,7-dihydropyrazolo[1,5-a]pyrazine-5(4H)-carboxylate (46.2 mg, 0.153 mmol) and compound 114 (60 mg, 0.127 mmol) was added XPhos Pd G4 (10.97 mg, 0.013 mmol), 2-dicyclohexylphosphino-2',4',6'-triisopropylbiphenyl (6.08 mg, 0.013 mmol) and Potassium phosphate (81 mg, 0.382 mmol). The resulting mixture was purged with nitrogen before dioxane (300 μL) and water (300 μL) were added and the yellow suspension was sparged with nitrogen for 20 min. The reaction vial was capped and stirred at 105° C. for 1.5 h. The RM was filtered through a pad of celite, washed on filters with THF (5 mL), filtrates were concentrated. The residue was treated with 1.5 mL of TFA at 55° C. for 1 h. The resulting mixture was concentrated and purified by preparative HPLC chromatography using a gradient (22 to 40%) of acetonitrile in water with 0.05% trifluoroacetic acid to yield a TFA salt of the title compound (17 mg) as a light yellow solid. $[M+H]^+$ calcd for $C_{23}H_{16}ClF_2N_7$ 464.11, found 464.2. $^1$H NMR (400 MHz, Methanol-$d_4$) δ 9.01 (d, J=2.2 Hz, 1H), 8.40 (s, 1H), 8.31 (dd, J=8.8, 0.8 Hz, 1H), 8.11 (s, 1H), 8.06 (dd, J=2.2, 0.8 Hz, 1H), 7.86-7.75 (m, 2H), 7.22 (t, J=9.4 Hz, 1H), 4.81 (s, 2H), 4.54 (t, J=5.9 Hz, 2H), 3.87 (t, J=5.9 Hz, 2H).

Example 99: Synthesis of 7-(1-((1H-imidazol-4-yl)methyl)-1H-1,2,3-triazol-4-yl)-2-(3-(5-chloro-2,4-difluorophenyl)-1H-pyrazol-4-yl)-1,5-naphthyridine (6-62)

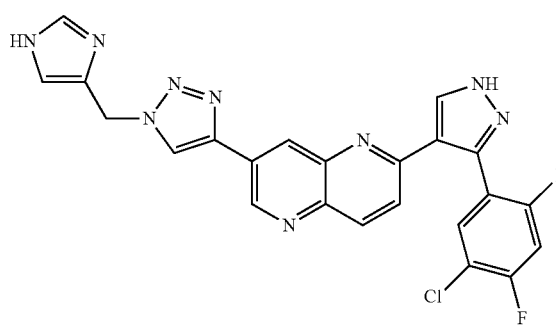

Step 1: Synthesis of azide. To a slurry of 4(5)-(hydroxymethyl)imidazole (100 mg, 1.019 mmol) in acetonitrile (1.2 mL) under nitrogen atmosphere was added thionyl chloride (0.5 mL, 6.85 mmol) and the resulting sticky mixture was stirred at RT for 2 h before being concentrated. The residue was dissolved in DMF (1.5 mL) and treated with sodium azide (199 mg, 3.06 mmol) which resulted in a red mixture which was then stirred at RT overnight. The reaction mixture was diluted with water (5 mL), ethyl acetate (20 mL) and sat NaHCO$_3$ (10 mL). The organic layer was separated and dried over sodium sulfate and then concentrated to give 4-(azidomethyl)-1H-imidazole as a green liquid (90 mg, 68% yield, 95% purity).

Step 2: To a vial containing 118 (14.48 mg, 0.032 mmol) and copper(I)thiophene-2-carboxylate (6.74 mg, 0.035 mmol) was added dichloroethane (250 μL). The reaction mixture was stirred at 55° C. for 1 h. Following that a stock solution of 4-(azidomethyl)-1H-imidazole (4.55 mg, 0.037 mmol) in 71 μL of DCE was added and the mixture was stirred at RT for 18 h. The crude reaction slurry was concentrated in vacuum and the residue was treated with TFA (0.370 ml, 4.80 mmol) at 55° C. for 1 h. The resulting mixture was concentrated and purified by preparative HPLC chromatography using a gradient (23 to 37%) of acetonitrile in water with 0.05% trifluoroacetic acid to yield a TFA salt of the title compound (13.6 mg) as a light yellow solid. $[M+H]^+$ calcd for $C_{23}H_{14}ClF_2N_9$ 490.10, found 489.9. $^1$H NMR (400 MHz, Methanol-$d_4$) δ 9.34 (d, J=2.1 Hz, 1H), 8.90 (d, J=1.4 Hz, 1H), 8.69 (s, 1H), 8.49 (dd, J=2.1, 0.9 Hz, 1H), 8.43 (s, 1H), 8.33 (dd, J=8.9, 0.9 Hz, 1H), 7.87 (d, J=8.9 Hz, 1H), 7.82-7.73 (m, 2H), 7.21 (t, J=9.4 Hz, 1H), 5.87 (d, J=0.7 Hz, 2H).

Example 100: Synthesis of 1-(7-bromo-1,5-naphthyridin-2-yl)-2-(5-chloro-2,4-difluorophenyl)ethane-1,2-dione (122)

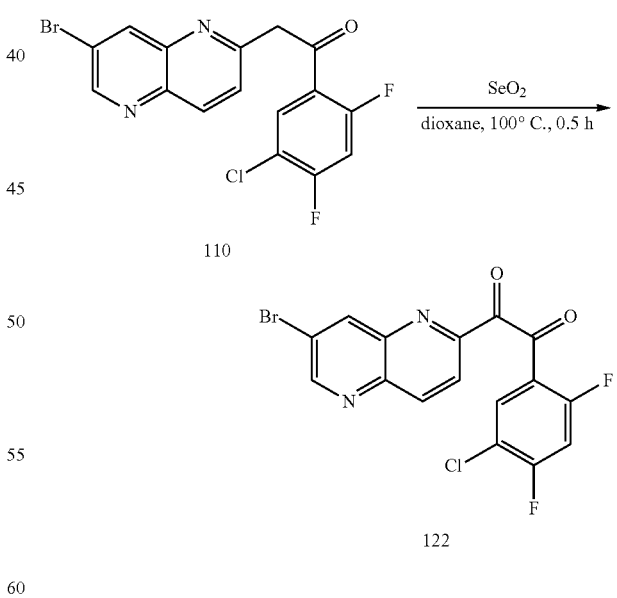

A solution of 110 (12.8 g, 32.2 mmol) and SeO$_2$ (17.9 g, 161 mmol) in dioxane (150 mL) was stirred at 100° C. for 0.5 h. The mixture was quenched with water (60 mL) and extracted by EA (2×60 mL). The organic layer was dried with Na$_2$SO$_4$ and filtered. The residue was concentrated in vacuum to obtain 12.1 g of crude 122 as black oil which was used in the following reaction.

Example 101: Synthesis of 7-bromo-2-(5-(5-chloro-2,4-difluorophenyl)-1H-imidazol-4-yl)-1,5-naphthyridine (123)

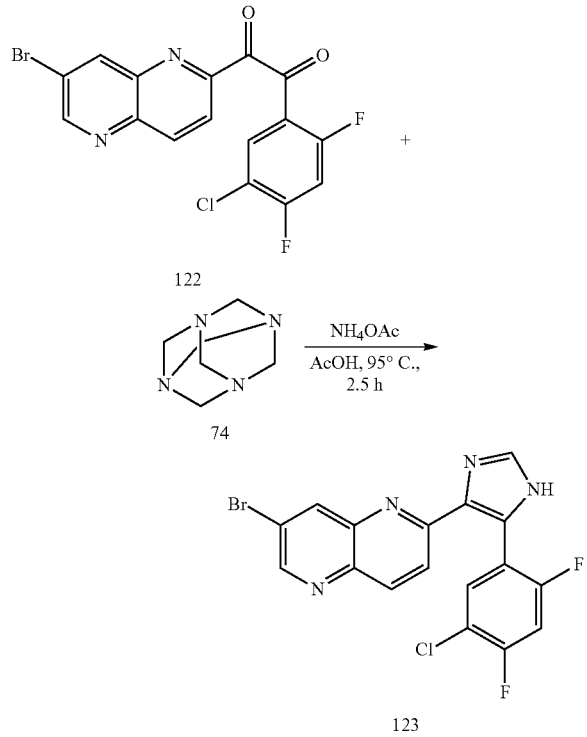

A solution of 122 (12.1 g, 14.5 mmol), 74 (6.1 g, 43.5 mmol) and NH₄OAc (6.7 g, 86.9 mmol) in AcOH (50 mL) was heated to 95° C. After 30 min, additional AcOH (50 mL) was added, and the reaction mixture was stirred for 2 h. The reaction mixture was concentrated in vacuum and basified with sat.aq NaHCO₃ (200 mL) to pH 10. The mixture was filtered. The filter residue was dried in vacuum to afford 123 as yellow solid (4.3 g, 70% yield, 93% purity). [M+H]+ calcd for C₁₇H₈BrClF₂N₄ 420.96, found 420.9.

Example 102: Synthesis of 7-bromo-2-(5-(5-chloro-2,4-difluorophenyl)-1-((2-(trimethylsilyl)ethoxy)methyl)-1H-imidazol-4-yl)-1,5-naphthyridine (124) and 7-bromo-2-(4-(5-chloro-2,4-difluorophenyl)-1-((2-(trimethylsilyl)ethoxy)methyl)-1H-imidazol-5-yl)-1,5-naphthyridine (125)

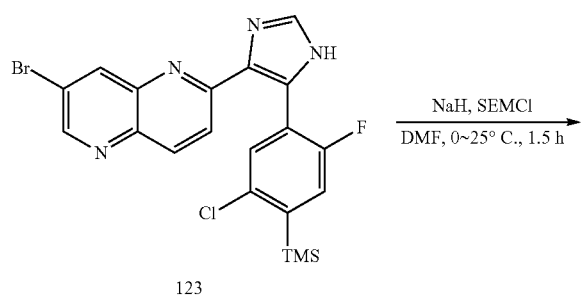

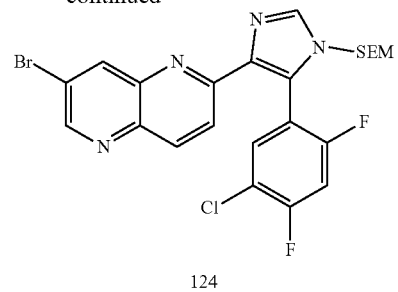

To a suspension of NaH (783 mg, 19.6 mmol) in DMF (20 mL) was added 123 (3.3 g, 7.83 mmol) in DMF (30 mL) at 0° C. and stirred at 0° C. for 0.5 h. Then SEMCl (3.3 g, 19.6 mmol) was added to the mixture at 0° C. and the reaction mixture was warmed to 25° C. and stirred for 1 h. The mixture was quenched with water (100 mL) and extracted with EA (3×80 mL). The organic layer was washed with brine (2×100 mL), dried with Na₂SO₄ and filtered. The liquor was concentrated in vacuum and purified by silica gel column (EA:PE 0-30%) to obtain 124 as yellow solid (880 mg, 15% yield, 98% purity). [M+H]+ calcd for $C_{23}H_{22}BrClF_2N_4OSi$ 551.04, found 551.0. ¹H NMR (400 MHz, Methanol-d₄) δ 9.21 (d, J=2.3 Hz, 1H), 8.88 (dd, J=2.3, 0.9 Hz, 1H), 8.54 (dd, J=8.8, 0.9 Hz, 1H), 8.40 (s, 1H), 7.99 (dd, J=8.3, 7.3 Hz, 1H), 7.84 (d, J=8.8 Hz, 1H), 7.34 (t, J=9.4 Hz, 1H), 6.12 (s, 2H), 3.69 (dd, J=8.4, 7.5 Hz, 2H), 0.92 (dd, J=8.4, 7.5 Hz, 2H), 0.00 (s, 9H). and 125 as yellow solid (1.3 g, 23% yield, 97% purity). [M+H]+ calcd for $C_{23}H_{22}BrClF_2N_4OSi$ 551.04, found 551.0. ¹H NMR (400 MHz, Methanol-d₄) δ 8.87 (d, J=2.3 Hz, 1H), 8.42-8.28 (m, 2H), 8.18 (s, 1H), 8.05 (dd, J=2.3, 0.8 Hz, 1H), 7.80 (dd, J=8.2, 7.2 Hz, 1H), 7.37 (t, J=9.2 Hz, 1H), 5.36 (s, 2H), 3.60-3.51 (m, 2H), 0.95-0.84 (m, 2H), 0.00 (s, 9H).

Example 103: Synthesis of 6-(5-(5-chloro-2,4-difluorophenyl)-1H-imidazol-4-yl)-N-(2-(piperazin-1-yl)ethyl)-1,5-naphthyridin-3-amine (7-1)

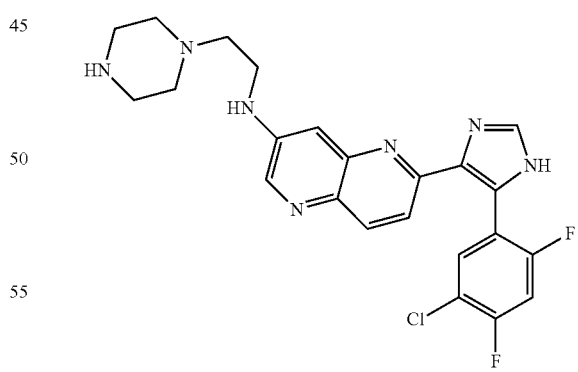

7-bromo-2-(5-(5-chloro-2,4-difluorophenyl)-1-((2-(trimethylsilyl)ethoxy)methyl)-1H-imidazol-4-yl)-1,5-naphthyridine (124) (30 mg, 0.054 mmol) and 4-(2-aminoethyl)-1-bocpiperazine (16.2 mg, 0.071 mmol) was added BrettPhos, (5.84 mg, 10.87 μmop, BrettPhos Pd G4 (10.01 mg, 10.87 μmop and cesium carbonate, (53.1 mg, 0.163 mmol). To the resulting mixture was added dioxane (544 μL) and subsequently sparged with nitrogen for 5 m. The resulting yellow reaction mixture was capped stirred at 85° C. for 16 h. The reaction was filtered through a plug of celite, washed with THF (10 mL) and concentrated in vacuo. The resulting residue was dissolved in 1,2-dichloroethane (0.2 mL) and then treated with 6N aq. HCl (0.2 mL) and stirred at 80° C. for 3 h. The crude product was concentrated in vacuo and purified by preparative HPLC chromatography using a gradient (8 to 22%) of acetonitrile in water with 0.05% trifluoroacetic acid to yield a TFA salt of the title compound (6.9 mg). [M+H]+ calcd for $C_{23}H_{22}ClF_2N_7$ 470.16 found 470.1.

Example 104: Synthesis of (R)-4-(6-(5-(5-chloro-2,4-difluorophenyl)-1H-imidazol-4-yl)-1,5-naphthyridin-3-yl)piperazine-2-carboxylic acid (7-3)

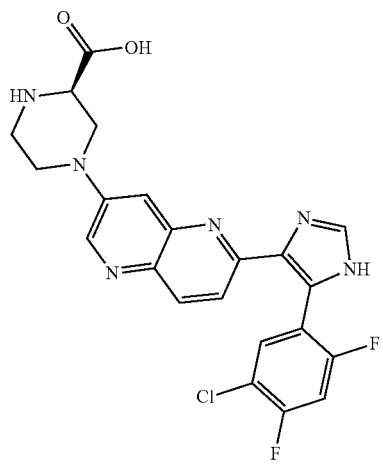 [SMILES: O=C(O)[C@H]1CN(c2cnc3ccc(-c4nc[nH]c4-c4cc(Cl)c(F)cc4F)nc3c2)CCN1]

7-bromo-2-(5-(5-chloro-2,4-difluorophenyl)-1-((2-(trimethylsilyl)ethoxy)methyl)-1H-imidazol-4-yl)-1,5-naphthyridine (124) (40 mg, 0.072 mmol) and (r)-1-n-bocpiperazine-2-carboxylic acid methyl ester (23.02 mg, 0.094 mmol) was added RuPhos, (6.76 mg, 0.014 mmol), RuPhos Pd G4 (12.33 mg, 0.014 mmol) and cesium carbonate, (70.8 mg, 0.217 mmol). To the resulting mixture was added dioxane (725 µL) and subsequently sparged with nitrogen for 5 min. The resulting yellow reaction mixture was capped stirred at 85° C. for 16 h. The reaction was filtered through a plug of celite, washed with THF (10 mL) and concentrated in vacuo. The resulting residue was dissolved in 1,2-dichloroethane (0.2 mL) and then treated with 6N aq. HCl (0.2 mL) and stirred at 80° C. for 3 h. The crude product was concentrated in vacuo, and purified by preparative HPLC chromatography using a gradient (10 to 24%) of acetonitrile in water with 0.05% trifluoroacetic acid to yield a TFA salt of the title compound (24.5 mg). [M+H]+ calcd for $C_{22}H_{17}ClF_2N_6O_2$ 471.11 found 471.1.

Example 105: Synthesis of 2-(4-(6-(5-(5-chloro-2,4-difluorophenyl)-1H-imidazol-4-yl)-1,5-naphthyridin-3-yl)-1H-pyrazol-1-yl)-N-methylethan-1-amine (7-4)

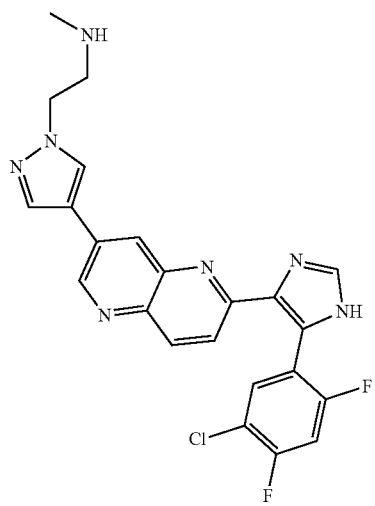 [SMILES: CNCCn1cc(-c2cnc3ccc(-c4nc[nH]c4-c4cc(Cl)c(F)cc4F)nc3c2)cn1]

To a vial containing charged 7-bromo-2-(5-(5-chloro-2,4-difluorophenyl)-1-((2-(trimethylsilyl)ethoxy)methyl)-1H-imidazol-4-yl)-1,5-naphthyridine (124) (30 mg, 0.071 mmol) was added tert-butyl methyl(2-(4-(4,4,5,5-tetramethyl-1,3,2-dioxaborolan-2-yl)-1H-pyrazol-1-yl)ethyl)carbamate (24.82 mg, 0.071 mmol) followed by sodium carbonate (23.05 mg, 0.217 mmol) and Pd(dppf)Cl$_2$ (7.95 mg, 10.87 µmop. The resulting mixture was purged with nitrogen before degassed water (109 µL) and 1,4-dioxane (435 µL) was added. The vial was capped and stirred at 85° C. for 16 h. The reaction was then cooled and concentrated in vacuo. The resulting residue was dissolved in 1,2-dichloroethane (0.2 mL) and then treated with 6N aq. HCl (0.2 mL) and stirred at 80° C. for 3 h. The crude product was concentrated in vacuo and purified by preparative HPLC chromatography using a gradient (10 to 25%) of acetonitrile in water with 0.05% trifluoroacetic acid to yield a TFA salt of the title compound (25.8 mg). [M+H]+ calcd for $C_{23}H_{18}ClF_2N_7$ 466.13, found 466.1.

Example 106: Synthesis of methyl 3,4-difluorobenzoate (127)

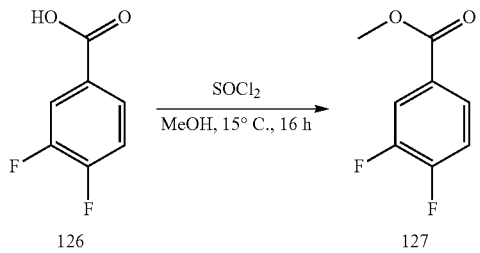

To a mixture of compound 126 (20.0 g, 127 mmol) in MeOH (200 mL) was added dropwise SOCl$_2$ (46.0 g, 380 mmol). Then the reaction was stirred at 15° C. for 16 h. The mixture was concentrated under reduced pressure. The residue was diluted with EA (200 mL), washed with sat. NaHCO₃ (2×50 mL), the organic layer was dried over Na₂SO₄, concentrated under reduced pressure and dried in vacuum to give compound 127 as white solid (18.3 g, 84% yield, 99% purity). $^1$H NMR (400 MHz, CDCl₃) δ 7.88-7.82 (2H, m), 7.27-7.22 (1H, m), 3.93 (3H, s).

Example 107: Synthesis of 2-(7-bromo-1,5-naphthyridin-2-yl)-1-(3,4-difluorophenyl)ethan-1-one (128)

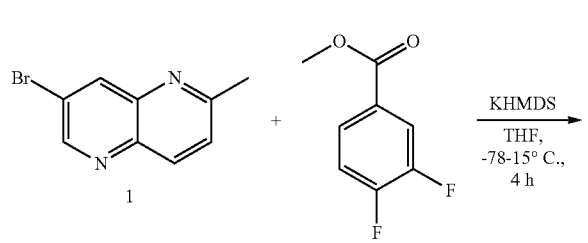

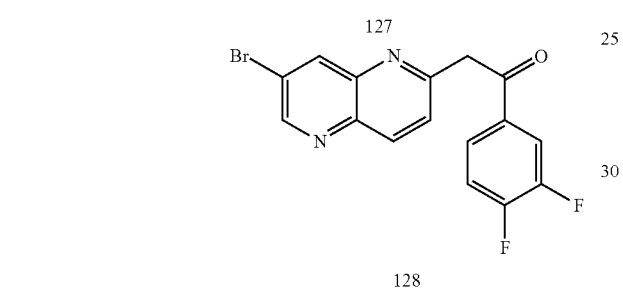

A solution of 1 (4.0 g, 18.0 mmol) and compound 127 (9.3 g, 54.0 mmol) in THF (120 mL) was added dropwise KHMDS (27.0 mL, 27.0 mmol, 1.0 M) at −78° C. The mixture was stirred at −78° C. for 2 h. Then the mixture was stirred at 15° C. for 2 h. The mixture was quenched with H₂O (80 mL), and extracted with EA (3×80 mL). The combined organic phase was dried over Na₂SO₄ and concentrated in vacuum. The residue was purified with PE/EA=10:1 (3×50 mL) to afford compound 128 as yellow solid (3.0 g, 46% yield).

Example 108: Synthesis of (Z)-2-(7-bromo-1,5-naphthyridin-2-yl)-1-(3,4-difluorophenyl)-3-(dimethylamino)prop-2-en-1-one (129)

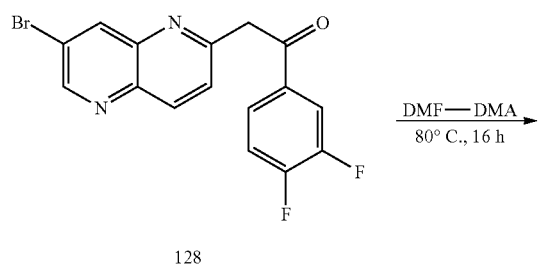

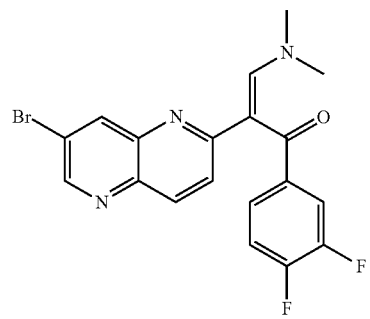

To a solution of compound 128 (3.0 g, 8.3 mmol) in DMF-DMA (60 mL) was stirred for 16 h at 80° C. under N₂ atmosphere. The mixture was concentrated in vacuum to obtain crude compound 129 (4.0 g) as black oil which was used in directly in next step of synthesis. [M+H]⁺ calcd for C₁₉H₁₄BrF₂N₃O, 418.04, found 418.1.

Example 109: Synthesis of 7-bromo-2-(3-(3,4-difluorophenyl)-1H-pyrazol-4-yl)-1,5-naphthyridine (130)

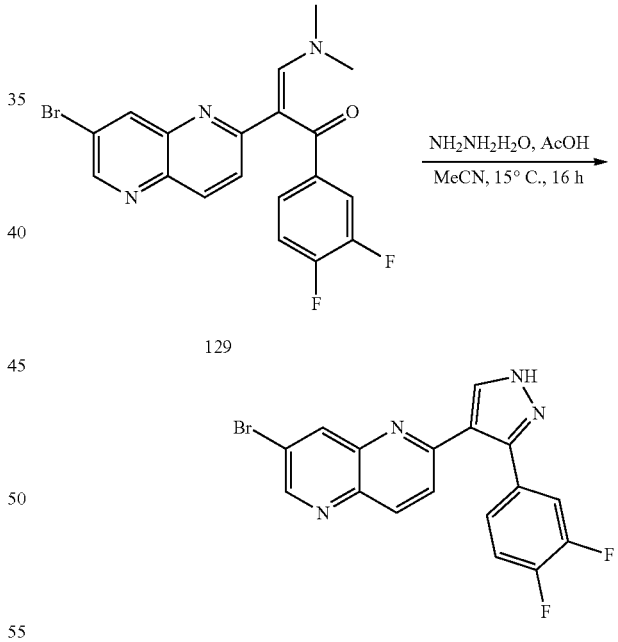

To a solution of compound 129 (4.0 g, 5.1 mmol, 53%) in MeCN (60 mL) was added AcOH (2.1 g, 36.2 mmol) and NH₂NH₂ H₂O (1.4 g, 28.1 mmol). The mixture was stirred at 15° C. for 16 h. The reaction was filtered and the filter caker was washed with MeCN (3×50 mL), then washed with H₂O (3×50 mL). The filter caker was concentrated in vacuum to obtain title compound 130 as yellow solid (1.8 g, 57% yield, 78% purity). [M+H]⁺ calcd for C₁₇H₉BrF₂N₄ 387.01, found 386.9.

Example 110: Synthesis of 7-bromo-2-(3-(3,4-difluorophenyl)-1-(tetrahydro-2H-pyran-2-yl)-1H-pyrazol-4-yl)-1,5-naphthyridine (131)

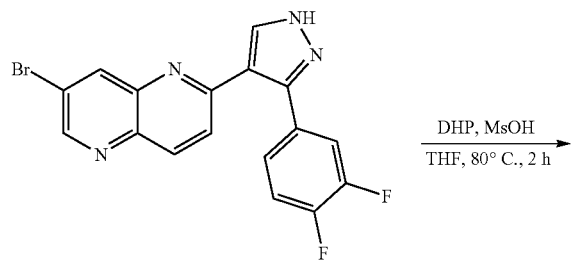

To a solution of compound 130 (1.8 g, 4.95 mmol) in THF (30 mL) was added MsOH (six drops, catalytic amount) and DHP (2.0 g, 23.25 mmol). The mixture was stirred for 2 h at 80° C. under N₂ atmosphere. The reaction was diluted with sat. NaHCO₃aq (50 mL) and extracted with EA (3×80 mL). The combined organic layers were dried (Na₂SO₄) and concentrated in vacuum. The residue was purified by column to yield compound 131 as yellow solid (1.8 g, 64% yield, 99% purity). [M+H]⁺ calcd for C₂₂H₁₇BrF₂N₄O 471.06, found 471.2. ¹H NMR (400 MHz, DMSO-d₆) δ 9.00 (d, J=2.2 Hz, 1H), 8.69 (s, 1H), 8.45 (dd, J=2.2, 0.9 Hz, 1H), 8.38 (dd, J=8.9, 0.9 Hz, 1H), 7.90 (d, J=8.9 Hz, 1H), 7.75-7.64 (m, 1H), 7.53-7.40 (m, 2H), 5.55 (dd, J=9.9, 2.3 Hz, 1H), 4.05-3.97 (m, 1H), 3.78-3.63 (m, 1H), 2.27-2.12 (m, 1H), 2.08-1.95 (m, 2H), 1.73 (s, 1H), 1.59 (h, J=4.2 Hz, 2H).

Example 111: Synthesis of tert-butyl 4-iodo-1H-pyrazole-1-carboxylate (133)

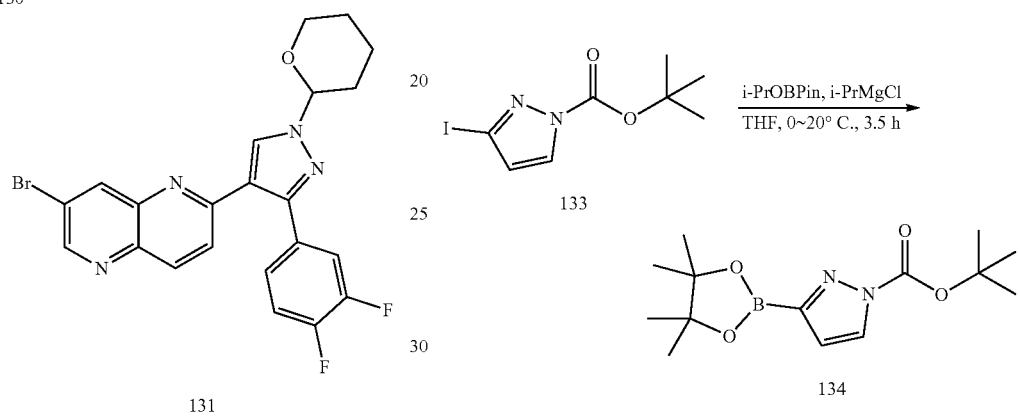

To a mixture of compound 132 (20.0 g, 103 mmol) and Boc₂O (34.0 g, 155 mmol) in THF (200 mL) was added DMAP (1.3 g, 10.3 mmol). The mixture was stirred at 15° C. for 3 h and combined with two additional reactions, quenched with H₂O (100 mL), and extracted with EA (3×200 mL). The organic layer was dried over Na₂SO₄, concentrated under reduced pressure. The residue was purified by column to give compound 133 as white solid (25.8 g, 76% yield, 99% purity). ¹H NMR (400 MHz, CDCl₃) δ 8.15 (1H, s), 7.70 (1H, s), 1.65 (9H, s).

Example 112: Synthesis of tert-butyl 3-(4,4,5,5-tetramethyl-1,3,2-dioxaborolan-2-yl)-1H-pyrazole-1-carboxylate (134)

To a mixture of compound 133 (23.8 g, 80.9 mmol), i-PrOBPin (22.6 g, 121 mmol) in THF (300 mL) was added i-PrMgCl (81 mL, 162 mmol) at 0° C. The reaction was stirred at 20° C. for 3.5 h. The reaction was quenched with H₂O (50 mL), extracted with DCM (2×300 mL). The combined organic layer was dried over Na₂SO₄, concentrated under reduced pressure and dried in vacuum to give crude produce 134, used directly in next step as white solid (20.0 g, 60% yield, 71% purity).

Example 113: Synthesis of 2-(3-(3,4-difluorophenyl)-1-(tetrahydro-2H-pyran-2-yl)-1H-pyrazol-4-yl)-7-(1H-pyrazol-4-yl)-1,5-naphthyridine (135)

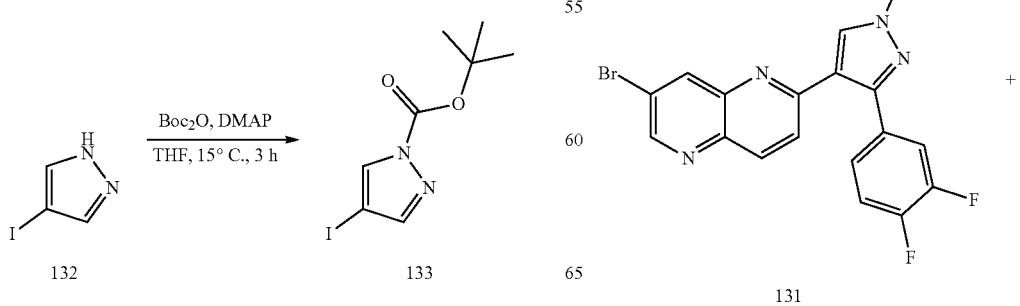

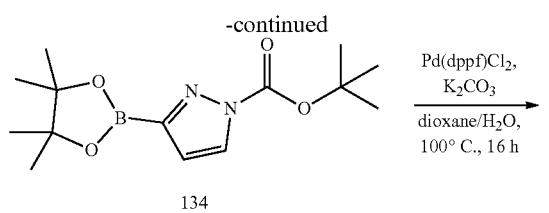

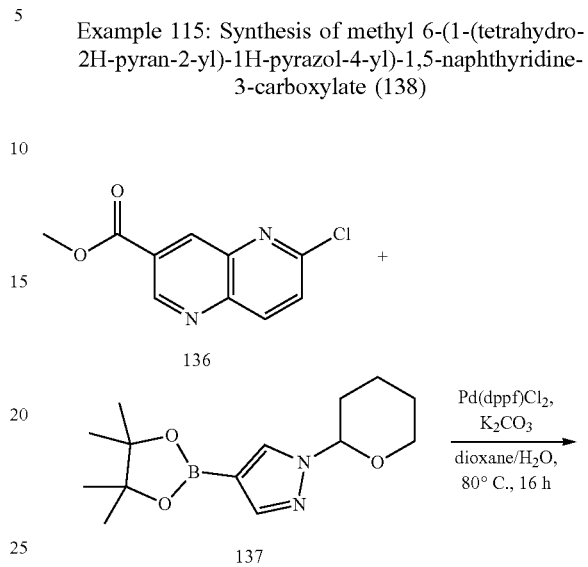

A mixture of Compound 131 (1.5 g, 3.18 mmol), compound 134 (4.0 g, 9.55 mmol), Pd(dppf)Cl$_2$ (466 mg, 0.637 mmol) and K$_2$CO$_3$ (880 mg, 6.37 mmol) in dioxane (20 mL) and H$_2$O (4 mL) was stirred at 100° C. under N$_2$ for 16 h. The mixture was combined with two additional reactions. The combined mixture was concentrated under reduced pressure. The residue was purified by column to give product 135 as light yellow solid (1.2 g, 59% yield, 97% purity). [M+H]$^+$ calcd for C$_{25}$H$_{20}$F$_2$N$_6$O 459.17, found 459.3. $^1$H NMR (400 MHz, Chloroform-d) δ 9.12 (d, J=2.2 Hz, 1H), 8.42 (t, J=2.2, 0.9 Hz, 1H), 8.32 (s, 1H), 8.21 (dd, J=8.8, 0.9 Hz, 1H), 8.09 (s, 2H), 7.76-7.65 (m, 2H), 7.38 (t, J=8.8 Hz, 1H), 5.55 (dd, J=6.9, 5.5 Hz, 1H), 4.21-4.13 (m, 1H), 3.78 (td, J=11.0, 3.0 Hz, 1H), 2.22 (q, J=5.6, 4.7 Hz, 2H), 2.11 (s, 2H), 1.88-1.50 (m, 2H).

Example 114: Synthesis of methyl 6-chloro-1,5-naphthyridine-3-carboxylate (136)

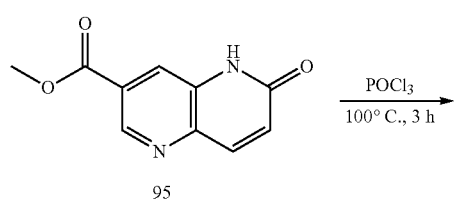

A solution of 95 (20.0 g, 44.0 mmol, 45% purity) in POCl$_3$ (200 mL) was stirred at 100° C. for 3 h. The mixture was poured into ice water and basified to pH 8 with sat. NaHCO$_3$aq. The resulting solid was filtered and trituration (PE:EA=5:1, 3×30 mL) to obtain crude 136 (5.2 g, 60% purity) as black solid. [M+H]$^+$ calcd for C$_{10}$H$_7$ClN$_2$O$_2$ 223.02, found 222.9.

Example 115: Synthesis of methyl 6-(1-(tetrahydro-2H-pyran-2-yl)-1H-pyrazol-4-yl)-1,5-naphthyridine-3-carboxylate (138)

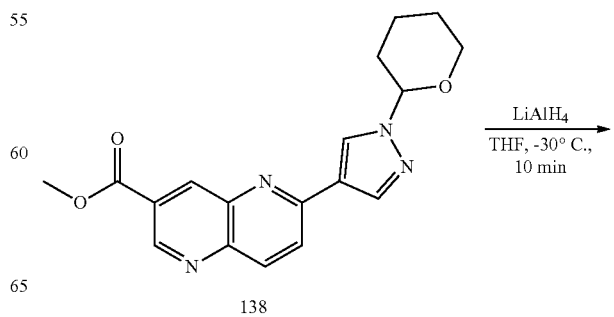

A mixture of 136 (5.2 g, 23.35 mmol), 137 (8.4 g, 30.36 mmol), K$_2$CO$_3$ (6.4 g, 46.70 mmol) and Pd(dppf)Cl$_2$ (1.7 g, 2.3 mmol) in dioxane (90 mL) and H$_2$O (15 mL) was stirred at 80° C. for 16 h under N$_2$. The mixture was concentrated in vacuum and purified by column (10%-100% of EA in PE) to obtain 138 (5.2 g, 29% yield, 85% purity) as a brown solid. [M+H]$^+$ calcd for C$_{18}$H$_{18}$N$_4$O$_3$ 339.14, found 339.0.

Example 116: Synthesis of (6-(1-(tetrahydro-2H-pyran-2-yl)-1H-pyrazol-4-yl)-1,5-naphthyridin-3-yl)methanol (139)

-continued

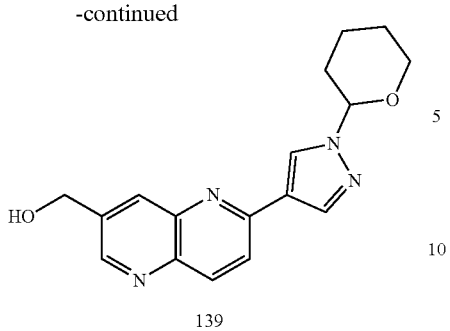
139

To a solution of 138 (4.2 g, 12.40 mmol) in THF (240 mL) stirred at −30° C. was added LiAlH$_4$ (941 mg, 24.80 mmol) in portions, the mixture was stirred at −30° C. for 10 min. The mixture was combined with another batch of the same reaction (starting with 2.0 g of 138), and the combined mixture was quenched with sat. sodium potassium tartrate (200 mL), then extracted with EA (3×300 mL). The combined organic layer was concentrated in vacuum and purified by column to obtain 139 (5.0 g, 94% yield) as yellow solid.

Example 117: Synthesis of 7-(((tert-butyldimethyl-silyl)oxy)methyl)-2-(1-(tetrahydro-2H-pyran-2-yl)-1H-pyrazol-4-yl)-1,5-naphthyridine (140)

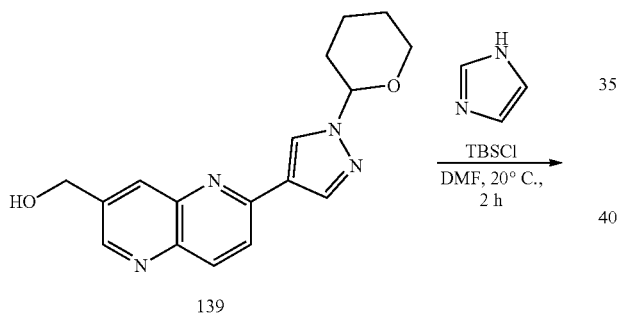
139 → 140

To a solution of 139 (3.0 g, 9.67 mmol) in DMF (50 mL) was added 1H-imidazole (2.0 g, 29.01 mmol) and TBSCl (4.4 g, 29.01 mmol), the mixture was stirred at 20° C. for 2 h. The mixture (combined with another batch of the same reaction starting from 2.0 g of 139) was diluted with H$_2$O (80 mL), extracted with EA (3×100 mL). The combined organic layers were washed with brine (3×150 mL), dried over Na$_2$SO$_4$ and concentrated in vacuum. The residue was purified by column (20-50% of EA in PE) to obtain 140 (6.3 g, 92% yield) as yellow oil.

Example 118: Synthesis of 7-(((tert-butyldimethyl-silyl)oxy)methyl)-2-(3-iodo-1-(tetrahydro-2H-pyran-2-yl)-1H-pyrazol-4-yl)-1,5-naphthyridine (141)

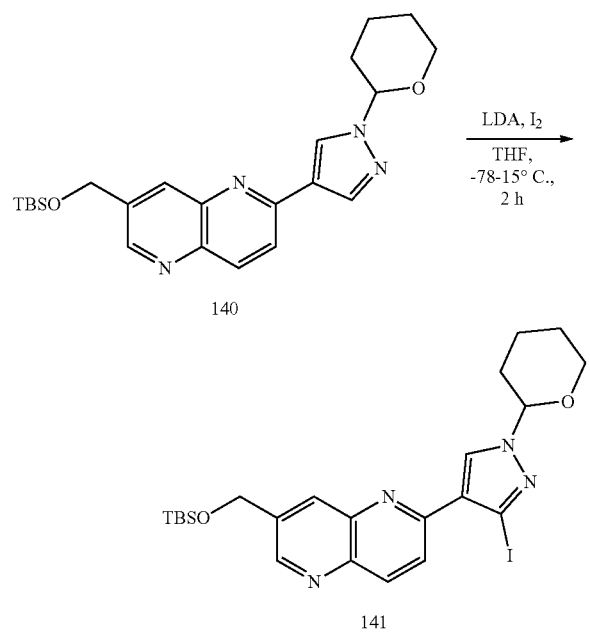
140 → 141

To a solution of 140 (11×200 mg, 11×0.47 mmol) in THF (11×10 mL) was added dropwise LDA (11×0.59 mL, 11×1.17 mmol) (in 2 min) stirred at −78° C. for 0.5 h. Then I$_2$ (11×239 mg, 11×0.94 mmol) dissolved in THF (11×2 mL) was added dropwise. The mixture was stirred at 15° C. for 1.5 h. The combined mixture was quenched with sat. aq. NH$_4$Cl (200 mL) and extracted with EA (2×200 mL). The combined organic layer was concentrated in vacuum and purified by column (0-30% of EA in PE) to obtain 141 (2.3 g, 80% yield).

Example 119: Synthesis of (6-(3-iodo-1-(tetrahydro-2H-pyran-2-yl)-1H-pyrazol-4-yl)-1,5-naphthyridin-3-yl)methanol (142)

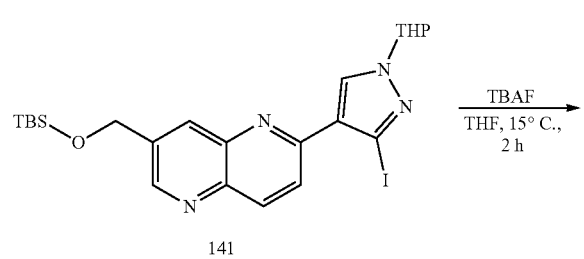
141

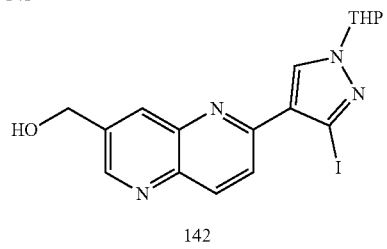
142

To a mixture of 141 (3.2 g, 5.81 mmol) in THF (64 mL) was added TBAF (11.6 mL, 11.62 mmol). The mixture was stirred at 15° C. for 2 h. The mixture (combined with another batch of the same reaction starting with 500 mg of 141) was diluted with H$_2$O (100 mL) and extracted with EA (3×80 mL). The combined organic layer concentrated in vacuum and purified by column (0-10% of EA in PE) to obtain 142 (2.9 g, 96% yield, 97% purity) as red solid. [M+H]$^+$ calcd for C$_{17}$H$_{17}$IN$_4$O$_2$ 437.04, found 437.0.

Example 120: Synthesis of 6-(3-iodo-1-(tetrahydro-2H-pyran-2-yl)-1H-pyrazol-4-yl)-1,5-naphthyridine-3-carbaldehyde (143)

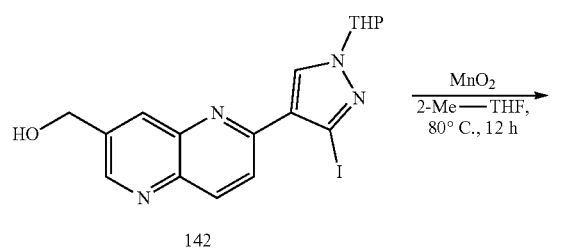

A mixture of 142 (5×480 mg, 5×1.10 mmol) and MnO$_2$ (5×478 mg, 5×5.50 mmol) in 2-Me-THF (5×10 mL) was stirred at 80° C. for 12 h. The mixture was filtered and concentrated in vacuum. The residue was purified by column (10%-60% of EA in PE) to obtain 143 (1.7 g, 71% yield) as light yellow solid.

Example 121: Synthesis of 6-(3-iodo-1-(tetrahydro-2H-pyran-2-yl)-1H-pyrazol-4-yl)-1,5-naphthyridine-3-carbaldehyde (145)

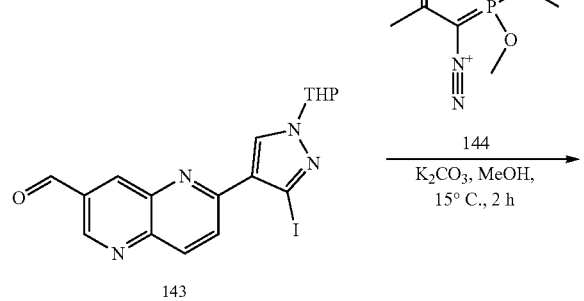

-continued

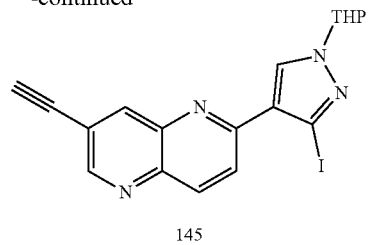

145

A mixture of 143 (900 mg, 2.07 mmol) and K$_2$CO$_3$ (572 mg, 4.14 mmol) in MeOH (15 mL) was added 144 (596 mg, 3.10 mmol) stirred at 15° C. for 2 h. The mixture (combined with another batch of the same reaction starting with 800 mg of 143) was diluted with H$_2$O (50 mL) and extracted with EA (4×50 mL). The combined organic layer was concentrated in vacuum and purified by column (0-30% of EA in PE), then purified by trituration (PE/EA=10/1, 3×10 mL) to obtain 145 (850 mg, 43% yield, 95% purity) as white solid. [M+H]$^+$ calcd for C$_{18}$H$_{15}$IN$_4$O 431.0, found 430.9. $^1$H NMR (400 MHz, DMSO-d$_6$) δ 8.98 (d, J=2.0 Hz, 1H), 8.52-8.42 (m, 2H), 8.33 (s, 1H), 8.26 (d, J=8.8 Hz, 1H), 5.63 (dd, J=9.8, 2.5 Hz, 1H), 4.67 (s, 1H), 4.02-3.94 (m, 1H), 3.74-3.62 (m, 1H), 2.46-2.35 (m, 1H), 2.05 (d, J=13.2 Hz, 1H), 1.96 (dd, J=13.1, 3.1 Hz, 1H), 1.76 (s, 1H), 1.58 (s, 2H).

Example 122: Synthesis of 6-(3-(3,4-difluorophenyl)-1H-pyrazol-4-yl)-N-(2-(4-isopropylpiperazin-1-yl)ethyl)-1,5-naphthyridin-3-amine (8-1)

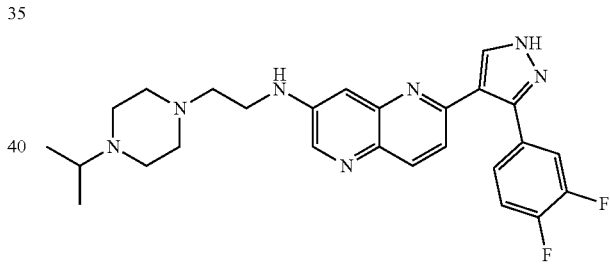

To a vial charged with 131 (35.2 mg, 0.075 mmol) and cesium carbonate (73.0 mg, 0.224 mmol) was added BrettPhos Pd G4 (6.88 mg, 7.47 µmol), BrettPhos (4.01 mg, 7.47 µmol) and 2-(4-isopropylpiperazin-1-yl)ethan-1-amine (17.68 µL, 0.097 mmol). The resulting mixture was purged with N$_2$ before degassed dioxane (299 µL) was added. The resulting yellow reaction mixture was stirred at 105° C. overnight for 15 h. The mixture was filtered through a plug of celite, washed on a filter with THF (5 mL) and the filtrates were concentrated in vacuum. The residue was treated with TFA (1 mL) at 55° C. for 1 h. The resulting mixture was concentrated and purified by preparative HPLC chromatography using a gradient (16 to 31%) of acetonitrile in water with 0.05% trifluoroacetic acid to yield a TFA salt of the title compound (28.5 mg) as a yellow solid. [M+H]$^+$ calcd for C$_{26}$H$_{29}$F$_2$N$_7$ 478.25, found 478.2. $^1$H NMR (400 MHz, Methanol-d$_4$) δ 8.64 (d, J=2.6 Hz, 1H), 8.41 (d, J=8.6 Hz, 1H), 8.32 (s, 1H), 7.57-7.47 (m, 1H), 7.39 (d, J=8.6 Hz, 1H), 7.37-7.28 (m, 2H), 7.06 (d, J=2.6 Hz, 1H), 3.58-3.46 (m, 1H), 3.42 (t, J=6.1 Hz, 2H), 3.26-3.09 (m, 4H), 2.83 (t, J=6.1 Hz, 2H), 2.66-2.36 (m, 4H), 1.37 (d, J=6.6 Hz, 6H).

Example 123: Synthesis of 2-(3-(3,4-difluorophenyl)-1H-pyrazol-4-yl)-7-(4-(4-methylpiperazin-1-yl)piperidin-1-yl)-1,5-naphthyridine (8-3)

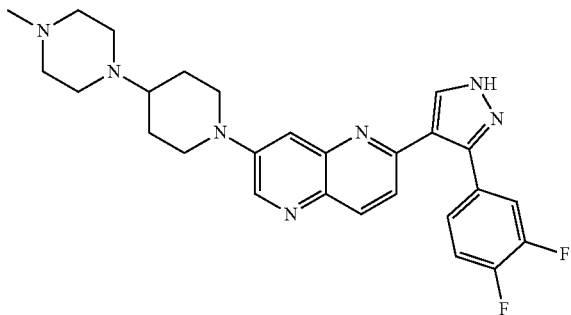 [SMILES: CN1CCN(C2CCN(c3cnc4ccc(-c5c[nH]nc5-c5ccc(F)c(F)c5)nc4c3)CC2)CC1]

To a vial containing 131 (35 mg, 0.074 mmol) was added 1-methyl-4-(piperidin-4-yl)piperazine (17.70 mg, 0.097 mmol), 2-dicyclohexylphosphino-2',6'-diisopropoxybiphenyl, (3.47 mg, 7.43 µmol) and RuPhos Pd G2 (5.77 mg, 7.43 µmol) followed by potassium tert-butoxide (25.00 mg, 0.223 mmol) and the resulting mixture was purged with nitrogen before being treated with dioxane (371 µL) and being stirred at 90° C. for 14 h. The mixture was filtered through a plug of celite. washed on a filter with 3 mL THF, filtrates were concentrated and treated with TFA 1 mL at 55° C. for 1 h. The resulting mixture was concentrated and purified by preparative HPLC chromatography using a gradient (15 to 45%) of acetonitrile in water with 0.05% trifluoroacetic acid to yield a TFA salt of the title compound (14.6 mg) as a light yellow solid. [M+H]$^+$ calcd for $C_{27}H_{29}F_2N_7$ 490.25, found 490.3. $^1$H NMR (400 MHz, Methanol-$d_4$) δ 9.04 (d, J=2.8 Hz, 1H), 8.48 (dd, J=8.7, 0.7 Hz, 1H), 8.39 (s, 1H), 7.58-7.43 (m, 3H), 7.40-7.27 (m, 2H), 4.24 (d, J=13.3 Hz, 2H), 3.56-3.44 (m, 3H), 3.42-3.32 (m, 2H), 3.16 (t, J=11.7 Hz, 4H), 3.10-2.99 (m, 2H), 2.88 (s, 3H), 2.15 (d, J=12.5 Hz, 2H), 1.85-1.71 (m, 2H).

Example 124: Synthesis of 2-(4-(6-(3-(3,4-difluorophenyl)-1H-pyrazol-4-yl)-1,5-naphthyridin-3-yl)-1H-pyrazol-1-yl)-N-methylethan-1-amine (8-12)

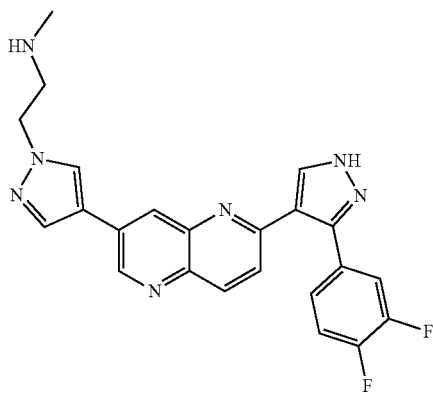 [SMILES: CNCCn1cc(-c2cnc3ccc(-c4c[nH]nc4-c4ccc(F)c(F)c4)nc3c2)cn1]

To a vial containing 135 (35.2 mg, 0.075 mmol) was added tert-butyl methyl(2-(4-(4,4,5,5-tetramethyl-1,3,2-dioxaborolan-2-yl)-1H-pyrazol-1-yl)ethyl)carbamate (31.5 mg, 0.090 mmol) followed by potassium phosphate tribasic (47.6 mg, 0.224 mmol), Xphos Pd G4 (6.43 mg, 7.47 µmop, and Xphos (3.56 mg, 7.47 µmol. The resulting mixture was purged with nitrogen before degassed water (149 µL) and 1,4-dioxane (149 µL) was added. The vial was capped and stirred at 105° C. for 1.5 h. The reaction was then cooled, filtered through a plug of celite, washed with THF (5 mL) and concentrated in vacuo. The resulting residue was treated with 1.2 mL of TFA and stirred at 55° C. for 1 h. The crude product was concentrated in vacuo, and purified by preparative HPLC chromatography using a gradient (21 to 36%) of acetonitrile in water with 0.05% trifluoroacetic acid to yield a TFA salt of the title compound (25.2 mg). [M+H]+ calcd for $C_{23}H_{19}F_2N_7$ 432.17 found 432.2. $^1$H NMR (400 MHz, Methanol-$d_4$) δ 9.17 (d, J=2.2 Hz, 1H), 8.39-8.37 (m, 2H), 8.29 (dd, J=8.8, 0.8 Hz, 1H), 8.28 (s, 1H), 8.20 (d, J=0.7 Hz, 1H), 7.69 (d, J=8.8 Hz, 1H), 7.54 (ddd, J=11.6, 7.7, 1.8 Hz, 1H), 7.39-7.24 (m, 2H), 4.64-4.56 (m, 2H), 3.62-3.54 (m, 2H), 2.78 (s, 3H).

Example 125: Synthesis of 2-(4-(6-(3-(3,4-difluorophenyl)-1H-pyrazol-4-yl)-1,5-naphthyridin-3-yl)-1H-pyrazol-1-yl)ethan-1-ol (8-21)

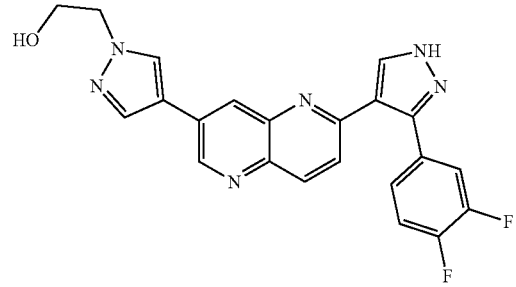 [SMILES: OCCn1cc(-c2cnc3ccc(-c4c[nH]nc4-c4ccc(F)c(F)c4)nc3c2)cn1]

To a vial containing 2-chloroethoxytrimethylsilane (10.82 mg, 0.071 mmol) was added 2-(3-(3,4-difluorophenyl)-1-(tetrahydro-2H-pyran-2-yl)-1H-pyrazol-4-yl)-7-(1H-pyrazol-4-yl)-1,5-naphthyridine (25 mg, 0.055 mmol) followed by cesium carbonate (35.5 mg, 0.109 mmol). The resulting mixture was purged with nitrogen before acetonitrile (500 µL) was added and the vial was capped and stirred at 85° C. for 18 h. The reaction was then cooled and concentrated in vacuo. The resulting residue was treated with 1 mL of TFA and stirred at 50° C. for 1 h. The crude product was concentrated in vacuo, and purified by preparative HPLC chromatography using a gradient (10 to 45%) of acetonitrile in water with 0.05% trifluoroacetic acid to yield a TFA salt of the title compound (4.6 mg). [M+H]+ calcd for $C_{22}H_{16}F_2N_6O$ 419.14, found 419.1. $^1$H NMR (400 MHz, Methanol-$d_4$) δ 9.19 (d, J=2.1 Hz, 1H), 8.39 (d, J=2.0 Hz, 1H), 8.35 (s, 1H), 8.31-8.28 (m, 2H), 8.13 (s, 1H), 7.67 (d, J=8.8 Hz, 1H), 7.54 (ddd, J=11.6, 7.5, 1.5 Hz, 1H), 7.37-7.29 (m, 2H), 4.32 (t, J=5.3 Hz, 2H), 3.95 (t, J=5.3 Hz, 2H).

Example 126: Synthesis of 2-(3-(3,4-difluorophenyl)-1H-pyrazol-4-yl)-7-(1-methyl-2,5-dihydro-1H-pyrrol-3-yl)-1,5-naphthyridine (8-22)

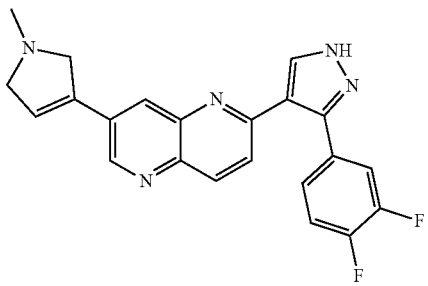 [SMILES: CN1CC=C(c2cnc3ccc(-c4c[nH]nc4-c4ccc(F)c(F)c4)nc3c2)C1]

To a vial charged with compound 8-20 (10.62 mg, 0.028 mmol) dissolved in methanol (0.25 mL) was added formaldehyde 37% in H$_2$O (4.21 µL, 0.057 mmol) followed by sodium triacetoxyborohydride (17.99 mg, 0.085 mmol). The resulting mixture was capped and let stir at RT for 16 h. Afterwards, the reaction was quenched by the addition of H$_2$O, and concentrated in vacuo. The resulting material was purified by preparative HPLC chromatography using a gradient (22 to 40%) of acetonitrile in water with 0.05% trifluoroacetic acid to yield a TFA salt of the title compound (6.6 mg). [M+H]+ calcd for C$_{22}$H$_{17}$F$_2$N$_5$ 390.15, found 390.1.

Example 127: Synthesis of 4-(6-(3-(3,4-difluorophenyl)-1H-pyrazol-4-yl)-1,5-naphthyridin-3-yl)-N-isopropylcyclohex-3-en-1-amine (8-24)

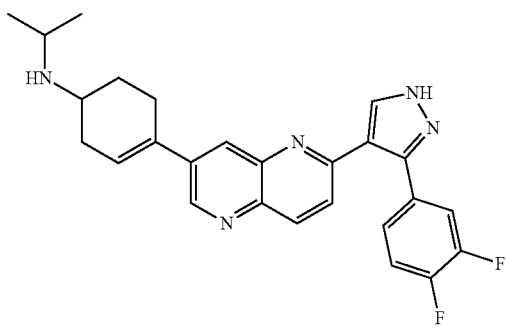 [SMILES: CC(C)NC1CC=C(c2cnc3ccc(-c4c[nH]nc4-c4ccc(F)c(F)c4)nc3c2)CC1]

To a vial charged with compound 8-19 (10.58 mg, 0.026 mmol) dissolved in methanol (0.25 mL) was added acetone in H$_2$O (3.85 µL, 0.052 mmol) followed by sodium triacetoxyborohydride (16.67 mg, 0.079 mmol). The resulting mixture was capped and let stir at RT for 16 h. Afterwards, the reaction was quenched by the addition of H$_2$O, and concentrated in vacuo. The resulting material was purified by preparative HPLC chromatography using a gradient (15 to 55%) of acetonitrile in water with 0.05% trifluoroacetic acid to yield a TFA salt of the title compound (6.4 mg). [M+H]+ calcd for C$_{26}$H$_{25}$F$_2$N$_5$ 446.21 found 446.0.

Example 128: Synthesis of 2-(4-(6-(3-(3,4-difluorophenyl)-1H-pyrazol-4-yl)-1,5-naphthyridin-3-yl)-1H-1,2,3-triazol-1-yl)-N-methylethan-1-amine (8-27)

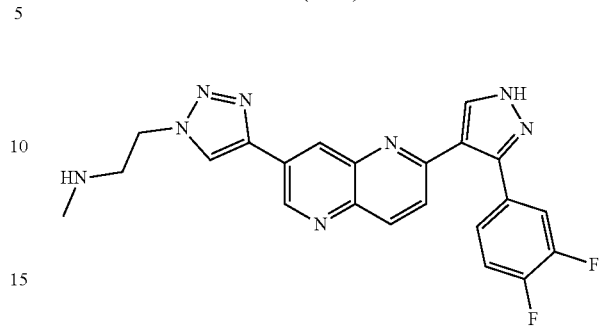

To a vial containing compound 145 (25 mg, 0.058 mmol) and copper(I) thiophene-2-carboxylate (14.4 mg, 0.075 mmol) was added DCM (0.2 mL). The vial was capped and stirred at 55° C. for 1 h. Afterwards, tert-butyl (2-azidoethyl)(methyl)carbamate (12.8 mg, 0.064 mmol) was added, and let stir at 55° C. for 1 h. The reaction mixture was concentrated in vacuo, yielding a crude mixture containing tert-butyl (2-(4-(6-(3-iodo-1-(tetrahydro-2H-pyran-2-yl)-1H-pyrazol-4-yl)-1,5-naphthyridin-3-yl)-1H-1,2,3-triazol-1-yl)ethyl)(methyl)carbamate. To this material was added sodium carbonate (15.13 mg, 0.143 mmol), Pd(dppf)Cl$_2$ (6.96 mg, 9.52 µmol), and 3,4-difluorophenylboronic acid (9.02 mg, 0.057 mmol) followed by 1,4-dioxane (317 µL) and H$_2$O (159 µL). The reaction was sparged with nitrogen for 5 min before being sealed and stirred at 85° C. for 16 h. Afterwards, the reaction was cooled and concentrated in vacuo. To the dried material was added TFA (0.2 mL) and let stir at 50° C. for 1 h. Afterwards, the reaction was cooled and concentrated in vacuo, and purified by preparative HPLC chromatography using a gradient (10 to 50%) of acetonitrile in water with 0.05% trifluoroacetic acid to yield a TFA salt of the title compound (1.2 mg). [M+H]+ calcd for C$_{22}$H$_{18}$F$_2$N$_8$ 433.16 found 433.0.

Example 129: Synthesis of 1-(7-bromo-1,5-naphthyridin-2-yl)-2-(3,4-difluorophenyl)ethane-1,2-dione (146)

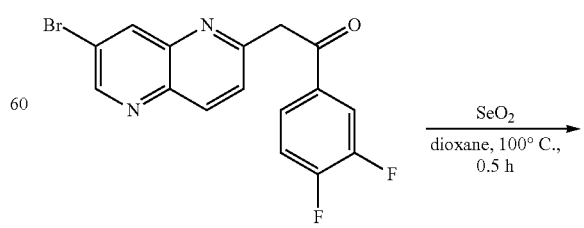

128

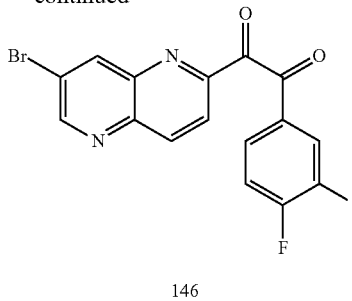

146

A solution of 128 (7.2 g, 19.8 mmol) and selenium dioxide (11.0 g, 99.1 mmol) in dioxane (140 mL) was stirred at 100° C. for 0.5 h. The mixture was filtered. The filtrate was concentrated in vacuum to obtain crude 146 as black oil (14.7 g, crude, 51% purity). [M+H]+ calcd for $C_{16}H_7BrF_2N_2O_2$ 376.98, found 376.8.

Example 130: Synthesis of 7-bromo-2-(5-(3,4-difluorophenyl)-1H-imidazol-4-yl)-1,5-naphthyridine (147)

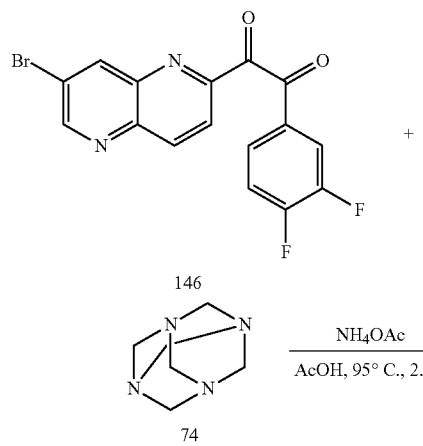

A solution of 146 (14.7 g, 19.8 mmol), 74 (8.3 g, 59.4 mmol) and ammonium acetate (9.1 g, 119 mmol) in acetic acid (120 mL) was stirred at 95° C. for 2.5 h. The reaction mixture was concentrated in vacuum and basified with sat. aq. sodium bicarbonate to pH 8. The mixture was extracted with EA (3×500 mL). Combined organic phase was washed with brine (2×100 mL), dried over sodium sulfate, filtered, and concentrated under vacuum to give a residue that was purified by silica gel column chromatography (EA in PE 20-60%) to afford 147 as yellow solid (3.5 g, 46%).

Example 131: Synthesis of 7-bromo-2-(5-(3,4-difluorophenyl)-1-((2-(trimethylsilyl)ethoxy)methyl)-1H-imidazol-4-yl)-1,5-naphthyridine (148) and 7-bromo-2-(4-(3,4-difluorophenyl)-1-((2-(trimethylsilyl)ethoxy)methyl)-1H-imidazol-5-yl)-1,5-naphthyridine (149)

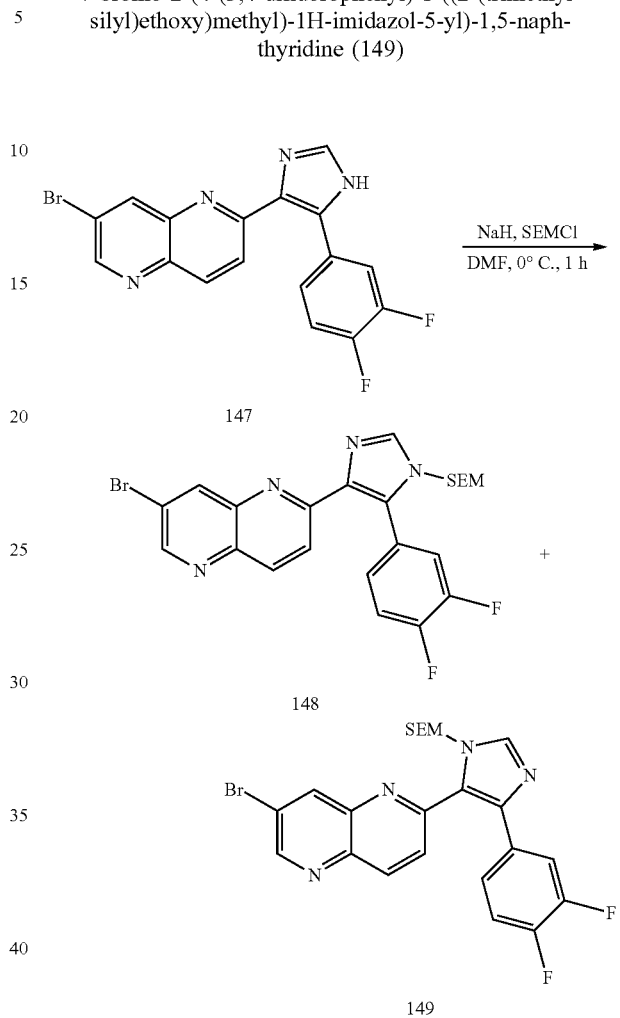

To a solution of 147 (3.5 g, 9.04 mmol) in DMF (50 mL) was added sodium hydride (724 mg, 18.1 mmol) at 0° C. under $N_2$. The mixture was stirred at 0° C. for 0.5 h before SEM-chloride (1.8 g, 10.8 mmol) was added at 0° C. under $N_2$. The reaction was stirred at 0° C. for another 0.5 h and quenched with sat. aq. ammonium chloride (50 mL). The mixture was extracted with EA (3×100 mL). Combined organic phase was washed with brine (2×50 mL), dried over sodium sulfate, filtered, and concentrated under vacuum. The residue was purified by column to afford 148 as yellow oil (740 mg, 16% yield, 100% purity) and 149 as yellow solid (1.9 g, 41% yield, 100% purity). [M+H]+ calcd for $C_{23}H_{23}BrF_2N_4OSi$ 517.09, found 517.2. 1H NMR (400 MHz, Chloroform-d) 148 δ 8.99 (d, J=2.2 Hz, 1H), 8.56 (dd, J=2.2, 0.9 Hz, 1H), 8.27 (dd, J=8.8, 0.9 Hz, 1H), 7.82 (s, 1H), 7.59 (d, J=8.8 Hz, 1H), 7.39 (ddd, J=11.4, 7.7, 2.1 Hz, 1H), 7.22-7.13 (m, 1H), 7.08 (dt, J=10.1, 8.3 Hz, 1H), 5.73 (s, 2H), 3.47-3.37 (m, 2H), 0.84-0.70 (m, 2H), −0.15 (s, 9H). and 1H NMR (400 MHz, Chloroform-d) 149 δ 8.85 (d, J=2.2 Hz, 1H), 8.28 (dd, J=8.9, 0.8 Hz, 1H), 8.28-8.14 (m, 2H), 7.81 (s, 1H), 7.52-7.42 (m, 1H), 7.34-7.21 (m, 2H), 5.17 (s, 2H), 3.65-3.49 (m, 2H), 1.03-0.83 (m, 2H), 0.00 (s, 9H).

Example 132: Synthesis of 6-(5-(3,4-difluorophenyl)-1H-imidazol-4-yl)-N-(2-(piperazin-1-yl)ethyl)-1,5-naphthyridin-3-amine (9-1)

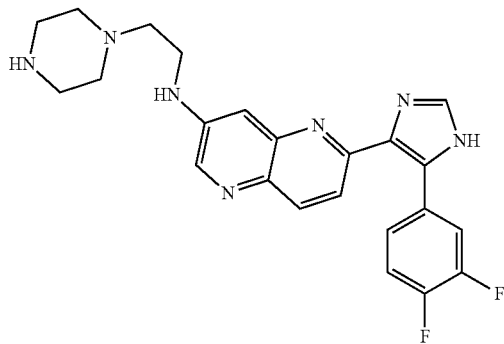 [SMILES: Fc1ccc(-c2[nH]cnc2-c2ccc3ncc(NCCN4CCNCC4)cc3n2)cc1F]

A vial containing 148 (30 mg, 0.058 mmol), 4-(2-aminoethyl)-1-boc-piperazine (17.28 mg, 0.075 mmol), BrettPhos Pd G4 (10.67 mg, 0.012 mmol), BrettPhos (6.22 mg, 0.012 mmol), and cesium carbonate (56.7 mg, 0.174 mmol) in 1,4-dioxane (580 µL) was sparged with $N_2$ for 5 min before being heated to 85° C. for 16 h. The reaction mixture was cooled down to RT, filtered through a pad of celite and the filtrate was concentrated in vacuum. 200 µL of 6N aq. hydrochloric acid and 200 µL of dichloroethane were added to the residue and the mixture was heated to 80° C. for 3 hours. The resulting mixture was concentrated and purified by preparative HPLC chromatography using a gradient (6 to 36%) of acetonitrile in water with 0.05% trifluoroacetic acid to yield a TFA salt of the title compound (15.8 mg). [M+H]$^+$ calcd for $C_{23}H_{23}F_2N_7$ 436.20, found 436.1. $^1$H NMR (400 MHz, Methanol-$d_4$) δ 8.61 (d, J=2.8, 1H), 8.60 (s, 1H), 8.28 (d, J=8.7 Hz, 1H), 7.65 (ddd, J=10.2, 7.2, 1.7 Hz, 1H), 7.52-7.44 (m, 2H), 7.43 (d, J=8.7 Hz, 1H), 7.24 (dd, J=2.8, 0.8 Hz, 1H), 3.43 (t, J=6.1 Hz, 2H), 3.29-3.25 (m, 2H), 2.86-2.76 (m, 8H).

Example 133: Synthesis of 2-(4-(6-(5-(3,4-difluorophenyl)-1H-imidazol-4-yl)-1,5-naphthyridin-3-yl)-1H-pyrazol-1-yl)-N-methylethan-1-amine (9-3)

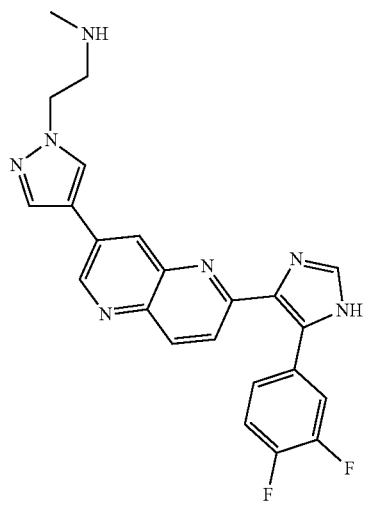 [SMILES: CNCCn1cc(-c2cnc3ccc(-c4nc[nH]c4-c4ccc(F)c(F)c4)nc3c2)cn1]

A vial of 148 (30 mg, 0.058 mmol), tert-butyl methyl(2-(4-(4,4,5,5-tetramethyl-1,3,2-dioxaborolan-2-yl)-1H-pyrazol-1-yl)ethyl)carbamate (26.5 mg, 0.075 mmol), [1,1'-bis(diphenylphosphino)ferrocene]dichloropalladium(II) (8.48 mg, 0.012 mmol), and sodium carbonate (24.58 mg, 0.232 mmol) in 1,4-dioxane (464 µL) and water (116 µL) was sparged with nitrogen for 5 min before being heated to 85° C. for 16 h. The reaction mixture was cooled down to RT, filtered through a pad of celite and the filtrate was concentrated in vacuum. 200 µL of 6N aq. HCl and 200 µL of dichloroethane were added to the residue and the mixture was heated to 80° C. for 3 h. The resulting mixture was concentrated and purified by preparative HPLC chromatography using a gradient (10 to 38%) of acetonitrile in water with 0.05% trifluoroacetic acid to yield a TFA salt of the title compound (25.8 mg). [M+H]$^+$ calcd for $C_{23}K_9F_2N_7$ 432.17, found 432.2. $^1$H NMR (400 MHz, Methanol-$d_4$) δ 9.23 (d, J=2.1 Hz, 1H), 8.65 (s, 1H), 8.53 (dd, J=2.1, 0.9 Hz, 1H), 8.41 (d, J=0.8 Hz, 1H), 8.34 (dd, J=8.9, 0.9 Hz, 1H), 8.23 (d, J=0.8 Hz, 1H), 7.77 (d, J=8.9 Hz, 1H), 7.68 (ddd, J=11.4, 7.4, 1.8 Hz, 1H), 7.53-7.38 (m, 2H), 4.65-4.57 (m, 2H), 3.63-3.55 (m, 2H), 2.79 (s, 3H).

Example 134: Synthesis of 2-methyl-7-(1-(tetrahydro-2H-pyran-2-yl)-1H-pyrazol-4-yl)-1,5-naphthyridine (150)

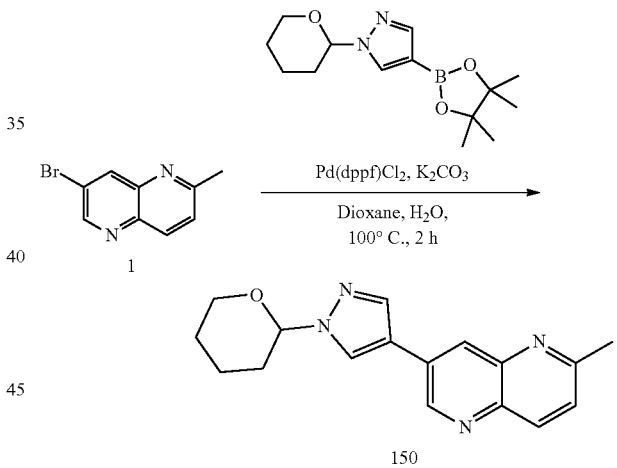

A mixture of compound 1 (4.8 g, 21.5 mmol) and 1-(tetrahydro-2H-pyran-2-yl)-4-(4,4,5,5-tetramethyl-1,3,2-dioxaborolan-2-yl)-1H-pyrazole (7.2 g, 25.8 mmol), Pd(dppf)Cl$_2$ (1.6 g, 2.2 mmol), potassium carbonate (5.9 g, 43.0 mmol) in dioxane (50 mL) and water (5 mL) was sparged with nitrogen and then stirred at 100° C. for 2 h. The reaction progress was monitored by TLC. The reaction mixture was filtered through a pad of celite. The filtrate was concentrated in vacuum and purified by silica gel column chromatography (EA:PE=1:10 to 1:1) to afford 150 (5.8 g, 87%) as a yellow solid. [M+H]$^+$ calcd for $C_{17}H_{18}N_4O$ 295.15, found 295.1. $^1$H NMR (400 MHz, Chloroform-d) δ 9.07 (d, J=2.1 Hz, 1H), 8.34 (d, J=2.1 Hz, 1H), 8.23 (d, J=8.6 Hz, 1H), 8.06 (s, 1H), 8.00 (s, 1H), 7.45 (d, J=8.6 Hz, 1H), 5.46 (dd, J=8.1, 4.3 Hz, 1H), 4.15-4.06 (m, 1H), 3.75 (td, J=11.0, 3.0 Hz, 1H), 2.77 (s, 3H), 2.16 (q, J=4.4 Hz, 2H), 2.16-2.01 (m, 1H), 1.82-1.52 (m, 3H).

Example 135: Synthesis of 2-(3-(2,4-difluorophenyl)-1H-pyrazol-4-yl)-7-(1H-pyrazol-4-yl)-1,5-naphthyridine (10-1)

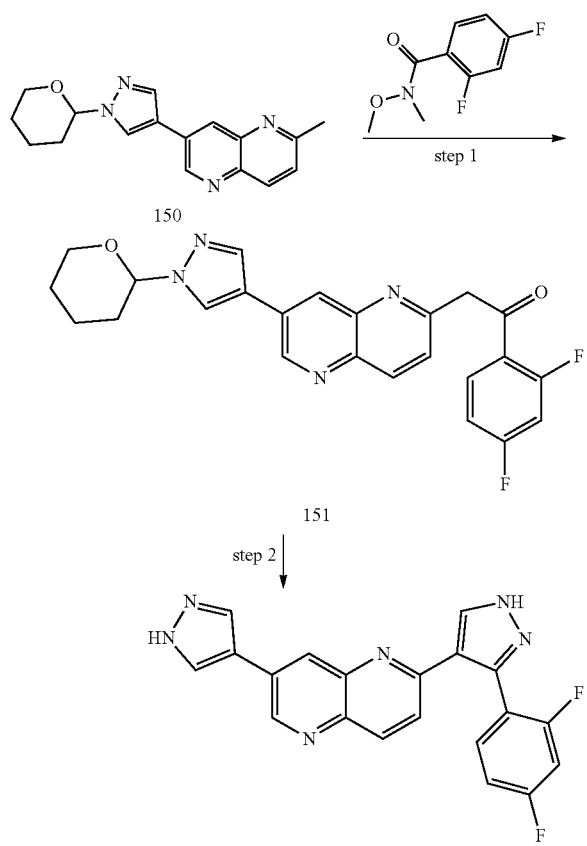

Step 1: In an oven-dried flask was charged 2,4-difluoro-N-methoxy-N-methylbenzamide (54.9 mg, 0.273 mmol) and 150 (80 mg, 0.273 mmol). The resulting mixture was purged with nitrogen and THF (0.7 mL) was added. The mixture was cooled to −78° C. and potassium bis(trimethylsilyl)amide, 0.5 M in toluene (655 µL, 0.328 mmol) was added dropwise over a course of 10 min resulting in a deep red mixture. The resultant mixture was stirred at −78° C. for 2 h. Dry ice bath was removed and the mixture was warmed to room temperature and stirred at room temperature for 2 h before being quenched with water (5 mL). The mixture was extracted with EA (3×7 mL), dried over anhydrous sodium sulfate, concentrated and purified by silica gel column chromatography (EA in hexanes 0 to 100% gradient) to yield intermediate 1-(2,4-difluorophenyl)-2-(7-(1-(tetrahydro-2H-pyran-2-yl)-1H-pyrazol-4-yl)-1,5-naphthyridin-2-yl)ethan-1-one 151 (32 mg, 27%) as a white solid. [M+H]+ calcd for $C_{24}H_{20}F_2N_4O_2$ 435.16, found 435.

Step 2: To a vial containing 151 (32 mg, 0.074 mmol) was added N,N-dimethylformamide dimethyl acetal (250 µL, 1.882 mmol) and the resulting was stirred at 80° C. for 3.5 h before being concentrated. The dark residue was dissolved in ethanol (407 µL) and treated with acetic acid (23 µL, 0.402 mmol) and hydrazine hydrate (20.36 µL, 0.407 mmol). The mixture was stirred at RT for 2 h before being concentrated in vacuum and treated with TFA (0.7 mL) at 50° C. for 1 h. The resulting dark mixture was concentrated and purified by preparative HPLC chromatography using a gradient (20 to 50%) of acetonitrile in water with 0.05% trifluoroacetic acid to yield a TFA salt of the title compound (23.7 mg). [M+H]+ calcd for $C_{20}H_{12}F_2N_6$ 375.12, found 375.1. $^1$H NMR (400 MHz, Acetonitrile-d$_3$) δ 9.02 (s, 1H), 8.40 (s, 1H), 8.27 (dd, J=9.1, 1.8 Hz, 1H), 8.24-8.22 (m, 1H), 7.97 (s, 2H), 7.49 (dt, J=9.1, 1.2 Hz, 1H), 7.40 (dt, J=9.5, 7.7 Hz, 1H), 6.89 (dd, J=9.5, 7.4 Hz, 1H), 6.86-6.79 (m, 1H), 6.34 (s, br 2H).

Example 136: Synthesis of 6-(3-(2,4-difluorophenyl)-1H-pyrazol-4-yl)-N-(2-(4-isopropylpiperazin-1-yl)ethyl)-1,5-naphthyridin-3-amine (10-2)

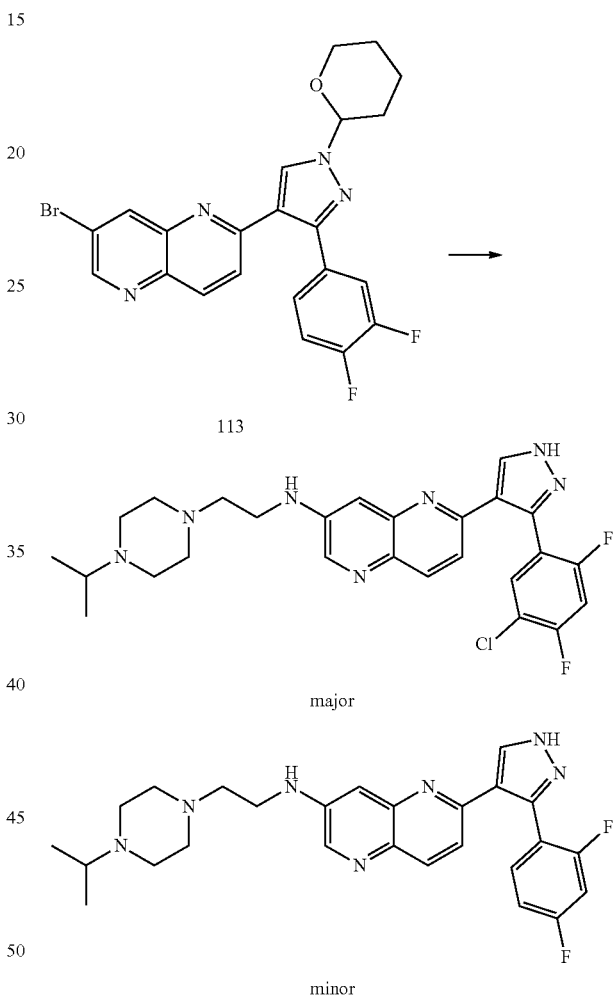

To a vial charged with 113 (100 mg, 0.198 mmol) and 2-(4-isopropyl-piperazin-1-yl)-ethylamine (41.4 µL, 0.227 mmol) was added BrettPhos (10.61 mg, 0.020 mmol), BrettPhos Pd G4 (18.20 mg, 0.020 mmol) and cesium carbonate (193 mg, 0.593 mmol). The resulting mixture was purged with nitrogen and dioxane (791 µL) was added. The resulting yellow reaction mixture was capped with a green cap and stirred at 105° C. overnight. The dark mixture was filtered through a plug of celite, washed with THF (10 mL) and concentrated. The residue was treated with 2 mL of TFA and stirred at 55° C. and for 1 h. The resultant mixture was concentrated, re-dissolved in 1:2 ACN:H$_2$O (10 mL), filtered and purified by preparative HPLC chromatography using a gradient (20 to 35%) of acetonitrile in water with 0.05% trifluoroacetic acid to yield a TFA salt of the title compound as a minor side product (2.1 mg). [M+H]+ calcd for C26H29F2N7 478.25, found 478.0.

Example 137: Synthesis of 7-bromo-2-(3-(2-fluorophenyl)-1-(tetrahydro-2H-pyran-2-yl)-1H-pyrazol-4-yl)-1,5-naphthyridine (154)

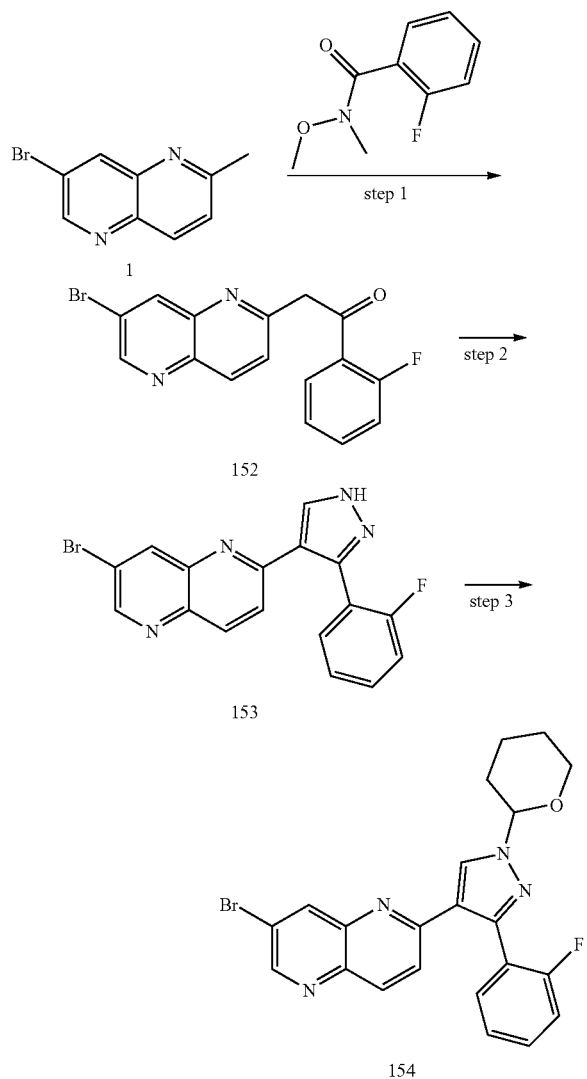

Step 1: In an oven-dried flask was charged 2-fluoro-N-methoxy-N-methylbenzamide (82 mg, 0.448 mmol) and 1 (100 mg, 0.448 mmol). The resulting mixture was purged with nitrogen and THF (1.1 mL) was added. The mixture was cooled to −78° C. and potassium bis(trimethylsilyl) amide, 0.5M in toluene (1.076 mL, 0.538 mmol) was added dropwise over a course of 10 min resulting in a deep red mixture. The resultant mixture was stirred at −78° C. for 2 h. Dry ice bath was removed and the mixture was warmed to room temperature and stirred at room temperature for 2 h before being quenched with water (5 mL). The mixture was extracted with EA (3×7 mL), dried over anhydrous sodium sulfate, concentrated and purified by silica gel column chromatography (EA in hexanes 0 to 100% gradient) to yield intermediate 2-(7-bromo-1,5-naphthyridin-2-yl)-1-(2-fluorophenyl)ethan-1-one 152 (23 mg, 15%) as a yellow solid. [M+H]+ calcd for C16H10BrFN2O, 344.00, found 345.0.

Step 2: To a vial containing 152 2-(7-bromo-1,5-naphthyridin-2-yl)-1-(2-fluorophenyl)ethan-1-one (23 mg, 0.067 mmol) was added N,N-dimethylformamide dimethyl acetal (179 μL, 1.505 mmol) and the resulting was stirred at 80° C. for 4 h before being concentrated. The dark residue was dissolved in ethanol (333 μL) and treated with acetic acid (23 μL, 0.402 mmol) and hydrazine hydrate (1.68 μL, 0.333 mmol). The mixture was stirred at RT for 1.5 h before being concentrated in vacuum and purified by silica gel column chromatography (EA in hexanes 0 to 80% gradient) to yield intermediate 153 (17.7 mg, 63%) as yellow solid. [M+H]+ calcd for C17H10BrFN4 369.01, found 369.

Step 3: To a vial containing 153 (15.5 mg, 0.042 mmol) or 7-bromo-2-(3-(5-chloro-2-fluorophenyl)-1H-pyrazol-4-yl)-1,5-naphthyridine (16.95 mg, 0.042 mmol) was added p-toluenesulfonic acid monohydrate (1.198 mg, 6.30 μmol), followed by DMF (280 μL) and 3,4-dihydro-2H-pyran 100 ml (11.49 μL, 0.126 mmol). The resulting mixture was purged with nitrogen and stirred at 85° C. for 3 h. The reaction mixture was treated with 20 μL of triethylamine, concentrated in vacuum before being purified by silica gel column chromatography (EA in hexanes 0 to 80% gradient) to yield 154 (13.5 mg, 64%) as yellow solid. [M+H]+ calcd for C17H10BrFN4 453.06, found 453.

Example 138: Synthesis of 2-(3-(2-fluorophenyl)-1H-pyrazol-4-yl)-7-(4-(4-methylpiperazin-1-yl)piperidin-1-yl)-1,5-naphthyridine (11-1)

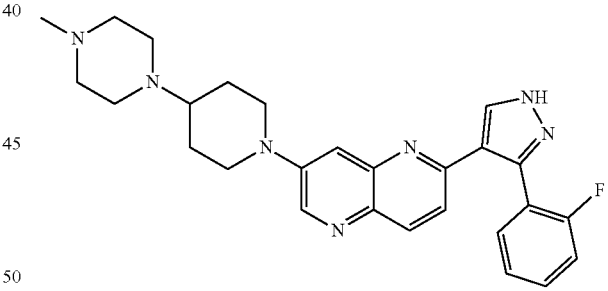

To a vial was added 1-methyl-4-(piperidin-4-yl)piperazine (3.23 mg, 0.018 mmol), RuPhos 2-dicyclohexylphosphino-2',6'-diisopropoxybiphenyl (0.824 mg, 1.765 μmop and RuPhos Pd G2 (1.371 mg, 1.765 μmop followed by sodium tertbutoxide (5.09 mg, 0.053 mmol) and the resulting mixtures were purged with nitrogen before being treated with 154 (8 mg, 0.018 mmol) dissolved in dioxane (77 μL). The resulting mixture was stirred at 85° C. for 15 h. The mixture was cooled down, filtered through a plug of celite, washed on a filter with THF (3 mL). The combined filtrates were concentrated and purified by preparative HPLC chromatography using a gradient (8 to 48%) of acetonitrile in water with 0.05% trifluoroacetic acid to yield a TFA salt of the title compound (12.2 mg) as a yellow solid. [M+H]+ calcd for C27H30FN7 472.25, found 472.3.

Example 139: Synthesis of 1-(6-(3-(2-fluorophenyl)-1H-pyrazol-4-yl)-1,5-naphthyridin-3-yl)pyrrolidin-3-amine (11-2)

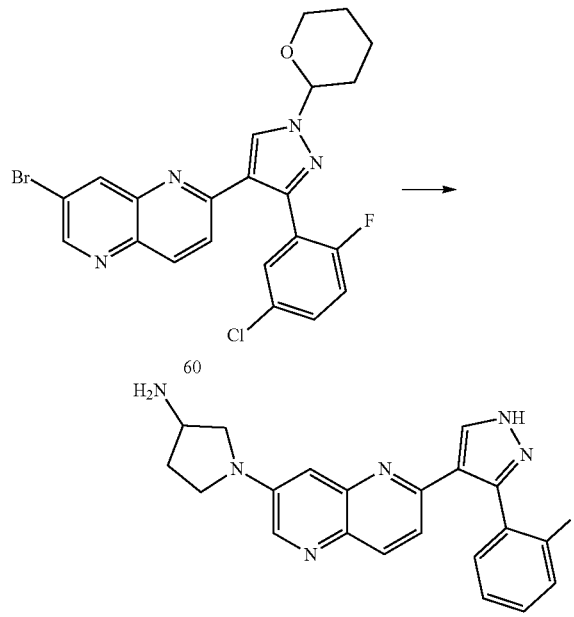

To a vial was added 60 (20 mg, 0.041 mmol) and 3-(tert-butoxycarbonylamino)pyrrolidine (8.0 mg, 0.045 mmol) and then Dioxane (400 μL). The reactions were then sparged with N₂ for 5 min, followed by the addition of RuPhos G2 Pd (3.18 mg, 4.10 μmol, RuPhos (1.913 mg, 4.10 μmol, and cesium carbonate (40.1 mg, 0.123 mmol), followed by additional sparging with N₂ for 5 min. The reaction vial then capped and heated to 105° C. for 20 h before the resulting mixture was concentrated in vacuum. The residue was treated with 1 mL 1:1 TFA/DCM and warmed to 45° C. for 4 h. The resulting dark mixture was concentrated and purified by preparative HPLC chromatography using a gradient (12 to 27%) of acetonitrile in water with 0.05% trifluoroacetic acid to yield a TFA salt of the title compound (10.3 mg) as a yellow solid. [M+H]⁺ calcd for $C_{21}H_{19}FN_6$ 375.17, found 375.2. ¹H NMR (400 MHz, Methanol-d₄) δ 8.68 (d, J=2.7 Hz, 1H), 8.37 (s, 1H), 8.32 (d, J=8.6 Hz, 1H), 7.68-7.46 (m, 2H), 7.37-7.28 (m, 2H), 7.23-7.12 (m, 2H), 4.15 (m, 1H), 3.90 (dd, J=11.4, 6.2 Hz, 1H), 3.84-3.75 (m, 1H), 3.68 (ddd, J=14.8, 10.0, 4.4 Hz, 2H), 2.58 (m, 1H), 2.34-2.17 (m, 1H).

Example 140: Synthesis of methyl 6-((2-fluorophenyl)ethynyl)-1,5-naphthyridine-3-carboxylate (156)

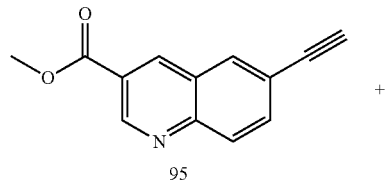

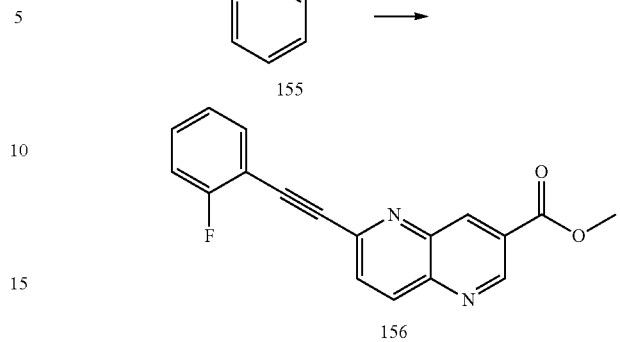

To a vial of 95 (50 mg, 0.236 mmol) in THF (310 μL) was added 1-fluoro-2-iodobenzene 155 (78 mg, 0.353 mmol) and NET3 (310 μL). The reaction mixture was sparged for 5 min with N₂. Copper (I) iodide (8.97 mg, 0.047 mmol) and Pd(PPh₃)₄ (27.2 mg, 0.024 mmol) were then added. The reaction was allowed to stir at 80° C. overnight, filtered through a pad of celite and the crude product was used in the following reaction after solvent removal in vacuum. [M+H]⁺ calcd for $C_{18}H_{11}FN_2O_2$ 307.09, found 307.0.

Example 141: Synthesis of methyl 6-(4-(2-fluorophenyl)-1H-1,2,3-triazol-5-yl)-1,5-naphthyridine-3-carboxylate (12-1)

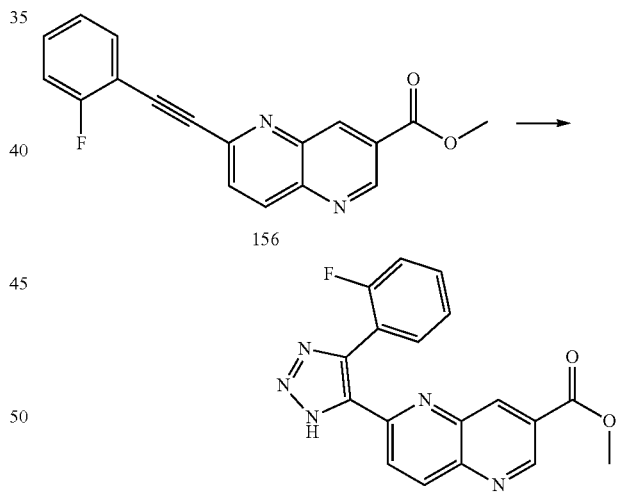

To a solution of crude 156 (30 mg, 0.098 mmol) in dry DMF (653 μL) was added trimethylsilyl azide, 95% (51.8 μL, 0.392 mmol). The reaction mixture was allowed to stir at 100° C. overnight. The resulting mixture was concentrated and purified by preparative HPLC chromatography, gradient (25 to 45%) of acetonitrile in water with 0.05% trifluoroacetic acid to yield a TFA salt of the title compound (5.6 mg). [M+H]⁺ calcd for $C_{18}H_{12}FN_5O_2$ 350.11, found 350.0. ¹H NMR (400 MHz, Methanol-d₄) δ 9.38 (d, J=2.0 Hz, 1H), 8.63 (s, br, 1H), 8.48 (dd, J=8.9, 0.9 Hz, 1H), 8.35 (s, br, 1H), 7.68 (td, J=7.5, 1.8 Hz, 1H), 7.62-7.51 (m, 1H), 7.35 (td, J=7.5, 1.1 Hz, 1H), 7.22 (td, J=9.3 Hz, 1.8 Hz 1H), 4.00 (s, 3H).

Example 142: Synthesis of methyl 5-((tert-butyldimethylsilyl)oxy)-2-methylbenzoate (158)

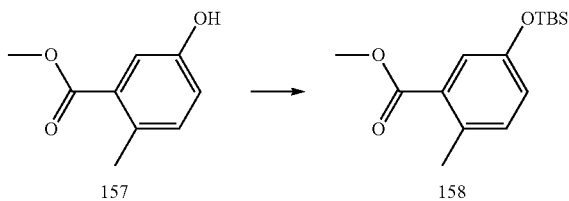 [SMILES: COC(=O)c1cc(O)ccc1C ; COC(=O)c1cc(O[Si](C)(C)C(C)(C)C)ccc1C]

To a vial containing a solution of methyl 5-hydroxy-2-methylbenzoate 157 (100 mg, 0.602 mmol) and imidazole (49.2 mg, 0.722 mmol) in DCM (6 mL) was added tert-butyldimethylsilyl chloride (100 mg, 0.662 mmol) and the resulting cloudy mixture was stirred at RT overnight. Additional amounts of tert-butyldimethylsilul chloride (50 mg, 0.332 mmol) and imidazole (30 mg, 0.441 mmol) were introduced into reaction mixture and stirred at RT for 22 h. When TLC analysis indicated that majority of the starting material was converted to the product, the reaction mixture was diluted with DCM (10 mL) and washed with 0.1M aqueous HCl (2×10 mL), water (2×10 mL) and brine (10 mL). The combined organics were dried over sodium sulfate and concentrated. The resulting crude product 158 (85% purity, 190 mg, 96%) was used in the next step without additional purification. $^1$H NMR (400 MHz, Chloroform-d) δ 7.35 (d, J=2.7 Hz, 1H), 7.07 (d, J=8.2 Hz, 1H), 6.86 (dd, J=8.2, 2.7 Hz, 1H), 3.86 (s, 3H), 2.49 (s, 3H), 0.96 (s, 9H), 0.17 (s, 6H).

Example 143: Synthesis of 2-(7-bromo-1,5-naphthyridin-2-yl)-1-(5-((tert-butyldimethylsilyl)oxy)-2-methylphenyl)ethan-1-one (159)

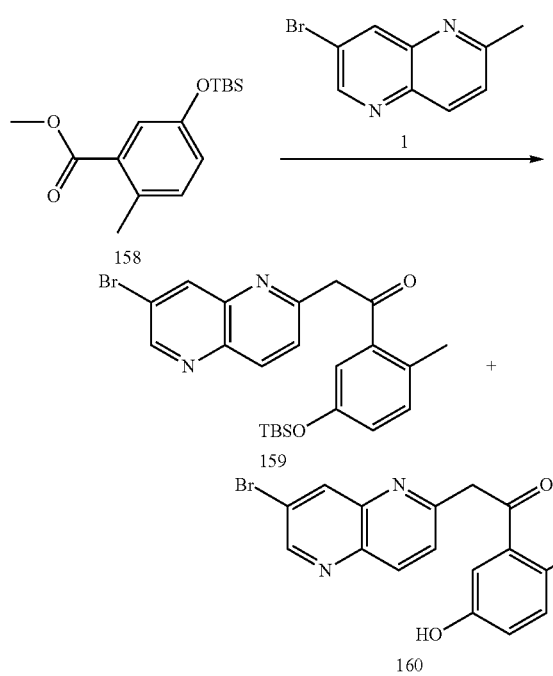

To an oven-dried round bottom flask containing 158 (150 mg, 0.535 mmol) and 1 (119 mg, 0.535 mmol) and purged with nitrogen was added dry THF (2 mL) and the resulting mixture was cooled to −78° C. After 15 min of cooling potassium bis(trimethylsilyl)amide solution, 1 M in THF (0.669 mL, 0.669 mmol) was added dropwise and the resulting mixture was stirred and allowed to slowly warm up to RT overnight. The reaction was quenched with 1 mL MeOH and concentrated prior to be purified on silica gel column (0 to 100% EA in hexanes gradient) to yield desired product 159 (12 mg, 5%), [M+H]$^+$ calcd for $C_{23}H_{27}BrN_2O_2Si$, 471.1, found 471, and deprotected product 160 (50 mg, 26%) as white solids.

Example 144: Synthesis of 7-bromo-2-(3-(5-((tert-butyldimethylsilyl)oxy)-2-methylphenyl)-1H-pyrazol-4-yl)-1,5-naphthyridine (161)

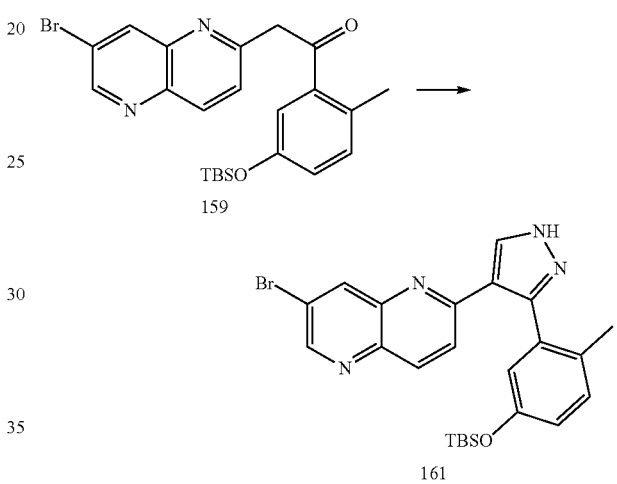

To a vial containing 159 (12 mg, 0.025 mmol) was added N,N-dimethylformamide dimethyl acetal (85 µL, 0.636 mmol) and the resulting mixture was stirred at 80° C. for 3 h. The mixture was concentrated in hi-vacuum. The residue was then re-dissolved in EtOH (127 µL) and treated with acetic acid (7.29 µL, 0.127 mmol) and hydrazine hydrate (6.37 µL, 0.127 mmol). The mixture was stirred at RT for 2.5 days before being purified on silica gel column (0 to 10% methanol in DCM gradient) to yield desired product 161 (5.6 mg, 44%) as yellowish solid. [M+H]$^+$ calcd for $C_{24}H_{27}BrN_4OSi$ 395.1, found 395.

Example 145: Synthesis of 4-methyl-3-(4-(7-(1-(2-(methylamino)ethyl)-1H-pyrazol-4-yl)-1,5-naphthyridin-2-yl)-1H-pyrazol-3-yl)phenol (13-1)

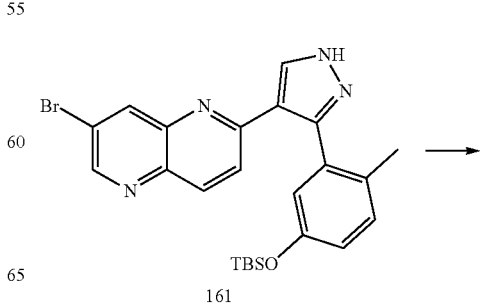

-continued

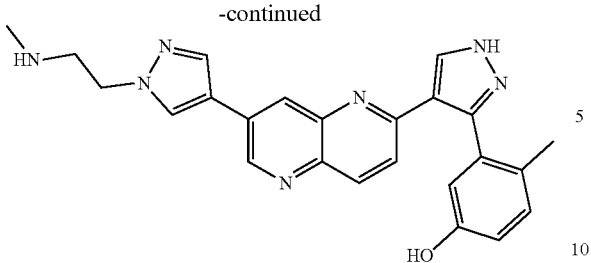

To a vial containing 161 (5.8 mg, 0.012 mmol) and tert-butyl methyl(2-(4-(4,4,5,5-tetramethyl-1,3,2-dioxaborolan-2-yl)-1H-pyrazol-1-yl)ethyl)carbamate (4.93 mg, 0.014 mmol) was added XPhos Pd G4 (1.007 mg, 1.171 µmol), 2-dicyclohexylphosphino-2',4',6'-triisopropylbiphenyl (0.558 mg, 1.171 µmol), potassium phosphate (7.45 mg, 0.035 mmol) and dioxane (58.5 µL) followed by water (58.5 µL). The resulting mixture was sparged with nitrogen before being stirred at 85° C. for 16 h. Additional tert-butyl methyl(2-(4-(4,4,5,5-tetramethyl-1,3,2-dioxaborolan-2-yl)-1H-pyrazol-1-yl)ethyl)carbamate (4.93 g, 14.05 mmol) and XPhos Pd G4 (1.007 g, 1.171 mmol) were added and stirring was continued at 105° C. for 4 h. The reaction mixture was filtered through a plug of celite and washed on a filter with 3 mL THF before being concentrated in vacuo. The residue was then treated with 0.3 mL DCM and 0.3 mL TFA and the resulting product was stirred at RT for 1 h. The resulting dark mixture was concentrated and purified by preparative HPLC chromatography using a gradient (10 to 40%) of acetonitrile in water with 0.05% trifluoroacetic acid to yield a TFA salt of the title compound (2.8 mg). [M+H]$^+$ calcd for C$_{24}$H$_{23}$N$_7$O, 426.20, found 426.1.

Example 146: Synthesis of methyl 3-(hydroxymethyl)benzoate (163)

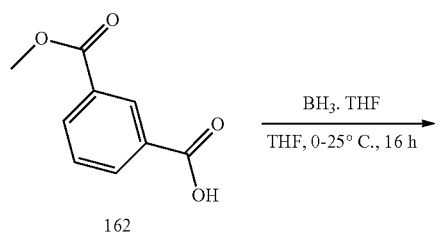

To a solution of 162 (20.0 g, 111 mmol) in THF (300 mL) was added BH$_3$THF (333 mL, 333 mmol). The mixture was stirred at 0° C. for 0.5 h. Then the mixture was warmed to 25° C. for 15.5 h. The mixture was combined with a second lot and quenched with MeOH (400 mL) and concentrated in vacuum. The residue was diluted with H$_2$O (200 mL), the aqueous phase was extracted with EA (3×400 mL). The organic phase was washed with brine, dried over anhydrous Na$_2$SO$_4$, filtered and concentrated in vacuum to give colorless oil (21.0 g, 91% yield).

Example 147: Synthesis of methyl 3-(methoxymethyl)benzoate (164)

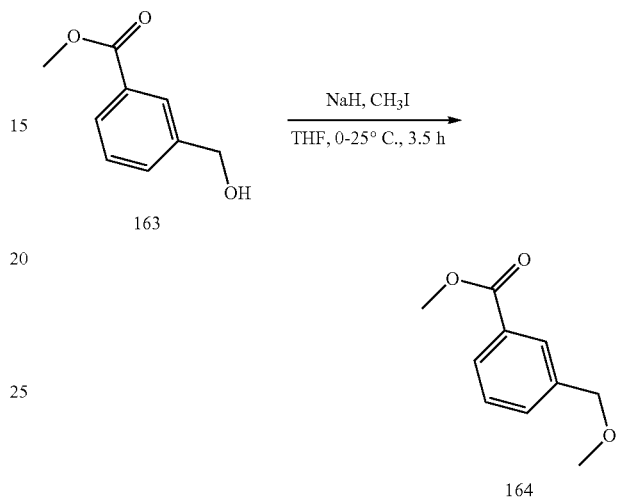

To a solution of 163 (23.0 g, 138 mmol) in THF (300 mL) was added NaH (8.3 g, 207 mmol) at 0° C. Then the mixture was stirred at 25° C. for 30 min. Then CH$_3$I (72.5 g, 511 mmol) was added dropwise and the mixture was stirred at 25° C. for 3 h. The mixture was quenched with HCl (1M) (240 mL) at 0° C. The reaction mixture was combined with a second reaction and extracted with EA (3×400 mL). The organic phase was washed with brine, dried over anhydrous Na$_2$SO$_4$, filtered and concentrated under vacuum to the residue. The residue was purified by column (PE:EA=10:1 to 5:1) to afford 164 as yellow oil (12.0 g, 53% yield, 88% purity). [M+H]$^+$ calcd for C$_{10}$H$_{12}$O$_3$ 181.09 found 181.3.

Example 148: Synthesis of 2-(7-bromo-1,5-naphthyridin-2-yl)-1-(3-(methoxymethyl)phenyl)ethan-1-one (165)

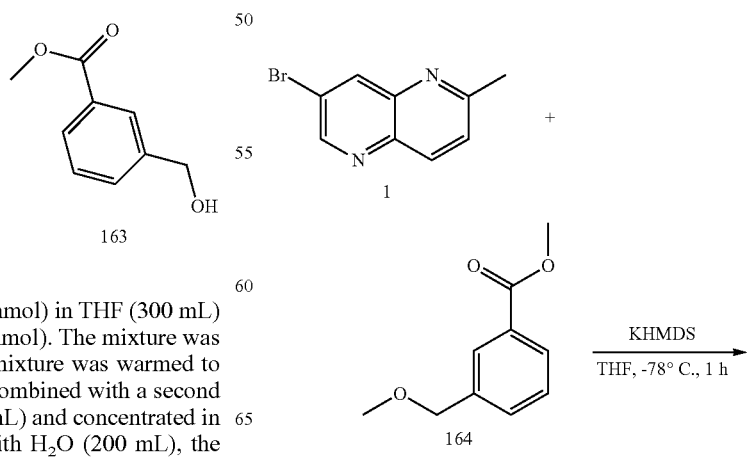

-continued

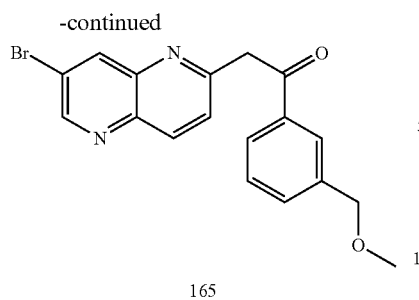

165

To a solution of 1 (5.0 g, 22.4 mmol) and 164 (6.1 g, 33.6 mmol) in THF (80 mL) was added KHMDS (45 mL, 44.8 mmol) dropwise at −78° C. The mixture was stirred at −78° C. for 1 h. The mixture was quenched with H$_2$O (100 mL) at −78° C. The mixture with a second reaction and the total mixture was extracted with EA (3×200 mL). The combined organic phase was dried over Na$_2$SO$_4$, concentrated in vacuum to afford 165 as yellow oil (7.5 g, 79% yield, 87% purity). [M+H]$^+$ calcd for C$_{18}$H$_{15}$BrN$_2$O$_2$ 371.14, found 371.2.

Example 149: Synthesis of (E)-2-(7-bromo-1,5-naphthyridin-2-yl)-3-(dimethylamino)-1-(3-(methoxymethyl)phenyl)prop-2-en-1-one (166)

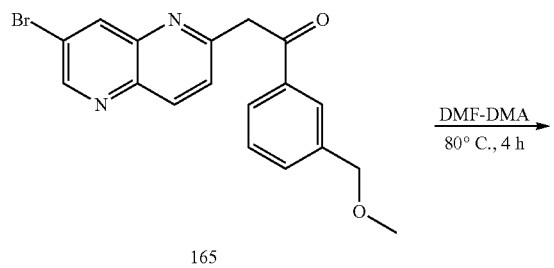

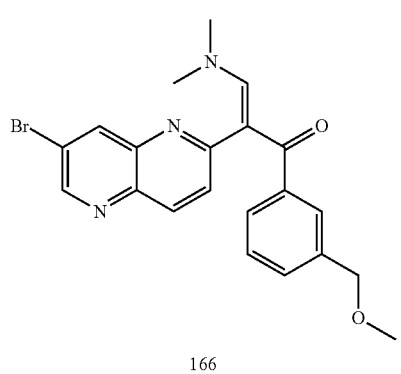

166

To a solution of 165 (7.4 g, 19.9 mmol) in DMF-DMA (80 mL) was stirred for 4 h at 80° C. The mixture was concentrated in vacuum to give 166 as brown oil (8.4 g). The crude product was used directly in the next step.

Example 150: Synthesis of 7-bromo-2-(3-(3-(methoxymethyl)phenyl)-1H-pyrazol-4-yl)-1,5-naphthyridine (167)

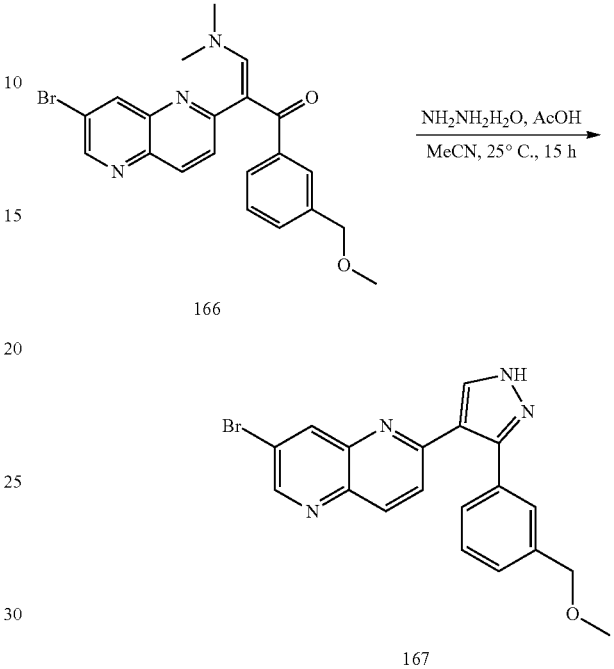

To a solution of 166 (8.4 g, 19.7 mmol) in MeCN (100 mL) was added AcOH (8.4 g, 140 mmol) and NH$_2$NH$_2$·H$_2$O (5.4 g, 108 mmol). The mixture was stirred for 15 h at 25° C. The mixture was combined with a second reaction and was concentrated in vacuum. The residue was washed with H$_2$O (2×40 mL) and MeCN (40 mL), filtered. The cake was dried in vacuum to afford 167 as a yellow solid (7.0 g, 75% yield, 84% purity). [M+H]$^+$ calcd for C$_{19}$H$_{15}$BrN$_4$O, 395.05, found 395.2.

Example 151: Synthesis of 7-bromo-2-(3-(3-(methoxymethyl)phenyl)-1-(tetrahydro-2H-pyran-2-yl)-1H-pyrazol-4-yl)-1,5-naphthyridine (168)

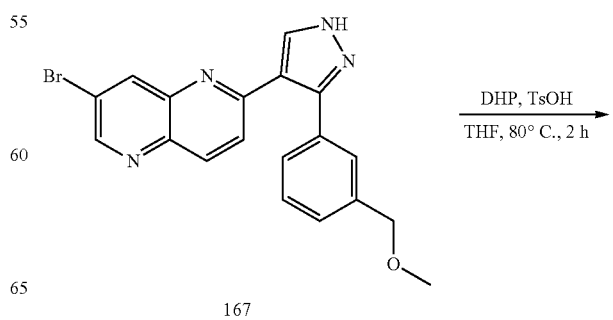

167

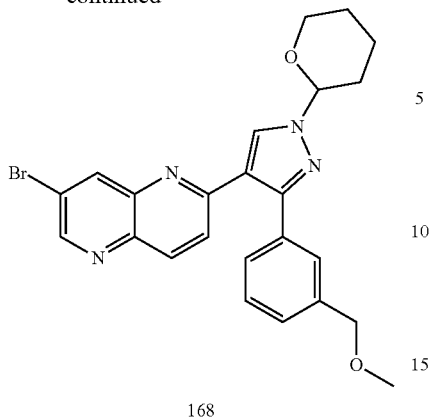

168

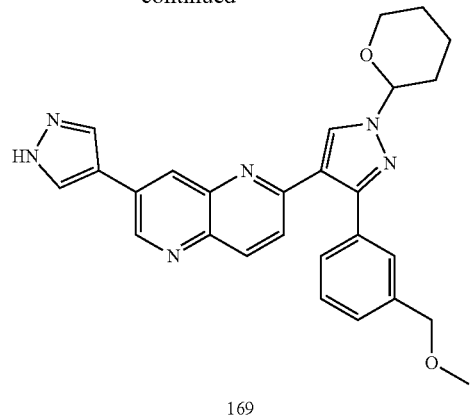

169

To a solution of 167 (6.9 g, 14.7 mmol) in THF (80 mL) was added MsOH (280 mg, 1.47 mmol) and DHP (12.4 g, 147 mmol). The mixture was stirred for 2 h at 80° C. The mixture (combined with a second reaction) was diluted with H$_2$O (100 mL), the aqueous phase was extracted with EA (3×200 mL). The organic phase was washed with brine, dried over anhydrous Na$_2$SO$_4$, filtered and concentrated in vacuum. The residue was purified by column to afford to afford 168 as yellow oil (7.1 g, 97% yield, 97% purity). [M+H]$^+$ calcd for C$_{24}$H$_{23}$BrN$_4$O$_2$ 479.11, found 479.2. $^1$H NMR (400 MHz, DMSO-d$_6$) δ 8.96 (d, J=2.2 Hz, 1H), 8.60 (s, 1H), 8.47 (dd, J=2.2, 0.8 Hz, 1H), 8.30 (d, J=8.9 Hz, 1H), 7.75 (d, J=8.9 Hz, 1H), 7.66 (d, J=1.7 Hz, 1H), 7.53-7.45 (m, 1H), 7.41-7.30 (m, 2H), 5.54 (dd, J=9.9, 2.3 Hz, 1H), 4.42 (s, 2H), 4.06-3.96 (m, 1H), 3.76-3.64 (m, 1H), 3.27 (s, 3H), 2.27-2.12 (m, 1H), 2.09-1.93 (m, 2H), 1.79-1.67 (m, 1H), 1.67-1.48 (m, 2H).

Example 152: Synthesis of 2-(3-(3-(methoxymethyl)phenyl)-1-(tetrahydro-2H-pyran-2-yl)-1H-pyrazol-4-yl)-7-(1H-pyrazol-4-yl)-1,5-naphthyridine (169)

To a solution of 168 (970 mg, 2.02 mmol), t-BuOK (680 mg, 6.06 mmol) and 134 (3.6 g, 12.1 mmol) in dioxane (20 mL) and H$_2$O (2 mL) was added Pd(dppf)Cl$_2$ (739 mg, 1.01 mmol) under N$_2$. The reaction mixture was stirred at 100° C. for 12 h. The mixture was filtered and concentrated in vacuum to give the residue. The residue was purified by silica column (PE:EA=1:1 to 0:1) and prep-HPLC (Xtimate C18 10 μm, 250 mm×50 mm, water (0.5% ammonia hydroxide v/v-ACN, 32% to 62% MeCN in H$_2$O) to afford 169 as yellow solid (460 mg, 42% yield, 100% purity). [M+H]$^+$ calcd for C$_{27}$H$_{26}$N$_6$O$_2$ 467.22, found 467.3. [M+H]$^+$ calcd for C$_{27}$H$_{26}$N$_6$O$_2$ 467.22, found 467.3. $^1$H NMR (400 MHz, DMSO-d$_6$) δ 13.17 (s, 1H), 9.29 (d, J=2.2 Hz, 1H), 8.54 (s, 1H), 8.47-8.38 (m, 3H), 8.26 (d, J=8.8 Hz, 1H), 7.64-7.54 (m, 2H), 7.48 (dt, J=7.5, 1.7 Hz, 1H), 7.45-7.32 (m, 2H), 5.56 (dd, J=10.0, 2.4 Hz, 1H), 4.42 (s, 2H), 4.06-3.96 (m, 1H), 3.73 (dd, J=9.3, 4.9 Hz, 1H), 3.24 (s, 3H), 2.21 (q, J=9.4 Hz, 1H), 2.10-1.96 (m, 2H), 1.74 (s, 1H), 1.60 (dt, J=9.3, 5.3 Hz, 2H).).

Example 153: Synthesis of 1-(6-(3-(3-(methoxymethyl)phenyl)-1H-pyrazol-4-yl)-1,5-naphthyridin-3-yl)-N-methylpiperidin-4-amine (14-1)

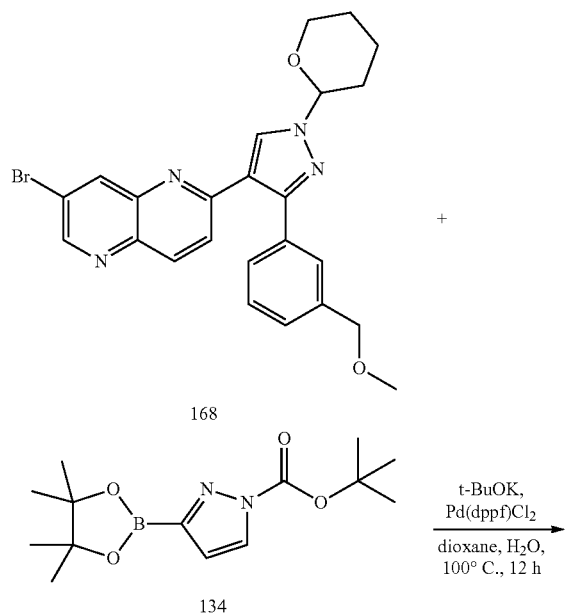

To a vial charged with 168 (21 mg, 0.044 mmol) and tert-butyl methyl(piperidin-4-yl)carbamate (14 mg, 0.066 mmol) was added RuPhos, (2.05 mg, 4.40 μmol), RuPhos Pd G2 (3.42 mg, 4.40 μmol) and sodium tert-butoxide, (13 mg, 0.132 mmol). To the resulting mixture was added dioxane (400 μL) and subsequently sparged with nitrogen for 5 min. The resulting yellow reaction mixture was capped stirred at 105° C. for 16 h. The reaction was filtered through a plug of celite, washed with THF (5 mL) and concentrated in vacuo.

The resulting residue was treated with 1 mL of TFA and stirred at 45° C. for 4 h. The crude product was concentrated in vacuo, and purified by preparative HPLC chromatography using a gradient (12 to 35%) of acetonitrile in water with 0.05% trifluoroacetic acid to yield a TFA salt of the title compound (22.2 mg). [M+H]+ calcd for $C_{25}H_{28}N_6O$ 429.23, found 429.2. $^1$H NMR (400 MHz, Methanol-$d_4$) δ 9.03 (d, J=2.8 Hz, 1H), 8.44-8.40 (m, 1H), 8.38 (s, 1H), 7.57 (d, J=2.6 Hz, 1H), 7.51 (m, 1H), 7.46-7.40 (m, 4H), 4.46 (s, 2H), 4.28 (m, 2H), 3.43-3.35 (m, 1H), 3.33 (s, 3H), 3.22-3.13 (m, 2H), 2.76 (s, 3H), 2.28 m, 2H), 1.77 (qd, J=12.5, 4.3 Hz, 2H).

Example 154: Synthesis of 2-(4-(6-(3-(3-(methoxymethyl)phenyl)-1H-pyrazol-4-yl)-1,5-naphthyridin-3-yl)-1H-pyrazol-1-yl)-N-methylethan-1-amine (14-8)

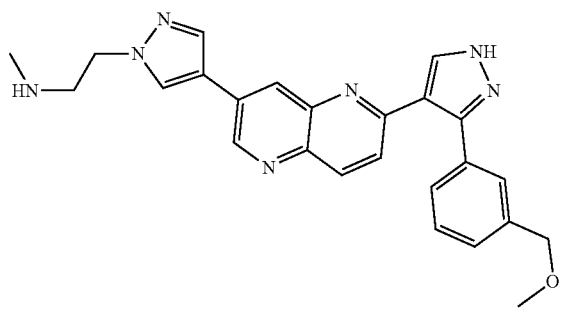 [SMILES: CNCCn1cc(-c2cnc3ccc(-c4c[nH]nc4-c4cccc(COC)c4)nc3c2)cn1]

To a vial containing charged with 168 (70 mg, 0.146 mmol) was added tert-butylmethyl(2-(4-(4,4,5,5-tetramethyl-1,3,2-dioxaborolan-2-yl)-1H-pyrazol-1-yl)ethyl) carbamate (59.0 mg, 0.168 mmol) followed by potassium phosphate tribasic (93 mg, 0.438 mmol), Xphos Pd G4 (12.57 mg, 0.015 mmol), and Xphos (6.69 mg, 0.015 mmol). The resulting mixture was purged with nitrogen before degassed water (292 µL) and 1,4-dioxane (292 µL) was added. The vial was capped and stirred at 105° C. for 1.5 h. The reaction was then cooled, filtered through a plug of celite, washed with THF (5 mL) and concentrated in vacuo. The resulting residue was treated with 1.5 mL of TFA and stirred at 55° C. for 1 h. The crude product was concentrated in vacuo, and purified by preparative HPLC chromatography using a gradient (18 to 33%) of acetonitrile in water with 0.05% trifluoroacetic acid to yield a TFA salt of the title compound (61.3 mg). [M+H]+ calcd for $C_{25}H_{25}N_7O$ 440.21, found 440.2. $^1$H NMR (400 MHz, Methanol-$d_4$) δ 9.18 (d, J=1.9 Hz, 1H), 8.47 (d, J=1.4 Hz, 1H), 8.40 (s, 1H), 8.30-8.19 (m, 3H), 7.60 (d, J=8.8 Hz, 1H), 7.54 (s, 1H), 7.51-7.40 (m, 3H), 4.64-4.56 (m, 2H), 4.45 (s, 2H), 3.62-3.55 (m, 2H), 3.31 (s, 3H), 2.79 (s, 3H).

Example 155: Synthesis of 4-(6-(3-(3-(methoxymethyl)phenyl)-1H-pyrazol-4-yl)-1,5-naphthyridin-3-yl)-N,N-dimethylcyclohex-3-en-1-amine (14-14)

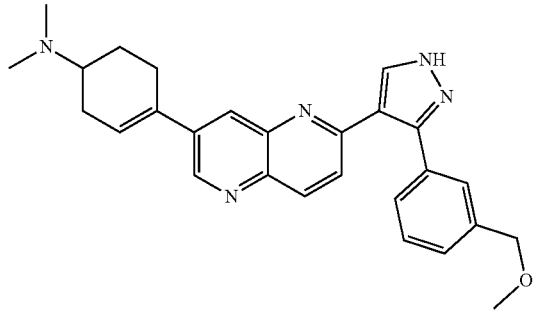 [SMILES: COCc1cccc(-c2n[nH]cc2-c2ccc3ncc(C4=CCC(N(C)C)CC4)cc3n2)c1]

To a vial charged with 4-(6-(3-(3-(methoxymethyl)phenyl)-1H-pyrazol-4-yl)-1,5-naphthyridin-3-yl)cyclohex-3-en-1-amine (10.79 mg, 0.026 mmol) dissolved in methanol (0.25 mL) was added formaldehyde 37 wt. % in $H_2O$ (3.90 µL, 0.052 mmol) followed by sodium triacetoxyborohydride (16.67 mg, 0.079 mmol). The resulting mixture was capped and let stir at RT for 16 h. Afterwards, the reaction was quenched by the addition of $H_2O$, and concentrated in vacuo. The resulting material was purified by preparative HPLC chromatography using a gradient (10 to 50%) of acetonitrile in water with 0.05% trifluoroacetic acid to yield a TFA salt of the title compound (4.2 mg). [M+H]+ calcd for $C_{27}H_{29}N_5O$, 440.24 found 440.1.

Example 156: Synthesis of 2-(4-(6-(3-(3-(methoxymethyl)phenyl)-1H-pyrazol-4-yl)-1,5-naphthyridin-3-yl)-1H-1,2,3-triazol-1-yl)-N-methyl-ethan-1-amine (14-15)

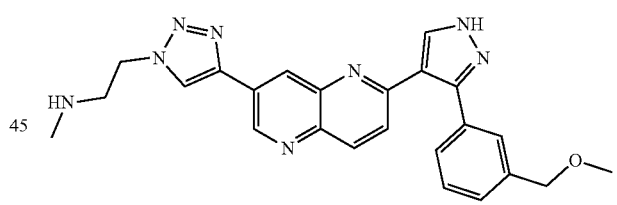

To a vial containing 7-ethynyl-2-(3-iodo-1-(tetrahydro-2H-pyran-2-yl)-1H-pyrazol-4-yl)-1,5-naphthyridine (25 mg, 0.058 mmol) and copper(I) thiophene-2-carboxylate (14.4 mg, 0.075 mmol) was added DCM (0.2 mL). The vial was capped and stirred at 55° C. for 1 h. Teat-butyl (2-azidoethyl)(methyl)carbamate (12.8 mg, 0.064 mmol) was then added, and let stir at 55° C. for 1 hr. The reaction mixture was concentrated in vacuo, yielding a crude mixture containing tert-butyl (2-(4-(6-(3-iodo-1-(tetrahydro-2H-pyran-2-yl)-1H-pyrazol-4-yl)-1,5-naphthyridin-3-yl)-1H-1,2,3-triazol-1-yl)ethyl)(methyl)carbamate. To this material was added sodium carbonate (15.13 mg, 0.143 mmol), Pd(dppf)Cl$_2$ (6.96 mg, 9.52 µmop, and (3-methoxyphenyl)boronic acid (9.48 mg, 0.057 mmol) followed by 1,4-dioxane (317 µL) and $H_2O$ (159 µL). The reaction was sparged with nitrogen for 5 min before being sealed and stirred at 85° C. for 16 h. The reaction was then cooled and concentrated in vacuo. To the dried material was added TFA (0.2 mL) and let stir at 50° C. for 1 h. The reaction was cooled and concentrated in vacuo, and purified by preparative HPLC chromatography using a gradient (5 to 45%) of acetonitrile in water with 0.05% trifluoroacetic acid to yield a TFA salt of the title compound (2.2 mg). [M+H]+ calcd for $C_{24}H_{24}N_8O$, 441.21, found 441.1.

Example 157: Synthesis of 1-(7-bromo-1,5-naphthyridin-2-yl)-2-(3-(methoxymethyl) phenyl)ethane-1,2-dione (170)

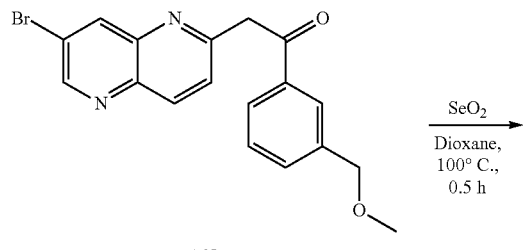

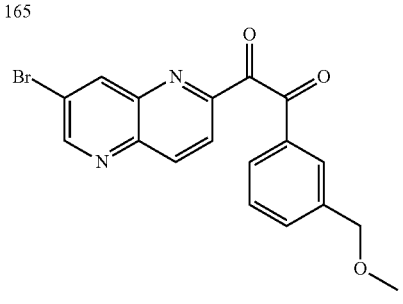

A solution of 165 (7.4 g, 19.9 mmol), SeO$_2$ (11.0 g, 99.5 mmol) in dioxane (100 mL) was stirred at 100° C. for 0.5 h. The reaction mixture was combined with a second reaction and filtered through a pad of celite. The filtrate was concentrated in vacuo to afford 170 as a yellow solid (8.0 g, 62% yield, 60% purity). [M+H]+ calcd for $C_{18}H_{13}BrN_2O_3$ 385.02, found 385.1.

Example 158: Synthesis of 7-bromo-2-(5-(3-(methoxymethyl)phenyl)-1H-imidazol-4-yl)-1,5-naphthyridine (171)

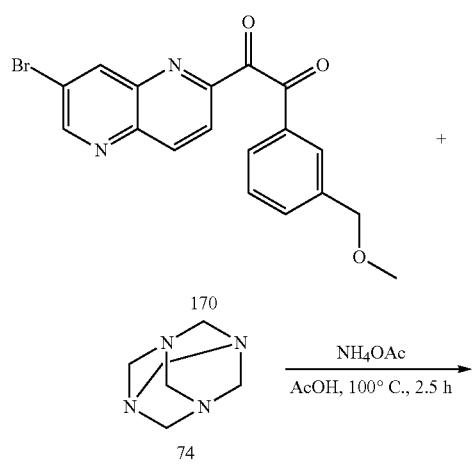

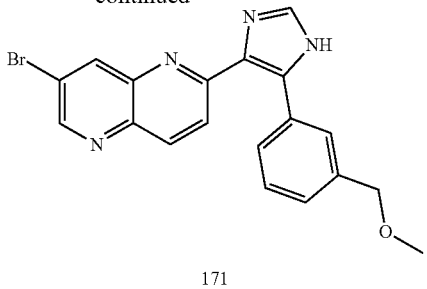

A solution of 170 (7.9 g, 12.3 mmol), 74 (5.2 g, 36.9 mmol) and NH$_4$OAc (5.7 g, 73.8 mmol) in AcOH (100 mL). The reaction mixture was stirred for 2.5 h at 100° C. The reaction mixture was combined with a second reaction, concentrated in vacuum, and basified with sat. NaHCO$_3$ (200 mL) to pH 9. The mixture was extracted with EA (3×400 mL). The combined organic phases were washed with brine (2×200 mL), dried over Na$_2$SO$_4$, filtered, and concentrated in vacuum to give a residue. The residue was purified by column (EA:MeOH=1:0 to 10:1) to afford 171 as yellow solid (3.5 g, 71% yield, 97% purity). [M+H]+ calcd for $C_{19}H_{15}BrN_4O$, 395.05, found 395.2.

Example 159: Synthesis of 7-bromo-2-(5-(3-(methoxymethyl)phenyl)-1-((2-(trimethylsilyl)ethoxy)methyl)-1H-imidazol-4-yl)-1,5-naphthyridine (172)

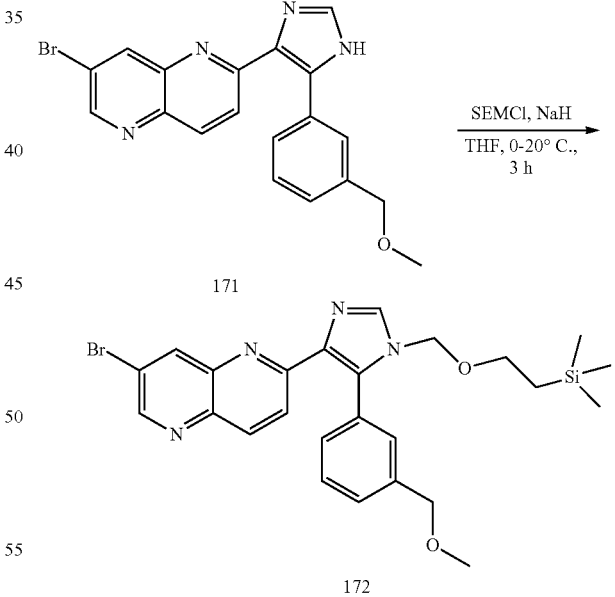

To a solution of 171 (3.4 g, 8.60 mmol) in THF (70 mL) was added NaH (1.0 g, 25.8 mmol) at 0° C. The reaction mixture was stirred at 0° C. for 1 h. To the mixture was added SEMCl (2.9 g, 17.2 mmol). The reaction mixture was stirred at 20° C. for 2 h. The reaction mixture was combined with a second reaction, diluted with H$_2$O (100 mL), extracted with EA (3×200 mL). The organic layer was washed with brine (2×100 mL), dried over Na$_2$SO$_4$, filtered, and concentrated in vacuum. The residue was purified by column to afford 172 as yellow oil (3.5 g, 74% yield, 99% purity). [M+H]+ calcd for $C_{25}H_{29}BrN_4O_2Si$ 525.13, found 524.9. $^1$H NMR (400 MHz, DMSO-$d_6$) δ 8.33 (s, 2H), 8.16 (s, 1H), 8.88 (d, J=2.3 Hz, 1H), 8.08 (d, J=2.3 Hz, 1H), 7.65 (s, 1H), 7.54-7.35 (m, 3H), 5.26 (s, 2H), 4.45 (s, 2H), 3.44 (d, J=8.0 Hz, 2H), 3.32 (s, 3H), 0.78 (t, J=8.1 Hz, 3H), −0.08 (s, 6H).

Example 160: Synthesis of 6-(5-(3-(methoxymethyl)phenyl)-1H-imidazol-4-yl)-N-(2-(piperazin-1-yl)ethyl)-1,5-naphthyridin-3-amine (15-1)

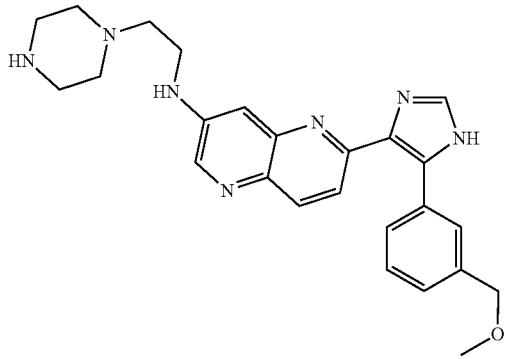 [SMILES: COCc1cccc(-c2[nH]cnc2-c2ccc3ncc(NCCN4CCNCC4)cc3n2)c1]

Compound 172 (30 mg, 0.057 mmol) and 4-(2-aminoethyl)-1-bocpiperazine (17.02 mg, 0.074 mmol) was added BrettPhos, (6.13 mg, 0.011 mmol), BrettPhos Pd G4 (10.51 mg, 0.011 mmol) and cesium carbonate, (55.8 mg, 0.171 mmol). To the resulting mixture was added dioxane (571 μl) and subsequently sparged with nitrogen for 5 m. The resulting yellow reaction mixture was capped stirred at 85° C. for 16 h. The resulting mixture was cooled and concentrated in vacuo. The resulting residue was dissolved in 1,2-dichloroethane (0.2 mL) and then treated with 6N aq. HCl (0.2 mL) and stirred at 80° C. for 3 h. The crude product was concentrated in vacuo, and purified by preparative HPLC chromatography using a gradient (12 to 27%) of acetonitrile in water with 0.05% trifluoroacetic acid to yield a TFA salt of the title compound (5.4 mg). [M+H]+ calcd for $C_{25}H_{29}N_7O$, 444.24, found 444.1.

Example 161: Synthesis of 2-(4-(6-(5-(3-(methoxymethyl)phenyl)-1H-imidazol-4-yl)-1,5-naphthyridin-3-yl)-1H-pyrazol-1-yl)-N-methylethan-1-amine (15-3)

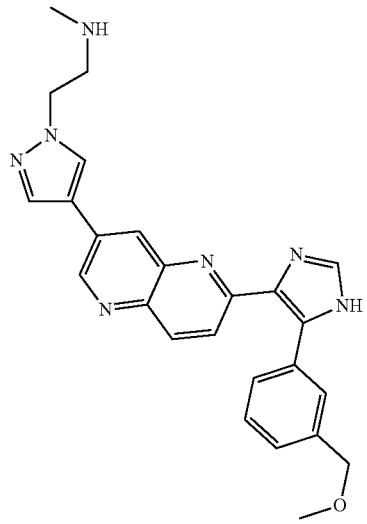 [SMILES: CNCCn1cc(-c2cnc3ccc(-c4nc[nH]c4-c4cccc(COC)c4)nc3c2)cn1]

To a vial containing 172 (30 mg, 0.057 mmol) was added tert-butyl methyl(2-(4-(4,4,5,5-tetramethyl-1,3,2-dioxaborolan-2-yl)-1H-pyrazol-1-yl)ethyl)carbamate (26.1 mg, 0.074 mmol) followed by sodium carbonate (24.20 mg, 0.228 mmol) and Pd(dppf)Cl$_2$ (8.35 mg, 0.011 mmol). The resulting mixture was purged with nitrogen before degassed water (114 μL) and 1,4-dioxane (457 μL) was added. The vial was capped and stirred at 85° C. for 16 h. The reaction was then cooled and concentrated in vacuo. The resulting residue was dissolved in 1,2-dichloroethane (0.2 mL) and then treated with 6N aq. HCl (0.2 mL) and stirred at 80° C. for 3 h. The crude product was concentrated in vacuo, and purified by preparative HPLC chromatography using a gradient (10 to 25%) of acetonitrile in water with 0.05% trifluoroacetic acid to yield a TFA salt of the title compound (21.7 mg). [M+H]+ calcd for $C_{25}H_{25}N_7O$, 440.21 found 440.1.

Example 162: Synthesis of 5-chloro-2-fluoro-N-methoxy-N-methylbenzamide (173)

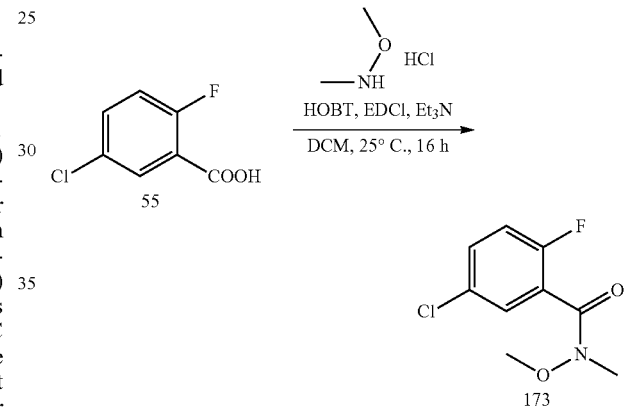

To a solution of 55 (9.0 g, 51.6 mmol), N,O-dimethylhydroxylamine hydrochloride (7.5 g, 77.3 mmol), HOBT (8.4 g, 61.9 mmol), EDCI (11.9 g, 61.9 mmol) in DCM (200 mL) was added Et$_3$N (20.9 g, 206 mmol) stirred at 25° C. for 16 h. The reaction mixture was concentrated in vacuum and purified by silica gel column (0 to 10% of EA in PE) to obtain 173 (10.0 g, 89% purity, 99% purity) as colorless oil. [M+H]+ calcd for $C_9H_9ClFNO_2$ 218.03, found 218.2.

Example 163: Synthesis of 5-chloro-2-fluorobenzaldehyde (174)

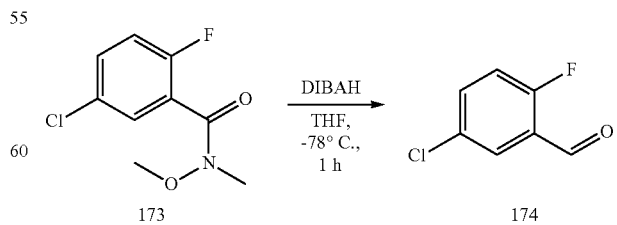

To a solution of 173 (10.0 g, 46.0 mmol) in THF (200 mL) was dropwise added DIBAH (92 mL, 92.0 mmol) at −78° C. and stirred at −78° C. for 1 h. The mixture was stirred at 0°

C. and diluted with (i-Pr)₂O (100 mL). Then water (3.7 mL) was added to the mixture, then NaOH solution (3.7 mL, 15%) was added and then water (9.2 mL) was added. After addition, the mixture was warmed to 25° C. and stirred for 15 min. The mixture was dried with Na₂SO₄ and filtered. The filtrate was concentrated in vacuum and purified by silica gel column (0 to 10% of EA in PE) to obtain 174 (6.4 g, 87% yield) as colorless oil.

Example 164: Synthesis of diphenyl ((5-chloro-2-fluorophenyl)(phenylamino)methyl)phosphonate (175)

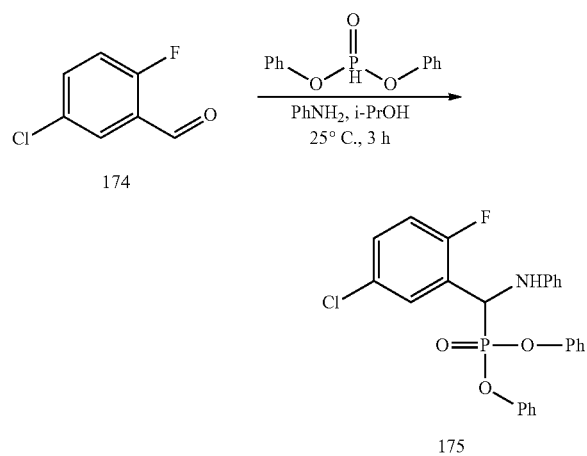

To a mixture of 174 (5.4 g, 34.1 mmol), PhNH₂ (3.8 g, 40.9 mmol) in i-PrOH (100 mL) was added diphenyl phosphonate (13.8 g, 44.3 mmol) at 25° C. The mixture was diluted with water (200 mL) and extracted with EA (2×100 mL). The organic layer was concentrated in vacuum and purified by silica gel column (0 to 10% of EA in PE) to obtain 175 (12.8 g, 80% yield) as white solid.

Example 165: Synthesis of 2-(3-bromoquinolin-6-yl)-1-(5-chloro-2-fluorophenyl)ethan-1-one (177)

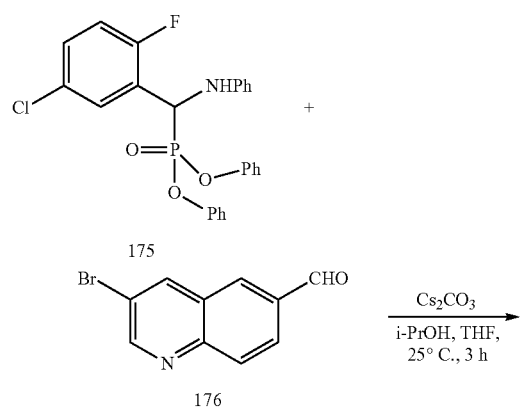

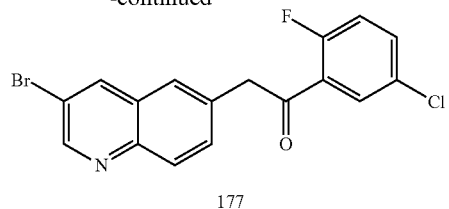

To a mixture of 175 (12.8 g, 28.0 mmol), Cs₂CO₃ (13.7 g, 41.9 mmol) in THF (100 mL) and i-PrOH (20 mL) was added 176 (6.6 g, 28.0 mmol) at 25° C. The reaction mixture was stirred at 25° C. for 12 h. The reaction mixture was diluted with 3.0 M HCl (60 mL), and stirred at 25° C. for 1 h. The reaction mixture was basified with solid NaOH to pH 8, extracted with EA (3×200 mL). The organic layer was washed with brine (2×100 mL), dried over Na₂SO₄, filtered, and concentrated in vacuum. The residue was purified by preparative HPLC chromatography using a gradient (55 to 85%) of acetonitrile in water with 0.1% trifluoroacetic acid to yield a TFA salt of 177 (7.3 g, 60% yield, 99% purity) as yellow solid. [M+H]⁺ calcd for $C_{17}H_{10}BrClFNO$ 377.96, found 377.9. ¹H NMR (400 MHz, DMSO-d₆) δ 8.92 (d, J=2.3 Hz, 1H), 8.68 (d, J=2.3 Hz, 1H), 8.00 (d, J=8.6 Hz, 1H), 7.93 (dd, J=6.2, 2.8 Hz, 1H), 7.81 (d, J=1.9 Hz, 1H), 7.75 (ddd, J=8.8, 4.2, 2.8 Hz, 1H), 7.70 (dd, J=8.6, 1.9 Hz, 1H), 7.47 (dd, J=10.6, 8.9 Hz, 1H), 4.60 (d, J=2.2 Hz, 2H).

Example 166: Synthesis of 3-bromo-6-(3-(5-chloro-2-fluorophenyl)-1-(tetrahydro-2H-pyran-2-yl)-1H-pyrazol-4-yl)quinoline (178)

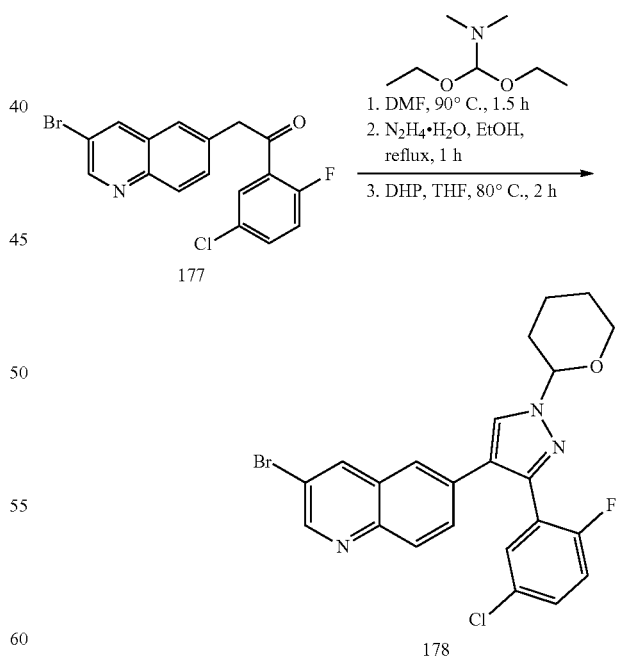

To a vial of 177 (0.500 g, 1.321 mmol) in DMF (4.58 mL) was added N,N-dimethylformamide diethyl acetal (2.88 ml, 16.64 mmol) and heated to 90° C. for 1.5 h. The reaction mixture was concentrated in vacuum. The residue was redissolved in EtOH (4.58 mL). Hydrazine hydrate (0.321 mL, 6.60 mmol) was added and the reaction mixture was brought to a reflux for 1 h. The reaction mixture was concentrated in vacuum and the crude material (0.833 g) was taken on to the next step without further purification. 3-bromo-6-(3-(5-chloro-2-fluorophenyl)-1H-pyrazol-4-yl)quinoline (0.833 g, 2.069 mmol, crude) and 3,4-dihydro-2H-pyran (5.66 mL, 62.1 mmol) were dissolved in THF (6.0 mL). Methanesulfonic acid (0.027 mL, 0.414 mmol) was added. The mixture was heated to 80° C. for 2 h. The crude material was concentrated in vacuum and the residue was purified via normal phase chromatography (0 to 60% of EA in hexanes) yielding 178 (540 mg, 53.6% yield) as a yellow oil. [M+H]$^+$ calcd for $C_{23}H_{18}BrClFN_3O$, 486.03, found 486.0.

Example 167: Synthesis of 2-(4-(6-(3-(5-chloro-2-fluorophenyl)-1H-pyrazol-4-yl)quinolin-3-yl)-1H-pyrazol-1-yl)-N-methylethan-1-amine (16-1)

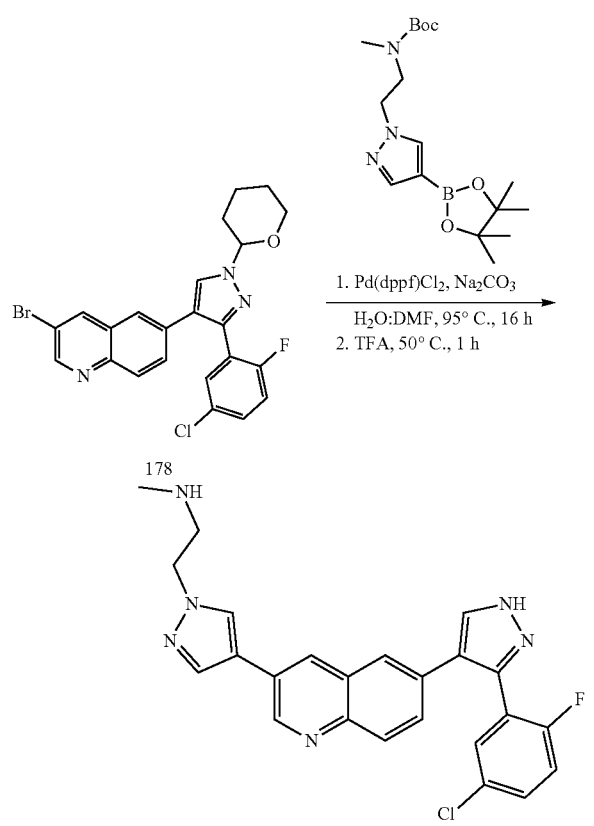

A vial of tert-butyl methyl (2-(4-(4,4,5,5-tetramethyl-1,3,2-dioxaborolan-2-yl)-1H-pyrazol-1-yl)ethyl)carbamate (32.5 mg, 0.092 mmol), 178 (30 mg, 0.062 mmol), sodium carbonate (19.60 mg, 0.185 mmol), and Pd(dppf)Cl$_2$ (10.07 mg, 0.012 mmol) in degassed water (154 μL):DMF (308 μL) was heated to 95° C. for 16 h. The reaction mixture was filtered through a pad of celite and concentrated in vacuum. TFA (300 μL) was added to the residue and heated to 50° C. for 1 h. TFA was removed in vacuum and the residue was purified by preparative HPLC chromatography using a gradient (5 to 65%) of acetonitrile in water with 0.05% trifluoroacetic acid to yield a TFA salt of the title compound (15.1 mg). [M+H]$^+$ calcd for $C_{24}H_{20}ClFN_6$ 447.14, found 447.1. $^1$H NMR (400 MHz, Methanol-d$_4$) δ 9.30 (d, J=2.0 Hz, 1H), 8.89 (d, J=1.8 Hz, 1H), 8.41 (s, 1H), 8.21 (s, 1H), 8.16 (s, 1H), 8.06 (d, J=8.8 Hz, 1H), 7.98 (d, J=1.8 Hz, 1H), 7.85 (dd, J=8.9, 1.9 Hz, 1H), 7.56 (dd, J=6.1, 2.7 Hz, 1H), 7.47 (ddd, J=8.8, 4.3, 2.7 Hz, 1H), 7.14 (t, J=9.1 Hz, 1H), 4.60 (dd, J=6.2, 5.0 Hz, 2H), 3.62-3.54 (m, 2H), 2.77 (s, 3H).

Example 168: Synthesis of (S)-1-(6-(3-(5-chloro-2-fluorophenyl)-1H-pyrazol-4-yl)quinolin-3-yl)-N,N-dimethylpyrrolidin-3-amine (16-3)

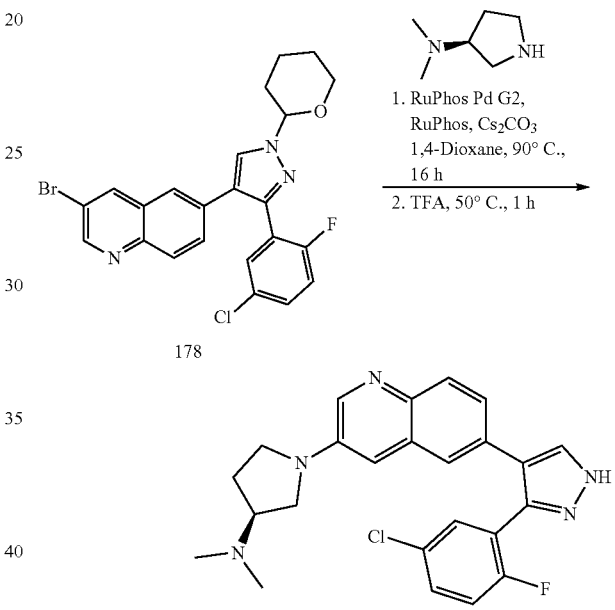

A vial of 178 (30 mg, 0.062 mmol), (S)—N,N-dimethylpyrrolidin-3-amine (7.74 mg, 0.068 mmol), RuPhos (2.88 mg, 6.16 μmol), cesium carbonate (60.2 mg, 0.185 mmol), and RuPhos Pd G2 (4.79 mg, 6.16 μmop in 1,4-dioxane (205 μL) (degassed with N$_2$) was heated to 90° C. for 16 h. The reaction mixture was filtered through a pad of celite and concentrated in vacuum. TFA (300 μL) was added to the residue and heated to 50° C. for 1 h. TFA was removed in vacuum and the residue was purified by preparative HPLC chromatography using a gradient (5 to 75%) of acetonitrile in water with 0.05% trifluoroacetic acid to yield a TFA salt of the title compound (6.1 mg). [M+H]$^+$ calcd for $C_{24}H_{23}ClFN_5$ 436.16, found 436.1. $^1$H NMR (400 MHz, Methanol-d$_4$) δ 8.68 (d, J=2.8 Hz, 1H), 8.11 (s, 1H), 7.93 (dt, J=8.8, 0.7 Hz, 1H), 7.83 (t, J=2.3 Hz, 2H), 7.60 (dd, J=8.9, 1.8 Hz, 1H), 7.53 (dd, J=6.1, 2.7 Hz, 1H), 7.45 (ddd, J=8.8, 4.3, 2.7 Hz, 1H), 7.17-7.08 (m, 1H), 4.14 (p, J=7.3 Hz, 1H), 3.95 (dd, J=10.8, 7.4 Hz, 1H), 3.80 (td, J=11.1, 10.3, 6.3 Hz, 2H), 3.56 (dt, J=9.7, 7.9 Hz, 1H), 3.01 (s, 6H), 2.66 (dtd, J=13.0, 7.4, 3.5 Hz, 1H), 2.41 (dq, J=13.1, 8.4 Hz, 1H).

Example 169: Synthesis of 6-(3-(5-chloro-2-fluorophenyl)-1H-pyrazol-4-yl)-N-(2-(4-isopropylpiperazin-1-yl)ethyl)quinolin-3-amine (16-5)

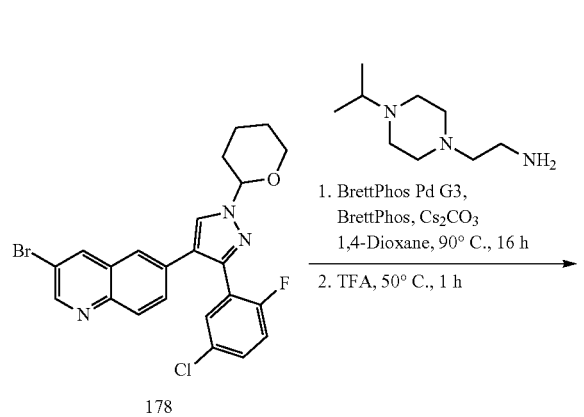

A vial of 178 (30 mg, 0.062 mmol), 2-(4-isopropylpiperazin-1-yl)-ethylamine (12.35 µL, 0.068 mmol), cesium carbonate (60.2 mg, 0.185 mmol), BrettPhos (3.31 mg, 6.16 µmol), BrettPhos Pd G3 (5.59 mg, 6.16 µmop in 1,4-dioxane (308 µL) (degassed with N₂) was heated to 90° C. for 16 h. The reaction mixture was filtered through a pad of celite and concentrated in vacuum. TFA (300 µL) was added to the residue and heated to 50° C. for 1 h. TFA was removed in vacuum and the residue was purified by preparative HPLC chromatography using a gradient (5 to 75%) of acetonitrile in water with 0.05% trifluoroacetic acid to yield a TFA salt of the title compound (5.0 mg). [M+H]⁺ calcd for C₂₇H₃₀ClFN₆ 493.22, found 493.1.

Example 170: Synthesis of 1-(3-bromoquinolin-6-yl)-2-(5-chloro-2-fluorophenyl)ethane-1,2-dione (179)

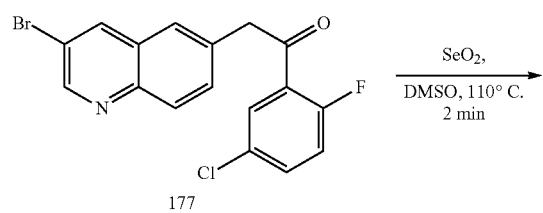

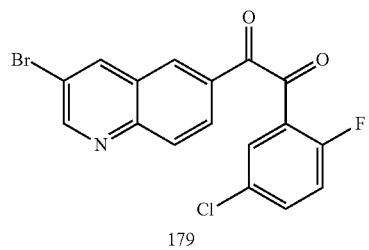

To a vial of 177 (800 mg, 2.113 mmol) in DMSO (9.4 mL) was added selenium dioxide (391 mg, 3.53 mmol). The reaction mixture was sealed and heated to 110° C. for 2 min in the microwave. The reaction was filtered and concentrated in the Genevac. The residue was purified via normal phase chromatography (0 to 65% of EA in hexanes) yielding 179 (823 mg, 89% yield) as a yellow powder. [M+H]⁺ calcd for C₁₇H₈BrClFNO₂ 391.96, found 392.0.

Example 171: Synthesis of 3-bromo-6-(5-(5-chloro-2-fluorophenyl)-1H-imidazol-4-yl)quinoline (180)

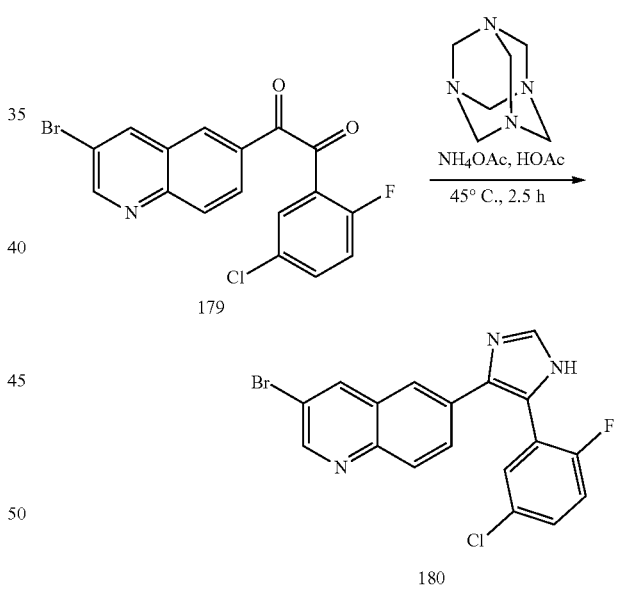

A vial of hexamine (1.76 g, 12.58 mmol), 179 (0.823 g, 2.097 mmol), and ammonium acetate (4.85 mg, 62.9 mmol) in acetic acid (23.500 mL) was heated to 120° C. for 1 h. The reaction mixture was concentrated and basified with sat. aq. NaHCO₃ to pH 8. The mixture was extracted with EA (3×30 mL). The organic layers were combined and washed with brine. The organic layer was dried over Na₂SO₄, filtered, and concentrated in vacuum yielding 180 (2.09 g, crude). [M+H]⁺ calcd for C$_{is}$H₁₀BrClFN₃ 401.97, found 402.0.

Example 172: Synthesis of 3-bromo-6-(5-(5-chloro-2-fluorophenyl)-1-((2 (trimethylsilyl)ethoxy)-methyl)-1H-imidazol-4-yl)quinoline (181)

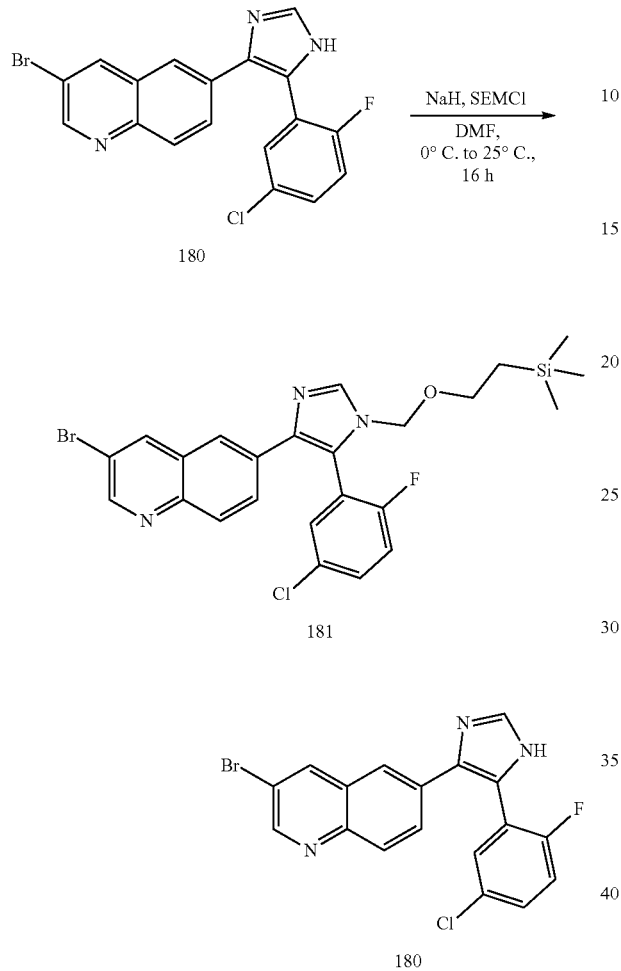

A vial of crude 180 (2.09 g, 5.19 mmol) was redissolved in anhydrous DMF (51.9 mL) and cooled to 0° C. NaH (0.477 g, 11.94 mmol) was added. The mixture was allowed to stir for 45 min at 0° C. before adding SEM-Cl (1.837 mL, 10.38 mmol) dropwise. The resulting mixture was warmed to room for 3 h. The reaction was quenched with sat. $NH_4Cl$ and extracted with DCM (3×80 mL). The organic layers were combined and washed with brine. The organic layer was dried over $Na_2SO_4$, filtered, and concentrated in vacuum. The residue was purified via normal phase chromatography (0 to 100% of EA in hexanes) yielding 181 (263 mg, 9.5% yield, 23.5% yield BRSM) as a yellow oil [M+H]$^+$ calcd for $C_{24}H_{24}BrClFN_3OSi$ 532.04, found 532.0. Starting material 180 (465.6 mg, 55.1%) was recovered during purification as a yellow powder. [M+H]$^+$ calcd for $C_{18}H_{10}BrClFN_3$ 401.97, found 402.0.

Example 173: Synthesis of (6-(5-(5-chloro-2-fluorophenyl)-1H-imidazol-4-yl)quinolin-3-yl)boronic acid (182)

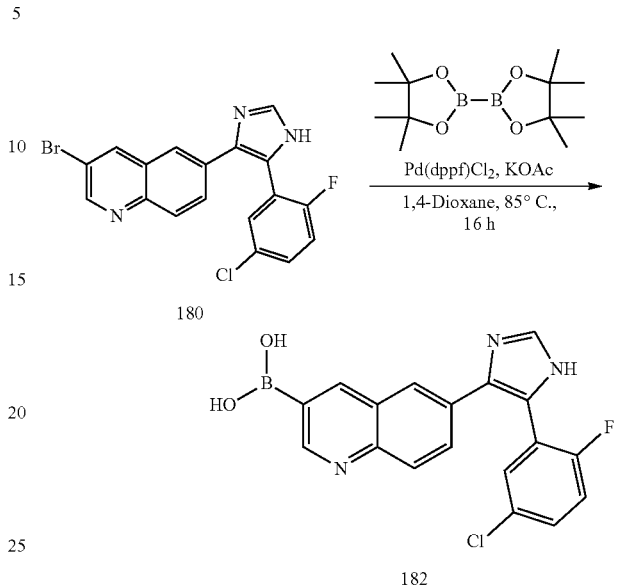

A vial of 180 (300 mg, 0.745 mmol), bis(pinacolato)diboron (265 mg, 1.044 mmol), Pd(dppf)Cl$_2$ (109 mg, 0.149 mmol), and potassium acetate (220 mg, 2.237 mmol) in 1,4-dioxane (3.55 mL) was sparged with N$_2$ for 5 min before heating to 85° C. for 16 h. The reaction was concentrated in vacuum. Crude 182 was used in the next reaction without further purification. [M+H]$^+$ calcd for $C_{18}H_{12}BClFN_3O_2$ 368.07, found 368.0.

Example 174: Synthesis of 6-(5-(5-chloro-2-fluorophenyl)-1H-imidazol-4-yl)-3-(1H-pyrazol-4-yl)quinoline (17-1)

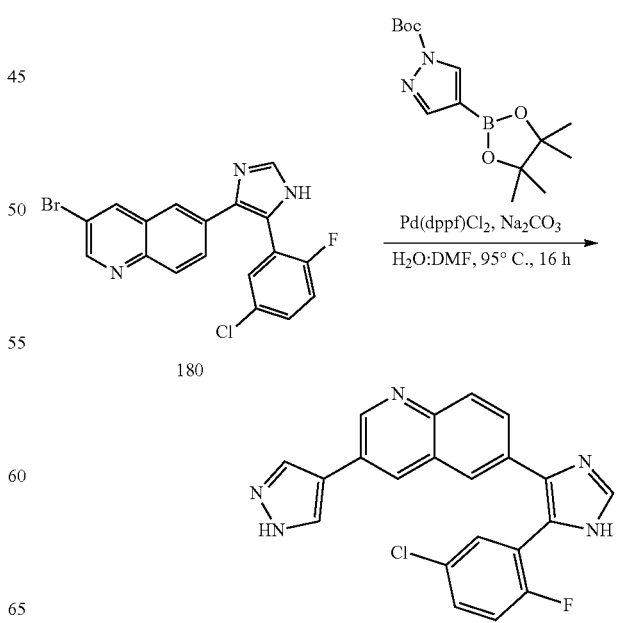

A vial of 1-boc-pyrazole-4-boronic acid pinacol ester (32.9 mg, 0.112 mmol), 180 (30 mg, 0.075 mmol, crude), sodium carbonate (23.69 mg, 0.224 mmol), and Pd(dppf)Cl₂ (12.17 mg, 0.015 mmol) in degassed water (248 µL):DMF (497 µL) was heated to 95° C. for 16 h. The reaction mixture was filtered through a pad of celite and concentrated in vacuum. The boc group is removed during the Suzuki reaction. The residue was purified by preparative HPLC chromatography using a gradient (2 to 60%) of acetonitrile in water with 0.05% trifluoroacetic acid to yield a TFA salt of the title compound (15.2 mg). [M+H]⁺ calcd for $C_{21}H_{13}ClFN_5$ 390.0, found 390.1.

Example 175: Synthesis of 6-(5-(5-chloro-2-fluorophenyl)-1H-imidazol-4-yl)-N-(2-(4-isopropylpiperazin-1-yl)ethyl)quinolin-3-amine (17-3)

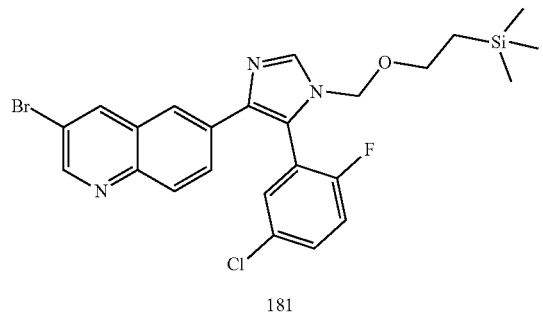

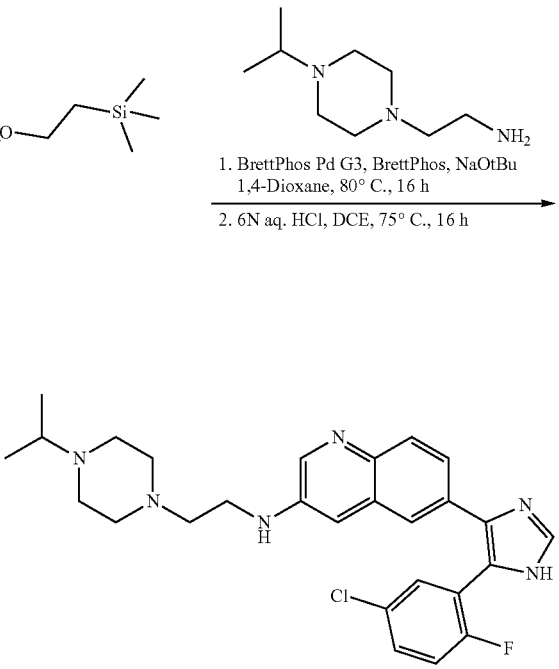

A vial of 181 (30 mg, 0.056 mmol), 2-(4-isopropylpiperazin-1-yl)-ethylamine (0.012 ml, 0.068 mmol), sodium tert-butoxide (16.23 mg, 0.169 mmol), BrettPhos (3.02 mg, 5.63 µmol), and BrettPhos Pd G3 (5.10 mg, 5.63 µmop in 1,4-dioxane (0.300 mL) (degassed with N₂) was heated to 80° C. for 16 h. The reaction mixture was filtered through a pad of celite and concentrated in vacuum. The crude material was dissolved in DCE (0.300 mL) and 6 M aq. HCl (0.200 ml) was added. The mixture was heated to 75° C. for 16 h. The reaction mixture was concentrated in vacuum and the residue was purified by preparative HPLC chromatography using a gradient (2 to 60%) of acetonitrile in water with 0.05% trifluoroacetic acid to yield a TFA salt of the title compound (6.7 mg). [M+H]⁺ calcd for $C_{27}H_{30}ClFN_6$ 493.22, found 493.2.

Example 176: Synthesis of 6-(5-(5-chloro-2-fluorophenyl)-1H-imidazol-4-yl)-3-(piperazin-1-yl)quinoline (17-4)

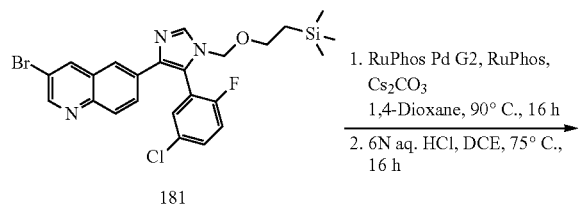

-continued

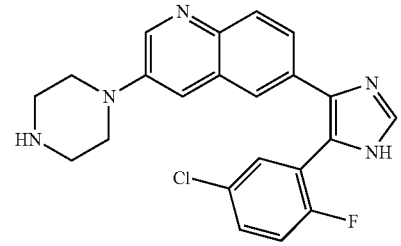

A vial of 181 (30 mg, 0.056 mmol), 1-boc-piperazine (12.58 mg, 0.068 mmol), sodium tert-butoxide (16.23 mg, 0.169 mmol), SPhos (4.62 mg, 0.011 mmol), and SPhos Pd G3 (8.78 mg, 0.011 mmol) in 1,4-dioxane (0.300 mL) (degassed with N₂) was heated to 80° C. for 16 h. The reaction mixture was filtered through a pad of celite and concentrated in vacuum. The crude material was dissolved in DCE (0.300 mL) and 6 M aq. HCl (0.200 ml) was added. The mixture was heated to 75° C. for 16 h. The reaction mixture was concentrated in vacuum and the residue was purified by preparative HPLC chromatography using a gradient (2 to 60%) of acetonitrile in water with 0.05% trifluoroacetic acid to yield a TFA salt of the title compound (4.4 mg). [M+H]⁺ calcd for $C_{22}H_{19}ClFN_5$ 408.13, found 408.2.

Example 177: Synthesis of 6-(5-(5-chloro-2-fluorophenyl)-1H-imidazol-4-yl)-3-(2,3-dihydro-1H-imidazo[1,2-a]imidazol-5-yl)quinoline (17-9)

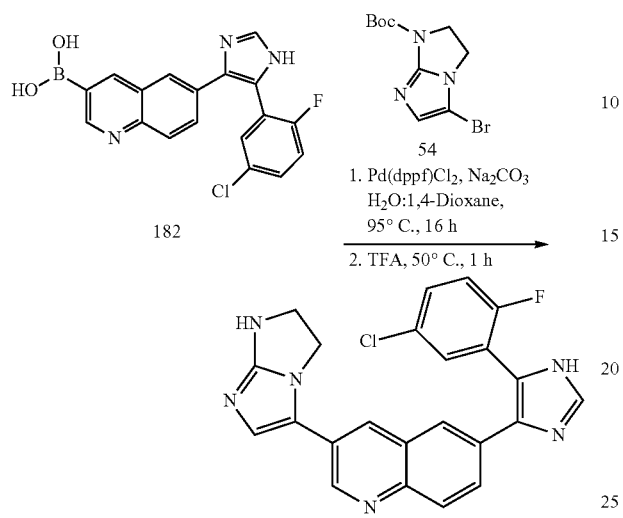

A vial of 182 (29.4 mg, 0.080 mmol, crude), 54 (34 mg, 0.120 mmol), sodium carbonate (0.025 g, 0.240 mmol), and Pd(dppf)Cl$_2$ (9.21 mg, 0.016 mmol) in water (0.150 mL):1,4-dioxane (0.300 mL) was sparged for 10 min with N$_2$ before heating to 95° C. for 16 h. TFA (300 µL) was added to the residue and heated to 50° C. for 1 h. TFA was removed in vacuum and the residue was purified by preparative HPLC chromatography using a gradient (5 to 75%) of acetonitrile in water with 0.05% trifluoroacetic acid to yield a TFA salt of the title compound (15.3 mg). [M+H]$^+$ calcd for C$_{23}$H$_{16}$ClFN$_6$ 431.11, found 431.1.

Example 178: Synthesis of 3-bromo-6-ethynylquinoline (183)

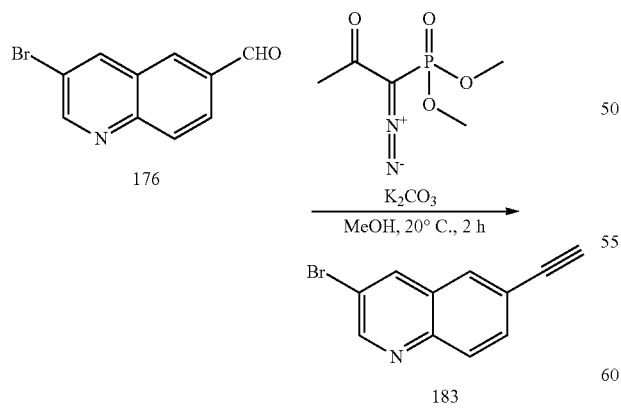

To a suspension of 176 (6.0 g, 25.4 mmol) and K$_2$CO$_3$ (7.0 g, 50.8 mmol) in MeOH (100 mL) was added dropwise dimethyl (1-diazo-2-oxopropyl)phosphonate (9.8 g, 50.8 mmol) and stirred at 25° C. for 2 h. The mixture was diluted with water (100 mL) and extracted with EA (2×100 mL). The organic layer was concentrated in vacuum. The residue was purified by silica gel column (0 to 7% of EA in PE) to obtain 183 (11.0 g, 80% yield, 90% purity) as white solid. [M+H]$^+$ calcd for C$_H$H$_6$BrN 231.97, found 231.9. $^1$H NMR (400 MHz, Chloroform-d) δ 8.90 (d, J=2.2 Hz, 1H), 8.26 (d, J=2.2 Hz, 1H), 8.02 (d, J=8.7 Hz, 1H), 7.90 (d, J=1.4 Hz, 1H), 7.76 (dt, J=8.7, 1.4 Hz, 1H), 3.22 (s, 1H).

Example 179: Synthesis of 3-bromo-6-((5-chloro-2-fluorophenyl)ethynyl)quinoline (184)

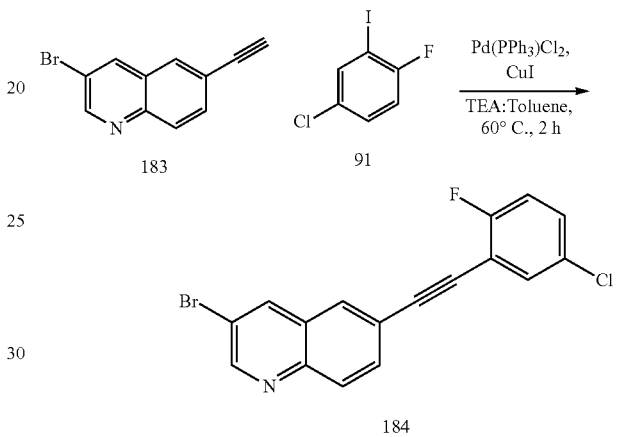

A vial of 183 (100 mg, 0.431 mmol), 91 (166 mg, 0.646 mmol), Pd(PPh$_3$)Cl$_2$ (30.2 mg, 0.043 mmol), and copper (I) iodide (16.41 mg, 0.086 mmol) in 2:1 TEA (958 µL): toluene (479 µL) was sparged with N$_2$ for 5 min before heating to 60° C. for 2 h. The reaction was filtered through a pad of celite and concentrated in vacuum. The residue was purified by silica gel column (0 to 50% of EA in hexanes) to obtain 184 (136 g, 88% yield) as a pale orange powder. [M+H]$^+$ calcd for C$_{17}$H$_8$BrClFN 359.95, found 360.0. $^1$H NMR (400 MHz, Chloroform-d) δ 8.90 (d, J=2.3 Hz, 1H), 8.30-8.25 (m, 1H), 8.05 (dt, J=8.6, 0.8 Hz, 1H), 7.94 (dd, J=1.8, 0.5 Hz, 1H), 7.81 (dd, J=8.7, 1.8 Hz, 1H), 7.53 (dd, J=6.1, 2.7 Hz, 1H), 7.34-7.25 (m, 1H), 7.07 (t, J=8.8 Hz, 1H).

Example 180: Synthesis of 3-bromo-6-(5-(5-chloro-2-fluorophenyl)-1H-1,2,3-triazol-4-yl)quinoline (185)

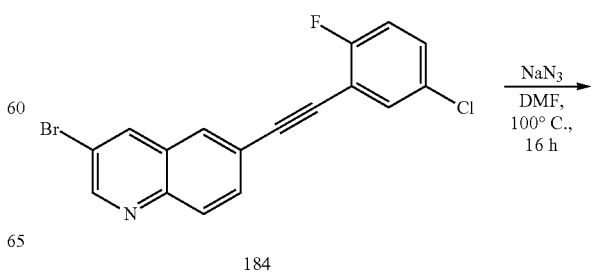

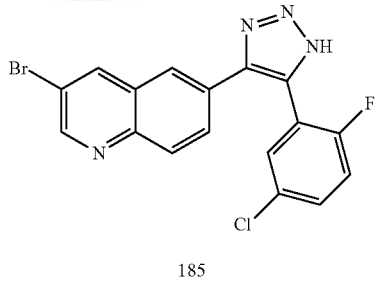

185

A vial of 184 (200 mg, 0.555 mmol) and sodium azide (108 mg, 1.664 mmol) in DMF (5.55 mL) was heated 100° C. for 16 h. The reaction was quenched with water (15 mL) and extracted with DCM (3×30 mL). The organic layer was dried over $Na_2SO_4$, filtered, and concentrated in vacuum. The residue was purified via normal phase chromatography (0 to 20% MeOH in DCM) yielding 185 (168 mg, 75% yield) as a yellow solid. $[M+H]^+$ calcd for $C_{17}H_9BrClFN_4$ 402.97, found 403.0.

Example 181: Synthesis of 2-(4-(6-(5-(5-chloro-2-fluorophenyl)-1H-1,2,3-triazol-4-yl)quinolin-3-yl)-1H-pyrazol-1-yl)-N-methylethan-1-amine (18-1)

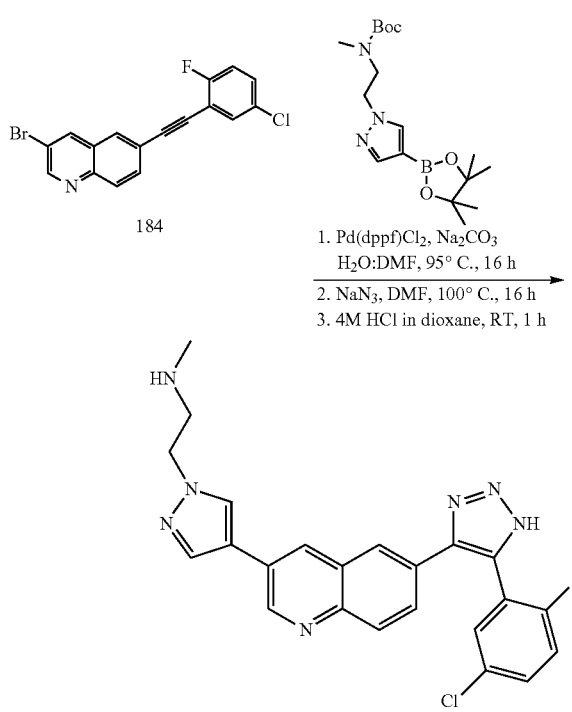

A vial of 184 (50 mg, 0.139 mmol), $Pd(dppf)Cl_2$ (20.29 mg, 0.028 mmol), sodium carbonate (44.1 mg, 0.416 mmol), and tert-butyl methyl(2-(4-(4,4,5,5-tetramethyl-1,3,2-dioxaborolan-2-yl)-1H-pyrazol-1-yl)ethyl)carbamate (73.1 mg, 0.208 mmol) in degassed 2:1 DMF (462 μL):water (231 μL) was heated to 95° C. for 16 h. The reaction mixture was filtered through a pad of celite and concentrated in vacuum. The crude material was purified via normal phase chromatography (0-5% MeOH in DCM) yielding tert-butyl (2-(4-(6-((5-chloro-2-fluorophenyl)ethynyl)quinolin-3-yl)-1H-pyrazol-1-yl)ethyl)(methyl) carbamate (50.5 mg, 72.1% yield). $[M+H]^+$ calcd for $C_{28}H_{26}ClFN_4O_2$ 505.17, found 505.0. To a vial of tert-butyl (2-(4-(6-((5-chloro-2-fluorophenyl)ethynyl)quinolin-3-yl)-1H-pyrazol-1-yl)ethyl)(methyl)carbamate (50.5 mg, 0.100 mmol) in anhydrous DMF (1 mL) was added sodium azide (26.00 mg, 0.400 mmol). The reaction mixture was heated to 100° C. for 16 h. The reaction mixture was concentrated in vacuum. The residue was redissolved in 1,4-dioxane (0.300 mL) and 4 M HCl in dioxane (0.100 mL) was added. The reaction mixture was stirred for 1 h and concentrated in vacuum. The residue was purified by preparative HPLC chromatography using a gradient (10 to 80%) of acetonitrile in water with 0.05% trifluoroacetic acid to yield a TFA salt of the title compound (12.3 mg). $[M+H]^+$ calcd for $C_{23}K_9ClFN_7$ 448.14, found 448.1. $^1H$ NMR (400 MHz, Methanol-$d_4$) δ 9.15 (d, J=2.2 Hz, 1H), 8.49 (d, J=2.1 Hz, 1H), 8.36-8.31 (m, 1H), 8.18 (d, J=0.8 Hz, 1H), 8.09-7.99 (m, 2H), 7.86 (d, J=8.8 Hz, 1H), 7.63 (dd, J=6.1, 2.7 Hz, 1H), 7.52 (ddd, J=8.8, 4.2, 2.7 Hz, 1H), 7.22 (t, J=9.1 Hz, 1H), 4.58 (t, J=5.6 Hz, 2H), 3.70-3.63 (m, 2H), 2.78 (s, 3H).

Example 182: Synthesis of 6-(5-(5-chloro-2-fluorophenyl)-1H-1,2,3-triazol-4-yl)-N-(2-(4-isopropylpiperazin-1-yl)ethyl)quinolin-3-amine (18-3)

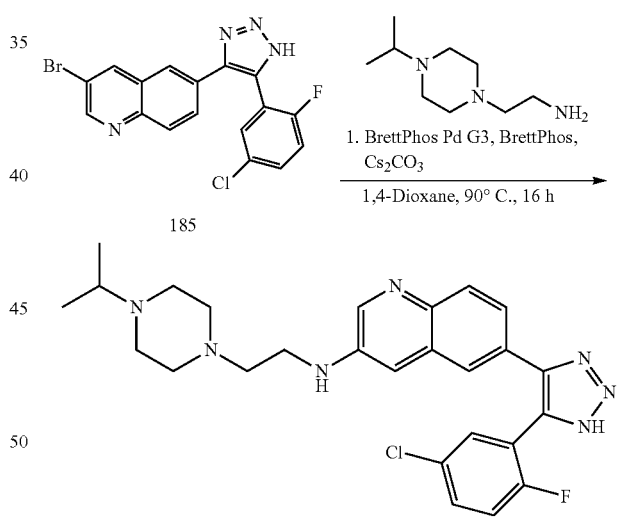

A vial of 185 (25 mg, 0.062 mmol), 2-(4-isopropylpiperazin-1-yl)-ethylamine (13.50 μL, 0.074 mmol), sodium tert-butoxide (17.81 mg, 0.185 mmol), BrettPhos (19.89 mg, 0.036 mmol), and BrettPhos Pd G3 (33.60 mg, 0.036 mmol) in 1,4-dioxane (309 μL) (degassed with $N_2$) was heated to 90° C. for 48 h. The reaction mixture was concentrated in vacuum. The residue was purified by preparative HPLC chromatography using a gradient (5 to 75%) of acetonitrile in water with 0.05% TFA to yield a TFA salt of the title compound (5 mg). $[M+H]^+$ calcd for $C_{26}H_{29}ClFN_7$ 494.22, found 494.2.

Example 183: Synthesis of (S)-1-(6-(5-(5-chloro-2-fluorophenyl)-1H-1,2,3-triazol-4-yl)quinolin-3-yl)-N,N-dimethylpyrrolidin-3-amine (18-4)

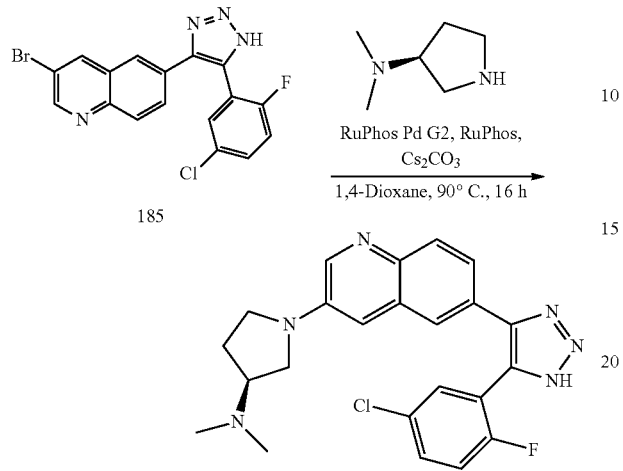

A vial of 185 (25 mg, 0.062 mmol), RuPhos (5.78 mg, 0.012 mmol), (S)—N,N-dimethylpyrrolidin-3-amine (10.61 mg, 0.093 mmol), sodium tert-butoxide (17.86 mg, 0.186 mmol), and RuPhos Pd G2 (48.10 mg, 0.062 mmol) in 1,4-dioxane (206 μL) was heated to 90° C. for 32 h. The reaction mixture was concentrated in vacuum. The residue was purified by preparative HPLC chromatography using a gradient (5 to 75%) of acetonitrile in water with 0.05% trifluoroacetic acid to yield a TFA salt of the title compound (5.7 mg). [M+H]$^+$ calcd for $C_{23}H_{22}ClFN_6$ 437.92, found 437.2.

Example 184: Synthesis of 3-bromo-6-(2-(5-chloro-2-fluorophenyl)imidazo[1,2-a]pyridin-3-yl)quinoline (186)

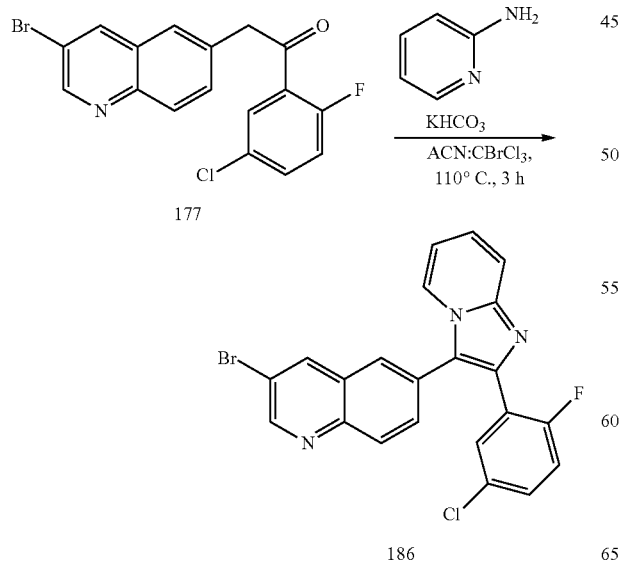

A vial of 177 (300 mg, 0.792 mmol), 2-aminopyridine (82 mg, 0.872 mmol) and potassium bicarbonate (79 mg, 0.792 mmol) in 9:2 ACN (1.29 mL):CBrCl$_3$ (0.288 mL) was sealed and heated to 110° C. for 3 h in the microwave. The reaction was concentrated in vacuum and the residue was purified via normal phase chromatography (0 to 80% EA in Hex) yielding 186 (158 mg, 44% yield) as a yellow powder. [M+H]$^+$ calcd for $C_{22}H_{12}BrClFN_3$ 451.99, found 452.0.

Example 185: Synthesis of 2-(4-(6-(2-(5-chloro-2-fluorophenyl)imidazo[1,2-a]pyridin-3-yl)quinolin-3-yl)-1H-pyrazol-1-yl)-N-methylethan-1-amine (19-1)

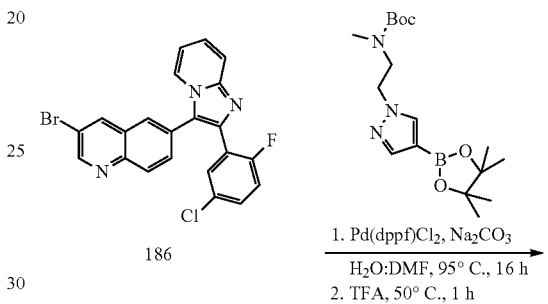

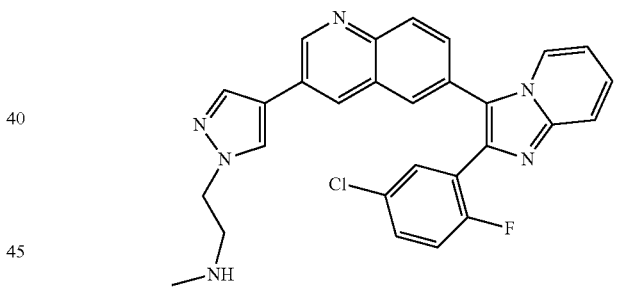

A vial of tert-butyl methyl(2-(4-(4,4,5,5-tetramethyl-1,3,2-dioxaborolan-2-yl)-1H-pyrazol-1-yl)ethyl)carbamate (34.9 mg, 0.099 mmol), 186 (30 mg, 0.066 mmol), sodium carbonate (21.07 mg, 0.199 mmol), and Pd(dppf)Cl$_2$ (10.82 mg, 0.013 mmol) in degassed water (166 μL):DMF (331 μL) was heated to 95° C. for 16 h. The reaction mixture was filtered through a pad of celite and concentrated in vacuum. 4 M HCl in dioxane (200 μL) was added to the residue and stirred for 1 h. The reaction mixture was concentrated in vacuum and the residue was purified by preparative HPLC chromatography using a gradient (5 to 75%) of acetonitrile in water with 0.05% trifluoroacetic acid to yield a TFA salt of the title compound (26.4 mg). [M+H]$^+$ calcd for $C_{28}H_{22}ClFN_6$ 497.16, found 497.1.

Example 186: Synthesis of 6-(2-(5-chloro-2-fluorophenyl)imidazo[1,2-a]pyridin-3-yl)-3-(piperazin-1-yl)quinoline (19-4)

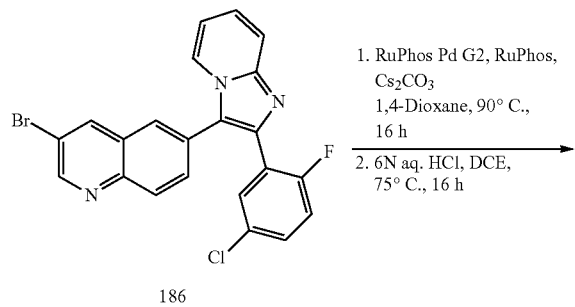

1. RuPhos Pd G2, RuPhos, Cs₂CO₃
   1,4-Dioxane, 90° C., 16 h
2. 6N aq. HCl, DCE, 75° C., 16 h

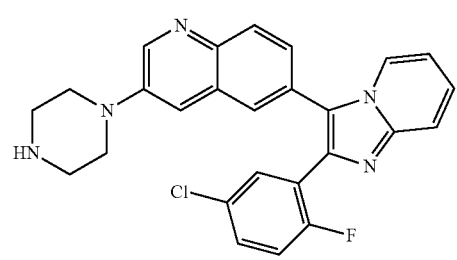

186

A vial of 186 (30 mg, 0.066 mmol), RuPhos (6.18 mg, 0.013 mmol), 1-boc-piperazine (18.51 mg, 0.099 mmol), sodium tert-butoxide (19.11 mg, 0.199 mmol), and RuPhos Pd G2 (10.29 mg, 0.013 mmol) in 1,4-dioxane (221 µL) was heated to 90° C. 16 h. The reaction mixture was concentrated in vacuum. 4 M HCl in dioxane (500 µL, 0.066 mmol) was added and allowed to stir for 2 h. The reaction mixture was concentrated in vacuum and the residue was purified by preparative HPLC chromatography using a gradient (5 to 75%) of acetonitrile in water with 0.05% trifluoroacetic acid to yield a TFA salt of the title compound (13.4 mg). [M+H]⁺ calcd for $C_{26}H_{21}ClFN_5$ 458.15, found 458.0.

Example 187: Synthesis of 6-(2-(5-chloro-2-fluorophenyl)imidazo[1,2-a]pyridin-3-yl)-N-(2-(4-isopropylpiperazin-1-yl)ethyl)quinolin-3-amine (19-6)

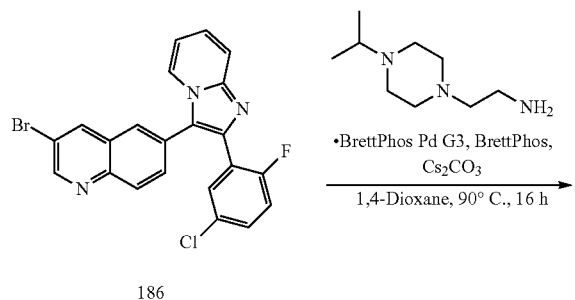

BrettPhos Pd G3, BrettPhos, Cs₂CO₃
1,4-Dioxane, 90° C., 16 h

186

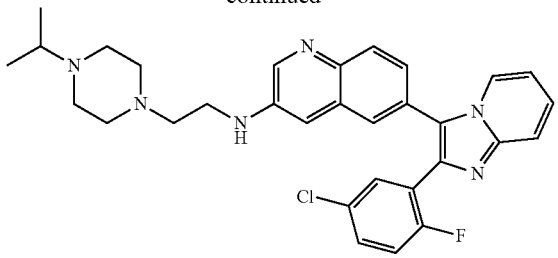

A vial of 186 (30 mg, 0.066 mmol), 2-(4-isopropyl-piperazin-1-yl)-ethylamine (17.03 mg, 0.099 mmol), sodium tert-butoxide (19.11 mg, 0.199 mmol), BrettPhos, (3.56 mg, 6.63 µmol), and BrettPhos Pd G3 (6.01 mg, 6.63 µmop in degassed 1,4-dioxane (331 µL) was heated to 90° C. for 16 h. The reaction mixture was concentrated in vacuum and the residue was purified by preparative HPLC chromatography using a gradient (5 to 75%) of acetonitrile in water with 0.05% trifluoroacetic acid to yield a TFA salt of the title compound (28.1 mg). [M+H]⁺ calcd for $C_{31}H_{32}ClFN_6$ 543.24, found 543.1.

Example 188: Synthesis of 3-bromo-6-(4-(5-chloro-2-fluorophenyl)-1-(pyridin-3-ylmethyl)-1H-1,2,3-triazol-5-yl)quinoline (187)

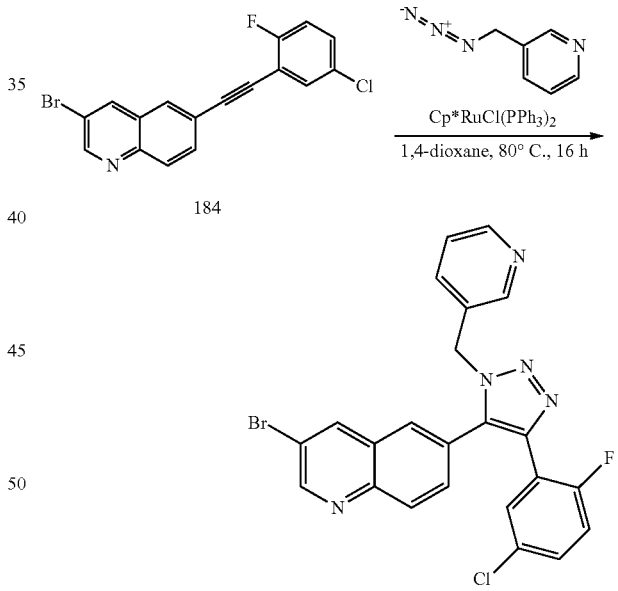

A vial of 184 (80 mg, 0.222 mmol), 3-(azidomethyl)pyridine (83.4 mg, 0.622 mmol), and Cp*RuCl(PPh₃)₂ (8.83 mg, 0.011 mmol) in 1,4-dioxane (2.22 mL) was sparged with N₂ for 10 minutes. The reaction mixture was then heated to 80° C. for 16 h. Two isomers were formed. The reaction mixture was filtered through a pad of celite and concentrated in vacuum. The residue was purified via normal phase chromatography (0 to 70% of EA in Hex) the yielding 187 as a clear oil. [M+H]⁺ calcd for $C_{23}H_{14}BrClFN_5$ 494.01, found 494.0.

Example 189: Synthesis of 2-(4-(6-(4-(5-chloro-2-fluorophenyl)-1-(pyridin-3-ylmethyl)-1H-1,2,3-triazol-5-yl)quinolin-3-yl)-1H-pyrazol-1-yl)-N-methyl-ethan-1-amine (20-1)

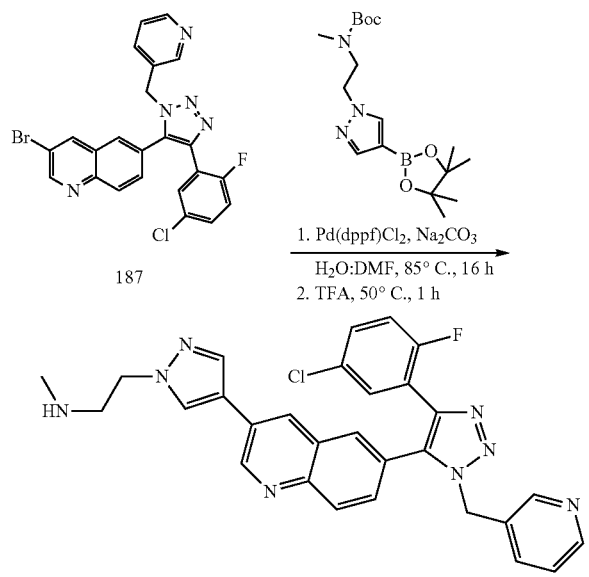

A mixture of isomers 187 (50 mg, 0.101 mmol), tert-butyl methyl(2-(4-(4,4,5,5-tetramethyl-1,3,2-dioxaborolan-2-yl)-1H-pyrazol-1-yl)ethyl)carbamate (46.1 mg, 0.131 mmol), Pd(dppf)Cl₂ (14.79 mg, 0.020 mmol), and sodium carbonate (32.1 mg, 0.303 mmol) in 1,4-dioxane (808 µL):water (202 µL) was sparged with N₂ for 5 min before heating to 85° C. for 16 h. The reaction mixture was filtered through a pad of celite and concentrated in vacuum. TFA (500 µL) was added to the residue and heated to 50° C. for 1 h until fully deprotected. The reaction was concentrated in vacuum. The isomers were separated via preparative HPLC chromatography using a gradient (2 to 60%) of acetonitrile in water with 0.05% trifluoroacetic acid to yield a TFA salt of the title compound (6.7 mg, 8.64% yield). [M+H]⁺ calcd for $C_{29}H_{24}ClFN_8$ 539.18, found 539.1.

Example 190: Synthesis of ((5-chloro-2-fluorophenyl)ethynyl)trimethylsilane (189)

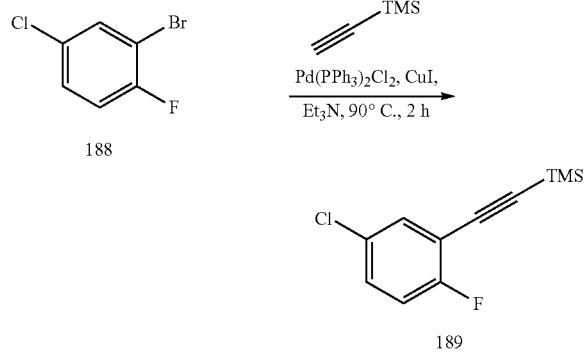

A mixture of 188 (7.0 g, 33.4 mmol), ethynyltrimethylsilane (11.5 g, 117.0 mmol), Pd(PPh₃)₂Cl₂ (1.2 g, 1.7 mmol) and copper (I) iodide (637 mg, 3.3 mmol) in Et₃N (70 mL) was stirred at 90° C. for 2 h under N₂. The mixture was concentrated under reduced pressure. The residue was purified by silica gel column (PE) to give 189 (9.5 g, crude) as red oil.

Example 191: Synthesis of 4-chloro-2-ethynyl-1-fluorobenzene (190)

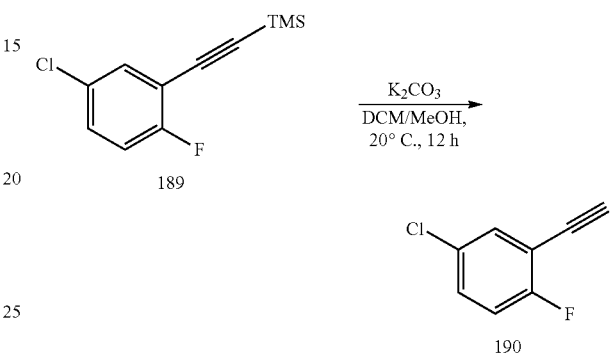

To a solution of 189 (9.5 g, 33.4 mmol, crude) in DCM (100 mL) and MeOH (50 mL) was added K₂CO₃ (12.0 g, 83.8 mmol), the mixture was stirred at 20° C. for 12 h. The reaction mixture was filtered and the filtrate was diluted with H₂O (200 mL), the aqueous phase was extracted with DCM (3×100 mL). The combined organic layer was washed with brine (3×100 mL), dried over Na₂SO₄, filtered and concentrated in vacuum to afford 190 (4.7 g, 70% yield) as a red oil.

Example 192: Synthesis of 2-((5-chloro-2-fluorophenyl)ethynyl)pyridin-3-amine (192)

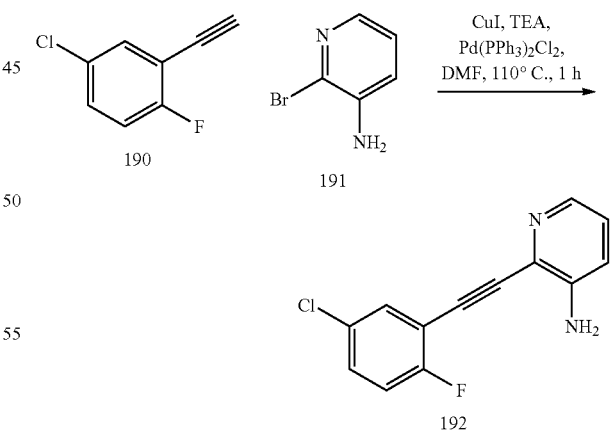

To a solution of 190 (2.3 g, 14.74 mmol) and 191 (1.7 g, 9.83 mmol) in DMF (30 mL) was added TEA (16.9 g, 167.04 mmol), copper (I) iodide (94 mg, 0.49 mmol) and Pd(PPh₃)₂Cl₂ (138 mg, 0.20 mmol). The mixture was stirred at 110° C. for 1 h under N₂. The mixture was diluted with H₂O (200 mL), the aqueous was extracted with EA (4×150 mL), the organic layer was washed with brine, dried over Na₂SO₄, concentrated in vacuum to give a residue, then the residue was purified by column (PE:EA=3:1 to 1:1) to afford 192 (2.3 g, 94% yield, 98% purity) as a brown solid.

Example 193: Synthesis of N-(2-((5-chloro-2-fluorophenyl)ethynyl)pyridin-3-yl)-2,2,2-trifluoroacetamide (193)

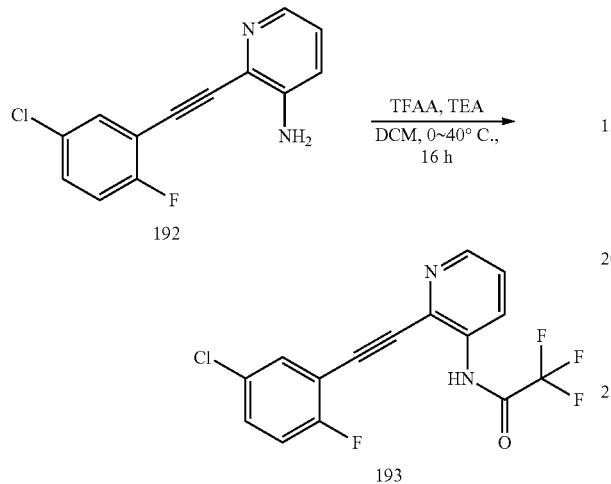

To a solution of 192 (2.0 g, 8.23 mmol), TEA (5.0 g, 49.38 mmol) in DCM (30 mL) was added TFAA (6.9 g, 32.92 mmol) at 0° C. The mixture was heated to 40° C. and stirred at 40° C. for 16 h. The mixture was diluted with sat. NaHCO₃aq. (100 mL), the aqueous phase was extracted with EA (3×80 mL), the combined organic layer was dried over Na₂SO₄ and concentrated under reduced pressure, the residue was purified by column (PE:EA=4:1 to 3:1) and trituration (PE:EA=10:1 (50 mL)) to give 193 (1.0 g, 30% yield, 100% purity) as a white solid. [M+H]⁺ calcd for $C_{15}H_7ClF_4N_2O$ 343.02, found 342.9. ¹H NMR (400 MHz, Chloroform-d) δ 8.79 (s, 1H), 8.74 (dd, J=8.5, 1.5 Hz, 1H), 8.49 (dd, J=4.8, 1.5 Hz, 1H), 7.59 (dd, J=5.9, 2.7 Hz, 1H), 7.47-7.35 (m, 2H), 7.14 (t, J=8.7 Hz, 1H).

Example 194: Synthesis of quinolin-6-yl acetate (196)

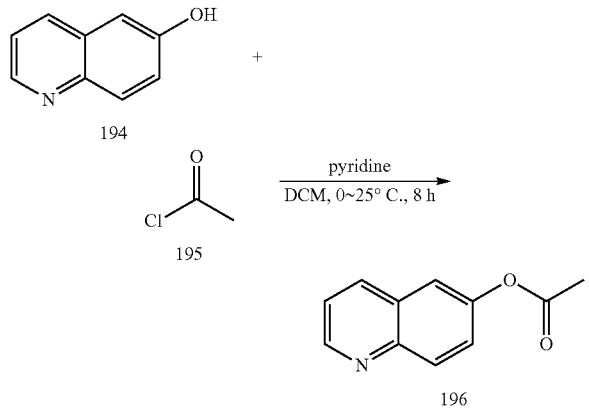

To a solution of 194 (24.0 g, 165 mmol) and pyridine (15.7 g, 198 mmol) in DCM (300 mL) was added 195 (15.5 g, 198 mmol) dropwise at 0° C. Then the mixture was stirred at 25° C. for 8 h under N₂. The mixture was basified by sat. NaHCO₃ solution to pH 8 and extracted by EA (2×300 mL). The organic layer was concentrated in vacuum and purified by silica gel column (0 to 36% of EA in PE) to obtain 196 (26.8 g, 86% yield, 99% purity) as yellow solid. [M+H]⁺ calcd for $C_{11}H_9NO_2$ 188.06, found 188.0.

Example 195: Synthesis of 3-bromoquinolin-6-yl acetate (197)

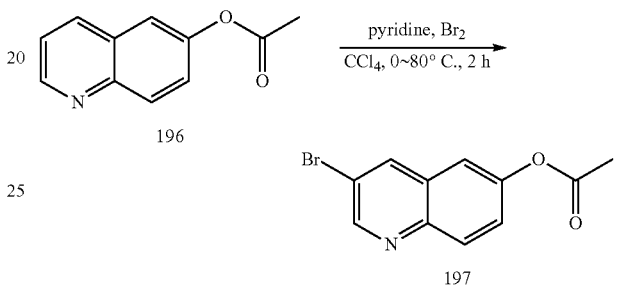

To a solution of 196 (26.8 g, 143 mmol) and pyridine (24.9 g, 315 mmol) in CCl₄ (400 mL) was added Br₂ (45.7 g, 286 mmol) at 0° C. The mixture was stirred at 80° C. for 2 h. The mixture was filtered and the filtrate was concentrated in vacuum. The residue was purified by trituration (10% of EA in PE (50 mL)) to obtain 197 (32.8 g, 86% yield, 87% purity) as white solid. [M+H]⁺ calcd for $C_{11}H_8BrNO_2$ 265.97, found 265.8.

Example 196: Synthesis of tert-butyl (2-chloroethyl)carbamate (199)

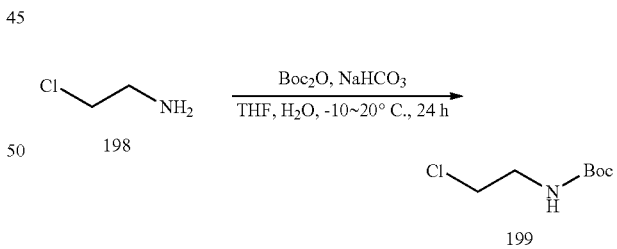

To a mixture of 198 (127.0 g, 1095 mmol), NaHCO₃ (263.0 g, 4380 mmol) in THF (1.0 L) and H₂O (1.2 L) was added Boc₂O (368.0 g 1204 mmol) in THF (200 mL) dropwise at −10° C. The reaction mixture was warmed to 20° C. and stirred at this temperature for 24 h. The residue was filtered through celite. The reaction mixture was diluted with EA (3×500 mL). The organic layer was washed with brine (2×300 mL), dried over Na₂SO₄, filtered. The filtrate was concentrated in vacuum to afford 199 (220.0 g, 100% yield) as a yellow oil.

Example 197: Synthesis of tert-butyl (2-chloroethyl)(methyl)carbamate (78)

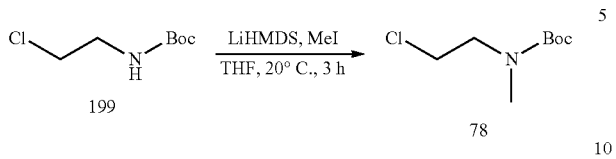

To a mixture of 199 (30.00 g, 167 mmol), MeI (107.53 g, 757 mmol) in THF (500 mL) was added LiHMDS (251 mL, 251 mmol) dropwise at 20° C. The reaction mixture was stirred at 20° C. for 3 h. The residue was diluted with H$_2$O (400 mL), extracted with EA (3×300 mL). The organic layer was dried over Na$_2$SO$_4$, filtered. The filtrate was concentrated in vacuum to afford 78 (27.9 g, 86% yield) as yellow oil.

Example 198: Synthesis of tert-butyl (2-(4-iodo-1H-pyrazol-1-yl)ethyl)(methyl)carbamate (79)

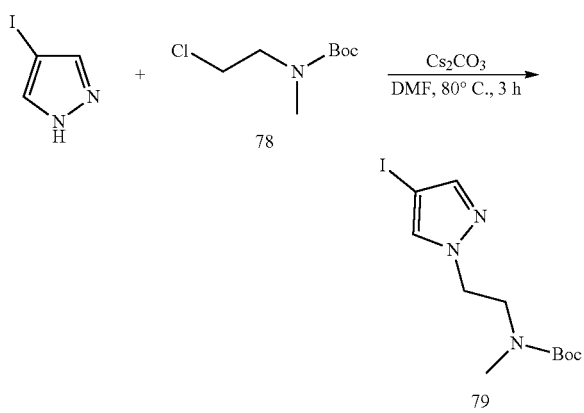

A mixture of 3-iodo-1H-pyrazole (24.0 g, 124 mmol), 78 (47.9 g, 247 mmol), Cs$_2$CO$_3$ (80.5 g, 247 mmol) in DMF (400 mL) was stirred at 80° C. for 3 h. The mixture was filtered. The filtrate was diluted with brine (1 L) and extracted with EA (2×500 mL). The organic layer was concentrated in vacuum and purified by silica gel column (0 to 20% of EA in PE) to obtain 79 (40.0 g, 93% yield, 97% purity) as yellow oil. [M+H]$^+$ calcd for C$_{11}$H$_{18}$INO$_2$ 352.04, found 351.9.

Example 199: Synthesis of tert-butyl methyl (2-(4-(4,4,5,5-tetramethyl-1,3,2-dioxaborolan-2-yl)-1H-pyrazol-1-yl)ethyl)carbamate

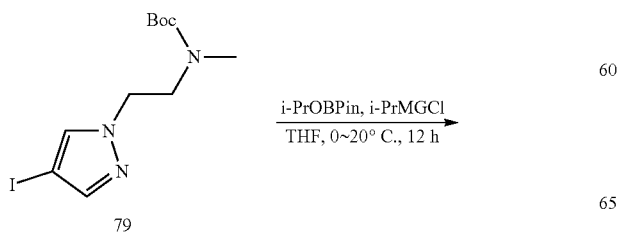

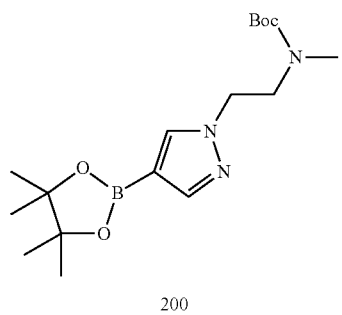

To a mixture of 79 (40.0 g, 114 mmol), i-PrOBPin (31.8 g, 171 mmol) in THF (300 mL) was added i-PrMgCl (114 mL, 228 mmol) at 0° C. The reaction was stirred at 20° C. for 12 h. The reaction mixture was concentrated in vacuum to afford 200 (91.0 g, 51% purity) as yellow solid which was used directly. [M+H]$^+$ calcd for C$_{17}$H$_{30}$BN$_3$O$_4$ 352.23, found 352.0.

Example 200: Synthesis of 3-(1-(2-((tert-butoxycarbonyl)(methyl)amino)ethyl)-1H-pyrazol-4-yl)quinolin-6-yl acetate (201)

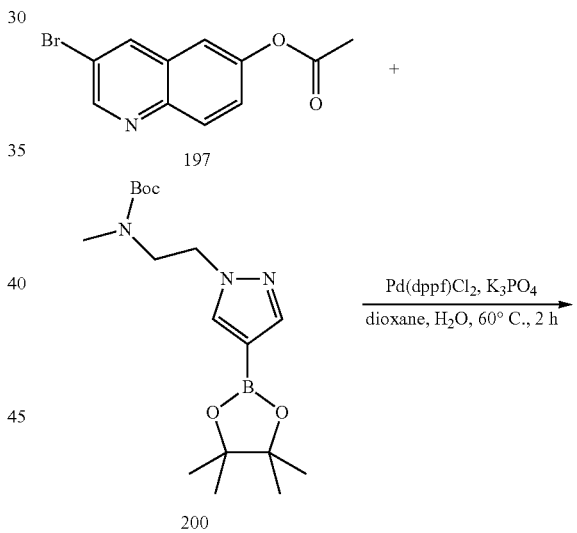

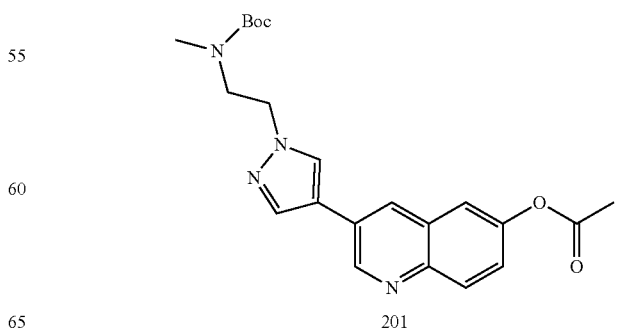

To a solution of 197 (9.2 g, 34.6 mmol), 200 (30.0 g, 38.1 mmol) and K₃PO₄ (14.7 g, 69.3 mmol) in dioxane (160 mL) and H₂O (32 mL) was added Pd(dppf)Cl₂ (2.5 g, 3.46 mmol). The mixture was stirred at 60° C. for 2 h under N₂. The mixture was concentrated in vacuum and purified by silica gel column to obtain 201 as black oil (6.3 g, 41% yield).

Example 201: Synthesis of tert-butyl (2-(4-(6-hydroxyquinolin-3-yl)-1H-pyrazol-1-yl)ethyl)(methyl)carbamate (202)

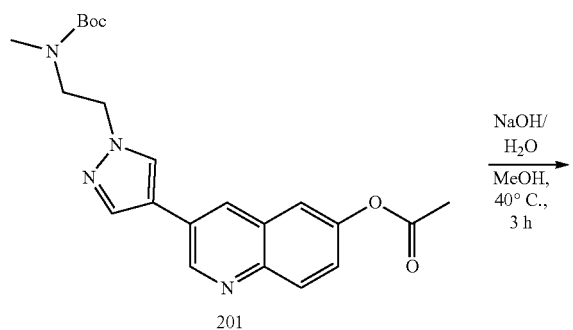

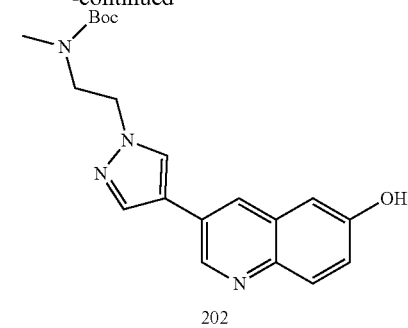

A solution of 201 (6.3 g, 15.3 mmol) in NaOH/H₂O (14 mL, 40%) and MeOH (80 mL) was stirred at 40° C. for 3 h. TLC showed starting material was consumed. The mixture was concentrated in vacuum. The residue was acidified by HCl (2M) to pH 7. The mixture was diluted with water (100 mL) and extracted with EA (3×100 mL). The organic layer was concentrated in vacuum and purified by silica gel column (40 to 90% of EA in PE) to obtain 202 (4.6 g, 81% yield) as white solid.

Example 202: Synthesis of 3-(1-(2-((tert-butoxycarbonyl)(methyl)amino)ethyl)-1H-pyrazol-4-yl)quinolin-6-yl trifluoromethanesulfonate (203)

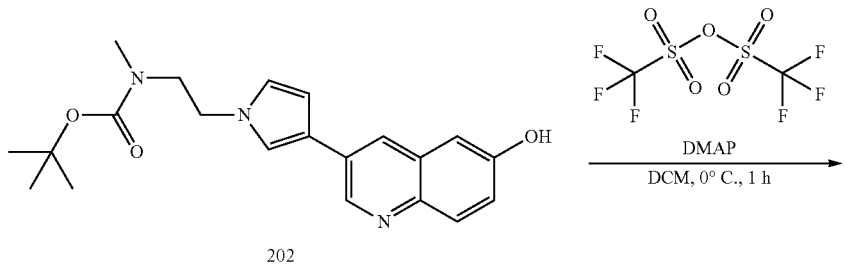

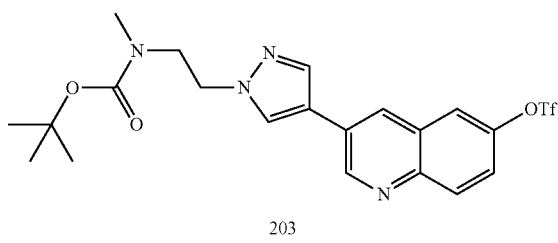

To a solution of 202 (4.6 g, 12.5 mmol) and DMAP (3.1 g, 25.0 mmol) in DCM (50 mL) was dropwise added trifluoromethanesulfonic anhydride (4.2 g, 15.0 mmol) over 0.5 h at 0° C. The mixture was stirred at 0° C. for 0.5 h. The mixture was concentrated in vacuum and purified by silica gel column (30 to 60% of EA in PE) to obtain 203 (4.0 g, 64% yield) as white solid.

Example 203: Synthesis of tert-butyl methyl(2-(4-(6-(4,4,5-trimethyl-1,3,2-dioxaborolan-2-yl)quinolin-3-yl)-1H-pyrazol-1-yl)ethyl)carbamate (204)

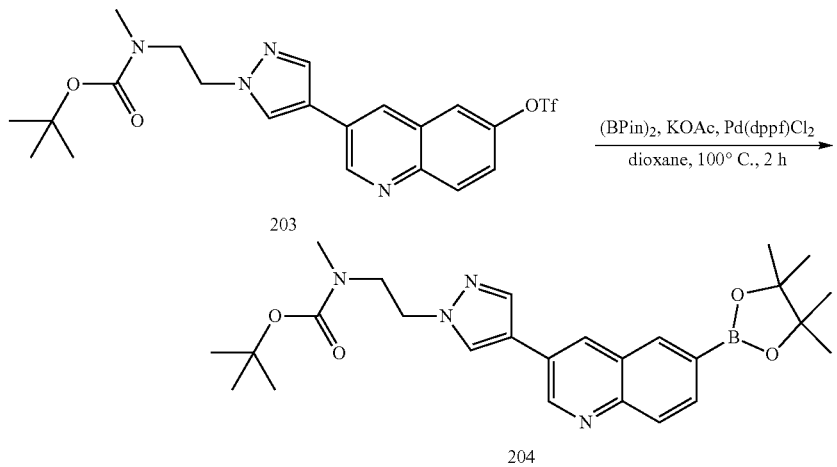

To a mixture of 203 (4.0 g, 7.99 mmol) and (BPin)$_2$ (2.4 g, 9.59 mmol) in dioxane (60 mL) was added Pd(dppf)Cl$_2$ (584 mg, 0.799 mmol) and KOAc (1.6 g, 16.0 mmol). The mixture was stirred at 100° C. for 2 h under N$_2$ atmosphere. The mixture was concentrated in vacuum and purified by silica gel column (30 to 70% of EA in PE) to obtain 204 (4.1 g, 76% yield, 99% purity) as white solid. $^1$H NMR (400 MHz, DMSO-d$_6$) δ 9.23 (d, J=2.3 Hz, 1H), 8.59 (d, J=2.3 Hz, 1H), 8.40-8.31 (m, 2H), 8.13 (s, 1H), 7.97 (d, J=8.3 Hz, 1H), 7.87 (dd, J=8.3, 1.4 Hz, 1H), 4.31 (t, J=5.8 Hz, 2H), 3.61 (t, J=5.8 Hz, 2H), 2.73 (s, 3H), 1.36 (s, 9H).

Example 204: Synthesis of 2-(4-(6-(2-(5-chloro-2-fluorophenyl)-1H-pyrrolo[3,2-b]pyridin-3-yl)quinolin-3-yl)-1H-pyrazol-1-yl)-N-methylethan-1-amine (21-1)

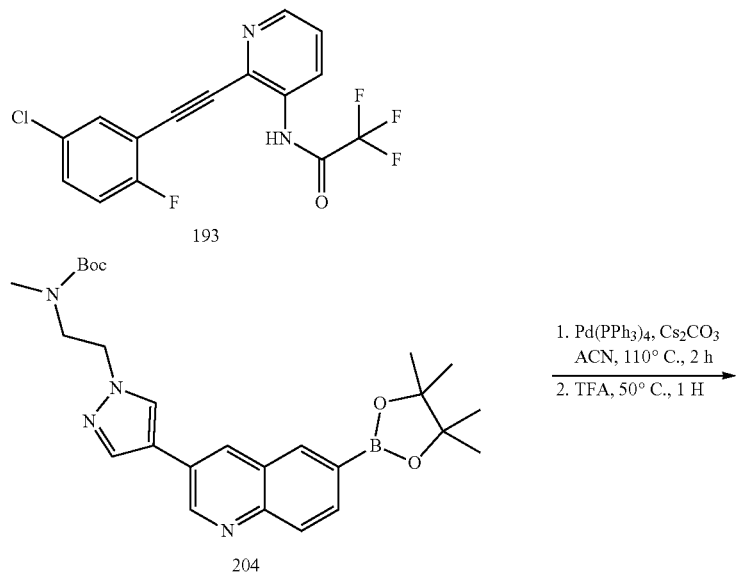

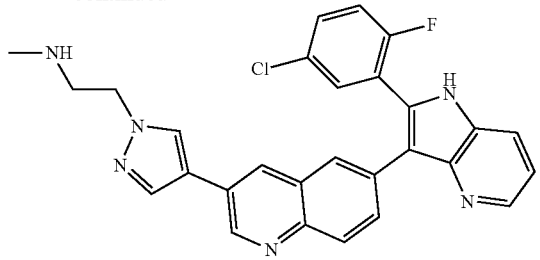

A vial of 193 (20 mg, 0.058 mmol), cesium carbonate (38.0 mg, 0.117 mmol), Pd(PPh$_3$)$_4$ (6.74 mg, 5.84 μmol), and 204 (46.3 mg, 0.117 mmol) in ACN (292 μL) was heated for 2 h at 110° C. The reaction mixture was concentrated in vacuum. TFA (500 μL) was added to the reaction and heated to 50° C. for 1 h until fully deprotected. The reaction mixture was concentrated in vacuum and the residue was purified by preparative HPLC chromatography using a gradient (10 to 80%) of acetonitrile in water with 0.05% trifluoroacetic acid to yield a TFA salt of the title compound (7.5 mg). [M+H]$^+$ calcd for C$_{28}$H$_{22}$ClFN$_6$ 497.16, found 497.0.

Example 205: Synthesis of diphenyl ((5-chloro-2,4-difluorophenyl)(phenylamino) methyl)phosphonate (206)

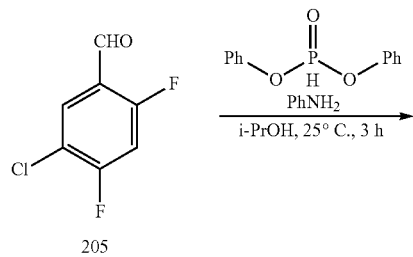

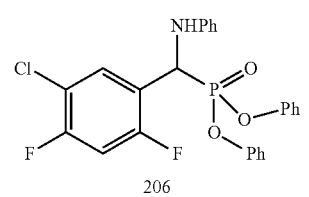

To a mixture of 205 (9.0 g, 51.0 mmol), PhNH$_2$ (5.7 g, 61.2 mmol) in i-PrOH (100 mL) was added diphenyl phosphonate (20.7 g, 66.3 mmol) at 25° C. The reaction mixture was stirred at 25° C. for 3 h. The mixture was filtered. The filter residue was dried in vacuum to afford 206 (22.0 g, 89% yield) as white solid.

Example 206: Synthesis of 2-(3-bromoquinolin-6-yl)-1-(5-chloro-2,4-difluorophenyl)ethan-1-one (207)

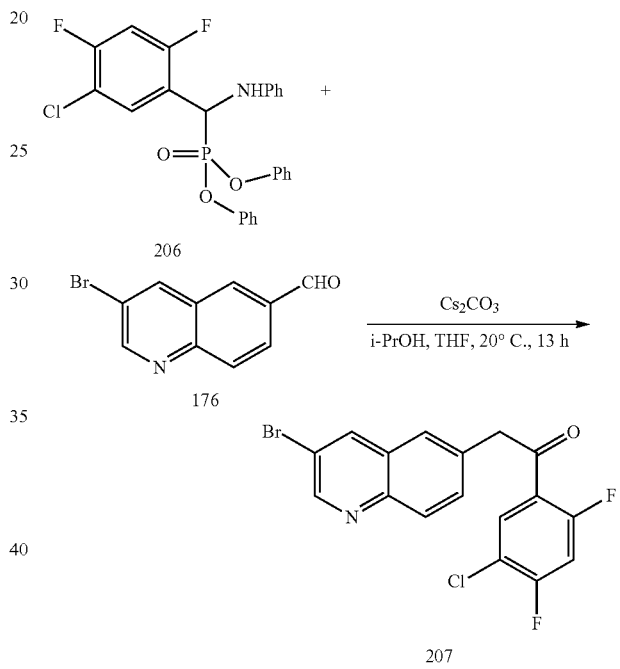

To a mixture of 206 (15.5 g, 31.9 mmol), Cs$_2$CO$_3$ (10.3 g, 31.9 mmol) in THF (100 mL) and i-PrOH (20 mL) was added 176 (5.0 g, 21.3 mmol) at 20° C. The reaction mixture was stirred at 20° C. for 12 h. The reaction mixture was diluted with 3.0 M HCl (16 mL), and stirred at 20° C. for 1 h. The mixture was basified with solid NaOH to pH 8 and filtered. The filtrate cake was washed by EA (10 mL) and dried in vacuum to obtain 207 (9.0 g, 75% yield, 99% purity) as white solid. The mother liquor was extracted by EA (3×50 mL). The organic layer was concentrated in vacuum and purified by silica gel column (0-20% of EA in PE) to obtain 207 (2.0 g, 11% yield, 70% purity) as yellow solid. [M+H]$^+$ calcd for C$_{17}$H$_9$BrClF$_2$NO 395.95, found 396.0. $^1$H NMR (400 MHz, Chloroform-d) δ 8.88 (d, J=2.3 Hz, 1H), 8.26 (dd, J=2.3, 0.8 Hz, 1H), 8.09-7.96 (m, 2H), 7.59 (dq, J=4.3, 2.0 Hz, 2H), 7.02 (dd, J=10.4, 8.3 Hz, 1H), 4.44 (d, J=2.9 Hz, 2H).

Example 207: Synthesis of 1-(3-bromoquinolin-6-yl)-2-(5-chloro-2,4-difluorophenyl)ethane-1,2-dione (208)

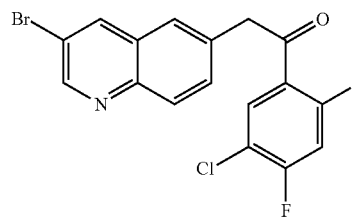

Example 208: Synthesis of 3-bromo-6-(5-(5-chloro-2,4-difluorophenyl)-1H-imidazol-4-yl)quinoline (209)

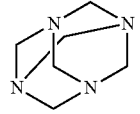

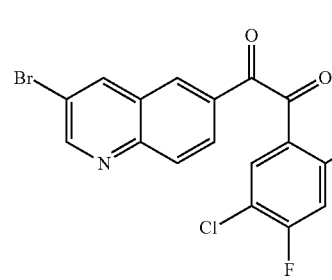

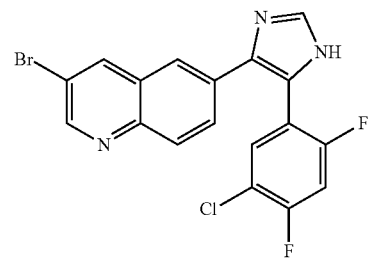

209
Exact Mass: 418.96

A solution of 207 (4.0 g, 10.1 mmol) and SeO$_2$ (5.6 g, 50.4 mmol) in dioxane (60 mL) was stirred at 100° C. for 16 h. The mixture was filtered. The filtrate was diluted with water (100 mL) and extracted with EA (3×100 mL). The organic layer was concentrated in vacuum to obtain 208 (5.0 g, 80% purity, crude) as black solid. [M+H]$^+$ calcd for C$_{17}$H$_7$BrClF$_2$NO$_2$ 409.93, found 409.8.

A solution of 208 (6.0 g, 11.7 mmol, crude), hexamine (26.45 g, 189 mmol) and NH$_4$OAc (5.4 g, 70.2 mmol) in AcOH (50 mL) was stirred at 95° C. for 2.5 h. The reaction mixture was concentrated in vacuum and basified with sat. aq. NaHCO$_3$ to pH 8. The mixture was extracted by EA (3×150 mL). The organic layer was concentrated in vacuum and purified by silica gel column (25-75% of EA in PE) to obtain 209 (3.5 g, 83% yield, 99% purity) as yellow solid. [M+H]$^+$ calcd for C$_{18}$H$_9$BrClF$_2$N$_3$ 419.96, found 419.8.

Example 209: Synthesis of 3-bromo-6-(5-(5-chloro-2,4-difluorophenyl)-1-((2-(trimethylsilyl) ethoxy) methyl)-1H-imidazol-4-yl)quinoline (210) and 3-bromo-6-(4-(5-chloro-2,4-difluorophenyl)-1-((2-(trimethylsilyl)ethoxy)methyl)-1H-imidazol-5-yl) quinoline (211)

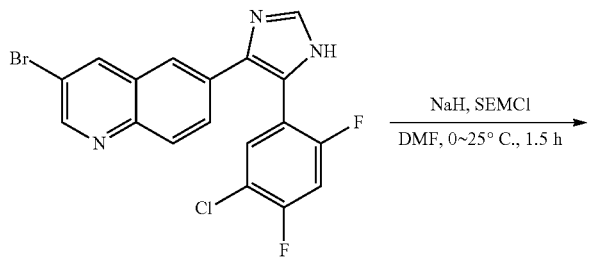

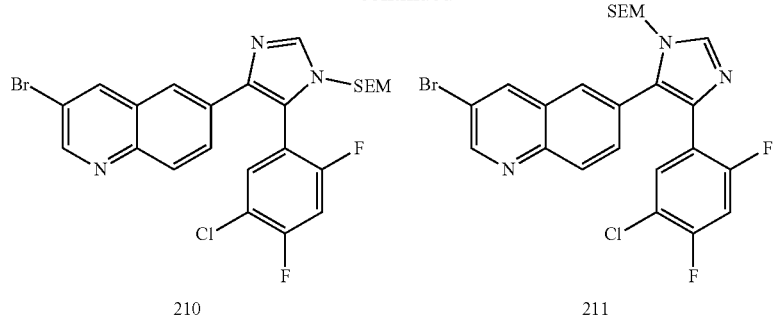

210  211

To a suspension of NaH (666 mg, 16.6 mmol) in DMF (40 mL) was added 209 (3.5 g, 8.32 mmol) in DMF (40 mL) at 0° C. and stirred at 0° C. for 0.5 h. Then SEMCl (2.8 g, 16.6 mmol) was added to the mixture at 0° C. and the reaction mixture was warmed to 25° C. and stirred for 1 h. The mixture was quenched by water (60 mL) and extracted by EA (3×100 mL). The organic layer was washed by brine (3×70 mL). Then organic layer was concentrated in vacuum and purified by silica gel column (0-25% of EA in PE) to obtain a mixture (1:1.6 ratio) of isomers 210 and 211 (3.3 g, 56% yield, 99% purity) as yellow solid. [M+H]$^+$ calcd for $C_{24}H_{23}BrClF_2N_3OSi$ 549.05, found 549.9. $^1$H NMR—mixture of regioisomers—(400 MHz, Chloroform-d) δ 8.92 (d, J=2.3 Hz, 1H), 8.82 (d, J=2.3 Hz, 2H), 8.26 (d, J=2.3 Hz, 1H), 8.19 (d, J=2.2 Hz, 3H), 8.07 (d, J=8.7 Hz, 1H), 7.98-7.89 (m, 4H), 7.89-7.61 (m, 7H), 7.52 (t, J=7.6 Hz, 2H), 7.09 (t, J=8.6 Hz, 2H), 6.73 (t, J=9.2 Hz, 1H), 5.22 (s, 2H), 5.14 (s, 4H), 3.58 (dd, J=8.8, 7.6 Hz, 2H), 3.46 (t, J=8.2 Hz, 4H), 1.00-0.90 (m, 2H), 0.87 (dd, J=9.0, 7.4 Hz, 4H), −0.00 (s, 9H), −0.03 (s, 14H).

Example 210: Synthesis of (1R,2R)-2-((tert-butoxycarbonyl)amino)cyclohexyl methanesulfonate (213)

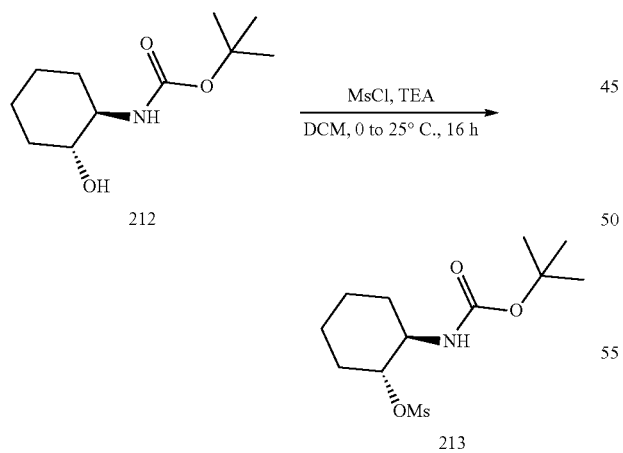

To a vial charged with tert-butyl 212 (70 mg, 0.325 mmol) was added DCM (2.3 mL) and triethylamine (113 μL, 0.813 mmol). The mixture was cooled to 0° C. before being treated with methanesulfonyl chloride (45.3 μL, 0.585 mmol). The resulting clear solution was stirred at 0° C. and slowly allowed to warm up to 25° C. and stirred for 16 h. The reaction mixture was quenched with sat. NaHCO$_3$(3 mL).

The aqueous layer was extracted with DCM (3×10 mL), dried over Na$_2$SO$_4$, and concentrated in vacuum yielding 213 (89.5 mg, crude) as a white solid which was used in the next step directly.

Example 211: Synthesis of (1R,2R)-2-(4-(6-(5-(5-chloro-2,4-difluorophenyl)-1H-imidazol-4-yl)quinolin-3-yl)-1H-pyrazol-1-yl)cyclohexan-1-amine (22-1)

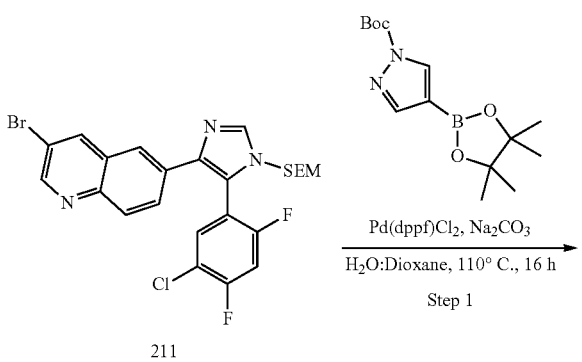

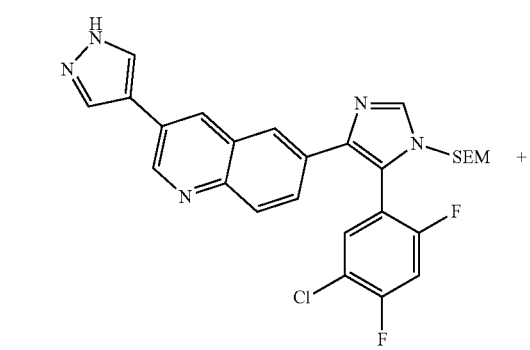

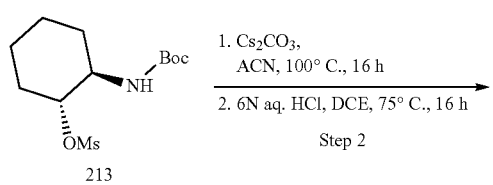

-continued

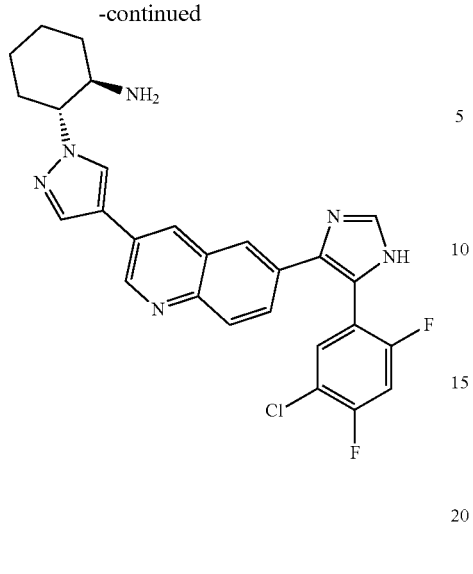

Step 1: A vial of 211 (44.5 mg, 0.081 mmol), sodium carbonate (42.8 mg, 0.404 mmol), 1-boc-pyrazole-4-boronic acid pinacol ester (40.4 mg, 0.137 mmol), and Pd(dppf)Cl$_2$ (11.81 mg, 0.016 mmol) in 1,4-dioxane (323 μL):water (81 μL) was sparged with N$_2$ for 10 min before heating to 110° C. for 16 h. The boc group is removed during the Suzuki reaction. The reaction mixture was filtered and concentrated in vacuum. The residue was purified via normal phase chromatography (0 to 100% of EA in hexanes) yielding 6-(5-(5-chloro-2,4-difluorophenyl)-1-((2(trimethylsilyl)ethoxy)methyl)-1H-imidazol-4-yl)-3-(1H-pyrazol-4-yl)quinoline (27 mg, 62% yield) as a yellow oil. [M+H]$^+$ calcd for C$_{27}$H$_{26}$ClF$_2$N$_5$OSi 538.16, found 538.0.

Step 2: To the vial containing 213 (22.79 mg, 0.078 mmol) was added cesium carbonate (33.8 mg, 0.104 mmol) followed by a solution containing 6-(5-(5-chloro-2,4-difluorophenyl)-1-((2(trimethylsilyl)ethoxy)methyl)-1H-imidazol-4-yl)-3-(1H-pyrazol-4-yl)quinoline (27 mg, 0.050 mmol) in acetonitrile (1 mL) and the resulting mixture was capped and stirred at 100° C. for 16 h. The reaction was concentrated in vacuum. The residue was dissolved in DCE (0.300 mL) and 6 M aq. HCl (0.200 ml) was added. The mixture was heated to 75° C. for 16 h. The reaction mixture was concentrated in vacuum and the residue was purified by preparative HPLC chromatography using a gradient (5 to 75%) of acetonitrile in water with 0.05% trifluoroacetic acid to yield a TFA salt of the title compound (4.4 mg). [M+H]$^+$ calcd for C$_{27}$H$_{23}$ClFN$_6$ 505.16, found 505.1. The stereochemistry of the product was confirmed by NOE.

Example 212: Synthesis of 2-(4-(6-(5-(5-chloro-2,4-difluorophenyl)-1H-imidazol-4-yl)quinolin-3-yl)-1H-pyrazol-1-yl)-N-methylethan-1-amine (22-2)

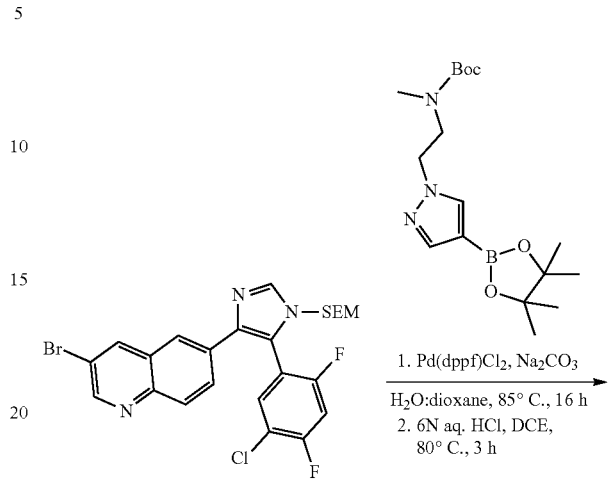

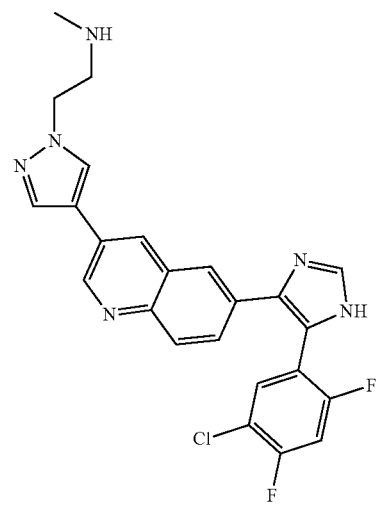

A vial of tert-butyl methyl(2-(4-(4,4,5,5-tetramethyl-1,3,2-dioxaborolan-2-yl)-1H-pyrazol-1-yl)ethyl)carbamate (24.87 mg, 0.071 mmol), 211 (30 mg, 0.054 mmol), sodium carbonate (23.09 mg, 0.218 mmol), and Pd(dppf)Cl$_2$ (7.97 mg, 0.011 mmol) in degassed water (109 μL):1,4-dioxane (436 μL) was sparged with N$_2$ for 10 min before heating to 85° C. for 16 h. The reaction mixture was filtered through a pad of celite and concentrated in vacuum. The crude material was dissolved in DCE (0.300 mL) and 6 M aq. HCl (0.200 mL) was added. The mixture was heated to 80° C. for 3 h. The reaction mixture was concentrated in vacuum and the residue was purified by preparative HPLC chromatography using a gradient (5 to 75%) of acetonitrile in water with 0.05% trifluoroacetic acid to yield a TFA salt of the title compound (9.8 mg). [M+H]$^+$ calcd for C$_{24}$H$_{19}$ClF$_2$N$_6$ 465.13, found 465.0.

Example 213: Synthesis of 6-(5-(5-chloro-2,4-difluorophenyl)-1H-imidazol-4-yl)-N-(2-(4-isopropylpiperazin-1-yl)ethyl)quinolin-3-amine (22-4)

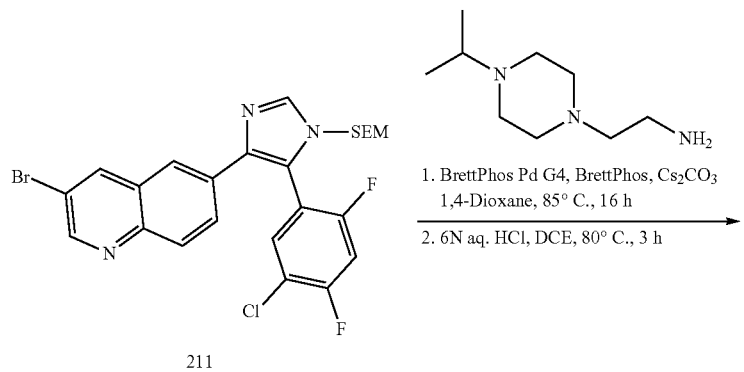

A vial of 211 (30 mg, 0.054 mmol), 2-(4-isopropyl-piperazin-1-yl)-ethylamine (0.013 ml, 0.071 mmol), cesium carbonate (53.2 mg, 0.163 mmol), BrettPhos (5.85 mg, 10.03 μmol), and BrettPhos Pd G4 (10.03 mg, 10.89 μmol) in 1,4-dioxane (0.545 mL) (degassed with $N_2$) was heated to 85° C. for 16 h. The reaction mixture was filtered through a pad of celite and concentrated in vacuum. The crude material was dissolved in DCE (0.300 mL) and 6 M aq. HCl (0.200 mL) was added. The mixture was heated to 80° C. for 3 h. The reaction mixture was concentrated in vacuum and the residue was purified by preparative HPLC chromatography using a gradient (5 to 65%) of acetonitrile in water with 0.05% trifluoroacetic acid to yield a TFA salt of the title compound (13.6 mg). $[M+H]^+$ calcd for $C_{27}H_{29}ClF_2N_6$ 511.21, found 511.1.

Example 214: Synthesis of diphenyl ((3,4-difluorophenyl)(phenylamino)methyl)phosphonate (214)

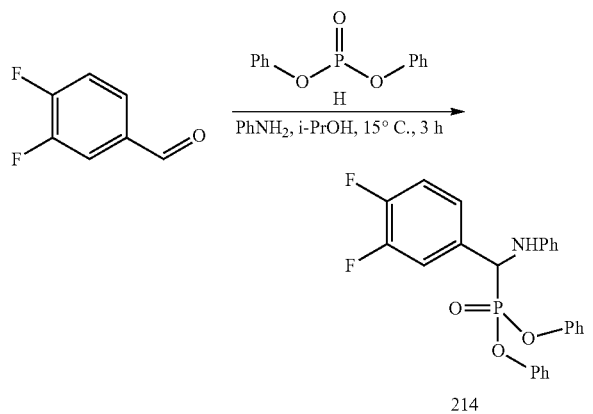

To a mixture of 3,4-difluorobenzaldehyde (8.0 g, 56.3 mmol), $PhNH_2$ (7.9 g, 84.5 mmol) in i-PrOH (100 mL) was added diphenyl phosphonate (19.8 g, 84.5 mmol) at 15° C. The reaction mixture was stirred at 15° C. for 3 h. The mixture was filtered and the filter cake was washed with i-PrOH (3×30 mL). Then the filter cake was dried to obtain 214 (21.5 g, 84% yield) as white solid.

Example 215: Synthesis of 2-(3-bromoquinolin-6-yl)-1-(3,4-difluorophenyl)ethan-1-one (215)

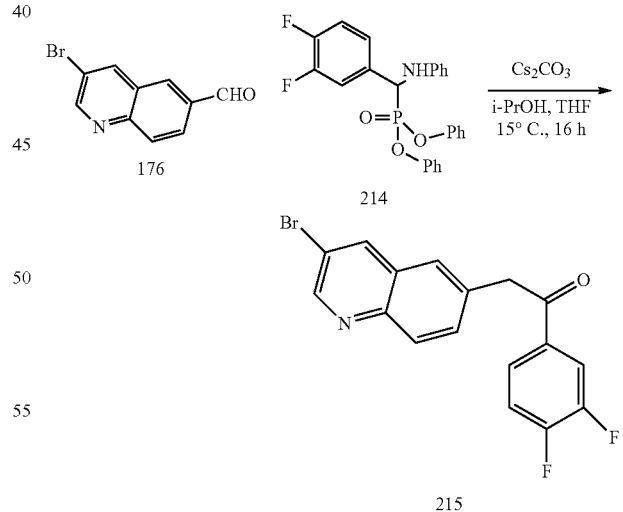

To a solution of 176 (5.0 g, 21.2 mmol), $Cs_2CO_3$ (13.8 g, 42.4 mmol) in THF (100 mL) and i-PrOH (25 mL) was added 214 (14.3 g, 31.8 mmol). The mixture was stirred at 15° C. for 15 h. Then the reaction was acidified with 2.0 M HCl aq. to pH 2 and stirred at 15° C. for 1 h. The mixture was adjusted to pH 8 by added sat. aq. $NaHCO_3$ and further diluted with $H_2O$ (150 mL) and extracted with EA (3×200 mL). The combined organic layer was concentrated in vacuum. The residue was purified by column (0 to 20% of EA in PE) to obtain 215 (7.2 g, 75% yield) as light yellow solid.

Example 216: Synthesis of 1-(3-bromoquinolin-6-yl)-2-(3,4-difluorophenyl)ethane-1,2-dione (216)

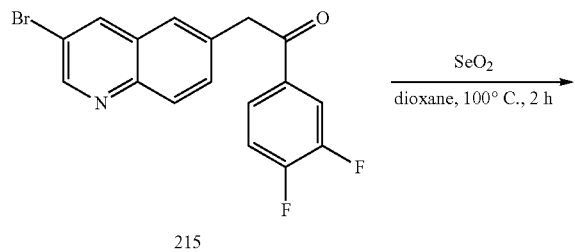

215

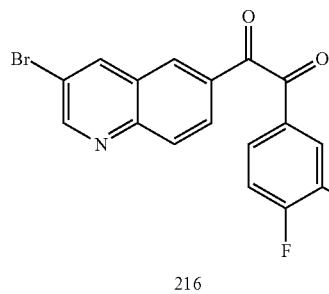

216

To a solution of 215 (2.0 g, 5.52 mmol) in dioxane (30 mL) was added SeO₂ (3.1 g, 27.60 mmol). The mixture was filtered and the organic layer was concentrated in vacuum to obtain crude 216 (2.0 g) as brown solid.

Example 217: Synthesis of 3-bromo-6-(5-(3,4-difluorophenyl)-1H-imidazol-4-yl)quinoline (217)

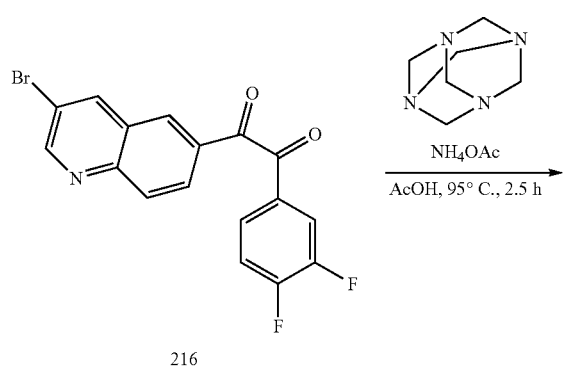

217

A solution of 216 (2.0 g, 5.52 mmol), hexamine (2.3 g, 16.56 mmol) and NH₄OAc (2.5 g, 33.12 mmol) in AcOH (30 mL) was stirred at 95° C. for 2.5 h. The reaction mixture was concentrated in vacuum and basified with sat. NaHCO₃aq to pH 8. The mixture was extracted with EA (3×100 mL). The combined organic phase was washed with brine (2×100 mL), dried over Na₂SO₄, filtered and concentrated in vacuum. The residue was purified by column (20 to 100% of EA in PE) to obtain 217 (1.2 g, 56% yield) as red solid.

Example 218: Synthesis of 3-bromo-6-(5-(3,4-difluorophenyl)-1-((2-(trimethylsilyl)ethoxy) methyl)-1H-imidazol-4-yl)quinoline (218) and 3-bromo-6-(4-(3,4-difluorophenyl)-1-((2-(trimethylsilyl)ethoxy) methyl)-1H-imidazol-5-yl)quinoline (219)

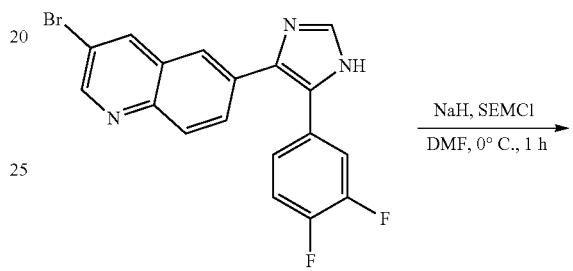

217

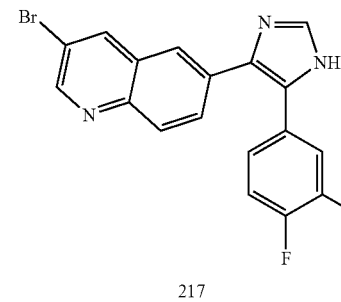

218

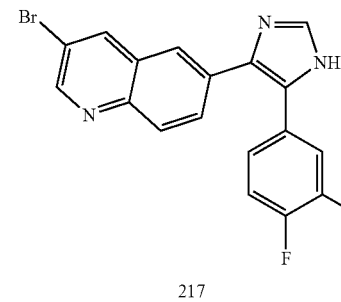

219

To a solution of 217 (1.2 g, 3.11 mmol) in DMF (20 mL) stirred at 0° C. was added NaH (249 mg, 6.22 mmol) in portions. The reaction was stirred at 0° C. for 0.5 h. Then SEMCl (621 mg, 3.73 mmol) was added and the mixture was stirred at 0° C. for another 0.5 h. The mixture was diluted with H₂O (50 mL) and extracted with EA (3×50 mL). The combined organic layer was washed with brine (3×100 mL) and concentrated in vacuum. The residue was purified by column (10 to 50% of EA in PE) to obtain a mixture (1:0.9 ratio) of 218 and 219 (2.8 g, 87% yield, 100% purity) as red oil. [M+H]⁺ calcd for C₂₄H₂₄BrF₂N₃OSi 516.08, found 516.0. ¹H NMR—mixture of regioisomers—(400

MHz, Chloroform-d) δ 8.98 (d, J=2.3 Hz, 1H), 8.82 (d, J=2.3 Hz, 1H), 8.31 (dd, J=2.3, 0.8 Hz, 1H), 8.21-8.11 (m, 2H), 7.97-7.85 (m, 3H), 7.81-7.77 (m, 2H), 7.72 (ddd, J=12.3, 8.8, 1.9 Hz, 2H), 7.39-7.14 (m, 4H), 7.19-7.06 (m, 1H), 6.96 (dt, J=10.3, 8.4 Hz, 1H), 5.14 (s, 4H), 3.60-3.49 (m, 4H), 0.98-0.83 (m, 4H), 0.01 (s, 9H), −0.01 (s, 9H).

Example 219: Synthesis of 2-(4-(6-(5-(3,4-difluorophenyl)-1H-imidazol-4-yl)quinolin-3-yl)-1H-pyrazol-1-yl)ethan-1-amine (23-1)

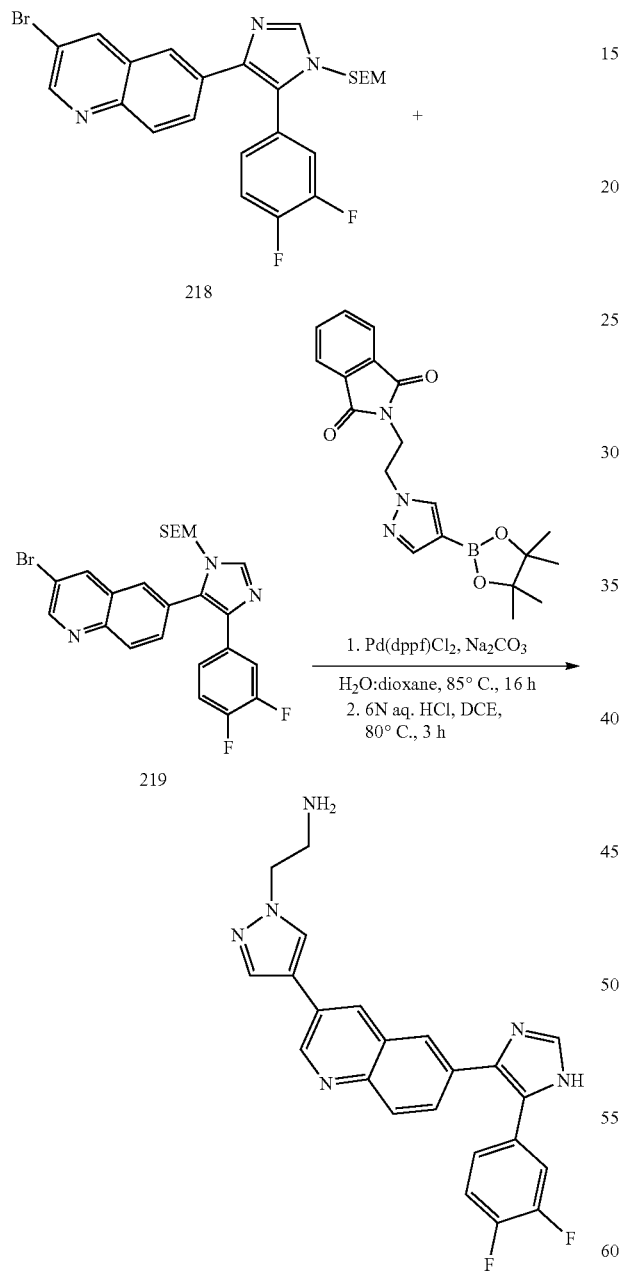

dioxane (465 µL) was sparged with N₂ for 10 min before heating to 85° C. for 16 h. The reaction mixture was filtered through a pad of celite and concentrated in vacuum. The crude material was dissolved in DCE (0.300 mL) and 6 M aq. HCl (0.200 mL) was added. The mixture was heated to 80° C. for 3 h until fully deprotected. The reaction mixture was concentrated in vacuum and the residue was purified by preparative HPLC chromatography using a gradient (5 to 75%) of acetonitrile in water with 0.05% trifluoroacetic acid to yield a TFA salt of the title compound (15.6 mg). [M+H]⁺ calcd for $C_{23}H_{18}F_2N_6$ 417.16, found 417.1. ¹H NMR (400 MHz, Methanol-d₄) δ 9.26 (d, J=2.1 Hz, 1H), 9.14 (s, 1H), 8.64 (d, J=2.1 Hz, 1H), 8.38 (d, J=0.7 Hz, 1H), 8.18 (t, J=1.7 Hz, 2H), 8.11 (d, J=8.8 Hz, 1H), 7.78 (dd, J=8.8, 2.0 Hz, 1H), 7.49 (ddd, J=11.0, 7.4, 2.1 Hz, 1H), 7.39 (dt, J=10.1, 8.2 Hz, 1H), 7.32 (dddd, J=8.6, 4.1, 2.1, 1.0 Hz, 1H), 4.55 (dd, J=6.3, 5.2 Hz, 2H), 3.56-3.46 (m, 2H).

Example 220: Synthesis of (1R,2R)-2-(4-(6-(5-(3,4-difluorophenyl)-1H-imidazol-4-yl)quinolin-3-yl)-1H-pyrazol-1-yl)cyclohexan-1-amine (23-3)

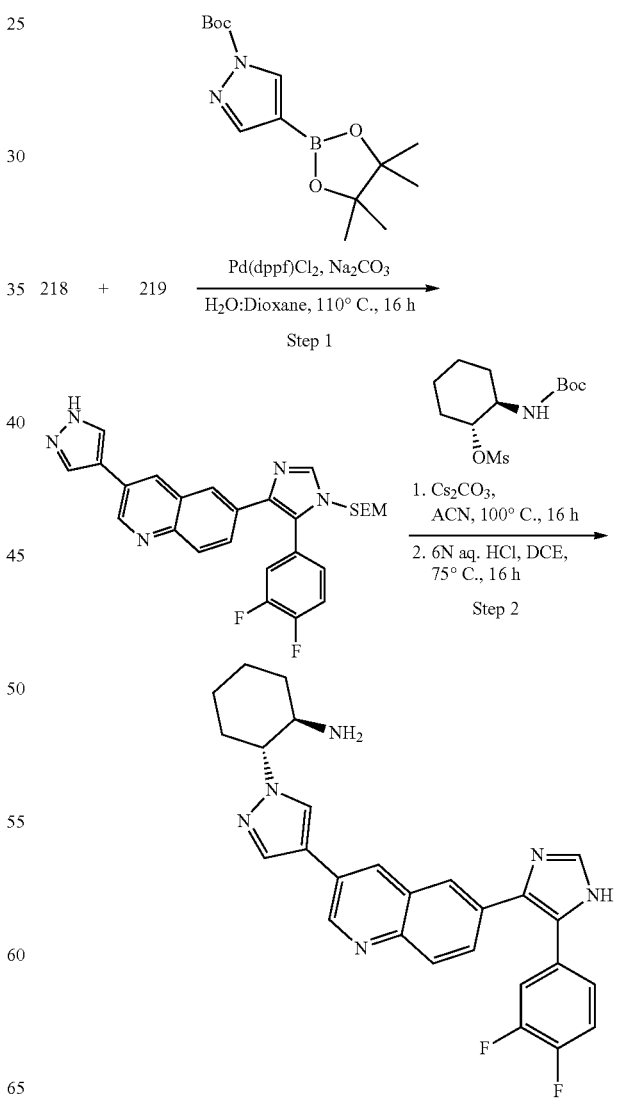

A vial of 2-(2-(4-(4,4,5,5-tetramethyl-1,3,2-dioxaborolan-2-yl)-1H-pyrazol-1-yl)ethyl)isoindoline-1,3-dione (26.50 mg, 0.076 mmol), 218 and 219 (30 mg, 0.058 mmol), sodium carbonate (24.63 mg, 0.232 mmol), and Pd(dppf)Cl₂ (8.50 mg, 0.012 mmol) in degassed water (116 µL):1,4-

Step 1: A vial of 218 and 219 (41.7 mg, 0.081 mmol), sodium carbonate (42.8 mg, 0.404 mmol), 1-boc-pyrazole-4-boronic acid pinacol ester (40.4 mg, 0.137 mmol), and Pd(dppf)Cl₂ (11.81 mg, 0.016 mmol) in 1,4-dioxane (323 μL):water (81 μL) was sparged with N₂ for 10 min before heating to 110° C. for 16 h. The boc group is removed during the Suzuki reaction. The reaction mixture was filtered and concentrated in vacuum. The residue was purified via normal phase chromatography (0 to 100% of EA in hexanes) yielding 6-(5-(3,4-difluorophenyl)-1-((2-(trimethylsilyl)ethoxy)methyl)-1H-imidazol-4-yl)-3-(1H-pyrazol-4-yl)quinoline (34 mg, 84% yield) as a yellow oil. [M+H]+ calcd for $C_{27}H_{27}F_2N_5OSi$ 504.20, found 504.0.

Step 2: To the vial containing 6-(5-(3,4-difluorophenyl)-1-((2-(trimethylsilyl)ethoxy)methyl)-1H-imidazol-4-yl)-3-(1H-pyrazol-4-yl)quinoline (22.79 mg, 0.078 mmol) was added cesium carbonate (33.8 mg, 0.104 mmol) followed by a solution containing 6-(5-(3,4-difluorophenyl)-1-((2-(trimethylsilyl)ethoxy)methyl)-1H-imidazol-4-yl)-3-(1H-pyrazol-4-yl)quinoline (26.1 mg, 0.052 mmol) in acetonitrile (1 mL) and the resulting mixture was capped and stirred at 100° C. for 16 h. The reaction was concentrated in vacuum. The residue was dissolved in DCE (0.300 mL) and 6 M aq. HCl (0.200 mL) was added. The mixture was heated to 75° C. for 16 h. The reaction mixture was concentrated in vacuum and the residue was purified by preparative HPLC chromatography using a gradient (5 to 75%) of acetonitrile in water with 0.05% trifluoroacetic acid to yield a TFA salt of the title compound (13.2 mg). [M+H]+ calcd for $C_{27}H_{24}F_2N_6$ 471.20, found 471.1. The stereochemistry of the product was confirmed by NOE.

Example 221: Synthesis of 6-(5-(3,4-difluorophenyl)-1H-imidazol-4-yl)-N-(2-(4-isopropylpiperazin-1-yl)ethyl)quinolin-3-amine (23-4)

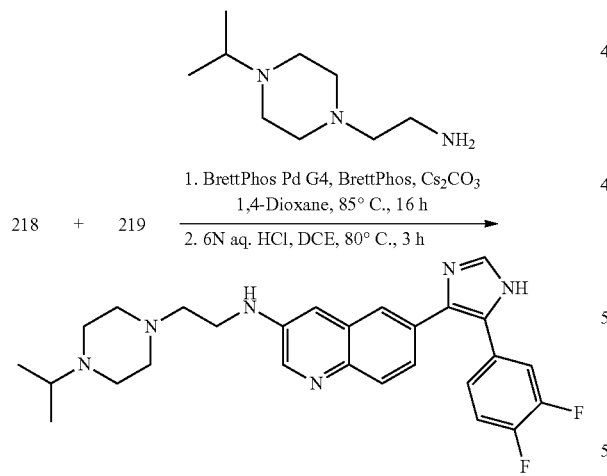

A vial of 218 and 219 (30 mg, 0.058 mmol), 2-(4-isopropyl-piperazin-1-yl)-ethylamine (0.014 ml, 0.076 mmol), cesium carbonate (56.8 mg, 0.174 mmol), BrettPhos (6.24 mg, 0.012 mmol), and BrettPhos Pd G4 (10.69 mg, 0.012 mmol) in 1,4-dioxane (0.581 mL) (degassed with N₂) was heated to 85° C. for 16 h. The reaction mixture was filtered through a pad of celite and concentrated in vacuum. The crude material was dissolved in DCE (0.300 mL) and 6 M aq. HCl (0.200 mL) was added. The mixture was heated to 80° C. for 3 h. The reaction mixture was concentrated in vacuum and the residue was purified by preparative HPLC chromatography using a gradient (5 to 75%) of acetonitrile in water with 0.05% trifluoroacetic acid to yield a TFA salt of the title compound (16.5 mg). [M+H]+ calcd for $C_{27}H_{30}F_2N_6$ 477.25, found 477.2.

Example 222: Synthesis of 3-chloro-N-methoxy-N-methylbenzamide (221)

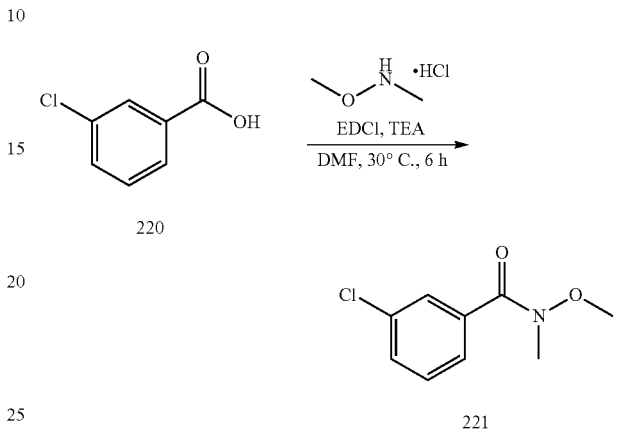

To a mixture of 220 (5.0 g, 31.9 mmol) in DMF (100 mL) N,O-dimethylhydroxylamine hydrochloride was added (3.7 g, 38.3 mmol), TEA (3.4 g, 33.5 mmol) and EDCI (6.4 g, 33.5 mmol). The mixture was stirred at 30° C. for 6 h. The reaction mixture was diluted with H₂O (100 mL) and the aqueous phase was extracted with EA (4×80 mL). The combined organic layer was washed with brine (4×100 mL) and concentrated in vacuum to afford 221 (5.2 g, 82% yield, 94% purity) as a light yellow oil. [M+H]+ calcd for $C_9H_{10}C_1NO_2$ 200.04, found 200.1.

Example 223: Synthesis of 3-chlorobenzaldehyde (222)

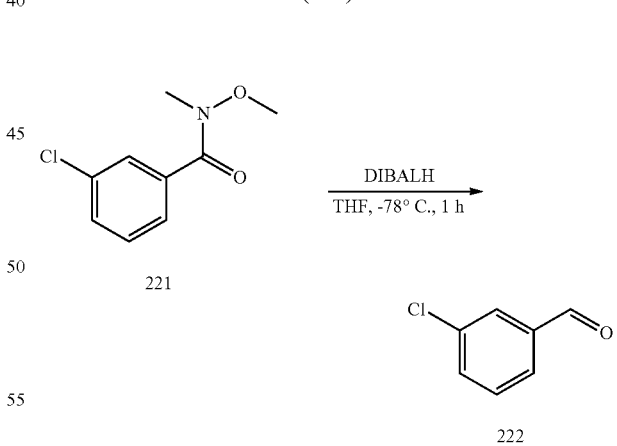

To a mixture of 221 (5.2 g, 26.0 mmol) in THF (100 mL) was added DIBALH (52.1 mL, 52.1 mmole). The resulting mixture was stirred at −78° C. for 1 h. The reaction mixture diluted with H₂O (100 mL). The aqueous phase was extracted with EA (3×80 mL). The combined organic layer was washed with brine (4×100 mL) and concentrated in vacuum. The residue was purified by silica gel chromatography (PE:EA=10:1) to afford 222 (1.5 g, 42% yield, 90% purity) as a light yellow oil.

Example 224: Synthesis of diphenyl ((3-chlorophenyl)(phenylamino)methyl)phosphonate (223)

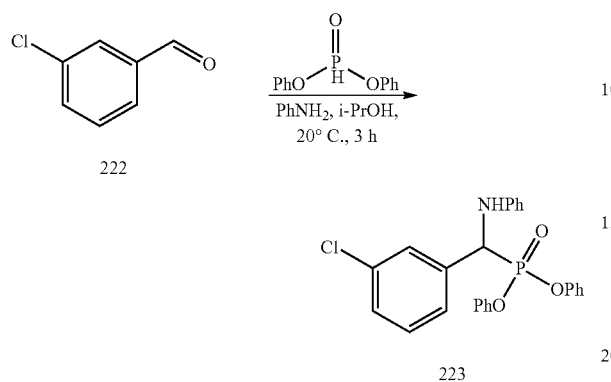

To a mixture of 222 (1.5 g, 11.0 mmol), PhNH$_2$ (1.5 g, 16.5 mmol) in i-PrOH (45 mL) was added diphenyl phosphonate (3.9 g, 16.5 mmol). The reaction mixture was stirred at 20° C. for 3 h. The mixture was filtered and the filter cake was washed with i-PrOH (50 mL). Then the filter cake was dried in vacuum to obtain 223 (3.1 g, 65% yield) as a white solid.

Example 225: Synthesis of 2-(3-bromoquinolin-6-yl)-1-(3-chlorophenyl)ethan-1-one (224)

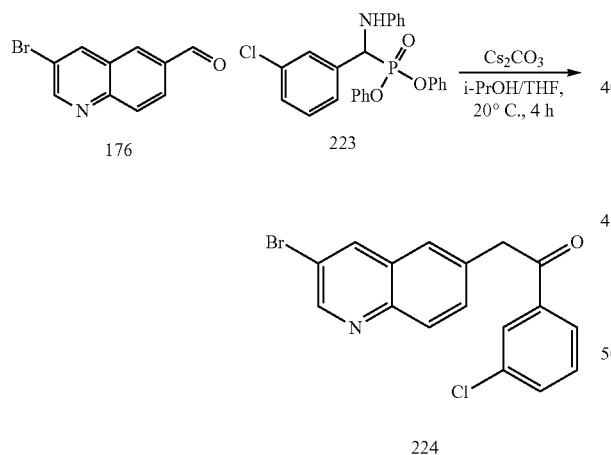

A mixture of 176 (1.5 g, 6.3 mmol), 223 (3.1 g, 7.0 mmol) and Cs$_2$CO$_3$ (2.7 g, 8.3 mmol) in i-PrOH (15 mL) and THF (60 mL) was stirred at 20° C. for 3 h. 3M HCl was added to adjust pH 2-3 and the mixture was stirred for 1 h. The mixture was basified with sat. NaHCO$_3$ to pH 7. The aqueous phase was extracted with EA (3×60 mL). The combined organic layers were dried over Na$_2$SO$_4$ and concentrated under reduced pressure. The residue was purified by silica gel column (0 to 20% of EA in PE) to give 224 (2.0 g, 87% yield, 90% purity) as a white solid. [M+H]$^+$ calcd for C$_{17}$H$_{11}$BrClNO 359.97, found 359.9.

Example 226: Synthesis of 1-(3-bromoquinolin-6-yl)-2-(3-chlorophenyl)ethane-1,2-dione (225)

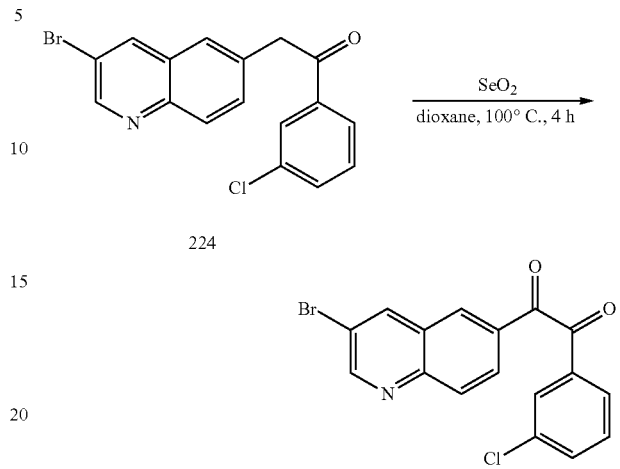

A mixture of 224 (2.0 g, 5.55 mmol) and SeO$_2$ (1.3 g, 11.09 mmol) in dioxane (40 mL) was stirred at 100° C. for 4 h. The mixture was filtered and the filtrate was concentrated under reduced pressure to give 225 (3.1 g, crude, 70% purity) as yellow oil which was used in the next step directly. [M+H]$^+$ calcd for C$_{17}$H$_9$BrClNO$_2$ 373.95, found 373.9.

Example 227: Synthesis of 3-bromo-6-(5-(3-chlorophenyl)-1H-imidazol-4-yl)quinoline (226)

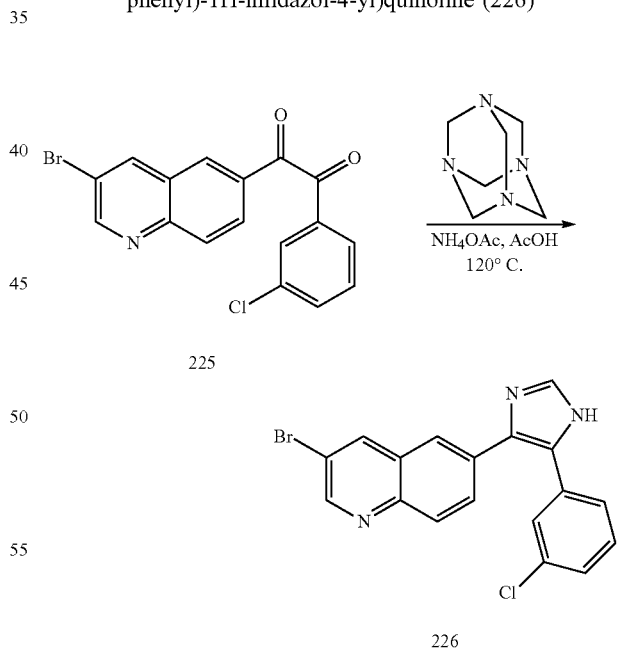

A mixture of 225 (3.1 g, 8.28 mmol), hexamine (3.5 g, 24.83 mmol) and NH$_4$OAc (3.8 g, 49.65 mmol) in AcOH (40 mL) was stirred at 95° C. for 5 h. The mixture was concentrated in vacuum to about 40 mL. The residue was diluted with H$_2$O (100 mL), basified with solid NaOH at 0° C. to pH 7. The mixture was extracted with DCM (3×150 mL), the combined organic layers were concentrated under reduced pressure and dried in vacuum to give 226 (2.4 g, 76% yield, 96% purity) as a brown solid. [M+H]$^+$ calcd for $C_{18}H_{11}BrClN_3$ 383.92, found 383.9.

Example 228: Synthesis of 3-bromo-6-(5-(3-chlorophenyl)-1-((2-(trimethylsilyl)ethoxy)methyl)-1H-imidazol-4-yl)quinoline (227) and 3-bromo-6-(4-(3-chlorophenyl)-1-((2-(trimethylsilyl)ethoxy)methyl)-1H-imidazol-5-yl)quinoline (228)

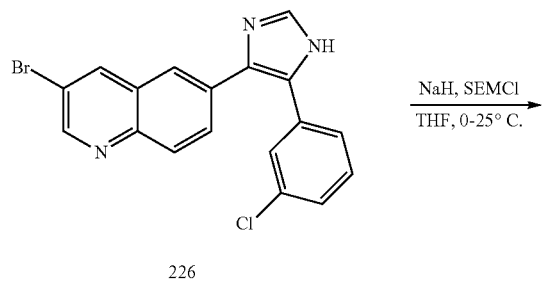

226

NaH, SEMCl
———————→
THF, 0-25° C.

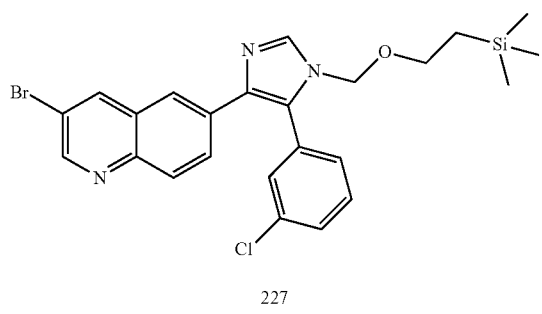

227

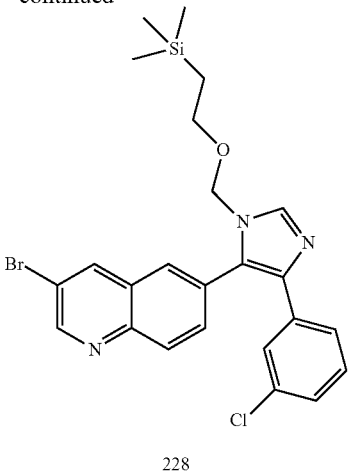

228

To a solution of 226 (1.2 g, 3.12 mmol) in THF (15 mL) was added NaH (230 mg, 9.36 mmol) stirred at 0° C. for 0.5 h. SEMCl (624 mg, 3.74 mmol) was added and the mixture was stirred at 25° C. for 3 h. The mixture was quenched with sat. $NH_4C_1$ (100 mL). The mixture was extracted with EA (3×80 mL), the organic layer was dried over $Na_2SO_4$, concentrated under reduced pressure. The residue was purified by silica gel column (20 to 30% of EA in PE) to give 227 (300 mg, 19% yield, 99% purity) as a yellow solid and 228 (280 mg, 18% yield, 98% purity) as a yellow solid. [M+H]$^+$ calcd for $C_{24}H_{25}BrClN_3OSi$ 514.06 found 514.0. $^1$H NMR (400 MHz, Chloroform-d) δ 8.97 (d, J=2.3 Hz, 1H), 8.31 (d, J=2.3 Hz, 1H), 8.14 (d, J=8.7 Hz, 1H), 7.89 (d, J=1.9 Hz, 1H), 7.78 (s, 1H), 7.72 (dd, J=8.7, 2.0 Hz, 1H), 7.60 (t, J=1.8 Hz, 1H), 7.27-7.12 (m, 2H), 7.08 (t, J=7.8 Hz, 1H), 5.15 (s, 2H), 3.61-3.50 (m, 2H), 0.97-0.83 (m, 2H), -0.01 (s, 8H). and $^1$H NMR (400 MHz, Chloroform-d) δ 8.81 (d, J=2.3 Hz, 1H), 8.20-8.14 (m, 1H), 7.98-7.86 (m, 2H), 7.81-7.73 (m, 1H), 7.51-7.46 (m, 1H), 7.40 (t, J=7.7 Hz, 1H), 7.31 (dt, J=7.6, 1.4 Hz, 1H), 5.14 (s, 2H), 3.56-3.42 (m, 2H), 1.01-0.85 (m, 2H), 0.00 (s, 9H).

Example 229: Synthesis of 2-(4-(6-(5-(3-chlorophenyl)-1H-imidazol-4-yl)quinolin-3-yl)-1H-pyrazol-1-yl)-N-methylethan-1-amine (24-1)

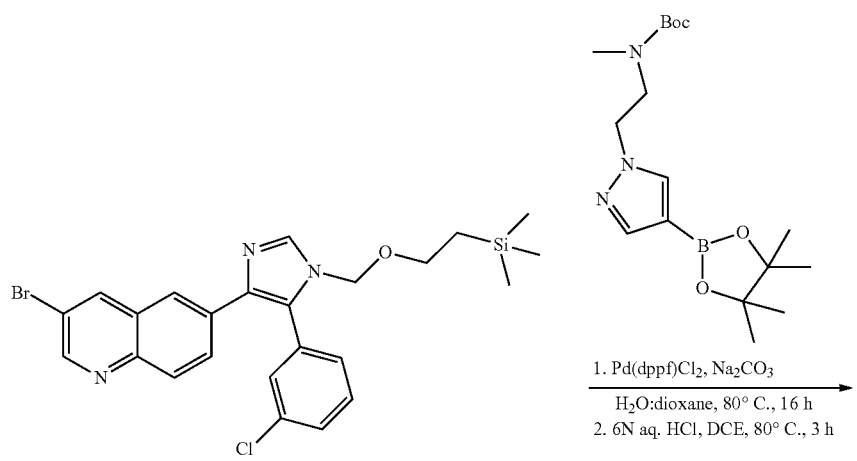

228

1. Pd(dppf)Cl$_2$, Na$_2$CO$_3$
———————————————→
H$_2$O:dioxane, 80° C., 16 h
2. 6N aq. HCl, DCE, 80° C., 3 h

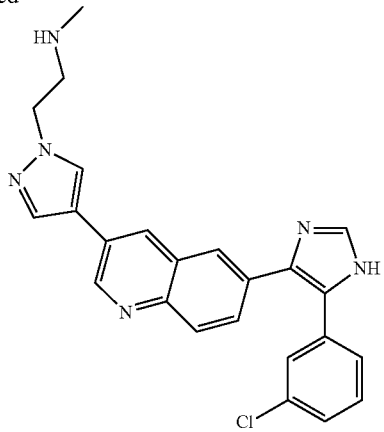

A vial of tert-butyl methyl(2-(4-(4,4,5,5-tetramethyl-1,3,2-dioxaborolan-2-yl)-1H-pyrazol-1-yl)ethyl)carbamate (24.56 mg, 0.070 mmol), 228 (30 mg, 0.058 mmol), sodium carbonate (24.70 mg, 0.233 mmol), and Pd(dppf)Cl$_2$ (8.53 mg, 0.012 mmol) in degassed water (117 µL):1,4-dioxane (466 µL) was sparged with N$_2$ for 10 min before heating to 80° C. for 16 h. The reaction mixture was filtered through a pad of celite and concentrated in vacuum. The crude material was dissolved in DCE (0.300 mL) and 6 M aq. HCl (0.200 mL) was added. The mixture was heated to 80° C. for 3 h. The reaction mixture was concentrated in vacuum and the residue was purified by preparative HPLC chromatography using a gradient (5 to 75%) of acetonitrile in water with 0.05% trifluoroacetic acid to yield a TFA salt of the title compound (8.0 mg). [M+H]$^+$ calcd for C$_{24}$H$_{21}$ClN$_6$ 429.15, found 429.0.

Example 230: Synthesis of 6-(5-(3-chlorophenyl)-1H-imidazol-4-yl)-N-(2-(4-isopropylpiperazin-1-yl)ethyl)quinolin-3-amine (24-2)

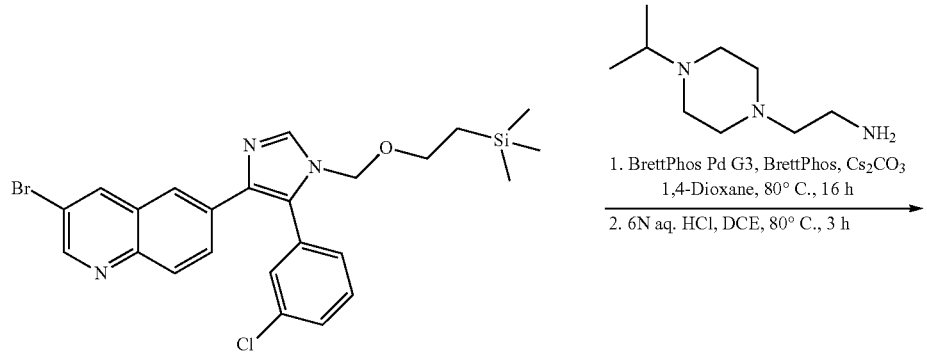

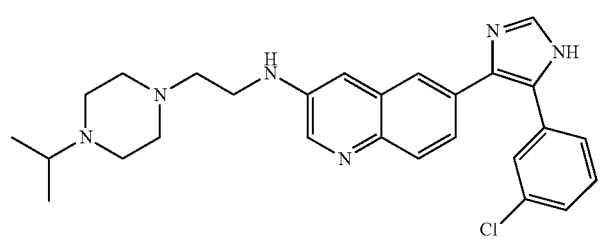

A vial of 228 (30 mg, 0.058 mmol), 2-(4-isopropyl-piperazin-1-yl)-ethylamine (0.012 ml, 0.064 mmol), cesium carbonate (56.9 mg, 0.175 mmol), BrettPhos (5.25 mg, 0.012 mmol), and BrettPhos Pd G3 (10.56 mg, 0.012 mmol) in 1,4-dioxane (0.583 mL) (degassed with $N_2$) was heated to 80° C. for 16 h. The reaction mixture was filtered through a pad of celite and concentrated in vacuum. The crude material was dissolved in DCE (0.300 mL) and 6 M aq. HCl (0.200 mL) was added. The mixture was heated to 80° C. for 3 h. The reaction mixture was concentrated in vacuum and the residue was purified by preparative HPLC chromatography using a gradient (5 to 75%) of acetonitrile in water with 0.05% trifluoroacetic acid to yield a TFA salt of the title compound (13.1 mg). $[M+H]^+$ calcd for $C_{27}H_{31}C_1N_6$ 475.23, found 475.1. $^1H$ NMR (400 MHz, Methanol-$d_4$) δ 9.15 (s, 1H), 8.68 (d, J=2.8 Hz, 1H), 8.06-7.95 (m, 2H), 7.66 (dd, J=2.8, 0.8 Hz, 1H), 7.63-7.53 (m, 2H), 7.55-7.45 (m, 1H), 7.50-7.35 (m, 2H), 3.64-3.51 (m, 3H), 3.48 (s, 5H), 3.43-3.37 (m, 2H), 3.14 (t, J=6.0 Hz, 2H), 2.90 (s, 1H), 1.37 (d, J=6.7 Hz, 6H).

Example 231: Synthesis of 7-bromo-2-chloro-1,5-naphthyridine (229)

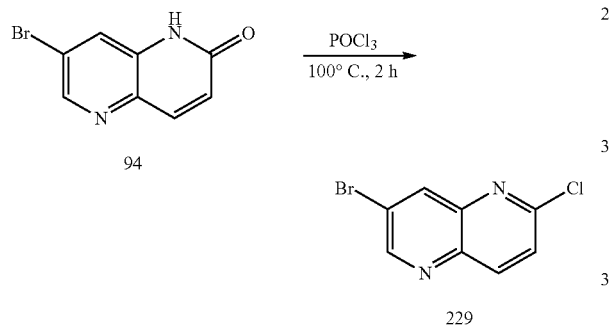

A solution of 94 (12.0 g, 53.3 mmol) in $POCl_3$ (220.0 g) was stirred for 2 h at 100° C. The reaction mixture was concentrated in vacuum. The reaction mixture was quenched with $H_2O$ (200 mL), basified with 3.0 M NaOH to pH=8 and filtered. The cake was washed with $H_2O$ (100 mL). The residue was dried in vacuum to afford 229 (13.0 g, 80% yield, 91% purity) as a gray solid. $[M+H]^+$ calcd for $C_8H_4BrClN_2$ 242.92, found 242.9.

Example 232: Synthesis of 2-chloro-7-(1-(tetrahydro-2H-pyran-2-yl)-1H-pyrazol-4-yl)-1,5-naphthyridine (231)

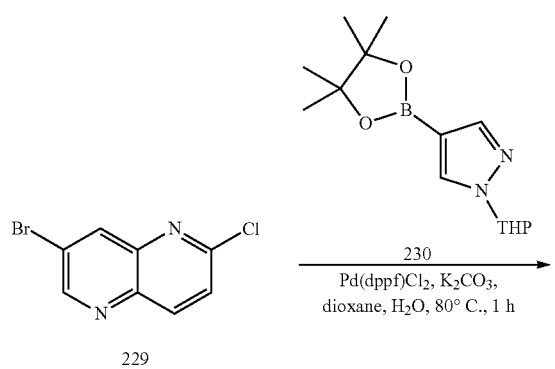

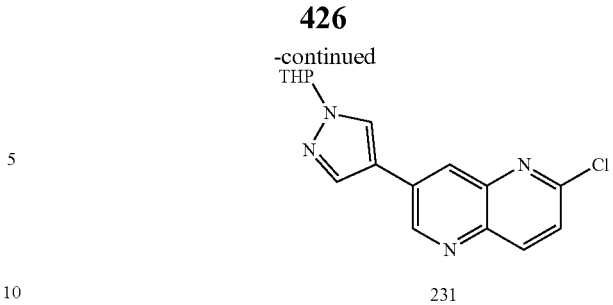

To a mixture of 229 (9.0 g, 37.0 mmol), 230 (10.3 g, 37.0 mmol), $K_2CO_3$ (15.3 g, 111 mmol), Pd(dppf)$Cl_2$ (2.7 g, 3.70 mmol) in dioxane (150 mL) and $H_2O$ (15 mL) was stirred under $N_2$ for 1 h at 80° C. The reaction was monitored by TLC. The reaction mixture was purified by column (EA/PE=1/5 to 1/1) to afford 231 (5.7 g, 50% yield) as a yellow solid.

Example 233: Synthesis of 2-iodo-7-(1H-pyrazol-4-yl)-1,5-naphthyridine (232)

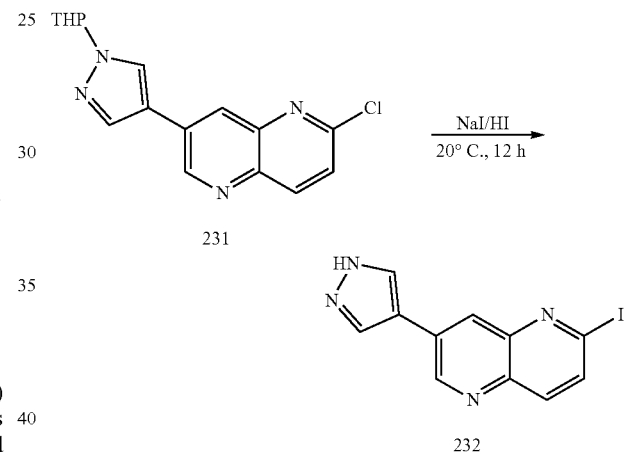

To a mixture of 231 (5.0 g, 15.9 mmol), NaI (14.3 g, 95.4 mmol) in HI (100 mL) was stirred for 12 h at 20° C. The reaction mixture was monitored by TLC. The reaction mixture was basified with solid $NaHCO_3$ to pH=8, extracted with EA (200 mL×3). The organic layer was washed with $Na_2SO_3$ (100 mL), dried over $Na_2SO_4$, filtered. The filtrate was concentrated in vacuum to afford 232 (3.5 g, 70% yield) as a yellow solid.

Example 234: Synthesis of tert-butyl (2-(4-(6-iodo-1,5-naphthyridin-3-yl)-1H-pyrazol-1-yl)ethyl)(methyl)carbamate (233)

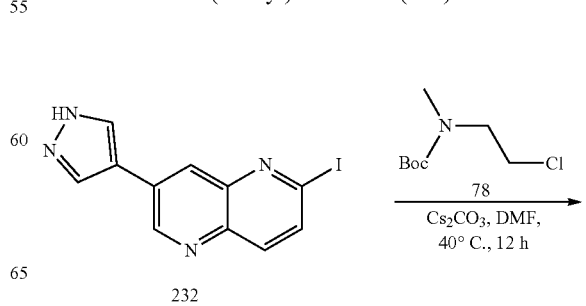

-continued

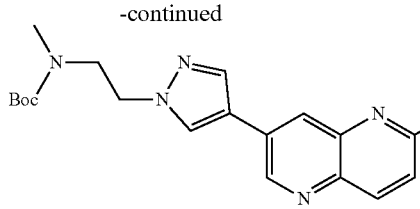

233

To a mixture of 232 (2.0 g, 1.55 mmol), 78 (598 mg, 3.10 mmol), Cs$_2$CO$_3$ (1.5 g, 4.65 mmol) in DMF (20 mL) was stirred for 12 h at 40° C. The reaction mixture was concentrated in vacuum. The residue was purified by column (EA/PE=1/5 to 2/1) to afford 233 (560 mg, 19% yield, 93% purity) as a white solid. [M+H]$^+$ calcd for C$_{19}$H$_{22}$IN$_5$O$_2$ 480.08, found 480.0. $^1$H NMR (400 MHz, Chloroform-d) δ 9.05 (d, J=2.2 Hz, 1H), 8.26 (dd, J=2.2, 0.8 Hz, 1H), 7.93-7.86 (m, 2H), 7.83 (d, J=8.6 Hz, 1H), 7.76 (s, 1H), 7.71 (s, 1H), 4.31 (s, 1H), 3.63 (t, J=6.0 Hz, 2H), 2.70 (s, 1H), 2.61 (s, 2H), 1.36 (s, 9H).

Example 235: Synthesis of 2-[4-[6-[2-(5-chloro-2-fluoro-phenyl)-1H-pyrrolo[3,2-b]pyridin-3-yl]-1,5-naphthyridin-3-yl]pyrazol-1-yl]-N-methyl-ethanamine (25-2)

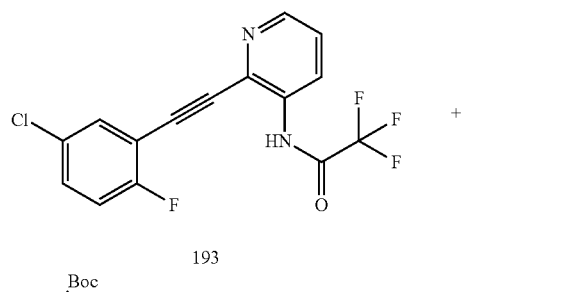

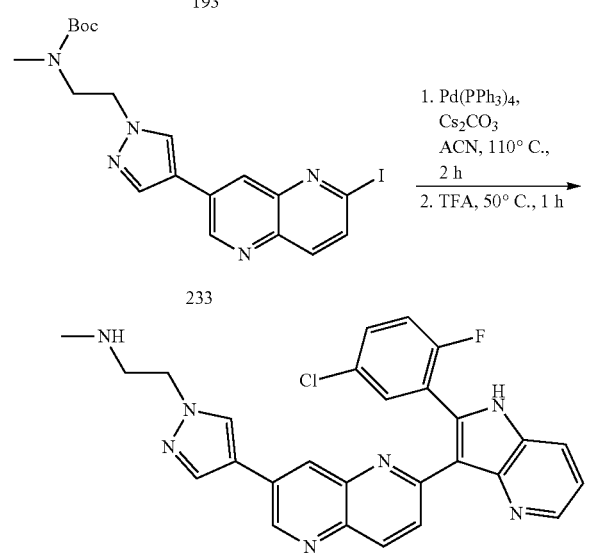

A vial of 193 (30 mg, 0.088 mmol), cesium carbonate (57.0 mg, 0.175 mmol), Pd(PPh$_3$)$_4$ (10.12 mg, 8.75 µmol), and 233 (84 mg, 0.175 mmol) in ACN (292 µL) was heated for 2 h at 110° C. The reaction mixture was concentrated in vacuum. TFA (500 µL) was added to the reaction and heated to 50° C. for 1 h until fully deprotected. The reaction mixture was concentrated in vacuum and the residue was purified by preparative HPLC chromatography using a gradient (10 to 80%) of acetonitrile in water with 0.05% trifluoroacetic acid to yield a TFA salt of the title compound (63.6 mg). [M+H]$^+$ calcd for C$_{27}$H$_{21}$ClFN$_7$ 498.15, found 498.0.

Example 236: Synthesis of 7-bromo-1-(4-methoxy-benzyl)-1,5-naphthyridin-2(1H)-one (234)

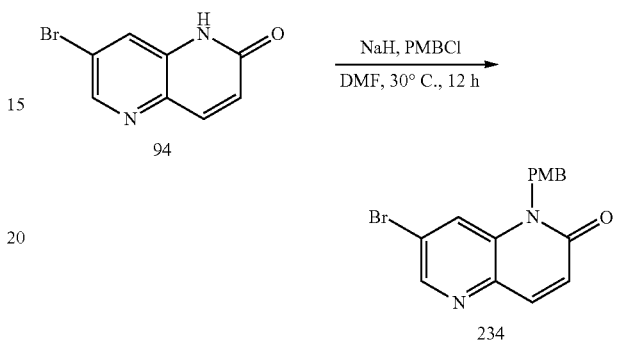

To a solution of 94 (25.0 g, 111 mmol) in DMF (300 mL) was added NaH (6.7 g, 167 mmol) at 30° C. The reaction mixture was stirred at 30° C. for 1 h. Then to the reaction mixture was added PMBCl (26.1 g, 167 mmol). The reaction mixture was stirred at 30° C. for 11 h. The reaction mixture was quenched with H$_2$O (200 mL), extracted with EA (200 mL×3). The organic layer was washed with brine (200 mL×2), dried over Na$_2$SO$_4$, and filtered. The filtrate was concentrated in vacuum. The residue was purified by silica gel column (EA/PE=1/10 to 1/1) to afford 234 (20.0 g, 51% yield) as a yellow solid.

Example 237: Synthesis of 7-(4-(methylamino)piperidin-1-yl)-1,5-naphthyridin-2(1H)-one (235)

A mixture of 234 (8.0 g, 23.2 mmol), tert-butyl methyl (piperidin-4-yl)carbamate (6.0 g, 27.8 mmol), Pd₂(dba)₃ (1.1 g, 1.16 mmol), Xantphos (670 mg, 1.16 mmol), Cs₂CO₃ (22.7 g, 69.6 mmol) in dioxane (100 mL) was stirred at 100° C. under N₂ for 4 h. The reaction mixture was concentrated in vacuum. The residue was purified by silica column (EA/PE=1/10 to 2/1) to afford tert-butyl (1-(5-(4-methoxybenzyl)-6-oxo-5,6-dihydro-1,5-naphthyridin-3-yl)piperidin-4-yl)(methyl)carbamate (5.0 g, 45% yield) as a yellow solid. TFA (100.0 mL) was added to the solid and stirred at 80° C. for 12 h. The reaction mixture was concentrated in vacuum to afford 235 (2.5 g, 92% yield) as a yellow solid.

Example 238: Synthesis of 1-(6-chloro-1,5-naphthyridin-3-yl)-N-methylpiperidin-4-amine (236)

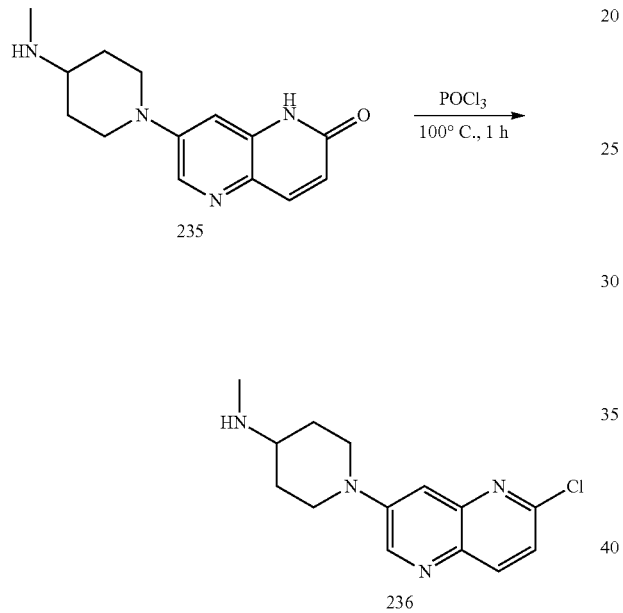

A solution of 235 (2.5 g, 9.69 mmol) in POCl₃ (168 g) was stirred at 100° C. for 1 h. The reaction mixture was concentrated in vacuum. The residue was diluted with H₂O (100 mL), basified with solid, NaHCO₃ to pH=8. The mixture was filtered. The cake was dried in vacuum to afford 236 (2.5 g, 93% yield) as a yellow solid.

Example 239: Synthesis of 1-(6-iodo-1,5-naphthyridin-3-yl)-N-methylpiperidin-4-amine (237)

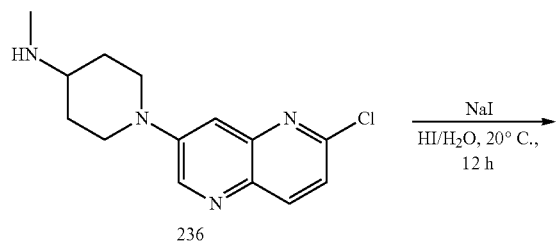

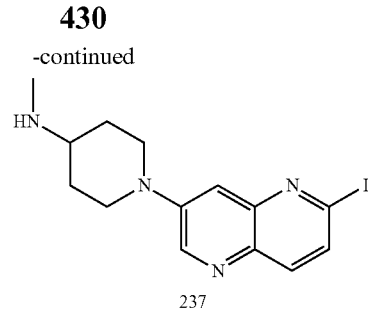

A mixture of 236 (2.5 g, 9.06 mmol), NaI (13.6 g, 90.6 mmol) in HI/H₂O (50 mL) was stirred at 20° C. for 12 h. The reaction mixture was diluted with H₂O (50 mL), basified with solid Na₂CO₃ to pH=8. The mixture was filtered. The cake was dried in vacuum to afford 237 (3.0 g, 90% yield) as a brown solid.

Example 240: Synthesis of tert-butyl (1-(6-iodo-1,5-naphthyridin-3-yl)piperidin-4-yl)(methyl)carbamate (238)

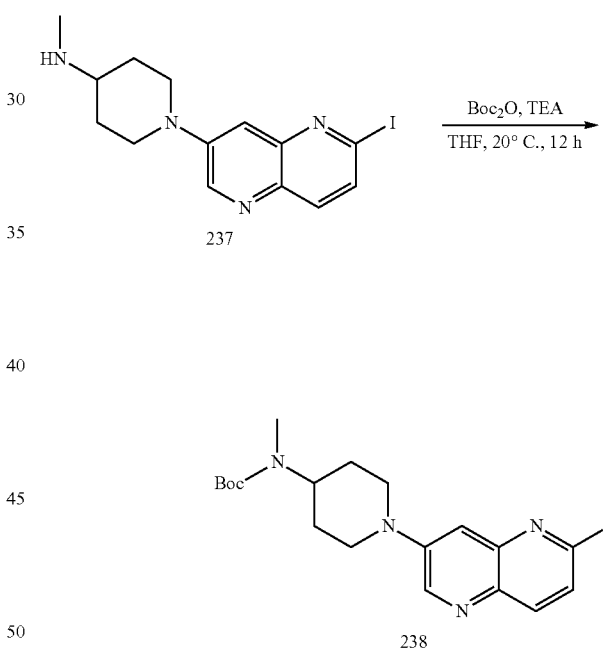

A mixture of 237 (3.0 g, 8.15 mmol), Boc₂O (2.7 g, 12.2 mmol), TEA (2.5 g, 24.5 mmol) in THF (50 mL) was stirred at 20° C. for 12 h. The reaction mixture was concentrated in vacuum. The residue was purified by column (EA/PE=1/10 to 1/2) and trituration from EA (15 mL) to afford 238 (1.0 g, 26% yield, 95% purity) as a yellow solid, and the mother solution was concentrated in vacuum to afford 238 (1.0 g, 80% purity) as a yellow solid. [M+H]⁺ calcd for $C_{19}H_{25}IN_4O_2$ 469.10, found 462.2. ¹H NMR (400 MHz, Chloroform-d) δ 8.83 (d, J=2.9 Hz, 1H), 7.84 (dd, J=8.5, 0.8 Hz, 1H), 7.73 (d, J=8.5 Hz, 1H), 7.50 (dd, J=2.9, 0.8 Hz, 1H), 4.26 (s, 1H), 4.00 (dq, J=10.9, 2.3 Hz, 2H), 3.03 (t, J=12.2 Hz, 2H), 2.77 (s, 3H), 1.87 (d, J=24.9 Hz, 1H), 1.84 (s, 3H), 1.50 (s, 9H).

Example 241: Synthesis of 1-[6-[2-(5-chloro-2-fluoro-phenyl)-1H-pyrrolo[3,2-b]pyridin-3-yl]-1,5-naphthyridin-3-yl]-N-methyl-piperidin-4-amine (25-1)

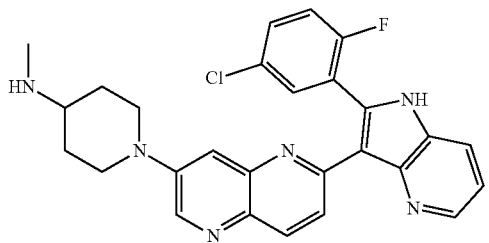 [SMILES: CNC1CCN(c2cnc3ccc(-c4c(-c5cc(Cl)ccc5F)[nH]c5cccnc45)nc3c2)CC1]

The procedure provided in Example 235 was also used to make the title compound except that 233 was substituted for 238 (82 mg, 0.175 mmol). The material was purified by preparative HPLC chromatography using a gradient (10 to 80%) of acetonitrile in water with 0.05% trifluoroacetic acid to yield a TFA salt of the title compound (28.7 mg). [M+H]$^+$ calcd for $C_{27}H_{24}ClFN_6$ 487.17, found 487.0.

Example 242: Synthesis of 2-[4-[6-[2-(5-chloro-2,4-difluoro-phenyl)-1H-pyrrolo[3,2-b]pyridin-3-yl]-1,5-naphthyridin-3-yl]pyrazol-1-yl]-N-methyl-ethanamine (26-1)

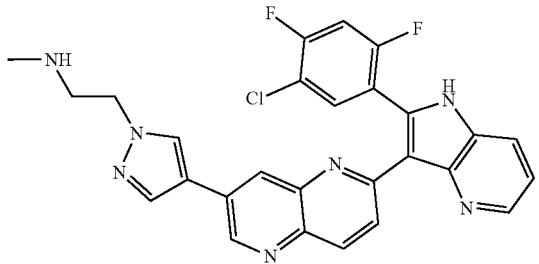 [SMILES: CNCCn1cc(-c2cnc3ccc(-c4c(-c5cc(Cl)c(F)cc5F)[nH]c5cccnc45)nc3c2)cn1]

The procedure provided in Example 235 was also used to make the title compound except that 193 was substituted for N-(2-((5-chloro-2,4-difluorophenyl)ethynyl)pyridin-3-yl)-2,2,2-trifluoroacetamide (22.1 mg, 0.061 mmol), which was made following Example 192 using 1-chloro-5-ethynyl-2,4-difluorobenzene instead of 190. The material was purified by preparative HPLC chromatography using a gradient (10 to 80%) of acetonitrile in water with 0.05% trifluoroacetic acid to yield a TFA salt of the title compound (15.5 mg). [M+H]$^+$ calcd for $C_{28}H_{22}ClFN_6$ 516.14, found 516.0.

Example 243: Synthesis of 2-[4-[6-[2-(3,4-difluoro-phenyl)-1H-pyrrolo[3,2-b]pyridin-3-yl]-1,5-naphthyridin-3-yl]pyrazol-1-yl]-N-methyl-ethanamine (27-1)

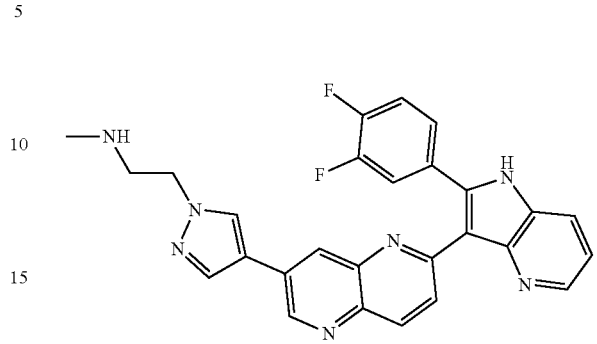

The procedure provided in Example 235 was also used to make the title compound except that 193 was substituted for N-(2-((3,4-difluorophenyl)ethynyl)pyridin-3-yl)-2,2,2-trifluoroacetamide (20 mg, 0.061 mmol), which was made following Example 192 using 4-ethynyl-1,2-difluorobenzene instead of 190. The material was purified by preparative HPLC chromatography using a gradient (10 to 80%) of acetonitrile in water with 0.05% trifluoroacetic acid to yield a TFA salt of the title compound (43.5 mg). [M+H]$^+$ calcd for $C_{28}H_{22}ClFN_6$ 482.18, found 482.0.

Example 244: Synthesis of 2-(7-bromo-1,5-naphthyridin-2-yl)-1-(3-chlorophenyl)ethan-1-one (240)

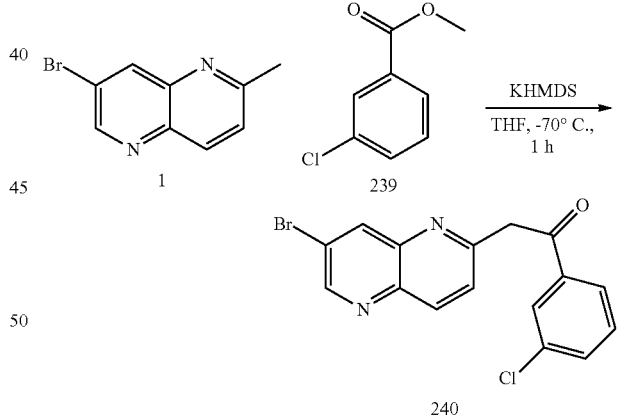

To a mixture of 1 (1.0 g, 4.48 mmol) in THF (20 mL) was added KHMDS (9.0 mL, 9.0 mmol) at −70° C. under $N_2$. It was stirred at −70° C. for 0.5 h. Then 239 (1.1 g, 6.72 mmol) was added. It was stirred at −70° C. for another 0.5 h. It was quenched with sat. $NH_4Cl$ at −70° C. It was extracted with DCM (50 mL×3). The combined organic layers were concentrated in vacuum. It was purified by trituration (PE: EA=1:1, 30 mL) to afford 240 (1.1 g, 68% yield) as a yellow solid. [M+H]$^+$ calcd for $C_{16}H_{10}BrClN_2O$, 360.97 found 360.9.

Example 245: Synthesis of 7-bromo-2-(3-(3-chlorophenyl)-1H-pyrazol-4-yl)-1,5-naphthyridine (241)

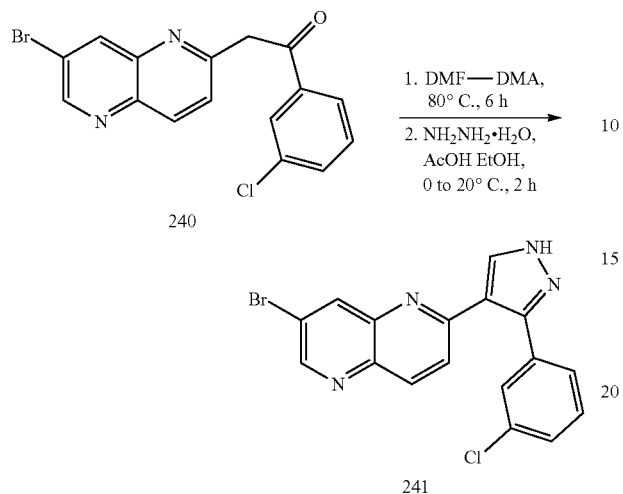

A mixture of 240 (1.0 g, 2.77 mmol) in DMF-DMA (20 mL) was stirred at 80° C. for 6 h. The reaction mixture was concentrated in vacuo. AcOH (1.0 g, 16.8 mmol) in EtOH (20 mL) and NH$_2$NH$_2$·H$_2$O (601 mg, 12.0 mmol) was added to the residue at 0° C. The resulting mixture was stirred at 20° C. for 2 h. It was concentrated in vacuo. The residue was combined with an additional lot of 241. It was purified by silica gel column (PE:EA=1:1) to afford 241 (400 mg, 34% over 2 steps) as yellow solid. [M+H]$^+$ calcd for C$_{17}$H$_{10}$BrClN$_4$ 384.98 found 384.9.

Example 246: Synthesis of 7-bromo-2-(3-(3-chlorophenyl)-1-(tetrahydro-2H-pyran-2-yl)-1H-pyrazol-4-yl)-1,5-naphthyridine (242)

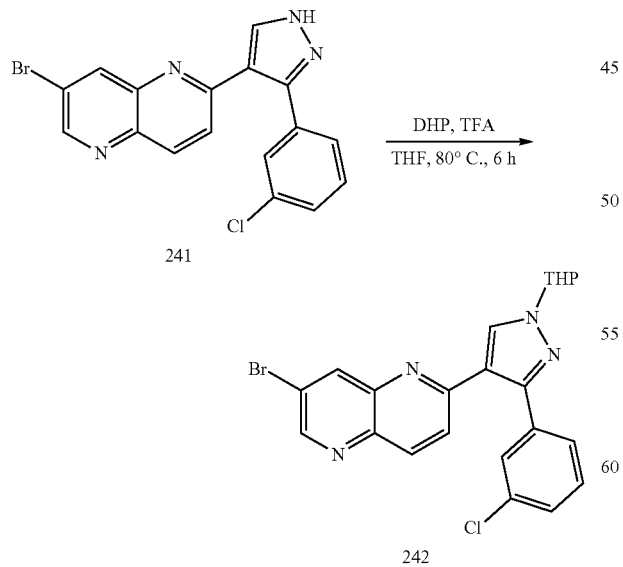

To a mixture of 241 (300 mg, 0.778 mmol) and DHP (654 mg, 7.78 mmol) in THF (10 mL) was added TFA (10 drops).

It was stirred at 80° C. for 6 h. The reaction mixture was concentrated in vacuum. The residue was combined with an additional lot of 242. It was purified by silica column (PE:EA=1:1) to afford 242 (305 mg, 63% yield, 97% purity) as yellow oil. [M+H]$^+$ calcd for C$_{22}$H$_{18}$BrClN$_4$O 469.04 found 469.9. $^1$H NMR (400 MHz, Chloroform-d) δ 8.93 (d, J=2.2 Hz, 1H), 8.50 (dd, J=2.3, 0.9 Hz, 1H), 8.30 (s, 1H), 8.21 (dd, J=8.8, 0.9 Hz, 1H), 7.71 (t, J=1.9 Hz, 1H), 7.54 (d, J=8.8 Hz, 1H), 7.50-7.33 (m, 2H), 7.31 (t, J=7.8 Hz, 1H), 5.57-5.48 (m, 1H), 4.22-4.09 (m, 1H), 3.85-3.70 (m, 1H), 3.54 (d, J=20.2 Hz, 1H), 2.39-2.17 (m, 2H), 2.11 (s, 1H), 1.80-1.65 (m, 1H), 1.33-1.21 (m, 1H).

Example 247: Synthesis of 6-(3-(3-chlorophenyl)-1H-pyrazol-4-yl)-N-(2-(4-isopropylpiperazin-1-yl)ethyl)-1,5-naphthyridin-3-amine (28-1)

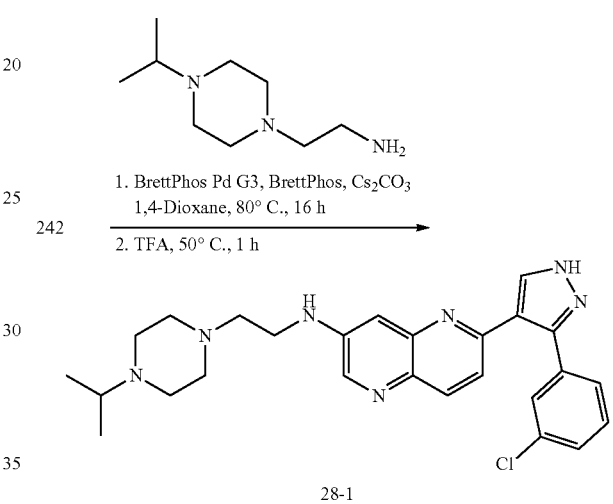

A vial of 242 (30 mg, 0.064 mmol), 2-(4-isopropylpiperazin-1-yl)-ethylamine (0.015 ml, 0.083 mmol), cesium carbonate (56.9 mg, 0.175 mmol), BrettPhos (6.86 mg, 0.013 mmol), and BrettPhos Pd G3 (11.58 mg, 0.013 mmol) in 1,4-dioxane (0.639 ml) (degassed with N$_2$) was heated to 80° C. for 16 h. The reaction mixture was filtered through a pad of celite and concentrated in vacuum. TFA (0.50 ml) was added to the residue and heated to 50° C. for 1 h. The reaction mixture was concentrated in vacuum. The residue was purified by preparative HPLC chromatography using a gradient (5 to 75%) of acetonitrile in water with 0.05% trifluoroacetic acid to yield a TFA salt of the title compound (6.7 mg). [M+H]$^+$ calcd for C$_{26}$H$_{30}$ClN$_7$ 476.23 found 476.2.

Example 248: Synthesis of 1-(7-bromo-1,5-naphthyridin-2-yl)-2-(3-chlorophenyl)ethane-1,2-dione (243)

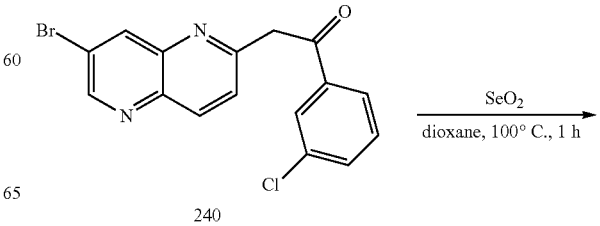

-continued

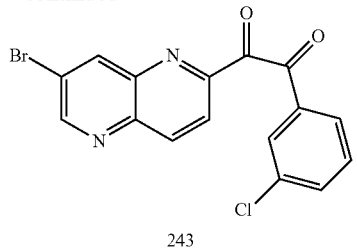

243

A mixture of 240 (5.1 g, 14.1 mmol) and SeO₂ (3.1 g, 28.2 mmol) in dioxane (80 mL) was stirred at 100° C. for 1 h. The mixture was filtered and the filtrate was concentrated under reduced pressure to give 243 as yellow solid. 240 (5.3 g, crude) was used into next step directly. [M+H]⁺ calcd for $C_{16}H_8BrClN_2O_2$ 374.95 found 374.8.

Example 249: Synthesis of 7-bromo-2-(5-(3-chlorophenyl)-1H-imidazol-4-yl)-1,5-naphthyridine (244)

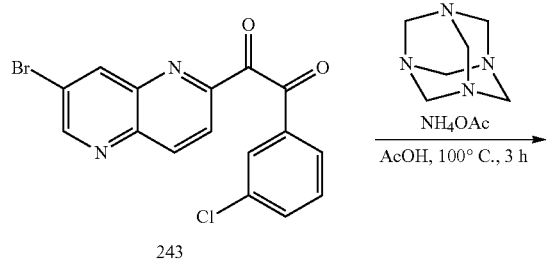

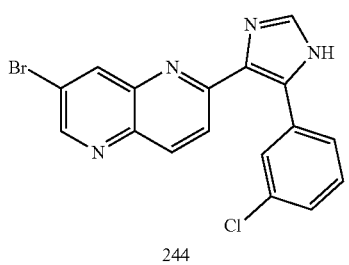

244

A mixture of 243 (5.3 g, 14.1 mmol), hexamine (5.9 g, 42.3 mmol) and NH₄OAc (6.5 g, 84.6 mmol) in AcOH (100 mL) was stirred at 100° C. for 3 h. The mixture (combined with an additional lot of 243) was concentrated in vacuum. The residue was diluted with H₂O (100 mL), basified with solid NaHCO₃ to pH=7. The mixture was extracted with EA (300 mL×3). The combined organic layers were concentrated under reduced pressure. The residue was purified by silica gel column (EA/MeOH=1/0~10/1) to afford 244 (3.2 g, 53% yield, 96% purity) as yellow solid. [M+H]⁺ calcd for $C_{17}H_{10}BrClN_4$ 384.98 found 384.9.

Example 250: Synthesis of 7-bromo-2-(5-(3-chlorophenyl)-1-((2-(trimethylsilyl)ethoxy)methyl)-1H-imidazol-4-yl)-1,5-naphthyridine (245)

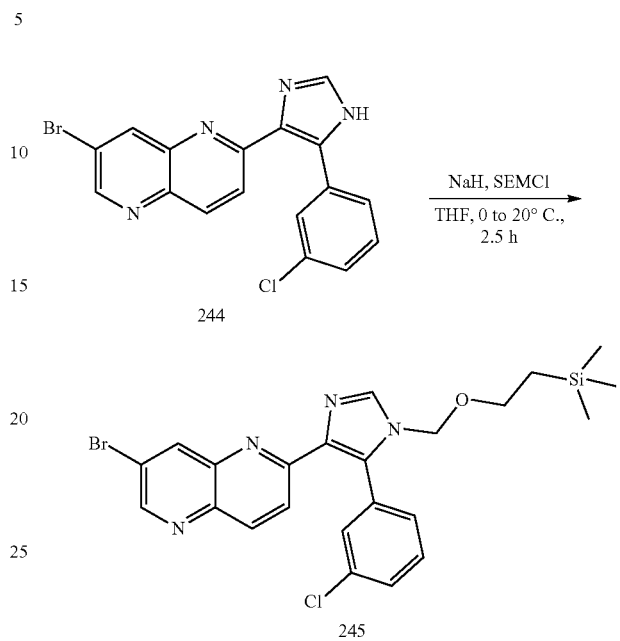

To a solution of NaH (416 mg, 10.4 mmol) in THF (50 mL) was added 244 (2.0 g, 5.18 mmol). The mixture was stirred at 25° C. for 1 h. Then to the mixture was added SEMCl (2.6 g, 15.5 mmol) at 0° C. The mixture was stirred at 25° C. for 1.5 h. The reaction mixture (combined with additional lot of 244) was quenched with sat. NH₄Cl (100 mL). The mixture was extracted with EA (300 mL×3) and the organic layer was dried over Na₂SO₄. The organic layer was concentrated under reduced pressure. The residue was purified by silica gel column (EA/MeOH=1/0 to 10/1) and preparative HPLC (50 to 80% of acetonitrile in water with 0.05% HCl) to give 245 (1.0 g, 37% yield, 98% purity) as yellow solid. [M+H]⁺ calcd for $C_{23}H_{24}BrClN_4OSi$ 515.06 found 515.0. ¹H NMR (400 MHz, Chloroform-d) δ 8.85 (d, J=2.2 Hz, 1H), 8.26 (dd, J=8.9, 0.8 Hz, 2H), 8.21 (dd, J=2.2, 0.9 Hz, 2H), 8.16 (d, J=8.9 Hz, 2H), 7.83 (s, 2H), 7.67-7.61 (m, 2H), 7.54-7.45 (m, 2H), 7.47-7.37 (m, 3H), 5.19 (s, 3H), 3.57-3.47 (m, 3H), 0.97-0.86 (m, 2H).

Example 251: Synthesis of 6-(5-(3-chlorophenyl)-1H-imidazol-4-yl)-N-(2-(4-isopropylpiperazin-1-yl)ethyl)-1,5-naphthyridin-3-amine (29-1)

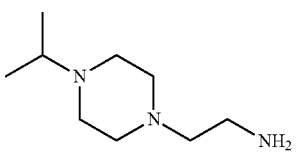

1. BrettPhos Pd G3, BrettPhos, Cs₂CO₃
1,4-Dioxane, 80° C., 16 h 2. 6N aq. HCl, DCE, 80° C., 3 h

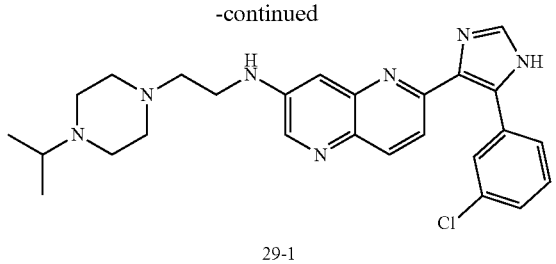

29-1

A vial of 245 (30 mg, 0.058 mmol), 2-(4-isopropyl-piperazin-1-yl)-ethylamine (0.012 ml, 0.064 mmol), cesium carbonate (56.8 mg, 0.174 mmol), BrettPhos (6.24 mg, 0.012 mmol), and BrettPhos Pd G3 (10.54 mg, 0.012 mmol) in 1,4-dioxane (0.581 mL) (degassed with $N_2$) was heated to 80° C. for 16 h. The reaction mixture was filtered through a pad of celite and concentrated in vacuum. The crude material was dissolved in DCE (0.300 mL) and 6 M aq. HCl (0.200 mL) was added. The mixture was heated to 80° C. for 3 h. The reaction mixture was concentrated in vacuum and the residue was purified by preparative HPLC chromatography using a gradient (5 to 75%) of acetonitrile in water with 0.05% trifluoroacetic acid to yield a TFA salt of the title compound (7.4 mg). $[M+H]^+$ calcd for $C_{26}H_{30}ClN_7$ 476.23, found 476.1.

Example 252: Synthesis of 2-(4-(6-(5-(3-chlorophe-nyl)-1H-imidazol-4-yl)-1,5-naphthyridin-3-yl)piper-azin-2-yl)acetic acid (29-4)

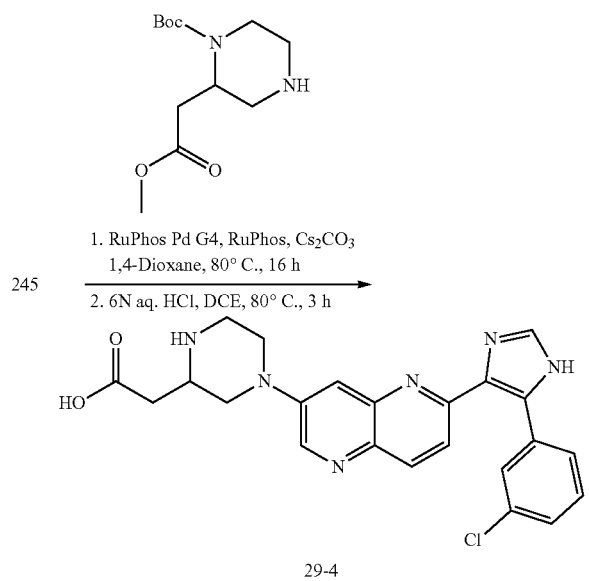

29-4

A vial of 245 (86 mg, 0.0161 mol), 1-boc-2-methoxycar-bonylmethylpiperazine (50.0 mg, 0.194 mmol), cesium carbonate (158 mg, 0.484 mmol), RuPhos Pd G4 (13.73 mg, 0.016 mmol), RuPhos (15.07 mg, 0.032 mmol) in 1,4-dioxane (807 μL) was sparged with $N_2$ before heating to 80° C. for 16 h. The mixture was concentrated in vacuum and treated with 200 μL of 6 N aq HCl and 200 μL of dichloroethane. The reaction mixture was heated to 80° C. for 3 h until fully deprotected and ester hydrolyzed to carboxylic acid. The resulting mixture was concentrated and purified by preparative HPLC chromatography using a gradient (5 to 75%) of acetonitrile in water with 0.05% trifluoroacetic acid to yield a TFA salt of the title compound (4.2 mg). $[M+H]+$ calcd for $C_{23}H_{21}ClN_6O_2$ 449.14, found 449.1.

Example 253: Synthesis of methyl 2-(4-(6-(5-(3-chlorophenyl)-1H-imidazol-4-yl)-1,5-naphthyridin-3-yl)piperazin-2-yl)acetate (29-3)

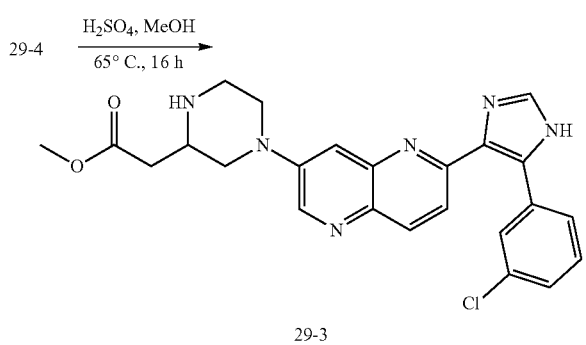

29-3

A mixture of crude 29-4 (30 mg, 0.067 mmol) and sulfuric acid (3.56 μl, 0.067 mmol) in MeOH (0.50 ml) was heated to a reflux overnight. The resulting mixture was concentrated and purified by preparative HPLC chromatography using a gradient (5 to 75%) of acetonitrile in water with 0.05% trifluoroacetic acid to yield a TFA salt of the title compound (16.1 mg). $[M+H]+$ calcd for $C_{24}H_{23}ClN_6O_2$ 463.16, found 463.0.

Example 254: Biochemical ALK5 (TGF-βR1) Assay to Measure pKi

Apparent pKi values for compounds of the present disclosure were determined using a recombinant human ALK5 (TGF-βR1) protein (Product No. PR9075A or equivalent, Life Technologies) and a commercially-available kinase assay (LANCE® (lanthanide chelate excite) Ultra ULight™ kinase assay, Product Nos. TRF0130-M and TRF02108-M, Perkin Elmer) as described below.

The assays were performed in a 384-well plate (24 columns×16 wells/rows). An Echo® 550 Liquid Handler (Labcyte) was used to prepare various intermediate concentrations of compounds of the present disclosure in 100% DMSO. From the intermediate concentrations, a range of concentrations (from 10 μM to 25 pM corresponding to volumes up to 105 nL) were prepared and ejected into a final assay plate to be used to create individual dose response curves for each of the subject compounds. To a separate column within the assay plate, 105 nL of DMSO in each well was used to establish a maximum assay signal. Additionally, 105 nL of 100 μM SD-208, a selective TGF-βR1 inhibitor (Catalog #S7624, Selleck Chemicals), was used in another column of wells to establish a minimal assay signal.

With a multidrop dispenser, 8 μL of enzyme mixture (1.25× final) was added to each well. The enzyme mixture consisted of 250 pM ALK5 enzyme and 62.5 nM peptide substrate (LANCE® (lanthanide chelate excite) Ultra ULight™-DNA Topoisomerase 2-alpha (Thr1342)) prepared in assay buffer (50 mM HEPES, 10 mM $MgCl_2$, 1 mM EGTA, 0.01% Tween-20, pH 7.5 at room temperature) with 2 mM DTT added prior to use. The plate was then sealed with an adhesive seal and allowed to equilibrate for 60 minutes at room temperature.

Next, 2 μL of 125 μM ATP (5× final, 125 μM ATP prepared in assay buffer with 2 mM DTT) was added to the incubated mixtures, covered with a MicroClime® Environmental Lid (Product No. LLS-0310, Labcyte) and immediately transferred to 37° C. The reactions were allowed to proceed at 37° C. for 60 minutes before terminating with the addition of 10 μL of detection antibody (LANCE® (lanthanide chelate excite) Ultra Europium-anti-phospo-DNA Topoisomerase 2-alpha (Thr1342)) in detection mixture (12 mM EDTA, 4 nM detection antibody prepared in detection buffer (50 mM Tris-HCl, 150 mM NaCl, 0.5% BSA (Fraction V), pH 7.0)) at room temperature. The plate was then read on a Perkin Elmer EnVision Plate Reader using europium specific reader settings with excitation and emission wavelengths set to 320 or 340 nm and 665 nm, respectively. These data were used to calculate percent enzyme inhibition values based on DMSO and SD-208 background controls.

For dose-response analyses, percent inhibition versus compound concentrations were plotted, and $pIC_{50}$ values were determined from a 4-parameter robust fit model with GraphPad Prism V5 Software (GraphPad Software, Inc., La Jolla, Calif.). This model obtains $pIC_{50}$ values by fitting the sigmodial dose-response (variable slope) equation to the data. Results were expressed as $pIC_{50}$ (negative logarithm of $IC_{50}$) and subsequently converted to $pK_i$ (negative logarithm of dissociate constant, $K_i$) using the Cheng-Prusoff equation.

The higher the value of $pK_i$ (lower value of $K_i$), the greater the inhibition of ALK5 activity. Certain compounds disclosed herein exhibited $pK_i$ values of greater than 8 or greater than 9 when tested in the biochemical ALK5 assay.

Table 2 shows biological activities of selected compounds in a biochemical ALK5 assay. Compound numbers correspond to the numbers and structures provided in Table 1 and Examples 1-253.

TABLE 2

| | 7.5 to 8.4 (+) | 8.5 to 9.4 (++) | 9.5 to 10.4 (+++) | ≥10.5 (++++) |
|---|---|---|---|---|
| ALK5 $pK_i$ | 1-5, 1-9, 1-35, 1-42, 1-73, 1-75, 1-98, 1-99, 2-27, 2-32, 2-38, 4-2, 5-2, 6-50, 6-65, 8-1, 8-2, 8-4, 8-8, 8-16, 9-2, 10-2, 11-3, 11-4, 12-1, 12-2, 14-1, 14-3, 14-4, 14-5, 14-7, 14-16, 14-17, 15-1, 15-2, 18-7, 22-6, 23-4, 23-5, 25-1, 27-1 | 1-4, 1-6, 1-19, 1-25, 1-33, 1-38, 1-48, 1-50, 1-54, 1-59, 1-61, 1-62, 1-63, 1-65, 1-66, 1-67, 1-68, 1-72, 1-74, 1-80, 1-81, 1-82, 1-101, 1-102, 1-104, 1-117, 1-119, 1-120, 1-129, 1-130, 1-134, 2-7, 2-13, 2-28, 2-30, 2-31, 3-10, 4-1, 5-1, 6-7, 6-8, 6-11, 6-12, 6-15, 6-16, | 1-1, 1-2, 1-3, 1-7, 1-8, 1-10, 1-11, 1-12, 1-13, 1-14, 1-15, 1-16, 1-17, 1-18, 1-20, 1-21, 1-22, 1-23, 1-24, 1-26, 1-28, 1-29, 1-30, 1-31, 1-32, 1-36, 1-37, 1-39, 1-40, 1-41, 1-43, 1-44, 1-45, 1-46, 1-47, 1-49, 1-51, 1-52, 1-53, 1-56, 1-57, 1-58, 1-60, 1-64, 1-69, 1-70, 1-77, 1-78, 1-79, 1-84, 1-88, 1-90, 1-91, 1-92, 1-93, 1-95, 1-100, 1-105, 1-107, 1-109, 1-110, 1-112, 1-113, 1-114, 1-115, 1-116, 1-118, 1-121, 1-122, 1-123, 1-124, 1-125, 1-126, 1-128, 1-131, 1-132, 1-133, 1-135, 1-136, 2-1, 2-2, 2-3, 2-4, 2-5, 2-6, 2-8, 2-10, 2-11, 2-14, 2-16, 2-17, 2-18, 2-19, 2-20, 2-21, 2-22, 2-23, 2-24, 2-25, 2-26, 2-29, 2-33, 2-34, 2-35, 2-36, 2-37, 3-1, 3-2, 3-3, 3-4, 3-5, 3-6, 3-7, 3-8, 3-9, 6-1, 6-2, 6-3, 6-4, 6-5, 6-6, 6-9, 6-10, 6-13, 6-14, 6-17, 6-18, 6-19, 6-21, 6-22, 6-23, 6-25, 6-30, 6-31, 6-32, 6-36, 6-37, 6-38, 6-39, 6-42, 6-43, 6-44, 6-45, 6-46, 6-49, 6-52, 6-53, 6-54, 6-55, 6-56, 6-58, 6-59, 6-61, 6-62, 6-63, 6-72, 6-74, 7-1, 7-2, 7-4, 7-5, 7-6, 7-7, 8-19, 8-21, 8-25, 8-26, 8-27, 10-1, 14-8, 14-11, 14-13, 14-14, 14-18, 15-3, 15-4, 16-2, 16-3, 17-1, 17-5, 17-7, 17-9, 17-11, 17-13, 17-14, 17-15, 18-2, 19-1, 19-2, 19-4, 19-5, 19-7, 20-1, 22-2, 22-3, 22-4, 22-5, 23-1, 23-2, 23-3, 26-1, 28-1 | 1-27, 1-34, 1-55, 1-71, 1-76, 1-83, 1-85, 1-86, 1-87, 1-89, 1-94, 1-96, 1-97, 1-103, 1-106, 1-108, 1-111, 1-127, 2-9, 2-15, 6-29, 6-34, 6-35, 6-40, 6-41, 6-67, 8-12, 8-15, 8-17, 8-24, 9-3, 16-1, 17-2, 18-1, 22-1, 24-1 |

TABLE 2-continued

| 7.5 to 8.4 (+) | 8.5 to 9.4 (++) | 9.5 to 10.4 (+++) | ≥10.5 (++++) |
|---|---|---|---|
| 6-20, 6-24, 6-26, 6-27, 6-28, 6-33, 6-47, 6-48, 6-51, 6-57, 6-60, 6-64, 6-66, 6-68, 6-71, 6-73, 6-75, 7-3, 8-3, 8-5, 8-6, 8-7, 8-9, 8-10, 8-11, 8-13, 8-14, 8-18, 8-20, 8-22, 8-23, 9-1, 11-1, 11-2, 13-1, 14-2, 14-6, 14-9, 14-10, 14-12, 14-15, 16-4, 16-5, 17-3, 17-4, 17-6, 17-8, 17-10, 17-12, 18-3, 18-4, 18-5, 18-6, 19-3, 19-6, 19-8, 21-1, 24-2, 24-3, 24-4, 25-2, 29-1, 29-2, 29-3, 29-4 | | | |

Example 255: Cellular ALK5 Potency Assay to Measure $pIC_{50}$, Inhibition of TGF-β Stimulated pSMAD3 Formation in BEAS-2B Cells The potency of compounds of the present disclosure for inhibition of TGF-β-stimulated SMAD3 phosphorylation was measured in BEAS-2B cells, a human lung epithelial cell line. TGF-β signals through activin receptor-like kinase 5 (ALK5) immediately prior to SMAD3 phosphorylation. As the AlphaLISA SureFire Ultra kit (Perkin Elmer) quantitatively measures pSMAD3 levels in lysate, the assay demonstrates the ALK5 cellular potency of a test compound.

BEAS-2B cells were grown using 50% DMEM (Life Technologies) and 50% F-12 (Life Technologies) media, supplemented with 10% Fetal Bovine Serum (ATCC), 25 mM HEPES (Life Technologies), and 1×Pen-Strep (Life Technologies). Cells were cultured in a humidified incubator set at 37° C., 5% $CO_2$, and trypsonized using 0.25% Trypsin with 0.5% polyvinylpyrrolidone (PVP).

For the assay, BEAS-2B cells were seeded at 7,500 cells/well (25 μL/well) in a 384-well plate and cultured overnight. Before dosing, growth media was aspirated and the wells were rinsed with HBSS Buffer (HBSS with Calcium and Magnesium, Life Technologies) supplemented with 25 mM HEPES (Life Technologies) and 1% Bovine Serum Albumin (Roche). Compounds were serially diluted in DMSO, then further diluted with supplemented HBSS Buffer (50 µL/well) to create a compound plate 3× of the final assay concentration, at 0.3% DMSO. The diluted compounds were then added to the cells (8 µL/well) and incubated at 37° C., 5% $CO_2$ for 1 hour. After the compound incubation, TGF-β (R&D Systems) reconstituted in supplemented HBSS Buffer was added to the cells (12 µL/well, final concentration 10 ng/mL) and incubated for a further 30 minutes, after which the cells were immediately lysed with AlphaLISA lysis buffer (PerkinElmer). AlphaLISA Acceptor and Detector beads (PerkinElmer) were added 2 hours apart, then incubated overnight to be read the next day. The potency of the compound was determined through analysis of dose-dependent quantified changes in pSMAD3 signal from baseline (non-compound treated TGF-β stimulated cells). Data are expressed as $pIC_{50}$ (negative decadic logarithm $IC_{50}$) values. Certain compounds disclosed herein exhibited $pIC_{50}$ values of greater than 6 or greater than 7 when tested in BEAS-2B cells.

Table 3 shows biological activities of selected compounds in a cellular ALK5 potency assay. Compound numbers correspond to the numbers and structures provided in Table 1 and Examples 1-253.

TABLE 3

| | 5 to 5.8 (+) | 5.9 to 6.7 (++) | 6.8 to 7.6 (+++) | ≥7.7 (++++) |
|---|---|---|---|---|
| BEAS2B $pIC_{50}$ | 3-10, 22-6, 29-4 | 1-6, 1-9, 1-35, 1-84, 1-98, 1-99, 1-110, 1-117, 1-127, 1-128, 1-129, 1-130, 1-132, 1-133, 2-13, 2-14, 2-28, 2-30, 2-32, 2-33, 2-34, 2-37, 3-2, 3-4, 3-5, 4-1, 4-2, 6-10, 6-64, 6-65, 6-66, 6-68, 9-1, 12-1, 13-1, 14-16, 14-17, 15-1, 15-2, 18-7, 19-2, 19-4, 19-5, 19-6, 19-7, 19-8, 21-1, 23-5, 25-1, 25-2, 26-1 | 1-1, 1-4, 1-5, 1-15, 1-16, 1-17, 1-18, 1-19, 1-21, 1-22, 1-23, 1-24, 1-25, 1-26, 1-27, 1-28, 1-29, 1-30, 1-32, 1-33, 1-34, 1-36, 1-37, 1-38, 1-40, 1-41, 1-42, 1-43, 1-44, 1-46, 1-47, 1-50, 1-51, 1-53, 1-54, 1-57, 1-58, 1-59, 1-60, 1-61, 1-62, 1-63, 1-65, 1-66, 1-67, 1-68, 1-70, 1-72, 1-73, 1-74, 1-75, 1-76, 1-77, 1-78, 1-80, 1-81, 1-82, 1-85, 1-86, 1-88, 1-89, 1-94, 1-95, 1-100, 1-103, 1-104, 1-105, 1-106, 1-107, 1-109, 1-111, 1-112, 1-113, 1-114, 1-115, 1-116, 1-119, 1-120, 1-121, 1-122, 1-123, 1-124, 1-125, 1-126, 1-134, 1-135, 2-1, 2-2, 2-3, 2-4, 2-5, 2-6, 2-7, 2-9, 2-10, 2-15, 2-16, 2-17, 2-18, 2-19, 2-20, 2-21, 2-22, 2-23, 2-24, 2-25, 2-27, 2-29, 2-31, 2-35, 2-36, 2-38, 3-1, 3-3, 3-6, 3-7, 3-8, 3-9, 5-1, 5-2, 6-1, 6-4, 6-5, 6-7, 6-8, 6-9, 6-11, 6-12, 6-13, 6-14, 6-15, 6-16, 6-17, 6-18, 6-19, 6-20, 6-21, 6-22, 6-23, 6-24, 6-25, 6-26, 6-27, 6-28, 6-30, 6-32, 6-33, 6-36, 6-37, 6-38, 6-39, 6-41, 6-42, 6-45, 6-46, 6-47, 6-48, 6-49, 6-50, 6-51, 6-52, 6-53, 6-54, 6-55, 6-56, 6-57, 6-58, 6-59, 6-60, 6-61, 6-62, 6-63, 6-67, 6-71, 6-72, 6-73, 6-74, 6-75, 7-1, 7-2, 7-3, 7-4, 7-5, 7-6, 7-7, 8-1, 8-2, 8-3, 8-4, 8-5, 8-6, 8-7, 8-8, 8-9, 8-10, 8-11, 8-14, 8-15, 8-16, 8-18, 8-20, 8-22, 8-23, 8-25, 8-26, 8-27, 9-2, 10-2, 11-1, 11-2, 11-3, 11-4, 12-2, 14-1, 14-2, 14-3, 14-4, 14-5, 14-6, 14-7, 14-8, 14-10, 14-11, 14-12, 14-13, 14-14, 14-15, 14-18, 15-3, 15-4, 16-3, 16-4, 16-5, 17-2, 17-3, 17-4, 17-5, 17-6, 17-7, 17-8, 17-9, 17-10, 17-12, 17-14, 17-15, 18-1, 18-3, 18-4, 18-5, 18-6, 19-1, 19-3, 20-1, 22-1, 22-2, 22-3, 22-4, 22-5, 23-1, 23-2, 23-3, 23-4, 24-2, 24-3, 24-4, 27-1, 28-1, 29-2, 29-3 | 1-2, 1-3, 1-7, 1-8, 1-10, 1-11, 1-12, 1-13, 1-14, 1-20, 1-31, 1-39, 1-45, 1-48, 1-49, 1-52, 1-55, 1-56, 1-64, 1-69, 1-71, 1-79, 1-83, 1-87, 1-90, 1-91, 1-92, 1-93, 1-96, 1-97, 1-101, 1-102, 1-108, 1-118, 1-131, 1-136, 2-8, 2-11, 2-26, 6-2, 6-3, 6-6, 6-29, 6-31, 6-34, 6-35, 6-40, 6-43, 6-44, 8-12, 8-13, 8-17, 8-19, 8-21, 8-24, 9-3, 10-1, 14-9, 16-1, 16-2, 17-1, 17-11, 17-13, 18-2, 24-1, 29-1 |

Example 256: Cytotoxicity Measured by Premature Chromosome Condensation [15]($pCC_{15}$)

The impact of a compound of the present disclosure on cellular adenosine triphosphate (ATP) levels was measured in Beas2B cells, a human lung epithelial cell line. Levels of ATP are correlated with the viability of cells and are often measured to determine the potential cytotoxicity of compounds. CellTiter-Glo, which lyses the cells and produces a luminescent signal proportional to the amount of ATP present, was used to determine the effect of test compound on cell viability.

Beas2B cells were grown in 50% DMEM (Life Technologies) and 50% F-12 (Life Technologies) media, supplemented with 10% Fetal Bovine Serum (ATCC), 25 mM HEPES (Life Technologies), and 1×Pen-Strep (Life Technologies). Cells were cultured in a humidified incubator set at 37° C., 5% $CO_2$, and trypsinized using 0.25% Trypsin with 0.5% polyvinylpyrrolidone (PVP).

For the assay, Beas2B cells were seeded at 500 cells/well (25 µL/well) in a 384-well plate and cultured overnight. Compounds were serially diluted in DMSO, then further diluted with growth media (40 µL/well) to create a compound plate 6× of the final assay concentration, at 0.6% DMSO. The diluted compounds were then added to the cells (5 µL/well) and incubated at 37° C., 5% $CO_2$ for 48 hours. After the compound incubation, CellTiter-Glo (Promega) was added directly to the cells (30 µL/mL). The assay plate was sealed and shaken at 700 rpm for 15 minutes in a darkened environment, then centrifuged for 2 minutes at 1500 rpm to settle the lysate at the bottom of the well. The effect of the compound on cell viability was determined through analysis of dose-dependent quantified changes in ATP from baseline (non-compound treated cells) and wells treated with 60 µM AT9283, a well-characterized cytotoxic compound. Data are expressed as $pCC_{15}$ (negative decadic logarithm $CC_{15}$) values. Certain compounds disclosed herein exhibited $pCC_{15}$ values of less than 6 or less than 5.5 when tested in Beas2B cells.

Table 4 shows cytotoxicities of selected compounds in a premature chromosome condensation assay. Compound numbers correspond to the numbers and structures provided in Table 1 and Examples 1-253.

TABLE 4

| | ≤5 (+++) | 5.1 to 5.7 (++) | 5.8 to 7.0 (+) |
|---|---|---|---|
| Cytotoxicity $pCC_{15}$ | 1-22, 1-50, 1-65, 1-85, 1-101, 1-102, 1-104, 1-105, 1-110, 1-126, 1-127, 1-128, 1-129, 1-130, 1-133, 1-134, 2-3, 2-6, 2-7, 2-8, 2-13, 2-14, 2-20, 2-22, 2-23, 2-24, 2-25, 2-27, 2-28, 2-30, 2-31, 2-32, 2-33, 2-34, 2-35, 2-36, 2-37, 2-38, 3-1, 3-4, 3-9, 3-10, 4-1, 4-2, 5-1, 5-2, 6-6, 6-7, 6-38, 6-46, 6-48, 6-57, 6-61, 6-64, 6-65, 6-68, 6-71, 6-75, 7-3, 7-5, 7-6, 7-7, 8-5, 8-6, 8-9, 8-10, 8-16, 8-23, 9-1, 10-2, 11-4, 12-1, 12-2, 13-1, 14-1, 14-2, 14-3, 14-4, 14-5, 14-6, 14-7, 14-11, 14-13, 14-15, 14-16, 14-17, 15-1, 15-2, 15-4, 17-4, 17-6, 17-10, 18-1, 18-2, 18-4, 18-5, 18-6, 18-7, 19-3, 22-3, 22-5, 22-6, 23-5, 29-3, 29-4 | 1-1, 1-2, 1-5, 1-6, 1-8, 1-9, 1-10, 1-11, 1-12, 1-13, 1-14, 1-16, 1-17, 1-18, 1-19, 1-20, 1-21, 1-23, 1-26, 1-27, 1-28, 1-31, 1-32, 1-33, 1-34, 1-35, 1-40, 1-41, 1-43, 1-47, 1-48, 1-49, 1-51, 1-52, 1-53, 1-55, 1-58, 1-61, 1-62, 1-66, 1-68, 1-70, 1-72, 1-73, 1-74, 1-75, 1-77, 1-78, 1-80, 1-81, 1-84, 1-90, 1-95, 1-98, 1-99, 1-100, 1-103, 1-107, 1-109, 1-111, 1-112, 1-114, 1-115, 1-117, 1-118, 1-119, 1-123, 1-132, 2-1, 2-2, 2-4, 2-5, 2-9, 2-10, 2-11, 2-15, 2-16, 2-17, 2-19, 2-26, 2-29, 3-2, 3-3, 3-5, 3-6, 3-7, 6-1, 6-3, 6-4, 6-5, 6-8, 6-9, 6-11, 6-12, 6-13, 6-14, 6-18, 6-19, 6-20, 6-21, 6-22, 6-24, 6-25, 6-26, 6-27, 6-28, 6-30, 6-31, 6-32, 6-33, 6-37, 6-39, 6-41, 6-44, 6-45, 6-47, 6-49, 6-50, 6-51, 6-54, 6-56, 6-58, 6-59, 6-60, 6-62, 6-63, 6-66, 6-72, 6-73, 6-74, 7-1, 7-2, 7-4, 8-1, 8-2, 8-3, 8-4, 8-7, 8-8, 8-11, 8-13, 8-18, 8-20, 8-25, 8-27, 9-2, 11-1, 11-2, 11-3, 14-8, 14-10, 14-12, 14-14, 14-18, 15-3, 16-2, 16-3, 16-4, 16-5, 17-1, 17-2, 17-3, 17-5, 17-7, 17-8, 17-11, 17-12, 17-13, 17-14, 17-15, 18-3, 19-1, 19-4, 19-5, 19-6, 19-7, 19-8, 20-1, 21-1, 22-1, 22-2, 23-1, 23-3, 23-4, 24-2, 24-3, 24-4, 25-1, 25-2, 27-1, 29-2 | 1-3, 1-4, 1-7, 1-15, 1-24, 1-25, 1-29, 1-30, 1-36, 1-37, 1-38, 1-39, 1-42, 1-44, 1-45, 1-46, 1-54, 1-56, 1-57, 1-59, 1-60, 1-63, 1-64, 1-67, 1-69, 1-71, 1-76, 1-79, 1-82, 1-83, 1-86, 1-87, 1-88, 1-89, 1-91, 1-92, 1-93, 1-94, 1-96, 1-97, 1-106, 1-108, 1-113, 1-116, 1-120, 1-121, 1-122, 1-124, 1-125, 1-131, 1-135, 1-136, 2-18, 2-21, 3-8, 6-2, 6-10, 6-15, 6-16, 6-17, 6-23, 6-29, 6-34, 6-35, 6-36, 6-40, 6-42, 6-43, 6-52, 6-53, 6-55, 6-67, 8-12, 8-14, 8-15, 8-17, 8-19, 8-21, 8-22, 8-24, 8-26, 9-3, 10-1, 14-9, 16-1, 17-9, 19-2, 22-4, 23-2, 24-1, 26-1, 28-1, 29-1 |

Example 257: In Vitro Human Liver Microsome Intrinsic Clearance (HLM $Cl_{int}$)

Liver microsomes were used for in vitro determination of hepatic clearance of compounds of the present disclosure. A microsomal incubation cofactor solution was prepared with 100 mM potassium phosphate buffered to pH 7.4 (BD Biosciences, Woburn, Mass.) supplemented with 2 mM NADPH (Sigma-Aldrich, St. Louis, Mo.). 10 mM DMSO stocks of test compound were diluted and spiked into the cofactor solution to yield a 0.2 µM concentration (0.02% v/v DMSO). Aliquots of frozen human liver microsomes (Bioreclamation IVT, Baltimore Md.) were thawed and diluted into 100 mM potassium phosphate buffer to yield microsomal protein concentrations of 0.2 mg/mL. Cofactor/drug and microsomal solutions were pre-warmed separately for 4 minutes in a water bath held at 37° C. Incubations (n=1) were started by the combination of equal volumes of cofactor/drug solution with microsomal solution. The final concentration of test compound was 0.1 µM with a final protein concentration of 0.1 mg/mL and final NADPH concentration of 1 mM. Samples were collected at times 0, 3, 8, 15, 30, and 45 minutes to monitor the disappearance of test compound. At each time point, 50 µL of incubation sample was removed and spiked into 25 µL of water plus 3% formic acid plus Internal Standard for reaction termination. Samples were then injected onto an AB Sciex API 4000 triple quadrupole mass spectrometer for quantitation by LC-MS/MS. Mobile Phase A consisted of HPLC grade water with 0.2% formic acid and Mobile Phase B consisted of HPLC grade acetonitrile with 0.2% formic acid with all samples run through a Thermo HyPURITY C18 50×2.1 mm column (Waltham, Mass.). HLM $Cl_{int}$ data was reported in units of µL/min/mg. See Riley, R. J., et al., *Drug Metab. Dispos.*, 2005, September, 33(9), pp. 1304-1311. Certain compounds disclosed herein exhibited HLM $Cl_{int}$ of greater than 50 µL/min/mg or greater than 100 µL/min/mg.

Example 258: Lung PK/PD

In-Life Portion $C_{57}$bl/6n mice were acclimated for at least 3 days before use. On the day of the experiment, animals were grouped into sample sizes of 5 (n=10 for the TGF-β stimulated group). Compounds of the present disclosure (formulated in 3% glycerol in PBS; pH=4) were pre-treated via oral aspiration (OA; animals are forced to aspirate solution into the lungs by covering their nose). All oral aspirations were performed using a 50 µL dosing volume and accompanied by the appropriate vehicle control groups. Following compound OA treatment, the animals were returned to their home cages and monitored. Compound pre-treatment occurred 4 hours prior to harvest for screening and dose-response studies; duration studies had variable compound pre-treatment times. One hour prior to harvest, animals were challenged via oral aspiration a second time with PBS vehicle or recombinant human TGF-β1 protein (0.01 µg per animal dissolved in 1 part 4 mM HCl and 2 parts 3% glycerol in PBS). Five minutes prior to harvest, animals were deeply anesthetized under isoflurane and euthanized via cervical dislocation. Bronchoalveolar lavage fluid (BALF), plasma and left lung lobes were collected during harvest.

Sample Collection and Processing

Blood plasma was collected via open cardiac puncture. After whole blood collection, the samples were placed in EDTA-coated tubes to prevent coagulation. Blood samples were spun at 15300×g's for 4 minutes at 4° C. to separate the plasma. Plasma was immediately isolated, frozen and submitted for bioanalytical (BA) analysis.

In order to collect BALF, the lungs were flushed via the trachea with 0.7 mL of PBS 3 times.

The BALF, which consists almost entirely of tissue-derived macrophages, was immediately centrifuged at 700× g's for 15 minutes. After centrifugation, the supernatant was removed, the BALF was re-suspended in 1× cell lysis buffer, and immediately frozen. Prior to BA submission, the BALF was dethawed and sonicated for 30 minutes on cold water to lyse open the cells Left lung lobes were harvested immediately after BALF collection. Lung samples were homogenized in 500 µL of 1× cell lysis buffer. After homogenization, the samples were split: half of the sample was immediately placed on a rotisserie for 10 minutes while the other half was immediately frozen for BA analysis. The samples placed on the rotisserie were then centrifuged at 10,000×g's for 10 minutes in order to separate the protein in the supernatant from pelleted debris. Following collection of the supernatant, a total protein quantification assay (Bradford) was performed to normalize the concentrations of all samples. Using the Hamilton star liquid handling system, each sample was diluted in 1× cell lysis buffer to 2 mg/ml of protein. Samples were stored at −80° C. or immediately processed using the Meso-scale Discovery system.

Phospho-SMAD3 (pSMAD3) and Total-SMAD3 (tSMAD3) Quantification Using Meso-Scale Discovery Meso-scale Discovery (MSD) is an electrochemical protein quantification assay that requires specialized microplates with carbon electrodes attached to the bottom. These carbon electrodes allow for greater attachment of biological reagent to microplates, thus allowing for a more sensitive read-out when compared to a traditional ELISA. Similar to a standard sandwich ELISA, MSD requires use of a coating antibody that binds the target protein(s) within the sample. After sample incubation, a primary antibody is used to bind the epitope of interest. Following addition of the primary antibody, a secondary-antibody with a SULFO-TAG detection is used to allow for quantification of the epitope of interest. Lastly, the microplate is read via an electric pulse that causes the SULFO-TAG to emit light, which serves as the final read-out of the assay.

The coating antibody (SMAD3, clone=5G-11) was incubated overnight in the specialized MSD microplates at 4° C. The next day, the microplates were blocked in 3% BSA (bovine serum albumin) for 70 minutes to prevent non-specific protein binding to the bottom of the microplate. After a wash step, 50 µg of lung samples were loaded into the MSD-plate and incubated for 2 hours at room temperature. The plates were washed again to remove unbound sample; either phospo-SMAD3 (pSMAD3; clone=EP568Y) or total-SMAD3 (tSMAD3) primary antibody were incubated for 1 hour. Following a wash step, the anti-rabbit SULFO-tag detection antibody was incubated for 50 minutes. After a final wash step, MSD-read buffer was added to each sample. pSMAD3 and tSMAD3 quantification was performed using an MSD-specific plate reader (Sector S 600).

Data Analysis

Samples were immediately analyzed using an outlier analysis (Grubbs test, α=0.05). After outlier removal, the raw pSMAD3 were divided by the tSMAD3 luminescent readings. In screening and dose-response studies, the pSMAD3/tSMAD3 ratio was normalized to the TGF-β induction group (set to 100%) in order to minimize the variability between stimulation. First, the 3% glycerol/PBS group was compared with the 3% glycerol/TGF-β with a student's t-test (cut-off: p=0.05) to ensure a pSMAD3 window was present. A one-way ANOVA (fisher's uncorrected LSD) was used to compare all drug treated groups with the 3% glycerol/TGF-β group to determine if statistically significant differences are observed. Percent pSMAD3 inhibition was calculated using the vehicle pSMAD3 as a baseline value and displayed as the final readout. Dose-response curves were fitted with a 4-parameter non-linear regression algorithm; the minimum response was set to 0% pSMAD3 inhibition and the maximum response set to 100% pSMAD3 inhibition. Compound potencies were obtained from the regression and reported as ID50s.

PK Study

Plasma, lung and macrophage drug concentrations were quantified. Total macrophage concentration was normalized to the total macrophage cell volume over the total drug recovered in the BALF. The alveolar macrophage volume used in the calculation was based on a publication by Krombach et al. (*Environmental Health Perspectives*, September 1997, Vol. 105, Supplement 5, pp. 1261-1263) which estimated the rat alveolar macrophage volume to be approximately 1200 µm$^3$ or 1.2e$^{-9}$ mL. The assumption was made that the mouse alveolar macrophage volume is similar to that of the rat. Normalized total macrophage concentration recovered=(total drug recovered from BALF)/(total cell counts*1.2e$^{-9}$ mL).

Certain compounds disclosed herein exhibited (lung AUC$_{0-t}$):(plasma AUC$_{0-t}$) ratios of greater than 10, such as greater than 50, greater than 75 or greater than 100. A compound intended for local delivery to the lung with minimal systemic exposure preferably exhibits a (lung AUC$_{0-t}$):(plasma AUC$_{0-t}$) ratio of greater than 50. Certain compounds provided in Table 2 having pK$_i$ values of greater than 9.5 exhibited a (lung AUC$_{0-t}$):(plasma AUC$_{0-t}$) ratio of greater than 75.

Example 259: Cardiac PK/PD

In-Life Portion

C$_{57}$bl/6n mice were acclimated for at least 3 days before use. On the day of the experiment, animals were grouped into sample sizes of 5-10. Test compounds were pre-treated via oral aspiration (OA; animals are forced to aspirate solution into the lungs by covering their nose). All oral aspirations were performed using a 50 µL dosing volume and accompanied by a vehicle control group (3% glycerol in PBS, pH=4). Following compound OA treatment, the animals were returned to their home cages and monitored. Compound pre-treatment occurred either 2 or 4 hours prior to harvest. One hour prior to harvest, animals were challenged via tail-vein intravenous injection with PBS vehicle or recombinant human TGF-β1 protein (1 µg per animal dissolved in 1 part 4 mM HCl and 2 parts 3% glycerol in PBS). Five minutes prior to harvest, animals were deeply anesthetized under isoflurane and euthanized via cervical dislocation. Plasma, left lung lobes and whole hearts were collected during harvest.

Sample Collection and Processing

Blood plasma was harvested as described above in the Lung PK/PD experiment. Whole hearts were processed in the same manners as left lung lobes in the Lung PK/PD experiment. Left lung lobes were homogenized in 500 µL, of water and submitted for BA Analysis.

Phospho-SMAD3 (pSMAD3) and Total-SMAD3 (tSMAD3) Quantification Using Meso-Scale Discovery Heart samples were processed using MSD in the same manner as the left lung lobes above. Data analysis was performed in the same manners as the lung PK/PD experiment. Plasma, lung and heart drug concentrations were quantified.

There was minimal target engagement systemically following treatment with one or more compound disclosed herein, as measured by SMAD3 phosphorylation inhibition. In some examples, a compound disclosed herein exhibited less than 10% target engagement systemically as measured by SMAD3 phosphorylation inhibition.

Example 260: Efficacy Study in Syngeneic Cancer Model

One or more compounds disclosed herein, e.g., a compound provided in Table 1 having an ALK5 $pK_i$ value of greater than 9.5, preferably greater than 10.5 (a measurement reflecting the ability of the compound to inhibit ALK5 activity, measured in accordance with Example 254), are expected to suppress tumor growth in syngeneic cancer models when administered alone or in combination with an immunotherapeutic agent. Six- to 8-week old BALB/c mice are used for in vivo efficacy studies in accordance with IACUC guidelines. Commercially available 4T1 cells (0.5-2.0×$10^4$ cells/mouse) are implanted subcutaneously into the right flanks of BALB/c mice. When the tumor reaches a palpable size of approximately 8-10 mm in diameter, the primary tumors are surgically removed, and the mice are randomly assigned to vehicle control or compound treatment groups. Alternatively, CT26 cells (0.5-2.0×$10^4$ cells/mouse) are injected intravenously into BALB/c mice to generate the cancer model. Two days following the surgery, or 7 days following injection of CT26 cells, the mice are treated with either (1) vehicle control, (2) a compound of the present disclosure at an appropriate amount and frequency (formulated in 3% glycerol in PBS; pH=4) via oral aspiration or intranasally, (3) an immunotherapeutic agent (e.g., pembrolizumab or durvalumab) at an appropriate amount and frequency, or (4) a compound of the present disclosure and an immunotherapeutic agent, each at an appropriate amount and frequency.

Body weight is measured twice weekly. Following 2- to 4-weeks of treatment, the lung and liver of each animal is harvested, and the number of metastatic cells in each tissue sample determined using a clonogenic metastasis assay. Cells may be further subjected to one or more of FACS analysis, T-cell function assay, and RNA extraction. It is expected that the animal group treated with one or more of the ALK5 inhibitors disclosed herein exhibits reduction in lung tumor burden. Activation of an immune response by the ALK5 inhibitor may stimulate both local and systemic antitumor T-cell activation, thus a reduction in liver tumor burden may also be observed. When administered in combination with an immunotherapeutic agent, a compound of the present disclosure, such as a compound provided in Table 1, is expected to produce an increased reduction in lung tumor burden relative to the reduction in tumor burden observed in animals treated with either single agent alone. The compounds described herein are expected to interact synergistically with an immunotherapeutic agent to suppress tumor growth and increase survival.

What is claimed is:
1. A compound of Formula (II), (III) or (VII):

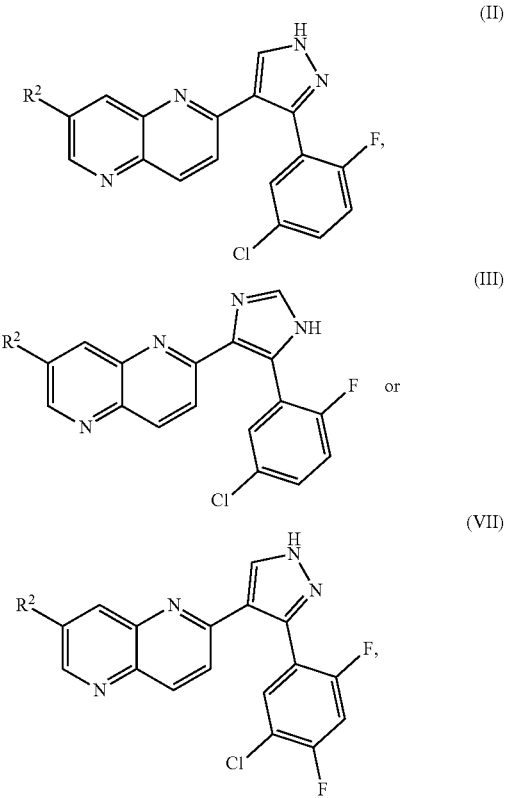

or a pharmaceutically acceptable salt thereof, wherein:
$R^2$ is selected from H; —NH—$(CH_2)_{0-3}R^5$; —NHCH$_2$C$(CH_3)_2R^5$; —NHCH$_2$C$(CH_3)(CH_2OCH_3)R^5$; —NHR$^5$; —NH—C$(CH_3)_2CH_2R^5$; —N$(CH_3)R^5$; —N$(CH_3)$CH$_2R^5$; —N$(CH_3)$CH$_2$CH$_2R^5$; phenyl-$R^5$; pyrrolinyl; pyrrolidinyl; 3,6-diazabicyclo[3.2.0]heptanyl; 1,4-diazepanyl; piperazinyl; (2R,5R)-1,2,5-trimethylpiperazinyl; 1-methylpyridin-2(1H)-onyl; and carboxylate; or
$R^2$ is selected from azetidinyl-$R^5$; piperazinyl-$R^5$; isopropylpiperazinyl-$R^5$; methylpiperazinyl-$R^5$; pyrrolidinyl-$R^5$; piperidinyl-$R^5$; pyrazolyl-$R^5$; triazolyl-$R^5$; 2,7-diazaspiro[4.4]nonanyl-$R^5$; 2,5-diazabicyclo[2.2.1]heptanyl-$R^5$; 5,6,7,8-tetrahydro-[1,2,4]triazolo[1,5-a]pyrazinyl; 5,6,7,8-tetrahydro-[1,2,4]triazolo[1,5-a]pyrazinyl-$R^5$; 5,6,7,8-tetrahydroimidazo[1,5-a]pyrazinyl; 3-(trifluoromethyl)-5,6,7,8-tetrahydroimidazo[1,5-a]pyrazinyl; 5,6,7,8-tetrahydroimidazo[1,2-a]pyrazinyl; 5,6,7,8-tetrahydroimidazo[1,2-a]pyrimidinyl; 5,6,7,8-tetrahydropyrido[4,3-c]pyridazinyl; 4,5,6,7-tetrahydro-[1,2,3]triazolo[1,5-a]pyrazinyl; 3,6-diazabicyclo[3.2.0]heptanyl-$R^5$; 2,3-dihydro-1H-imidazo[1,2-a]imidazolyl; 2,3-dihydro-1H-imidazo[1,5-a]imidazolyl; 4,5,6,7-tetrahydropyrazolo[1,5-a]pyrazinyl; 4,5,6,7-tetrahydropyrazolo[1,5-a]pyrazinyl-$R^5$; 5,6,7,8-tetrahydroimidazo[1,2-a]pyrazinyl; 5,6-dihydro-4H-imidazo[1,2-c][1,2,3]triazolyl; 2,4,5,6-tetrahydropyrrolo[2,3-c]pyrazolyl; (R)-2-methyl-1,4-diazepanyl-$R^5$; cyclohexenyl-$R^5$; and cyclohexanyl-$R^5$; and R⁵ is selected from:
piperazinyl, piperidinyl, pyrrolidinyl, azetidinyl, pyridinyl, pyrrolinyl, —CH₂—R⁶, and 1,4-diazabicyclo[2.2.2]octanyl, each of which is optionally substituted with one or more methyl, ethyl, i-propyl, n-propyl, substituted or unsubstituted piperazinyl, carboxyl, carboxylate, or benzyl; and
methyl amine; dimethyl amine; substituted or unsubstituted cyclopentanyl; substituted or unsubstituted cyclohexanyl; —(CH₂)₀₋₃OH; —(CH₂)₀₋₃OCH₃; methyl; ethyl; i-propyl; n-propyl; halo; —CF₃; carboxamide; methyl carboxamide; dimethyl carboxamide; isopropyl carboxamide; benzyl carboxamide; N-methylacetamide; —NH₂; —NH-benzyl; —CH₂NHCH₃; —CH₂CH₂NH₂; —CH₂CH₂N(CH₃)₂; —CH₂CH₂NHCH₃; —CH₂CH₂NHCH(CH₃)₂; —CH₂CH₂NH-benzyl; carboxyl; carboxylate; benzyl carboxylate; methyl carboxylate; isopropyl carboxylate; substituted or unsubstituted piperazinyl; ethylazetidinyl; and 1,5-diazabicyclo[3.3.2]decanyl;
R⁶ is selected from azetidinyl, imidazolyl, and 5,6,7,8-tetrahydro-1,6-naphthyridine.

2. The compound of claim 1, wherein the compound is a compound of Formula (II) or a pharmaceutically acceptable salt thereof.

3. The compound of claim 1, wherein the compound is a compound of Formula (III) or a pharmaceutically acceptable salt thereof.

4. The compound of claim 1, wherein the compound is a compound of Formula (VII) or a pharmaceutically acceptable salt thereof.

5. The compound of claim 1, wherein the compound, or a pharmaceutically acceptable salt thereof, is provided in at least 90% enantiomeric excess.

6. A compound selected from:
6-[3-(5-chloro-2-fluoro-phenyl)-1H-pyrazol-4-yl]-N-[2-[rac-(3R,5S)-3,5-dimethylpiperazin-1-yl]ethyl]-1,5-naphthyridin-3-amine;
6-[3-(5-chloro-2-fluoro-phenyl)-1H-pyrazol-4-yl]-N-[2-(4-isopropylpiperazin-1-yl)ethyl]-1,5-naphthyridin-3-amine;
6-[3-(5-chloro-2-fluoro-phenyl)-1H-pyrazol-4-yl]-N-(1-methyl-4-piperidyl)-1,5-naphthyridin-3-amine;
6-[3-(5-chloro-2-fluoro-phenyl)-1H-pyrazol-4-yl]-N-(1-methylazetidin-3-yl)-1,5-naphthyridin-3-amine;
N-[2-(azetidin-1-yl)ethyl]-6-[3-(5-chloro-2-fluoro-phenyl)-1H-pyrazol-4-yl]-1,5-naphthyridin-3-amine;
6-[3-(5-chloro-2-fluoro-phenyl)-1H-pyrazol-4-yl]-N-(1,4-diazabicyclo[2.2.2]octan-2-ylmethyl)-1,5-naphthyridin-3-amine;
6-[3-(5-chloro-2-fluoro-phenyl)-1H-pyrazol-4-yl]-N-[2-(4-ethylpiperazin-1-yl)ethyl]-1,5-naphthyridin-3-amine;
6-[3-(5-chloro-2-fluoro-phenyl)-1H-pyrazol-4-yl]-N-[2-(4-methylpiperazin-1-yl)ethyl]-1,5-naphthyridin-3-amine;
6-[3-(5-chloro-2-fluoro-phenyl)-1H-pyrazol-4-yl]-N-[2-(2,2-dimethylpyrrolidin-1-yl)ethyl]-1,5-naphthyridin-3-amine;
6-[3-(5-chloro-2-fluoro-phenyl)-1H-pyrazol-4-yl]-N-(2-pyrrolidin-1-ylethyl)-1,5-naphthyridin-3-amine;
6-[3-(5-chloro-2-fluoro-phenyl)-1H-pyrazol-4-yl]-N-(5-piperazin-1-yl-2-pyridyl)-1,5-naphthyridin-3-amine;
6-[3-(5-chloro-2-fluoro-phenyl)-1H-pyrazol-4-yl]-N-(pyrrolidin-3-ylmethyl)-1,5-naphthyridin-3-amine;
N-(azetidin-2-ylmethyl)-6-[3-(5-chloro-2-fluoro-phenyl)-1H-pyrazol-4-yl]-1,5-naphthyridin-3-amine;
N-(azetidin-3-yl)-6-[3-(5-chloro-2-fluoro-phenyl)-1H-pyrazol-4-yl]-1,5-naphthyridin-3-amine;
6-[3-(5-chloro-2-fluoro-phenyl)-1H-pyrazol-4-yl]-N-[[(2S)-pyrrolidin-2-yl]methyl]-1,5-naphthyridin-3-amine;
6-[3-(5-chloro-2-fluoro-phenyl)-1H-pyrazol-4-yl]-N-(2-piperazin-1-ylethyl)-1,5-naphthyridin-3-amine;
methyl 4-[2-[[6-[3-(5-chloro-2-fluoro-phenyl)-1H-pyrazol-4-yl]-1,5-naphthyridin-3-yl]amino]ethyl]piperazine-2-carboxylate;
6-[3-(5-chloro-2-fluoro-phenyl)-1H-pyrazol-4-yl]-N-(2-piperidylmethyl)-1,5-naphthyridin-3-amine;
6-[3-(5-chloro-2-fluoro-phenyl)-1H-pyrazol-4-yl]-N-(4-piperidyl)-1,5-naphthyridin-3-amine;
6-[3-(5-chloro-2-fluoro-phenyl)-1H-pyrazol-4-yl]-N-(piperazin-2-ylmethyl)-1,5-naphthyridin-3-amine;
6-[3-(5-chloro-2-fluoro-phenyl)-1H-pyrazol-4-yl]-N-(4-piperidylmethyl)-1,5-naphthyridin-3-amine;
N-(azetidin-3-ylmethyl)-6-[3-(5-chloro-2-fluoro-phenyl)-1H-pyrazol-4-yl]-1,5-naphthyridin-3-amine;
6-[3-(5-chloro-2-fluoro-phenyl)-1H-pyrazol-4-yl]-N-[5-(4-methylpiperazin-1-yl)-2-pyridyl]-1,5-naphthyridin-3-amine;
6-[3-(5-chloro-2-fluoro-phenyl)-1H-pyrazol-4-yl]-N-[5-(4-isopropylpiperazin-1-yl)-2-pyridyl]-1,5-naphthyridin-3-amine;
1-[6-[3-(5-chloro-2-fluoro-phenyl)-1H-pyrazol-4-yl]-1,5-naphthyridin-3-yl]-N,N-dimethyl-azetidin-3-amine;
1-[4-[6-[3-(5-chloro-2-fluoro-phenyl)-1H-pyrazol-4-yl]-1,5-naphthyridin-3-yl]piperazin-1-yl]cyclopentanecarboxamide;
rac-(3S)-1-[6-[3-(5-chloro-2-fluoro-phenyl)-1H-pyrazol-4-yl]-1,5-naphthyridin-3-yl]-N,N-dimethyl-pyrrolidin-3-amine;
2-[4-[6-[3-(5-chloro-2-fluoro-phenyl)-1H-pyrazol-4-yl]-1,5-naphthyridin-3-yl]piperazin-1-yl]ethanol;
6-[3-(5-chloro-2-fluoro-phenyl)-1H-pyrazol-4-yl]-N-methyl-N-(1-methyl-4-piperidyl)-1,5-naphthyridin-3-amine;
2-[3-(5-chloro-2-fluoro-phenyl)-1H-pyrazol-4-yl]-7-[rac-(3R)-3-(1-piperidyl)pyrrolidin-1-yl]-1,5-naphthyridine;
2-[3-(5-chloro-2-fluoro-phenyl)-1H-pyrazol-4-yl]-7-[3-(1-piperidyl)azetidin-1-yl]-1,5-naphthyridine;
N-(azetidin-3-ylmethyl)-6-[3-(5-chloro-2-fluoro-phenyl)-1H-pyrazol-4-yl]-N-methyl-1,5-naphthyridin-3-amine;
2-[3-(5-chloro-2-fluoro-phenyl)-1H-pyrazol-4-yl]-7-(4-isopropylpiperazin-1-yl)-1,5-naphthyridine;
2-[3-(5-chloro-2-fluoro-phenyl)-1H-pyrazol-4-yl]-7-(4-pyrrolidin-1-yl-1-piperidyl)-1,5-naphthyridine;
1-[6-[3-(5-chloro-2-fluoro-phenyl)-1H-pyrazol-4-yl]-1,5-naphthyridin-3-yl]-N,N-dimethyl-piperidin-4-amine;
7-[2-(4-benzylpiperazin-1-yl)-6,8-dihydro-5H-[1,2,4]triazolo[1,5-a]pyrazin-7-yl]-2-[3-(5-chloro-2-fluoro-phenyl)-1H-pyrazol-4-yl]-1,5-naphthyridine;
7-[2-(4-benzylpiperazin-1-yl)-6,7-dihydro-4H-pyrazolo[1,5-a]pyrazin-5-yl]-2-[3-(5-chloro-2-fluoro-phenyl)-1H-pyrazol-4-yl]-1,5-naphthyridine;
1-[6-[3-(5-chloro-2-fluoro-phenyl)-1H-pyrazol-4-yl]-1,5-naphthyridin-3-yl]-N-methyl-azetidin-3-amine;
rac-(2R)-4-[6-[3-(5-chloro-2-fluoro-phenyl)-1H-pyrazol-4-yl]-1,5-naphthyridin-3-yl]-N-methyl-piperazine-2-carboxamide;
1-[6-[3-(5-chloro-2-fluoro-phenyl)-1H-pyrazol-4-yl]-1,5-naphthyridin-3-yl]azetidin-3-amine;

6-[3-(5-chloro-2-fluoro-phenyl)-1H-pyrazol-4-yl]-N-methyl-N-(2-piperazin-1-ylethyl)-1,5-naphthyridin-3-amine;

1-[6-[3-(5-chloro-2-fluoro-phenyl)-1H-pyrazol-4-yl]-1,5-naphthyridin-3-yl]pyrrolidin-3-amine;

1-[6-[3-(5-chloro-2-fluoro-phenyl)-1H-pyrazol-4-yl]-1,5-naphthyridin-3-yl]-N-methyl-pyrrolidin-3-amine;

2-[4-[6-[3-(5-chloro-2-fluoro-phenyl)-1H-pyrazol-4-yl]-1,5-naphthyridin-3-yl]piperazin-1-yl]ethanamine;

(2S)-4-[6-[3-(5-chloro-2-fluoro-phenyl)-1H-pyrazol-4-yl]-1,5-naphthyridin-3-yl]-N-methyl-piperazine-2-carboxamide;

1-[6-[3-(5-chloro-2-fluoro-phenyl)-1H-pyrazol-4-yl]-1,5-naphthyridin-3-yl]-N-methyl-piperidin-4-amine;

2-[3-(5-chloro-2-fluoro-phenyl)-1H-pyrazol-4-yl]-7-(3,6-diazabicyclo[3.2.0]heptan-3-yl)-1,5-naphthyridine;

2-[3-(5-chloro-2-fluoro-phenyl)-1H-pyrazol-4-yl]-7-(6-isopropyl-3,6-diazabicyclo[3.2.0]heptan-3-yl)-1,5-naphthyridine;

2-[4-[6-[3-(5-chloro-2-fluoro-phenyl)-1H-pyrazol-4-yl]-1,5-naphthyridin-3-yl]piperazin-1-yl]-N,N-dimethyl-ethanamine;

N-[2-[4-[6-[3-(5-chloro-2-fluoro-phenyl)-1H-pyrazol-4-yl]-1,5-naphthyridin-3-yl]piperazin-1-yl]ethyl]propan-2-amine;

rac-(2R)-4-[6-[3-(5-chloro-2-fluoro-phenyl)-1H-pyrazol-4-yl]-1,5-naphthyridin-3-yl]-N,1-dimethyl-piperazine-2-carboxamide;

rac-(2R)-4-[6-[3-(5-chloro-2-fluoro-phenyl)-1H-pyrazol-4-yl]-1,5-naphthyridin-3-yl]-1-isopropyl-N-methyl-piperazine-2-carboxamide;

6-[3-(5-chloro-2-fluoro-phenyl)-1H-pyrazol-4-yl]-N-methyl-N-[rac-(3R)-1-methylpyrrolidin-3-yl]-1,5-naphthyridin-3-amine;

2-[3-(5-chloro-2-fluoro-phenyl)-1H-pyrazol-4-yl]-7-[4-(4-methylpiperazin-1-yl)-1-piperidyl]-1,5-naphthyridine;

2-[3-(5-chloro-2-fluoro-phenyl)-1H-pyrazol-4-yl]-7-[2-(2,5-dihydro-1H-pyrrol-3-yl)-6,8-dihydro-5H-[1,2,4]triazolo[1,5-a]pyrazin-7-yl]-1,5-naphthyridine;

2-[3-(5-chloro-2-fluoro-phenyl)-1H-pyrazol-4-yl]-7-[2-(1-methyl-2,5-dihydropyrrol-3-yl)-6,8-dihydro-5H-[1,2,4]triazolo[1,5-a]pyrazin-7-yl]-1,5-naphthyridine;

2-[4-[6-[3-(5-chloro-2-fluoro-phenyl)-1H-pyrazol-4-yl]-1,5-naphthyridin-3-yl]pyrazol-1-yl]-N-methyl-ethanamine;

7-[1-(azetidin-3-ylmethyl)pyrazol-4-yl]-2-[3-(5-chloro-2-fluoro-phenyl)-1H-pyrazol-4-yl]-1,5-naphthyridine;

2-[4-[6-[3-(5-chloro-2-fluoro-phenyl)-1H-pyrazol-4-yl]-1,5-naphthyridin-3-yl]pyrazol-1-yl]ethanamine;

3-[6-[3-(5-chloro-2-fluoro-phenyl)-1H-pyrazol-4-yl]-1,5-naphthyridin-3-yl]-1-methyl-pyridin-2-one;

4-[6-[3-(5-chloro-2-fluoro-phenyl)-1H-pyrazol-4-yl]-1,5-naphthyridin-3-yl]cyclohex-3-en-1-amine;

2-[3-[6-[3-(5-chloro-2-fluoro-phenyl)-1H-pyrazol-4-yl]-1,5-naphthyridin-3-yl]pyrazol-1-yl]-N-methyl-ethanamine;

2-[3-(5-chloro-2-fluoro-phenyl)-1H-pyrazol-4-yl]-7-(2,5-dihydro-1H-pyrrol-3-yl)-1,5-naphthyridine;

N-[2-[4-[6-[3-(5-chloro-2-fluoro-phenyl)-1H-pyrazol-4-yl]-1,5-naphthyridin-3-yl]pyrazol-1-yl]ethyl]propan-2-amine;

N-benzyl-2-[4-[6-[3-(5-chloro-2-fluoro-phenyl)-1H-pyrazol-4-yl]-1,5-naphthyridin-3-yl]pyrazol-1-yl]ethanamine;

4-[6-[3-(5-chloro-2-fluoro-phenyl)-1H-pyrazol-4-yl]-1,5-naphthyridin-3-yl]-N,N-dimethyl-cyclohex-3-en-1-amine;

2-[3-(5-chloro-2-fluoro-phenyl)-1H-pyrazol-4-yl]-7-(5,6,7,8-tetrahydro-[1,2,4]triazolo[1,5-a]pyrazin-2-yl)-1,5-naphthyridine;

2-[3-(5-chloro-2-fluoro-phenyl)-1H-pyrazol-4-yl]-7-(6,7-dihydro-5H-imidazo[1,2-a]imidazol-3-yl)-1,5-naphthyridine;

2-[3-(5-chloro-2-fluoro-phenyl)-1H-pyrazol-4-yl]-7-(5,6,7,8-tetrahydroimidazo[1,2-a]pyrazin-3-yl)-1,5-naphthyridine;

2-[3-(5-chloro-2-fluoro-phenyl)-1H-pyrazol-4-yl]-7-(4,5,6,7-tetrahydropyrazolo[1,5-a]pyrazin-3-yl)-1,5-naphthyridine;

2-[3-(5-chloro-2-fluoro-phenyl)-1H-pyrazol-4-yl]-7-(4,5,6,7-tetrahydrotriazolo[1,5-a]pyrazin-3-yl)-1,5-naphthyridine;

2-[3-(5-chloro-2-fluoro-phenyl)-1H-pyrazol-4-yl]-7-[1-(1H-imidazol-4-ylmethyl)triazol-4-yl]-1,5-naphthyridine;

2-[3-(5-chloro-2-fluoro-phenyl)-1H-pyrazol-4-yl]-7-[1-(5,6,7,8-tetrahydro-1,6-naphthyridin-3-ylmethyl)triazol-4-yl]-1,5-naphthyridine;

2-[3-(5-chloro-2-fluoro-phenyl)-1H-pyrazol-4-yl]-7-(5,6,7,8-tetrahydroimidazo[1,5-a]pyrazin-1-yl)-1,5-naphthyridine;

2-[3-(5-chloro-2-fluoro-phenyl)-1H-pyrazol-4-yl]-7-(5,6,7,8-tetrahydroimidazo[1,5-a]pyrazin-3-yl)-1,5-naphthyridine;

2-[3-(5-chloro-2-fluoro-phenyl)-1H-pyrazol-4-yl]-7-(5,6,7,8-tetrahydroimidazo[1,2-a]pyrazin-2-yl)-1,5-naphthyridine;

2-[4-[6-[3-(5-chloro-2-fluoro-phenyl)-1H-pyrazol-4-yl]-1,5-naphthyridin-3-yl]-2,6-dimethyl-piperazin-1-yl]ethanamine;

2-[3-(5-chloro-2-fluoro-phenyl)-1H-pyrazol-4-yl]-7-(5,6-dihydro-4H-imidazo[1,2-c]triazol-3-yl)-1,5-naphthyridine;

2-[3-(5-chloro-2-fluoro-phenyl)-1H-pyrazol-4-yl]-7-(5,6,7,8-tetrahydroimidazo[1,2-a]pyrimidin-3-yl)-1,5-naphthyridine;

2-[3-(5-chloro-2-fluoro-phenyl)-1H-pyrazol-4-yl]-7-(2,4,5,6-tetrahydropyrrolo[2,3-c]pyrazol-3-yl)-1,5-naphthyridine;

methyl 3-[6-[3-(5-chloro-2-fluoro-phenyl)-1H-pyrazol-4-yl]-1,5-naphthyridin-3-yl]-7,8-dihydro-5H-pyrido[4,3-c]pyridazine-6-carboxylate;

2-[4-[6-[3-(5-chloro-2-fluoro-phenyl)-1H-pyrazol-4-yl]-1,5-naphthyridin-3-yl]triazol-1-yl]-N-methyl-ethanamine;

1-[6-[3-(5-chloro-2-fluoro-phenyl)-1H-pyrazol-4-yl]-1,5-naphthyridin-3-yl]piperidin-4-amine;

6-[5-(5-chloro-2-fluoro-phenyl)-1H-imidazol-4-yl]-N-[5-(4-methylpiperazin-1-yl)-2-pyridyl]-1,5-naphthyridin-3-amine;

6-[5-(5-chloro-2-fluoro-phenyl)-1H-imidazol-4-yl]-N-[2-(4-isopropylpiperazin-1-yl)ethyl]-1,5-naphthyridin-3-amine;

6-[5-(5-chloro-2-fluoro-phenyl)-1H-imidazol-4-yl]-N-[2-(2,2-dimethylpyrrolidin-1-yl)ethyl]-1,5-naphthyridin-3-amine;

6-[5-(5-chloro-2-fluoro-phenyl)-1H-imidazol-4-yl]-N-(5-piperazin-1-yl-2-pyridyl)-1,5-naphthyridin-3-amine;

6-[5-(5-chloro-2-fluoro-phenyl)-1H-imidazol-4-yl]-N-[5-(4-isopropylpiperazin-1-yl)-2-pyridyl]-1,5-naphthyridin-3-amine;

1-[6-[5-(5-chloro-2-fluoro-phenyl)-1H-imidazol-4-yl]-1,5-naphthyridin-3-yl]-N,N-dimethyl-piperidin-4-amine;
2-[5-(5-chloro-2-fluoro-phenyl)-1H-imidazol-4-yl]-7-piperazin-1-yl-1,5-naphthyridine;
1-[6-[5-(5-chloro-2-fluoro-phenyl)-1H-imidazol-4-yl]-1,5-naphthyridin-3-yl]-N-methyl-piperidin-4-amine;
2-[5-(5-chloro-2-fluoro-phenyl)-1H-imidazol-4-yl]-7-[4-(4-methylpiperazin-1-yl)-1-piperidyl]-1,5-naphthyridine;
rac-(3S)-1-[6-[5-(5-chloro-2-fluoro-phenyl)-1H-imidazol-4-yl]-1,5-naphthyridin-3-yl]-N,N-dimethyl-pyrrolidin-3-amine;
2-[5-(5-chloro-2-fluoro-phenyl)-1H-imidazol-4-yl]-7-[2-(1-methyl-2,5-dihydropyrrol-3-yl)-6,8-dihydro-5H-[1,2,4]triazolo[1,5-a]pyrazin-7-yl]-1,5-naphthyridine;
2-[3-[6-[5-(5-chloro-2-fluoro-phenyl)-1H-imidazol-4-yl]-1,5-naphthyridin-3-yl]pyrazol-1-yl]-N-methyl-ethanamine;
2-[5-(5-chloro-2-fluoro-phenyl)-1H-imidazol-4-yl]-7-[1-(3-piperidyl)pyrazol-4-yl]-1,5-naphthyridine;
2-[4-[6-[5-(5-chloro-2-fluoro-phenyl)-1H-imidazol-4-yl]-1,5-naphthyridin-3-yl]pyrazol-1-yl]-N-methyl-ethanamine;
2-[4-[6-[5-(5-chloro-2-fluoro-phenyl)-1H-imidazol-4-yl]-1,5-naphthyridin-3-yl]pyrazol-1-yl]ethanamine;
2-[5-(5-chloro-2-fluoro-phenyl)-1H-imidazol-4-yl]-7-(4,5,6,7-tetrahydropyrazolo[1,5-a]pyrazin-2-yl)-1,5-naphthyridine;
2-[5-(5-chloro-2-fluoro-phenyl)-1H-imidazol-4-yl]-7-(4,5,6,7-tetrahydropyrazolo[1,5-a]pyrazin-3-yl)-1,5-naphthyridine;
2-[5-(5-chloro-2-fluoro-phenyl)-1H-imidazol-4-yl]-7-(4,5,6,7-tetrahydrotriazolo[1,5-a]pyrazin-3-yl)-1,5-naphthyridine;
2-[5-(5-chloro-2-fluoro-phenyl)-1H-imidazol-4-yl]-7-(5,6,7,8-tetrahydroimidazo[1,2-a]pyrazin-3-yl)-1,5-naphthyridine;
2-[5-(5-chloro-2-fluoro-phenyl)-1H-imidazol-4-yl]-7-(5,6,7,8-tetrahydro-[1,2,4]triazolo[1,5-a]pyrazin-2-yl)-1,5-naphthyridine;
6-[5-(5-chloro-2-fluoro-phenyl)-1H-imidazol-4-yl]-N-(2-pyrrolidin-1-ylethyl)-1,5-naphthyridin-3-amine;
6-[5-(5-chloro-2-fluoro-phenyl)-1H-imidazol-4-yl]-N-[2-[rac-(3R,5S)-3,5-dimethylpiperazin-1-yl]ethyl]-1,5-naphthyridin-3-amine;
methyl 2-[1-[2-[[6-[5-(5-chloro-2-fluoro-phenyl)-1H-imidazol-4-yl]-1,5-naphthyridin-3-yl]amino]ethyl]piperazin-2-yl]acetate;
methyl 2-[4-[2-[[6-[5-(5-chloro-2-fluoro-phenyl)-1H-imidazol-4-yl]-1,5-naphthyridin-3-yl]amino]ethyl]piperazin-2-yl]acetate;
6-[3-(5-chloro-2,4-difluoro-phenyl)-1H-pyrazol-4-yl]-N-[2-(4-isopropylpiperazin-1-yl)ethyl]-1,5-naphthyridin-3-amine;
6-[3-(5-chloro-2,4-difluoro-phenyl)-1H-pyrazol-4-yl]-N-[2-(4-methylpiperazin-1-yl)ethyl]-1,5-naphthyridin-3-amine;
6-[3-(5-chloro-2,4-difluoro-phenyl)-1H-pyrazol-4-yl]-N-[2-(4-ethylpiperazin-1-yl)ethyl]-1,5-naphthyridin-3-amine;
6-[3-(5-chloro-2,4-difluoro-phenyl)-1H-pyrazol-4-yl]-N-(1,4-diazabicyclo[2.2.2]octan-2-ylmethyl)-1,5-naphthyridin-3-amine;
6-[3-(5-chloro-2,4-difluoro-phenyl)-1H-pyrazol-4-yl]-N-[2-(2,2-dimethylpyrrolidin-1-yl)ethyl]-1,5-naphthyridin-3-amine;
6-[3-(5-chloro-2,4-difluoro-phenyl)-1H-pyrazol-4-yl]-N-(2-piperazin-1-ylethyl)-1,5-naphthyridin-3-amine;
N-[2-(4-tert-butylpiperazin-1-yl)ethyl]-6-[3-(5-chloro-2,4-difluoro-phenyl)-1H-pyrazol-4-yl]-1,5-naphthyridin-3-amine;
2-[3-(5-chloro-2,4-difluoro-phenyl)-1H-pyrazol-4-yl]-7-[3-(1-piperidyl)azetidin-1-yl]-1,5-naphthyridine;
2-[3-(5-chloro-2,4-difluoro-phenyl)-1H-pyrazol-4-yl]-7-[4-(4-methylpiperazin-1-yl)-1-piperidyl]-1,5-naphthyridine;
1-[6-[3-(5-chloro-2,4-difluoro-phenyl)-1H-pyrazol-4-yl]-1,5-naphthyridin-3-yl]-N,N-dimethyl-piperidin-4-amine;
1-[6-[3-(5-chloro-2,4-difluoro-phenyl)-1H-pyrazol-4-yl]-1,5-naphthyridin-3-yl]-N,N-dimethyl-azetidin-3-amine;
2-[3-(5-chloro-2,4-difluoro-phenyl)-1H-pyrazol-4-yl]-7-[rac-(3R)-3-(1-piperidyl)pyrrolidin-1-yl]-1,5-naphthyridine;
rac-(3S)-1-[6-[3-(5-chloro-2,4-difluoro-phenyl)-1H-pyrazol-4-yl]-1,5-naphthyridin-3-yl]-N,N-dimethyl-pyrrolidin-3-amine;
1-[6-[3-(5-chloro-2,4-difluoro-phenyl)-1H-pyrazol-4-yl]-1,5-naphthyridin-3-yl]-N-methyl-piperidin-4-amine;
rac-(2R)-4-[6-[3-(5-chloro-2,4-difluoro-phenyl)-1H-pyrazol-4-yl]-1,5-naphthyridin-3-yl]-N-methyl-piperazine-2-carboxamide;
1-[1-[6-[3-(5-chloro-2,4-difluoro-phenyl)-1H-pyrazol-4-yl]-1,5-naphthyridin-3-yl]azetidin-3-yl]-N-methyl-methanamine;
1-[6-[3-(5-chloro-2,4-difluoro-phenyl)-1H-pyrazol-4-yl]-1,5-naphthyridin-3-yl]azetidin-3-amine;
1-[6-[3-(5-chloro-2,4-difluoro-phenyl)-1H-pyrazol-4-yl]-1,5-naphthyridin-3-yl]-N-methyl-azetidin-3-amine;
N-(azetidin-3-ylmethyl)-6-[3-(5-chloro-2,4-difluoro-phenyl)-1H-pyrazol-4-yl]-N-methyl-1,5-naphthyridin-3-amine;
1-[6-[3-(5-chloro-2,4-difluoro-phenyl)-1H-pyrazol-4-yl]-1,5-naphthyridin-3-yl]pyrrolidin-3-amine;
1-[6-[3-(5-chloro-2,4-difluoro-phenyl)-1H-pyrazol-4-yl]-1,5-naphthyridin-3-yl]-N-methyl-pyrrolidin-3-amine;
2-[4-[6-[3-(5-chloro-2,4-difluoro-phenyl)-1H-pyrazol-4-yl]-1,5-naphthyridin-3-yl]piperazin-1-yl]ethanamine;
6-[3-(5-chloro-2,4-difluoro-phenyl)-1H-pyrazol-4-yl]-N-[(3R)-1-isopropylpyrrolidin-3-yl]-N-methyl-1,5-naphthyridin-3-amine;
(2R)-4-[6-[3-(5-chloro-2,4-difluoro-phenyl)-1H-pyrazol-4-yl]-1,5-naphthyridin-3-yl]-1-isopropyl-N-methyl-piperazine-2-carboxamide;
N-[2-[4-[6-[3-(5-chloro-2,4-difluoro-phenyl)-1H-pyrazol-4-yl]-1,5-naphthyridin-3-yl]piperazin-1-yl]ethyl]propan-2-amine;
2-[3-[6-[3-(5-chloro-2,4-difluoro-phenyl)-1H-pyrazol-4-yl]-1,5-naphthyridin-3-yl]pyrazol-1-yl]-N-methyl-ethanamine;
2-[4-[6-[3-(5-chloro-2,4-difluoro-phenyl)-1H-pyrazol-4-yl]-1,5-naphthyridin-3-yl]pyrazol-1-yl]ethanamine;
7-[1-(azetidin-3-ylmethyl)pyrazol-4-yl]-2-[3-(5-chloro-2,4-difluoro-phenyl)-1H-pyrazol-4-yl]-1,5-naphthyridine;
2-[3-(5-chloro-2,4-difluoro-phenyl)-1H-pyrazol-4-yl]-7-(4,5,6,7-tetrahydropyrazolo[1,5-a]pyrazin-3-yl)-1,5-naphthyridine;
2-[3-(5-chloro-2,4-difluoro-phenyl)-1H-pyrazol-4-yl]-7-(5,6,7,8-tetrahydro-[1,2,4]triazolo[1,5-a]pyrazin-2-yl)-1,5-naphthyridine;

2-[3-(5-chloro-2,4-difluoro-phenyl)-1H-pyrazol-4-yl]-7-(5,6,7,8-tetrahydroimidazo[1,5-a]pyrazin-1-yl)-1,5-naphthyridine;
2-[3-(5-chloro-2,4-difluoro-phenyl)-1H-pyrazol-4-yl]-7-(5,6,7,8-tetrahydroimidazo[1,2-a]pyrazin-2-yl)-1,5-naphthyridine;
2-[3-(5-chloro-2,4-difluoro-phenyl)-1H-pyrazol-4-yl]-7-(6,7-dihydro-5H-imidazo[1,2-a]imidazol-3-yl)-1,5-naphthyridine;
2-[3-(5-chloro-2,4-difluoro-phenyl)-1H-pyrazol-4-yl]-7-(2,3-dihydro-1H-imidazo[1,5-a]imidazol-7-yl)-1,5-naphthyridine;
2-[3-(5-chloro-2,4-difluoro-phenyl)-1H-pyrazol-4-yl]-7-(4,5,6,7-tetrahydropyrazolo[1,5-a]pyrazin-2-yl)-1,5-naphthyridine;
2-[3-(5-chloro-2,4-difluoro-phenyl)-1H-pyrazol-4-yl]-7-(5,6-dihydro-4H-imidazo[1,2-c]triazol-3-yl)-1,5-naphthyridine;
2-[3-(5-chloro-2,4-difluoro-phenyl)-1H-pyrazol-4-yl]-7-(2,4,5,6-tetrahydropyrrolo[2,3-c]pyrazol-3-yl)-1,5-naphthyridine;
methyl 3-[6-[3-(5-chloro-2,4-difluoro-phenyl)-1H-pyrazol-4-yl]-1,5-naphthyridin-3-yl]-7,8-dihydro-5H-pyrido[4,3-c]pyridazine-6-carboxylate;
2-[3-(5-chloro-2,4-difluoro-phenyl)-1H-pyrazol-4-yl]-7-[1-(1H-imidazol-4-ylmethyl)triazol-4-yl]-1,5-naphthyridine;
2-[3-(5-chloro-2,4-difluoro-phenyl)-1H-pyrazol-4-yl]-7-[1-(5,6,7,8-tetrahydro-1,6-naphthyridin-3-ylmethyl)triazol-4-yl]-1,5-naphthyridine;
2-[4-[6-[3-(5-chloro-2,4-difluoro-phenyl)-1H-pyrazol-4-yl]-1,5-naphthyridin-3-yl]triazol-1-yl]-N-methyl-ethanamine;
2-[4-[2-[[6-[3-(5-chloro-2,4-difluoro-phenyl)-1H-pyrazol-4-yl]-1,5-naphthyridin-3-yl]amino]ethyl]piperazin-1-yl]propan-1-ol; and
6-[3-(5-chloro-2,4-difluoro-phenyl)-1H-pyrazol-4-yl]-N-[2-[rac-(3R,5S)-3,5-dimethylpiperazin-1-yl]ethyl]-1,5-naphthyridin-3-amine;
or a pharmaceutically acceptable salt thereof.

7. A pharmaceutical composition comprising the compound or pharmaceutically acceptable salt of claim 1 and a pharmaceutically acceptable carrier.

8. The pharmaceutical composition of claim 7, wherein the pharmaceutical composition is formulated for inhalation.

9. A method of treating an ALK5-mediated disease or condition in a subject, comprising administering to the subject a therapeutically effective amount of the compound or pharmaceutically acceptable salt of claim 1.

10. The method of claim 9, wherein the disease or condition is fibrosis.

11. The method of claim 10, wherein the fibrosis is selected from cardiac fibrosis, kidney fibrosis, pulmonary fibrosis, liver fibrosis, portal vein fibrosis, skin fibrosis, bladder fibrosis, intestinal fibrosis, peritoneal fibrosis, myelofibrosis, oral submucous fibrosis, and retinal fibrosis.

12. The method of claim 11, where the pulmonary fibrosis is selected from idiopathic pulmonary fibrosis (IPF), familial pulmonary fibrosis (FPF), interstitial lung fibrosis, fibrosis associated with asthma, fibrosis associated with chronic obstructive pulmonary disease (COPD), silica-induced fibrosis, asbestos-induced fibrosis, and chemotherapy-induced lung fibrosis.

13. The method of claim 10, wherein the fibrosis is idiopathic pulmonary fibrosis (IPF).

14. The method of claim 9, wherein the disease or condition is selected from breast cancer, colon cancer, prostate cancer, lung cancer, hepatocellular carcinoma, glioblastoma, melanoma, and pancreatic cancer.

15. The method of claim 14, wherein the lung cancer is non-small cell lung cancer.

16. The method of claim 9, comprising administering a second therapeutic agent.

17. The compound of claim 1, wherein $R^2$ is selected from —NH—$(CH_2)_{1-3}R^5$; —NHCH$_2$C(CH$_3$)$_2R^5$; —NHCH$_2$C(CH$_3$)(CH$_2$OCH$_3$)$R^5$; —NHR$^5$; —NH—C(CH$_3$)$_2$CH$_2R^5$; —N(CH$_3$)$R^5$; —N(CH$_3$)CH$_2R^5$; and —N(CH$_3$)CH$_2$CH$_2R^5$;

or a pharmaceutically acceptable salt thereof.

18. The compound of claim 1, wherein $R^2$ is selected from azetidinyl-$R^5$; piperazinyl-$R^5$; pyrrolidinyl-$R^5$; piperidinyl-$R^5$; pyrazolyl-$R^5$; triazolyl-$R^5$; cyclohexenyl-$R^5$; and cyclohexanyl-$R^5$, or a pharmaceutically acceptable salt thereof.

19. The compound of claim 1, wherein $R^5$ is selected from piperazinyl, piperidinyl, pyrrolidinyl, azetidinyl, pyridinyl, and pyrrolinyl, each of which is optionally substituted with one or more methyl, ethyl, i-propyl, or n-propyl; and methyl amine; dimethyl amine; methyl; ethyl; i-propyl; n-propyl; halo; —CF$_3$; —NH$_2$; —CH$_2$NHCH$_3$; —CH$_2$CH$_2$NH$_2$; —CH$_2$CH$_2$N(CH$_3$)$_2$; —CH$_2$CH$_2$NHCH$_3$; and —CH$_2$CH$_2$NHC(CH$_3$)$_2$;

or a pharmaceutically acceptable salt thereof.

20. The compound of claim 1, wherein $R^5$ is selected from piperazinyl, piperidinyl, pyrrolidinyl, and azetidinyl, each of which is optionally substituted with one or more methyl, ethyl, i-propyl, or n-propyl, or a pharmaceutically acceptable salt thereof.

21. The compound of claim 1, wherein:

$R^2$ is selected from —NH—$(CH_2)_{1-3}R^5$; —NHCH$_2$C(CH$_3$)$_2R^5$; —NHR$^5$; —NH—C(CH$_3$)$_2$CH$_2R^5$; —N(CH$_3$)$R^5$; —N(CH$_3$)CH$_2R^5$; —N(CH$_3$)CH$_2$CH$_2R^5$; and $R^5$ is selected from piperazinyl, piperidinyl, pyrrolidinyl, and pyridinyl, each of which is optionally substituted with one or more methyl, ethyl, i-propyl, or n-propyl; or $R^2$ is selected from piperazinyl-$R^5$; pyrrolidinyl-$R^5$; piperidinyl-$R^5$; pyrazolyl-$R^5$; and triazolyl-$R^5$; and $R^5$ is selected from methyl amine; dimethyl amine; methyl; ethyl; i-propyl; n-propyl; —NH$_2$; —CH$_2$NHCH$_3$; —CH$_2$CH$_2$NH$_2$; —CH$_2$CH$_2$N(CH$_3$)$_2$; and —CH$_2$CH$_2$NHCH$_3$;

or a pharmaceutically acceptable salt thereof.

22. The compound of claim 1, wherein $R^2$ is selected from:

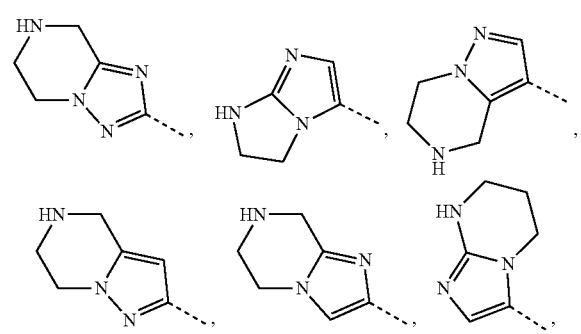

-continued
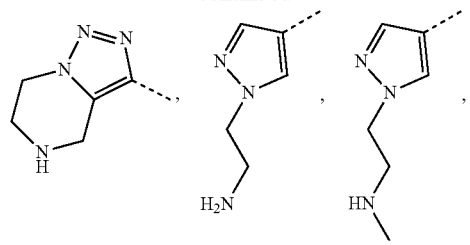
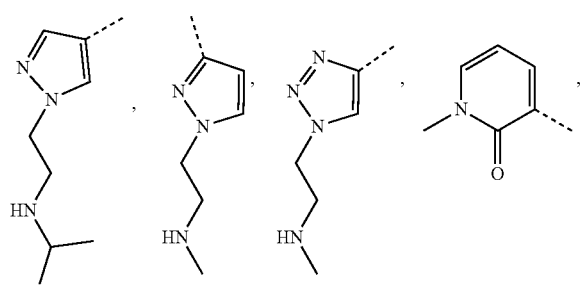
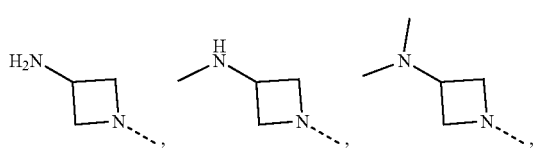
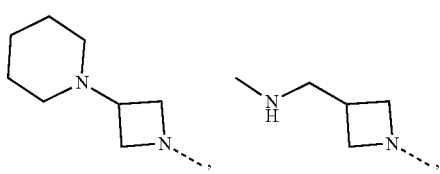
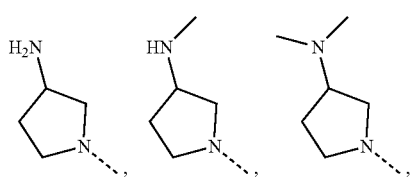
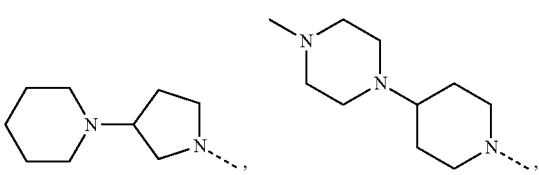
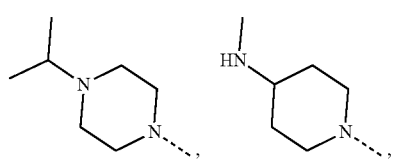
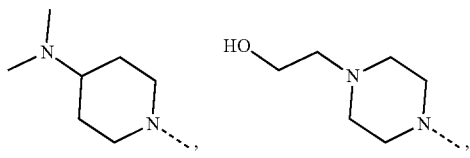
-continued
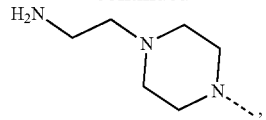
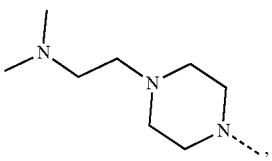
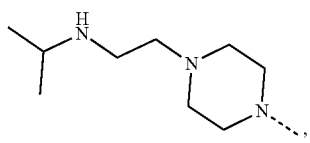
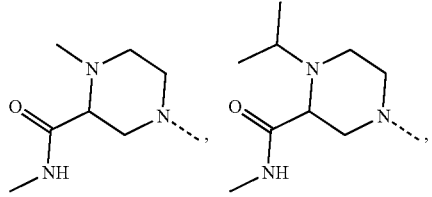
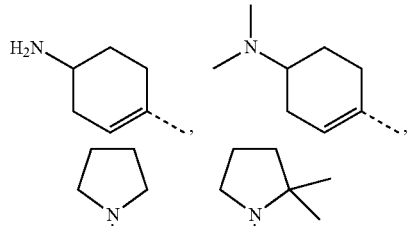
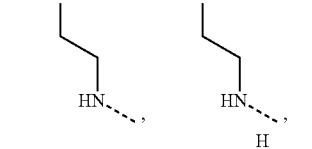
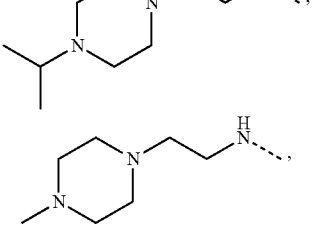
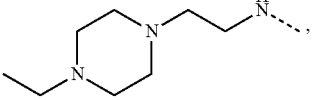
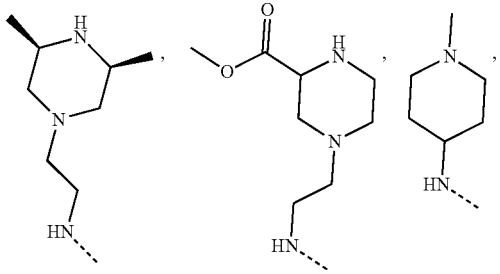

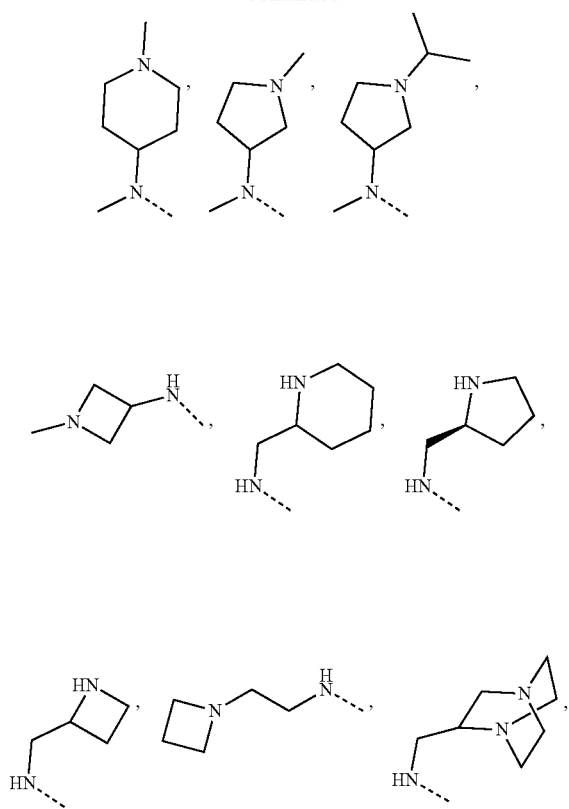

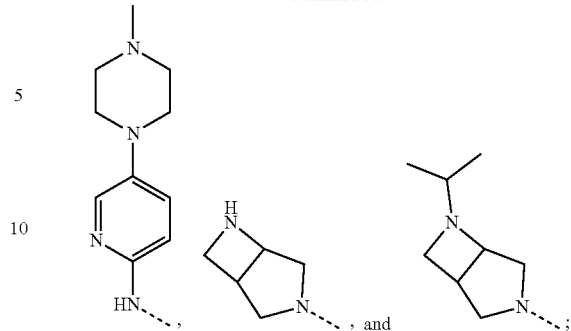

or a pharmaceutically acceptable salt thereof.

23. A pharmaceutical composition comprising the compound or pharmaceutically acceptable salt of claim 6 and a pharmaceutically acceptable carrier.

24. The pharmaceutical composition of claim 23, wherein the pharmaceutical composition is formulated for inhalation.

25. A method of treating an ALK5-mediated disease or condition in a subject, comprising administering to the subject a therapeutically effective amount of the compound or pharmaceutically acceptable salt of claim 6.

26. The method of claim 25, wherein the disease or condition is fibrosis.

27. The method of claim 26, wherein the fibrosis is idiopathic pulmonary fibrosis (IPF).

28. The method of claim 25, wherein the disease or condition is non-small cell lung cancer.

* * * * *